US009951342B2

(12) United States Patent
Barrangou et al.

(10) Patent No.: US 9,951,342 B2
(45) Date of Patent: Apr. 24, 2018

(54) CULTURES WITH IMPROVED PHAGE RESISTANCE

(71) Applicant: DUPONT NUTRITION BIOSCIENCES APS, Copenhagen K (DK)

(72) Inventors: Rodolphe Barrangou, Madison, WI (US); Christophe Fremaux, Poitiers (FR); Phillippe Horvath, Scorbe-Clairvaux (FR); Dennis Romero, Oregon, WI (US); Patrick Boyaval, La Meziere (FR)

(73) Assignee: DUPONT NUTRITION BIOSCIENCES APS (DK)

( * ) Notice: Subject to any disclaimer, the term of this patent is extended or adjusted under 35 U.S.C. 154(b) by 3 days.

(21) Appl. No.: 14/570,994

(22) Filed: Dec. 15, 2014

(65) Prior Publication Data

US 2015/0093473 A1 Apr. 2, 2015

Related U.S. Application Data

(62) Division of application No. 12/529,421, filed as application No. PCT/US2008/002714 on Feb. 29, 2008, now abandoned.

(60) Provisional application No. 60/904,721, filed on Mar. 2, 2007.

(51) Int. Cl.

| | |
|---|---|
| ***C12Q 1/68*** | (2018.01) |
| ***C12N 15/74*** | (2006.01) |
| ***A23C 9/123*** | (2006.01) |
| ***C12N 1/20*** | (2006.01) |
| ***C12Q 1/70*** | (2006.01) |

(52) U.S. Cl.

CPC ............ *C12N 15/746* (2013.01); *A23C 9/123* (2013.01); *A23C 9/1238* (2013.01); *C12N 1/20* (2013.01); *C12Q 1/70* (2013.01); *A23C 2220/202* (2013.01); *A23Y 2240/75* (2013.01); *C12N 2795/00011* (2013.01)

(58) Field of Classification Search

None

See application file for complete search history.

(56) References Cited

U.S. PATENT DOCUMENTS

| | | | |
|---|---|---|---|
| 2,225,783 | A | 12/1940 | Jensen et al. |
| 3,024,116 | A | 3/1962 | Engelland |
| 3,403,032 | A | 9/1968 | Etchells et al. |
| 3,897,307 | A | 7/1975 | Porubcan et al. |
| 3,932,674 | A | 1/1976 | Etchells et al. |
| 4,140,800 | A | 2/1979 | Kline |
| 4,423,079 | A | 12/1983 | Kline |
| 4,621,058 | A | 11/1986 | Reddy |
| 5,593,885 | A | 1/1997 | Klaenhammer et al. |
| 2003/0219778 | A1 | 11/2003 | Ferreira et al. |

FOREIGN PATENT DOCUMENTS

| | | |
|---|---|---|
| WO | 2007025097 | 3/2007 |
| WO | 2007136815 | 11/2007 |

OTHER PUBLICATIONS

Roe et al., DNA Isolation and Sequencing, 1996, Essential Techniques Series, John Wiley & Sons.
Sambrook et aI., Molecular Cloning: A Laboratory Manual, 2nd edition, 1989, Cold Spring Harbor Laboratory Press.
Altschul S.F. et aI., Basic Local Alignment Search Tool, J. Mol. Biol., 1990, 215, p. 403-410.
Amann R. et aI., Fluorescent-oligonucleotide probing of whole cells for determinative, phylogenetic, and environmental studies in microbiolog~, J. Bacteriology, 1990, vol. 172, No. 2, p. 762-770.
Ausubel et aI., Current Protocols in Molecular Biology, John Wiley & Sons, Inc., 1995, chapter 18.
Ausubel et aI., Current Protocols in Molecular Biology, John Wiley & Sons, Inc., 1999, p. 7-58 to 7-60.
Barrangou R. et aI., Identification and Characterization of Leuconostoc fallax Strains Isolated from an Industrial Sauerkraut Fermentation, Appl. Environ. Microbiol., 2002, vol. 68, No. 6, p. 2877-2884.
Bolotin A. et aI., “Clustered regularly interspaced short palindrome repeats (CRISPRs) have spacers of extrachromosomal origin”, Microbiology, 2005, vol. 151, No. 8, p. 2551-2561.
Bolton A. et aI, “Complete sequence and comparative genome analysis of the dairy bacterium *Streptococcus thermophiles*”, Nature Biotechnology, 2004, vol. 22, p. 1554-1558.
Breitbart and Rohwer, Trends Microbiol., 2005, vol. 13, p. 278.
Brussow H., Phages of dairy bacteria, Ann. Rev. Microbiol., 2001, vol. 55, p. 283-303.
Chibani-Chennoufi S. et aI., “Phage-host interaction: an ecological perspective”, 1. Bacteriol, 2004, vol. 186, No. 12, p. 3677-3686.
DeBoy R.T. et aI., Chromosome evolution in the Thermotogales: large-scale inversions and strain diversification ofCRISPR sequences, J. Bacteriol., 2006, vol. 188, p. 2364-2374.
Devereux J. et aI., A Comprehensive set of sequence analysis programs for the V AX, Nucleic Acids Research, 1984, vol. 12, No. 1, p. 387.

(Continued)

*Primary Examiner* — Jennifer Graser

(57) ABSTRACT

The present invention provides methods and compositions related to modulating the resistance of a cell against a target nucleic acid or a transcription product thereof. In some preferred embodiments, the present invention provides compositions and methods for the use of one or more cas genes or proteins for modulating the resistance of a cell against a target nucleic acid or a transcription product thereof. In some embodiments, the present invention provides methods and compositions that find use in the development and use of strain combinations and starter culture rotations. In additional embodiments, the present invention provides methods for labelling and/or identifying bacteria. In some preferred embodiments, the present invention provides methods for the use of CRISPR loci to determine the potential virulence of a phage against a cell and the use of CRISPR-cas to modulate the genetic sequence of a phage for increased virulence level. In still further embodiments, the present invention provides means and compositions for the development and use of phages as biocontrol agents.

25 Claims, 16 Drawing Sheets

(56) References Cited

OTHER PUBLICATIONS

Duplessis M. et al., Global gene expression analysis of two *Streptococcus thermophil* us bacteriophages using DNA microarray, Virology, 2005, vol. 340, p. 192-208.
Genbank accession No. DQ072990.
Godde JS and Bickerton, The repetitive DNA elements called CRISPRs and their associated genes: evidence of horizontal transfer among prokaryotes, 1. Mol. Evol., 2006, vol. 62, p. 718.
Groenen P.M.A. et al., Nature of DNA polymorphism in the direct repeat cluster of *Mycobacterium tuberculosis*; application for strain differentiation by a novel typing method, Mol. Microbio 1., 1993, vol. 10, No. 5, p. 1057-1065.
Haft D.H. et al., A Guild of 45 CRISPR-Associated (Cas) Protein Families and Multiple CRISPRJCas Subtypes Exist in Prokaryotic Genomes, PLoS. Comput. Biol., 2005, vol. 1, No. 6, e60.
Heap H.A. and Lawrence R.C., The selection of starter strains for cheesemaking, N. Z. 1. Dairy Sci. Technol.,1976,vo1.11,No. 1,p. 16.
Hendrix RW, et al, "Evolutionary relationships among diverse bacteriophages and prophages: All the world's a phage", Proc. Natl. Acad. Sci. USA, 1999, vol. 96, p. 2192-2197.
Hoe N. et al., Rapid Molecular Genetic Subtyping of Serotype M1 Group A *Streptococcus* Strains, Emerg. Infect. Dis., 1999, vol. 5, p. 254-263.
Ishino Y. et al., Nucleotide Sequence of the iap Gene, Responsible for Alkaline Phosphatase Isozyme Conversion in *Escherichia coli*, and identification of the gene product, J. Bacteriol., 1987, vol. 169, No. 12, p. 5429-5433.
Jansen R. et al., Identification of a Novel Family of Sequence Repeats Among Prokaryotes, OMICS J. Integ. Biol., 2002, vol. 6, p. 23-33.
Jansen R. et al., Identification of genes that are associated with DNA repeats in prokaryotes, Molecular Microbiology, 2002, vol. 43, No. 6, p. 1565-1575.
Kamerbeek et al., J. Clin. Microbiol., 1997, vol. 35, p. 907-914.
Klaenhammer T.R., Interactions of Bacteriophages with Lactic Streptococci, Advances in Applied Microbiology, 1984, vol. 30, p. 1-29.
Knorr (ed.) Food Biotechnology, 1987, p. 530-555.
Lawrence R.C. et al., Cheese Starters, J. Dairy Res., 1976, vol. 43, p. 141-193.
Lawrence et al., J. Dairy Science, 1978, vol. 61, p. 1181.
Levesque et al., Appl. Environ. Microbiol., 2005, vol. 71,4057-4068.
Lillestol R.K. et al., A putative viral defense mechanism in archaeal cells, Archaea, 2006, vol. 2, p. 59-72.
Limsowtin and Terzahi, N.Z. J. Dairy Sci. Technol., 1976, vol. 11, p. 251.
Limsowtin et at, N.ZJ. Dairy Sci. Technol., 1978, vol. 13, p. 1.
Makarova et al., Biol. Direct., 2006, vol. 1, p. 7.
Makarova K.S. et al., A DNA repair system specific for thermophilic Archaea and bacteria predicted by genomic context analysis, Nucleic Acids Research, 2002, vol. 30, No. 2, p. 482-496.
Masepohl B. et al., Long tandemly repeated repetitive (L TRR) sequences in filamentous *cyanobacterium Anabaena* sp. PCC 7120, Biochim. Biophys. Acta, 1996, vol. 1307, p. 26-30.
Moineau et al., CanJ. Microbiol., 1992, vol. 38, p. 875.
Mojica et al., Mol. Microbiol., 2000, vol. 36, p. 244-246.
Mojica FJ.M. et al., Intervening Sequences of Regularly Spaced Prokaryotic Repeats Derive from Foreign Genetic Elements, J. Mol. Evol., 2005, vol. 60, p. I74-182.
Mojica FJ.M. et al., Long stretches of short tandem repeats are present in the largest replicons of the Archaea Haloferax mediterranei and Haloferax volcanii and could be involved in replicon partitioning, Mol. Microbiol., 1995, 17:85-93.
Mongodin EF, Hance IR, DeBoy RT, Gill SR, Daugherty S, Huber R, Fraser CM, Stetter K, & KE Nelson (2005). Gene transfer and genome plasticity in Thermotoga maritima, a model hyperthermophilic species. Journal of Bacteriology 187:4935-4944.
Nakata A et al., Unusual Nucleotide Arrangement with Repeated Sequences in the *Escherichia coli* K-12 Chromosome, Journal of Bacteriology, 1989, vol. 171, No. 6, p. 3553-3556.
Pearce, N.Z. J. Dairy Sci. Technol., 1978, vol. 13, p. 166.
Pease AC. et al., Light-generated oligonucleotide arrays for rapid DNA sequence analysis, Proc. Natl. Acad. Sci. USA, 1994, vol. 91, No. 11, p. 5022-5026.
Pederson, Microbiology of Fermented Foods, 2nd edition, 1979, p. 105-135.
Pederson, Microbiology of Fermented Foods, 2nd edition, 1979, p. 135-152.
Pederson, Microbiology of Fermented Foods, 2nd edition, 1979, p. 210-234.
Pourcel C. et al., CRISPR elements in Yersinia pestis acquire new repeats by preferential uptake of bacteriophage DNA, and provide additional tools for evolutionary studies, Microbiol., 2005, vol. 151, p. 653-663.
Rajagopal S.N. et al. Associative Growth and Proteolysis of *Streptococcus thermophilus* and Lactobacillus bulgaricus in skim milk, Journal of Dairy Science, 1990, vol. 73,2—894-899.
Russell and Klaenhammer, Appl. Environ. Microbiol., 2001, vol. 67, p. 4361-4364.
Sanders and Klaenhammer, Appl. Environ. Microbiol., 1980, vol. 40, p. 500.
Sturino J.M. and Klaenhammer T.R., Engineered bacteriophage-defense systems in bioprocessing, Nat. Rev. Microbiol., 2006, vol. 4, No. 5, p. 395-404.
Tatusova T.A. et al., BLAST 2 SEQUENCES, A new tool for comparing protein and nucleotide sequences, FEMS Microbiol. Lett., 1999, vol. 174, No. 2, p. 247-250.
Tatusova T.A. et al., Erratum to BALST 2 SEQUENCES, a new tool for comparing protein and nucleotide sequences, FEMS Microbiol. Lett., 1999, vol. 177, No. 1, p. I87-188.
Thunell R.K. et al., Phage-Insensitive, Multiple-Strain Starter Approach to Cheddar Cheese Making, Journal Dairy Science, 1981, vol. 64, issue 11, p. 2270-2277.
van Embden J.D.A. et al., Genetic Variation and Evolutionary Origin of the Direct Repeat Locus of *Mycobacterium tuberculosis* Complex Bacteria, Journal of Bacteriology, 2000, vol. 182, No. 9, p. 2393-2401.
van Embden et al., J. Clin. Microbiol., 1993, vol. 31, p. 406-409.
White P.A. et al., Simplified hepatitis C virus genotyping by heteroduplex mobility analysis, 1. Clin. Microl., 2000, vol. 38, No. 2, p. 477-482.
Whitehead H.R. and Hunter GJ.E., 356. Bacteriophage in cheese manufacture: Contamination from farm equipment, Journal Dairy Research, 1947, vol. 15, issues 1-2, p. 112.
Courtin P. et al., "Interactions between microorganisms in a simple ecosystem: yogurt bacteria as a study model", LA1T, 2004, vol. 84, p. 125-134.
Barrangou R. et al., "CRISPR provides acquired resistance against viruses in prokaryotes", Science, 2007, vol. 315, No. 5819, p. 1709-1712.
Brouns SJJ et al., Small CRISPR RNAs Guide Antiviral Defense in Prokaryotes, Science, 2008, vol. 321, p. 960-964.
Deltcheva E et al., CRISPR RNA maturation by trans-encoded small RNA and host factor Rnase III, Nature, 2001 vol. 471, p. 602-606.
Deveau H et al., Phage Response in CRISPR-Encoded Resistance in *Streptococcus thermophilus*, Journal of Bacteriology, Feb. 2008, vol. 190, No. 4, p. 1390-1400.
Garneau JE et al., The CRISPRICas bacterial immune system cleaves bacteriophage and plasmid DNA, Nature, Nov. 4, 2010, vol. 468, p. 67-71.
Gasiunas G et al., Cas9-crRNA ribonucleoprotein complex mediates specific DNA cleavage for adaptive immunity in bacteria, Proc. Natl. Acad. Sci. USA, Sep. 25, 2012;109(39):E2579-86.
Hale CR et al., RNA-Guided RNA Cleavage by CRISPR RNA-Cas Protein Complex, Cell. Nov. 25, 2009;139(5):945-956.
Horvath P. et al., Comparative analysis of CRISPR loci in lactic acid bacteria genomes, International Journal of Food Microbiology, 2009, vol. 131, p. 62-70.

(56) References Cited

OTHER PUBLICATIONS

Horvath P. et al., CRISPRICas, the Immune System of Bacteria and Archaea, Science, Jan. 8, 2010, vol. 327, 167-170.
Ibrahim M et al., A genome-wide survey of short coding sequences in streptococci, Microbiology, 2007, vol. 153, p. 3631-3644.
Jinek M et al., A programmable dual-RNA-guided DNA endonuclease in adaptive bacterial immunity, Science, Aug. 17, 2012;337(6096):816-21.
Labrie SJ et al., Bacteriophage resistance mechanisms, Nature Reviews Microbiology, May 2010;8(5):317-27 and published online Mar. 29, 2010.
Makarova K. S. et al., Evolution and classification of the CRISPR-Cas systems, Nature Reviews 2011 v9 p. 467-477.
Marraffini LA et al., CRISTPR Interference Limits Horizontal Gene Transfer in Staphylococci by Targeting DNA, Science, vol. 322, Dec. 19, 2008, p. 1843-1845.
Pougach K et al., Transcription, processing and function of CRISPR cassettes in *Esherichia coli*, Molecular Microbiology, Sep. 2010;77(6):1367-79.
Pul U et al., Identification and characterization of *E.coli* CRISPR-cas Promoters and their Silencing by H-NS, Molecular Microbiology, Mar. 2010;75(6):1495-1512.
Sapranauskas R et al., The *Streptococcus thermophilus* CRISPRICas system provides immunity in *Escherichia coli*, Nucleic Acids Research, 2011, vol. 39, No. 21, p. 9275-9282.
Sashital D G et al., Mechanism of Foreign DNA Selection in a Bacterial Adaptive Immune System, Molecular Cell, 2012, vol. 46, p. 606-615.
Sinkunas T et al., Cas3 is a single-stranded DNA nuclease and ATP-dependent helicase in CRISPRICas immune system, EMBO Journal 2011, vol. 30, p. 1335-1342.
Westra ER et al., CRISPR Immunity Relies on the Consecutive Binding and Degradation of Negatively Supercoiled Invader DNA by Cascade and Cas3, Molecular Cell, 2012, vol. 46, p. 595-605.
Westra ER et al., H-NS-mediated repression of CRISPR-based immunity in *Escherichia coli* K12 can be relieved by the transcription activator LeuO, Molecular Microbiology, 2010, vol. 77, No. 6, p. 1380-1393.
Genbank accession No. DQ072991.
Heap H.A. and Lawrence R. C., The contribution of starter strains to the level of phage infection in a commercial cheese factory, N.Z. J. Dairy Sci. Technol., 1977, vol. 12, p. 213.
Bolotin, A., et al., "Complete sequence and comparative genome analysis of the dairy bacterium *Streptococcus thermophiles*," Nature Biotechnology, 2004, vol. 22, No. 12, pp. 1554-1558.
Duplessis, M., et al., "Characterization of *Streptococcus thermoplhilius* host range phage mutants, Applied and Environmental Microbiology," Apr. 2006, vol. 72, No. 4, pp. 3036-3041 XP002679467.
O'Flynn, G., et al., "Evaluation of a cocktail of three bacteriophages for biocontrol of *Escherichia coli* 0157:H7", Applied and Environmental microbiology, Jun. 2004, vol. 70, No. 6, pp. 3417-3421 XP002679469.
Li, Patrushev, "Gene expression, Part II, Artificial genetic systems," Chapter 7, Moscow, "Nauka", 2000, pp. 599-600.
"CRISPRs details NC_008054_2" retrieved from the Internet URL:http://crispr.u-psud.fr/cgi-bin/crispr/SpecieProperties.cgi?Taxon_id=390333 [retrieved on Oct. 29, 2013].
Madera, C., et al., Characterisation of technologically progicient wild Lactococcus lactis strains resistant to phage infection, International Journal of Food Microbiology, 2003, 86, pp. 213-222.
Reinheimer J A et al., Natural Milk Cultures for the Productin of Argentinian Cheeses, Journal of Food Protection, 1997, vol. 60, No. 1, pp. 59-63.

S1 and S2 both originate from phage 858. S1 is in ORF 38 at 31,381bp - S2 is in ORF 27 at 25,440bp FIGURE 11
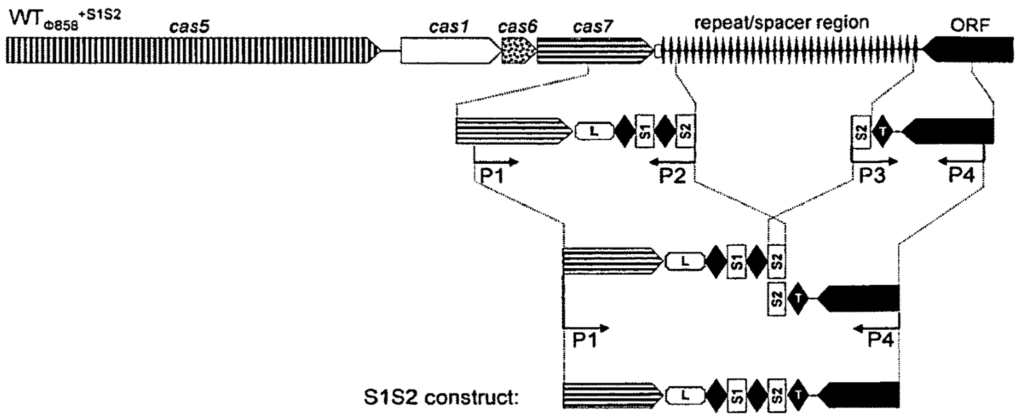
FIGURE 12
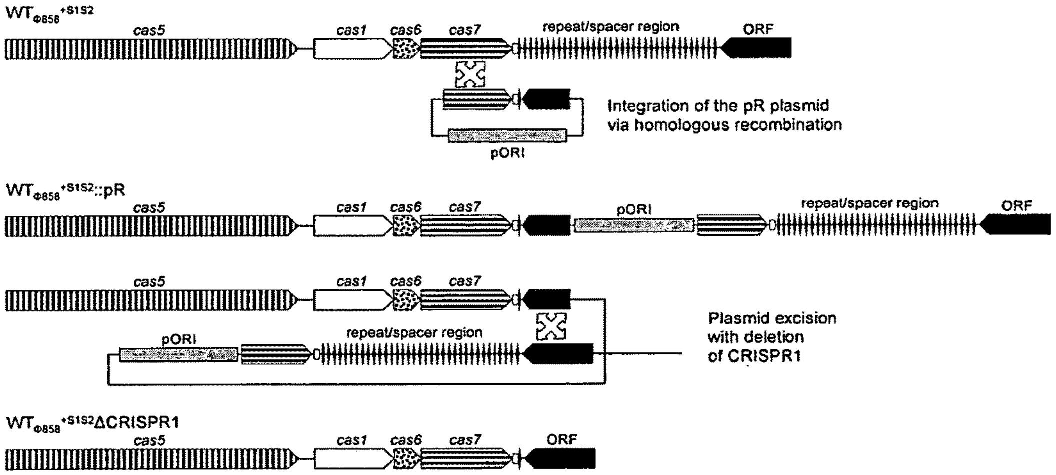
FIGURE 13
```
S1          CAACACATTCAACAGATTAATGAAGAATAC
Φ858        ..............................
Φ858-A      ............A.................
Φ858-B      ............................C.
```

CULTURES WITH IMPROVED PHAGE RESISTANCE

FIELD OF THE INVENTION

The present invention provides methods and compositions related to modulating the resistance of a cell against a target nucleic acid or a transcription product thereof. In some preferred embodiments, the present invention provides compositions and methods for the use of one or more cas genes or proteins for modulating the resistance of a cell against a target nucleic acid or a transcription product thereof. In some embodiments, the present invention provides methods and compositions that find use in the development and use of strain combinations and starter culture rotations. In additional embodiments, the present invention provides methods for labelling and/or identifying bacteria. In some preferred embodiments, the present invention provides methods for the use of CRISPR loci to determine the potential virulence of a phage against a cell and the use of CRISPR-cas to modulate the genetic sequence of a phage for increased virulence level. In still further embodiments, the present invention provides means and compositions for the development and use of phages as biocontrol agents.

BACKGROUND OF THE INVENTION

Cultures, and starter cultures, in particular are used extensively in the food industry in the manufacture of fermented products including milk products (e.g., yogurt, buttermilk, and cheese), meat products, bakery products, wine, and vegetable products. The preparation of cultures is labor intensive, occupying much space and equipment, and there is a considerable risk of contamination with spoilage bacteria and/or phages during the propagation steps. The failure of bacterial cultures due to bacteriophage (phage) infection and multiplication is a major problem with the industrial use of bacterial cultures. There are many different types of phages and new strains continue to emerge. In addition, there is a need for methods and compositions for tracking bacteria used in such cultures. Indeed, despite advances in culture development, there is a continuing need to improve cultures for use in industry.

SUMMARY OF THE INVENTION

The present invention provides methods and compositions related to modulating the resistance of a cell against a target nucleic acid or a transcription product thereof. In some preferred embodiments, the present invention provides compositions and methods for the use of one or more cas genes or proteins for modulating the resistance of a cell against a target nucleic acid or a transcription product thereof. In some embodiments, the present invention provides methods and compositions that find use in the development and use of strain combinations and starter culture rotations. In additional embodiments, the present invention provides methods for labelling and/or identifying bacteria. In some preferred embodiments, the present invention provides methods for the use of CRISPR loci to determine the potential virulence of a phage against a cell and the use of CRISPR-cas to modulate the genetic sequence of a phage for increased virulence level. In still further embodiments, the present invention provides means and compositions for the development and use of phages as biocontrol agents.

The present invention provides methods for generating at least one bacteriophage resistant variant strain, comprising the steps of: (a) exposing a parent bacterial strain comprising at least a portion of a CRISPR locus to at least one nucleic acid sequence to produce a mixture of bacteria comprising at least one bacteriophage resistant variant strain comprising a modified CRISPR locus; (b) selecting a bacteriophage resistant variant strain from the mixture of bacteria; (c) selecting the bacteriophage resistant variant strains comprising an additional nucleic acid fragment in the modified CRISPR locus from the bacteriophage resistant strains selected in step (b); and (d) isolating at least one bacteriophage resistant variant strain, wherein the strain comprises an additional nucleic acid fragment in the modified CRISPR locus. In some preferred embodiments, the methods further comprise the step of comparing the CRISPR locus or a portion thereof of the parent bacterial strain and the modified CRISPR locus of the bacteriophage resistant variant strain to identify bacteriophage resistant variant strains comprising at least one additional nucleic acid fragment in the modified CRISPR locus that is absent from the CRISPR locus of the parent bacterial strain. In some particularly preferred embodiments, the methods further comprise the step of selecting bacteriophage resistant variant strains comprising an additional nucleic acid fragment in the modified CRISPR locus. In some embodiments, the parent bacterial strain is exposed to two or more nucleic acid sequences. In some preferred embodiments, the parent bacterial strain is simultaneously exposed to two or more nucleic acid sequences, while in some alternative embodiments, the parent bacterial strain is sequentially exposed to two or more nucleic acid sequences. In some particularly preferred embodiments, the parent bacterial strain is exposed to the nucleic acid sequence through infection by at least one bacteriophage comprising the nucleic acid sequence. In some further preferred embodiments, the at least one bacteriophage is selected from the group of virus families consisting of: Corticoviridae, Cystoviridae, Inoviridae, Leviviridae, Microviridae, Myoviridae, Podoviridae, Siphoviridae, and Tectiviridae. In some additional preferred embodiments, the at least one bacteriophage is a naturally occurring bacteriophage, while in other preferred embodiments, the at least one bacteriophage is a mutated bacteriophage obtained through selective pressure using a bacteriophage resistant bacterial strain. In yet further preferred embodiments, the parent bacterial strain is exposed to the nucleic acid through a natural mechanism of nucleic acid uptake. In some embodiments, the natural mechanism of nucleic acid uptake comprises natural competence. In some additional embodiments, the natural mechanism of nucleic acid uptake parent bacterial strain by conjugation or transformation. In still other embodiments, the bacteriophage resistant strain is a bacteriophage insensitive mutant. In yet additional embodiments, the parent bacterial strain is a bacteriophage insensitive mutant. In some further embodiments, the 5' end and/or the 3' end of the CRISPR locus of the parent bacterial strain is compared with the modified CRISPR locus of the bacteriophage resistant variant strain. It some still further embodiments, the 5' and/or the 3' end of the at least the first CRISPR repeat or at least the first CRISPR spacer of the CRISPR locus of the parent bacterial strain is compared with the modified CRISPR locus of the bacteriophage resistant variant strain. In still further embodiments, the bacteriophage resistant variant strain comprises at least one additional nucleic acid fragment in the modified CRISPR locus. In some additional embodiments, at least a portion of the CRISPR locus of the parent bacterial strain and at least a portion of the modified CRISPR locus of the bacteriophage resistant variant strain are compared by amplifying at least a portion of the CRISPR locus and at least a portion of the modified CRISPR locus, to produce an amplified CRISPR locus sequence and an amplified modified CRISPR locus sequence. In still further embodiments, amplifying is conducted using the polymerase chain reaction. In some preferred embodiments, at least a portion of the CRISPR locus of the parent bacterial strain and at least a portion of the modified CRISPR locus of the bacteriophage resistant variant strain are compared by sequencing at least a portion of the CRISPR locus and at least a portion of the modified CRISPR locus. In some particularly preferred embodiments, the methods further comprise the step of sequencing the amplified CRISPR locus sequence and the amplified modified CRISPR sequence locus. In some additional embodiments, the additional nucleic acid fragment in the modified CRISPR locus is an additional repeat-spacer unit. In some preferred embodiments, the additional repeat-spacer unit comprises at least about 44 nucleotides. In some alternative preferred embodiments, additional repeat-spacer unit is comprises between about 44 and about 119 nucleotides. However, it is not intended that the present invention be limited to these specific size ranges, as other sizes find use in the present invention, as described herein. In some embodiments, the additional repeat-spacer unit comprises at least one nucleotide sequence that has at least about 95% identity to a CRISPR repeat in the CRISPR locus of the parent bacterial strain. In some further embodiments, the additional repeat-spacer unit comprises at least one nucleotide sequence that has at least about 95% identity to a nucleotide sequence in the genome of at least one bacteriophage. In some particularly preferred embodiments, the parent bacterial strain is an industrially useful strain. In some additional embodiments, the parent bacterial strain is susceptible to infection by at least one bacteriophage. In some further preferred embodiments, the parent bacterial strain comprises a culture selected from starter cultures, probiotic cultures, and dietary supplement cultures. In some preferred embodiments, the parent bacterial strain comprises a strain obtained from a culture. In some particularly preferred embodiments, the culture is a starter culture, a probiotic culture, and/or a dietary supplement culture. In yet additional embodiments, the parent bacterial strain is selected from *Escherichia, Shigella, Salmonella, Erwinia, Yersinma, Bacillus, Vibrio, Legionella, Pseudomonas. Neisseria, Bordetella, Helicobacter, Listeria, Agrobacterium, Staphylococcus, Streptococcus, Enterococcus, Clostridium, Corynebacterium, Mycobacterium, Treponema, Borrelia, Francisella, Brucella, Campylobacter, Klebsiella, Frankia, Bartonella. Rickettsia, Shewanella, Serratia, Enterobacter, Proteus, Providencia, Brochothrix, Bifidobacterium, Brevibacterium, Propionibacterium, Lactococcus, Lactobacillus, Pediococcus, Leuconostoc*, and *Oenococcus*.

The present invention also provides at least one bacteriophage resistant variant strain obtained using the methods set forth herein. In some preferred embodiments, the present invention provides bacteriophage resistant variant strains, wherein the bacteriophage resistant variant strain is an industrially useful strain. In some preferred embodiments, the bacteriophage resistant variant strain comprises an industrially useful strain that is at least one component of a starter culture, probiotic culture, dietary supplement culture, and/or other useful cultures.

The present invention also provides compositions comprising a bacteriophage resistant variant strain produced using the methods set forth herein. In some embodiments, the present invention provides compositions comprising at least two bacteriophage resistant variant strains produced using the methods set forth herein. The present invention also provides foods and/or feeds comprising at least one of these compositions. The present invention also provides methods for preparing food and/or feed comprising adding at least one of these compositions to the food or feed. The present invention also provides starter cultures, probiotic cultures, dietary supplement cultures, and other useful cultures that comprise at least one of these compositions. The present invention also provides fermentation methods comprising adding at least one of these compositions to a starter culture. In some embodiments, the present invention provides fermentation methods comprising adding at least one of these compositions to a fermentation medium, under conditions such that fermentation of the components of the fermentation medium occur. In some embodiments, the fermentation is unaffected by the presence of bacteriophages. In some embodiments, the fermentation medium is a food product. In some preferred embodiments, the food product is a dairy product. In some particularly preferred embodiments, the dairy product is milk. In some further embodiments, at least two different compositions comprising two or more bacteriophage resistant variant strains are sequentially exposed to the fermentation medium.

The present invention also provides methods for reducing the detrimental bacteriophage population in a fermentation medium comprising exposing a fermentation medium to at least one bacteriophage resistant variant strain produced using the methods set forth herein, under conditions such that the bacteriophage population is reduced.

The present invention also provides methods for generating at least one bacteriophage resistant variant strain, comprising the steps of: (a) exposing a parent bacterial strain comprising at least a portion of a CRISPR locus to at least one nucleic acid sequence to produce a mixture of bacteria comprising at least one bacteriophage resistant variant strain comprising a modified CRISPR locus; (b) selecting a bacteriophage resistant variant strain from the mixture of bacteria; (c) comparing the CRISPR locus or a portion thereof of the parent bacterial strain and the modified CRISPR locus of the bacteriophage resistant variant strain to identify bacteriophage resistant variant strains comprising at least one additional nucleic acid fragment in the modified CRISPR locus that is absent from the CRISPR locus of the parent bacterial strain; (d) selecting the bacteriophage resistant variant strains comprising an additional nucleic acid fragment in the modified CRISPR locus; (e) analyzing the at least one additional nucleic acid fragment in the modified CRISPR locus to identify the at least one bacteriophage resistant variant strain; and (f) isolating the at least one bacteriophage resistant variant strain.

The present invention also provides methods for generating CRISPR-escape phage mutants comprising: (a) obtaining: at least one parent phage and a phage-resistant bacterial strain comprising at least one CRISPR locus, wherein the CRISPR locus comprises a nucleic acid sequence that is at least about 95% identical to at least one protospacer sequence in the genome of the at least one parent phage; (b) exposing the at least one parent phage to the phage-resistant bacterial strain, under conditions such that at least one phage variant is produced; and (c) selecting the at least one phage variant, wherein the at least one phage variant exhibits the ability to infect the phage-resistant bacterial strain and is a CRISPR-escape phage mutant. In some embodiments, the phage-resistant bacterial strain is a bacteriophage-resistant variant strain obtained using the methods set forth herein. In some embodiments, the methods further comprise the step of comparing at least a portion of the at least one protospacer sequence and a CRISPR motif positioned near the at least one protospacer sequence in the phage variant with the at least one protospacer sequence and CRISPR motif of the parent phage. In yet additional embodiments, the methods further comprise the step of selecting the variant phages that infect the phage resistant bacterial strain, wherein the variant phages comprise the CRISPR-escape phage mutants, and wherein the CRISPR-escape phages comprise at least one mutation in the at least one protospacer sequence and/or in the CRISPR motif of the CRISPR-escape phage mutants. In yet additional embodiments, the methods are iteratively repeated one or more times using the CRISPR-escape phage mutants and different CRISPR phage-resistant bacterial strain comprising at least one CRISPR locus, wherein the CRISPR locus comprises a nucleic acid sequence that is at least about 95% identical to at least one protospacer sequence in the genome of the CRISPR-escape phage mutants. In yet additional embodiments, at least one bacteriophage is selected from the group of virus families consisting of: Corticoviridae, Cystoviridae, Inoviridae, Leviviridae, Microviridae, Myoviridae, Podoviridae, Siphoviridae, and Tectiviridae. In some preferred embodiments, the phage-resistant bacterial strain is selected from *Escherichia, Shigella. Salmonella, Erwinia, Yersinia, Bacillus, Vibrio, Legionella. Pseudomonas, Neisseria, Bordetella, Helicobacter. Listeria. Agrobacterium, Staphylococcus, Enterococcus. Clostridium, Camplyobacter, Corynebacterium, Mycobacterium, Treponema, Borrelia, Francisella, Brucella, Klebsiella, Frankia, Bartonella, Rickettsia, Shewanella, Serratia, Enterobacter, Proteus, Providencia, Brochothrix, Bifidobacterium, Brevibacterium, Propionibacterium, Lactococcus, Lactobacillus, Pediococcus, Leuconostoc, Streptococcus*, and *Oenococcus*.

The present invention also provides CRISPR-escape phage mutants obtained using the methods set forth herein. In some embodiments, the CRISPR-escape phage mutants comprise two or more mutations present in at least two protospacer sequences and/or in the CRISPR motif.

The present invention also provides CRISPR-escape phage mutants, wherein the genome of the CRISPR-escape phage mutants is genetically engineered to comprise mutations in at least one protospacer and/or the CRISPR motif. In some embodiments, at least one CRISPR motif is mutated in the CRISPR-escape phage mutants, while in some alternative embodiments, at least one CRISPR motif is deleted in the CRISPR-escape phage mutants. The present invention also provides compositions comprising at least one CRISPR-escape phage mutants.

The present invention also provides methods for controlling bacterial populations in a product comprising exposing compositions comprising at least one CRISPR-escape phage mutant to a fermentation medium wherein the fermentation medium contains at least one population of undesirable bacteria, under conditions such that the population of the undesirable bacteria is reduced, and the fermentation medium is used to generate the product. In some embodiments, the product is selected from foods, feeds, cosmetics, personal care products, health care products, veterinary products, and dietary supplements. In some further embodiments, the methods are repeated at least once and the different compositions and/or compositions comprising different CRISPR-escape phage mutants are used in rotation.

In some embodiments, the present invention provides methods and compositions for the use of one or more cas genes or proteins for modulating resistance in a cell against a target nucleic acid or a transcription product thereof. In some additional embodiments, the present invention provides compositions and methods for the use of a recombinant nucleic acid sequence comprising at least one cas gene and at least two CRISPR repeats together with at least one CRISPR spacer, wherein at least one CRISPR spacer is heterologous to at least one cas gene and/or at least two CRISPR repeats to modulate resistance against a target nucleic acid or transcription product thereof. In yet additional embodiments, the present invention provides at least one nucleic acid sequence comprising at least one cas gene.

In still further embodiments, the present invention provides at least one nucleic acid sequence comprising at least one cas gene and at least two CRISPR repeats. In some embodiments, the present invention provides a nucleic acid sequence comprising at least one cas gene and at least one CRISPR spacer. In yet further embodiments, the present invention provides a nucleic acid sequence comprising at least one cas gene, at least one CRISPR spacer and at least two CRISPR repeats. In further embodiments, the present invention provides a recombinant nucleic acid sequence comprising at least one cas gene and at least two CRISPR repeats together with at least one CRISPR spacer, wherein the CRISPR spacer is heterologous to the at least one cas gene and/or the at least two CRISPR repeats. The present invention also provides constructs comprising one or more of the nucleic acid sequences described herein. In yet additional embodiments, the present invention provides vectors comprising one or more of the nucleic acid sequences or one or more of the constructs described herein. In still further embodiments, the present invention provides cells comprising the nucleic acid sequence or the construct or the vector described herein.

The present invention also provides methods for modulating (e.g., conferring or increasing) the resistance of a cell against a target nucleic acid or a transcription product thereof comprising the steps of: (i) identifying a sequence (e.g., a conserved sequence) in an organism (in some embodiments, this is a sequence that is essential to the function or survival of the organism); (ii) preparing a CRISPR spacer which is homologous to the identified sequence; (iii) preparing a nucleic acid (e.g., a recombinant nucleic acid) comprising at least one cas gene and at least two CRISPR repeats together with the CRISPR spacer; and (iv) introducing the nucleic acid into a cell thus to render the cell resistant to the target nucleic acid or transcription product thereof.

The present invention also provides methods for modulating (e.g., conferring or increasing) the resistance of a cell against a target nucleic acid or a transcription product thereof comprising the steps of: (i) identifying one or more CRISPR spacers or pseudo CRISPR spacers in an organism resistant to the target nucleic acid or transcription product thereof; (ii) preparing a recombinant nucleic acid comprising at least one cas gene or protein and at least two CRISPR repeats together with the identified one or more spacers; and (iii) introducing the recombinant nucleic acid into a cell thus to render the cell resistant to the target nucleic acid or transcription product thereof.

The present invention also provides methods for modulating (e.g., conferring or increasing) the resistance of a cell comprising at least one or more cas genes or proteins and two or more CRISPR repeats against a target nucleic acid or a transcription product thereof comprising the steps of: (i) identifying one or more CRISPR spacers in an organism resistant to the target nucleic acid or transcription product thereof; and (ii) modifying the sequence of one or more CRISPR spacer(s) in the cell such that the CRISPR spacer(s) has homology to the CRISPR spacer(s) in the organism.

The present invention also provides methods for modulating (e.g., reducing or decreasing) the resistance of a cell comprising at least one or more cas genes or proteins and two or more CRISPR repeats against a target nucleic acid or a transcription product thereof comprising the steps of: (i) identifying one or more CRISPR spacers in an organism that is substantially resistant to the target nucleic acid or transcription product thereof; and (ii) modifying the sequence of at least one or more CRISPR spacer(s) in the cell such that the CRISPR spacer(s) has a reduced degree of homology to the spacer(s) in the organism.

The present invention also provides methods for modulating (e.g., reducing or decreasing) the resistance of a cell comprising at least one or more cas genes or proteins and two or more CRISPR repeats against a target nucleic acid or a transcription product thereof comprising modifying the one or more cas genes or proteins and/or two or more CRISPR repeats in the cell.

The present invention also provides methods for identifying a CRISPR spacer or pseudo CRISPR spacer for use in modulating the resistance of a cell against a target nucleic acid or a transcription product thereof comprising the steps of: (i) preparing a cell comprising at least two CRISPR repeats and at least one cas gene or protein; (ii) identifying at least one CRISPR spacer or pseudo CRISPR spacers in an organism that is substantially resistant to the target nucleic acid or transcription product thereof; (iii) modifying the sequence of the CRISPR spacer in the cell such that the CRISPR spacer has homology to the spacer of the organism; and (iv) determining if the cell modulates resistance against the target nucleic acid or transcription product thereof, wherein modulation of the resistance of the cell against the target nucleic acid or transcription product thereof is indicative that the CRISPR spacer modulates the resistance of the cell.

The present invention also provides methods for identifying a cas gene for use in modulating the resistance of a cell against a target nucleic acid or transcription product thereof comprising the steps of: (i) preparing a cell comprising at least one CRISPR spacer and at least two CRISPR repeats; (ii) engineering the cell such that it comprises at least one cas gene; and (iii) determining if the cell modulates resistance against the target nucleic acid or transcription product thereof, wherein modulation of the resistance of the cell against the target nucleic acid or transcription product thereof is indicative that the cas gene can be used to modulate the resistance of the cell.

The present invention also provides methods for identifying a CRISPR repeat for use in modulating the resistance of a cell against a target nucleic acid or transcription product thereof comprising the steps of: (i) preparing a cell comprising at least one CRISPR spacer and at least one cas gene; (ii) engineering the cell such that it contains the CRISPR repeat; and (iii) determining if the cell modulates resistance against the target nucleic acid or transcription product thereof, wherein modulation of the resistance of the cell against the target nucleic acid or transcription product thereof is indicative that the CRISPR repeat can be used to modulate resistance.

The present invention also provides methods for identifying a functional combination of a cas gene and a CRISPR repeat comprising the steps of: (a) determining the sequences of the cas gene and the CRISPR repeat; (b) identifying one or more clusters of cas genes as determined by sequence comparison analysis; (c) identifying one or more clusters of CRISPR repeats; and (d) combining those cas gene and CRISPR repeat sequences that fall within the same cluster, wherein the combination of the cas gene and CRISPR repeat sequences within the same cluster is indicative that the combination is a functional combination.

The present invention also provides methods for modulating the lysotype of a bacterial cell comprising one or more cas genes or proteins and two or more CRISPR repeats comprising the steps of: (i) identifying one or more pseudo CRISPR spacers in the genomic sequence of a bacteriophage against which resistance is to be modulated; and (ii) modifying the sequence of one or more CRISPR spacers of the bacterial cell such that the CRISPR spacer(s) of the bacterial cell has homology to the pseudo CRISPR spacer(s) of the bacteriophage against which resistance is to be modulated.

The present invention also provides methods for modulating (e.g., conferring or increasing) the resistance of a bacterial cell against a bacteriophage comprising the steps of: (i) identifying a sequence (e.g., a conserved sequence) in a bacteriophage (preferably, a sequence essential to the function or survival of the bacteriophage); (ii) preparing a CRISPR spacer which is homologous to the identified sequence; (iii) preparing a nucleic acid comprising at least one cas gene and at least two CRISPR repeats together with the CRISPR spacer; and (iv) introducing the nucleic acid into the bacterial cell thus to render the bacterial cell resistant to the target nucleic acid or transcription product thereof.

The present invention also provides methods for modulating (e.g., conferring or increasing) the resistance of a bacterial cell against a target nucleic acid or transcription product in a bacteriophage thereof comprising the steps of: (i) identifying one or more pseudo CRISPR spacers in a bacteriophage genome that is capable of providing resistance to the target nucleic acid or transcription product thereof; (ii) preparing a recombinant nucleic acid comprising at least one cas gene and at least two CRISPR repeats together with the identified one or more pseudo CRISPR spacers; and (iii) introducing the recombinant nucleic acid into the bacterial cell thus to render the bacterial cell resistant to the target nucleic acid or transcription product thereof.

The present invention also provides methods for modulating the resistance of a bacterial cell comprising one or more cas genes or proteins and two or more CRISPR repeats against a target nucleic acid or transcription product thereof in a bacteriophage comprising the steps of: (i) identifying one or more pseudo CRISPR spacers in a bacteriophage that is capable of providing resistance to a target nucleic acid or transcription product thereof; (ii) identifying one or more CRISPR spacers in a bacterial cell in which resistance is to be modulated; and (iii) modifying the sequence of the CRISPR spacer(s) in the bacterial cell in which resistance is to be modulated such that the CRISPR spacer(s) has a higher degree of homology to the pseudo CRISPR spacer(s) of the bacteriophage against which resistance is to be modulated.

The present invention also provides methods for determining the resistance of a cell against a target nucleic acid or a transcription product thereof comprising identifying one or more functional CRISPR repeat-cas combinations and one or more CRISPR spacers in the cell.

The present invention also provides cells obtained or obtained using the method(s) provided herein. In some embodiments, the present invention provides CRISPR spacers or pseudo CRISPR spacers obtained or obtainable by the method(s) described herein.

In some embodiments, the present invention provides cas genes obtained or obtainable by the method(s) described herein. In some further embodiments, the present invention provides CRISPR repeats obtained or obtainable by the method(s) described herein. In yet further embodiments, the present invention provides functional combinations obtained or obtainable by the method(s) described herein. In still further embodiments, the present invention provides recombinant CRISPR loci comprising at least one CRISPR spacer or pseudo CRISPR spacer, and/or at least one cas gene, and/or at least one CRISPR repeat and/or a functional combination.

In some embodiments, the present invention provides methods for the use of cells, at least one CRISPR spacer or pseudo CRISPR spacer, at least one cas gene, at least one CRISPR repeat, or a functional combination thereof for modulating the resistance of a cell against a target nucleic acid or a transcription product thereof.

In some further embodiments, the present invention provides cell cultures comprising at least one cell, at least one CRISPR spacer or pseudo CRISPR spacer, at least one cas gene, at least one CRISPR repeat or a functional combination for modulating the resistance of a cell against a target nucleic acid or a transcription product thereof.

In still further embodiments, the present invention provides food products and/or feed comprising cultures provided herein. In some additional embodiments, the present invention provides processes for preparing a food product and/or feed comprising cultures provided herein. In yet additional embodiments, the present invention provides food products and/or feed obtained or obtainable by the methods provided herein. In some preferred embodiments, the present invention provides methods for the use of the cultures provided herein for preparing food products and/or feed.

The present invention further provides nucleotide sequences comprising or consisting of the sequences set forth in any of SEQ ID NOS:7-10 and SEQ ID NOS:359-405, as well as variants, fragments, homologues and derivatives thereof. The present invention also provides amino acids encoded by the nucleotide sequences set forth herein. In yet further embodiments, the present invention provides constructs and/or vectors comprising one or more of the nucleotide sequences provided herein. The present invention also provides host cells comprising at least one of the constructs and/or nucleotide sequences provided herein.

In some embodiments, the one or more cas genes or proteins are used in combination with two or more CRISPR repeats. In some further embodiments, the one or more cas genes or proteins and/or the two or more CRISPR repeats are derived from the same cell. In some additional embodiments, the one or more cas genes or proteins and the two or more CRISPR repeats naturally co-occur in the same cell. In some still further embodiments, the one or more cas genes or proteins are used in combination with one or more CRISPR spacers.

In some embodiments, the CRISPR spacer(s) is derived from a different organism than the cell from which the one or more cas genes or proteins and/or the two or more CRISPR repeats are derived. In some embodiments, the spacer is obtained from a cell which is resistant to a target nucleic acid. In some embodiments, the CRISPR spacer is a synthetic nucleic acid sequence. In some further embodiments, the CRISPR spacer(s) have homology to the target nucleic acid. In some embodiments, the CRISPR spacer(s) have 100% identity to the target nucleic acid over at least the length of the CRISPR spacer core.

In some embodiments, the one or more cas genes or proteins are used in combination with at least one or more CRISPR spacers and at least two or more CRISPR repeats. In some embodiments, the target nucleic acid or transcription product thereof is derived from bacteriophage DNA. In yet further embodiments, the target nucleic acid or transcription product thereof is derived from at least one plasmid. In some further embodiments, the target nucleic acid or transcription product thereof is derived from at least one mobile genetic element DNA. In some embodiments, the target nucleic acid or transcription product thereof is derived from a transposable element and/or an insertion sequence. In some alternative embodiments, the target nucleic acid or transcription product thereof is derived from an antibiotic/antimicrobial resistance gene. In some further embodiments, the target nucleic acid or transcription product thereof is derived from a nucleic acid encoding at least one virulence factor. In some preferred embodiments, the virulence factor comprises toxins, internalins, hemolysins, and/or other virulence factors.

In some embodiments of the present invention, the one or more cas genes and the two or more CRISPR repeats are derived from the same cell. In some alternative embodiments, the one or more cas genes and the two or more CRISPR repeats naturally co-occur in the same cell. In yet further embodiments, the CRISPR spacers are derived from a different organism than the cell from which the one or more cas genes and/or the two or more CRISPR repeats are derived. In some embodiments, the cell is a recipient cell or a host cell.

In some embodiments, the one or more cas genes or proteins and/or the two or more CRISPR repeats are derived from the same cell. In some embodiments, the spacers are derived from a different organism than the cell comprising the one or more cas genes or proteins and/or the two or more CRISPR repeats.

In some embodiments, the one or more cas genes or proteins and the two or more CRISPR repeats naturally co-occur in the same cell.

In some embodiments, the modification comprises inserting one or more CRISPR spacers and/or pseudo CRISPR spacers into the cell. In some embodiments, the modification comprises genetically engineering the CRISPR spacer of the cell. In some embodiments, the spacer of the cell has 100% homology to the CRISPR spacer or pseudo CRISPR spacer of the organism. In some embodiments, all or part of the spacer in the cell is modified. In some embodiments, the modification comprises the modification of a recombinant spacer. In some embodiments, the modification occurs through spontaneous mutation or mutagenesis. In some embodiments, at least one or more CRISPR spacer(s) in the cell are deleted. In some embodiments, at least one or more CRISPR repeat(s) in the cell are deleted. In some embodiments, one or more cas genes are deleted. In some embodiments, CRISPR and/or one or more cas genes are deleted. In some embodiments, the one or more cas genes or proteins and/or two or more CRISPR repeats in the cell are deleted. In some embodiments, the nucleotide sequences of the cas gene and the CRISPR repeat are derived from the same or different strains. In some embodiments, the nucleotide sequences of the cas gene and the CRISPR repeat are derived from the same or different species.

In some embodiments, the nucleotide sequences of the cas gene and the CRISPR repeat are derived from the same or different genera. In some embodiments, the nucleotide sequences of the cas gene and the CRISPR repeat are derived from the same or different organisms.

In some embodiments of the present invention, the target nucleic acid in the bacteriophage is a highly conserved nucleic acid sequence. In some embodiments, the target nucleic acid in the bacteriophage encodes a host specificity protein. In some further embodiments, the target nucleic acid in the bacteriophage encodes a protein that is essential for survival, replication or growth of the bacteriophage. In some embodiments, the target nucleic acid in the bacteriophage encodes a helicase, a primase, a head or tail structural protein, a protein with a conserved domain (e.g., holin, lysin, etc.) or at least one conserved sequence amongst important phage genes.

In some embodiments, the method for determining the resistance of a cell to a target nucleic acid or a transcription product thereof comprises the additional step of comparing the sequence of the one or more CRISPR spacers in the cell with the sequence of the target nucleic acid. In some alternative embodiments, the method for determining the resistance of a cell to a target nucleic acid or a transcription product thereof comprises the additional step of determining the resistance profile of the cell.

In some embodiments, the culture is a starter culture or a probiotic culture.

The present invention also provides "labelled bacteria" that are resistant to phage (i.e., "bacteriophage-insensitive mutants"; "BIMs"). In some embodiments, the present invention provides bacteria comprising one or more sequences originating from at least one bacteriophage genome that is/are integrated into the CRISPR locus of the bacteria. This phage-derived sequence provides a label, which is identifiable by its location and/or sequence and/or adjacent sequence.

In some alternative embodiments, the present invention provides duplicated sequences (e.g., duplicated CRISPR repeats) that originate from a parent bacterium and are also integrated iteratively, sequentially, simultaneously or substantially simultaneously along with the sequence originating from the bacteriophage genome.

In addition, the present invention provides methods that facilitate the integration of one or more different bacteriophage sequences into the CRISPR locus of the bacterial strain. In some embodiments, the integration of different bacteriophage sequences in the CRISPR locus of the bacterial strain is a random event. In some alternative embodiments, the integration of different bacteriophage sequences in the CRISPR locus of the bacterial strain is not a random event. Thus, it is not always the same locus of the bacteriophage genome which is integrated into the CRISPR locus of the bacterium. However, once it is integrated it is maintained and thus becomes a robust tag to label and/or track the bacterium. Accordingly, the one or more sequences originating from the bacteriophage genome are not only new to the CRISPR locus of the parent bacterium but are also a label that is unique to each bacterium. There is therefore provided herein methods for labelling (e.g., tagging) and/or identifying bacteria.

In some embodiments, the methods of the present invention are "natural" and do not result in the production of genetically modified organisms. In some preferred embodiments, the present invention provides methods for labelling bacteria comprising the steps of: (a) exposing a parent bacterium to a bacteriophage; (b) selecting a bacteriophage insensitive mutant; (c) comparing a CRISPR locus or a portion thereof from the parent bacterium and the bacteriophage insensitive mutant; and (d) selecting a labelled bacterium comprising an additional DNA fragment in the CRISPR locus that is not present in the parent bacterium.

The present invention also provides labelled bacteria obtained using the methods of the present invention. In some embodiments, the present invention provides cell cultures comprising at least one labelled bacterial strain. In still further embodiments, the present invention provides food and/or feed comprising labelled bacteria, including but not limited to cell cultures comprising such labelled bacteria. The present invention also provides methods for preparing food and/or feed comprising at least one labelled bacterial strain. In some embodiments, the methods comprise adding at least one labelled bacterial strain or cell culture to the food and/or feed.

The present invention also provides methods for generating CRISPR variants comprising the steps of: (a) exposing a parent bacterium to a bacteriophage; (b) selecting a bacteriophage resistant bacterium (i.e., a "bacteriophage insensitive mutant"); (c) comparing the CRISPR locus or a portion thereof from the parent bacterium and the bacteriophage insensitive mutant; (d) selecting a labelled bacterium comprising an additional DNA fragment in the CRISPR locus that is not present in the parent bacterium; and (e) isolating and/or cloning and/or sequencing the additional DNA fragment. The present invention also provides CRISPR variants produced using the methods set forth herein. In some particularly preferred embodiments, the CRISPR variants are phage resistant mutant strains that have a modified CRISPR locus with an additional spacer.

In some additional embodiments, the present invention also provides methods for the use of at least one nucleotide sequence obtained or obtainable from a bacteriophage for tagging and/or identifying bacteria, wherein the nucleotide sequence is integrated within the CRISPR locus of the parent bacterium.

In still further embodiments, the present invention provides methods for the use of at least one nucleotide sequence for labelling and/or identifying a bacterium, wherein the nucleotide sequence is obtained or obtainable by: (a) exposing a parent bacterium to a bacteriophage; (b) selecting a bacteriophage insensitive mutant; (c) comparing a CRISPR locus or a portion thereof from the parent bacterium and the bacteriophage insensitive mutant; and (d) selecting a labelled bacterium comprising an additional DNA fragment in the CRISPR locus that is not present in the parent bacterium. In yet additional embodiments, the present invention provides methods for identifying a labelled bacterium comprising the step of screening the bacterium for an additional DNA fragment within a CRISPR locus of the bacterium is also provided in a further aspect of the present invention.

In yet further embodiments, the present invention provides methods for identifying labelled bacteria comprising the steps of: (a) screening the bacteria for an additional DNA fragment in a CRISPR locus; (b) determining the nucleotide sequence of the additional DNA fragment; (c) comparing the nucleotide sequence of the additional DNA fragment with a database of labelled bacteria obtained or obtainable by the method of the present invention; and (d) identifying a nucleotide sequence in the database of labelled bacteria that matches the additional DNA fragment.

In some preferred embodiments, the 5' end and/or the 3' end of the CRISPR locus of the parent bacterium is compared with the labelled bacteria. In some alternative preferred embodiments, at least the first CRISPR repeat or the first CRISPR spacer (e.g., the first CRISPR spacer core) at the 5' end of the CRISPR locus is compared. In yet further embodiments, at least the last CRISPR repeat or the last CRISPR spacer (e.g., the last CRISPR spacer core) at the 3' end of the CRISPR locus is/are compared.

In some preferred embodiments, the methods of the present invention comprise the step of selecting a labelled bacterium comprising an additional DNA fragment at the 5' end and/or at the 3' end of the CRISPR locus that is not present in the parent bacterium. In some alternative embodiments, the methods further comprise exposing the parent bacterium to two or more bacteriophages either simultaneously or sequentially. In yet further embodiments, the CRISPR locus or a portion thereof from the parent bacterium and the bacteriophage insensitive mutant are compared by amplifying the CRISPR locus or a portion thereof from the parent bacterium and/or bacteriophage insensitive mutant. In some particularly preferred embodiments, the amplification is performed using PCR. In some alternative embodiments, the CRISPR locus or a portion thereof from the parent bacterium and the bacteriophage insensitive mutant are compared by sequencing the CRISPR locus or a portion thereof from the parent bacterium and/or the bacteriophage insensitive mutant. In some preferred embodiments, the CRISPR locus or a portion thereof from the parent bacterium and the bacteriophage insensitive mutant are compared by amplifying and then sequencing the CRISPR locus or a portion thereof from the parent bacterium and/or the bacteriophage insensitive mutant. In some alternative preferred embodiments, the additional DNA fragment is at least 44 nucleotides in length. In some additional preferred embodiments, the labelled bacteria comprise two or three or more additional DNA fragments is selected. In yet further embodiments, the additional DNA fragment comprises at least one nucleotide sequence that has at least about 95% identity, or preferably, 100% identity to a CRISPR repeat in the CRISPR locus of the parent bacterium. In still further embodiments, the additional DNA fragment comprises at least one nucleotide sequence that has at least about 95% identity, and in some embodiments, preferably about 100% identity to a nucleotide sequence in the genome of the bacteriophage used for the selection of the labelled bacterium. In some embodiments, the present invention also provides at least one additional DNA fragment that comprises a first nucleotide sequence and a second nucleotide sequence wherein at least one of the nucleotide sequences have at least about 95% identity, or in some preferred embodiments, about 100% identity to a nucleotide sequence in the genome of the bacteriophage used for the selection of the labelled bacteria.

In some embodiments, the present invention provides parent bacteria that are suitable for use as starter cultures, probiotic cultures and/or dietary supplements. In some embodiments, the parent bacteria are selected any suitable genus, including but not limited to *Escherichia, Shigella, Salmonella, Erwinia, Yersinia, Bacillus, Vibrio, Legionella, Pseudomonas, Neisseria, Bordetella, Helicobacter, Listeria, Agrobacterium, Staphylococcus, Streptococcus, Enterococcus, Clostridium, Corynebacterium, Mycobacterium, Treponema. Borrelia, Francisella, Brucella, Bifidobacterium. Brevibacterium, Propionibacterium, Lactococcus, Lactobacillus, Pediococcus, Leuconostoc*, and *Oenococcus*. In some embodiments, the bacteriophage is selected from a suitable virus family, including but not limited to Corticoviridae, Cystoviridae, Inoviridae, Leviviridae, Microviridae, Myoviridae, Podoviridae, Siphoviridae, and Tectiviridae. In some embodiments, the present invention provides cell cultures that are selected from starter cultures, probiotic cultures and/or dietary supplements. In some particularly preferred embodiments, the present invention provides methods for identifying labelled bacteria, comprising the step of comparing at least one additional DNA fragment with a bacteriophage sequence database and/or a bacterial sequence database.

The present invention also provides *S. thermophilus* strains comprising a sequence obtained or obtainable from a bacteriophage, wherein the sequence comprises the CRISPR spacer from *Streptococcus thermophilus* strain DGCC7778, referred to herein as SEQ ID NO:680 (caacacattcaacagattaatgaagaatac; SEQ ID NO:680).

In yet additional embodiments, the present invention provides *S. thermophilus* strains comprising a sequence obtained or obtainable from a bacteriophage, wherein the sequence comprises SEQ ID NO:680 downstream (e.g., directly downstream) of the first CRISPR repeat in at least one CRISPR locus.

In further embodiments, the present invention provides *S. thermophilus* strains comprising a sequence obtained or obtainable from a bacteriophage, wherein the sequence comprises CRISPR spacer (5'-3') from *Streptococcus thermophilus* strain DGCC7778 (tccactcacgtacaaatagtgagtgtactc; SEQ ID NO:681). In yet additional embodiments, the present invention provides *S. thermophilus* strains comprising a sequence obtained or obtainable from a bacteriophage, wherein the sequence comprises SEQ ID NO:681 downstream (e.g., directly downstream) of the first CRISPR repeat in at least one CRISPR locus.

In still further embodiments, the present invention provides *S. thermophilus* strains comprising a sequence obtained or obtainable from a bacteriophage, wherein the sequence comprises SEQ ID NO:683:

CRISPR1 sequence (5'-3') of *Streptococcus thermophilus* strain DGCC7710-RH1
(SEQ ID NO: 683)

```
caaggacagttattgattttataatcactatgtgggtataaaaacgtcaa

aatttcatttgagGTTTTTGTACTCTCAAGATTTAAGTAACTGTACAACt

caacaattgcaacatcttataacccacttGTTTTTGTACTCTCAAGATTT

AAGTAACTGTACAACtgtttgacagcaaatcaagattcgaattgtGTTTT

TGTACTCTCAAGATTTAAGTAACTGTACAACaatgacgaggagctattgg

cacaacttacaGTTTTTGTACTCTCAAGATTTAAGTAACTGTACAACcga

tttgacaatctgctgaccactgttatcGTTTTTGTACTCTCAAGATTTAA

GTAACTGTACAACacacttggcaggcttattactcaacagcgaGTTTTTG

TACTCTCAAGATTTAAGTAACTGTACAACctgttccttgttcttttgttg

tatcttttcGTTTTTGTACTCTCAAGATTTAAGTAACTGTACAACttcat

tcttccgtttttgtttgcgaatcctGTTTTTGTACTCTCAAGATTTAAGT

AACTGTACAACgctggcgaggaaacgaacaaggcctcaacaGTTTTTGTA

CTCTCAAGATTTAAGTAACTGTACAACcatagagtggaaaactagaaaca

gattcaaGTTTTTGTACTCTCAAGATTTAAGTAACTGTACAACataatgc

cgttgaattacacggcaaggtcaGTTTTTGTACTCTCAAGATTTAAGTAA

CTGTACAACgagcgagctcgaaataatcttaattacaagGTTTTTGTACT

CTCAAGATTTAAGTAACTGTACAACgttcgctagcgtcatgtggtaacgt

atttaGTTTTTGTACTCTCAAGATTTAAGTAACTGTACAACggcgtccca

atcctgattaatacttactcgGTTTTTGTACTCTCAAGATTTAAGTAACT

GTACAACaacacagcaagacaagaggatgatgctatgGTTTTTGTACTCT

CAAGATTTAAGTAACTGTACAACcgacacaagaacgtatgcaagagttca

agGTTTTTGTACTCTCAAGATTTAAGTAACTGTACAACacaattcttcat
```

-continued

```
ccggtaactgctcaagtgGTTTTTGTACTCTCAAGATTTAAGTAACTGTA
CAACaattaagggcatagaaagggagacaacatgGTTTTTGTACTCTCAA
GATTTAAGTAACTGTACAACcgatatttaaaatcattttcataacttcat
GTTTTTGTACTCTCAAGATTTAAGTAACTGTACAACgcagtatcagcaag
caagctgttagttactGTTTTTGTACTCTCAAGATTTAAGTAACTGTACA
ACataaactatgaaattttataattttaagaGTTTTTGTACTCTCAAGA
TTTAAGTAACTGTACAACaataatttatggtatagcttaatatcattgGT
TTTTGTACTCTCAAGATTTAAGTAACTGTACAACtgcatcgagcacgttc
gagtttaccgtttcGTTTTTGTACTCTCAAGATTTAAGTAACTGTACAAC
tctatatcgaggtcaactaacaattatgctGTTTTTGTACTCTCAAGATT
TAAGTAACTGTACAACaatcgttcaaattctgttttaggtacatttGTTT
TTGTACTCTCAAGATTTAAGTAACTGTACAACaatcaatacgacaagagt
taaaatggtcttGTTTTTGTACTCTCAAGATTTAAGTAACTGTACAACgc
ttagctgtccaatccacgaacgtggatgGTTTTTGTACTCTCAAGATTTA
AGTAACTGTACAACcaaccaacggtaacagctacttttttacagtGTTTTT
GTACTCTCAAGATTTAAGTAACTGTACAACataactgaaggataggagct
tgtaaagtctGTTTTTGTACTCTCAAGATTTAAGTAACTGTACAACtaat
gctacatctcaaaggatgatcccagaGTTTTTGTACTCTCAAGATTTAAG
TAACTGTACAACaagtagttgatgacctctacaatggtttatGTTTTTGT
ACTCTCAAGATTTAAGTAACTGTACAACacctagaagcatttgagcgtat
attgattgGTTTTTGTACTCTCAAGATTTAAGTAACTGTACAACaatttt
gccccttctttgccccttgactagGTTTTTGTACTCTCAAGATTTAAGTA
ACTGTACAACaccattagcaatcatttgtgcccattgagtGTTTTTGTAC
TCTCAAGATTTAAGTAACTGTACAGTTtgattcaacataaaaagccagtt
caattgaacttggcttt
```

In yet additional embodiments, the present invention provides *S. thermophilus* strains comprising a sequence obtained or obtainable from a bacteriophage, wherein the sequence comprises SEQ ID NO:683 downstream (e.g., directly downstream) of the first CRISPR repeat in at least one CRISPR locus. *S. thermophilus* strains comprising a sequence obtained or obtainable from a bacteriophage, wherein the sequence comprises SEQ ID NO:685 (i.e., 5'-TACGTTTGAAAAGAATATCAAATCAATGA-3').

In yet additional embodiments, the present invention provides *S. thermophilus* strains comprising a sequence obtained or obtainable from a bacteriophage, wherein the sequence comprises SEQ ID NO:685 downstream (e.g., directly downstream) of the first CRISPR repeat in at least one CRISPR locus.

In some embodiments, the present invention provides methods and compositions that find use in the development and use of strain combinations and starter culture rotations. In some additional embodiments, the use of one or more CRISPR BIMs simultaneously in a starter cultures (i.e., a combination of BIMs) is provided. In some further embodiments, the use of one or more CRISPR BIMs in a rotation scheme is provided. In some further embodiments, the use of one or more CRISPR BIMs combinations in a rotation scheme is provided.

The present invention also provides means to analyze target organism CRISPRs, in order to allow comparisons between spacer sequences against biocontrol phage genome. In some embodiments, the present invention provides means to predict phage virulence and selection of at least one biocontrol phage against at least one target microorganism.

The present invention also provides methods and compositions to utilize CRISPR-cas (i.e., 50 natural mutagenesis, in some preferred embodiments) to construct at least one phage resistant CRISPR variant of at least target microorganism which is then used to generate mutant phage that circumvent CRISPR-cas resistance via mutation within the phage corresponding to a sequence selected from spacer sequences, pseudospacer sequences, proximal sequence, recognition motifs, etc., to enhance the virulence of the phage. In some preferred embodiments, phage with enhanced virulence find use as biocontrol agents.

In some embodiments, the present invention provides compositions and methods suitable for the production of phage having enhanced virulence, as compared to the parent phage. In some embodiments, at least one cloned spacer is introduced into an active CRISPR-cas locus, to produce a phage-resistant cell variant for use in the generation of mutant phage. In some preferred embodiments, the methods comprise introducing a sequence that serves as a specific target of a phage genome sequence (e.g., a region that is highly susceptible as a spacer target or recognition sequence for spacer host incorporation). In some additional embodiments, the present invention provides methods and compositions for the direct engineering of phage, such that the genome sequence corresponding to the spacer is mutated accordingly.

The present invention also provides methods to direct the evolution of a given phage using the acquired CRISPR phage resistance of a corresponding host strain to create a more virulent, therefore effective, biocontrol agent.

DESCRIPTION OF THE DRAWINGS

FIG. 11 provides a schematic showing the construction of the S1S2 construct.

FIG. 12 provides a schematic showing the construction of $WT_{\Phi858}^{+S1S2}\Delta$CRISPR1.

FIG. 13 provides an alignment of CRISPR spacer S1 (SEQ ID NO: 680) with the corresponding genomic region of phage 858 and the two mutant phages that have circumvented the CRISPR resistance of strain $WT_{\Phi858}^{+S1S2}$.

DESCRIPTION OF THE INVENTION

Figure 1:
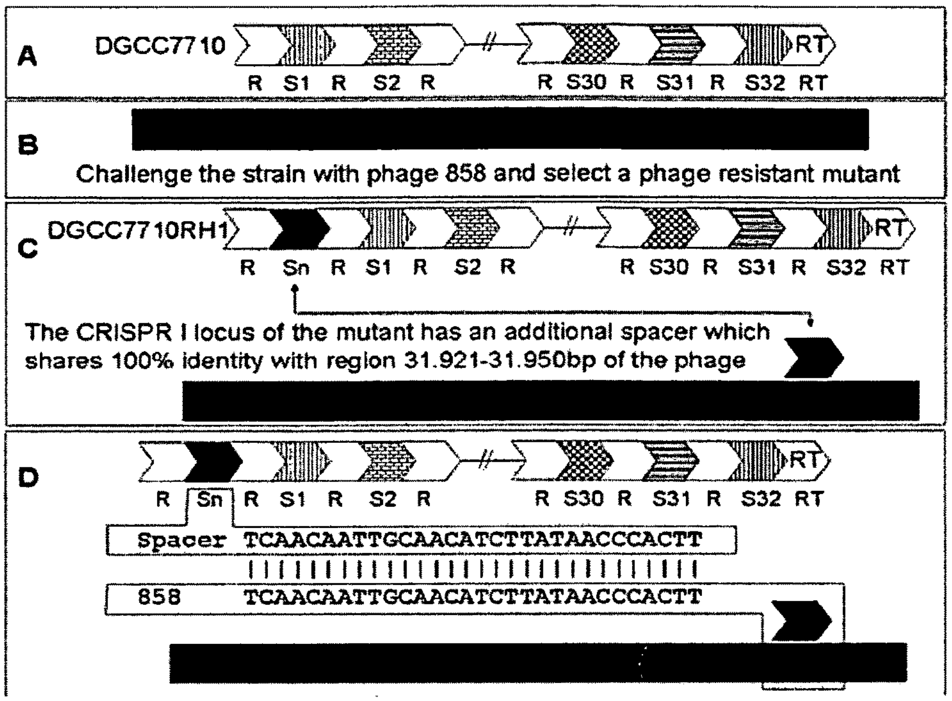
FIG. 1 provides a schematic showing that the integration of a CRISPR spacer into the CRISPR locus of *S. thermophilus* provides resistance against a bacteriophage to which the CRISPR spacer shows identity. The parent DGCC7710 is phage sensitive, and the BIM DGCC7710RH1 is phage resistant. The BIM DGCC7710RH1 has a new spacer (Sn) in the CRISPR locus, which shows 100% identity to phage sequence. As shown in step (B), the strain is challenged with phage 858 and a phage resistant mutant is selected. As shown in step (C), the CRISPR I locus of the mutant has an additional spacer which shares 100% identity with region 31.921-31.950 bp of the phage.

The present invention provides methods and compositions related to modulating the resistance of a cell against a target nucleic acid or a transcription product thereof. In some preferred embodiments, the present invention provides compositions and methods for the use of one or more cas genes or proteins for modulating the resistance of a cell against a target nucleic acid or a transcription product thereof. In some embodiments, the present invention provides methods and compositions that find use in the development and use of strain combinations and starter culture rotations. In additional embodiments, the present invention provides methods for labelling and/or identifying bacteria. In some preferred embodiments, the present invention provides methods for the use of CRISPR loci to determine the potential virulence of a phage against a cell and the use of CRISPR-cas to modulate the genetic sequence of a phage for increased virulence level. In still further embodiments, the present invention provides means and compositions for the development and use of phages as biocontrol agents.

*Streptococcus thermophilus* is a low G+C Gram-positive bacterial species that is a key species exploited in the formulation of dairy culture systems for the production of yogurt and cheese. Comparative genomics analyses of closely related *S. thermophilus* strains have previously revealed that genetic polymorphism primarily occurs at hypervariable loci, such as the eps and rps operons, as well as two clustered regularly interspaced short palindromic repeats (CRISPR) loci (See e.g., Jansen et al., Mol. Microbiol., 43:1565 [2002]; Bolotin et al., Microbiol., 151:2551 [2005]; and Bolotin et al., Nat. Biotechnol., 22:1554 [2004]). As described herein in greater detail, CRISPR loci typically consist of several non-contiguous direct repeats separated by stretches of variable sequences called spacers, and are often times adjacent to cas genes (CRISPR-associated). Although the function of CRISPR loci has not been established biologically, in silico analyses of the spacers have revealed sequence homology with foreign elements, including bacteriophage and plasmid sequences (See e.g., Bolotin et al., Microbiol., supra; Mojica et al., supra; and Pourcel et al., supra). Based exclusively on in silico analyses, several hypotheses have been put forward proposing roles for CRISPR and cas genes, that include providing immunity against foreign genetic elements via a mechanism based on RNA interference (See, Makarova et al., Biol. Direct., 1:7 [2006]). However, it is not intended that the present invention be limited to any particular mechanism and/or means of action.

Current strategies used in industry to minimize bacteriophage infection and the resultant failure of bacterial cultures, include the use of: (i) mixed starter cultures; and (ii) the use of alternating strains having different phage susceptibility profiles (i.e., strain rotation). Traditionally, starter cultures used in the dairy industry are mixtures of lactic acid bacterial strains. The complex composition of mixed starter cultures ensures that a certain level of resistance to phage attack is provided. However, repeated sub-culturing of mixed strain cultures leads to unpredictable changes in the distribution of individual strains and eventually often to undesired strain dominance. This in turn may lead to increased susceptibility to phage attack and risk of fermentation failures.

The rotation of selected bacterial strains which are sensitive to different phages is another approach currently used to limit phage development. However, it is difficult and cumbersome to identify and select a sufficient number of strains having different phage type profiles to provide an efficient and reliable rotation program. In addition, the continuous use of strains requires careful monitoring for new infectious phages and the need to quickly substitute an infected strain with a resistant bacterial strain. In manufacturing plants where large quantities of bulk starter cultures are prepared long before use, such a quick response is usually not possible. Thus, several attempts have been made to improve the resistance of cultures for use in industry.

In addition, although it would be useful to have starter cultures that are labelled such that their origin could be determined, this has not been done. Indeed, although it is feasible to insert a synthetic oligonucleotide into a strain to tag or label it, using recombinant DNA technologies, the labelled strain would be considered to be a genetically modified organism and may thereby face regulatory issues in commercial applications. Thus, there is a need in the art for natural methods and compositions suitable for introducing a unique sequence into bacteria that could be used to identify and/or track bacteria.

Bacteriophages are arguably the most abundant biological entity on the planet (See, Breitbart and Rohwer, Trends Microbiol., 13:278 [2005]). Their ubiquitous distribution and abundance have an important impact on microbial ecology and the evolution of bacterial genomes (See, Chibani-Chennoufi et al., J. Bacteriol., 186:3677 [2004]). Consequently, bacteria have developed a variety of natural defense mechanisms that target diverse steps of the phage life cycle, notably blocking adsorption, preventing DNA injection, restricting the incoming DNA and abortive infection systems. These antiviral barriers can also be engineered and manipulated to better control phage populations (See e.g., Chibani-Chennoufi et al., supra; and Sturino and Klaenhammer, Nat. Rev. Microbiol., 4:395 [2006]).

Numerous bacteria have been selected by humans and used extensively for fermentation and biotechnology processes. Unfortunately, domesticated bacteria used in industrial applications are often susceptible to phage attack, including those genera and species widely used as dairy cultures (See, Brussow, Ann. Rev. Microbiol., 55:283 [2001]). Accordingly, the industry has devised various strategies to combat phage based on strain diversity, bacteriophage insensitive mutants, and plasmids bearing phage-resistance mechanisms.

Definitions

Unless defined otherwise herein, all technical and scientific terms used herein have the same meaning as commonly understood by one of ordinary skill in the art to which this invention pertains.

Although any methods and materials similar or equivalent to those described herein find use in the practice of what is described herein, exemplary methods and materials are described herein. As used herein, the singular terms "a", "an," and "the" include the plural reference unless the context clearly indicates otherwise. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

It is intended that every maximum numerical limitation given throughout this Specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

As used herein, the term "naturally occurring" refers to elements and/or process that occur in nature.

As used herein, the terms "construct," "conjugate," "cassette," and "hybrid," include a nucleotide sequence directly or indirectly attached to another sequence (e.g., a regulatory sequence, such as a promoter). In some embodiments, the present invention provides constructs comprising a nucleotide sequence operably linked to such a regulatory sequence. The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences. As used herein, the term "regulatory sequences" includes promoters and enhancers and other expression regulation signals. As used herein, the term "promoter" is used in the normal sense of the art, e.g. an RNA polymerase binding site. In some embodiments, constructs comprise or express a marker, which allows for the selection of the nucleotide sequence construct in, for example, a bacterium. Various markers exist which may be used, for example those markers that provide for antibiotic/antimicrobial resistance.

In some embodiments, the construct comprises a vector (e.g., a plasmid). In some further embodiments, the present invention provides vectors comprising one or more of the constructs or sequences described herein. As used herein, the term "vector" includes expression vectors, transformation vectors, and shuttle vectors. The term "transformation vector" means a construct capable of being transferred from one entity to another entity, which may be of the same species or may be a different species. Constructs that are capable of being transferred from one species to another are sometimes referred to as "shuttle vectors. In some embodiments, the vectors are transformed into a suitable host cell as described herein. In some embodiments, the vectors are plasmid or phage vectors provided with an origin of replication, optionally a promoter for the expression of the polynucleotide, and optionally a regulator of the promoter. In some embodiments, the vectors contain one or more selectable marker nucleotide sequences. The most suitable selection systems for industrial micro-organisms are those formed by the group of selection markers which do not require a mutation in the host organism. In some embodiments, the vectors are used in vitro (e.g., for the production of RNA or used to transfect or transform a host cell). In some embodiments, polynucleotides are incorporated into a recombinant vector (typically a replicable vector), such as a cloning or expression vector. The vector finds use in the replication of the nucleic acid in a compatible host cell.

Introduction of a nucleic acid (e.g., a phage, construct or vector) into a cell can be effected by various methods. For example, in some embodiments, transduction, transformation, calcium phosphate transfection, DEAE-dextran mediated transfection, cationic lipid-mediated transfection, electroporation, transduction or infection may find use. Indeed, any suitable method known in the art finds use in the present invention. In some embodiments, cells containing exogenous nucleic acid (introduced by means of phage, construct, or a vector) are selected for using any suitable method known in the art.

Teachings on the transformation of cells are well documented in the art, for example see Sambrook et al (Molecular Cloning: A Laboratory Manual, 2nd edition, 1989, Cold Spring Harbor Laboratory Press) and Ausubel et al., Current Protocols in Molecular Biology (1995), John Wiley & Sons, Inc.

In the context of introducing a nucleic acid into a cell, in some embodiments, it is preferred that the term "introducing" means one or more of transforming, transfecting, conjugating or transducing. In some particularly preferred embodiments, bacterial strains (e.g., parent bacterial strains, variant bacterial strains, etc.) are "exposed" to at least one phage, such that the phage nucleic acid is introduced into the cells of the bacterial strain.

As used herein, the terms "nucleic acid sequence," "nucleotide sequence," and "nucleic acid," refer to any nucleic acid sequence, including DNA, RNA, genomic, synthetic, recombinant (e.g., cDNA). It is intended that the terms encompass double-stranded and/or single-stranded sequences, whether representing the sense or antisense strand or combinations thereof. Recombinant nucleic acid sequences are prepared by use of any suitable recombinant DNA techniques. In some embodiments, as described herein, nucleic acid sequences provided include gene sequences that encode CRISPR, Cas, and other sequences. Indeed, as used in context, the present invention encompasses nucleic acid sequences that encode various CRISPR sequences, including but not limited to spacers, pseudo-spacers, leaders, etc., as well as cas sequences, and other bacterial and phage ("bacteriophage") nucleic acid sequences.

The terms "nucleic acid molecule encoding," "nucleic acid sequence encoding," "DNA sequence encoding," and "DNA encoding," refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, conjugation, and transduction. In some particularly preferred embodiments, nucleic acid is introduced into recipient cells upon infection of the cells by bacteriophage(s).

In some embodiments, the nucleic acid sequences and the nucleic acids provided herein are isolated or substantially purified. By "isolated" or "substantially purified" is intended that the nucleic acid molecules, or biologically active fragments or variants, homologues, or derivatives thereof are substantially or essentially free from components normally found in association with the nucleic acid in its natural state. Such components include, but are not limited to other cellular material, culture media, materials from recombinant production, and various chemicals used in chemically synthesising the nucleic acids.

In some embodiments, an "isolated" nucleic acid sequence or nucleic acid is typically free of nucleic acid sequences that flank the nucleic acid of interest in the genomic DNA of the organism from which the nucleic acid was derived (e.g., coding sequences present at the 5' or 3' ends). However, the molecule may include some additional bases or moieties that do not deleteriously affect the basic characteristics of the composition.

As used herein, the term "modification" refers to changes made within nucleic acid and/or amino acid sequences. In some embodiments, modifications are accomplished using genetic engineering (e.g., recombinant) methods, while in other embodiments, modifications are made using naturally-occurring genetic mechanisms. It is intended that all or part of a sequence will be modified using the methods of the present invention. In some preferred embodiments, the nucleic acids modified include one or more naturally-occurring or recombinantly produced CRISPR spacers, cas genes or proteins, CRISPR repeats, CRISPR loci, as well as bacteriophage nucleic acids. Any suitable method known in the art finds use in the present invention, including but not limited to use of PCR, cloning, site-directed mutagenesis, etc. Indeed, commercially available kits find use in the present invention. In some embodiments, synthetic oligonucleotides are used. In some embodiments, methods such as homologous recombination find use (e.g., for insertion or deletion of CRISPR spacers). In some embodiments, genetic engineering includes the activation of one or more nucleic acid sequences (e.g., CRISPR loci, CRISPR repeats, CRISPR spacers, cas genes or proteins, functional combinations of cas genes or proteins and CRISPR repeats, or combinations thereof).

In some embodiments, one or more CRISPR spacers or pseudo CRISPR spacers are inserted into at least one CRISPR locus. In some further embodiments, the modification does not interrupt one or more cas genes of the at least one CRISPR locus. In other embodiments, the one or more cas genes remain intact. In some additional embodiments, the modification does not interrupt one or more CRISPR repeats of the at least one CRISPR locus. In some embodiments, the one or more CRISPR repeats remain intact. In some further embodiments, one or more CRISPR spacers or pseudo CRISPR spacers are inserted into or within at least one CRISPR locus. In some further embodiments, one or more CRISPR spacers or pseudo CRISPR spacers are inserted at the 5' end of at least one CRISPR locus.

In some embodiments, the modification comprises inserting at least one CRISPR spacer or pseudo CRISPR spacers into a cell (e.g., a recipient cell). In some other embodiments, the modification comprises inserting one or more CRISPR spacers or pseudo CRISPR spacers into (e.g., to modify or replace) one or more CRISPR spacers of a recipient cell. In some embodiments, the CRISPR spacers of the cell are the same, while in other embodiments, they are different. In some embodiments, the modification comprises inserting at least one CRISPR spacer or pseudo CRISPR spacer from a donor organism into a recipient cell. In some further embodiments, the modification comprises inserting one or more CRISPR spacers or pseudo CRISPR spacers from a donor organism into a recipient cell under conditions suitable to modify or replace one or more CRISPR spacers or pseudo CRISPR spacers of the recipient cell. In some embodiments, one or more CRISPR spacers or pseudo CRISPR spacers from a donor organism are inserted into one or more, preferably, two or more CRISPR repeats of the cell. In some preferred embodiments, at least one functional CRISPR repeat-cas combination remains intact in the cell.

In some further embodiments, insertion occurs adjacent to one or more (preferably two or more) CRISPR spacers or pseudo-spacers. As used herein, the term "adjacent" means "next to" in its broadest sense and includes "directly adjacent." Thus, in some embodiments, one or more CRISPR spacers or pseudo CRISPR spacers from an organism are inserted "directly adjacent" to one or more CRISPR spacers or pseudo CRISPR spacers of the recipient cell. (i.e., the CRISPR spacer(s) or pseudo CRISPR spacer(s) is inserted such that there are no intervening nucleotides between the spacers).

In some additional embodiments, the CRISPR spacer(s) or pseudo CRISPR spacer(s) are inserted such that there are at least about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 95, about 100, about 200, about 300, about 400, about 500, about 600, about 700, about 800, about 900, about 1000, about 10,000, 1 about 00,000, or about 1,000,000 or more intervening nucleotides between the spacers.

In some further embodiments, the intervening nucleotide is referred to as a "leader sequence." These terms are used interchangeably herein. The leader sequence can be of a different length in different bacteria. In some embodiments, the leader sequence is at least about 20, about 25, about 30, about 35, about 40, about 45, about 50, about 55, about 60, about 65, about 70, about 75, about 80, about 85, about 90, about 95, about 100, about 200, about 300, about 400, or about 500 or more nucleotides in length. In some preferred embodiments, the leader sequence is between the last cas gene (at the 3' end) and the first CRISPR repeat (at the 5' end) of the CRISPR locus. In some embodiments, the leader sequence is between about 20-500 nucleotides in length.

In some embodiments, one or more CRISPR spacers or pseudo CRISPR spacers from a donor organism are inserted adjacent to one or more cas genes of a recipient cell, wherein the cas genes are the same or different. In some additional embodiments, one or more CRISPR spacers or pseudo CRISPR spacers from a donor organism are inserted adjacent to the same or different spacers of the recipient cell.

In another embodiment, one or more CRISPR spacers or pseudo CRISPR spacers—such as one or more CRISPR spacers or pseudo CRISPR spacers from a donor organism—are each inserted adjacent to the same or different CRISPR repeats of the cell. In another embodiment, one or more CRISPR spacers or pseudo CRISPR spacers—such as one or more CRISPR spacers or pseudo CRISPR spacers from a donor organism—are each inserted adjacent to the same or different cas genes of the recipient cell.

In some further embodiments, the sequence of the one or more CRISPR spacer(s) from a donor organism are provided under conditions that the recipient cell is modified such that the CRISPR spacer has homology to the CRISPR spacer or pseudo CRISPR spacer of the donor organism. In some embodiments, the CRISPR spacer has 100% homology to the CRISPR spacer of the donor organism.

In some embodiments, the CRISPR spacer(s) or pseudo CRISPR spacers comprise DNA or RNA of genomic, synthetic or recombinant origin. In some embodiments, the CRISPR spacer (s) or pseudo CRISPR spacers are double-stranded, while in other embodiments, they are single-stranded, whether representing the sense or antisense strand or combinations thereof. It is contemplated that the CRISPR spacer (s) or pseudo CRISPR spacers be prepared by use of recombinant DNA techniques (e.g. recombinant DNA), as described herein.

In some embodiments, the modification comprises inserting one or more CRISPR spacers or pseudo CRISPR spacers from a donor organism that is/are substantially resistant to a target nucleic acid or a transcription product thereof into one or more CRISPR loci of a substantially sensitive cell. In some embodiments, the insertion occurs at or between a functional combination of at least two CRISPR repeats and at least one cas gene in a substantially sensitive cell. In some embodiments, the modification comprises modifying (e.g., mutating) the DNA of a recipient cell (e.g., plasmid DNA or genomic DNA), such that one or more cas genes are created in the DNA of the cell. In some embodiments, the cas genes are cloned into a construct, a plasmid or a vector, etc., which is then transformed into the cell, using any suitable method.

In some embodiments, the modification comprises modifying (e.g., mutating) the DNA of a recipient cell (e.g., such as plasmid DNA or genomic DNA), such that one or more, preferably, two or more CRISPR repeats are created in the DNA of the cell. In some embodiments, the CRISPR repeats are cloned into a construct, a plasmid or a vector, etc., which is then transformed into the cell, using any suitable method.

In some further embodiments, the modification comprises modifying (e.g., mutating) the DNA of a recipient cell (e.g., plasmid DNA or genomic DNA), such that one or more cas-CRISPR repeat functional combinations are created in the DNA of the cell. In some embodiments, the cas-CRISPR repeat functional combinations may be cloned into a construct, a plasmid or a vector, which is then transformed into the cell, using any suitable method.

In some embodiments, the modification comprises modifying (e.g., mutating) the DNA of a recipient cell (e.g., plasmid DNA or genomic DNA), such that one or more CRISPR spacers are created in the DNA of the cell. In some embodiments, the CRISPR spacers may be cloned into a construct, a plasmid or a vector, which is then transformed into the cell, using any suitable method. In some preferred embodiments, a CRISPR spacer is flanked by two CRISPR repeats (i.e., a CRISPR spacer has at least one CRISPR repeat on each side).

In some embodiments, the modification comprises inserting one or more CRISPR spacers (e.g., heterologous CRISPR spacers) in the vicinity of (e.g., adjacent to/directly adjacent to) one or more cas genes and/or the leader sequence. Thus, in some embodiments, the organization of the naturally occurring CRISPR locus is maintained following insertion of the one or more CRISPR spacers.

As used herein, the term "target nucleic acid" refers to any nucleic acid sequence or transcription product thereof, against which resistance in a cell (e.g., a recipient cell) is modulated. In some embodiments, the resistance is directed against the target nucleic acid sequence per se. Advantageously, this confers resistance to a cell against a donor organism from which the target nucleic acid(s) is derivable. Thus, in some embodiments, the insertion of a pseudo-CRISPR spacer derived from a bacteriophage or a CRISPR spacer(s) which is/are complementary or homologous to the one or more pseudo CRISPR spacer(s) into a recipient cell confers resistance to the bacteriophage. Thus, in some preferred embodiments, insertion between two CRISPR repeats of a pseudo-CRISPR spacer derived from a bacteriophage or CRISPR spacer(s) that is/are complementary or homologous to the one or more pseudo CRISPR spacer(s) into a recipient cell confers resistance to the bacteriophage.

In a further aspect, there is provided a method for modulating the resistance of a recipient cell against a target nucleic acid or a transcription product thereof.

The present invention also provides methods for determining the resistance profile of a cell against a target nucleic acid. As used herein, the term "resistance profile" means one or more entities against which the cell is sensitive or resistant. Accordingly, in some embodiments, the resistance profile of a cell reflects that the cell is resistant to a first bacteriophage, sensitive to a second bacteriophage, resistant to a first mobile genetic element, and sensitive to a first antibiotic resistance gene, etc.

In some embodiments, one or more cas genes or proteins, one or more CRISPR repeats, one or more cas genes, one or more cas-CRISPR repeat functional combinations, one or more CRISPR spacers, and/or one or more CRISPR spacers etc., within a cell are detected and/or sequenced so as to predict/determine the likely resistance profile of a particular cell. In some other embodiments, one or more CRISPR spacers within a cell are detected or sequenced so as to predict/determine the likely resistance profile of a particular cell. Suitable detection methods include, but are not limited to PCR, DNA-DNA hybridization, DNA-RNA hybridization, DNA microarrays, etc. Indeed, it is intended that any suitable method will find use in the present invention. In additional embodiments, the likely resistance profile of a particular bacterial cell to one or more bacteriophage is used as a lysotype predictor for microbial selection. In some further embodiments, one or more Cas genes and/or one or more CRISPR repeats are sequenced in addition to one or more CRISPR spacers, in order to verify the compatibility of the cas gene-CRISPR repeat combination or to identify new pairs of compatible cas/repeat combinations.

As used herein, the term "modulating resistance" refers suppressing, reducing, decreasing, inducing, conferring, restoring, elevating, increasing or otherwise affecting the resistance of a cell to a target nucleic acid, as taken in context.

As used herein, the term "resistance" is not meant to imply that a cell is 100% resistant to a target nucleic acid or a transcription product thereof, but includes cells that are tolerant of the target nucleic acid or a transcription product thereof.

As used herein the term "resistance to target nucleic acid or transcription product thereof" means that resistance is conferred against a cell or an organism (e.g., phage) that comprises or produces the target nucleic acid or transcription product thereof. In some embodiments, the minimal component required for conferring immunity or resistance against a target nucleic acid or expression product thereof is at least one cas gene (or one Cas protein) and at least two CRISPR repeats flanking a spacer.

In some embodiments, the present invention provides methods for modulating (e.g. conferring or increasing) the resistance of a cell against a target nucleic acid or a transcription product thereof comprising the steps of: identifying a sequence (e.g., a conserved sequence) in an organism (preferably, a sequence essential to the function or survival of the organism); preparing a CRISPR spacer which comprises a sequence homologous (e.g., 100% identical), to the identified sequence; preparing a nucleic acid comprising at least one cas gene and at least two CRISPR repeats together with the CRISPR spacer; and (iv) transforming a cell with the nucleic acid thus to render the cell resistant to the target nucleic acid or transcription product thereof.

As used herein, the term "conserved sequence" in the context of identifying a conserved sequence in an organism does not necessarily have to be conserved in its strictest sense, as the knowledge of one sequence from a given organism is sufficient. Furthermore, the sequence does not need to be part of an essential entity. However, in some embodiments, the conserved sequence is a sequence that is essential for function and/or survival and/or replication and/or infectivity and the like of an organism or a cell. In some embodiments, the conserved sequence comprises a helicase, a primase a head or tail structural protein, a protein with a conserved domain (e.g., holing, lysine, and others), or conserved sequences amongst important phage genes.

In some further embodiments, the present invention provides methods for modulating (e.g., conferring or increasing) the resistance of a cell against a target nucleic acid or a transcription product thereof comprising the steps of identifying one or more CRISPR spacers in an organism resistant to the target nucleic acid or transcription product thereof; preparing a recombinant nucleic acid comprising at least one cas gene or protein and at least two CRISPR repeats together with the identified one or more spacers; and transforming a cell with the recombinant nucleic acid thus to render the recipient cell resistant to the target nucleic acid or transcription product thereof.

In some embodiments, the present invention provides methods for modulating (e.g., conferring or increasing) the resistance of a cell comprising at least one or more cas genes or proteins and one or more, preferably, two or more CRISPR repeats against a target nucleic acid or a transcription product thereof comprising the steps of identifying one or more CRISPR spacers in an organism resistant to the target nucleic acid or transcription product thereof; and modifying the sequence of one or more CRISPR spacer(s) in the cell such that the CRISPR spacer(s) has homology to the CRISPR spacer(s) in the organism. In some embodiments, one or more CRISPR spacers in a recipient cell are modified (e.g., genetically engineered) such that the CRISPR spacer(s) have homology to one or more CRISPR spacer(s) in a donor organism that is substantially resistant to a target nucleic acid or a transcription product thereof, in order to render the cell resistant to the target nucleic acid. In some preferred embodiments, the one or more cas genes or proteins and one or more, preferably, two or more CRISPR repeats in the cell are a functional combination as described herein.

The genetic engineering methods include any suitable methods known in the art, including but not limited to, adding (e.g., inserting), deleting (e.g., removing) or modifying (e.g., mutating) the sequence of the one or more CRISPR spacers and/or one or more pseudo CRISPR spacers in a cell, such that the CRISPR spacer has homology (e.g., increased homology after the genetic engineering) to one or more CRISPR spacers of a donor organism. This engineering step results in a cell that was substantially sensitive to a target nucleic acid or a transcription product thereof being substantially resistant to the target nucleic acid or a transcription product thereof.

In some additional embodiments, the present invention provides methods for decreasing or reducing the resistance of a recipient cell comprising at least one or more cas genes or proteins and one or more, preferably, two or more CRISPR repeats against a target nucleic acid or a transcription product thereof.

In some embodiments, the methods comprise the steps of: identifying one or more CRISPR spacers in an organism that is substantially resistant to the target nucleic acid or a transcription product thereof; and modifying the sequence of one or more CRISPR spacer(s) in the cell such that the CRISPR spacer(s) has a reduced degree of homology to the CRISPR spacer(s) in the organism.

In other embodiments, the methods for modulating (e.g., decreasing) the resistance of a cell comprising one or more cas genes or proteins and one or more, preferably, two or more CRISPR repeats against a target nucleic acid or transcription product thereof comprise the steps of: identifying a CRISPR spacer or a pseudo CRISPR spacer in an organism comprising a target nucleic acid or transcription product thereof against which resistance is to be modulated; and identifying the CRISPR spacer in the organism in which resistance is to be modulated; and (iii) adapting the sequence of the CRISPR spacer in the organism in which resistance is to be modulated such that the CRISPR spacer has a lower degree of homology to the CRISPR spacer or pseudo CRISPR spacer of the organism comprising the target nucleic acid or transcription product thereof against which resistance is to be modulated.

One or more CRISPR spacers in a substantially resistant cell are engineered in order to render the cell sensitive to a target nucleic acid. The genetic engineering methods that find use include, but are not limited to, the addition (e.g., insertion), deletion (e.g., removal) or modification of one or more functional CRISPR repeat-cas combinations or portions or fragments thereof in the substantially resistant cell and/or the addition (e.g., insertion), deletion (e.g., removal) or modification of one or more CRISPR spacers or portions or fragments thereof in the substantially resistant cell. This engineering step results in a cell that was substantially resistant to a target nucleic acid or a transcription product thereof becoming substantially sensitive to a target nucleic acid or a transcription product thereof.

In some embodiments, in order to confer sensitivity to a cell, it is contemplated that one or more CRISPR spacers, one or more cas genes or proteins, one or more, preferably, two or more CRISPR repeats, and/or one or more functional CRISPR repeat-cas combinations from a substantially resistant cell will be removed, deleted or modified such that resistance is no longer conferred. In some embodiments, cells that are sensitive to a target nucleic acid or a transcription product thereof are prepared such that their levels within a given culture (e.g., a starter culture) may be modulated (e.g., decreased) as desired. Thus, in some embodiments, starter cultures comprising two or more bacterial strains are developed such that all members of the culture are sensitive to the same agent (e.g., the same bacteriophage). Thus, when the time comes that it is no longer desired for the culture to be alive, the culture is contacted with the same single agent in order to kill all members of the culture. In some embodiments, the sensitivity of cells are modulated to one or more agents (e.g., phages), such that the agent kills only a certain proportion of the cells in a given culture (e.g., about 10, about 20, about 30, about 40, about 50, about 60, about 70, about 80, about 90, or about 95% of the cells in the culture).

In some embodiments, a recipient cell is engineered such that it comprises a CRISPR spacer or a sequence corresponding to a pseudo CRISPR spacer, thereby rendering the cell resistant to a target nucleic acid or transcription product thereof. Suitably, the cell is engineered such that the CRISPR spacer or sequence corresponding to the pseudo CRISPR spacer is used together with a functional cas gene-CRISPR repeat combination, as described herein.

In some embodiments, a cell that is resistant to a target nucleic acid or transcription product thereof is engineered such that the CRISPR spacer conferring the immunity against the target nucleic acid or transcription product thereof is inserted into a cell that comprises a functional cas gene-CRISPR repeat combination, thereby rendering the cell resistant to the target nucleic acid or transcription product thereof.

In some further embodiments, the sequence of one or more CRISPR spacers or pseudo CRISPR spacers of a cell that is resistant to a target nucleic acid or transcription product thereof is determined. A recipient cell is then engineered such that it comprises the sequence of the CRISPR spacer and a functional cas gene-CRISPR repeat combination, thereby rendering the cell resistant to the target nucleic acid or transcription product thereof.

In some additional embodiments, a CRISPR spacer from a recipient cell and a functional cas gene-CRISPR repeat combination from the same or different cell (e.g., the same or different recipient cell) are prepared. A further recipient cell is then engineered such that is comprises the CRISPR spacer sequence and functional cas gene-CRISPR repeat combination thereby rendering the cell resistant to the target nucleic acid or transcription product thereof.

In some embodiments, the resistance is directed against a transcription product of the target nucleic acid sequence (e.g., a transcript of the target nucleic acid sequence, in particular an RNA or mRNA), a transcript (e.g., a sense or an antisense RNA transcript), or a polypeptide transcription product. In some embodiments, this confers resistance to a cell against a donor organism from which the transcription product is derived.

In some embodiments, the target nucleotide sequence comprises DNA or RNA of genomic, synthetic or recombinant origin. In some further embodiments, the nucleotide sequence is double-stranded, while in other embodiment it is single-stranded, whether representing the sense or antisense strand or combinations thereof. In yet additional embodiments, the nucleotide sequence is prepared by use of recombinant DNA techniques (e.g., recombinant DNA). In still further embodiments, the nucleotide sequence is the same as a naturally occurring form, while in other embodiments it is derived therefrom. In yet further embodiments, the target nucleic acid sequence is derived from a gene. In some other embodiments, the target nucleic acid sequence is derived from a variant, homologue, fragment or derivative of a gene. In some preferred embodiments, the target nucleic sequence is or is derived from bacteriophage. In some embodiments, the target nucleic sequence is derived from plasmid DNA. In some embodiments, the target nucleic sequence is derived from a mobile genetic element. In some additional embodiments, the target nucleic sequence is derived from a transposable element or an insertion sequence. In yet additional embodiments, the target nucleic sequence is derived from a gene that confers resistance. In some further embodiments, the target nucleic sequence is derived from a gene that confers resistance to an antibiotic or antimicrobial. In some embodiments, the target nucleic sequence is derived from a virulence factor. In some additional embodiments, the target nucleic sequence is derived from a toxin, an internalin or a hemolysin.

In some embodiments, the target nucleic sequence or a transcription product thereof is derived from one or more bacteria. Thus, in some preferred embodiments the resistance of bacterial cells is modulated using the methods and compositions of the present invention. In some preferred embodiments, the target nucleotide sequence is derived from a gene associated with resistance to plasmid transfer in bacteria. In some embodiments, one or more CRISPR spacers in the cell are modified such that the CRISPR spacer of the cell has homology to the CRISPR spacer and/or pseudo CRISPR spacer contained in the plasmid DNA of the bacterial cell, thereby providing resistance against the particular plasmid(s). Thus, the transfer of foreign DNA into the cell is prevented. In some preferred embodiments, particular regions within the plasmid DNA are targeted, so as to provide immunity against plasmid DNA. For example, in some embodiments, sequences within the plasmid's origin of replication or sequences within genes coding for replication proteins are targeted.

In some embodiments, the present invention provides methods comprising the steps of: identifying a CRISPR spacer and/or pseudo CRISPR spacer derived from the plasmid DNA of a bacterial cell against which resistance is to be modulated; and modifying the sequence of a CRISPR spacer in the cell in which resistance is to be modulated, such that the CRISPR spacer of the cell has homology to the CRISPR spacer and/or pseudo CRISPR spacer contained in the plasmid DNA of the bacterial cell.

In still further embodiments, the present invention provides methods for conferring resistance to a cell against plasmid transfer, comprising the steps of: identifying a CRISPR spacer and/or pseudo CRISPR spacer derived from plasmid DNA; identifying one or more functional CRISPR repeat-cas gene combinations in a cell that is substantially sensitive to the plasmid; and engineering the one or more CRISPR loci in the substantially sensitive cell such that they comprise one or more CRISPR spacers and/or pseudo CRISPR spacers from the plasmid, thereby rendering the cell resistant.

In some embodiments, the target nucleotide sequence is derived from a gene associated with resistance to one or more mobile genetic elements. In some embodiments, particular CRISPR spacers and/or pseudo CRISPR spacers derived from one or more mobile genetic elements are added within a CRISPR locus of a cell so as to provide resistance against mobile genetic elements (e.g., transposable elements and insertion sequences), thus preventing transfer of foreign DNA and genetic drift. In some embodiments, particular regions within transposons and insertion sequences are targeted so as to provide immunity against mobile genetic elements. For example, in some embodiments targets include, but are not limited to conjugative transposons (Tn916), class II transposons (Tn501), insertion sequences (IS26), and transposase genes.

In some embodiments, the present invention provides methods comprising the steps of: identifying a CRISPR spacer and/or pseudo CRISPR spacer derived from one or more mobile genetic elements of a cell against which resistance is to be modulated; and modifying the sequence of a CRISPR spacer in a cell in which resistance is to be modulated such that the CRISPR spacer and/or pseudo CRISPR spacer of the cell has homology to the CRISPR spacer contained in the mobile genetic element(s) of the cell.

In still a further embodiments, the present invention provides methods for conferring resistance to a cell against one or more mobile genetic elements comprising the steps of: identifying a CRISPR spacer and/or pseudo CRISPR spacer derived from one or more mobile genetic elements; identifying one or more functional CRISPR repeat-cas combinations in a cell that is substantially sensitive to the one or more mobile genetic elements; and engineering the one or more CRISPR loci in the substantially sensitive cell such that they comprise or have homology to one or more CRISPR spacers and/or pseudo CRISPR spacers from the one or more mobile genetic elements to render the cell resistant.

In some embodiments the target nucleotide sequence is derived from a gene associated with resistance to antibiotics and/or antimicrobials. As used herein, the term "antimicrobial" refers to any composition that kills or inhibits the growth or reproduction of microorganisms. It is intended that the term encompass antibiotics (i.e., compositions produced by other microorganisms), as well as synthetically produced compositions. Antimicrobial resistance genes include, but are not limited to $bla_{tem}$, $bla_{rob}$, $bla_{shv}$, aadB, aacC1, aacC2, aacC3, aacA4, mecA, vanA, vanH, vanX, satA, aacA-aphH, vat, vga, msrA sul, and/or int. The antimicrobial resistance genes include those that are obtained from bacterial species that include but are not limited to the genera *Escherichia, Klebsiella, Pseudomonas, Proteus, Streptococcus, Staphylococcus, Enterococcus, Haemophilus*, and *Moraxella*. The antimicrobial resistance genes also include those that are obtained from bacterial species that include but are not limited to *Escherichia coli, Klebsiella pneumoniae, Pseudomonas aeruginosa, Proteus mirabilis, Streptococcus pneumoniae, Staphylococcus aureus, Staphylococcus epidermidis, Enterococcus faecalis, Staphylococcus saprophyticus. Streptococcus pyogenes, Haemophilus influenzae*, and *Moraxella catarrhalis*. In some embodiments, particular CRISPR spacers and/or pseudo CRISPR spacers derived from antimicrobial resistance encoding genes are added within a CRISPR locus of a recipient cell, under conditions such that transfer of resistance genes is prevented. Thus, the risk of acquiring antimicrobial resistance genes (i.e., markers) is reduced. In some embodiments, targets also include vanR, (i.e., vancomycin resistance), tetR (i.e., tetracycline resistance), and/or resistance factors that provide beta-lactamase resistance.

In some embodiments, the present invention provides methods comprising the steps of: identifying one or more CRISPR spacers and/or pseudo CRISPR spacers derived from a cell that comprises one or more antimicrobial resistance genes or markers; and modifying the sequence of the CRISPR spacer in a cell that does not comprise or does not express the antimicrobial resistance genes or markers such that the CRISPR spacer of the cell has homology to the one or more CRISPR spacers and/or pseudo CRISPR spacers contained in the cell that comprises one or more antimicrobial resistance genes or markers.

In still a further embodiments, the present invention provides methods for modulating the acquisition of antimicrobial resistance markers in a cell comprising the steps of: identifying one or more CRISPR spacers and/or pseudo CRISPR spacers derived from a cell that comprises one or more antimicrobial resistance genes or markers; identifying one or more CRISPR loci in a cell that does not comprise or does not express the antimicrobial resistance genes or markers; and modifying the sequence of the CRISPR spacer in the cell that does not comprise or does not express the antimicrobial resistance genes or markers such that the CRISPR spacer and/or pseudo CRISPR spacers has homology to the CRISPR spacer contained in the cell resistant to the transfer of genes conferring resistance to one or more antimicrobials.

In some embodiments, the target nucleotide sequence is derived from at least one gene associated with virulence factor(s). In some embodiments, particular CRISPR spacers and/or pseudo CRISPR spacers derived from genes encoding virulence factors are added within a bacterial CRISPR locus to provide resistance against the transfer of genes conferring virulence into the bacteria. In some embodiments, factors that commonly contribute to microbial virulence (e.g., in pathogens) are targeted, such as toxins, internalins, hemolysins and other virulence factors.

The present invention also provides methods comprising the steps of: identifying one or more CRISPR spacers and/or pseudo CRISPR spacers derived from a cell that comprises one or more virulence factors; and modifying the sequence of the CRISPR spacer in a cell that does not comprise or does not express the virulence factor(s) or marker(s) such that the CRISPR spacer of the cell has homology to the one or more CRISPR spacers and/or pseudo CRISPR spacers contained in the cell that comprises one or more virulence factors.

In still further embodiments, the present invention provides methods for conferring resistance to a cell against one or more virulence factor(s) or marker(s) comprising the steps of: identifying a CRISPR spacer and/or pseudo CRISPR spacer derived from one or more virulence factor(s) or marker(s); identifying one or more functional CRISPR repeat-cas combinations in a cell that is substantially sensitive to the one or more virulence factor(s) or marker(s); and engineering the one or more CRISPR loci in the substantially sensitive cell such that they comprise one or more CRISPR spacers and/or pseudo CRISPR spacers from the one or more virulence factor(s) or marker(s) to render the cell resistant.

The present invention encompasses the use of variants, homologues, derivatives and fragments thereof, including variants, homologues, derivatives and fragments of CRISPR loci, CRISPR spacers, pseudo CRISPR spacers, cas genes or proteins, CRISPR repeats, functional CRISPR repeat-cas gene combinations and target nucleic acid sequences or transcription products thereof.

The term "variant" is used to mean a naturally occurring polypeptide or nucleotide sequences which differs from a wild-type sequence.

The term "fragment" indicates that a polypeptide or nucleotide sequence comprises a fraction of a wild-type sequence. It may comprise one or more large contiguous sections of sequence or a plurality of small sections. The sequence may also comprise other elements of sequence, for example, it may be a fusion protein with another protein. Preferably the sequence comprises at least 50%, more preferably at least 65%, more preferably at least 80%, more preferably at least 85%, more preferably at least 90%, more preferably at least 95%, more preferably at least 96%, more preferably at least 97%, more preferably at least 98%, most preferably at least 99% of the wild-type sequence.

Preferably, the fragment retains 50%, more preferably 60%, more preferably 70%, more preferably 80%, more preferably 85%, more preferably 90%, more preferably 95%, more preferably 96%, more preferably 97%, more preferably 98%, or most preferably 99% activity of the wild-type polypeptide or nucleotide sequence.

Preferably, a CRISPR spacer or pseudo CRISPR spacer comprises at least 50%, more preferably at least 65%, more preferably at least 80%, more preferably at least 85%, more preferably at least 90%, more preferably at least 95%, more preferably at least 96%, more preferably at least 97%, more preferably at least 98%, most preferably at least 99% of the wild-type sequence. Preferably, a CRISPR spacer retains 50%, more preferably 60%, more preferably 70%, more preferably 80%, more preferably 85%, more preferably 90%, more preferably 95%, more preferably 96%, more preferably 97%, more preferably 98%, or most preferably 99% activity of the wild-type polypeptide or nucleotide sequence.

Preferably, a cas gene comprises at least 50%, more preferably at least 65%, more preferably at least 80%, more preferably at least 85%, more preferably at least 90%, more preferably at least 95%, more preferably at least 96%, more preferably at least 97%, more preferably at least 98%, most preferably at least 99% of the wild-type sequence. Preferably, a cas gene retains 50%, more preferably 60%, more preferably 70%, more preferably 80%, more preferably 85%, more preferably 90%, more preferably 95%, more preferably 96%, more preferably 97%, more preferably 98%, or most preferably 99% activity of the wild-type polypeptide or nucleotide sequence.

Preferably, a Cas protein comprises at least 50%, more preferably at least 65%, more preferably at least 80%, more preferably at least 85%, more preferably at least 90%, more preferably at least 95%, more preferably at least 96%, more preferably at least 97%, more preferably at least 98%, most preferably at least 99% of the wild-type sequence. Preferably, a Cas protein retains 50%, more preferably 60%, more preferably 70%, more preferably 80%, more preferably 85%, more preferably 90%, more preferably 95%, more preferably 96%, more preferably 97%, more preferably 98%, or most preferably 99% activity of the wild-type polypeptide or nucleotide sequence.

Preferably, a CRISPR repeat comprises at least 50%, more preferably at least 65%, more preferably at least 80%, more preferably at least 85%, more preferably at least 90%, more preferably at least 95%, more preferably at least 96%, more preferably at least 97%, more preferably at least 98%, most preferably at least 99% of the wild-type sequence. Preferably, a CRISPR repeat retains 50%, more preferably 60%, more preferably 70%, more preferably 80%, more preferably 85%, more preferably 90%, more preferably 95%, more preferably 96%, more preferably 97%, more preferably 98%, or most preferably 99% activity of the wild-type polypeptide or nucleotide sequence.

Preferably, a functional CRISPR repeat-cas combination comprises at least 50%, more preferably at least 65%, more preferably at least 80%, more preferably at least 85%, more preferably at least 90%, more preferably at least 95%, more preferably at least 96%, more preferably at least 97%, more preferably at least 98%, most preferably at least 99% of the wild-type sequence. Preferably, functional CRISPR repeat-cas combination retains 50%, more preferably 60%, more preferably 70%, more preferably 80%, more preferably 85%, more preferably 90%, more preferably 95%, more preferably 96%, more preferably 97%, more preferably 98%, or most preferably 99% activity of the wild-type polypeptide or nucleotide sequence.

Preferably, a target nucleic acid sequence comprises at least 50%, more preferably at least 65%, more preferably at least 80%, more preferably at least 85%, more preferably at least 90%, more preferably at least 95%, more preferably at least 96%, more preferably at least 97%, more preferably at least 98%, most preferably at least 99% of the wild-type sequence. Preferably, a target nucleic acid sequence retains 50%, more preferably 60%, more preferably 70%, more preferably 80%, more preferably 85%, more preferably 90%, more preferably 95%, more preferably 96%, more preferably 97%, more preferably 98%, or most preferably 99% activity of the wild-type polypeptide or nucleotide sequence.

In some embodiments, the fragment is a functional fragment. By a "functional fragment" of a molecule is understood a fragment retaining or possessing substantially the same biological activity as the intact molecule. In all instances, a functional fragment of a molecule retains at least 10% and at least about 25%, about 50%, about 75%, about 80%, about 85%, about 90%, about 95%, about 96%, about 97%, about 98%, or about 99% of the biological activity of the intact molecule.

The term "homologue" means an entity having a certain homology with the subject amino acid sequences and the subject nucleotide sequences. Here, the term "homology" can be equated with "identity".

In the present context, a homologous sequence is taken to include an amino acid sequence, which may be at least 75, 85 or 90% identical, preferably at least 95%, 96%, 97%, 98% or 99% identical to the subject sequence. Although homology can also be considered in terms of similarity (i.e. amino acid residues having similar chemical properties/functions), in the context of the present invention it is preferred to express homology in terms of sequence identity.

In the present context, a homologous sequence is taken to include a nucleotide sequence, which may be at least 75, 85 or 90% identical, preferably at least 95%, 96%, 97%, 98% or 99% identical to the subject sequence. Although homology can also be considered in terms of similarity (i.e. amino acid residues having similar chemical properties/functions), in the context of the present invention it is preferred to express homology in terms of sequence identity.

Homology comparisons may be conducted by eye, or more usually, with the aid of readily available sequence comparison programs. These commercially available computer programs can calculate % homology between two or more sequences.

Percent (%) homology may be calculated over contiguous sequences (i.e. one sequence is aligned with the other sequence and each amino acid in one sequence is directly compared with the corresponding amino acid in the other sequence, one residue at a time). This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, *Nucleic Acids Research* 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410), the GENEWORKS suite of comparison tools and CLUSTAL. Both BLAST and FASTA are available for offline and online searching (see Ausubel et al., 1999 ibid, pages 7-58 to 7-60). However, for some applications, it is preferred to use the GCG Bestfit program. A new tool, called BLAST 2 Sequences is also available for comparing protein and nucleotide sequence (see FEMS Microbiol Lett 1999 174(2): 247-50; FEMS Microbiol Lett 1999 177(1): 187-8).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix—such as BLOSUM62.

Once the software has produced an optimal alignment, it is possible to calculate % homology, preferably % sequence identity. The software typically does this as part of the sequence comparison and generates a numerical result.

Should Gap Penalties be used when determining sequence identity, then suitably the following parameters are used:

| FOR BLAST | |
|---|---|
| GAP OPEN | 0 |
| GAP EXTENSION | 0 |

| FOR CLUSTAL | DNA | PROTEIN | |
|---|---|---|---|
| WORD SIZE | 2 | 1 | K triple |
| GAP PENALTY | 10 | 10 | |
| GAP EXTENSION | 0.1 | 0.1 | |

For polypeptide sequence comparison the following settings may be used: GAP creation penalty of 3.0 and GAP extension penalty of 0.1. Suitably, the degree of identity with regard to an amino acid sequence is determined over at least 5 contiguous amino acids, determined over at least 10 contiguous amino acids, over at least 15 contiguous amino acids, over at least 20 contiguous amino acids, over at least 30 contiguous amino acids, over at least 40 contiguous amino acids, over at least 50 contiguous amino acids, or over at least 60 contiguous amino acids.

The sequences may also have deletions, insertions or substitutions of amino acid residues, which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example, according to the Table below. Amino acids in the same block in the second column and preferably in the same line in the third column may be substituted for each other:

| | | |
|---|---|---|
| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) may occur i.e. like-for-like substitution—such as basic for basic, acidic for acidic, polar for polar etc. Non-homologous substitution may also occur i.e. from one class of residue to another or alternatively involving the inclusion of unnatural amino acids—such as omithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids—such as trifluorotyrosine*, p-Cl-phenylalanine*, p-Br-phenylalanine*, p-I-phenylalanine*, L-allyl-glycine*, β-alanine*, L-α-amino butyric acid*, L-γ-amino butyric acid*, L-α-amino isobutyric acid*, L-ε-amino caproic acid#, 7-amino heptanoic acid*, L-methionine sulfone#*, L-norleucine*, L-norvaline*, p-nitro-L-phenylalanine*, L-hydroxyproline#, L-thioproline*, methyl derivatives of phenylalanine (Phe)—such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid # and L-Phe (4-benzyl)*. The notation * has been utilised for the purpose of the discussion above (relating to homologous or non-homologous substitution), to indicate the hydrophobic nature of the derivative whereas # has been utilised to indicate the hydrophilic nature of the derivative, #* indicates amphipathic characteristics.

Variant amino acid sequences include suitable spacer groups that are suitable for insertion inserted between any two amino acid residues of the sequence including alkyl groups—such as methyl, ethyl or propyl groups—in addition to amino acid spacers—such as glycine or β-alanine residues. A further form of variation involves the presence of one or more amino acid residues in peptoid form will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are well known in the art.

The nucleotide sequences for use in the present invention may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences may be modified by any method available in the art. Such modifications may be carried out to enhance the in vivo activity or life span of nucleotide sequences useful in the present invention.

CRISPRs

CRISPRs (Clustered Regularly Interspaced Short Palindromic Repeats); also known as SPIDRs (SPacer Interspersed Direct Repeats) constitute a family of recently described DNA loci that are usually specific to a particular bacterial species. The CRISPR locus is a distinct class of interspersed short sequence repeats (SSRs) that were first recognized in *E. coli* (Ishino et al., J. Bacteriol., 169:5429-5433 [1987]; and Nakata et al., J. Bacteriol., 171:3553-3556 [1989]). Similar interspersed SSRs have been identified in *Haloferax mediterranei, Streptococcus pyogenes, Anabaena*, and *Mycobacterium tuberculosis* (See, Groenen et al., Mol. Microbiol., 10:1057-1065 [1993]; Hoe et al., Emerg. Infect. Dis., 5:254-263 [1999]; Masepohl et al., Biochim. Biophys. Acta 1307:26-30 [1996]; and Mojica et al., Mol. Microbiol., 17:85-93 [1995]). The CRISPR loci differ from other SSRs by the structure of the repeats, which have been termed short regularly spaced repeats (SRSRs) (Janssen et al., OMICS J. Integ. Biol., 6:23-33 [2002]; and Mojica et al., Mol. Microbiol., 36:244-246 [2000]). The repeats are short elements that occur in clusters that are always regularly spaced by unique intervening sequences with a constant length (Mojica et al., [2000], supra). Although the repeat sequences are highly conserved between strains, the number of interspersed repeats and the sequences of the spacer regions differ from strain to strain (van Embden et al., J. Bacteriol., 182:2393-2401 [2000]).

CRISPR loci consist of short and highly conserved partially palindromic DNA repeats typically of 24 to 40 bp, containing inner and terminal inverted repeats of up to 11 bp. These repeats have been reported to occur from 1 to 140 times. Although isolated elements have been detected, they are generally arranged in clusters (up to about 20 or more per genome) of repeated units spaced by unique intervening 20-58 bp sequences. To date, up to 20 distinct CRISPR loci have been found within a single chromosome.

CRISPRs are generally homogenous within a given genome with most of them being identical. However, there are examples of heterogeneity in, for example, the Archaea (Mojica et al., [2000], supra).

As used herein, the term "CRISPR locus" refers to the DNA segment which includes all of the CRISPR repeats, starting with the first nucleotide of the first CRISPR repeat and ending with the last nucleotide of the last (terminal) CRISPR repeat.

Although the biological function of CRISPR loci is unknown, some hypotheses have been proposed. For example, it has been proposed that they may be involved in the attachment of the chromosome to a cellular structure, or in the chromosome replication and replicon partitioning (Jansen et al., OMICS 6:23-33 [2002]; Jansen et al., Mol. Microbiol., 43:1565-1575 [2002]; and Pourcel et al., Microbiol., 151:653-663 [2005]). Mojica et al. (Mojica et al., J. Mol. Evol., 60:174-182 [2005]) hypothesize that CRISPR may be involved in conferring specific immunity against foreign DNA and Pourcel et al. (supra) hypothesize that CRISPRs are structures that are able to take up pieces of foreign DNA as part of a defense mechanism. Bolotin et al. (supra) suggest that the CRISPR spacer elements are the traces of past invasions by extrachromosomal elements, and hypothesize that they provide a cell with immunity against phage infection, and more generally foreign DNA expression, by coding an antisense RNA. Bolotin et al. (supra) also suggest that cas genes are necessary for CRISPR formation. However, it is not intended that the present invention be limited to any particular mechanism, function, theory, nor means of action.

The genome of *Streptococcus thermophilus* LMG18311 contains 3 CRISPR loci; the 36-bp repeated sequences are different in CRISPR1 (34 repeats), CRISPR2 (5 repeats), and CRISPR3 (a single sequence). Nevertheless, they are perfectly conserved within each locus. CRISPR1 and CRISPR2 repeats are respectively interspaced by 33 and 4 sequences of 30 bp in length. All these interspacing sequences are different from each other. They are also different from those found in strain CNRZ1066 (41 interspacing sequences within CRISPR1) and in strain LMD-9 (16 within CRISPR1 and 8 within CRISPR3), which both are *S. thermophilus*.

Various methods for identifying CRISPR loci are known in the art. For example, Jensen et al. (Jensen et al., [2002], supra) describe a computer-based approach in which nucleotide sequences are searched for CRISPR motifs using the PATSCAN program at the server of the Mathematics and Computer Science Division at the Argonne National Laboratory, Argonne, Ill., USA. The algorithm that was used for identifying CRISPR motifs was p1=a . . . b c . . . d p1 c . . . d p1 c . . . d p1, where a and b were the lower and upper size limit of the repeat and p1 and c and d were the lower and upper size limit of the spacer sequences. The values of a, b, c and d may be varied from about 15 to about 70 bp at increments of about 5 bp. In some preferred embodiments, CRISPR loci are identified using dotplots (e.g., by using the Dotter computer program).

Any suitable method known in the art finds use in analyzing sequence similarity. For example, analysis may be performed using NCBI BLAST with a microbial genomes database and GenBank, as known in the art. In addition, nucleotide sequences, including those provided herein are included in databases (e.g., GenBank or the JGI genome website). As used herein, "upstream" means in the 5' direction and "downstream" means in the 3' direction.

In additional embodiments, the methods of the present invention utilize amplification procedures (See e.g., Mojica et al., [2005], supra; and Pourcel et al., [2005], supra). Amplification of the desired region of DNA may be achieved by any method known in the art, including polymerase chain reaction (PCR). "Amplification" refers to the production of additional copies of a nucleic acid sequence. This is generally carried out using PCR technologies well known in the art. The "polymerase chain reaction" ("PCR") is well-known to those in the art. In the present invention, oligonucleotide primers are designed for use in PCR reactions to amplify all or part of a CRISPR locus.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced (i.e., in the presence of nucleotides and an inducing agent—such as DNA polymerase and at a suitable temperature and pH). In some embodiments, the primer is single stranded for maximum efficiency in amplification, although in other embodiments, the primer is double stranded. In some embodiments, the primer is an oligodeoxyribonucleotide. The primer must be sufficiently long to prime the synthesis of extension products in the presence of the inducing agent. The exact length of the primers depends on many factors, including temperature, source of primer, and the use of the method. PCR primers are typically at least about 10 nucleotides in length, and most typically at least about 20 nucleotides in length. Methods for designing and conducting PCR are well known in the art, and include, but are not limited to methods using paired primers, nested primers, single specific primers, degenerate primers, gene-specific primers, vector-specific primers, partially mismatched primers, etc.

In some preferred embodiments of the present invention, a CRISPR locus or a portion thereof from a parent bacterium and a labelled bacterium are compared using any suitable method known in the art. In some preferred embodiments of the present invention, the CRISPR locus or a portion thereof from the parent bacterium and the labelled bacterium are compared by amplifying the CRISPR locus or a portion thereof. In addition to well-known cycling amplification methods (e.g., PCR, ligase chain reaction, etc.), other methods, including but not limited to isothermal amplification methods find use in the present invention. Well-known isothermal amplification methods that find use in the present invention include, but are not limited to strand displacement amplification (SDA), Q-beta-replicase, nucleic acid-based sequence amplification (NASBA), and self-sustained sequence replication.

In some other preferred embodiments of the present invention, the CRISPR locus or a portion thereof from the parent bacterium and the labelled bacterium are compared by sequencing the of the present invention, the CRISPR locus or a portion thereof from the parent bacterium and the labelled bacterium are compared by amplifying and then sequencing the CRISPR loci or a portion thereof. In some embodiments, one end of the CRISPR loci are compared, while in other embodiments, both the 5' and 3' ends of the loci are compared. In some preferred embodiments, one end (e.g., the 5' end) of the CRISPR loci are compared. In yet other embodiments, at least the last CRISPR repeat at the 3' end of the CRISPR locus and/or at least the last CRISPR spacer (e.g., the last CRISPR spacer core) at the 3' end of the CRISPR locus and/or at least the first CRISPR repeat at the 5' end of the CRISPR locus and/or at least the first CRISPR spacer (e.g., the first CRISPR spacer core) at the 5' end of the CRISPR locus are compared. In some preferred embodiments, at least the first CRISPR repeat at the 5' end of the CRISPR locus and/or at least the first CRISPR spacer (e.g., the first CRISPR spacer core) at the 5' end of the CRISPR locus are compared. In some additional preferred embodiments, at least the last CRISPR spacer (e.g., the last CRISPR spacer core) at the 3' end of the CRISPR locus and/or at least the first CRISPR spacer (e.g., the first CRISPR spacer core) at the 5' end of the CRISPR locus are compared. In some further preferred embodiments, at least the first CRISPR spacer (e.g., the first CRISPR spacer core) at the 5' ends of the CRISPR loci are compared.

In some embodiments, the CRISPR loci comprise DNA, while in other embodiments, the CRISPR loci comprise RNA. In some embodiments, the nucleic acid is of genomic origin, while in other embodiments, it is of synthetic or recombinant origin. In some embodiments, the CRISPR loci are double-stranded, while in other embodiments, they are single-stranded, whether representing the sense or antisense strand or combinations thereof. In some embodiments, CRISPR loci are prepared by use of recombinant DNA techniques (e.g., recombinant DNA), as described herein.

The present invention also provides methods for generating CRISPR variants. These variants are expressed, isolated, cloned, and/or sequenced using any suitable method known in the art. In some particularly preferred embodiments, the CRISPR variants are phage resistant mutant strains that have a modified CRISPR locus with an additional spacer. In some additional embodiments, these variants find use as targets for detection/identification purposes, or for engineering resistance against nucleic acid molecules. In still further embodiments, these variants find use in the development of biocontrol agents.

In the context of the present invention, the CRISPR locus is oriented as described below. The CRISPR leader is a conserved DNA segment of defined size. The orientation of the *S. thermophilus* CRISPR1 locus is established using the following characteristics:

The relative position of CRISPR to the neighbouring cas (CRISPR-associated sequences) genes; CRISPR1 is located downstream of 4 cas genes (genes str0657, str0658, str0659, and str0660 within CNRZ1066 chromosome sequence);

This repeat sequence has the potential to form a hairpin secondary structure, although it is not fully palindromic, and the reverse complementary sequence; (5'-GTTGTACAGTTACTTAAATCTTGAGAGTACAAAAAC-3'; SEQ ID NO:695) is different from the direct sequence (5'-GTTTTTGTACTCTCAAGATTTAAGTAACTGTACAAC-3'; SEQ ID NO:1). Generally the 5' end of the direct sequence is richer in nucleotides G and T than the 5' end of the reverse complementary sequence. Furthermore, as G-T base pairing is better than A-C base pairing, the hairpin structure is generally stronger on the direct strand; and As used herein, the position of the terminal repeat is the end repeat which shows sequence variation at its 3' end is generally the terminal repeat.

The CRISPR leader is a conserved DNA segment of defined size which is located immediately upstream of the first repeat. For example, the leader sequence of *S. thermophilus* CRISPR1 is the DNA segment starting immediately after the stop codon of gene str0660, and ending just before the first repeat. The CRISPR leader is located at the 5' end of the CRISPR locus. The CRISPR leader is located immediately upstream of the first CRISPR repeat of the CRISPR locus.

The CRISPR trailer is a conserved DNA segment of defined size, which is located immediately downstream of the terminal repeat. For example, the trailer sequence of *S. thermophilus* CRISPR1 is the DNA segment starting immediately after the terminal repeat, and ending just before the stop codon of gene str0661 (located on the opposite DNA strand). The CRISPR trailer is located at the 3' end of the CRISPR locus. The CRISPR trailer is located immediately downstream of the terminal repeat.

For example, the CRISPR leader and CRISPR trailer sequences in the CRISPR1 locus of *Streptococcus thermophilus* strain CNRZ1066 are:

```
CRISPR leader:
                                    (SEQ ID NO: 688)
5'-CAAGGACAGTTATTGATTTTATAATCACTATGTGGGTATAAAAACGT
CAAAATTTCATTTGAG-3'

CRISPR trailer:
                                    (SEQ ID NO: 691)
5'-TTGATTCAACATAAAAAGCCAGTTCAATTGAACTTGGCTTT-3'
```

The CRISPR leader corresponds to positions 625038 to 625100, and the CRISPR trailer corresponds to positions 627845 to 627885 in the full genome (CP000024) of *S. thermophilus*.

As used herein, the term "upstream" means in the 5' direction and "downstream" means in the 3' direction. As used herein the term "portion thereof" in the context of a CRISPR locus means at least about 10 nucleotides, about 20 nucleotides, about 24 nucleotides, about 30 nucleotides, about 40 nucleotides, about 44 nucleotides, about 50 nucleotides, about 60 nucleotides, about 70 nucleotides, about 80 nucleotides, about 90 nucleotides, about 98 nucleotides or even about 100 or more nucleotides (e.g., at least about 44-98 nucleotides) of a CRISPR locus. In some preferred embodiments, the term "portion thereof" means at least about 10 nucleotides, about 20 nucleotides, about 24 nucleotides, about 30 nucleotides, about 40 nucleotides, about 44 nucleotides, about 50 nucleotides, about 60 nucleotides, about 70 nucleotides, about 80 nucleotides, about 90 nucleotides, about 98 nucleotides or about 100 or more nucleotides (e.g., at least about 44-98 nucleotides) from one or both ends (i.e., the 5' and/or 3' ends) of a CRISPR locus. In some preferred embodiments, the term "portion thereof" refers to at least about the first 44 nucleotides at the 5' end of a CRISPR locus or about the last 44 nucleotides at the 3' end of a CRISPR locus.

In some further embodiments, the term "portion thereof" in the context of a CRISPR locus means at least the first about 10 nucleotides, about 20 nucleotides, about 24 nucleotides, about 30 nucleotides, about 40 nucleotides, about 44 nucleotides, about 50 nucleotides, about 60 nucleotides, about 70 nucleotides, about 80 nucleotides, about 90 nucleotides, about 98 nucleotides, or about 100 or more nucleotides (e.g., at least about 44-98 nucleotides) downstream from the first nucleotide of the first CRISPR repeat at the 5' end of a CRISPR locus or upstream from the last nucleotide of the last CRISPR repeat at the 3' end of a CRISPR locus. In some preferred embodiments, the term "portion thereof" refers to the at least about the first 44 nucleotides downstream from the first nucleotide of the first CRISPR repeat at the 5' end of a CRISPR locus or at least about 44 nucleotides upstream from the last nucleotide of the last CRISPR repeat at the 3' end of a CRISPR locus.

In some embodiments, the minimum size of the duplicated sequence is about 24 nucleotides and minimum size of the tagging sequence is about 20 nucleotides. Thus, in some preferred embodiments, the term "portion thereof" in the context of a CRISPR locus, means at least 44 nucleotides.

In some embodiments, the maximum size of the duplicated sequence is about 40 nucleotides and the maximum size of the tagging sequence is about 58 nucleotides. Thus, in some embodiments, the term "portion thereof" when used in the context of a CRISPR locus means at least about 98 nucleotides. In some preferred embodiments, the term "portion thereof" in the context of a CRISPR locus means at least about 44-98 nucleotides.

When comparing the CRISPR locus or a portion thereof from the parent bacterium and a labelled bacterium, at least about 10 nucleotides, about 20 nucleotides, about 24 nucleotides, about 30 nucleotides, about 40 nucleotides, about 44 nucleotides, about 50 nucleotides, about 60 nucleotides, about 70 nucleotides, about 80 nucleotides, about 90 nucleotides, about 98 nucleotides, or about 100 nucleotides (e.g., at least about 44-98 nucleotides) of a CRISPR locus are compared. In some preferred embodiments, at least about 10 nucleotides, about 20 nucleotides, about 24 nucleotides, about 30 nucleotides, about 40 nucleotides, about 44 nucleotides, about 50 nucleotides, about 60 nucleotides, about 70 nucleotides, about 80 nucleotides, about 90 nucleotides, about 98 nucleotides, or about 100 or more nucleotides (e.g., at least about 44-98 nucleotides) at one or both ends of a CRISPR locus are compared.

In some preferred embodiments, at least the first about 10 nucleotides, about 20 nucleotides, about 24 nucleotides, about 30 nucleotides, about 40 nucleotides, about 44 nucleotides, about 50 nucleotides, about 60 nucleotides, about 70 nucleotides, about 80 nucleotides, about 90 nucleotides, about 98 nucleotides or about 100 or more nucleotides (e.g., at least about 44-98 nucleotides) at the 5' end of a CRISPR locus or at the 3' end of a CRISPR locus are compared. In some preferred embodiments, at least the first about 44 nucleotides at the 5' end of a CRISPR locus or the last about 44 nucleotides at the 3' end of a CRISPR locus are compared.

In some embodiments, at least the first about 10 nucleotides, about 20 nucleotides, about 24 nucleotides, about 30 nucleotides, about 40 nucleotides, about 44 nucleotides, about 50 nucleotides, about 60 nucleotides, about 70 nucleotides, about 80 nucleotides, about 90 nucleotides, about 98 nucleotides, or about 100 or more nucleotides (e.g., at least about 44-98 nucleotides) downstream from the first nucleotide of the first CRISPR repeat at the 5' end of a CRISPR locus or upstream from the last nucleotide of the last CRISPR repeat at the 3' end of a CRISPR locus are compared. In some preferred embodiments, at least about the first 44 nucleotides downstream from the first nucleotide of the first CRISPR repeat at the 5' end of a CRISPR locus or about at least 44 nucleotides upstream from the last nucleotide of the last CRISPR repeat at the 3' end of a CRISPR locus are compared.

In some embodiments, the minimum size of the duplicated sequence is about 24 nucleotides and minimum size of the tagging sequence is about 20 nucleotides. In some preferred embodiments, at least 44 nucleotides are compared. In some alternative embodiments, the maximum size of the duplicated sequence is about 40 nucleotides and the maximum size of the tagging sequence is about 58 nucleotides. In some preferred embodiments, at least 98 nucleotides are compared. In some alternative preferred embodiments, at least about 44-98 nucleotides are compared.

As used herein, the term “CRISPR repeat” has the conventional meaning as used in the art (i.e., multiple short direct repeats, which show no or very little sequence variation within a given CRISPR locus). As used herein, in context, “CRISPR repeat” is synonymous with the term “CRISPR.”

A CRISPR locus comprises one or more CRISPR repeats than there are CRISPR spacers. Thus, the CRISPR repeat corresponds to the repeated sequence within a CRISPR locus. For example, except for the terminal repeat, the typical repeat sequence of the *S. thermophilus* CRISPR1 sequence is:

```
                                    (SEQ ID NO: 1)
5'-GTTTTTGTACTCTCAAGATTTAAGTAACTGTACAAC-3'
```

Point variations of this repeat sequence have been observed but they are very rare. Compared to this typical repeat sequence, the terminal repeat sequence always shows the same variation at its 3' end. Point variations of this terminal repeat sequence have also been observed but they are rare. CRISPR repeats may naturally occur in the parent bacterium. Genbank accession numbers of CRISPR1 sequences include: CP000023, CP000024, DQ072985, DQ072986, DQ072987, DQ072988, DQ072989, DQ072990, DQ072991, DQ072992, DQ072993, DQ072994, DQ072995, DQ072996, DQ072997, DQ072998, DQ072999, DQ073000, DQ073001, DQ073002, DQ073003, DQ073004, DQ073005, DQ073006, DQ073007, DQ073008, and AAGS01000003.

As described in further detail herein, a duplicated sequence is derived, derivable, obtained or obtainable from a parent bacterium. In some preferred embodiments, the sequence comprises the genomic DNA of a parent bacterium. In some particularly preferred embodiments, the duplicated CRISPR repeat (e.g., in the same CRISPR locus) is integrated iteratively, sequentially, simultaneously or substantially simultaneously along with the tagging sequence into the parent bacterium to give rise to a labelled bacterium.

The number of nucleotides in a repeat is generally about 20 to about 40 base pairs (e.g., 36 base pairs), but in other embodiments is about 20 to about 39 base pairs, about 20 to about 37 base pairs, about 20 to about 35 base pairs, about 20 to about 33 base pairs, about 20 to about 30 base pairs, about 21 to about 40 base pairs, about 21 to about 39 base pairs, about 21 to about 37 base pairs, about 23 to about 40 base pairs, about 23 to about 39 base pairs, about 23 to about 37 base pairs, about 25 to about 40 base pairs, about 25 to about 39 base pairs, about 25 to about 37 base pairs, about 25 to about 35 base pairs, or about 28 or 29 base pairs.

The number of nucleotides in a repeat is generally about 20 to about 40 base pairs, but may be about 20 to about 39 base pairs, about 20 to about 37 base pairs, about 20 to about 35 base pairs, about 20 to about 33 base pairs, about 20 to about 30 base pairs, about 21 to about 40 base pairs, about 21 to about 39 base pairs, about 21 to about 37 base pairs, about 23 to about 40 base pairs, about 23 to about 39 base pairs, about 23 to about 37 base pairs, about 25 to about 40 base pairs, about 25 to about 39 base pairs, about 25 to about 37 base pairs, about 25 to about 35 base pairs, or about 28 or 29 base pairs. The number of repeats may range from about 1 to about 140, from about 1 to about 100, from about 2 to about 100, from about 5 to about 100, from about 10 to about 100, from about 15 to about 100, from about 20 to about 100, from about 25 to about 100, from about 30 to about 100, from about 35 to about 100, from about 40 to about 100, from about 45 to about 100, from about 50 to about 100, from about 1 to about 135, from about 1 to about 130, from about 1 to about 125, from about 1 to about 120, from about 1 to about 115, from about 1 to about 110, from about 1 to about 105, from about 1 to about 100, from about 1 to about 95, from about 1 to about 90, from about 1 to about 80, from about 1 to about 70, from about 1 to about 60, from about 1 to about 50, from about 10 to about 140, from about 10 to about 130, from about 10 to about 120, from about 10 to about 110, from about 10 to about 95, from about 10 to about 90, from about 20 to about 80, from about 30 to about 70, from about 30 to about 60, from about 30 to about 50, from about 30 to about 40, or about 32.

In some other embodiments, the number of nucleotides in a repeat is about 20 to about 39 base pairs, about 20 to about 37 base pairs, about 20 to about 35 base pairs, about 20 to about 33 base pairs, about 20 to about 30 base pairs, about 21 to about 40 base pairs, about 21 to about 39 base pairs, about 21 to about 37 base pairs, about 23 to about 40 base pairs, about 23 to about 39 base pairs, about 23 to about 37 base pairs, about 25 to about 40 base pairs, about 25 to about 39 base pairs, about 25 to about 37 base pairs, about 25 to about 35 base pairs, or about 28 or 29 base pairs.

In some embodiments, the number of repeats ranges from about 1 to about 144, from about 1 to about 100, from about 2 to about 100, from about 5 to about 100, from about 10 to about 100, from about 15 to about 100, from about 20 to about 100, from about 25 to about 100, from about 30 to about 100, from about 35 to about 100, from about 40 to about 100, from about 45 to about 100, from about 50 to about 100, from about 1 to about 135, from about 1 to about 130, from about 1 to about 125, from about 1 to about 120, from about 1 to about 115, from about 1 to about 110, from about 1 to about 105, from about 1 to about 100, from about 1 to about 95, from about 1 to about 90, from about 1 to about 80, from about 1 to about 70, from about 1 to about 60, from about 1 to about 50, from about 10 to about 140, from about 10 to about 130, from about 10 to about 120, from about 10 to about 110, from about 10 to about 95, from about 10 to about 90, from about 20 to about 80, from about 30 to about 70, from about 30 to about 60, from about 30 to about 50, from about 30 to about 40, or about 30, 31, 32, 33, 34 or 35 repeats.

In some embodiments, the number of repeats ranges from about 2 to about 140, from about 2 to about 100, from about 2 to about 100, from about 5 to about 100, from about 10 to about 100, from about 15 to about 100, from about 20 to about 100, from about 25 to about 100, from about 30 to about 100, from about 35 to about 100, from about 40 to about 100, from about 45 to about 100, from about 50 to about 100.

In some further embodiments, the number of repeats ranges from about 2 to about 135, from about 2 to about 130, from about 2 to about 125, from about 2 to about 120, from about 2 to about 115, from about 2 to about 110, from about 2 to about 105, from about 2 to about 100, from about 2 to about 95, from about 2 to about 90, from about 2 to about 80, from about 2 to about 70, from about 2 to about 60, from about 2 to about 50, from about 2 to about 40, from about 2 to about 30, from about 2 to about 20, from about 2 to about 10, from about 2 to about 9, from about 2 to about 8, from about 2 to about 7, from about 2 to about 6, from about 2 to about 5, from about 2 to about 4, or from about 2 to about 3.

In some embodiments, the CRISPR repeats comprise DNA, while in other embodiments, the CRISPR repeats comprise RNA. In some embodiments, the nucleic acid is of genomic origin, while in other embodiments, it is of synthetic or recombinant origin. In some embodiments, the CRISPR repeat genes are double-stranded or single-stranded whether representing the sense or antisense strand or combinations thereof. In some embodiments, CRISPR repeat genes are prepared by use of recombinant DNA techniques (e.g., recombinant DNA), as described herein.

In some embodiments, one or more of the CRISPR repeats are used to engineer a cell (e.g., a recipient cell). In some preferred embodiments, one or more, preferably, two or more CRISPR repeats are used to engineer a cell (e.g., a recipient cell), that in combination with one or more cas genes or proteins and one or more CRISPR spacers modulates the resistance of a cell against a target nucleic acid or a transcription product thereof. For example, in some embodiments, the CRISPR repeat(s) are inserted into the DNA of a cell (e.g., plasmid and/or genomic DNA of a recipient cell), using any suitable method known in the art. In additional embodiments, the CRISPR repeat(s) find use as a template upon which to modify (e.g., mutate) the DNA of a cell (e.g., plasmid and/or genomic DNA of a recipient cell), such that CRISPR repeat(s) are created or engineered in the DNA of the cell. In additional embodiments, the CRISPR repeat(s) are present in at least one construct, at least one plasmid, and/or at least one vector, etc. In further embodiments, the CRISPR repeats are introduced into the cell using any suitable method known in the art.

In additional embodiments, the present invention provides methods for identifying a CRISPR repeat for use in modulating the resistance of a cell against a target nucleic acid or transcription product thereof comprising the steps of: (i) preparing a cell comprising at least one CRISPR spacer and at least one cas gene; (ii) engineering the cell such that it contains a CRISPR repeat; and (iii) determining if the cell modulates resistance against the target nucleic acid or transcription product thereof, wherein modulation of the resistance of the cell against the target nucleic acid or transcription product thereof is indicative that the CRISPR repeat can be used to modulate resistance.

In some further embodiments, one or more cas genes or proteins are used together with or in combination with one or more, preferably, two or more CRISPR repeats and optionally one or more CRISPR spacers. In some particularly preferred embodiments, the cas gene(s) or protein(s) and CRISPR repeat(s) form a functional combination as described below. In some embodiments, the CRISPR repeats comprise any of the nucleotides set forth in SEQ ID NOS: 1-22. SEQ ID NOS:1-12 are from *S. thermophilus*, while SEQ ID NOS:13-16 are from *Streptococcus agalactiae*, SEQ NO:17 is from *S. mutans*, and SEQ ID NOS:18-22 are from *S. pyogenes*.

```
                                   (SEQ ID NO: 1)
GTTTTTGTACTCTCAAGATTTAAGTAACTGTACAAC

                                   (SEQ ID NO: 2)
GTTTTTGTATTCTCAAGATTTAAGTAACTGTACAGT

                                   (SEQ ID NO: 3)
GTTTTTGTACTCTCAAGATTTAAGTAACTGTACAGT

                                   (SEQ ID NO: 4)
GTTTTTGTACTCTCAAGATTTAAGTAACCGTACAAC

                                   (SEQ ID NO: 5)
GTTTTTGTACTCTCAAGATTTAAGTAACTGTGCAAC
```

-continued

```
                                   (SEQ ID NO: 6)
GTTTTTGTACTCTCAAGATTTAAGTAGCTGTACAGT

                                   (SEQ ID NO: 7)
GTTTTTGTACTCTCAAGATATAAGTAACTGTACAAC

                                   (SEQ ID NO: 8)
GTTTTTGTACTCTCAAGATCTAAGTAACTGTACAAC

                                   (SEQ ID NO: 9)
GTTTTTGTACTCTCAAGATGTAAGTAACTGTACAAC

                                  (SEQ ID NO: 10)
GTCTTTGTACTCTCAAGATTTAAGTAACTGTACAAC

                                  (SEQ ID NO: 11)
AAAAAAGTCCCCTCTCGAGGTAATTAGGTTTATATC

                                  (SEQ ID NO: 12)
GTTTCCGTCCCCTCTCGAGGTAATTAGGTTTATATC

                                  (SEQ ID NO: 13)
GTTTTAGAGCTGTGTTGTTTCGAATGGTTCCAAAAC

                                  (SEQ ID NO: 14)
GTTTTAAAGCTGTGCTGTTATTATGCTAGGGCACCA

                                  (SEQ ID NO: 15)
GTTTTAGAGCTGTGCTGTTTCGAATGGTTCCAAAAC

                                  (SEQ ID NO: 16)
GTTTTAGAGCTGTGCTGTTATTATGCTAGGACATCA

                                  (SEQ ID NO: 17)
GTTTTAGAGCCATGTTAGTTACTGATTTACTAAAAT

                                    SEQ ID NO: 18
GTTTTAGAGCTATGCTGTTTTGAATGGTCCCAAAAC

                                  (SEQ ID NO: 19)
GTTTTAGAGCTATGCTGTTTTGAATGGTCTCCATTC

                                  (SEQ ID NO: 20)
CTTTCAATCCACTCACCCATGAAGGGTGAGACG

                                  (SEQ ID NO: 21)
ATTTCAATCCACTCACCCATGAAGGGTGAGACT

                                  (SEQ ID NO: 22)
ATTTCAATCCACTCACCCATGAAGGGTGAGACC
```

CRISPR Spacer

As used herein, "CRISPR spacer" encompasses non-repetitive spacer sequences that are found between multiple short direct repeats (i.e., CRISPR repeats) of CRISPR loci. In some embodiments of the present invention, a "CRISPR spacer" refers to the nucleic acid segment that is flanked by two CRISPR repeats. It has been found that CRISPR spacer sequences often have significant similarities to a variety of mobile DNA molecules (e.g., bacteriophages and plasmids). In some preferred embodiments, CRISPR spacers are located in between two identical CRISPR repeats. In some embodiments, CRISPR spacers are identified by sequence analysis at the DNA stretches located in between two CRISPR repeats. In some preferred embodiments, CRISPR spacer is naturally present in between two identical multiple short direct repeats that are palindromic.

Interestingly, cells carrying these CRISPR spacers are unable to be infected by DNA molecules containing sequences homologous to the spacers (Mojica et al. 2005). In some preferred embodiments, the CRISPR spacer is homologous to the target nucleic acid or a transcription product thereof or an identified sequence. Although homology can also be considered in terms of similarity, in the context of the present invention it is preferred to express homology in terms of sequence identity. A homologous sequence is taken to include a CRISPR spacer, which may be at least about 70, about 75, about 80, about 85, or about 90% identical, or at least about 91, about 92, about 93, about 94, about 95, about 96, about 97, about 98, or about 99% identical to the target nucleic acid sequence or a transcription product thereof or an identified sequence. In some preferred embodiments, the CRISPR spacer is about 100% identical to the target nucleic acid sequence. It is also noted that the number of CRISPR spacers at a given CRISPR loci or locus can vary between species. In addition, the number of spacers ranges from about 1 to about 140, from about 1 to about 100, from about 2 to about 100, from about 5 to about 100, from about 10 to about 100, from about 15 to about 100, from about 20 to about 100, from about 25 to about 100, from about 30 to about 100, from about 35 to about 100, from about 40 to about 100, from about 45 to about 100, or from about 50 to about 100. In some preferred embodiments, the number of spacers ranges from about 1 to about 135, from about 1 to about 130, from about 1 to about 125, from about 1 to about 120, from about 1 to about 115, from about 1 to about 110, from about 1 to about 105, from about 1 to about 100, from about 1 to about 95, from about 1 to about 90, from about 1 to about 80, from about 1 to about 70, from about 1 to about 60, from about 1 to about 50, from about 1 to about 40, from about 1 to about 30, from about 1 to about 20, from about 1 to about 10, from about 1 to about 9, from about 1 to about 8, from about 1 to about 7, from about 1 to about 6, from about 1 to about 5, from about 1 to about 4, from about 1 to about 3, or from about 1 to about 2. In some preferred embodiments, CRISPR spacers are identified by sequence analysis as the DNA stretches located in between two repeats.

As described herein, the present invention provides methods and compositions that facilitate the use of one or more cas genes or proteins in combination with one or more, preferably, two or more CRISPR repeats suitable to confer specificity of immunity to at least one CRISPR spacer in a recipient cell. In some preferred embodiments, at least one cas genes or proteins and at least one CRISPR repeat are used in functional combinations to confer specificity of immunity to at least one CRISPR spacer in a cell.

As used herein, the term "specificity of immunity" means that immunity is conferred against a specific nucleic acid sequence or transcription product thereof, using a specific CRISPR spacer or pseudo-CRISPR spacer sequence. As indicated herein, a given CRISPR spacer does not confer resistance against any nucleic acid sequence or transcription product thereof but only to those sequences against which the CRISPR spacer or pseudo-CRISPR spacer is homologous (e.g., those that are about 100% identical).

In some embodiments, the CRISPR spacer(s) are obtained from a donor organism that is different from the recipient cell. In some preferred embodiments, the donor and recipient cells are different bacterial strains, species, and/or genera. In some preferred embodiments, at least one cas genes or proteins and/or at least one CRISPR repeats are obtained from a different organism than the recipient organism. In some preferred embodiments, at least two CRISPR repeats are transferred. In some additional preferred embodiments, the CRISPR spacers are obtained from an organism that is heterologous to the recipient or a further donor cell from which the at least one cas genes and/or proteins, and/or at least one CRISPR repeat are obtained. In some alternative preferred embodiments, the CRISPR spacers are obtained from an organism that is homologous to the recipient or a further donor cell from which the at least one cas genes and/or proteins, and/or at least one CRISPR repeat are obtained. In some preferred embodiments, the CRISPR spacer(s) is/are designed and produced using recombinant methods known in the art. Indeed, it is intended that the CRISPR spacers be produced using any suitable method known in the art.

In some embodiments, the CRISPR spacers are heterologous to the recipient cell from which at least one cas genes or proteins and/or the at least one, and in some embodiments, preferably, two or more, CRISPR repeats are obtained. In some alternative embodiments, the CRISPR spacers are homologous to the recipient cell from which at least one cas genes or proteins and/or the at least one, and in some embodiments, preferably, two or more, CRISPR repeats are obtained. Indeed, it is intended that any of the elements utilized in the methods be heterologous or homologous. In some embodiments, where multiple elements are used (e.g., any combination of CRISPR spacer(s), CRISPR repeat(s), cas gene(s), and Cas protein(s)), some elements are homologous with each other and some elements are heterologous to each other (e.g., in some embodiments, the CRISPR spacer(s) and cas genes are homologous, but the CRISPR repeat(s) is/are heterologous). Thus, in some embodiments, the CRISPR spacer is not naturally associated with the CRISPR repeat and/or cas genes and/or functional CRISPR repeat-cas gene combination. Indeed, it is intended that any combination of heterologous and homologous elements find use in the present invention. In yet additional embodiments, the donor and recipient cells are heterologous, while in further embodiments, they are homologous. It is also intended that the elements contained within the donor and recipient cells be homologous and/or heterologous. The elements (e.g., CRISPR spacers) are introduced into plasmid and/or genomic DNA of the recipient cell utilizing any suitable method known in the art.

In some preferred embodiments, at least one CRISPR spacer is used to engineer a cell (e.g., a recipient cell). In some additional embodiments, one or more CRISPR spacers are used in combination with one or more cas genes or proteins and/or one or more, preferably, two or more CRISPR repeats (in some preferred embodiments, one or more functional combinations thereof are used) to modulate the resistance of a cell against a target nucleic acid or a transcription product thereof, to produce an engineered cell. In some further embodiments, CRISPR spacers are used as a template upon which to modify (e.g., mutate) the plasmid and/or genomic DNA of a cell (e.g., a recipient cell), such that CRISPR spacers are created in the DNA of the cell. In some embodiments, the CRISPR spacer(s) is/are cloned into at least one construct, plasmid or other vector, with which the recipient cell is then transformed, using any suitable method known in the art.

In some further embodiments, the present invention provides methods for identifying a CRISPR spacer for use in modulating the resistance of a cell against a target nucleic acid or a transcription product thereof, comprising the steps of: preparing a cell comprising at least two CRISPR repeats and at least one cas gene or protein; identifying at least one CRISPR spacer in an organism (e.g., a donor organism); modifying the sequence of the CRISPR spacer of the cell such that it has homology to the CRISPR spacer of the donor organism comprising the target nucleic acid; and determining whether the cell modulates resistance against the target nucleic acid, wherein modulation of the resistance of the cell against the target nucleic acid or transcription product thereof is indicative that the CRISPR spacer modulates the resistance of the cell against the target nucleic acid.

In some preferred embodiments, the CRISPR spacers comprise or consist of the nucleotide sequence set forth any one or more of in any of SEQ ID NO:23-460 and/or SEQ ID NOS:522-665. SEQ ID NOS:23-339, 359-408, 522-665 are from *S. thermophilus*, while SEQ ID NOS:340-358 are from *S. vestibularis*, SEQ ID NOS:409-446 are from *S. agalactiae*, SEQ ID NOS:447-452 are from *S. mutans*, and SEQ ID NOS:453-460 are from *S. pyogenes*.

(SEQ ID NO: 23)
AGAACGTATTCCAAAACCTCTTTACGATTA (SEQ ID NO: 24)
TTAACTGTTATCAAAATGATAAGATAGTCT (SEQ ID NO: 25)
CGTTGATGTTTATTCAAGTAAAATAATTAA (SEQ ID NO: 26)
TCCTTTCACGGGTAGCACACTAACATACAC (SEQ ID NO: 27)
GTTGGCAATGCAAACAACCTTTATGAACCG (SEQ ID NO: 28)
TTTATTTCCTTGCGATAACGTTCCACCTTT (SEQ ID NO: 29)
AGATTATAAGGAACACAACCAACTATATAG (SEQ ID NO: 30)
ACGACATCAAGCTGATTGTCTTCTACATAA (SEQ ID NO: 31)
TTTGGAATACTGAATGTTTTACTGAAAATC (SEQ ID NO: 32)
ACACCACTATCTTTTCCTCCTGAAAATGAA (SEQ ID NO: 33)
GTAATTCCACGAAATTATCAACCTTATGCA (SEQ ID NO: 34)
TTGGAGGATTGCCCCATATTCCCAAGAGT (SEQ ID NO: 35)
GAGAGGCGTTAAATATAGAAATGCAAGATT (SEQ ID NO: 36)
TTTTAACGTCATCAGTCCACCGCCTTAAAT (SEQ ID NO: 37)
CACCTCTTTCGATGGAAAGGTATCCTTCTA (SEQ ID NO: 38)
GACCAAAGTTTGATTATAGAGCTATACACC (SEQ ID NO: 39
ACCATCATTCTTACCATTACAACTGTAATG (SEQ ID NO: 40)
ATACGAATTCGGTTCGCACAATTACAATTC (SEQ ID NO: 41)
TATCAACGCAATCATTACAACAACTTCAAACA (SEQ ID NO: 42)
ATCTACGTGTCAATACATATCACAAAACAG (SEQ ID NO: 43)
ATTTTTAGAAATTTCTGATATAATAATGA (SEQ ID NO: 44)
TTGTTGGAACAAGGACGACTTGGTAAACTA (SEQ ID NO: 45)
CATATTAAGCTGACTGGGCCTAATGCTTTT (SEQ ID NO: 46)
TTCATAGCATACCGTAGTTGTAAAATCTAT

-continued (SEQ ID NO: 47)
AACATTTAGGGAATGAAATTGATAAGACTG (SEQ ID NO: 48)
AACATGAGAAACTGTAGAAAACAAGCAATA (SEQ ID NO: 49)
TGGTGAAGATGGCAGTCATAAATGGCACATT (SEQ ID NO: 50)
AAGGGTTGAAAAATGTTGGTATATCAAACG (SEQ ID NO: 51)
TTCTGGTAGTGGATTTAGTCAAACAGATGT (SEQ ID NO: 52)
TCCATAGAGCGTCTTAAACAAAGAATAGTC (SEQ ID NO: 53)
TTATGATTGAATGACATGGTTGTATAAGTA (SEQ ID NO: 54)
TTTCTTTAGGAATACCAGGGAGTTCAGCTT (SEQ ID NO: 55)
TGGCAGAGATTACACAGCAACGGAAACAGC (SEQ ID NO: 56)
GGGTATCATTGTATCTAGTGATGGACCTGA (SEQ ID NO: 57)
ATTTGAAAAAATGCACAACAGCGTTTGATAG (SEQ ID NO: 58)
GAGCTACCAGCTACCCCGTATGTCAGAGAG (SEQ ID NO: 59)
CGTTCCTTTTTTCAAGGTAATCTTTGAAAG (SEQ ID NO: 60)
AAGTCCGTAAGCACCAGTTCCAATCGTCAT (SEQ ID NO: 61)
TTGAATACCAATGCCAGCTTCTTTTAAGGC (SEQ ID NO: 62)
AACCTCATACATGGGGAAAATTGGTAAGTA (SEQ ID NO: 63)
TAACTTCATTAGTGTAGTTGTAATTAGCAT (SEQ ID NO: 64)
TTAGCTACCCAAATATCTTCTGTTTTCCAA (SEQ ID NO: 65)
GAGTTTTCAATATTGGCACAGGAGACAATT (SEQ ID NO: 66)
TGATACTATTTTAGTCAGATATGAAATATC (SEQ ID NO: 67)
TCATCAATGTTTAAAGCCCAACAATACATGA (SEQ ID NO: 68)
TAGATTTAATCAGTAATGAGTTAGGCATAA (SEQ ID NO: 69)
AGGAAAATAGCATGAGCGTACAACAATCTA (SEQ ID NO: 70)
TGTCTATCACGCTTCCTAAGTGCATGAAAA (SEQ ID NO: 71)
ATGTCACCAATCACTAAAGAACCTACGCTG (SEQ ID NO: 72)
AACATCTTCCTCTCCGATTGCAAATAGTGC (SEQ ID NO: 73)
CATATTTGGTGCCCGTTCGATAAAGAGTA -continued (SEQ ID NO: 74)
CATTAAATCGCTTGAAGCAGACATTGAAGC (SEQ ID NO: 75)
GACTTATCTTGGAAGGTAGTGAAGGCACTT (SEQ ID NO: 76)
TCCTTGCCATCTGCACTGTAAGCCCAAGCA (SEQ ID NO: 77)
TAGTACGCATAATCAATTCATCAAGCTTGA (SEQ ID NO: 78)
GTAGTGACCCAAAATTCTATGACCTTGAAA (SEQ ID NO: 79)
AGATTGTGGTGCTTACGGAAAATTCCTTGT (SEQ ID NO: 80)
TGGCAAGAAGTGTAAGAGATGCAATGGATA (SEQ ID NO: 81)
TTTATTATCATTATTCTTCTTCCCAAGCGT (SEQ ID NO: 82)
TTTTATAGAATTTGGTGGTGAACTTTTTCA (SEQ ID NO: 83)
AATGGGTCACAGATTGCCATAATAAGGAG (SEQ ID NO: 84)
CCGAGGTCACTTTAGAACCCACAAAATAAG (SEQ ID NO: 85)
ATGAGAGAACACAGTATAGACCCTGATACA (SEQ ID NO: 86)
CAGTATTAATGAGGTTTGGGTGGTCATTCC (SEQ ID NO: 87)
CCATACTCTCTATCAGTTCATTTAATTCTTC (SEQ ID NO: 88)
TAATATGTCGCTCTACTGATTCCAAAACGG (SEQ ID NO: 89)
ATGAATTACATTCATGATTTTATCGAGTTT (SEQ ID NO: 90)
CGTGCCATTGTTTCGGTCGGACGTGGGCA (SEQ ID NO: 91)
CTTTCTAAGTTGAATTAAATTCAAGTTTTG (SEQ ID NO: 92)
TCGCTACTATGGTTAACGATGAGGAACTCT (SEQ ID NO: 93)
AGCAACTTTAAAACTAAAAGAGCTACTTGA (SEQ ID NO: 94)
AAAACCCTACACAGTGTGTGAGATGTGTCA (SEQ ID NO: 95)
AATGGGTCACAGATTGCCATAATAAGGAGG (SEQ ID NO: 96)
TTTTTTAAAATCCGTCATGCTATACTATAT (SEQ ID NO: 97)
AATTCAAACTTTCTCCAATAATACCCTCCA (SEQ ID NO: 98)
CATGCTTTCAGTTAATAAGACGTGGGACTA (SEQ ID NO: 99)
TGGAAGGGGTGTCTAGTGAAGAAATTGTCG (SEQ ID NO: 100)
CTCGAAGCGCTTCATTGCCCTATTCCTTTC -continued (SEQ ID NO: 101)
ATGTCTAAGGTATCCACTCGTGAAATCAT (SEQ ID NO: 102)
ATATTAATGGAAATTTCATTCAAACGCAGT (SEQ ID NO: 103)
TAGAGAGTTTATATCCTGATGGAATCGATG (SEQ ID NO: 104)
TGGCGAATTAGAGAGCCAATGGCAAGCAAG (SEQ ID NO: 105)
AGAAGACCAATAAACTTGAGAAAAAGCAAG (SEQ ID NO: 106)
AAATGGTCGTTTAATTGTTAATGTCAAAGC (SEQ ID NO: 107)
CAATTGATTCTAAAATGCTTGGTACACGTA (SEQ ID NO: 108)
TCTTCGTGTTATCACAGCTTCTACACGTTG (SEQ ID NO: 109)
GAAATCTCATTGAAACCAACTTCAAGACCA (SEQ ID NO: 110)
TGCTTGGTAGTTGATGCACTGCATTAGTAA (SEQ ID NO: 111)
AATGTACCGGAATAGCGTTACATTGCACAT (SEQ ID NO: 112)
TTCATAAATTCTCACTTTTCCTTGCTATTC (SEQ ID NO: 113)
TGTCGAAAAAATTACCTAGTCACGACAGAC (SEQ ID NO: 114)
CAACAATTACTTATGCATTAGGAACATCTG (SEQ ID NO: 115)
AATTCGTGAAAAACAATAAAAACAAAAAAA (SEQ ID NO: 116)
TAACATTTCTGTCCATTTCTTCCTTGATGC (SEQ ID NO: 117)
CAAGGCAACTCAACCAACCAAATTGACC (SEQ ID NO: 118)
CTAAAATCGTAAATGGTAAGTTGCACGATG (SEQ ID NO: 119)
AACGTAAGGAGTTTTTTTATTTCTTTGTTA (SEQ ID NO: 120)
GTGGAAAATTTCACACCCTACATATATCAA (SEQ ID NO: 121)
CCTCTGCTAATGACTTAAACGGCTCGTTTT (SEQ ID NO: 122)
AAAATCAAAGTTTTGGGTTTGTCTACGTTG (SEQ ID NO: 123)
ATATGTACATACCTAAAGAAAACACGGGCA (SEQ ID NO: 124)
CGTTGTCAAAATATGTGATTACTTTGTATT (SEQ ID NO: 125)
CCATAGCTGTAATGTTGTTTGTGACTGCTT (SEQ ID NO: 126)
CGCTAAGTTTGGCTTTAAGTATAACAAGCT (SEQ ID NO: 127)
AAAGTACGCTTCAAGGCACGTTGAAGACAT -continued (SEQ ID NO: 128)
CTTTTTAACGTGTTAGCGTCTTTAGCTTTG (SEQ ID NO: 129)
TTGGCTTCGTGAATAATTTTTAAAACGCAT (SEQ ID NO: 130)
TGTTGAATCAATACGCTGAAACACACTCCC (SEQ ID NO: 131)
CGTTATCAGTTGAAAGTTTCAACTCGTAAG (SEQ ID NO: 132)
TAAACTAGTTGGCATCTATGCTCCAGGAAG (SEQ ID NO: 133)
TAGACCACCATAGCCGAGTTGTCTTTTTCG (SEQ ID NO: 134)
ACATCCCACTTTCTGGGTTTTTTAGCCATG (SEQ ID NO: 135)
AGTATGGCTATTGTCCTGATACTCATCCAC (SEQ ID NO: 136)
CGCTCTTGACGTGGCTGGTGACATCTACGC (SEQ ID NO: 137)
GAGTACATGGAGTTTCTGCTAGATACACTA (SEQ ID NO: 138)
TAAGTTATGAAATATAAAGTTATTGTCTA (SEQ ID NO: 139)
AACGTTATGACATTTAGGAGCTTCCAAATT (SEQ ID NO: 140)
AACACAGCAAGACAAAAGGATGACACTTT (SEQ ID NO: 141)
CAACCATAACTTACGCATCAGGTACATCTG (SEQ ID NO: 142)
ACACGCGCTTACCTCGTATATCAAATTCA (SEQ ID NO: 143)
TGCCCGCAAACTAGCGATACACAACAGCAT (SEQ ID NO: 144)
CTCAAGCTCTTCATCTGTGATAGGTGTTTTG (SEQ ID NO: 145)
ATCACTCTTTGATAGTATCTCAAACGCTGG (SEQ ID NO: 146)
GAAACAGTCAGACCAGCTAATTCGCCAATT (SEQ ID NO: 147)
ATATTTCGAAAGATACAAGGACACTTACAC (SEQ ID NO: 148)
GCGGATGAAACACAACTTCAATTGTATTCA (SEQ ID NO: 149)
TAATGCTACATCTCAAAGGATGATCCCAGA (SEQ ID NO: 150)
ACGTCTGTCTAACTGGAAAGTACCTGCTAAT (SEQ ID NO: 151)
CTGTTCTCTAATCGAGAGGCGCGTGATTGA (SEQ ID NO: 152)
AAACCTCACTAGTCACTTAGTGCGGTTAGG (SEQ ID NO: 153)
TATTAAGTTTAGTCCCAGGTTTCTTATCGT (SEQ ID NO: 154)
AAACCAATAAACATACCGATTGCTGCCAAT -continued (SEQ ID NO: 155)
GCAAACGTTAGCCCAGGAAAGCATCATGAA (SEQ ID NO: 156)
AAGAGCAAAAAATAACTCTAGCTCTCGTCC (SEQ ID NO: 157)
AAGAAACCTCTAAGTTGAGCATTTAATGAT (SEQ ID NO: 158)
ATATAGTTTTAAACTTTCTTGACCTTCTG (SEQ ID NO: 159)
ACGTTGATGAATATTGTTGATAAACTTTA (SEQ ID NO: 160)
CAAGAAGTGAACAAAGTACACGCTGGAAGT (SEQ ID NO: 161)
GACAGCAAGATACACGTAGTTGATGAATTG (SEQ ID NO: 162)
TAAGAAATCAACGCAGATTTTTAGCCAACA (SEQ ID NO: 163)
TAACCCAATAATTACAGTGAAGCACAATAG (SEQ ID NO: 164)
CAGGCGTAAGGTATGCTAATTATAACGAT (SEQ ID NO: 165)
GCTATCGAACTAATAGCTTAGAGGAACTCA (SEQ ID NO: 166)
GTGGAATATTAAGCCCGAATTGTTGCAGCA (SEQ ID NO: 167)
TATTGCAATATTTGCGTTTGGGAAACCTTC (SEQ ID NO: 168)
CGTCTGTCTAACTGGAAAGTACCGGCTAAT (SEQ ID NO: 169)
AAAGAGATGTACCCATCCATTCTAACAGGT (SEQ ID NO: 170)
GGGGAGTTGATTTCTTACATCAAAACAATG (SEQ ID NO: 171)
CATCAAAGTTGAAAAGGACTACAACAGCCC (SEQ ID NO: 172)
CTTAAATTTAGAGCGTGGGATCTTGAATAT (SEQ ID NO: 173)
ATATACCGATGGCACATCTGAAACTGGCTG (SEQ ID NO: 174)
TAACTCATATGTATCTTGACCAACTATTTT (SEQ ID NO: 175)
AAATAGCACCTCTAAGCGTTAATGGTATTC (SEQ ID NO: 176)
AATATCTACAGGTCACTACAAAGCTACGCT (SEQ ID NO: 177)
GTTGGGGTGTGTTTGTAACGGCGTATGCTA (SEQ ID NO: 178)
TCAATCAGGTGACGGTGATGCTTATATTAA (SEQ ID NO: 179)
CATACATGATAGTTTGTCAACACTTTTGAT (SEQ ID NO: 180)
TCAGCATTTGGTTTACATGACCCACGTCTG (SEQ ID NO: 181)
CAATCAACAGGTTTGACTGATTATAACGGT -continued (SEQ ID NO: 182)
TAGCTACACATGAATTTTATTACAATGGTG (SEQ ID NO: 183)
CTTACGTTTGAAAAGAATATCAAATCAATG (SEQ ID NO: 184)
TTAAAAAAGGGCCTTTCTCTAAATCAAGTA (SEQ ID NO: 185)
TGCTGAACGTATCTGTCCACTGTGTGGCCA (SEQ ID NO: 186)
CCGTTCTTCAAACGTTAAATTCCAAGGTGT (SEQ ID NO: 187)
GCTGCGATTATGACAATGCTGTCTGTAAGG (SEQ ID NO: 188)
GAAGAATTTATTAATAAAGATGGTTCTGCT (SEQ ID NO: 189)
AGGCAGAAAAGAAGTATTTTGGTAAGTATG (SEQ ID NO: 190)
AAATGGTTTATCGACAAGAAAATGAAGCT (SEQ ID NO: 191)
CCAAATTTGCATTATACAAAACGCTCCTTC (SEQ ID NO: 192)
ATCCTAACTGCTTTGCTAACTACATCATGG (SEQ ID NO: 193)
TAACAAGATAAGATTAGCGTCTTCAACAT (SEQ ID NO: 194)
AAAAGCCTATGTTTGCCCACTTTGTGGAAG (SEQ ID NO: 195)
TGTCACTTTCTCTTTCTGGGTTGTGCCAAT (SEQ ID NO: 196)
CATACTTTTCCATCTGTTTGTTGTTTGAAAA (SEQ ID NO: 197)
TGAGAGTGTCTGATGGATTTATTGGCAGCC (SEQ ID NO: 198)
GGGGTTATTTTCCATTTTACCGTCTATCTA (SEQ ID NO: 199)
TATCACGCCCATTTTCATTTCGCCATCTGT (SEQ ID NO: 200)
AACATTTTAATATAATTTCTAAATCTATTG (SEQ ID NO: 201)
TACAAAATTCCTTCAAACGCTATTTATTGA (SEQ ID NO: 202)
AGAGTTTGAAAATTATTTTTCAGTTTCTA (SEQ ID NO: 203)
TTCCTCATCTTTCTCCGCTTTTGCTAGCTT (SEQ ID NO: 204)
TTGAGCGTTCTAGTGTGTGGCTTGTAATGAA (SEQ ID NO: 205)
TGAAAGAAATACAATACAACGATAATGACC (SEQ ID NO: 206)
CTAGTTTTAAGAGATAGCTCTCTAAGTAGG (SEQ ID NO: 207)
AAATTCGACATAAGCACTACAGTTATATT (SEQ ID NO: 208)
CTATTTTCGAGAGAACGTCAGTCATTTTAA -continued (SEQ ID NO: 209)
GTGCTAACTATATCAGTCGCATCAATAACA (SEQ ID NO: 210)
TTAGCGGTGATTGGAATAGAATAAGCGAAT (SEQ ID NO: 211)
CTTCTACAGCAGTTTAAGACACATTATCAT (SEQ ID NO: 212)
CGTATCGAAAACGGCGATAATCCAACAGT (SEQ ID NO: 213)
CAATACCTTTTTTTAATTCATCTTGATAAGT (SEQ ID NO: 214)
TTAAGAACAATATCATCAATACGACTTTCA (SEQ ID NO: 215)
CATCTATCAAATTCAAATTCGGATAAACTA (SEQ ID NO: 216)
TGAGAGTGTCTGATGGATTTATTGGTAACC (SEQ ID NO: 217)
ACCTCATACATGGGGAAAACTTGTAAGTA (SEQ ID NO: 218)
TATTTCACGAATTTCTACACTTTTCAACCT (SEQ ID NO: 219)
CTGAAACCTTGTTTTGAAGCGCTTGGAAGT (SEQ ID NO: 220)
GTCAATTGATACTGCAATCTCTTTAACATT (SEQ ID NO: 221)
ACTTCAATATGGTCAACATCTTGATCACCGA (SEQ ID NO: 222)
TAAACTCGACAAAAGCACTACATGAATATT (SEQ ID NO: 223)
ATTTTTTAAGGAAAGGAGGAAAATAATATA (SEQ ID NO: 224)
CGTTCAAAACAGCGAAAACTTAACCCTAAC (SEQ ID NO: 225)
CATTAAGTCGCTTGAGGCAGACATTGAAGC (SEQ ID NO: 226)
CCAAACTCAAATTGTCTATAATAATAACCG (SEQ ID NO: 227)
TATCTCTATTTCAGGTGGTTTAAAACATTC (SEQ ID NO: 228)
AAACGAAGATGGAAGCGTTGATGTTTATTC (SEQ ID NO: 229)
GATTGCATTTGCCAGTATTTCTTTTGATTA (SEQ ID NO: 230)
TGAAGACAACGGAAACAATCAACCTATTA (SEQ ID NO: 231)
ACTTCTTTTTTAATGTCATCTAAGACAATA (SEQ ID NO: 232)
GCCAATGATGTTCAATTCGTTAATGGAATT (SEQ ID NO: 233)
TCAACATGGGATATTTCGTTGGTCAGGATG (SEQ ID NO: 234)
TATGGCTCTCTTGTTGGAATAAAGATGATT (SEQ ID NO: 235)
ATAACATAGCAGTCTATTTCTTTGCTGATG -continued (SEQ ID NO: 236)
GTTACCACGCGCCCTACTGTATTAGTGGAG (SEQ ID NO: 237)
TACATACCCAAGGTTGTAAGTCGTTAAATT (SEQ ID NO: 238)
TGTAAGTAGTCAATATTCACTTCTGATAAC (SEQ ID NO: 239)
GATAGCAATAGCTTTCTTGACCTAAAAGAC (SEQ ID NO: 240)
GAGGTCTGTAATTTCATTCCCTCGTAATCT (SEQ ID NO: 241)
AAAGGTTTCTCTAAACACATGCGGAATAT (SEQ ID NO: 242)
GTCATAGTACCAAGCACAAATAACGTTAGT (SEQ ID NO: 243)
GTGTATTTAGTAATGGTGATTTTTTAAATT (SEQ ID NO: 244)
CATTCATTTTTTATATATCAATAAAACTTT (SEQ ID NO: 245)
GGGGATTCTTATTTCACTGTAGTTACGATG (SEQ ID NO: 246)
CAAAAATTGATGTCACAATTAATAAAGGTG (SEQ ID NO: 247)
CTATTTCTGACAATGGTTGAAATTGTGTTC (SEQ ID NO: 248)
CTTTTTTTAAATTAATTTATCGTAAGCAA (SEQ ID NO: 249)
AACAAACTTATGAGAACGGTTGAACGGCTT (SEQ ID NO: 250)
AGCCCGCTTATTGCTTCAGTTGGTTTATAT (SEQ ID NO: 251)
TGGAGCAACAAGAATGATTAACTCTAATGC (SEQ ID NO: 252)
TTTGATGGATATCATTGATAAACTATACGA (SEQ ID NO: 253)
TAACGAAAGCAATACCAATCGTGCTAAAGC (SEQ ID NO: 254)
TATTCCTATGGTCGATATTCGAACAGTCAA (SEQ ID NO: 255)
CAGGGGACAAGGACTTTGACCCAACAGAAG (SEQ ID NO: 256)
AGAAACACCTAATGGTCTCTTAGAACCCGA (SEQ ID NO: 257)
AAGAAGTTAAAGACAACTTTGTTAAAGACT (SEQ ID NO: 258)
GAAAAAGCATCCATGATAGTGCTTAGACCT (SEQ ID NO: 259)
CGGAATGGTATAAAGAATACAAAGAAAACG (SEQ ID NO: 260)
CCAAGTATCACGCAAAGAAATCAACGAGA (SEQ ID NO: 261)
TTGACCTGTTTATCCTTGTTAACTAGAATAG (SEQ ID NO: 262)
AGAGCACTAGCATACTGTTTAGTCCGAACG -continued (SEQ ID NO: 263)
AGGCAAGGTATTTGATCCAACAGAAGCCAA (SEQ ID NO: 264)
CATGATTTACAACCACGCGCTAGACCAAG (SEQ ID NO: 265)
ACCTAGAAGCATTTGAGCGTATATTGATTG (SEQ ID NO: 266)
AATTTTGCCCCTTCTTTGCCCCTTGACTAG (SEQ ID NO: 267)
TAATAGTTTACCAAATCGTCCTTGTTCCAA (SEQ ID NO: 268)
ACCATTAGCAATCATTTGTGCCCATTGAGT (SEQ ID NO: 269)
ACGTCTGTCTAACTGGAAAGTACCTGTTAAT (SEQ ID NO: 270)
TTTTTATACTTTGGGTAATTACAAAATAG (SEQ ID NO: 271)
AAGAAAGAAATATTCTAGATATAGATATAA (SEQ ID NO: 272)
CAACGACCAACACAACAACTAAAGTTACTG (SEQ ID NO: 273)
TGATTATGGGTGTTAAACAAGGAGCTTATG (SEQ ID NO: 274)
TGAGTGGTAAGTACAAATACGCAGGACTGA (SEQ ID NO: 275)
TTATTTCCTCCTTTCCTTAAAAAAATTAGA (SEQ ID NO: 276)
GGATGTATCTGTTGAAAGAGGTGTGTATAT (SEQ ID NO: 277)
AATAGGTGAAAAATATGCAAGTCACACAAA (SEQ ID NO: 278)
AAAATGGCATTAAAAATTAACATAGGAATA (SEQ ID NO: 279)
TATCAGCTCGTAAATGTTCGATAGACTCTT (SEQ ID NO: 280)
ATTCCATTAACGTATTTGACTTCACTAGCT (SEQ ID NO: 281)
CTGTTACCGATCCAAGAGCAGACATCATAC (SEQ ID NO: 282)
AAGAAGCGGTTAAATGCTTCAACTGAATAG (SEQ ID NO: 283)
AATTGCTAAACATCTAAAAGACTTAACGGG (SEQ ID NO: 284)
GATGAAGATTTGACTGATGATAAAGAGAAA (SEQ ID NO: 285)
GACATCAGAAAGCAGTTTATAAATATTTTA (SEQ ID NO: 286)
TTTGAATTTAACAACCTTGATTTTGATATC (SEQ ID NO: 287)
TGATACGGTCAAAGTTTTTCCACTAATAGCG (SEQ ID NO: 288)
ATGGTTTTCATTTCCTGAACCCCTAAGAGG (SEQ ID NO: 289)
AAGTTATTGAAAAACGCCAACATGATGAGT -continued (SEQ ID NO: 290)
ATATAAGTCCTCCTATTAATATCCACAATA (SEQ ID NO: 291)
TTGCCTCAAGAGATCCTGCTTGTTGCCAAG (SEQ ID NO: 292)
TCCCATAGTTTTAATGAGTCGGTTAACTTA (SEQ ID NO: 293)
GTGTACTAAAAGTGTGCTAAGTTCATAAGG (SEQ ID NO: 294)
ATATAGTGATTGTATCCAGCTGCGGCGTAG (SEQ ID NO: 295)
AAAAGCAAATCGCGAGTATAAAGGATATA (SEQ ID NO: 296)
TTTTAATTGATCTAGACACCCTATGAAATA (SEQ ID NO: 297)
ACAGAGGAGAGAAACCATGGCTATTTTAGA (SEQ ID NO: 298)
TGGCAGCAGTGAATTCGATGCCGAGCAAT (SEQ ID NO: 299)
CCAAGGAATACCAGGTCCTAAAGGTGCCGA (SEQ ID NO: 300)
CTAAATGAACTACAACAACAGCTTGATGA (SEQ ID NO: 301)
TACCTTAACATTTTCGATATTTTTCAAATT (SEQ ID NO: 302)
TTTGACTGCTTTTTTATCTGAATTGTAATT (SEQ ID NO: 303)
CAGTAACCTAAAGCTCTATCAAGCCTATTT (SEQ ID NO: 304)
CGTCAAGCTGACAGACCTTGACAACAAATC (SEQ ID NO: 305)
AGGCATAAATAACATTGATAACCCTAACA (SEQ ID NO: 306)
GCCAACGAGGTCAAATATGTCAACGGCATT (SEQ ID NO: 307)
GAAATAGGAACTTCAAAGGTAATTTCTTTA (SEQ ID NO: 308)
ATTTAGAGCAAGGAAAGCAGTACATCATTA (SEQ ID NO: 309)
CTGTAATCATTTTTAAATCAGGATTATCAA (SEQ ID NO: 310)
TTAAATGTATCCTAGTATTTTTGTACTATA (SEQ ID NO: 311)
CCATCAGCCAACTGTATCGGCTACTTTCTA (SEQ ID NO: 312)
ATGCTCTTGGCGACTATCTCATGGAGCGTG (SEQ ID NO: 313)
AGGAAAAAAACCCAAACAACCCAAAATGTTA (SEQ ID NO: 314)
TCTAATTCTGTCACCACGACTATATCGCCA (SEQ ID NO: 315)
AATCTGTGTGGGAAGTAAAGATTGAAGATG (SEQ ID NO: 316)
ATAGTTTGTTAAGTCATACCCATTAAATTG -continued (SEQ ID NO: 317)
TCCACATGATTACAAAGCCACGCAAGACCT (SEQ ID NO: 318)
GAAGACCAAAATTTGACAATGAGTCCTGC (SEQ ID NO: 319)
ATTATATTTAAGTTGTAAATGTTGCTTTTC (SEQ ID NO: 320)
GCAGACATTGGCTCAACAAGTGATTATGAA (SEQ ID NO: 321)
TGTTCTCATAAATTGCCTTTCCTTTTTATG (SEQ ID NO: 322)
CTTATCAAACATCAAGGATTGTAGATGAGG (SEQ ID NO: 323)
ATTTCATTAGTAGCTTGATAAATGTTTCTA (SEQ ID NO: 324)
GAAAATACTATACTTTAAAAGAAATTTTAA (SEQ ID NO: 325)
TCTCCTCCGACATAATCTTTTGTCTTTCCG (SEQ ID NO: 326)
ACAAAAGCACTGCCACCTATAGAAGCATTT (SEQ ID NO: 327)
AAAAACTTTATGCTATCCGTGTCAGTATAT (SEQ ID NO: 328)
TTTTCAATGATTGAAAGCCCATAACTAACA (SEQ ID NO: 329)
CTTTCATAGTTGTTACGAAATGTTTGGCAT (SEQ ID NO: 330)
CGATTTGCAATATGATGATATTGATGAATT (SEQ ID NO: 331)
TTTAGATGCTAGTCCTAAGACTGTAGAGAC (SEQ ID NO: 332)
GTAATCAAGCGTATATAAGTCAGGACTATC (SEQ ID NO: 333)
ATAACAGAAGGAGTAGGGGACGTAGGCGCG (SEQ ID NO: 334)
TTATTTGATAGGAATGTCAGTAATTTTTGA (SEQ ID NO: 335)
AACATTTCAGCGCTTACTTATCAATCTAAT (SEQ ID NO: 336)
GTATTAGTAGGCATACGATTATGGAAGTA (SEQ ID NO: 337)
CATATATATATATATATTTATTTTAAATAT (SEQ ID NO: 338)
TTGTCATAATAATTAAATCCAATAGGACTT (SEQ ID NO: 339)
GAAAATTTCTGTTGTGTTCTTAATATTAGC (SEQ ID NO: 340)
GTACTTCAAAGGTTCTAACTACATAACACA (SEQ ID NO: 341)
TAAAACCAGATGGTGGTTCTTCTGATACTA (SEQ ID NO: 342)
CATTTTCTTCAGTCAATTCGTTCTCAAGCG (SEQ ID NO: 343)
AAAGGACGGGGGCAATGAACAAACGACAAC -continued (SEQ ID NO: 344)
TAATATCATTGATAGCTTCATCAAAGGCT (SEQ ID NO: 345)
TAAATTGTTCCTTGACTCCGAACTGCCCT (SEQ ID NO: 346)
AAACAATCGTTTATCTATCCTCAAAGGATG (SEQ ID NO: 347)
ATAAAAAAACGCCTCAAAAACCGAGACAAC (SEQ ID NO: 348)
TGGAAATCCCTTATATCGACAAATACGTTA (SEQ ID NO: 349)
TTCCCAGTCGTTGATTTTTATTGAATACCC (SEQ ID NO: 350)
GGACATCGAACAAGTCAATGCCGTAAGCTT (SEQ ID NO: 351)
AATCTTTAACCGGATTGTAGAACCGTTCGG (SEQ ID NO: 352)
TGCCTTTAAAATAACTAGATTTTACCATCA (SEQ ID NO: 353)
GAGCAAGCACAAGCAAGCTTTACTATCCT (SEQ ID NO: 354)
CAGATTGGTTTATCGAACAAGGTCGCAAGT (SEQ ID NO: 355)
CAAAAGCTGTTGGTTAACGGTGCTTTGGGCA (SEQ ID NO: 356)
CTTGTTTTTCCTCTGGGGTCTCTGCGACTT (SEQ ID NO: 357)
GAAATAAACTGCCCAAACATTTTTATTTTC (SEQ ID NO: 358)
TGAGTAAGCGACAAGCTAGAAATCAAGTCA (SEQ ID NO: 359)
ATAGCTAAGATGGAAGAAGCATCAAGCACC (SEQ ID NO: 360)
CAGTATCTCAAACGCTGGATACAACAAGAT (SEQ ID NO: 361)
CCTACTCAGTGGACACCTGCAATTGAAGAC (SEQ ID NO: 362)
CGATTGGAACGGGTGCTTATGGCCTTAAC (SEQ ID NO: 363)
GCGAACAATTGAATTTGTTAGAAAATGTCG (SEQ ID NO: 364)
GAAGCATTTATTAATATAGATGGTTCTGCT (SEQ ID NO: 365)
TGCTGACGTATCTGTCCACTGTGTGCCA (SEQ ID NO: 366)
TTTTTATACTTTGGGTAAATTACAAAATAG (SEQ ID NO: 367)
TCAAGGTGTCGCCTTATGGAAAAGATGCTTG (SEQ ID NO: 368)
TGTAAAAATTTCTAGACGTTTAGACACTTTA (SEQ ID NO: 369)
AAATGATGATTGAATGCTTGAGATAGCAGT (SEQ ID NO: 370)
AATAAGAAGTTCTTGACGACCAACCGACAT -continued (SEQ ID NO: 371)
TCGTCAACGTCGATACAGAACAACGTGCTT (SEQ ID NO: 372)
TGATTAGCAAATTTAAAACAGGATATTTGG (SEQ ID NO: 373)
AAAGACAAGCCCAAGGGATTGAACTAGCAA (SEQ ID NO: 374)
CGAACAGTTGGCGAGAAATCCGTCTGGCGT (SEQ ID NO: 375)
CTACATTATTGATCATGTTTTTTCTCCTGT (SEQ ID NO: 376)
TAGAAGGCTCTGGAAATACAAAGCAATTCT (SEQ ID NO: 377)
TAGAAGGCTCTGGTAAATACAAAGCAATTCT (SEQ ID NO: 378)
TCTGATGGCTCTTGGTAGGGAACTGGATAT (SEQ ID NO: 379)
TTTGATGGCTCTTGGTAGGGAACTGGATAT (SEQ ID NO: 380)
TTTTGATGGCTCTTGGTAGGGAACTGGATAT (SEQ ID NO: 381)
ACAGAACAAAATGGTAGAATATATCATCT (SEQ ID NO: 382)
CCCTGGACAAGCTATCAGCACATATCCTTG (SEQ ID NO: 383)
CGCTGTTGATGTAACCCGCTTTATATATAT (SEQ ID NO: 384)
GAATGAATGTATTAGAGCAAGCACTTGACC (SEQ ID NO: 385)
TAGACGAAAAGGAAGGAAAATAGCATGAGC (SEQ ID NO: 386)
ATAACTCGATTGCTAACTTAAGCAAGCAGT (SEQ ID NO: 387)
CTGCATGTGTAACCATGACTTCTTCGTCGT (SEQ ID NO: 388)
CTTCGCTGGAAACTTCGTAGTCATACATAC (SEQ ID NO: 389)
AAGACCGCTGTACTGGTTGGTATTCGTACC (SEQ ID NO: 390)
CAACCAAGCGAACACAGCAGTAGCACCGCA (SEQ ID NO: 391)
ATGATGATGAAGTATCGTCATCTACTAAC (SEQ ID NO: 392)
CTTCACCTCAAATCTTAGAGATGGACTAAA (SEQ ID NO: 393)
AAAAGGTGCGTATGAAACTCATCCCAGCGG (SEQ ID NO: 394)
AAGGGTTTAAGTCCTTCATAGAGTGGAAAA (SEQ ID NO: 395)
CCTCAAAGCTTAAAATTGGGCTGAAGTAGA (SEQ ID NO: 396)
GCAATTTATTCGCTTGATGTACTCACGTTT (SEQ ID NO: 397)
TATTTATTGCAAATGGTTACCATATTTTTA -continued (SEQ ID NO: 398)
TATTTTAGCACTACGGTATCAGCGTATCTC (SEQ ID NO: 399)
TGCTACGTGCTCTGGACGGGCGCTATCAGC (SEQ ID NO: 400)
AAATGAACAGACAAGAAGCAACAGAAATTG (SEQ ID NO: 401)
AAGTTGATCGTATCTATTTAGAATATCGCA (SEQ ID NO: 402)
ATTCACTTTGACAGATACTAATGCTACATC (SEQ ID NO: 403)
CAAGCAGTGTAAAGGTGGTTTATATGTTAA (SEQ ID NO: 404)
CATAGTATAGCCGTCTTCTTTGATTGATTG (SEQ ID NO: 405)
CCATGGGTGCTAAAGGTGATGACTACCGCT (SEQ ID NO: 406)
TTTCTAGGAATGGGTAATTATAGCGAGCTAGAAAGC (SEQ ID NO: 407)
AGTTGGGAAGGTCTTGGAAAATCTATGGCAAAAAACCT (SEQ ID NO: 408)
TATATGGTTCAAATGCGATTCAAAGACTATTCAAA (SEQ ID NO: 409)
TAATTGCCAATGCTTACAATATCTTCGTCA (SEQ ID NO: 410)
ATGTTCTGAATTACCTTTCTCGACACTCCG (SEQ ID NO: 411)
ACCATCAAGGCTCTTATCTGCAGATTGTTA (SEQ ID NO: 412)
AAATGGTTGCCAATGACTTTCTAGAGTGAT (SEQ ID NO: 413)
ACAAAATCTTTTGTTGCTCCTGGACGTATT (SEQ ID NO: 414)
ATGTAAGGTATTGTAAAACTTCTTCTTGCG (SEQ ID NO: 415)
ACTGTTCCTATAATTAAAATAAAAGAGGTA (SEQ ID NO: 416)
TGTTCCAGTAAAAAGTAATTTTAAAGCATT (SEQ ID NO: 417)
CGCTCGATTGATGCTATCAACTATATTGAA (SEQ ID NO: 418)
TTCTTCAAGAGAACTTGTAGAACAGCTTCA (SEQ ID NO: 419)
AAGGTACTTTTAGCTTGTTCTTGTGGTGTT (SEQ ID NO: 420)
ACAGCTACTGTAAATTCTGCTTTTACGGTT (SEQ ID NO: 421)
TAGTGCAGTTGTCAAGGAGATTGTGAGCGA (SEQ ID NO: 422)
TTTAACCTTTGAAAATGTGAAAGGCTCGTA (SEQ ID NO: 423)
GCGATGATGGTAAGTCATCATGGACAGCGT (SEQ ID NO: 424)
TTTTACACACGATGTCAGATATAATGTCAA -continued (SEQ ID NO: 425)
AGTACTGCACTAGGAATTGTAGAGATCAAA (SEQ ID NO: 426)
CGTACCATCTATCAATTTACCGCAAGCTGT (SEQ ID NO: 427)
TTAAAAGATTTAAACTATCAAGCGTCAATT (SEQ ID NO: 428)
TTCTAAATGCTGGTGACTGCTTTGCATAAA (SEQ ID NO: 429)
TTGCTGCTAGACCCAAACAGTTTATTTTTAG (SEQ ID NO: 430)
TCCTTTTTTAGATAATGTGCGATCACGGAC (SEQ ID NO: 431)
TTTTACCAATGCTTCCATATCGCTTATAT (SEQ ID NO: 432)
TGGTTATACATTTACTAATCCATCAGCATT (SEQ ID NO: 433)
AAGCTAATTCTCATCTCACCGAGATGGATA (SEQ ID NO: 434)
AAAAACTCTTACCACTTACATACATGTATG (SEQ ID NO: 435)
GCTGGAGATTTTACAAGCAGTTTGAATTTC (SEQ ID NO: 436)
ATCACACCAGTCGTTATGATGGATGACTAT (SEQ ID NO: 437)
TGTCAACAGTACGTGAGACGAGTGTGTAGG (SEQ ID NO: 438)
TGAAGTTGATGGATATGTTGATTTAGAGCT (SEQ ID NO: 439)
TAATCATTTTATGAGAGATACCGCCTCAAG (SEQ ID NO: 440)
TTTAAAGAGATATCTGTTTCATCTTGCGGA (SEQ ID NO: 441)
AATCACTTCTGCATAAATATCTTTTACTTC (SEQ ID NO: 442)
AAACATCCGCAACGGGATAAATAAAGCTAG (SEQ ID NO: 443)
AGTTTCTTGTGGGTTAGCTTGTCCACCGTA (SEQ ID NO: 444)
GAACATGAAAGATTTTAAAAAAGAACATTT (SEQ ID NO: 445)
AGAGGGGAAAATATCAATGCCGAATGCTGA (SEQ ID NO: 446)
GATGGTACAAAATCATTTGTTGGTACTGAT (SEQ ID NO: 447)
AAAAGGAAACGCCATTAATTAATATGGTGA (SEQ ID NO: 448)
GATTGAACCAGCTAGCGCAGTTAGTGCTCT (SEQ ID NO: 449)
CGCTAAAAGCTGTTGTGTCATCATAGTTAG (SEQ ID NO: 450)
TAAATATTTTCAATTAGACAATAGACAAAC (SEQ ID NO: 451)
TGCCTATGTATTCGGACATGACTTGCCACA -continued (SEQ ID NO: 452)
ATGTGAAAAGAAAGTAACTACTACATTTGA (SEQ ID NO: 453)
TGCGCTGGTTGATTTCTTCTTGCGCTTTTT (SEQ ID NO: 454)
TTATATGAACATAACTCAATTTGTAAAAAA (SEQ ID NO: 455)
AGGAATATCCGCAATAATTAATTGCGCTCT (SEQ ID NO: 456)
TAAATTTGTTTAGCAGGTAAACCGTGCTTT (SEQ ID NO: 457)
TTCAGCACACTGAGACTTGTTGAGTTCCAT (SEQ ID NO: 458)
CTGTGACATTGCGGGATGTAATCAAAGTAAAAA (SEQ ID NO: 459)
AAAGCAAACCTAGCAGAAGCAGAAAATGACTT (SEQ ID NO: 460)
TGATGTAATTGGTGATTTTCGTGATATGCTTTTT (SEQ ID NO: 522)
CAACACATTCAACAGATTAATGAAGAATAC (SEQ ID NO: 523)
TCCACTCACGTACAAATAGTGAGTGTACTC (SEQ ID NO: 524)
GCCCTTCTAATTGGATTACCTTCCGAGGTG (SEQ ID NO: 525)
CTCAGTCGTTACTGGTGAACCAGTTTCAAT (SEQ ID NO: 526)
ATTGTCTATTACGACAACATGGAAGATGAT (SEQ ID NO: 527)
GAGTTTCTTTGTCAGACTCTAACACAGCCGC (SEQ ID NO: 528)
TTACTAGAGCGTGTCGTTAACCACTTTAAA (SEQ ID NO: 529)
TTCGTTAAAGTCACCTCGTGCTAGCGTTGC (SEQ ID NO: 530)
ATAACGGTAGCAAATATAAACCTGTTACTG (SEQ ID NO: 531)
GAAGTAGCCATACAAGAAGATGGATCAGCA (SEQ ID NO: 532)
ATGTCACTGAGTGTCTAAGCATTGCGTAC (SEQ ID NO: 533)
TGAATAAGCAGTTCTTGACGACCAACCGAC (SEQ ID NO: 535)
TTACGTTTGAAAAGAATATCAAATCAATGA (SEQ ID NO: 536)
GCTCTACGACTTCTTCCACGAGTTCCTGCC (SEQ ID NO: (SEQ ID NO: 537)
AACACAGCAAGACAAGAGGATGATGCTATG (SEQ ID NO: 538)
AAGTAGTTGATGACCTCTACAATGGTTTAT (SEQ ID NO: 539)
AATAATTTATGGTATAGCTTAATATCATTG (SEQ ID NO: 540)
AATCAATACGACAAGAGTTAAAATGGTCTT -continued (SEQ ID NO: 541)
AATCGTTCAAATTCTGTTTTAGGTACATTT (SEQ ID NO: 542)
AATGACGAGGAGCTATTGGCACAACTTACA (SEQ ID NO: 543)
AATTAAGGGCATAGAAAGGGAGACAACATG (SEQ ID NO: 544)
ACAATTCTTCATCCGGTAACTGCTCAAGTG (SEQ ID NO: 545)
ACACTTGGCAGGCTTATTACTCAACAGCGA (SEQ ID NO: 546)
ATAAACTATGAAATTTTATAATTTTTAAGA (SEQ ID NO: 547)
ATAACTGAAGGATAGGAGCTTGTAAAGTCT (SEQ ID NO: 548)
ATAATGCCGTTGAATTACACGGCAAGTCA (SEQ ID NO: 549)
CAACCAACGGTAACAGCTACTTTTTACAGT (SEQ ID NO: 550)
CATAGAGTGGAAAACTAGAAACAGATTCAA (SEQ ID NO: 551)
CGACACAAGAACGTATGCAAGAGTTCAAG (SEQ ID NO: 552)
CGATATTTAAAATCATTTTCATAACTTCAT (SEQ ID NO: 553)
CGATTTGACAATCTGCTGACCACTGTTATC (SEQ ID NO: 554)
CTGTTCCTTGTTCTTTTGTTGTATCTTTTC (SEQ ID NO: 555)
GAGCGAGCTCGAAATAATCTTAATTACAAG (SEQ ID NO: 556)
GCAGTATCAGCAAGCAAGCTGTTAGTTACT (SEQ ID NO: 557)
GCTGGCGAGGAAACGAACAAGGCCTCAACA (SEQ ID NO: 558)
GCTTAGCTGTCCAATCCACGAACGTGGATG (SEQ ID NO: 559)
GGCGTCCCAATCCTGATTAATACTTACTCG (SEQ ID NO: 560)
GTTCGCTAGCGTCATGTGGTAACGTATTTA (SEQ ID NO: 561)
TCTATATCGAGGTCAACTAACAATTATGCT (SEQ ID NO: 562)
TGCATCGAGCACGTTCGAGTTTACCGTTTC (SEQ ID NO: 563)
TGTTTGACAGCAAATCAAGATTCGAATTGT (SEQ ID NO: 564)
TTCATTCTTCCGTTTTTGTTTGCGAATCCT (SEQ ID NO: 565)
TGACTTAGCGAATTTAATCGCTAAGATATC (SEQ ID NO: 566)
TTTATACTTTATCTTTTTAAAGAATGTATT (SEQ ID NO: 567)
CCTAAAATCATTTTCAACGAGTTGCGATAC -continued (SEQ ID NO: 568)
AATAAATTGCTATGATACAGCGTACCGATA (SEQ ID NO: 569)
TGCTCTCTATGCGATTGGACGTCTGTCTAA (SEQ ID NO: 570)
AAGAAAGATAAGAAAAAAGTAACACTACTT (SEQ ID NO: 571)
TCTCTTTCCATCGGTACTGGTATATCTCAT (SEQ ID NO: 572)
ATTGGTAGCCAAGTAAATATCACCATTGAT (SEQ ID NO: 573)
TTCTTCAAATTCACCGACTGCAAAATTACA (SEQ ID NO: 574)
GCTTCCTAAGTGCATGAAAATCGCAAACGG (SEQ ID NO: 575)
TATACCTGTCTATGTAAGGGAATTTAACTC (SEQ ID NO: 576)
GGTGTAGGTGCTGTTGGTAAGTTGTTTAAT (SEQ ID NO: 577)
GTGAAACAGGTTATCAAAAAACGTATATTG (SEQ ID NO: 578)
TTATTCTTGGAATTATTACAGACCCTACTA (SEQ ID NO: 579)
GCTTTCATTATATCACTTACTCATAAATCT (SEQ ID NO: 580)
TAATCACCCCTTTTTCTAGCTCTTGATTGA (SEQ ID NO: 581)
CAAGCAGTGTAAAGGTGGTTTAAATGTTAA (SEQ ID NO: 582)
AACCCGCGTGGTTATGGGCTTGAGGAGTGT (SEQ ID NO: 583)
ATATTAATAGCGATTCTATGCTACAACGTG (SEQ ID NO: 584)
TCATCTTCTAAGTAAATACCACTGTCAGGG (SEQ ID NO: 585)
TTTTCGCAAAGTAAGCGAAGCTCTACGTG (SEQ ID NO: 586)
TTCTGTAGCCACTCCGTGGATGCCTTCAGC (SEQ ID NO: 587)
TTCTTTAGTTCGGACACCCTCAACACCTAT (SEQ ID NO: 588)
GCTTTGATTGGACGGAAAATGGTATCCCTG (SEQ ID NO: 589)
TTCCTCATCTTTCTCCGCTTTTGCTAGACTT (SEQ ID NO: 590)
TTAGACCAGATGGACAGATATTCTTCATCG (SEQ ID NO: 591)
TCATCAGAGTCAACAATCACGGGAAAGACCT (SEQ ID NO: 592)
ACACTCATCCTTATCCTGTAGTTCAAAACA (SEQ ID NO: 593)
CAGCACTAGCCGCAAGCCCTTGTATATTAA (SEQ ID NO: 594)
TAGAAATCAAGGAACTTGGATGAAAAGTAA -continued (SEQ ID NO: 595)
ATATGAAAGGGAAATGATATGAAGAATGAA (SEQ ID NO: 596)
TTTTGGGATACAACACGCAGTCGTTGACTTG (SEQ ID NO: 597)
GTTTGAGATGCCAATGTTTTTCAATCCTTG (SEQ ID NO: 598)
GTATCAAAAGACGCATTCATGAAGCGAGCT (SEQ ID NO: 599)
AAAAACAATTGAAATTCATAATCAGCGCTT (SEQ ID NO: 660)
GCTTTTAACGTTTTAAGAGAATACCCTCT (SEQ ID NO: 601)
GTGACGCTGCAATGACTTGCCATAGTAATT (SEQ ID NO: 602)
ATACTGGTATATAGTAATTCATACTTCATC (SEQ ID NO: 603)
TTGGTTTCATATTTACTCCTTTGTGTTTTG (SEQ ID NO: 604)
CTGATTTGGTCTTGTTCTTTTGTCCCTTTT (SEQ ID NO: 605)
GCAGCAGTTGAGAACTTTAGCGTCCAGTGG (SEQ ID NO: 606)
TGCTACTATGAAGGACGCTGTTGATACTTT (SEQ ID NO: 607)
TCTTCTTTAATCTTTTTTAACGTCAACGTT (SEQ ID NO: 608)
GTATCCATTAATATAGTAGCATTTCTATCA (SEQ ID NO: 609)
ATTCATTAATATCTGCAAGGATGTCTTGTT (SEQ ID NO: 610)
GAGAAAGTAGCCCATTCGGCCCATTCGGGG (SEQ ID NO: 611)
TACTTGAGTTAGCTCTGGAAGTCATTTATC (SEQ ID NO: 612)
CTGCATTTGTAACCATGACTTCTTCGTCGT (SEQ ID NO: 613)
AATTTGTCATCGACATCTACCAACGCCCAG (SEQ ID NO: 614)
ATAAAATTATGCCACGTTTTGGCACTAGAT (SEQ ID NO: 615)
ATGTCTCTGAGGCTGTAGTAATTTACTTGT (SEQ ID NO: 616)
CTTTAAAGAGTTGATTAAGTGCGTTACTGT (SEQ ID NO: 617)
AAATGGGTTATGCTGTTCAATATGCGTCCC (SEQ ID NO: 618)
AAACTGAAAACAACACAGACAATTCAACAA (SEQ ID NO: 619)
GCCCAAAATGCTAGACGTTTGAATGACGGC (SEQ ID NO: 620)
ATGAAGAACGTGATTCACCTACGGTATGCT (SEQ ID NO: 621)
GCTTTTGCAGAATTGTCTCCAGTGCCGATTT -continued (SEQ ID NO: 622)
TGTACTCTATTGATTGCTTCATCTTTATTA (SEQ ID NO: 623)
CTTTCAAGATACTCATCAACCATTGATGTCA (SEQ ID NO: 624)
CTATGTCTTTACTGTTCTTCCAAAACCACC (SEQ ID NO: 625)
TGCTACGTGCTCTGTACGGGCGCTATCAGC (SEQ ID NO: 626)
CGTGGCAGCGTGGTCGGGTTTAATAGCCCG (SEQ ID NO: 627)
AAGCCCAAGTCAGAGCATCCGTCCAAGCC (SEQ ID NO: 628)
ATTGGGTTTCGGTAAGAACTAAACATACCA (SEQ ID NO: 629)
CACAAAATAATTCGGTAGTTTTTACTAACT (SEQ ID NO: 630)
TTTGACCGTTTATTTAGACGTGCTAAAGT (SEQ ID NO: 631)
CTTCACCTCAAATCTTAGAGCTGGACTAAA (SEQ ID NO: 632)
ATGTCTGAAAAATAACCGACCATCATTACT (SEQ ID NO: 633)
GAAGCTCATCATGTTAAGGCTAAAACCTAT (SEQ ID NO: 634)
TAGTCTAAATAGATTTCTTGCACCATTGTA (SEQ ID NO: 635)
ATTCGTGAAAAAATATCGTGAAATAGGCAA (SEQ ID NO: 636)
TCTAGGCTCATCTAAAGATAAATCAGTAGC (SEQ ID NO: 637)
TAAAAACATGGGGCGGCGGTAATAGTGTAAG (SEQ ID NO: 638)
ACAACCAGCAAAGAGAGCGCCGACAACATT (SEQ ID NO: 639)
TATAACACAGGTTTAGAGGATGTTATACTT (SEQ ID NO: 640)
CTAGAAGCTCAAGCGGTAAAAGTTGATGGCG (SEQ ID NO: 641)
CTTTGAGGGCAAGCCCTCGCCGTTCCATTT (SEQ ID NO: 642)
AACTACCAAGCAAATCAGCAATCAATAAGT (SEQ ID NO: 643)
CTATAAGTGACAATCAGCGTAGGGAATACG (SEQ ID NO: 644)
ATCAGTGCGGTATATTTACCCTAGACGCTA (SEQ ID NO: 645)
AACAGTTACTATTAATCACGATTCCAACGG (SEQ ID NO: 646)
AATTAGGGCGTCTTCCTTTATTCCGTGGTT (SEQ ID NO: 647)
ATAGCTTCATTGCGCTTTTTAATTTGACCT (SEQ ID NO: 648)
AACAACAAAGCAAATACAACAGTAACAACC -continued (SEQ ID NO: 649)
CTAAACTACGTTTGAAGGTCTCAACTCCGT (SEQ ID NO: 650)
GAGGTTGAATAGTGAGTGCACCATGTTTGT (SEQ ID NO: 651)
AGTAGAGAGACCAGCACACTACTGTACTAC (SEQ ID NO: 652)
CTTCGCACGAAAGTTTATTAGACAACTCGC (SEQ ID NO: 653)
TGATAGAGCTAGAATTGTCTTTTTTACCGA (SEQ ID NO: 654)
AGATACTCTTGCTCGCCTCTGAACAACCAG (SEQ ID NO: 655)
GGTGAAAAAGGTTCACTGTACGAGTACTTA (SEQ ID NO: 656)
TCAATGAGTGGTATCCAAGACGAAAACTTA (SEQ ID NO: 657)
CCTTGTCGTGGCTCTCCATACGCCCATATA (SEQ ID NO: 658)
TGTTTGGGAAACCGCAGTAGCCATGATTAA (SEQ ID NO: 659)
ACAGAGTACAATATTGTCCTCATTGGAGACAC (SEQ ID NO: 660)
CTCATATTCGTTAGTTGCTTTTGTCATAAA (SEQ ID NO: 661)
AGAACTTTATCAAGATAAAACTACTTTAAA (SEQ ID NO: 662)
ATAGTATTAATTTCATTGAAAAATAATTGT (SEQ ID NO: 663)
GCTTTCTAGCTCGCTATAATTACCCATTCCTAGAAA (SEQ ID NO: 664)
TCAAAATATGTTATTACCTTGTATTTCATAATTCAATTAA (SEQ ID NO: 665)
CCACTTGCTGTGTACATCCTACCAGTTCCGCCTATGATG In particularly preferred embodiments, CRISPR spacers are flanked by two CRISPR repeats (i.e., a CRISPR spacer has at least one CRISPR repeat on each side). Although it is not intended that the present invention be limited to any particular mechanism, theory, or hypothesis, it is contemplated that the further a given CRISPR spacer is from the 5' end of the CRISPR locus comprising the cas gene(s) and/or the leader sequence, the lower the resistance conferred by that CRISPR spacer is. Thus, in some embodiments of the present invention, one or more of the first 100 CRISPR spacers from the 5' end of the CRISPR locus are modified, while in other embodiments, one or more of the first 50 CRISPR spacers from the 5' end of the CRISPR locus are modified. In some additional embodiments, one or more of the first 40 CRISPR spacers from the 5' end of the CRISPR locus are modified, while in some still further embodiments, one or more of the first 30 CRISPR spacers from the 5' end of the CRISPR locus are modified, and in yet additional embodiments, one or more of the first 20 CRISPR spacers from the 5' end of the CRISPR locus are modified, and in still more embodiments, one or more of the first 15 CRISPR spacers from the 5' end of the CRISPR locus are modified. In some preferred embodiments, one or more of the first 10 CRISPR spacers from the 5' end of the CRISPR locus are modified. As indicated herein, different bacteria have different numbers of CRISPR spacers, thus in some embodiments, various spacers are modified.

CRISPR Spacer Core

For a specific CRISPR type within a microbial species, the CRISPR spacer is typically represented by a defined predominant length, although the size may vary. CRISPR types described to date have been found to contain a predominant spacer length of between about 20 bp and about 58 bp.

As used herein, the term "CRISPR spacer core" refers to the length of the shortest observed spacer within a CRISPR type. Thus, for example, within *S. thermophilus* CRISPR Type 1 (CRISPR1), the dominant spacer length is 30 bp, with a minority of spacers between 28 bp and 32 bp in size. Thus, in *S. thermophilus* CRISPR Type 1, the CRISPR spacer core is defined as a continuous stretch of 28 bp.

In some preferred embodiments of the present invention, the CRISPR spacer core is homologous to the target nucleic acid, a transcription product thereof, or an identified sequence over the length of the core sequence. As indicated above, although homology can also be considered in terms of similarity, in some preferred embodiments of the present invention, homology is expressed in terms of sequence identity. Thus, in some embodiments, a homologous sequence encompasses a CRISPR spacer core, which may be at least about 90% identical, or at least about 91, about 92, about 93, about 94, about 95, about 96, about 97, about 98 or about 99% identical to the target nucleic acid sequence, a transcription product thereof, or an identified sequence over the length of the core sequence. In some particularly preferred embodiments, the CRISPR spacer core is about 100% identical to the target nucleic acid sequence, transcription product thereof, or an identified sequence over the length of the core sequence.

During the development of the present invention, the CRISPR sequences of various *S. thermophilus* strains, including closely related industrial strains and phage-resistant variants were analyzed. Differences in the number and type of spacers were observed primarily at the CRISPR1 locus. Notably, phage sensitivity appeared to be correlated with CRISPR1 spacer content. Specifically, the spacer content was nearly identical between parental strains and phage-resistant derivatives, except for additional spacers present in the latter. These findings suggested a potential relationship between the presence of additional spacers and the differences observed in the phage sensitivity of a given strain. This observation prompted the investigation of the origin and function of additional spacers present in phage-resistant mutants.

Pseudo-CRISPR Spacer

As used herein, the term "pseudo-CRISPR spacer" refers to a nucleic acid sequence present in an organism (e.g., a donor organism, including but not limited to bacteriophage), which is preferably essential for function and/or survival and/or replication and/or infectivity, etc., and which comprises a CRISPR spacer sequence. In some embodiments, the pseudo-CRISPR spacers find use in producing CRISPR spacer sequences that are complementary to or homologous to the pseudo-CRISPR spacer. In some particularly preferred embodiments, these sequences find use in modulating resistance.

In some embodiments, at least one pseudo-CRISPR spacer and CRISPR spacer(s) that is/are complementary or homologous to at least one pseudo-CRISPR spacer(s) are used to engineer a recipient cell. In some preferred embodiments, at least one pseudo-CRISPR spacers or CRISPR spacer(s) that is/are complementary or homologous to the at least one pseudo-CRISPR spacer(s) are used in combination with one or more cas genes or proteins and/or one or more CRISPR repeats (e.g., one or more functional combinations thereof), to engineer a recipient cell, such that the resistance of the recipient cell is modulated against a target nucleic acid or a transcription product thereof.

In some embodiments, the pseudo-CRISPR spacers or CRISPR spacer(s) that is/are complementary or homologous to the one or more pseudo-CRISPR spacer(s) are inserted into the plasmid and/or genomic DNA of a recipient cell using any suitable method known in the art.

In some additional embodiments, the pseudo-CRISPR spacers are used as a template upon which to modify (e.g., mutate) the plasmid and/or genomic DNA of a recipient cell, such that CRISPR spacers are created in the plasmid and/or genomic DNA of the cell. In some further embodiments, the pseudo-CRISPR spacers or CRISPR spacer(s) that is/are complementary or homologous to the one or more pseudo-CRISPR spacer(s) are cloned into a construct, plasmid and/or vector, etc. is/are introduced into the host cell using any suitable method known in the art.

CAS and cas Genes

As used herein, the term "cas gene" has the conventional meaning as used in the art and refers to one or more cas genes that are generally coupled, associated or close to or in the vicinity of flanking CRISPR loci. A comprehensive review of the Cas protein family is presented by Haft et al. (Haft et al., PLoS. Comput. Biol., 1(6): e60 [2005]), in which 41 newly recognized CRISPR-associated (cas) gene families are described, in addition to the four previously known gene families. As indicated therein. CRISPR systems belong to different classes, with different repeat patterns, sets of genes, and species ranges. As indicated herein, the number of cas genes at a given CRISPR locus can vary between species.

In some embodiments, the present invention provides methods and compositions for the use of one or more cas genes or proteins, alone or in any combination with one or more CRISPR spacers for modulating resistance in a cell (e.g., a recipient cell) against a target nucleic acid or a transcription product thereof.

In some embodiments, one or more of the cas genes and/or proteins naturally occur in a recipient cell and one or more heterologous spacers is/are integrated or inserted adjacent to the one or more of the cas genes or proteins. In some embodiments, one or more of the cas genes and/or proteins is/are heterologous to the recipient cell and one or more of the spacers is/are homologous or heterologous. In some preferred embodiments, the spacers are integrated or inserted adjacent to the one or more of the cas gene or proteins.

In some further embodiments, the present invention provides methods and compositions for the use of one or more cas genes or proteins and at least two CRISPR repeats for modulating resistance in a cell (e.g., a recipient cell) against a target nucleic acid or a transcription product thereof.

In yet additional embodiments, the present invention provides methods and compositions for the use of one or more cas genes or proteins, at least two CRISPR repeats and at least one CRISPR spacer for modulating resistance in a cell (e.g., a recipient cell) against a target nucleic acid or a transcription product thereof.

CRISPR structures are typically found in the vicinity of four genes named cas1 to cas4. The most common arrangement of these genes is cas3-cas4-cas1-cas2. The Cas3 protein appears to be a helicase, whereas Cas4 resembles the RecB family of exonucleases and contains a cysteine-rich motif, suggestive of DNA binding. Cas1 is generally highly basic and is the only Cas protein found consistently in all species that contain CRISPR loci. Cas2 remains to be characterized. cas1-4 are typically characterized by their close proximity to the CRISPR loci and their broad distribution across bacterial and archaeal species. Although not all cas1-4 genes associate with all CRISPR loci, they are all found in multiple subtypes.

In addition, there is another cluster of three genes associated with CRISPR structures in many bacterial species, referred to herein as cas1B, cas5 and cas6 (See, Bolotin et al., [2005], supra). It is noted that the nomenclature of the cas genes is in flux. Thus, the text herein must be taken in context. In some embodiments, the cas gene is selected from cas1, cas2, cas3, cas4, cas1B, cas5 and/or cas6. In some preferred embodiments, the cas gene is cas1. In yet other embodiments, the cas gene is selected from cas1, cas2, cas3, cas4, cas1B, cas5 and/or cas6 fragments, variants, homologues and/or derivatives thereof. In some additional embodiments, a combination of two or more cas genes find use, including any suitable combinations, including those provided in WO 07/025097, incorporated herein by reference. In some embodiments, a plurality of cas genes is provided. In some embodiments, there is a plurality of different and/or same cas genes, or any combination thereof, as provided in WO 07/025097.

In some embodiments, the cas genes comprise DNA, while in other embodiments, the cas comprise RNA. In some embodiments, the nucleic acid is of genomic origin, while in other embodiments, it is of synthetic or recombinant origin. In some embodiments, the cas genes are double-stranded or single-stranded whether representing the sense or antisense strand or combinations thereof. In some embodiments, cas genes are prepared by use of recombinant DNA techniques (e.g., recombinant DNA), as described herein.

As described herein, in some embodiments, the cas gene comprises a fragment of a cas gene (i.e., this fragment of the cas gene comprises a portion of a wild-type sequence). In some embodiments, the sequence comprises at least about 30%, at least about 40%, at least about 50%, at least about 60%, at least about 65%, at least about 70%, at least about 75%, at least about 80%, at least about 85%, at least about 90%, at least about 95%, at least about 96%, at least about 97%, at least about 98%, or least about 99% of the wild-type sequence.

In some embodiments it is preferred that the cas gene is the cas gene that is closest to the leader sequence or the first CRISPR repeat at the 5' end of the CRISPR locus—such as cas4 or cas6.

In some embodiments, the Cas protein is selected from Cas1, Cas2, Cas3, Cas4, Cas1B, Cas5 and/or Cas6, as well as fragments, variants, homologues and/or derivatives thereof. In some further embodiments, the Cas protein is selected from Cas1, Cas2, Cas3, Cas4, Cas1B, Cas5 and/or Cas6, and combinations thereof, as described in WO 07/025097. In yet additional embodiments, the Cas protein is selected from one or more of Cas1, Cas2, Cas3, Cas4, Cas1B, Cas5 and/or Cas6 or a plurality of same and/or different Cas proteins, in any suitable number and/or combination.

The term "Cas protein" also encompasses a plurality of Cas proteins (e.g., between about 2 and about 12 Cas proteins, more preferably, between about 3 and about 11 Cas proteins, more preferably, between about 4 and about 10 Cas proteins, more preferably, between about 4 and about 9 Cas proteins, more preferably, between about 4 and about 8 Cas proteins, and more preferably, between about 4 and about 7 proteins genes; such as 4, 5, 6, or 7 Cas proteins).

In some embodiments, the Cas proteins are encoded by cas genes comprising DNA, while in other embodiments, the cas comprise RNA. In some embodiments, the nucleic acid is of genomic origin, while in other embodiments, it is of synthetic or recombinant origin. In some embodiments, the cas genes encoding the Cas proteins are double-stranded or single-stranded whether representing the sense or antisense strand or combinations thereof. In some embodiments, cas genes are prepared by use of recombinant DNA techniques (e.g., recombinant DNA), as described herein.

The present invention also provides methods for identifying a cas gene for use in modulating the resistance of a cell against a target nucleic acid or transcription product thereof comprising the steps of: preparing a cell comprising at least one CRISPR spacer and at least two CRISPR repeats; engineering the cell such that it comprises at least one cas gene; and determining whether the cell modulates resistance against the target nucleic acid or transcription product thereof, wherein modulation of the resistance of the cell against the target nucleic acid or transcription product thereof is indicative that the cas gene is useful in modulating the resistance of the cell.

In some further embodiments, the present invention provides methods and one or more of the cas genes useful in the engineering of cells (e.g., recipient cells). In some preferred embodiments, one or more cas genes are used to engineer a cell (e.g., a recipient cell), that in combination with one or more, preferably, two or more CRISPR repeats and one or more CRISPR spacers finds use in modulating the resistance of a cell against a target nucleic acid or a transcription product thereof. For example, in some embodiments the cas gene(s) is/are inserted into the DNA of a cell (e.g., plasmid and/or genomic DNA of a recipient cell) using any suitable method known in the art. In some additional embodiments, the cas genes are used as a template upon which to modify (e.g., mutate) the DNA of a cell (e.g., plasmid and/or genomic DNA of a recipient cell), such that cas genes are created or formed in the DNA of the cell. In some embodiments, the cas genes are present in at least one construct, at least one plasmid, and/or at least one vector which is/are then introduced into the cell, using any suitable method known in the art.

In some embodiments, the cas genes comprise at least one cas cluster selected from any one or more of SEQ ID NOS:461, 466, 473, 478, 488, 493, 498, 504, 509, and 517. In further embodiments, the cas genes comprise any one or more of SEQ ID NOS:462-465, 467-472, 474-477, 479-487, 489-492, 494-497, 499-503, 505-508, 510-517, used alone or together in any suitable combination. In some preferred embodiments, the cluster(s) is/are used in combination with one or more, preferably, two or more CRISPR repeats and optionally one or more CRISPR spacers. In some additional embodiments, one or more cas genes or proteins is/are used in suitable combinations.

As indicated herein, a given set of cas genes or proteins is always associated with a given repeated sequence within a particular CRISPR locus. Thus, cas genes or proteins appear to be specific for a given DNA repeat (i.e., cas genes or proteins and the repeated sequence form a functional pair).

Accordingly, particular combinations of one or more cas genes or proteins and one or more, preferably, two or more CRISPR repeats are used in order for a CRISPR spacer to confer resistance against a target nucleic acid or transcription product thereof in a cell (e.g., a recipient cell). Accordingly, it has been surprisingly found that it is not possible to merely use any cas genes or proteins or any CRISPR repeat. Instead it is a feature of the present invention that the combination is functional.

In the context of the CRISPR repeat-cas gene or protein combination described herein, the term "functional" means that the combination is able to confer resistance to a target nucleic acid or a transcription product thereof when used together with a CRISPR spacer that aligns with or is homologous to a target nucleic acid or transcription product thereof. As used herein the terms "functional CRISPR repeat-cas combination" and "functional CRISPR repeat-cas gene combination" includes a functional combination in which cas is a cas gene or a Cas protein.

Suitably, the one or more cas genes or proteins and/or the one or more, preferably, two or more CRISPR repeats are derived from the same cell (e.g., the same recipient cell). In some embodiments, the term "derivable" is synonymous with the term "obtainable," as used in context. In some preferred embodiments, the term "derivable" is also synonymous with "derived," as used in context, as it is not intended that the present invention be specifically limited to elements that are "derived." In some embodiments, the term "derived" is synonymous with the term "obtained," as used in context.

In some embodiments, the one or more cas genes or proteins and/or the one or more, preferably, two or more CRISPR repeats are derived from the same CRISPR locus within a genome or plasmid, preferably a genome or plasmid of the same strain, species or genera. In some further embodiments, one or more cas genes or proteins and/or one or more, preferably, two or more CRISPR repeats are derived from the same CRISPR locus within a single genome or plasmid, preferably a single genome or plasmid of the same strain, species or genera. In some embodiments, one or more cas genes or proteins and one or more, preferably, two or more CRISPR repeats naturally co-occur. In yet additional embodiments, the one or more cas genes or proteins and one or more, preferably, two or more CRISPR repeats naturally co-occur in the same cell (e.g., recipient cell). In further embodiments, one or more cas genes or proteins and one or more, preferably, two or more CRISPR repeats naturally co-occur in the same genome of a cell (e.g., recipient cell). In still additional embodiments, one or more cas genes or proteins and one or more, preferably, two or more CRISPR repeats naturally co-occur in the same genome of a strain, species or genera. In some further preferred embodiments, the present invention provides any suitable combination of nucleic acids consisting essentially of at least two CRISPR repeats and at least one cas gene or protein.

In some embodiments, the term "consists essentially of" refers to a combination of at least two CRISPR repeats and at least one cas gene or protein and excluding at least one further component of a CRISPR locus (e.g., the absence of one or more CRISPR spacer(s) and/or the absence of one or more common leader sequence(s) of a CRISPR locus). In some alternative embodiments, the term "consists essentially of" refers to a combination of at least two CRISPR repeats and at least one cas gene or protein only and excluding all other components of a CRISPR locus (e.g., a naturally occurring CRISPR locus). In some further embodiments, the term "consists essentially of" refers to a combination of at least two CRISPR repeats and at least one cas gene or protein only and excluding at least one further component of a CRISPR locus, preferably excluding at least one further component of a naturally occurring CRISPR locus. In some still further embodiment, the term "consists essentially of" refers to a combination of at least two CRISPR repeats and at least one cas gene or protein, with the proviso that at least one further component of the natural CRISPR locus is absent (e.g., substantially absent). Thus, it is intended that the term find use in context. In some embodiments, the present invention provides any suitable combination of at least two CRISPR repeats and at least one cas gene or protein, with the proviso that all other components of the CRISPR locus are absent (e.g., substantially absent), preferably that all other components of the CRISPR locus of the natural combination of CRISPR repeat(s) and cas gene(s) are absent. In some further embodiments, one or more cas genes or proteins are used in combination or together with one or more CRISPR spacers. In some additional embodiments, one or more cas genes or proteins are used in combination or together with at least one or more CRISPR spacers and at least one or more, preferably, two or more CRISPR repeats. In some embodiments, the CRISPR spacer(s) are or are derived from an organism (e.g., a donor organism) that is different than the cell (e.g., the recipient cell) from which the one or more cas genes or proteins and/or the one or more, preferably, two or more CRISPR repeats are derived.

Various arrangements of CRISPR repeats(s) and cas gene(s) or protein(s), particularly functional CRISPR repeat-cas combinations, are provided. In some embodiments, the combination comprise, consist or consist essentially of at least any of about 9, about 10, about 11, about 12, about 13, about 14, about 15, about 16, about 17, about 18, about 19, or about 20 CRISPR repeat(s) in combination with any of about 1, about 2, about 3, about 4, about 5, about 6, about 7, about 8, about 9, about 10, about 11, about 12, about 13, about 14, about 15, about 16, about 17, about 18, about 19, or about 20 cas genes or proteins (e.g., 16 CRISPR repeat and 12 cas genes or proteins or 18 CRISPR repeats and 20 cas genes or proteins or any other combinations thereof). The present invention provides CRISPR repeat(s) and cas gene(s) arranged in various ways, as provided in WO 07/025097. In some embodiments in which the combination of a cas gene and a CRISPR repeat comprises more than one cas gene, it will be understood that the CRISPR repeat is inserted at the 3' end of the cas genes, the 5' end of the cas genes, or in between the cas genes, provided that at least one of the cas genes remains functional.

In some embodiments, a first CRISPR repeat-cas gene or protein combination (comprising at least one cas gene or protein and at least two CRISPR repeats, wherein both are derived from the same CRISPR locus within a genome) are used in combination with a second CRISPR repeat-cas gene or protein combination (comprising at least one cas gene or protein and at least two CRISPR repeats, wherein both are derived from the same or a different CRISPR locus within a genome). Accordingly, in these embodiments of the invention, the first and second combinations are derived from the same or different CRISPR loci within a genome. Thus, in some embodiments, the first and second CRISPR repeat-cas gene or protein combinations are from different genomes (e.g., from different genomes within the same cluster), as described in further detail herein.

In still further embodiments of the present invention, a first and/or a second CRISPR repeat-cas gene or protein combination (comprising at least one cas gene and at least two CRISPR repeats derived from the same CRISPR locus within a genome) are used in combination with about 3, about 4, about 5, about 6, about 7, about 8, about 9, or about 10 or more CRISPR repeat-cas gene or protein combinations (each comprising at least one cas gene or protein and at least two CRISPR repeats derived from the same or a different CRISPR loci within a genome). Accordingly, in these embodiments of the invention, the combinations are derived from the same or different CRISPR loci within a genome. In some further embodiments of the invention, the combinations are from different genomes (e.g., different genomes within the same cluster), as described in further detail herein.

Thus, in some embodiments, for the CRISPR-repeat-cas gene or protein combination to confer resistance, the CRISPR-repeat(s) and cas gene(s) or protein(s) naturally co-occur within a given CRISPR locus of a genome. In some embodiments, the CRISPR-repeat(s) and cas gene(s) or protein(s) naturally co-occur within the same CRISPR locus of a genome. In some embodiments, these functional combinations taken together, confer resistance against a target nucleic acid or a transcription product thereof.

In some further embodiments, the present invention provides methods for identifying a functional combination of a cas gene or protein and a CRISPR repeat comprising the steps of: analyzing the sequences (e.g., nucleic acid or protein sequences) of the cas gene or protein and the CRISPR repeat; identifying one or more clusters of cas genes or proteins; identifying one or more clusters of CRISPR repeats; and combining those cas gene or protein and CRISPR repeat sequences that fall within the same cluster.

In some additional embodiments, the present invention provides methods for identifying a functional combination of a cas gene or protein and a CRISPR repeat for use in modulating the resistance of a cell against a target nucleic acid or a transcription product thereof comprising the steps of: preparing a cell comprising a combination of one or more cas genes or proteins and one or more, preferably, two or more CRISPR repeats; engineering the cell such that it contains one or more CRISPR spacers; and determining if the cell modulates resistance against a target nucleic acid, wherein modulation of the resistance of the cell against the target nucleic acid or a transcription product thereof is indicative that the combination can be used to modulate the resistance of the cell against the target nucleic acid.

In some embodiments, the sequences of the cas gene and/or protein and/or the CRISPR repeat are or derived from the same or different strains, species, genera, and/or organisms. In some embodiments, the combination comprises DNA and/or RNA of genomic, recombinant, and/or synthetic origin. In some embodiments, the CRISPR repeat(s) comprise(s) DNA and/or RNA of genomic, recombinant and/or synthetic origin. In some embodiments, the cas gene(s) comprise(s) DNA and/or RNA of genomic, recombinant and/or synthetic origin. Indeed it is intended that the present invention encompass any combination of DNA and/or RNA for each of the elements (e.g., cas gene and/or CRISPR repeat). In some embodiments, the elements are analyzed using any suitable method known in the art. In some preferred embodiments, the analysis is conducted using dotplot analysis. In some embodiments, the CRISPR repeat and/or cas gene are double-stranded, while in other embodiments, either are single-stranded, whether representing the sense or antisense strand or combinations thereof.

In some embodiments, one or more of the functional combinations described herein are used to engineer a cell (e.g., a recipient cell). In some preferred embodiments, one or more functional combinations are used to engineer a cell (e.g., a recipient cell), that in combination with one or more CRISPR spacers find use in modulating the resistance of a cell against a target nucleic acid or a transcription product thereof. In some embodiments, the functional combinations are inserted into the DNA of a recipient cell (e.g., as plasmid or genomic DNA of a cell) using any suitable methods known in the art. In some additional embodiments, the functional combinations are used as a template upon which to modify (e.g., mutate) the DNA of a recipient cell (e.g., plasmid DNA or genomic DNA), such that functional combinations are created in the DNA of the cell. In yet additional embodiments, functional combinations are cloned into a construct, plasmid, or vector, etc., which is then transformed into the cell, using methods such as those described herein and known in the art.

In some embodiments, the functional combination is obtained or obtainable by a method comprising the steps of: analyzing the sequences of a cas gene and a CRISPR repeat; identifying one or more clusters of cas genes; identifying one or more clusters of CRISPR repeats; and combining those cas gene and CRISPR repeat sequences that fall within the same cluster, wherein the combination of the cas gene and CRISPR repeat sequences within the same cluster is indicative that the combination is a functional combination.

As indicated above, it was surprisingly found that it is not possible to merely exchange CRISPR repeat-cas combinations between any cells (e.g., any strains, species or genera of cells), as this does not necessarily result in functional CRISPR repeat-cas combinations. Indeed, for the CRISPR repeat-cas combination(s) to be functional, they need to be compatible. Thus, it is contemplated that it is not possible to switch cas genes or CRISPR repeats between different CRISPR loci unless they are from the same cluster. Even more surprising is that the clusters do not follow the "organism" phylogeny. Specifically, within one organism, there may be more than one CRISPR. These CRISPR(s) can belong to different clusters, even though they are present in the same organism. As a result, it is believed that a functional CRISPR repeat-cas combination requires that the combination be switched within a cluster as opposed to within an organism.

For the avoidance of doubt, the term "cluster" as used herein does not refer to a cluster of genes located at the same locus (typically forming an operon) but to the output from sequence comparison analysis (e.g., multiple sequence comparison analysis and/or multiple sequence alignments and/or dot plot analysis). Accordingly, in some embodiments, cluster analysis of CRISPR loci is performed using various methods that are known in the art (e.g., such as dot-plot analysis as described herein) or multiple alignment followed by dendrogram calculation. In some embodiments, the cluster is a class, a family or a group of sequences.

Advantageously, the use of naturally co-occurring CRISPR repeat-cas combination(s) provides for the interchange of the combination both within and between a given species, thereby making it possible to engineer the resistance of one strain using the combination from a different strain.

Bacteriophage

As used herein, the term "bacteriophage" (or "phage") has its conventional meaning as understood in the art (i.e., a virus that selectively infects one or more bacterial species). Many bacteriophages are specific to a particular genus or species or strain of bacteria. In some preferred embodiments, the phages are capable of infecting parent bacteria and/or host cells. In some embodiments, bacteriophages are virulent to the parent bacterium. In some embodiments, the phage are lytic, while in other embodiments, the phage are lysogenic.

A lytic bacteriophage is one that follows the lytic pathway through completion of the lytic cycle, rather than entering the lysogenic pathway. A lytic bacteriophage undergoes viral replication leading to lysis of the cell membrane, destruction of the cell, and release of progeny bacteriophage particles capable of infecting other cells.

A lysogenic bacteriophage is one capable of entering the lysogenic pathway, in which the bacteriophage becomes a dormant, passive part of the cell's genome through prior to completion of its lytic cycle.

Bacteriophages that find use in the present invention include, but are not limited to bacteriophages that belong to any of the following virus families: Corticoviridae, Cystoviridae, Inoviridae, Leviviridae, Microviridae, Myoviridae, Podoviridae, Siphoviridae, or Tectiviridae. In some embodiments, bacteriophage that infect bacteria that are pathogenic to plants and/or animals (including humans) find particular use. In some particularly preferred embodiments, the resistance of a cell against a bacteriophage is modulated.

In some particularly preferred embodiments, the bacteriophage of the present invention include, but are not limited to, those bacteriophage capable of infecting a bacterium that naturally comprises one or more CRISPR loci. CRISPR loci have been identified in more than 40 prokaryotes (See e.g., Jansen et al., Mol. Microbiol., 43:1565-1575 [2002]; and Mojica et al., [2005]) including, but not limited to *Aeropyrum, Pyrobaculum, Sulfolobus, Archaeoglobus, Halocarcula, Methanobacterium, Methanococcus, Methanosarcina, Methanopyrus, Pyrococcus, Picrophilus, Thermoplasma, Corynebacterium, Mycobacterium, Streptomyces, Aquifex, Porphyromonas, Chlorobium, Thermus, Bacillus, Listeria, Staphylococcus, Clostridium, Thermoanaerobacter, Mycoplasma, Fusobacterium, Azarcus, Chromobacterium, Neisseria, Nitrosomonas, Desulfovibrio, Geobacter, Myxococcus, Campylobacter, Wolinella, Acinetobacter, Erwinia, Escherichia, Legionella, Methylococcus, Pasteurella, Photobacterium, Salmonella, Xanthamonas, Yersinia, Treponema* and *Thermotoga.*

In some embodiments, the bacteriophage include, but are not limited to, those bacteriophage capable of infecting bacteria belonging to the following genera: *Escherichia, Shigella, Salmonella, Erwinia, Yersinia, Bacillus, Vibrio, Legionella, Pseudomonas, Neisseria, Bordetella, Helicobacter, Listeria, Agrobacterium, Staphylococcus, Streptococcus, Enterococcus, Clostridium, Corynebacterium, Mycobacterium, Treponema. Borrelia, Francisella, Brucella* and *Xanthomonas.*

In yet additional embodiments, the bacteriophage include, but are not limited to, those bacteriophage capable of infecting (or transducing) lactic acid bacteria, *Bifidobacterium, Brevibacterium, Propionibacterium, Lactococcus, Streptococcus, Lactobacillus* (e.g., *L. acidophilus*), *Enterococcus, Pediococcus, Leuconostoc*, and *Oenococcus.*

In still further embodiments, the bacteriophage include, but are not limited to, those bacteriophage capable of infecting *Lactococcus lacti* (e.g., *L. lactis* subsp. *lactis* and *L. lactis* subsp. *cremoris*, and *L. lactis* subsp. *lactis biovar diacetylactis*), *Streptococcus thermophilus, Lactobacillus delbrueckii* subsp. *bulgaricus, Lactobacillus helveticus, Bifidobactertum lactis, Lactobacillus acidophilus, Lactobacillus casei, Bifidobacterium infantis, Lactobacillus paracasei, Lactobacillus salivarius, Lactobacillus plantarum, Lactobacillus reuteri, Lactobacillus gasseri, Lactobacillus johnsonii* or *Bifidobacterium longum.*

In yet further embodiments, the bacteriophages include, but are not limited to, those bacteriophage capable of infecting any fermentative bacteria susceptible to disruption by bacteriophage infection, including but not limited to processes for the production of antibiotics, amino acids, and solvents. Products produced by fermentation which have been known to experience bacteriophage infection, and the corresponding infected fermentation bacteria, include cheddar and cottage cheese (*Lactococcus lactis* subsp. *lactis, Lactococcus lactis* subsp. *cremoris*), yogurt (*Lactobacillus delbrueckii* subsp. *bulgaricus, Streptococcus thermophilus*), Swiss cheese (*S. thermophilus. Lactobacillus lactis, Lactobacillus helveticus*), blue cheese (*Leuconostoc cremoris*), Italian cheese (*L. bulgaricus, S. thermophilus*), viili (*Lactococcus lactis* subsp. *cremoris, Lactococcus lactis* subsp. *lactis biovar diacetylactis, Leuconostoc cremoris*), yakult (*Lactobacillus casei*), casein (*Lactococcus lactis* subsp. *cremoris*), *natto* (*Bacillus subtilis* var. *natto*), wine (*Leuconostoc oenos*), sake (*Leuconostoc mesenteroides*), polymyxin (*Bacillus polymyxa*), colistin (*Bacillus colistrium*), bacitracin (*Bacillus licheniformis*), L-glutamic acid (*Brevibacterium lactofermentum, Microbacterium ammoniaphilum*), and acetone and butanol (*Clostridium acetobutylicum, Clostridium saccharoperbutylacetonicum*).

In some preferred embodiments, the bacteria that find use in the present invention include, but are not limited to *S. thermophilus, L. delbrueckii* subsp. *bulgaricus* and/or *L. acidophilus.*

In some particularly preferred embodiments, the bacteriophages include, but are not limited to, those bacteriophages capable of infecting bacteria that comprise one or more heterologous CRISPR loci. In some embodiments, the bacteria comprise one or more heterologous CRISPR loci, and/or one or more heterologous cas genes, and/or one or more heterologous CRISPR repeats, and/or one or more heterologous CRISPR spacers.

Infection of bacteria by phage results from the injection or transfer of phage DNA into cells. In some embodiments, infection leads to expression (i.e., transcription and translation) of the bacteriophage nucleic acid within the cell and continuation of the bacteriophage life cycle. In some embodiments involving recombinant bacteriophage, recombinant sequences within the phage genome (e.g., reporter nucleic acids), are also expressed.

It has been found that CRISPR spacer sequences in prokaryotes often have significant similarities to a variety of DNA molecules, including such genetic elements as chromosomes, bacteriophages, and conjugative plasmids. It has been reported that cells carrying these CRISPR spacers are unable to be infected by DNA molecules containing sequences homologous to the spacers (See, Mojica et al., [2005]).

In some embodiments of the present invention, one or more particular pseudo-spacers derived from bacteriophage DNA or CRISPR spacer(s) which is/are complementary or homologous to the one or more pseudo-CRISPR spacer(s) are added within a CRISPR locus of a cell (e.g., a recipient cell), in order to modulate (e.g., provide) resistance against a particular bacteriophage, thus substantially preventing phage attack.

In some preferred embodiments, particular regions within the phage genome are targeted to prepare the pseudo-spacers, including but not limited to genes coding for host specificity proteins, including those that provide particular phage-host recognition, such as helicases, primase, head or tail structural proteins, proteins with a conserved domain (e.g., holing, lysine, and others) or conserved sequences amongst important phage genes.

Any nucleic acid originating from the phage genome may confer immunity against the phage when inserted, for example, between two repeats in an active CRISPR locus. In some embodiments, immunity is more “efficient” when the CRISPR spacer corresponds to an internal sequence of a phage gene. In some particularly preferred embodiments, immunity is made even more “efficient” when the gene encodes an “essential” protein (e.g. the antireceptor).

In some preferred embodiments, the present invention provides methods for conferring resistance to a cell (e.g., a bacterial cell) against a bacteriophage comprising the steps of: (a) providing one or more pseudo CRISPR spacers from at least one bacteriophage; (b) identifying one or more functional CRISPR repeat-cas combinations in at least one cell that is substantially sensitive to the bacteriophage; and (c) engineering the one or more CRISPR loci in the substantially sensitive cell such that they comprise one or more pseudo CRISPR spacers from a bacteriophage or one or more CRISPR spacer(s) which is/are complementary or homologous to the one or more pseudo CRISPR spacer(s) to render the cell resistant.

In yet additional embodiments, the present invention provides methods for conferring resistance to a cell (e.g., a bacterial cell) against a bacteriophage comprising the steps of: (a) providing one or more pseudo CRISPR spacers from at least one bacteriophage; (b) identifying one or more functional CRISPR repeat-cas combinations in at least one cell that is substantially sensitive to the bacteriophage; and (c) inserting one or more pseudo CRISPR spacers from the bacteriophage or one or more CRISPR spacer(s) which is/are complementary or homologous to the one or more pseudo CRISPR spacer(s) into the substantially sensitive cell such that the cell is rendered substantially resistant to the bacteriophage.

In yet additional embodiments, the present invention provides methods for modulating the lysotype of a bacterial cell comprising the steps of: (a) providing one or more pseudo CRISPR spacers from at least one bacteriophage; (b) identifying one or more functional CRISPR repeat-cas combinations in at least one cell that is substantially sensitive to the bacteriophage; and (c) engineering the one or more CRISPR loci in the substantially sensitive cell such that they comprise one or more pseudo CRISPR spacers from a bacteriophage or one or more CRISPR spacer(s) which is/are complementary or homologous to the one or more pseudo CRISPR spacer(s).

In still further embodiments, the present invention provides methods for modulating the lysotype of a bacterial cell comprising the steps of: (a) providing one or more pseudo CRISPR spacers from at least one bacteriophage; (b) identifying one or more functional CRISPR repeat-cas combinations in at least one cell that is substantially sensitive to the bacteriophage; and (c) inserting one or more one or more pseudo CRISPR spacers from the bacteriophage or one or more CRISPR spacer(s) which is/are complementary or homologous to the one or more pseudo CRISPR spacer(s) into the substantially sensitive cell.

In some further preferred embodiments, the present invention provides methods for conferring resistance to a cell (e.g., a bacterial cell) against a bacteriophage comprising the steps of: (i) identifying a pseudo CRISPR spacer in a bacteriophage comprising a target nucleic acid or a transcription product thereof against which resistance is to be modulated; and (ii) modifying the sequence of the CRISPR spacer of the cell such that the CRISPR spacer of the cell has homology to the pseudo CRISPR spacer of the bacteriophage comprising the target nucleic acid.

In some further embodiments, the present invention provides methods for conferring resistance to a cell (e.g., a bacterial cell) against a bacteriophage comprising the steps of: (i) identifying a pseudo CRISPR spacer in a bacteriophage comprising a target nucleic acid or a transcription product thereof against which resistance is to be modulated; and (ii) modifying the sequence of the CRISPR spacer of the cell such that the CRISPR spacer of the cell has 100% homology or identity to the pseudo CRISPR spacer of the bacteriophage comprising the target nucleic acid.

In yet additional embodiments, the present invention provides methods for modulating the lysotype of a bacterial cell comprising the steps of: comprising the steps of: (i) identifying a pseudo CRISPR spacer in a bacteriophage comprising a target nucleic acid or a transcription product thereof against which resistance is to be modulated; and (ii) modifying the sequence of the CRISPR spacer of the cell such that the CRISPR spacer of the cell has homology to the pseudo CRISPR spacer of the bacteriophage comprising the target nucleic acid.

In some further embodiments, the present invention provides methods for modulating the lysotype of a bacterial cell comprising the steps of: (i) identifying a pseudo CRISPR spacer in a bacteriophage comprising a target nucleic acid or a transcription product thereof against which resistance is to be modulated; and (ii) modifying the sequence of the CRISPR spacer of the cell such that the CRISPR spacer of the cell has 100% homology or identity to the pseudo CRISPR spacer of the bacteriophage comprising the target nucleic acid.

In some embodiments, the CRISPR spacer of the bacterial cell has 100% homology or identity to a sequence (e.g., as a pseudo CRISPR spacer) in the bacteriophage comprising the target nucleic acid.

In some alternative embodiments, the CRISPR spacer of the bacterial cell forms a component part of a CRISPR locus comprising a functional CRISPR repeat-cas combination as described herein.

In some particularly preferred embodiments, the target nucleic acid or a transcription product thereof in the bacteriophage is a highly conserved nucleic acid sequence. In some further embodiments, the target nucleic acid or transcription product thereof in the bacteriophage is a gene coding for a host specificity protein. In some additional embodiments, the target nucleic acid or transcription product thereof in the bacteriophage encodes an enzyme that is essential for survival, replication and/or growth of the bacteriophage. In yet additional embodiments, the target nucleic acid or transcription product thereof in the bacteriophage encodes a helicase, a primase, a head or tail structural protein, or a protein with a conserved domain (e.g., holing, lysine, etc.).

In some preferred embodiments, bacterial cells are prepared that have “reduced susceptibility to bacteriophage multiplication or infection.” As used herein, this term refers to the bacteria as having a low or no susceptibility to bacteriophage multiplication or infection when compared to the wild-type bacteria when cultured (e.g., in a dairy medium).

In some embodiments, some bacterial cells exhibit “low susceptibility to bacteriophage multiplication.” This term refers to the level of bacteriophage multiplication in a bacterium being below a level, which would cause a deleterious effect to a culture in a given period of time. Such deleterious effects on a culture include, but are not limited to, no coagulation of milk during production of fermented milk products (e.g., yogurt or cheese), inadequate or slow lowering of the pH during production of fermented milk products (e.g., yogurt or cheese), slow ripening of cheese, and/or deterioration of a food's texture to the point where it is unappetizing or unsuitable for consumption.

For an equivalent set of culture conditions the bacterial susceptibility towards a bacteriophage of the present invention is generally expressed in comparison to the wild-type bacteria. In some embodiments, the bacteria have about 100 times lower (efficiency of plaquing [EOP]=$10^{-2}$), preferably about 1000 times lower (EOP=$10^{-3}$), more preferably 10,000 times lower (EOP=$10^{-4}$), and most preferably about 100,000 times lower (EOP=$10^{-5}$). In some preferred embodiments, the level of bacteriophage multiplication in a culture is measured after about 14 hours incubation of the culture, more preferably after about 12 hours, even more preferably after about 7 hours, still more preferably after about 6 hours, yet more preferably after about 5 hours, and most preferably after about 4 hours.

In additional embodiments, the present invention provides methods for conferring sensitivity to a cell (e.g., a bacterial cell) against a bacteriophage comprising the steps of: (a) providing a pseudo CRISPR spacer from at least one bacteriophage; (b) identifying one or more functional CRISPR repeat-cas combinations in a cell that is substantially resistant to the bacteriophage; and (c) engineering the one or more CRISPR loci in the substantially sensitive cell such that they comprise one or more pseudo CRISPR spacers or one or more CRISPR spacer(s) which is/are complementary or homologous to the one or more pseudo CRISPR spacer(s) that have a reduced degree of homology as compared to the one or more CRISPR loci in the substantially resistant cell.

In further embodiments, the present invention provides methods for modulating (e.g., reducing) the lysotype of a cell (e.g., a bacterial cell), comprising one or more cas genes or proteins and one or more, preferably, two or more CRISPR repeats comprising the steps of: (i) identifying a pseudo CRISPR spacer in a bacteriophage against which resistance is to be modulated; and (ii) modifying the sequence of the CRISPR spacer of the cell such that the CRISPR spacer of the cell has a reduced degree of homology to the pseudo CRISPR spacer of the bacteriophage comprising the target nucleic acid.

In still a further embodiments, the present invention provides methods for modulating (e.g., reducing or decreasing) the resistance of a bacterial cell comprising one or more cas genes or proteins and one or more, preferably, two or more CRISPR repeats against a bacteriophage comprising the steps of: (i) identifying one or more pseudo CRISPR spacers in a bacteriophage against which resistance is to be modulated; (ii) identifying a CRISPR spacer in the bacterial cell in which resistance is to be modulated that is homologous to the pseudo CRISPR spacer(s); and (iii) modifying the sequence of the CRISPR spacer in the bacterial cell in which resistance is to be modulated such that the CRISPR spacer has a lower degree of homology to the pseudo CRISPR spacer(s) of the bacteriophage against which resistance is to be modulated.

In some embodiments, the CRISPR spacer of the cell has a reduced degree of homology (e.g., about 1, about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 90, or about 95% reduction in homology) as compared to the pseudo CRISPR spacer(s) of the bacteriophage against which resistance is to be modulated.

In some embodiments, bacterial cells are prepared using the methods of the present invention such that the cells have an "increased susceptibility to bacteriophage multiplication." As used herein, this term refers to bacteria that have an increased or higher susceptibility to bacteriophage multiplication when compared to the wild-type bacteria when cultured (e.g., in a dairy medium).

In some embodiments, the term "high susceptibility to bacteriophage multiplication" refers to the level of bacteriophage multiplication in a bacterium being above a level, which would cause a deleterious effect to a culture in a given period of time. Such deleterious effects on a culture include, but are not limited to, no coagulation of milk during production of fermented milk products (e.g., yogurt or cheese), inadequate or slow lowering of the pH during production of fermented milk products (e.g., yogurt or cheese), slow ripening of cheese, and/or deterioration of a food's texture to the point where it is unappetizing or unsuitable for consumption.

For an equivalent set of culture conditions the bacterial susceptibility towards a bacteriophage of the present invention is generally expressed in comparison to the wild-type bacteria. In some embodiments, the bacteria have about 100 times lower (efficiency of plaquing [EOP]=$10^{-2}$), preferably about 1000 times lower (EOP=$10^{-3}$), more preferably 10,000 times lower (EOP=$10^{-4}$), and most preferably about 100,000 times lower (EOP=$10^{-5}$). In some preferred embodiments, the level of bacteriophage multiplication in a culture is measured after about 14 hours incubation of the culture, more preferably after about 12 hours, even more preferably after about 7 hours, still more preferably after about 6 hours, yet more preferably after about 5 hours, and most preferably after about 4 hours.

In some preferred embodiments, a CRISPR spacer is flanked by two CRISPR repeats (i.e., a CRISPR spacer has at least one CRISPR repeat on each side).

In some embodiments of the present invention, the parent bacterium (e.g., "parental bacterial strain") is exposed (e.g., iteratively, sequentially, simultaneously or substantially simultaneously) to more than one bacteriophage (e.g., a mixture of one or more phages). In some embodiments, the parental bacterial strain is sensitive to each of the bacteriophages that it is exposed to in the mixture, while in other embodiments, the bacterial strain is sensitive to some of the bacteriophages, but resistant to others.

As used herein, the term "tagging sequence" refers to the portion of an additional DNA fragment that is derived from the genome of one or more bacteriophage (e.g., the plus strand of the genome of the one or more bacteriophage) that the parent bacterium is exposed to in accordance with the methods of the present invention and is used as a label or a tag (e.g., providing a unique label or a unique tag).

The tagging sequence is typically a sequence that is a naturally occurring sequence in the bacteriophage. Preferably, the tagging sequence has at least about 90%, about 95%, about 96%, about 97%, about 98% or about 99% identity to the naturally occurring sequence in the bacteriophage (e.g., the genome of the bacteriophage from which it is derived). In some most preferred embodiments, the tagging sequence has about 100% identity to the naturally occurring sequence in the bacteriophage (e.g., the genome of the bacteriophage from which it is derived).

In some embodiments, the tagging sequence has less than about 40%, about 30%, about 20%, about 10%, about 5%, about 4%, about 3%, about 2%, about 1%, or about 0% identity to any other CRISPR spacers or CRISPR spacer cores in the one or more CRISPR loci of the labelled bacterium.

In some embodiments, the tagging sequence has less than about 40%, about 30%, about 20%, about 10%, about 5%, about 4%, about 3%, about 2%, about 1%, or about 0% identity to any other sequence in the one or more CRISPR loci of the labelled bacterium.

In some additional embodiments, the tagging sequence has a sequence that is identical to a sequence (e.g., as a CRISPR spacer) in the CRISPR locus of the bacterium. In some further embodiments, the tagging sequence has a sequence that is identical to a sequence (e.g., a CRISPR spacer) in the CRISPR locus of the bacterium aside from one or more single nucleotide polymorphisms (e.g., one or two single nucleotide polymorphisms).

In some preferred embodiments, the tagging sequence is at least about 20 nucleotides in length, while in some particularly preferred embodiments it is about 20 to about 58 nucleotides in length In some particularly preferred embodiments, at least one tagging sequence is integrated into the parent bacterium. In some additional embodiments, at least one duplicated sequence (e.g., a duplicated CRISPR repeat sequence) derived from the parent bacterium's genome or one or more of the parent bacterium's plasmids (e.g., megaplasmids) is also integrated. It is not intended that the present invention be limited to any particular mechanism or theory. However, it is believed that the at least one duplicated sequence is copied or replicated from the genome of the parent bacterium. In particular, it is believed that typically the CRISPR repeat sequence in a CRISPR locus is duplicated and the tagging sequence is integrated in the bacterium's genome immediately after (i.e., downstream) the new duplicated CRISPR repeat.

In some particularly preferred embodiments, the at least one duplicated sequence is a CRISPR repeat sequence that has at least about 90%, about 95%, about 96%, about 97%, about 98%, or about 99% identity to the CRISPR repeats in the one or more CRISPR loci of the parent bacterium and/or labelled bacterium. Most preferably, the at least one duplicated sequence is a CRISPR repeat sequence that has at least about 100% identity to the CRISPR repeats in the one or more CRISPR loci of the parent bacterium and/or labelled bacterium. In some preferred embodiments, the duplicated sequence is at least about 24 nucleotides in length, while in some particularly preferred embodiments it is about 24 to about 40 nucleotides in length.

In some preferred embodiments, at least one tagging sequence and at least one duplicated sequence are integrated into the parent bacterium. It is not intended that the present invention be limited to any particular mechanism or theory. However, it is believed that each time a tagging sequence is integrated into the genome of the parent bacterium, this is accompanied by the iterative, sequential, simultaneous or substantially simultaneous integration of at least one duplicated sequence. Accordingly, at least one pair of sequences comprising the tagging sequence and the duplicated sequence are integrated into the parent bacterium, thereby resulting in a labelled bacterium.

In some preferred embodiments, at least one tagging sequence and at least one duplicated sequence integrate adjacent to each other. More preferably, at least one tagging sequence and at least one duplicated sequence are integrated directly adjacent to each other such that there are no intervening nucleotides between the sequences.

In some embodiments, the duplicated sequence is attached, linked or fused to one end (e.g., the 5' or the 3' end) of the tagging sequence. Preferably, the duplicated sequence is attached, linked or fused to the 5' end of the tagging sequence. Accordingly, following the integration of a single pair of sequences, the duplicated sequence is the first sequence at the 5' end of the CRISPR locus and the tagging sequence will be the second (e.g., the next) sequence in the CRISPR locus, downstream of the duplicated sequence. In some preferred embodiments, the sequences are directly attached, directly linked or directly fused such that there are no intervening nucleotides between the duplicated sequence and the tagging sequence.

Thus, in some embodiments, a duplicated sequence and a tagging sequence pair are integrated into the genome of the parent bacterium to give rise to a labelled bacterium. The duplicated sequence is derived, derivable, obtained or obtainable from the parent bacterium's genome and the tagging sequence is derived, derivable, obtained or obtainable from the genome of the bacteriophage that is used to infect the parent bacterium.

Surprisingly, it has even been found that in some embodiments, multiple pairs of sequences are integrated into the genome of the parent bacterium. According to these embodiments, the multiple pairs comprise a first pair comprising a duplicated sequence and a tagging sequence, and a second pair comprising a second duplicated sequence and a second tagging sequence. The second duplicated sequence typically comprises the same sequence (e.g., greater than about 95%, about 96,%, about 97%, about 98%, about 99%, or about 100% identity) as the first duplicated sequence. The tagging sequence typically comprises a different sequence (e.g., less than about 40%, about 30%, about 20%, about 10%, about 5%, about 4%, about 3%, about 2%, about 1%, or about 0% identity) to the first tagging sequence. This is also the case in embodiments in which additional pairs of sequences are integrated.

Accordingly, the configuration of the multiple pairs typically comprises:

[duplicated sequence-tagging sequence]$_n$ wherein n=2, 3, 4, 5, 6, or more.

Preferably, the configuration of the multiple pairs typically comprises:

[CRISPR repeat-tagging sequence]$_n$ wherein n=2, 3, 4, 5, 6, or more.

In some embodiments, the configuration of the multiple pairs is:

5'-[duplicated sequence-tagging sequence]$_n$-3' wherein n=2, 3, 4, 5, 6, or more.

Preferably, the configuration of the multiple pairs is:

5'-[CRISPR repeat-tagging sequence]$_n$-3' wherein n=2, 3, 4, 5, 6, or more.

Accordingly, in some embodiments, multiple pairs of sequences are integrated into the parent bacterium. In some embodiments, the tagging sequence integrates adjacent to: (i) a duplicated sequence that is homologous (e.g., identical) to a naturally occurring sequence in the parent bacterium; (ii) a duplicated sequence that is homologous (e.g., identical) to a naturally occurring sequence in the CRISPR locus of the parent bacterium; or (iii) most preferably, a duplicated sequence that is homologous (e.g., identical) to a naturally occurring CRISPR repeat in the CRISPR locus of the parent bacterium.

Following each exposure of a parent bacterium to a given bacteriophage in independent experiments, the tagging sequence in each of the labelled bacterium presents a different nucleotide sequence, thereby creating a sequence that is unique to each bacterium. Thus, without being bound by any particular theory, it is believed that upon exposure of a parent bacterium to a given bacteriophage, the tagging sequence that is integrated into a parent bacterium is apparently randomly selected from the genome of the bacteriophage. However, it is not intended that the present invention be limited to random integration events.

Advantageously, this surprising finding is utilized in the context of the present invention by virtue of the fact that the randomly selected tagging sequence provides a unique tag or label in the labelled bacterium. Surprisingly, it has also be found that when the same parent bacterium is exposed to the same bacteriophage the tagging sequence that is integrated in independent/distinct experiments is of a different sequence, thereby resulting in a unique label in the labelled bacterium following each exposure.

In some embodiments, the randomly selected tagging sequence is identified in the labelled bacterium by virtue of one or more of the following properties of the tagging sequence:

(1) The location of the tagging sequence in the one or more CRISPR loci of the bacteriophage insensitive mutant. As described herein, the tagging sequence is typically located at one and/or both ends (e.g., the 5' and/or 3' end, more preferably, the 5' end) of the CRISPR locus of the labelled bacterium (2) The tagging sequence has a high degree of homology or identity (e.g., 100% identity) to a sequence in the bacteriophage genome that the parent bacterium was exposed to; and/or (3) The tagging sequence is fused, linked or attached to (e.g., directly fused, linked or attached to) at least one sequence (e.g., a CRISPR repeat) that is duplicated from the genome of the parent bacterium. Typically, as described herein, this additional pair of sequences is located at one and/or both ends (e.g., the 5' and/or 3' end, preferably, the 5' end) of the CRISPR locus of the labelled bacterium.

In some tagging/labelling embodiments provided herein, one or more tagging sequences and/or the one or more duplicated sequences (eg. the duplicated CRISPR repeat from the parent bacterium) integrate into the CRISPR locus of the parent bacterium. In some preferred embodiments, one or more duplicated-sequence-tagging sequence pairs as described herein integrate into the CRISPR locus of the parent bacterium. In some embodiments, the tagging sequence(s) and/or the duplicated sequence(s) integrate within the CRISPR locus of the parent bacterium. In some other embodiments, the tagging sequence(s) and/or the duplicated sequence(s) integrate at one or both ends of the CRISPR locus of the parent bacterium. In yet further embodiments, the tagging sequence(s) and/or the duplicated sequence(s) integrate at both ends of the CRISPR locus of the parent bacterium such that the sequences are at the 5' end and the 3' end of the CRISPR locus. One of the duplicated sequences will typically be the first sequence at the 5' end of the CRISPR locus and the tagging sequence will be immediately downstream of the duplicated sequence. The other duplicated sequence will be the last sequence at the 3' end of the CRISPR locus and the tagging sequence will be immediately upstream of the duplicated sequence.

In some embodiments, the tagging sequence(s) and/or the duplicated sequence(s) integrate into one or more CRISPR loci. In yet further embodiments, the tagging sequence(s) and/or the duplicated sequence(s) integrate at one end of the CRISPR locus of the parent bacterium such that the sequence(s) are at the 3' end of the CRISPR locus. The duplicated sequence will be the last sequence at the 3' end of the CRISPR locus and the tagging sequence will be immediately upstream of the duplicated sequence. Preferably, the tagging sequence(s) and/or the duplicated sequence(s) integrate at one end of the CRISPR locus of the parent bacterium such that the sequences are at the 5' end of the CRISPR locus. The duplicated sequence is the first sequence at the 5' end of the CRISPR locus and the tagging sequence is immediately downstream of the duplicated sequence.

As described herein, the tagging sequence(s) is a strain specific tag in the sense that the tagging sequence that is integrated or inserted from the bacteriophage into the parent bacterium is different each time the parent bacterium (e.g., the same parent bacterium) is exposed to the bacteriophage (e.g., the same bacteriophage). Hence the tagging sequence find use as a unique tag for a given bacterial strain.

The tagging sequence(s) and/or the duplicated sequence(s) integrate into one or more different CRISPR loci, while in other embodiments, two or more different tagging sequence(s) and/or duplicated sequence(s) integrate into one CRISPR locus, and is still further embodiments, two or more different tagging sequence(s) and/or duplicated sequence(s) each integrate into two or more different CRISPR loci. Each of the tagging sequences from each of the bacteriophage and/or each of the duplicated sequences (e.g., the duplicated CRISPR repeat) from the parent bacterium may integrate into the same CRISPR locus.

In some embodiments, each of the tagging sequences and/or each of the duplicated sequences integrate at one or both ends of the same CRISPR locus. In some further embodiments, each of the tagging sequences and/or each of the duplicated sequences integrate at the 5' and/or the 3' end of the same CRISPR locus. Preferably, each of the tagging sequences and/or each of the duplicated sequences integrate at the 5' end of the same CRISPR locus. In some additional embodiments, each of the tagging sequences and/or each of the duplicated sequences from the parent bacterium integrate iteratively, simultaneously or substantially simultaneously. In some embodiments, each of the tagging sequences and/or each of the duplicated sequences integrate sequentially, whereby the first tagging sequence and/or the first duplicated sequence is integrated into the parent bacterium. A second tagging sequence from a second bacteriophage and/or another duplicated sequence then integrates into the parent bacterium. Suitably, the tagging sequence and/or the duplicated sequence integrate into the chromosomal DNA of the parent bacterium.

In some embodiments, each of the tagging sequences and/or each of the duplicated sequences integrate into one end (e.g., the 5' end) of the same CRISPR locus adjacent (e.g., next to) each other. Thus, in some embodiments, each of the tagging sequences and/or duplicated sequences integrate sequentially, whereby the first sequences are integrated into the parent bacterium at one end (e.g., within or at the 5' and/or the 3' end) of the CRISPR locus. A second tagging sequence and/or duplicated sequence may then integrate into the parent bacterium adjacent (e.g., directly adjacent) to the first pair of sequences. In some embodiments, the second sequences integrate into the parent bacterium adjacent (e.g., directly adjacent) to the 5' or the 3' end of the first sequences. Preferably, the second sequences integrate into the parent bacterium adjacent (e.g., directly adjacent) to the 3' end of the first sequences and so on. In some embodiments, each of the sequences integrate adjacent (e.g., next to) each other within or at the 3' end and/or at the 5' end of the same CRISPR locus of the parent bacterium. In some preferred embodiments, each of the sequences integrate adjacent (e.g., next to) each other at the 5' end of the same CRISPR locus of the parent bacterium. More preferably, each of the sequences integrate adjacent (e.g., next to) each other upstream of the 5' end of the CRISPR locus of the parent bacterium. More preferably, each of the sequences integrate adjacent (e.g., next to) each other upstream of the 5' CRISPR repeat of the CRISPR locus of the parent bacterium. Most preferably, each of the sequences integrate adjacent (e.g., next to) each other upstream of the first 5' CRISPR repeat of the CRISPR locus of the parent bacterium.

Labelled Bacteria

As used herein, the term "labelled bacteria" and "labelled bacterium" refers to a parent bacterium, parent bacteria, or parental bacterial strain in which one or more CRISPR loci or a portion thereof have been modified (e.g., mutated) in such a way that it is insensitive to the one or more bacteriophage that it has been exposed to. As described in further detail herein, in some embodiments, the labelled bacterium is exposed to more than one bacteriophage (e.g., either iteratively, sequentially or simultaneously), such that it accumulates one or more genomic modifications within one or more CRISPR loci in such a way that it becomes insensitive to each of the bacteriophages to which it has been exposed To infect cells, a bacteriophage injects or transfers its nucleic acid into the cell with the phage nucleic acid existing independently of the cell's genome. In some embodiments, infection results in the expression (i.e., transcription and translation) of the bacteriophage nucleic acid within the cell and continuation of the bacteriophage life cycle.

In some embodiments of the present invention, following exposure to the bacteriophage, the labelled bacterium has a reduced or no susceptibility to bacteriophage infection and/or multiplication when compared to the parent bacterium. As used herein, the term "reduced susceptibility to bacteriophage infection and/or multiplication" means that the level of bacteriophage infection and/or multiplication in the labelled bacterium does not cause a deleterious effect to the labelled bacterium.

Thus, in some embodiments of the present invention, a parent bacterium is not killed following exposure to the bacteriophage, due to mutation of the parent bacterium in such a way that it becomes insensitive to the bacteriophage.

In some embodiments, the labelled bacterium is insensitive or substantially insensitive to further infection and/or multiplication by the bacteriophage. In additional embodiments, the labelled bacterium is insensitive or substantially insensitive to one or more of the mechanisms that the bacteriophage uses to infect and/or multiply in a bacterium. In still further embodiments, the labelled bacterium is insensitive or substantially insensitive to all of the mechanisms that the bacteriophage uses to infect and/or multiply in a bacterium. In yet additional embodiments, the labelled bacterium develops one or more mechanisms that attenuate, inactivate or destroy the bacteriophage during the infection cycle. In some further embodiments, the present invention provides labelled strains selected by standard screening procedures that are known in the art to isolate bacteriophage insensitive mutants.

In some embodiments of the present invention, a labelled bacterium comprising a tagging sequence in the CRISPR locus that is not present in the parent bacterium is selected following the comparison of the CRISPR locus or a portion thereof from the parent bacterium and the labelled bacterium.

In some preferred embodiments, a labelled bacterium comprising an additional DNA fragment within or at the 5' and/or the 3' end of the CRISPR locus that is not present in the parent bacterium is selected. More preferably, a labelled bacterium comprising a tagging sequence adjacent (e.g., directly adjacent) the 3' end of a newly duplicated sequence in the CRISPR locus of the labelled bacterium that is not present in the parent bacterium is selected. Most preferably, a labelled bacterium comprising a tagging sequence adjacent (e.g., directly adjacent) the 3' end of the first CRISPR repeat of the CRISPR locus in the labelled bacterium that is not present in the parent bacterium is selected.

In some embodiments, the tagging sequence (e.g., the one or more tagging sequences) is isolated and/or cloned. In some further embodiments, the tagging sequence (e.g., the one or more tagging sequences) is sequenced. These embodiments provide advantages, as they not only provide information about the location of the tagging sequence within the CRISPR locus, but also the specific sequence thereof, as well. In some embodiments, this information is stored in a database, thereby providing a unique label for the given bacterium and also a means for subsequently tracking and/or identifying the bacterium.

Once the sequence of the tagging sequence in the labelled bacterium is known, the tagging sequence alone finds use in identifying bacteria. Using various methods that are known in the art and described herein, the sequence and/or location of the tagging sequence are determined. This sequence is then matched against, for example, a bacterial sequence database and/or a bacteriophage sequence database and/or a database or labels/tags in order to identify the bacterium.

Donor Organism

As used in some embodiments herein, the term "donor organism" refers to an organism or cell from which the CRISPR repeat and/or cas gene and/or combination(s) thereof and/or CRISPR spacers are derived. These can be the same or different. In some embodiments, the term "donor organism" refers to an organism or cell from which the one or more, preferably, two or more CRISPR repeats and/or one or more cas gene and/or combination(s) thereof and/or CRISPR spacers are derived. These can be the same or different. In some embodiments, the CRISPR spacer and/or pseudo CRISPR spacer is synthetically derived. In yet further embodiments, the donor organism or cell comprises one or more CRISPR spacers, which confers the specific of immunity against a target nucleic acid or transcription product thereof. In additional embodiments, the donor organism or cell from which the cas gene and/or CRISPR repeat and/or combination thereof is derived is also the recipient cell/organism for the recombinant CRISPR locus. These can be the same or different. In other embodiments, the donor organism or cell from which the CRISPR spacer is derived is also the recipient cell/organism for the recombinant CRISPR locus. These can be the same or different. In embodiments in which the donor organism is a bacterial cell then the donor organism typically comprises a CRISPR spacer which confers the specific immunity against the target nucleic acid or transcription product thereof. In some embodiments, the organism is a bacterial cell while in other embodiments it is a bacteriophage.

Host Cell

As used herein, the term "host cell" refers to any cell that comprises the combination, the construct or the vector and the like according to the present invention. In some embodiments, host cells are transformed or transfected with a nucleotide sequence contained in a vector (e.g., a cloning vector). In some embodiments, a nucleotide sequence may be carried in a vector for the replication and/or expression of the nucleotide sequence. The cells are chosen to be compatible with the vector and in some embodiments, prokaryotic (e.g., bacterial) cells.

Recipient Cell

As used herein, the term "recipient cell" refers to any cell in which resistance against a target nucleic acid or a transcription product thereof is modulated or is to be modulated.

In some embodiments, the recipient cell refers to any cell comprising the recombinant nucleic acid according to the present invention. In some embodiments, the recipient cell comprises one or more, preferably, two or more CRISPR repeats and one or more cas genes or proteins. Suitably, the CRISPR repeats and the cas genes or proteins form a functional combination in the recipient cell, as described herein. In some further embodiments, the recipient cell comprises one or more modified CRISPR repeats and/or one or more modified cas genes or proteins. Suitably, the modified CRISPR repeats and/or the modified cas genes or proteins form a functional combination in the recipient cell, as described herein. In some embodiments, the recipient cell comprises one or more genetically engineered CRISPR repeats and/or one or more genetically engineered cas genes or proteins. Suitably, the genetically engineered CRISPR repeats and/or the genetically engineered cas genes or proteins form a functional combination in the recipient cell, as described herein. In some alternative embodiments, the recipient cell comprises one or more recombinant CRISPR repeats and/or one or more recombinant cas genes or proteins. Suitably, the recombinant CRISPR repeats and/or the recombinant cas genes or proteins form a functional combination in the recipient cell, as described herein. In yet additional embodiments, the recipient cell comprises one or more naturally occurring CRISPR repeats and one or more naturally occurring cas genes or proteins. Suitably, the CRISPR repeats(s) and the cas gene(s) or proteins form a functional combination.

In some embodiments, the recipient cell comprises combinations of one or more modified, genetically engineered, recombinant or naturally occurring CRISPR repeats and one or more modified, genetically engineered, recombinant or naturally occurring cas genes or proteins. Suitably, the one or more modified, genetically engineered, recombinant or naturally occurring CRISPR spacer(s) or the one or more modified, genetically engineered, recombinant or naturally occurring cas gene(s) or proteins form a functional combination.

In some embodiments, the recipient cell is a prokaryotic cell. In some preferred embodiments, the recipient cell is a bacterial cell. Suitable bacterial cells are described herein. In some embodiments, the bacterial cell is selected from a lactic acid bacteria species, a *Bifidobacterium* species, a *Brevibacterium* species, a *Propionibacterium* species, a *Lactococcus* species, a *Streptococcus* species, a *Lactobacillus* species including the *Enterococcus* species, *Pediococcus* species, a *Leuconostoc* species and *Oenococcus* species. Suitable species include, but are not limited to *Lactococcus lactis*, including *Lactococcus lactis* subsp. *lactis* and *Lactococcus lactis* subsp. *cremoris, Lactococcus lactis* subsp. *cremoris, Leuconostoc* sp., *Lactococcus lactis* subsp. *lactis* biovar, *Streptococcus thermophilus, Lactobacillus delbrueckii* subsp. *bulgaricus* and *Lactobacillus helveticus, Bifidobacterium lactis, Lactobacillus acidophilus, Lactobacillus casei.*

In some embodiments, in which the cell's resistance is to be modulated, the bacterial cell is used for the fermentation of meat (including beef, pork, and poultry) including, but not limited to, lactic acid bacteria, *Pediococcus cerevisiae, Lactobacillus plantarum, Lactobacillus brevis, Micrococcus species, Lactobacillus sakei, Lactobacillus curvatus, Pediococcus pentosaceus, Staphylococcus xylosus* and *Staphylococcus vitulinus* and mixtures thereof, as known in the art. In some alternative embodiments, the bacterial cell is used for the fermentation of vegetables (e.g., carrots, cucumbers, tomatoes, peppers, and cabbage) including, but not limited to, *Lactobacillus plantatum, Lactobacillus brevis, Leuconostoc mesenieroides, Pediococcus pentosaceus*, and mixtures thereof, as known in the art. In some alternative embodiments, the bacterial cell is used for the fermentation of dough formed from cereals (e.g., wheat, rye, rice, oats, barley, and corn). In some further embodiments, the bacterial cell is used for the production of wine. Typically, this is achieved by the fermentation of fruit juice, typically grape juice. In still further embodiments, the bacterial cell is used for the fermentation of milk to produce cheese (e.g., *Lactobacillus delbrueckii* subsp. *bulgaricus, Lactobacillus helveticus, Streptococcus thermophilus, Lactococcus lactis* subsp. *lactis, Lactococcus lactis* subsp. *cremoris, Lactococcus lactis* subsp. *lactis biovar diacetylactis, Lactococcus, Bifidobacterium*, and *Enterococcus*, etc. and mixtures thereof), as known in the art. In still further embodiments, the bacterial cell is used for the fermentation of egg (e.g., *Pediococcus pentosaceus, Lactobacillus plantarum*, and mixtures thereof), as known in the art. In some further embodiments, the bacterial cell is used in cosmetic or pharmaceutical compositions.

In some embodiments, the cell in which resistance is to be modulated is a bacterium that naturally comprises one or more CRISPR loci. CRISPR loci have been identified in more than 40 prokaryotes (See, Haft et al., 2005, supra) including, but not limited to *Aeropyrum, Pyrobaculum, Sulfolobus, Archaeoglobus, Halocarcula, Methanobacterium, Methanococcus, Methanosarcina, Methanopyrus, Pyrococcus, Picrophilus, Thermoplasma, Corynebacterium, Mycobacterium, Streptomyces, Aquifex, Porphyromonas, Chlorobium, Thermus, Bacillus, Listeria, Staphylococcus, Clostridium. Thermoanaerobacter, Mycoplasma, Fusobacterium, Azarcus, Chromobacterium, Neisseria, Nitrosomonas, Desulfovibrio, Geobacter, Myxococcus, Campylobacter, Wolinella, Acinetobacter, Erwinia, Escherichia, Legionella, Methylococcus, Pasteurella, Photobacterium, Salmonella, Xanthamonas, Yersinia, Treponema*, and *Thermotoga.*

Parent Bacterial Strain

As used herein the terms "parent bacterium" "parent bacteria" and "parental strain" refer to any bacterium/bacteria/strains that is/are exposed to one or more bacteriophage(s). In some embodiments, the bacteriophage are virulent for the parent bacterial strain, while in other embodiments, they are non-virulent. In some particularly preferred embodiments, the parent bacteria are sensitive to the virulent phage. In some preferred embodiments, the parental strain is infected by the bacteriophage. In some particularly preferred embodiments, the infection by phage renders the parent bacterium/bacteria/strain or a subpopulation thereof insensitive to further infection by the bacteriophage. In some preferred embodiments, the infection of a "parent bacterium" by one or more bacteriophage results in the creation of a labelled strain that can be selected based on its insensitivity to the bacteriophage. In some preferred embodiments, "bacteriophage resistant mutant" are bacteria that are tagged or labelled according to the methods of the present invention. In some embodiments, the parent bacteria are wild-type bacterial strains. In some preferred embodiments, the parent bacteria are wild-type strains of bacteria that have not been previously infected with any bacteriophage. In some preferred embodiments, the parent bacteria are wild-type strains of bacteria that have not been previously tagged or labelled, while in some alternative embodiments, the patent bacteria are bacteriophage resistant mutants that have been previously tagged or labelled.

In some particularly preferred embodiments, the parent bacterium is selected from any bacterium that naturally comprises one or more CRISPR loci. As indicated above, CRISPR loci have been identified in more than 40 prokaryotes (See, Haft et al., [2005], supra) including, but not limited to *Aeropyrum, Pyrobaculum, Sulfolobus, Archaeoglobus, Halocarcula, Methanobacterium, Methanococcus, Methanosarcina, Methanopyrus, Pyrococcus, Picrophilus, Thermoplasma, Corynebacterium, Mycobacterium, Streptomyces, Aquifex, Porphyromonas, Chlorobium, Thermus, Bacillus, Listeria, Staphylococcus, Clostridium. Thermoanaerobacter, Mycoplasma, Fusobacterium, Azarcus, Chromobacterium, Neisseria, Nitrosomonas, Desulfovibrio, Geobacter, Myxococcus, Campylobacter, Wolinella, Acinetobacter, Erwinia, Escherichia. Legionella, Methylococcus, Pasteurella, Photobacterium, Salmonella, Xanthamonas, Yersinia, Treponema*, and *Thermotoga.*

In some embodiments, the parent bacterium comprises one or more heterologous CRISPR spacers, one or more heterologous CRISPR repeats, and/or one or more heterologous cas genes. In some alternative embodiments, the parent bacterium comprises one or more heterologous CRISPR loci, preferably, one or more complete CRISPR loci. In some further embodiments, the parent bacterium naturally comprises one or more CRISPR loci and also comprises one or more heterologous CRISPR spacers, one or more heterologous CRISPR repeats, and/or one or more heterologous cas genes. In some additional embodiments, the parent bacterium naturally comprises one or more CRISPR loci and also comprises one or more heterologous CRISPR loci, preferably, one or more complete CRISPR loci.

In some preferred embodiments, the phage-resistant subpopulation created by exposure of the parent bacteria to at least one phage is a pure culture. However, it is not intended that the present invention be limited to pure cultures of bacterial strains, variants, or phage. Indeed, it is intended that the present invention encompasses mixed cultures of cells and phage. In some embodiments, the mixed culture is a mix of different mutants corresponding to different integration events at the same and/or at different CRISPR loci.

Although it is not intended that the present invention be so limited, preferred parental bacterial genera are *Streptococcus* and *Lactobacillus*. Indeed, it is intended that any bacterial species will find use in the present invention, including but not limited to *Escherichia, Shigella, Salmonella, Erwinia, Yersinia, Bacillus, Vibrio, Legionella. Pseudomonas, Neisseria, Bordetella, Helicobacter, Listeria, Agrobacterium, Staphylococcus, Streptococcus, Enterococcus, Clostridium, Corynebacterium, Mycobacterium, Treponema. Borrelia, Francisella, Brucella, Bifidobacterium, Brevibacterium, Propionibacterium, Lactococcus, Lactobacillus, Enterococcus, Pediococcus, Leuconostoc, Oenococcus*, and/or *Xanthomonas*. In some embodiments, the parent bacteria are or are derived from lactic acid bacteria, including but not limited to *Bifidobacterium, Brevibacterium, Propionibacterium, Lactococcus, Streptococcus, Lactobacillus* (e.g., *L. acidophilus*), *Enterococcus, Pediococcus, Leuconostoc*, and/or *Oenococcus*. In further embodiments, the parent bacteria are or are derived from *Lactococcus lactis* (e.g., *L. lactis* subsp. *lactis* and *L. lactis* subsp. *cremoris*, and *L. lactis* subsp. *lactis biovar diacetylactis*), *L. delbrueckii* subsp. *bulgaricus. L. helveticus, L. acidophilus, L. casei, L. paracasei, L. salivarius, L. plantarum, L. reuteri, L. gasseri, L. johnsonii, Bifidobacterium lactis, B. infantis, B. longum*, and/or *Streptococcus thermophilus.*

In some embodiments of the present invention, the parent bacterium is a "food-grade bacterium" (i.e., a bacterium that is used and generally regarded as safe for use in the preparation and/or production of food and/or feed). In some preferred embodiments, the parent bacterium is suitable for use as a starter culture, a probiotic culture, and/or a dietary supplement. In additional embodiments, the parent bacterium finds use in the fermentation of meat (e.g., beef, pork, lamb, and poultry) including, but not limited to, lactic acid bacteria, *Pediococcus cerevisiae, Lactobacillus plantarum, L. brevis, L. sakei, L. curvatus, Micrococcus species, Pediococcus pentosaceus, Staphylococcus xylosus, S. vitulinus* and mixtures thereof (See e.g., Knorr (ed.), *Food Biotechnology*, at 538-39 [1987]; and Pederson, *Microbiology of Fermented Foods*, at 210-34, 2d ed., [1979]; and U.S. Pat. No. 2,225,783, herein incorporated by reference in its entirety). In yet additional embodiments, the parent bacterium finds use in the fermentation of vegetables (e.g., carrots, cucumbers, tomatoes, peppers, and cabbage) including, but not limited to, *L. plantatum, L. brevis, Leuconostoc mesenteroides, Pediococcus pentosaceus*, and mixtures thereof (See e.g., Knorr, supra; Pederson, supra; and U.S. Pat. Nos. 3,024,116, 3,403,032, 3,932,674, and 3,897,307). In yet further embodiments, the parent bacterium finds use in the fermentation of dough formed from cereals (e.g., wheat, rye, rice, oats, barley, and corn). In still further embodiments, the parent bacterium finds use in the production of wine through fermentation of fruit juice (e.g., grape juice). In some additional embodiments, parent bacterium finds use in the fermentation of milk (e.g., *L. delbrueckii* subsp. *bulgaricus, L. acidophilus, S. thermophilus*, and mixtures thereof (See, Knorr, supra; and Pederson supra, at pages 105-35). In some preferred embodiments, the parent bacterium find use in the production of cheese, including but not limited to *L. delbrueckii* subsp. *bulgaricus, L. helveticus, L. lactis* subsp. *lactis, L lactis* subsp. *cremoris, L. lactis* subsp. *lactis biovar diacetylactis, S. thermophilus, Bifidobacterium Enterococcus*, etc., and mixtures thereof (See e.g., Knorr, supra, and Pederson, supra, at 135-51). In yet further embodiments, the parent bacterium finds use in the fermentation of eggs, including but not limited to *Pediococcus pentosaceus, Lactobacillus plantarum*, and mixtures thereof (See. Knorr, supra). In some embodiments, the parent bacterium is finds use in fermentation to produce various products, including but not limited to cheddar and cottage cheese (e.g., *L. lactis* subsp. *lactis, L. lactis* subsp. *cremoris*), yogurt (*L. delbrueckii* subsp. *bulgaricus*, and *S. thermophilus*), Swiss cheese (e.g., *S. thermophilus, L. lactis*, and *L. helveticus*), blue cheese (*Leuconostoc cremoris*), Italian cheese (*L. bulgaricus* and *S. thermophilus*), viili (*L. lactis* subsp. *cremoris, L. lactis* subsp. *lactis biovar diacetylactis, Leuconostoc cremoris*), yakult (*L. casei*), casein (*L. lactis* subsp. *cremoris*), *natto* (*Bacillus subtilis* var. *natto*), wine (*Leuconostoc oenos*), sake (*Leuconostoc mesenteroides*), polymyxin (*Bacillus polymyxa*), colistin (*Bacillus colistrium*), bacitracin (*Bacillus licheniformis*), L-Glutamic acid (*Brevibacterium lactofermentum* and *Microbacterium ammoniaphilum*), and acetone and butanol (*Clostridium acetobutyricum*, and *Clostridium saccharoperbutylacetonicum*). In some preferred embodiments, the parent bacterial species are selected from *S. thermophilus, L. delbrueckii* subsp. *bulgaricus* and/or *L. acidophilus.*

In yet additional embodiments, the parent bacteria find use in methods including but not limited to antibiotic production, amino acid production, solvent production, and the production of other economically useful materials. In still other embodiments the parent bacteria find use in cosmetic, therapeutic, and/or pharmaceutical compositions. In some embodiments the compositions have particular activities, including but not limited to regenerating the skin, including but not limited to anti-wrinkle properties, erasing old scars, repairing burn-damaged tissues, promoting skin healing, eliminating pigmentary spots, etc. In some embodiments, the compositions either promote or inhibit the growth of nails, hair or hairs. In some additional embodiments, the compositions comprise at least one microbial culture and/or labelled bacterium and/or a cell culture produced using the methods and compositions of the present invention In further embodiments, the parent bacteria are bacteriophage insensitive mutants. Thus, in some embodiments, the parent bacteria are insensitive to one or more bacteriophage. In some preferred embodiments, the parent bacterium is not a bacteriophage insensitive mutant for the bacteriophage that it is to be exposed to during use of the present invention.

Starter Cultures

Starter cultures are used extensively in the food industry in the manufacture of fermented products including milk products (e.g., yoghurt and cheese), as well as meat products, bakery products, wine and vegetable products.

Starter cultures used in the manufacture of many fermented milk, cheese and butter products include cultures of bacteria, generally classified as lactic acid bacteria. Such bacterial starter cultures impart specific features to various dairy products by performing a number of functions.

Commercial non-concentrated cultures of bacteria are referred to in industry as "mother cultures," and are propagated at the production site, for example a dairy, before being added to an edible starting material, such as milk, for fermentation. The starter culture propagated at the production site for inoculation into an edible starting material is referred to as the "bulk starter."

Suitable starter cultures for use in the present invention include any organism which is of use in the food, cosmetic or pharmaceutical industry (i.e., "industrially useful cultures" or "industrially useful strains").

Starter cultures are prepared by techniques well known in the art (See e.g., U.S. Pat. No. 4,621,058, incorporated herein by reference). In some embodiments, starter cultures are prepared by the introduction of an inoculum, for example a bacterium, to a growth medium (e.g., a fermentation medium or product) to produce an inoculated medium and incubating the inoculated medium to produce a starter culture.

Dried starter cultures are prepared by techniques well known in the art (See e.g., U.S. Pat. Nos. 4,423,079 and 4,140,800). Any suitable form of dried starter cultures find use in the present invention, including solid preparations (e.g., tablets, pellets, capsules, dusts, granules and powders) which are wettable, spray-dried, freeze-dried or lyophilized. In some embodiments, the dried starter cultures for use in the present invention are in either a deep frozen pellet form or freeze-dried powder form. Dried starter cultures in a deep frozen pellet or freeze-dried powder form are prepared according to any suitable method known in the art.

In some embodiments, the starter cultures used in the present invention are in the form of concentrates which comprise a substantially high concentration of one or more bacterial strains. In some embodiments, the concentrates are diluted with water or resuspended in water or other suitable diluents, (e.g., an appropriate growth medium, mineral oil, or vegetable oil). The dried starter cultures of the present invention in the form of concentrates are prepared according to the methods known in the art (e.g., centrifugation, filtration or a combination of such techniques).

In some embodiments, the starter culture is suitable for use in the dairy industry. When used in the dairy industry the starter culture is often selected from a lactic acid bacteria species, a *Bifidobacterium* species, a *Brevibacterium* species, a *Propionibacterium* species. Suitable starter cultures of the lactic acid bacteria group include commonly used strains of a *Lactococcus* species, a *Streptococcus* species, a *Lactobacillus* species including the *Lactobacillus acidophilus, Enterococcus* species, *Pediococcus* species, a *Leuconostoc* species and *Oenococcus* species.

Cultures of lactic acid bacteria are commonly used in the manufacture of fermented milk products (e.g., buttermilk, yoghurt or sour cream), and in the manufacture of butter and cheese (e.g., brie or havarti). *Lactococcus* species include the widely used *Lactococcus lactis*, including *Lactococcus lactis* subsp. *lactis* and *Lactococcus lactis* subsp. *cremoris*.

Other lactic acid bacteria species include *Leuconostoc* sp., *Streptococcus thermophilus, Lactobacillus delbrueckii* subsp. *bulgaricus* and *Lactobacillus helveticus*. In addition, probiotic strains (e.g., *Lactococcus* species), include the widely used *Lactococcus lactis*, including *Lactococcus lactis* subsp. *lactis*, and *Lactococcus lactis* subsp. *cremoris*.

Mesophilic cultures of lactic acid bacteria commonly used in the manufacture of fermented milk products such as buttermilk, yoghurt or sour cream, and in the manufacture of butter and cheese (e.g., brie or havarti). Other *Lactococcus* species include *Lactococcus lactis* subsp. *cremoris, Lactococcus lactis, Leuconostoc* sp., *Lactococcus lactis* subsp. *lactis* biovar, *Streptococcus thermophilus, Lactobacillus delbrueckii* subsp. *bulgaricus* and *Lactobacillus helveticus*. In addition, in some embodiments, probiotic strains such as *Bifidobacterium lactis, Lactobacillus acidophilus, Lactobacillus casei* are added during manufacturing to enhance flavour or to promote health.

Cultures of lactic acid bacteria commonly used in the manufacture of cheddar and monterey jack cheeses include *Streptococcus thermophilus, Lactococcus lactis* subsp. *lactis* and *Lactococcus lactis* subsp. *cremoris* or combinations thereof.

Thermophilic cultures of lactic acid bacteria commonly used in the manufacture of Italian cheeses such as pasta filata or parmesan, include *Streptococcus thermophilus* and *Lactobacillus delbrueckii* subsp *bulgaricus*. Other *Lactobacillus* species (e.g., *Lactobacillus helveticus*) are added during manufacturing to obtain a desired flavour.

In some preferred embodiments, the starter culture organism comprises or consists of a genetically modified strain prepared according to the methods provided herein, of one of the above lactic acid bacteria strains or any other starter culture strain.

The selection of organisms for the starter culture of the invention will depend on the particular type of products to be prepared and treated. Thus, for example, for cheese and butter manufacturing, mesophillic cultures of *Lactococcus* species, *Leuconostoc* species and *Lactobacillus* species are widely used, whereas for yoghurt and other fermented milk products, thermophillic strains of *Streptococcus* species and of *Lactobacillus* species are typically used.

In some embodiments, the starter culture is a dried starter culture, a dehydrated starter culture, a frozen starter culture, or a concentrated starter culture. In some embodiments, the starter culture is used in direct inoculation of fermentation medium or product.

In some embodiments, the starter culture comprises a pure culture (i.e., comprising only one bacterial strain). In some alternative embodiments, the starter culture is a mixed culture (i.e., comprising at least two different bacterial strains).

Lactic Acid Bacteria

Particularly suitable starter cultures, in particular dried starter cultures, for use in the present invention comprise lactic acid bacteria.

As used herein the term "lactic acid bacteria" refers to Gram positive, microaerophillic or anaerobic bacteria which ferment sugar with the production of acids including lactic acid as the predominantly produced acid, acetic acid, formic acid and propionic acid. The industrially most useful lactic acid bacteria are found among *Lactococcus* species, such as *Lactococcus lactis, Lactobacillus species, Bifidobacterium species, Streptococcus species, Leuconostoc species, Pediococcus* species and *Propionibacterium* species.

The starter cultures of the present invention may comprise one or more lactic acid bacteria species such as, *Lactococcus lactis, Lactobacillus delbrueckii* subsp. *bulgaricus* and *Streptococcus thermophilus* or combinations thereof.

Lactic acid bacteria starter cultures are commonly used in the food industry as mixed strain cultures comprising one or more species. For a number of mixed strain cultures, such as yoghurt starter cultures comprising strains of *Lactobacillus delbrueckii* subsp. *bulgaricus* and *Streptococcus thermophilus*, a symbiotic relationship exists between the species wherein the production of lactic acid is greater compared to cultures of single strain lactic acid bacteria (See e.g., Rajagopal et al., J. Dairy Sci., 73:894-899 [1990]).

Products

Suitable products for use in the present invention include, but are not limited to, a foodstuffs, cosmetic products or pharmaceutical products. Any product, which is prepared from, or comprises, a culture is contemplated in accordance with the present invention. These include, but are not limited to, fruits, legumes, fodder crops and vegetables including derived products, grain and grain-derived products, dairy foods and dairy food-derived products, meat, poultry, seafood, cosmetic and pharmaceutical products.

The term "food" is used in a broad sense and includes feeds, foodstuffs, food ingredients, food supplements, and functional foods.

As used herein the term "food ingredient" includes a formulation, which is or can be added to foods and includes formulations which can be used at low levels in a wide variety of products that require, for example, acidifying or emulsifying.

As used herein, the term "functional food" means a food which is capable of providing not only a nutritional effect and/or a taste satisfaction, but is also capable of delivering a further beneficial effect to consumer. Although there is no legal definition of a functional food, most of the parties with an interest in this area agree that there are foods marketed as having specific health effects.

The term "food" covers food for humans as well as food for animals (i.e., a feed). In a preferred aspect, the food is for human consumption.

In some embodiments, the cells described herein comprise or are added to a food ingredient, a food supplement, or a functional food. In some embodiments, the food is in a liquid form (e.g., a solution), gel, emulsion, or solid, as called for by the mode of application and/or administration.

The cells described herein find use in the preparation of food products such as one or more of: confectionery products, dairy products, meat products, poultry products, fish products and bakery products. In some embodiments, the bacteria find use as ingredients to soft drinks, fruit juices, beverages comprising whey protein, health teas, cocoa drinks, milk drinks, lactic acid bacteria drinks, yoghurt, drinking yoghurt, and wine, etc.

There is also provided a method of preparing a food, the method comprising admixing the cells according to the present invention with a food ingredient (such as a starting material for a food). The method for preparing a food is also another aspect of the present invention.

Suitably a food as described herein is a dairy product. In some preferred embodiments, the dairy product is yoghurt, cheese (e.g., acid curd cheese, hard cheese, semi-hard cheese, cottage cheese, etc.), buttermilk, quark, sour cream, kefir, crème fraiche, fermented whey-based beverage, koumiss, milk drink, or yoghurt drink.

As used herein the term term "food" is very broad sense, as it is intended to cover food for humans as well as food for non-human animals (i.e., feed). In some preferred embodiments, the food is for human consumption. The term "feed," as used herein includes raw and processed plant material and non-plant material. The term encompasses any feed suitable for consumption by an animal, including, but not limited to livestock, poultry, fish, crustacean, and/or pets.

Development of Phage-Resistant Strains and Starter Cultures

During the development of the present invention, phage resistance involving the CRISPR-cas genes, as well as their role in resistance to incoming alien DNA and on the role of the spacers inserted within the CRISPR on the specificity of this resistance, have been elucidated. Importantly, the present invention provides methods and compositions for the development of phage-resistant strains and starter cultures. In some embodiments, a parental strain "A" is exposed to phage "P" and a phage resistant variant (Variant "A1.0") selected. Variant A1.0 is analyzed (for example by PCR, and/or DNA sequencing) to confirm the presence of an additional inserted spacer within a CRISPR locus. The nucleotide sequence of the additional spacer (Spacer Sp1.0) is then determined. Typically, spacer Sp1.0 is a fragment of approximately 30 nucleotides in size from the phage P, and gives resistance to phage P and related phages ("related phages" are those containing the sequence of the spacer in their genomes, and define a family of phages).

Independently from the first phage exposure, the same parental strain A is exposed to the same phage P and a second phage resistant variant (Variant A2.0) is selected. Variant A2.0 is selected in order to also have an additional spacer inserted (Spacer Sp2.0) within a CRISPR locus but with the sequence of spacer Sp2.0 being different from that of spacer Sp1.0. Typically, spacer Sp2.0 is a fragment of approximately 30 nucleotides in size from the phage P, and gives resistance to phage P and related phages. Similarly, in some embodiments, variant A3.0 to variant Ax.0 are generated through the exposure of the sane strain A to the same phage P. All the "A" variants are selected in order to also have an additional spacer inserted (Spacer Sp3.0 to Spx.0) within a CRISPR locus but with the sequence of all the "Sp" spacers being different from each of the others. Typically, "Sp" spacers are fragments of approximately 30 nucleotides in size from the phage P, and all give resistance to phage P and related phages.

Although these variants are useful, they are limited in terms of the scope of their resistance. Thus, in some embodiments, it is advantageous to develop second level phage resistant strains. Indeed, it is advantageous to further develop these phage resistant variants by increasing and expanding their resistance to phages. Typically, it can be estimated that the level of resistance will be approximately that of a single mutation occurring within the phage genome within the sequence corresponding to the spacer (i.e., roughly $10^{-4}$ to $10^{-6}$). Consequently, phage resistant strains that accumulate different spacers within the CRISPR locus have an increased level of resistance to the phage containing the sequence of these spacers within their genome (i.e., since multiple single mutations need to occur within the phage genome).

Figure 15:
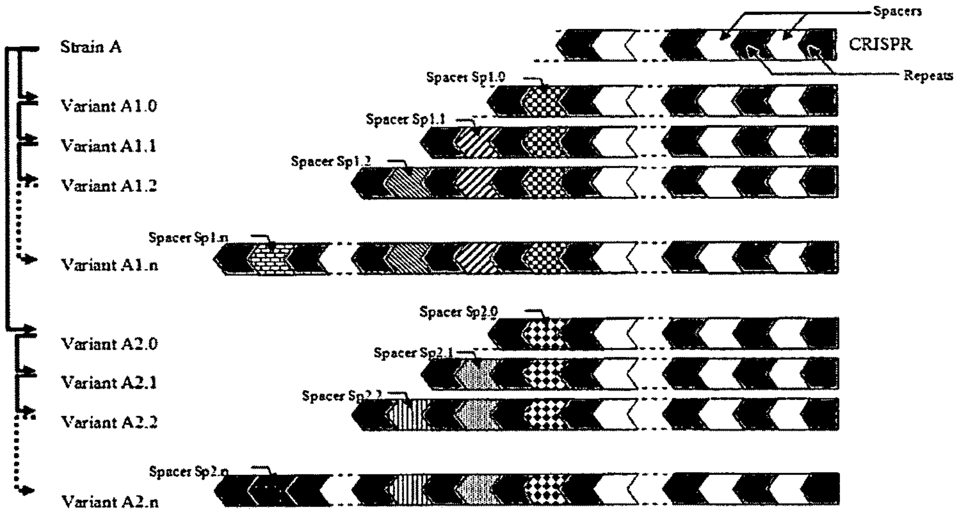
FIG. 15 provides a schematic representation of second level of phage resistant variants presenting increased resistance to phages. Final variants (A1.n and A2.n) originate from strain A and have a sequential integration of additional spacers within its CRISPR, with all spacers being different from each of the others and originating from phage P.

In some embodiments, the second level variants are produced by isolating a mutated phage through exposure of variant A1.0 to phage P. Typically, this mutated phage (phage P1.0) has a mutation (deletion, point mutation, etc.) in its genome within the region containing the sequence of spacer Sp1.0. Variant A1.0 is sensitive to phage P1.0. Then, variant A1.0 is exposed to phage P1.0 and a phage resistant variant (Variant A1.1) selected (See, FIG. 15). Variant A1.1 is also selected such that it has an additional spacer inserted (Spacer Sp1.1) within a CRISPR locus but with the sequence of spacer Sp1.1 being different from that of spacers Sp1.0, Sp2.0 to Spx.0. Typically, spacer Sp1.1 is a fragment of approximately 30 nucleotides in size from the phage P1.0, and will give resistance to phage P1.0 and related phages. Variant A1.1 is resistant to phage P1.0 and preferably, has an increased resistance to phage P because of the accumulation of spacer Sp1.0 and Sp1.1.

In additional embodiments, a newly mutated phage (phage P1.1) is generated through exposure of variant A1.1 to phage P1.0. Then, upon exposure of variant A1.1 to phage P1.1 a new variant A1.2 is obtained that contains one new additional spacer (Sp1.2). This spacer gives resistance to phage P1.1 and preferably increases the resistance to phage P1.0 and P (i.e., due to the accumulation of spacers Sp1.0, Sp1.1, Sp1.2). In yet additional embodiments, different spacers (e.g., 2, 3 or 4) are iteratively accumulated within strain A through variant A1, then variant A1.1, then variant A1.2, etc to obtain a variant highly resistant to phages (variant A1.n). In still further embodiments, additional different spacers can be accumulated in the same strain through variant A2, then variant A2.1, then variant A2.2, etc to generate another variant of strain A highly resistant to phages (variant A2.n) in parallel. The same strategy finds use with variants A3.0 to Ax.0

Figure 16:
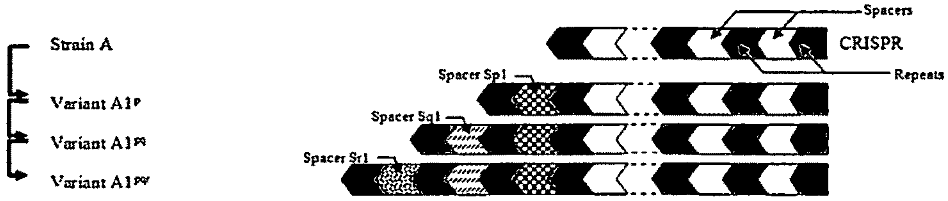
FIG. 16 provides a schematic representation of second level of phage resistant variants presenting enlarged resistance to phages. Final variant ($A1^{pqr}$) originates from strain A and has a sequential integration of additional spacers within its CRISPR originating from 3 different phages (i.e., from phage P, Q and R).

In some embodiments, strains that are resistant to more than one family of phages are provided. As a given strain can be sensitive to more than one family of phages, in some embodiments, it is desired to enlarge the strain resistance to multiple phage families by introducing additional spacer(s) within a CRISPR locus originating from the other families of phages (See, FIG. 16). For example, phages P, Q, and R are representative phages from three families of phages able to infect strain A. Using the method outlined above and herein, variants resistant to all three phage families are produced. In some embodiments, phage P is used to generate variant $A1^{p}$ (containing spacer Sp1) that is resistant to phage P. Then, variant $A1^{p}$ is exposed to phage Q and a phage resistant variant (Variant $A1^{pq}$) is selected. Variant $A1^{pq}$ has one additional spacer (Sq1) inserted within a CRISPR locus. Typically, spacer Sq1 is a fragment of approximately 30 nucleotides in size from the phage Q, and gives resistance to phage Q and related phages. Variant $A1^{pq}$ is resistant to both P and Q phages. Next, variant $A1^{pq}$ is exposed to phage R and a phage resistant variant (Variant $A1^{pqr}$) is selected. Variant $A1^{pqr}$ has a third additional spacer (Sr1) inserted within a CRISPR locus. Typically, Sr1 is a fragment of approximately 30 nucleotides in size from the phage R, and also gives resistance to phage R and related phages. Variant $A1^{pqr}$ is resistant to all three phages. In some particularly preferred embodiments, the variant is also resistant to related phages.

In additional embodiments, the above methods are used in combination to produce increased and expanded resistance to phages. In some particularly preferred embodiments, these variants have high resistances to multiple phage families. In still further embodiments, strains are produced that are resistant to particular phages or families of phages that are problematic in particular factories and/or fermenters.

CRISPR-Mediated Immunity and Applications for Phage-Resistant Strains

In contrast to the teachings of the prior art which hypothesize that CRISPR or CRISPR spacers could be involved in conferring specific immunity, the present invention is based, in part, on the surprising finding that cas genes or proteins are required for immunity against a target nucleic acid or a transcription product thereof. However, it is not intended that the present invention be limited to any particular mechanism, function, nor means of action.

Even more surprisingly, during the development of the present invention, it was found that one or more cas genes or proteins are associated with two or more CRISPR repeats within CRISPR loci. In other words, cas genes or proteins appear to be specific for a given DNA CRISPR repeat, meaning that cas genes or proteins and the repeated sequence form a functional pair. Accordingly, one or more CRISPR spacers find use together with one or more of these functional pairs (i.e., CRISPR repeats and cas genes) in order to modulate the resistance of a cell against a target nucleic acid or a transcription product thereof.

In one embodiment, for one or more CRISPR spacers to confer immunity to the cell, the CRISPR repeat(s) and the cas gene(s) or proteins form a functional combination (i.e., the CRISPR repeat(s) and the cas gene(s) or proteins are compatible).

In additional preferred embodiments, the present invention provides cas genes/proteins that influence resistance of bacteria to phages. In additional further preferred embodiments, the present invention provides at least two CRISPR repeats and at least one cas gene/protein useful in predicting, determining and/or modifying bacterial resistance to phages. Indeed, the present invention provides methods for modifying the lysotype (i.e., the resistance/sensitivity to various phages) of bacteria. Consequently, identification and detection of CRISPR loci in cells and phages provides means to determine, predict and modify the resistance profile of cells, as well as phage-host interactions.

Advantageously, the application of one or more CRISPR loci, two or more CRISPR repeats, one or more cas genes or proteins and/or one or more CRISPR spacers in genetic engineering provides means to produce resistant or sensitive variants of cells for use within a wide variety of applications in the biotechnology industry.

As discussed in greater detail below, phages are natural parasites of bacteria that may develop during fermentation. Upon infection by phages, bacteria are killed, which impairs the fermentation process. In dairy fermentation, these phage infections often have major economic impacts, ranging from a reduced quality of the fermented product up to the complete loss of the product.

To overcome phage problems, starter culture companies have developed various strategies. Traditional starter culture programs have depended on phage defence rotation strategies (PDRS) to minimize failures due to phage attack (See e.g., Klaenhammer, Adv. Appl. Microbiol., 30:1 [1984]; Lawrence et al., J. Dairy Res. 43:141 [1976]; and Whitehead and Hunter, J. Dairy Res., 15:112 [1947]). These strategies rely on multiple genetically unrelated strains that are likely to present different spectrum of phage sensitivity (i.e., different lysotypes). When a phage appears during a fermentation process using a defined strain, a strain which is ideally of a different lysotype (i.e., with a different sensitivity pattern to phages) is use in replacement for the fermentation. History has proven, however, that it is difficult to identify sufficient numbers of different lysotypes to successfully utilize these strategies. Indeed, many strains of industrial interest present rare functional traits (e.g., fast acidifying texturing *S. thermophilus*). In addition, not all of the strains present appropriate traits for being produced as starter cultures. Further, because of their rareness and the increase of the size of dairy factories, these strains are intensively used.

There are additional problems with traditional starter culture rotation strategies. Although some stains are not attacked by existing phages when introduced, phage often eventually appear due to phage mutation, modification, and build-up that attack the newly introduced strain (See e.g., Heap and Lawrence, N. Z. J. Dairy Sci. Technol., 11:16 [1976]; Limsowtin and Terzaghi, N. Z. J. Dairy Sci. Technol., 11:251 [1976]; Pearce, N. Z. J. Dairy Sci. Technol., 13:166 [1978]; and Sanders and Klaenhammer, Appl. Environ. Microbiol., 40:500 [1980]). Moreover, in many cases, the longevity and starter activity of complex strain rotations is unpredictable and often leads to early failure (See e.g., Limsowtin et al., N. Z. J. Dairy Sci. Technol., 13:1 [1977]; and Thunell et al., J. Dairy Sci., 64, 2270 [1981]). Furthermore, prolonged rotations involving numerous strains increase the level and diversity of phage contaminating the plant (See e.g., Heap and Lawrence, N. Z. J. Dairy Sci. Technol., 12:213 [1981]; Lawrence et al., J. Dairy Sci., 61:1181 [1978]; and Thunell et al., J. Dairy Sci. 64, 2270 [1981]).

In order to fight phage proliferation, traditional starter culture programs have depended on the use of strains presenting the same or similar technological functionalities but different phage sensitivities. The strains are used in rotation to perform successive fermentation. These programs traditionally rely on multiple genetically unrelated strains that consequently presents different spectrum of phage sensitivity (lysotype). Alternative approaches (See e.g., U.S. Pat. No. 5,593,885) utilizes starter culture programs based on the use of sets of isogenic strains that present different phage sensitivity, instead of genetically unrelated strains presenting different lysotypes. The term "set of isogenic strains" as used herein defines strains that are identical from a chromosomal point of view but that each differs by the presence of one or more phage resistance mechanisms that are plasmid-borne. In such starter culture rotation program, when a phage appears during a fermentation process using a defined strain, a strain which is ideally of a different lysotype (i.e., with a different spectrum of sensitivity to phages) is used in replacement for the fermentation. Due to this different lysotype, the second strain is not affected by the phages that stay dormant in the environment. Most of the population of dormant phages are then be washed out by successive fermentation and sanitation, and eradicated by the time the first strain is used again for the fermentation, if the system works as intended.

The present invention provides improved methods and compositions suitable for addressing these problems in the fermentation industry. Indeed, the present invention provides methods and compositions for the fermentation industry, and in particular the dairy industry with a selection of strains suitable to fulfill the needs of phage defence rotation strategies. In addition, the present invention provides methods and compositions suitable to customize strains having lysotypes that are adapted to a particular phage environment. In particular, the present invention provides methods and compositions suitable for directing the evolution of a given strain to various lysotypes, in order to produce strains that differ from each others only by their spectrum of phage sensitivity (lysotype). This difference of lysotype is a function of the CRISPR-cas system, as described herein. In some preferred embodiments, different lysotypes are obtained through the "modulation" of phage resistance. In some particularly preferred embodiments, although the lysotypes are different, strains of this type have identical metabolism (e.g., of carbon, nitrogen, etc.) and thus identical functionalities (e.g., acidification, flavour, texture, etc.). This provides means for amplifying the construction of starter rotation. In addition, industrial processability of the phage resistant strain are identical (e.g., nutrition needs, resistance to processing operation, etc.), thus reducing the need of development of specific production processes. Indeed, the present invention provides methods and compositions suitable for minimizing fermentation failures due to phage attack. In some embodiments, methods and compositions are provided for the production of highly phage resistant starter cultures, by the association of multiple phage resistant strains differing by their lysotype. In some alternative embodiments, methods and compositions are provided to produce starter cultures with strictly identical industrial functionalities to be used in rotation dairy fermentation. In further embodiments, methods and compositions are provided that are suitable to replace existing starters by preventing frequent phage attacks in dairy plants, by introducing a new bacterial strain that is resistant to the phages involved in these phage attack. In some embodiments, these methods and compositions are used iteratively, in order to combat sequential phage attacks.

In some additional embodiments, the starter culture is a mixed bacterial culture. In some particularly preferred embodiments, the starter comprises equal amounts of multiple (i.e., at least 2) phage resistant variants that only differ in their CRISPRs and their sensitivity to phages. In some embodiments, these variants are of the first level of phage resistant variants (e.g., variants A1.0 plus A2.0, as described above). In some preferred embodiments, the variants are selected from those in the second level of phage resistant variants (e.g., variants A1.4 plus A2.4, as described above). In some particularly preferred embodiments, the variants are selected among the third level of phage resistant variants. In such mixed bacterial cultures, when one of the variants is attacked by a given phage the other variants are not be attacked by the phage, due to their different phage sensitivities and the fermentation is not adversely affected.

In some further embodiments, a principal starter and a back-up starter are used. The principal starter is composed of a single strain. In some embodiments, this strain is of the first level of phage resistant variants, while in other preferred embodiments the strain is of the second level, and in still other more preferred embodiments, the strain is of the third level. In some preferred embodiments, the back up starter is based on a phage resistant variant obtained independently from the same parental strain. This second phage resistant variant differs from the other variant by its CRISPRs and is of the first level of phage resistant variants, while in other preferred embodiments the strain is of the second level, and in still other more preferred embodiments, the strain is of the third level. For example, in some embodiments, the principal starter is made of variant A1.4 and the back-up starter is made of strain A2.4. Upon first appearance of a phage during fermentation with the principal starter, this starter is discarded and replaced by the back up starter. In some more preferred embodiments, a third starter is also prepared as the back up starter that will serve as a back up for the back up. In some preferred embodiments, the starters are each made of multiply phage-resistant variants.

In yet further embodiments, the present invention provides methods and compositions suitable in rotation strategies. In some embodiments, instead of discarding the starter often attacked by phages, the starters are used in a cyclic way even if phage attack is observed. This strategy limits the number of starters to be developed. In some particularly preferred embodiments, the starters are each made of multiple phage resistant strains instead of a single one. This provides increased robustness to emerging phage. In still further embodiments, customized starters are provided. In some preferred embodiments, the phage resistant variants are produced to specifically combat phages that are present in a given fermentation plant or facility.

Typing

In a further aspect of the present invention, there is provided a method for identifying (eg. typing) a labelled bacterium.

In one embodiment, the identification step is performed by amplifying (eg. PCR amplifying) the CRISPR locus or a portion thereof.

A first primer may be designed to hybridize to a sequence that is located upstream of the first CRISPR repeat of a CRISPR locus. By way of example, the first primer may hybridize to part of the common leader sequence of the CRISPR locus. By way of further example, the first primer may hybridize to a neighboring gene that is located upstream of the CRISPR locus.

The second primer may hybridize downstream from at least the first CRISPR spacer or the at least first CRISPR spacer core. The second primer may hybridize as far as in the trailer or even in a downstream neighboring gene. Preferably, the second primer hybridizes within the CRISPR locus. Preferably, the second primer hybridizes at least partially to a downstream CRISPR spacer or CRISPR spacer core.

Following amplification, the tagging sequence may be identified using various methods that are known in the art.

By way of example, the tagging sequence may be identified by determining the amplification product restriction pattern. Accordingly, once the DNA comprising the CRISPR locus or a portion thereof has been amplified, it may be digested (eg. cut) with one or more restriction enzymes.

As used herein, the term "restriction enzymes" refers to enzymes (eg. bacterial enzymes), each of which cut double-stranded DNA at or near a specific nucleotide sequence. Restriction enzymes are well known in the art and may be readily obtained, for example, from variety of commercial sources (for example, New England Biolabs, Inc., Beverly, Mass.). Similarly, methods for using restriction enzymes are also generally well known and routine in the art. Restriction enzymes that produce between 10 and 24 fragments of DNA when cutting the CRISPR locus or a portion thereof may be used. Examples of such enzymes include, but are not limited to, AluI, MseI, and Tsp5091. Fragments of DNA obtained using restriction enzymes may be detected, for example, as bands by gel electrophoresis. Restriction enzymes may be used to create Restriction Fragment Length Polymorphisms (RFLPs).

RFLPs are generated by cutting ("restricting") a DNA molecule with a restriction endonuclease. Many hundreds of such enzymes have been isolated, as naturally made by bacteria. In essence, bacteria use such enzymes as a defensive system, to recognise and then cleave (restrict) any foreign DNA molecules that might enter the bacterial cell (e.g., a viral infection). Each of the many hundreds of different restriction enzymes has been found to cut (i.e., "cleave" or "restrict") DNA at a different sequence of the 4 basic nucleotides (A, T, G, C) that make up all DNA molecules, e.g., one enzyme might specifically and only recognise the sequence A-A-T-G-A-C, while another might specifically and only recognise the sequence G-T-A-C-T-A, etc. Depending on the unique enzyme involved, such recognition sequences may vary in length, from as few as 4 nucleotides to as many as 21 nucleotides. The larger the recognition sequence, the fewer restriction fragments will result, as the larger the recognition site, the lower the probability that it will repeatedly be found throughout the DNA.

By way of further example, the tagging sequence may be identified by determining or also determining the difference in size of the amplification product.

Separation may be achieved by any method suitable for separating DNA, including, but not limited to, gel electrophoresis, high performance liquid chromatography (HPLC), mass spectroscopy, and use of a microfluidic device. In one embodiment, the amplification products or DNA fragments are separated by agarose gel electrophoresis. Gel electrophoresis separates different sized charged molecules by their rate of movement through a stationary gel under the influence of an electric current. These separated amplification products or DNA fragments can easily be visualised, for example, by staining with ethidium bromide and by viewing the gel under UV illumination. The banding pattern reflects the sizes of the restriction digested DNA or the amplification products.

By way of further example, the tagging sequence may be identified by sequencing the amplification products.

The sequence of the amplified products may be obtained by any method known in the art, including automatic and manual sequencing methods. See, for example, Sambrook et al. (1989) *Molecular Cloning: A Laboratory Manual* (2d ed., Cold Spring Harbor Laboratory Press, Plainview, N.Y.; Roe et al. (1996) *DNA Isolation and Sequencing* (Essential Techniques Series, John Wiley & Sons).

Hybridisation methods are also within the scope of the present invention, either using a nucleic acid molecule as a probe, or a nucleic acid molecule capable of hybridising to a particular nucleotide sequence. See, for example, Sambrook et al. (1989) *Molecular Cloning: Laboratory Manual* (2d ed., Cold Spring Harbor Laboratory Press, Plainview, N.Y.).

In hybridisation techniques, the hybridisation probe(s) may be genomic DNA fragments, PCR-amplified products, or other oligonucleotides, and may comprise all or part of a known nucleotide sequence. In addition, it may be labelled with a detectable group such as $^{32}P$, or any other detectable marker, such as other radioisotopes, a fluorescent compound, an enzyme, or an enzyme co-factor. The term "labelled," with regard to the probe, is intended to encompass direct labelling of the probe by coupling (i.e., physically linking) a detectable substance to the probe, as well as indirect labelling of the probe by reactivity with another reagent that is directly labelled. Examples of indirect labelling include end-labelling of a DNA probe with biotin such that it can be detected with fluorescently labelled streptavidin.

Methods that encompass hybridisation techniques to detect or differentiate bacterial strains are also encompassed. These include, but are not limited to, Southern blotting (see, for example, Van Embden et al. (1993) *J. Clin. Microbiol.* 31:406-409), shift mobility assays (see, for example, U.S. Published Application No. 20030219778), sequencing assays using oligonucleotide arrays (see, for example, Pease et al. (1994) *Proc. Natl. Acad. Sci. USA* 91:5022-5026), spoligotyping (see, for example, Kamerbeek et al. (1997) *J. Clin. Microbiol.* 35:907-914), Fluorescent In Situ Hybridization (FISH) (see, for example, Amann et al. (1990) *J. Bacteriol.* 172:762-770) and heteroduplex tracking assays or heteroduplex mobility analysis (see, for example, White et al. (2000) *J. Clin. Micro.* 38:477-482).

The tagging sequence that is identified may be compared to with a phage sequence database and/or a bacterial sequence database. Typically, the tagging sequence will match with one or more sequences in the phage sequence database but not with the bacterial sequence database.

As new labeled bacteria are prepared using the methods described herein, a database of labels may be created allowing for the specific identification of bacteria that have been labeled.

In one aspect there is provided the use of a sequence obtained or obtainable from a bacteriophage (e.g., in the manufacture of a labelled bacterium) for labelling and/or identifying a bacterium, wherein said sequence is integrated at one end of the CRISPR locus of the parent bacterium.

In a further aspect there is provided the use of a sequence obtained or obtainable from a bacteriophage (eg. in the manufacture of a labelled bacterium) for labelling and/or identifying a bacterium, wherein said sequence comprises: (i) at least one sequence that is homologous (eg. identical) to a CRISPR repeat in the CRISPR locus of said bacterium; and (ii) a tagging sequence.

In a further aspect, there is provided the use of a sequence for labelling and/or identifying a bacterium (eg. in the manufacture of a labelled bacterium), wherein said sequence is obtained or obtainable by: (a) exposing a parent bacterium to a bacteriophage; (b) selecting a bacteriophage insensitive mutant; (c) comparing the CRISPR locus or a portion thereof from the parent bacterium and the bacteriophage insensitive mutant; and (d) selecting a sequence in the CRISPR locus or a portion thereof of the bacteriophage insensitive mutant that is not present in the parent bacterium.

CRISPR and Eukaryotes

As detailed herein, CRISPR has been shown to provide resistance against incoming nucleic acid in prokaryotes. Specifically, it was shown that CRISPR spacers showing homology to viral DNA (e.g., bacteriophage nucleic acid) provide resistance against the virus sharing sequence identity with at least one spacer sequence. However, it is also contemplated that the CRISPR system, including cas genes and/or proteins along with spacers, repeats, leader and trailer to cells not currently containing CRISPR loci will find use in providing resistance against nucleic acid de novo. Indeed in some embodiments, such manipulations find use with various eukaryotes, including but not limited to humans, other animals, fungi, etc. It is contemplated that the CRISPR system be transferred into eukaryotic cells utilizing any suitable method known in the art, including, but not limited to transformation via plasmids. In these embodiments, the CRISPR loci, as well as necessary transcription/translation signals are included in the plasmid DNA, to all for expression and function of the sequences in eukaryotic cells.

In some additional embodiments, the spacer sequences are engineered such that they have identity with viral sequences of interest infect the host involved. In some preferred embodiments, these methods and compositions provide resistance to the host cell against viruses that share sequence identity with the CRISPR spacer introduced into the cell. In some particularly preferred embodiments, the viruses include, but are not limited to HIV, orthomyxoviruses, paramyxoviruses, pseudomyxoviruses, RSV, influenza, rubeola, varicella, rubella, coronaviruses, hepatitis viruses, caliciviruses, poxviruses, herpesviruses, adenoviruses, papovaviruses, papillomaviruses, enteroviruses, arboviruses, rhabdoviruses, arenaviruses, arboviruses, rhinoviruses, reoviruses, coronaviruses, reoviruses, rotaviruses, retroviruses, etc. In further embodiments, specific targeting of highly conserved nucleic acid sequences in CRISPR spacers provides increased resistance against such viruses in eukaryotic cells. In some particularly preferred embodiments, the eukaryotic cells are human cells.

CRISPR and Generation of Phage-Resistant Mutants

During the development of the present invention, experiments were conducted to determine whether CRISPR loci are altered during the natural generation of phage-resistant mutants. A phage-host model system was selected, consisting of a phage-sensitive wild-type *S. thermophilus* strain widely used in the dairy industry, DGCC7710 (WT) and two distinct, but closely related virulent bacteriophages isolated from industrial yogurt samples, namely phage 858 and phage 2972 (Levesque et al., Appl. Environ. Microbiol., 71:4057 [2005]). Nine phage-resistant mutants were independently generated by challenging the WT strain with phage 858, phage 2972 or simultaneously with both, and their CRISPR loci were analyzed. Differences were consistently observed at the CRISPR1 locus, where 1 to 4 additional spacers were inserted next to the 32 spacers present in the WT strain (See, FIG. 9). The addition of new spacers in response to phage infection appeared to be polarized towards one end of the CRISPR1 locus. This is consistent with previous observations of spacer hypervariability at the leader end of the CRISPR locus in various strains (See e.g., See, Pourcel et al., Microbiol., 151:653 [2005]; and Lillestol et al., Archaea 2:59 [2006]). Sequence analysis of the additional spacers inserted in the CRISPR1 locus of the various phage-resistant mutants revealed similarity to sequences found within the genomes of the phages used in the challenge. Similarities were observed throughout the phage genomes, in most functional modules, both on the coding and non-coding strands. No particular sequence, gene or functional group seemed to be targeted specifically. These results indicate that upon becoming resistant to bacteriophages, the CRISPR1 locus was modified by the integration of novel spacers apparently derived from phage DNA. However, it is not intended that the present invention be limited to any specific mechanism.

Figure 9:
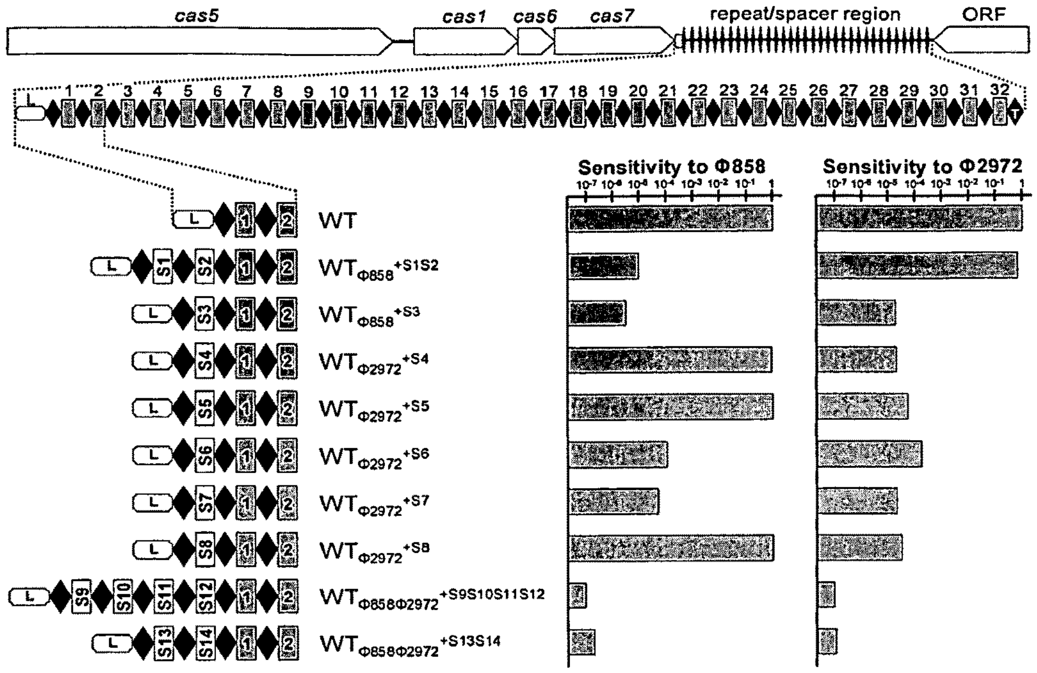
FIG. 9 provides a graphical representation showing an overview of the *S. thermophilus* CRISPR1 locus, the newly acquired spacers in phage-resistant mutants, and corresponding phage sensitivity. The CRISPR1 locus of DGCC7710 (WT) is at the top. The repeat/spacer region of WT is in the middle: repeats (black diamonds), spacers (numbered gray boxes), leader (L, white box) and terminal repeat (T, black diamond). At the bottom, the spacer content on the leader side of the locus in phage-resistant mutants is detailed on the left, with newly acquired spacers (white boxes, S1-S14). On the right, the sensitivity of each strain to phages 858 and 2972 is represented as a histogram of the efficiency of plaquing (EOP), which is the plaque count ratio of a mutant strain to that of the wild-type.

Surprisingly, it was observed that some strains were resistant to both phages while others were resistant only to the phage used in the challenge (See, FIG. 9). The phage-resistance profile seemed to be correlated to the spacer content whereby strains with spacers showing 100% identity to sequences conserved in both phages were resistant to both phages, such as spacers S3, S6 and S7. In contrast, when nucleotide polymorphisms were observed between the spacer and the phage sequence (from 1 to 15 SNPs over 29 or 30 nucleotides), the spacer did not seem to provide resistance, such as spacers S1, S2, S4, S5 and S8 (See, FIG. 9).

Additionally, when several spacers were inserted (S9-S14), phage-resistance levels were higher. These findings indicate that the CRISPR1 locus is subject to dynamic and rapid evolutionary changes driven by phage exposure. These results indicate that CRISPR loci can indeed be altered during the generation of phage-resistant mutants and establish a link between CRISPR content and phage sensitivity. Thus, it is contemplated that the presence of a CRISPR spacer identical to a phage sequence provides resistance against phages containing this particular sequence.

To determine whether CRISPR spacer content defines phage resistance, the CRISPR1 locus was altered by adding and deleting spacers, and the strain sensitivity to phages was tested. All constructs were generated and integrated into the *S. thermophilus* chromosome using methods known in the art (See e.g., Russell and Klaenhammer, Appl. Environ. Microbiol., 67:4361 [2001]). The spacers and repeats in the CRISPR1 locus of strain $WT_{\Phi 858}{}^{+S1S2}$ were removed and replaced with a single repeat without any spacer. The resulting strain $WT_{\Phi 858}{}^{+S1S2}\Delta$CRISPR1 was sensitive to phage 858, indicating that the phage resistance of the original phage-resistant mutant ($WT_{\Phi 858}{}^{+S1S2}$) was probably linked to the presence of S1 and S2 (See, FIG. 10).

In addition, to determine whether adding spacers provides novel phage resistance, the CRISPR1 locus of strain $WT_{\Phi 2972}{}^{+S4}$ was replaced with a version only containing spacers S1 and S2. The phage sensitivity of the resultant construct was then tested. The resulting strain $WT_{\Phi 2972}{}^{+S4}$::pS1S2 gained resistance to phage 858, suggesting that these two spacers have the ability to provide phage resistance de novo (See, FIG. 10). These observed modifications establish a link between the CRISPR spacer content and phage resistance.

Figure 10:
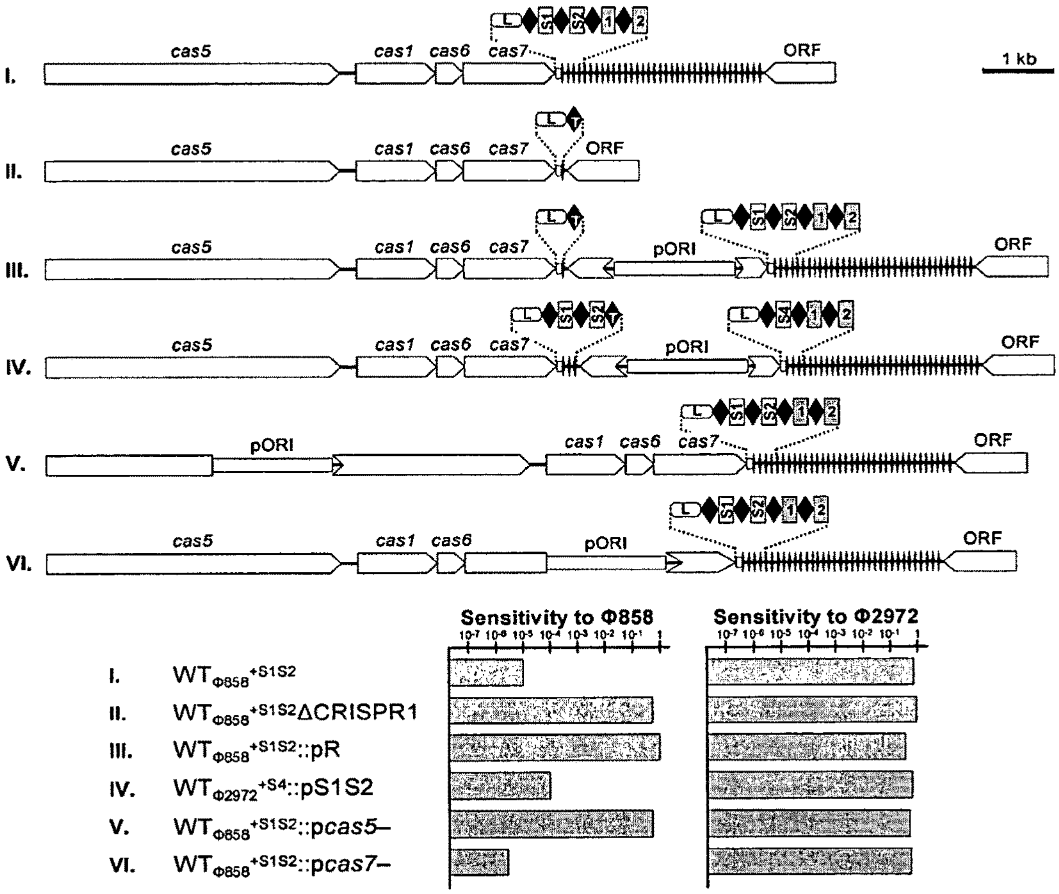
FIG. 10 provides CRISPR spacer engineering, cas gene inactivation and corresponding phage sensitivity. I, mutant $WT_{\Phi858}^{+S1S2}$; II, mutant $WT_{\Phi858}^{+S1S2}\Delta$CRISPR1 where CRISPR1 was deleted; III, mutant $WT_{\Phi858}^{+S1S2}$::pR where CRISPR1 was displaced and replaced with a unique repeat; IV, $WT_{\Phi2972}^{+S4}$::pS1S2, mutant of strain $WT_{\Phi2972}^{+S4}$ where CRISPR1 was displaced and replaced with a version containing S1 and S2; V, $WT_{\Phi858}^{+S1S2}$::pcas5- with cas5 inactivated; VI, $WT_{\Phi858}^{+S1S2}$::pcas7- with cas7 inactivated. pORI indicates the integrated plasmid (12). The phage sensitivity of each strain to phages 858 and 2972 is represented at the bottom as a histogram of the efficiency of plaquing (EOP).

In the process of generating strain $WT_{\Phi 858}{}^{+S1S2}\Delta$CRISPR1, $WT_{\Phi 858}{}^{+S1S2}$::pR, a variant that contains the integration vector with a single repeat inserted between the cas genes and the native CRISPR1 locus was created (See, FIG. 10). Unexpectedly, strain $WT_{\Phi 858}{}^{+S1S2}$::pR was sensitive to phage 858, although spacers S1 and S2 remained present on the chromosome (See, FIG. 10). Similarly, the $WT_{\Phi 2972}{}^{+S4}$::pS1S2 construct lost the resistance to phage 2972, although spacer S4 is present in the chromosome (See, FIG. 10). These results indicated that spacers alone did not provide resistance, and perhaps they have to be in a particular genetic context to be effective.

Although early experiments suggested involvement in DNA repair (Makarova et al., Nucl. Acids Res., 30:482 [2002]), the current hypothesis is that cas genes (Jansen et al., Mol. Microbiol., 43:1565 [2002]; and Haft et al., PloS Comput. Biol., 1:e60 [2005]) are involved in CRISPR-mediated immunity (Makarova et al., Biol. Direct. 1:7 [2006]). In additional experiments, two cas genes in strain $WT_{\Phi 858}{}^{+S1S2}$ were inactivated, namely cas5 (COG3513) and cas7, which are equivalent to str0657/stu0657 and str0660/stu0660, respectively (See, Bolotin et al., Nat. Biotechnol., 22:1554 [2004]; and Bolotin et al., Microbiol., 151:2551 [2005]). The cas5 inactivation resulted in loss of the phage resistance (See, FIG. 10). In addition, it is possible that Cas5 acts as a nuclease, since it contains a HNH-type nuclease motif. In contrast, inactivating cas7 did not alter the resistance to phage 858 (See, FIG. 10). However, it is not intended that the present invention be limited to any particular mechanism. In addition, experiments to generate CRISPR1 phage-resistant mutants from the cas7 knockout did not work. Although it is not intended that the present invention be limited to any particular mechanism, this may be because Cas7 is involved in the synthesis and/or insertion of new spacers and additional repeats.

Upon testing sensitivity of the phage-resistant mutants, it was found that plaque formation was dramatically reduced, but that a relatively small population of bacteriophage retained the ability to infect the mutants. Phage variants derived from phage 858 that retained the ability to infect $WT_{\Phi 858}{}^{+S1S2}$ were further analyzed. In particular, the sequences of the genome region corresponding to additional spacers S1 and S2 in two virulent phage variants were investigated. In both cases, the genome sequence of the phage variant was mutated and two distinct single nucleotide polymorphisms were identified in the sequence corresponding to spacer S1 (See, FIG. 13).

Overall, prokaryotes appear to have evolved a nucleic-acid based "immunity" system whereby specificity is dictated by the CRISPR spacer content, while the resistance is provided by the Cas enzymatic machinery. Additionally, it was speculated that some of the cas genes that do not directly provide resistance are actually involved in the insertion of additional CRISPR spacers and repeats, as part of an adaptive "immune" response. This nucleic-acid based system contrasts with amino-acid based counterparts in eukaryotes whereby adaptative immunity is not inheritable. The inheritable nature of CRISPR spacers supports the use of CRISPR loci as targets for evolutionary, typing and comparative genomic studies (See, Pourcel et al., supra; Groenen et al., Mol. Microbiol., 10:1057 [1993]; Mongodin et al., J. Bacteriol., 187:4935 [2005]; and DeBoy et al., J. Bacteriol., 188:2364 [2006]). Because this system is reactive to the phage environment, it likely plays a significant role in prokaryotic evolution and ecology and provides a historical perspective of phage exposure, as well as a predictive tool for phage sensitivity. However, it is not intended that the present invention be limited to any particular mechanism. Nonetheless, the present invention provides methods and compositions for utilizing the CRISPR/cas system as a virus defense means, and also potentially to reduce the dissemination of mobile genetic elements and the acquisition of undesirable traits such as antimicrobial resistance genes and virulence markers. In some embodiments, it is further contemplated from a phage evolution perspective, the integrated phage sequences within CRISPR loci also provide additional anchor points to facilitate recombination during subsequent phage infections, thus increasing the gene pool to which phages have access (See, Hendrix et al., Proc. Natl. Acad. Sci. USA 96:2192 [1999]). Since CRISPR loci are found in the majority of bacterial genera, and are ubiquitous in Archaea (See, Jansen et al., supra; Lillestol et al., supra; and Goode and Bickerton J. Mol. Evol., 62:718 [2006]), they provide new insights in the relationship and co-directed evolution between prokaryotes and their predators.

Biocontrol Phages

The present invention also provides methods and compositions for the development of phages as biocontrol agents. As indicated herein, bacteria can become resistant to phage attack by incorporating phage derived sequences (spacers) into an active CRISPR loci. Phage can escape this resistance by mutation within the genome sequence corresponding to the spacer or the CRISPR motif recognition sequence that corresponds to a given Cas-CRISPR system. Through iterative rounds of phage challenge to create host strain CRISPR-mediated phage resistant derivatives and isolation of phage escape mutants, the present invention provides phages that have been altered within CRISPR target sequences and/or putative CRISPR recognition sites that direct spacer insertion. Further, the present invention provides phages that have been synthetically designed such that the CRISPR motif sequence for a given Cas-CRISPR system has been eliminated. These "altered" phages, applied as a cocktail or in a "sequential rotation scheme" reduce the ability of target bacteria to adapt resistance via the CRISPR system. Indeed, the present invention provides a diverse set of virulent phage for use as biocontrol agents. In particularly preferred embodiments, this diversity is targeted at the CRISPR directed mechanism of phage resistance, such that the ability of the host organism to rapidly evolve against phage attack (via CRISPR) is severely reduced or eliminated. The administration of the diverse phage, either as a cocktail or in a sequential rotation further reduces the possibility of the host organism to adapt or evolve CRISPR-directed phage resistance.

Phages are natural antimicrobial agents that have been extensively studied as an alternative therapeutic agent to antibiotics. This interest has been recently renewed, due to the proliferation of multiple-antibiotic resistant pathogens. As with antibiotics, bacteria have developed multiple mechanisms to overcome phage attack. The present invention provides methods and compositions involving the use of Cas-CRISPR in mediating phage resistance to generate a diverse phage population, to create synthetic phages devoid of CRISPR motif sequences, as well as methods for administering such phage that will reduce the ability of a target organism to develop resistance against the phage.

As detailed herein, Cas-CRISPR systems have been described in a wide range of organisms which include examples of pathogenic genera. Upon phage infection, bacteria escaping lysis can be found to contain new spacer sequence(s) within a CRISPR locus. The new spacer is typically of a defined length that is characteristic for a given CRISPR locus and derived from the attacking phage genome to which it confers resistance. As the level of resistance conferred by a single spacer is often not complete, phage can escape the mechanism. Analysis of "escape-phages" indicated that the genomes were mutated in or proximal to the corresponding spacer sequence found in the resistant host variant. Furthermore, the "escape-phages" are fully virulent to the CRISPR-mediated host variant from which they were derived.

One unique aspect of therapeutic phage, distinguishing it from traditional antibiotics, is the ability to propagate exponentially in conjunction with the infected bacteria. While this can be advantageous from a pharmacological perspective, it also provides unique opportunities for the phage to evolve towards adaptive response of the targeted bacteria to phage attack.

Bacteria have developed several defense mechanisms against virulent phage. As indicated herein, the Cas-CRISPR loci play a role in conferring bacterial phage resistance. Following phage infection, analysis of surviving bacteria found that some isolates had inserted a new spacer element within their resident CRISPR locus, the sequence of which was identical to that found in the corresponding phage genome. When challenged with phage, these first generation CRISPR-mediated phage resistant variants give rise to plaques; the phage of which were found to be fully infective on both parent and derivative. Analysis of these "CRISPR-escape" phage indicated that their genomes were mutated in the sequence corresponding to the CRISPR spacer harbored by the phage resistant variant or in a proximal sequence believed to direct spacer insertion and identified as the CRISPR motif specific to a given Cas-CRISPR system. Therefore the "CRISPR-escape" phage is potentially more virulent than the parent and first-generation variants, as this phage is capable of infecting both the parent strain and the first generation CRISPR variant.

As indicated above, CRISPR loci have been identified in several genera/species of bacteria that include examples of known pathogens and spoilage microorganisms. Also as described herein, the present invention provides methods and compositions for utilization of CRISPR loci in combination with Cas proteins to confer "immunity" to invading foreign DNA, in particular, bacteriophages. Also as described herein, bacterial strains harbouring "active" CRISPR-cas loci containing a spacer that is identical to a corresponding sequence within a phage genome (i.e., a "protospacer"), confers upon that bacterial strain, resistance to the phage. In some preferred embodiments, the genome sequences of the biocontrol phage are known. In some particularly preferred methods, the isolated target microorganism is examined for the presence of CRISPR loci. In some preferred embodiments, PCR using specific primers for conserved sequences that flank CRISPR loci of the target microorganism finds use. In some preferred embodiments, amplification product(s) are sequenced compared with the genome sequence of the biocontrol phage. In some preferred embodiments, the generation of CRISPR phage resistant variants and analysis of the spacer/protospacer provides means to identify the specific CRISPR motif. Once identified, the sequence information is used to design and synthesize a phage devoid of the CRISPR motif Thus, the resulting phage is insensitive to CRISPR-cas mediated resistance. In these assessments, the absence of spacers with similarity to the phage genome indicates the susceptibility of the target microorganism to the biocontrol phage. Thus, the biocontrol phage has a greater degree of virulence and efficacy as a biocontrol agent.

The present invention provides methods and compositions suitable for use in the food, feed, medical and veterinary industries to generate phage with broader host range and method of application for more effective biocontrol of bacteria. The present invention provides means to produce a sufficient number of altered phage (in response to CRISPR) to significantly reduce the ability of the native bacteria to evolve an effective CRISPR-mediated resistance. The present invention also provides methods of application/administration designed such that the rate of evolution by the native bacteria is significantly reduced.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: ° C. (degrees Centigrade); rpm (revolutions per minute); $H_2O$ (water); HCl (hydrochloric acid); aa (amino acid); bp (base pair); kb (kilobase pair); kD (kilodaltons); gm (grams); μg and ug (micrograms); mg (milligrams); ng (nanograms); μl and ul (microliters); ml (milliliters); mm (millimeters); nm (nanometers); μm and um (micrometer); M (molar); mM (millimolar); μM and uM (micromolar); U (units); V (volts); MW (molecular weight); sec (seconds); min(s) (minute/minutes); hr(s) (hour/hours); MOI (multiplicity of infection); EOP (efficiency of plaquing); PFU (plaque-forming units); $MgCl_2$ (magnesium chloride); NaCl (sodium chloride); $OD_{420}$ (optical density at 420 nm); PAGE (polyacrylamide gel electrophoresis); EtOH (ethanol); PBS (phosphate buffered saline [150 mM NaCl, 10 mM sodium phosphate buffer, pH 7.2]); SDS (sodium dodecyl sulfate); Tris (tris(hydroxymethyl)aminomethane); w/v (weight to volume); v/v (volume to volume); Amicon (Amicon, Inc., Beverly, Mass.); ATCC (American Type Culture Collection, Manassas, Va.); Amersham (Amersham Biosciences, Inc., Piscataway, N.J.); NEB (New England Biolabs, Beverly, Mass.); Becton Dickinson (Becton Dickinson Labware, Lincoln Park, N.J.); BioRad (BioRad, Richmond, Calif.); Clontech (CLONTECH Laboratories, Palo Alto, Calif.); Difco (Difco Laboratories, Detroit, Mich.); GIBCO BRL or Gibco BRL (Life Technologies, Inc., Gaithersburg, Md.); Sigma (Sigma Chemical Co., St. Louis, Mo.); and Sorvall (Sorvall Instruments, a subsidiary of DuPont Co., Biotechnology Systems, Wilmington, Del.).

The present invention utilizes, unless otherwise indicated, conventional techniques of chemistry, molecular biology, microbiology, recombinant DNA and immunology, which are within the capabilities of a person of ordinary skill in the art. Such techniques are well known to those of skill in the art.

As used herein, DGCC7710 is also referred to as "WT"; DGCC7710RH1 is also referred to as "DGCC7710-RH1" and "RH1"; DGCC7710RH2 is also referred to as "DGCC7710-RH2" and "RH-2"; DGCC7778cas1 is also referred to as "DGCC7778cas1KO," "CAS1KO," and "cas1 KO"; DGCC7778cas4 is also referred to as "DGCC7778cas4KO"; DGCC7778 is also referred to as "WTΦ858+S1S2"; DGCC7778RT is also referred to as "WTΦ858+S1S2::pR"; DGCC7778RT' is also referred to as "WTΦ858+S1S2ΔCRISPR1"; DGCC7710-R2 is also referred to as "WTΦ2972+S4"; and DGCC7710-R2S1S2 is also referred to as "$WT_{\Phi 2972}^{+S4}$::pS1S2."

Example 1

Manipulation of Phage-Specific Spacers

In this Example, experiments conducted to manipulate phage-specific spacers are described. In some experiments, a phage specific spacer was inserted into an existing, functional CRISPR to provide resistance to the corresponding phage are described. The bacterial strain used was *Streptococcus thermophilus* ST0089 and the phage was phage 2972. *S. thermophilus* ST0089 is an industrially important strain used in the manufacture of yogurt. It is genetically amenable to manipulation, and susceptible to the well-known virulent phage 2972.

The CRISPR loci were determined in strain ST0089. This was determined preferentially by sequencing the entire genome of ST0089. Alternatively, the CRISPR loci are identified via PCR using primer sets with sequences identical to *S. thermophilus* CRISPR elements previously identified.

Once identified, the CRISPR loci sequences were determined as well as the proximal regions containing the relevant cas genes.

At least one particular CRISPR-cas locus was selected for further manipulation. Functionality of this locus was ascertained through in silico analysis of the spacer regions and their homologies to phage DNA sequences (i.e., absence and/or presence of spacer sequences and correlation to phage infectivity with strain ST0089). In the absence of this correlation, functionality was assumed, based on the presence of all documented elements (i.e., repeats, spacers, leader sequences, and cas genes that putatively encode full length proteins).

A suitable spacer sequence(s) was chosen from the genome of phage 2972. The criteria used to select the spacer were generally based on the length of the spacers within the selected CRISPR locus and the identity (preferably approximately 100%) to the phage sequence. Indeed, any suitable phage sequence finds use in various embodiments of the present invention.

In some embodiments, a CRISPR unit consisting of a phage 2972 spacer sequence, flanked by two repeating elements (identical to the selected CRISPR locus) was chemically synthesized. By definition, this synthetic "CRISPR unit" is approximately 100 bp in length and is too short for ensuring integration into the CRISPR locus.

Therefore, additional flanking DNA was constructed along with the CRISPR unit. A minimum of 500 bp of homologous DNA, identical to the targeted CRISPR locus that flanks the synthetic CRISPR unit, was produced in order to facilitate integration.

In additional embodiments, there are multiple approaches. In one embodiment, a construct emulates the addition of a new spacer onto the existing CRISPR. In some alternative embodiments, the entire CRISPR locus is replaced with the synthetic CRISPR unit.

The resulting CRISPR integrant was verified through DNA sequencing of the CRISPR locus prior to biological testing. In addition, phage sensitivity patterns of the CRISPR integrant against phage 2972 were tested and compared with the parental strain.

The constructed CRISPR integrant successfully demonstrated the direct correlation between the presence of a specific spacer within the proper context of CRISPR-cas.

In additional experiments, insertion of a spacer homologous to a phage DNA into a recipient cell was performed. In these experiments, a new CRISPR spacer was designed from phage DNA (with 100% identity to phage DNA) within the anti-receptor gene and inserted into the cell in a CRISPR locus. The anti-receptor gene was targeted because CRISPR spacers from other strains have been found to show similarity to phage anti-receptor genes. Four strains bearing spacers showing identity to phage anti-receptor genes were resistant to the particular phage. The mutant was exposed to phage and found to be resistant.

In additional experiments, a spacer was inserted into an original host, but not in a CRISPR locus. The resulting mutant retained its sensitivity to the phage. Thus, these experiments showed that the spacer needs to be in a particular environment within the context of a CRISPR and cas genes.

In other experiments, a particular CRISPR spacer was deleted from a naturally occurring CRISPR locus. This deletion removed immunity against a given phage and the host became sensitive (i.e., loses resistance) to the phage to which the spacer was homologous. Results from these experiments are provided in FIG. 10.

In yet additional experiments, whole CRISPR repeat-cas combinations were inserted into a recipient cell in order to provide immunity against incoming nucleic acid.

In additional experiments, a plasmid comprising a CRISPR spacer was prepared using the methods set forth herein. Attempts to transfer this plasmid into cells that contain the same spacer were unsuccessful. However, plasmids that do not contain the spacer can be transformed into cells. FIGS. 11 and 12 illustrate these results.

In further experiments, CRISPR-cas combinations present in two different strains were exchanged. This exchange of spacers was shown to modify their phenotypes (phage sensitivity/resistance). As indicated herein when S1S2 is introduced into a strain with S4, phage sensitivity was switched (See, FIG. 10).

In additional experiments, different cas-CRISPR-repeat combinations are prepared. Not only are cas genes or proteins required, but specific cas-CRISPR repeat pairs are required for functionality. When cas genes or proteins are provided from another CRISPR locus, the strain remains sensitive to the phage.

In still additional experiments, one or more cas genes (from a functional CRISPR-cas unit) were deleted. Cas genes are necessary for immunity to be provided. Cas mutants are still sensitive to the phage, despite the presence of the spacer identical to phage DNA. In these experiments, cas5 (formerly known as cas1) and cas7 (formerly known as cas4) were deleted. Cas5 was shown to be required for resistance. In addition, cas7 was shown to be required for integration of new spacers.

In additional experiments, cas genes are provided in trans to the host. Where the cas gene is knocked out, immunity is restored.

Example 2

Integration of CRISPR Spacer(s)

In these experiments, integration of a CRISPR spacer into the CRISPR locus was shown to provide resistance against a bacteriophage to which the CRISPR spacer shows identity. In these experiments, *S. thermophilus* strain DGCC7710RH1 was produced.

*Streptococcus thermophilus* strain DGCC7710 (deposited at the French "Collection Nationale de Cultures de Micro-organismes" under number CNCM 1-2423) possesses at least 3 CRISPR loci: CRISPR1, CRISPR2, and CRISPR3. In *S. thermophilus* strains CNRZ1066 and LMG18311 for which the complete genome sequence is known (Bolotin et al., Microbiol., 151:2551-1561 [2005]. CRISPR1 is located at the same chromosomal locus: between str0660 (or stu0660) and str0661 (or stu0661).

In strain DGCC7710, CRISPR1 is also located at the same chromosomal locus, between highly similar genes. CRISPR1 of strain DGCC7710 contains 33 repeats (including the terminal repeat), and thus 32 spacers.

All these spacers are different from each other. Most of these spacers are new (i.e, not previously described within CRISPR loci), but four spacers close to the CRISPR1 trailer are identical to already known CRISPR1 spacers:

- the $28^{th}$ spacer of DGCC7710 is 100% identical to the $31^{st}$ CRISPR1 spacer of strain CNRZ1575 (Genbank accession number DQ072991);
- the $30^{th}$ spacer of DGCC7710 is 100% identical to the $27^{th}$ CRISPR1 spacer of strain CNRZ703 (Genbank accession number DQ072990);
- the $31^{st}$ spacer of DGCC7710 is 100% identical to the $28^{th}$ CRISPR1 spacer of strain CNRZ703 (Genbank accession number DQ072990);
- the $32^{nd}$ spacer of DGCC7710 is 100% identical to the $30^{th}$ CRISPR1 spacer of strain CNRZ703 (Genbank accession number DQ072990).

During the development of the present invention, *S. thermophilus* strain DGCC7710RH1 was isolated as a natural phage resistant mutant using DGCC7710 as the parental strain, and phage D858 as the virulent phage. D858, a bacteriophage belonging to the Siphoviridae family of viruses was used.

CRISPR1 of strain DGCC7710-RH1 contains 34 repeats (including the terminal repeat), and thus 33 spacers. When compared to the CRISPR1 sequence of *S. thermophilus* strain DGCC7710, the CRISPR1 sequence of *S. thermophilus* strain DGCC7710-RH1 possesses one additional new spacer (and one additional repeat which flanks the new spacer) at one end of the CRISPR locus (i.e., close to the leader, at the 5' end of the CRISPR locus). All the other spacers of CRISPR1 locus remained unchanged.

The CRISPR1 sequence (5'-3') of strain DGCC7710-RH1 is provided below:

```
                                                   (SEQ ID NO: 682)
caaggacagttattgattttataatcactatgtgggtataaaaacgtcaaaatttcatttgag

GTTTTTGTACTCTCAAGATTTAAGTAACTGTACAACtcaacaattgcaacatcttataacccactt

GTTTTTGTACTCTCAAGATTTAAGTAACTGTACAACtgtttgacagcaaatcaagattcgaattgt

GTTTTTGTACTCTCAAGATTTAAGTAACTGTACAACaatgacgaggagctattggcacaacttaca

GTTTTTGTACTCTCAAGATTTAAGTAACTGTACAACcgatttgacaatctgctgaccactgttatc

GTTTTTGTACTCTCAAGATTTAAGTAACTGTACAACacacttggcaggcttattactcaacagcga

GTTTTTGTACTCTCAAGATTTAAGTAACTGTACAACctgttccttgttcttttgttgtatcttttc

GTTTTTGTACTCTCAAGATTTAAGTAACTGTACAACttcattcttccgtttttgtttgcgaatcct

GTTTTTGTACTCTCAAGATTTAAGTAACTGTACAACgctggcgaggaaacgaacaaggcctcaaca

GTTTTTGTACTCTCAAGATTTAAGTAACTGTACAACcatagagtggaaaactagaaacagattcaa

GTTTTTGTACTCTCAAGATTTAAGTAACTGTACAACataatgccgttgaattacacggcaaggtca

GTTTTTGTACTCTCAAGATTTAAGTAACTGTACAACgagcgagctcgaaataatcttaattacaag

GTTTTTGTACTCTCAAGATTTAAGTAACTGTACAACgttcgctagcgtcatgtggtaacgtattta

GTTTTTGTACTCTCAAGATTTAAGTAACTGTACAACggcgtcccaatcctgattaatacttactcg

GTTTTTGTACTCTCAAGATTTAAGTAACTGTACAACaacacagcaagacaagaggatgatgctatg

GTTTTTGTACTCTCAAGATTTAAGTAACTGTACAACcgacacaagaacgtatgcaagagttcaag

GTTTTTGTACTCTCAAGATTTAAGTAACTGTACAACacaattcttcatccggtaactgctcaagtg
```

-continued

```
GTTTTTGTACTCTCAAGATTTAAGTAACTGTACAACaattaagggcatagaaagggagacaacatg

GTTTTTGTACTCTCAAGATTTAAGTAACTGTACAACcgatatttaaaatcattttcataacttcat

GTTTTTGTACTCTCAAGATTTAAGTAACTGTACAACgcagtatcagcaagcaagctgttagttact

GTTTTTGTACTCTCAAGATTTAAGTAACTGTACAACataaactatgaaattttataatttttaaga

GTTTTTGTACTCTCAAGATTTAAGTAACTGTACAACaataatttatggtatagcttaatatcattg

GTTTTTGTACTCTCAAGATTTAAGTAACTGTACAACtgcatcgagcacgttcgagtttaccgtttc

GTTTTTGTACTCTCAAGATTTAAGTAACTGTACAACtctatatcgaggtcaactaacaattatgct

GTTTTTGTACTCTCAAGATTTAAGTAACTGTACAACaatcgttcaaattctgttttaggtacattt

GTTTTTGTACTCTCAAGATTTAAGTAACTGTACAACaatcaatacgacaagagttaaaatggtctt

GTTTTTGTACTCTCAAGATTTAAGTAACTGTACAACgcttagctgtccaatccacgaacgtggatg

GTTTTTGTACTCTCAAGATTTAAGTAACTGTACAACcaaccaacggtaacagctactttttacagt

GTTTTTGTACTCTCAAGATTTAAGTAACTGTACAACataactgaaggataggagcttgtaaagtct

GTTTTTGTACTCTCAAGATTTAAGTAACTGTACAACtaatgctacatctcaaaggatgatcccaga

GTTTTTGTACTCTCAAGATTTAAGTAACTGTACAACaagtagttgatgacctctacaatggtttat

GTTTTTGTACTCTCAAGATTTAAGTAACTGTACAACacctagaagcatttgagcgtatattgattg

GTTTTTGTACTCTCAAGATTTAAGTAACTGTACAACaattttgccccttctttgccccttgactag

GTTTTTGTACTCTCAAGATTTAAGTAACTGTACAACaccattagcaatcatttgtgcccattgagt

GTTTTTGTACTCTCAAGATTTAAGTAACTGTACAGT

Ttgattcaacataaaaagccagttcaattgaacttggcttt
```

In the above sequence, the leader has the sequence:

```
                                         (SEQ ID NO: 688)
5' caaggacagttattgattttataatcactatgtgggtataaaaacgt

caaaatttcatttgag 3'
```

The integrated sequence (GTTTTTGTACTCTCAAGATTTAAGTAACTGTACAACtcaacaattgcaacatcttataacccactt: SEQ ID NO:689) comprising a CRISPR repeat is shown in upper case and a CRISPR spacer (i.e., tagging sequence) in lower case. The terminal repeat and trailer sequences of the CRISPR repeat are shown below:

```
Terminal repeat:
                                                 (SEQ ID NO: 3)
5' gtttttgtactctcaagatttaagtaactgtacagt 3'

Trailer sequence:
                                               (SEQ ID NO: 691)
5' ttgattcaacataaaaagccagttcaattgaacttggcttt 3'
```

The sequence of the new spacer 5-TCAACAATTGCAACATCTTATAACCCACTT (SEQ ID NO:534) exists within the D858 phage genome.

The sequence of the spacer is found between positions 31921 and 31950 bp (i.e., on the plus strand) of D858's genome (and has 100% identity to the D858 genomic sequence over 30 nucleotides):

```
Spacer     1 tcaacaattgcaacatcttataacccactt    30 (SEQ ID NO: 534)
             ||||||||||||||||||||||||||||||
D858   31921 tcaacaattgcaacatcttataacccactt 31950 (SEQ ID NO: 534)
```

The new spacer that is integrated into the CRISPR1 locus of *S. thermophilus* strain DGCC7710-RH1 confers resistance to phage D858 to this strain, as shown in FIG. 1 and Table 2-1.

TABLE 2-1

| | | Phage 2972 | | Phage 858 | |
|---|---|---|---|---|---|
| Strains | BIM on[1] | Phage sensitivity[2] | Spacer-phage homology[3] | Phage sensitivity[2] | Spaceer-Phage homology[3] |
| DGCC7710 | — | S | Ctrl | S | Ctrl |
| DGCC7778 | 858 | S | >10 SNPs | R | 100% (2 spacers) |

TABLE 2-1-continued

| | | Phage 2972 | | Phage 858 | |
|---|---|---|---|---|---|
| Strains | BIM on[1] | Phage sensitivity[2] | Spacer-phage homology[3] | Phage sensitivity[2] | Spaceer-Phage homology[3] |
| DGCC7710-RH1 | 858 | R | 100% | R | 100% |
| DGCC7710-RH2 | 858 | R | 100% | R | 100% |
| DGCC7778RT | 858 | S | >10 SNPs | S | 100% but not next to cas |
| DGCC7778RT' | 858 | S | >10 SNPs | S | No spacers left |
| DGCC7778cas1 | 858 | S | >10 SNPs | S | 100% (2 spacers) but cas1 KO |
| DGCC7778cas4 | 858 | S | >10 SNPs | R | 7100% (2 spacers) but cas4 KO |
| DGCC7710-R2 | 2972 | R | 100% (1 spacer) | S | 5 SNPs |
| DGCC7710-R2S1S2 | 2972 | S | 100% but not next to cas | R | S1S2 are 100% identical to phage 858 |

[1]Phage used to generate Bacteriophage Insensitive Mutants (BIMs).
[2]Phage sensitivity of the strain, S = sensitive, R = resistant as determined by spot and plaque assays
[3]Homology between the new spacer of the mutant, and the DNA sequence of the phage used to generate the mutant. Phages retained the ability to adsorb to the mutants.

In addition, during the development of the present invention, *S. thermophilus* strain DGCC7710-RH2 was isolated as a natural phage resistant mutant using *S. thermophilus* strain DGCC7710 as the parental strain, and phage D858 as the virulent phage.

CRISPR1 of *S. thermophilus* strain DGCC7710-RH2 contains 34 repeats (including the terminal repeat), and thus 33 spacers. When compared to the CRISPR1 sequence of *S. thermophilus* strain DGCC7710, the CRISPR1 sequence of *S. thermophilus* strain DGCC7710-RH2 possesses one additional new spacer (and one additional repeat which flanks the new spacer) at one end of the CRISPR locus (i.e., close to the leader, at the 5' end of the CRISPR locus). All the other spacers of CRISPR1 locus remained unchanged.

The CRISPR1 sequence (5'-3') of strain DGCC7710-RH2 is shown below:

caaggacagttattgattttataatcactatgtgggtataaaaacgtcaaaatttcatttgag

GTTTTTGTACTCTCAAGATTTAAGTAACTGTACAACttacgtttgaaaagaatatcaaatcaatga

GTTTTTGTACTCTCAAGATTTAAGTAACTGTACAACtgtttgacagcaaatcaagattcgaattgt

GTTTTTGTACTCTCAAGATTTAAGTAACTGTACAACaatgacgaggagctattggcacaacttca

GTTTTTGTACTCTCAAGATTTAAGTAACTGTACAACcgatttgacaatctgctgaccactgttatc

GTTTTTGTACTCTCAAGATTTAAGTAACTGTACAACacacttggcaggcttattactcaacagcga

GTTTTTGTACTCTCAAGATTTAAGTAACTGTACAACctgttccttgttcttttgttgtatcttttc

GTTTTTGTACTCTCAAGATTTAAGTAACTGTACAACttcattcttccgtttttgtttgcgaatcct

GTTTTTGTACTCTCAAGATTTAAGTAACTGTACAACgctggcgaggaaacgaacaaggcctcaaca

GTTTTTGTACTCTCAAGATTTAAGTAACTGTACAACcatagagtggaaaactagaaacagattcaa

GTTTTTGTACTCTCAAGATTTAAGTAACTGTACAACataatgccgttgaattacacggcaaggtca

GTTTTTGTACTCTCAAGATTTAAGTAACTGTACAACgagcgagctcgaaataatcttaattacaag

GTTTTTGTACTCTCAAGATTTAAGTAACTGTACAACgttcgctagcgtcatgtggtaacgtattta

GTTTTTGTACTCTCAAGATTTAAGTAACTGTACAACggcgtcccaatcctgattaatacttactcg

GTTTTTGTACTCTCAAGATTTAAGTAACTGTACAACaacacagcaagacaagaggatgatgctatg

GTTTTTGTACTCTCAAGATTTAAGTAACTGTACAACcgacacaagaacgtatgcaagagttcaag

GTTTTTGTACTCTCAAGATTTAAGTAACTGTACAACacaattcttcatccggtaactgctcaagtg

GTTTTTGTACTCTCAAGATTTAAGTAACTGTACAACaattaagggcatagaaagggagacaacatg

GTTTTTGTACTCTCAAGATTTAAGTAACTGTACAACcgatatttaaaatcattttcataacttcat

GTTTTTGTACTCTCAAGATTTAAGTAACTGTACAACgcagtatcagcaagcaagctgttagttact

GTTTTTGTACTCTCAAGATTTAAGTAACTGTACAACataaactatgaaattttataatttttaaga

GTTTTTGTACTC~~TCAAG~~ATTTAAGTAACTGTACAACaataatttatggtatagcttaatatcattg

-continued

```
GTTTTTGTACTCTCAAGATTTAAGTAACTGTACAACtgcatcgagcacgttcgagtttaccgtttc

GTTTTTGTACTCTCAAGATTTAAGTAACTGTACAACtctatatcgaggtcaactaacaattatgct

GTTTTTGTACTCTCAAGATTTAAGTAACTGTACAACaatcgttcaaattctgttttaggtacattt

GTTTTTGTACTCTCAAGATTTAAGTAACTGTACAACaatcaatacgacaagagttaaaatggtctt

GTTTTTGTACTCTCAAGATTTAAGTAACTGTACAACgcttagctgtccaatccacgaacgtggatg

GTTTTTGTACTCTCAAGATTTAAGTAACTGTACAACcaaccaacggtaacagctactttttacagt

GTTTTTGTACTCTCAAGATTTAAGTAACTGTACAACataactgaaggataggagcttgtaaagtct

GTTTTTGTACTCTCAAGATTTAAGTAACTGTACAACtaatgctacatctcaaaggatgatcccaga

GTTTTTGTACTCTCAAGATTTAAGTAACTGTACAACaagtagttgatgacctctacaatggtttat

GTTTTTGTACTCTCAAGATTTAAGTAACTGTACAACacctagaagcatttgagcgtatattgattg

GTTTTTGTACTCTCAAGATTTAAGTAACTGTACAACaatttgccccttctttgccccttgactag

GTTTTTGTACTCTCAAGATTTAAGTAACTGTACAACaccattagcaatcatttgtgcccattgagt

GTTTTTGTACTCTCAAGATTTAAGTAACTGTACAGT

ttgattcaacataaaaagccagttcaattgaacttggcttt
```

In the above sequence, the leader sequence is:

```
                                        (SEQ ID NO: 688)
5'-caaggacagttattgattttataatcactatgtgggtataaaaacgt

caaaatttcatttgag-3'
```

The integrated sequence comprising a CRISPR repeat is shown in upper case and a CRISPR spacer (i.e., tagging sequence) in lower case. (GTTTTTGTACTCTCAAGATTTAAGTAACTGTACAACttacgtttgaaaagaatatcaaatcaatga; SEQ ID NO:694). The terminal repeat and trailer sequences of the CRISPR repeat are shown below:

```
Terminal repeat:
                                        (SEQ ID NO: 3)
5'-gtttttgtactctcaagatttaagtaactgtacagt-3'

Trailer sequence:
                                        (SEQ ID NO: 691)
5'-ttgattcaacataaaaagccagttcaattgaacttggcttt-3'
```

It has been shown that the sequence of the new spacer exists within the D858 phage genome.

The sequence of the spacer (SEQ ID NO:535) is found between positions 17215 and 17244 bp (i.e., on the plus strand) of D858's genome (and has 100% identity to the D858 genomic sequence over 30 nucleotides):

```
Spacer     1 ttacgtttgaaaagaatatcaaatcaatga    30 (SEQ ID NO: 535)
             ||||||||||||||||||||||||||||||
D858   17215 ttacgtttgaaaagaatatcaaatcaatga 17244 (SEQ ID NO: 690)
```

Figure 2:
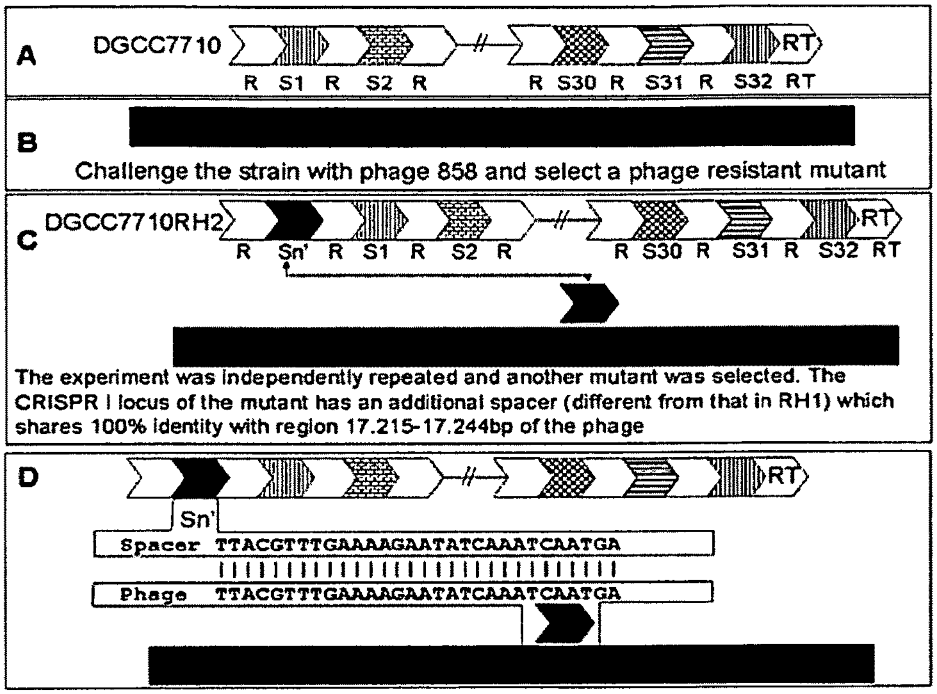
FIG. 2 provides a schematic showing that integration of a CRISPR spacer into the CRISPR locus of *S. thermophilus* provides resistance against a bacteriophage to which the CRISPR spacer shows identity. The parent DGCC7710 is phage sensitive, and the BIM DGCC771ORH2 is phage resistant. The BIM DGCC77 1ORH2 has a new spacer (Sn) in the CRISPR locus, which shows 100% identity to 25 phage sequence. As shown in step (B), the strain is challenged with phage 858 and a phage resistant mutant is selected. As shown in step (C,) the experiment was independently repeated and another mutant was selected. The CRISPR I locus of the mutant has an additional spacer (different from that in RH1) which shares 100% identity with region 17.125-17.244 bp of the phage. The sequence of the spacer and phage shown in step (D) corresponds to SEQ ID NO: 535.

The new spacer that is integrated into the CRISPR1 locus of *S. thermophilus* strain DGCC7710-RH2 confers resistance against phage D858 to *S. thermophilus* strain DGCC7710-RH2, as shown in FIG. 2 and Table 2-1 (See also, FIG. 10).

Example 3

Construct Integration and Knockout

In this Example, methods used for construct integration and knockout are described.

The strains used in these experiments were:

*S. thermophilus* DGCC7710 parent strain, sensitive to phages 858 and 2972
*S. thermophilus* DGCC7778 CRISPR mutant resistant to 858
*S. thermophilus* DGCC7778cas1KO
*S. thermophilus* DGCC7778cas4KO
*S. thermophilus* DGCC7778RT
*S. thermophilus* DGCC7778RT'
*S. thermophilus* DGCC7710R2 CRISPR mutant resistant to 2972
*S. thermophilus* DGCC7710R2S1S2
*E. coli* EC1,000 provided pORI28 (See, Russell and Klaenhammer, Appl. Environ. Microbiol., 67:43691-4364 [2001])
*Escherichia coli* pCR2.1TOPO provided pTOPO (See, Invitrogen catalog #K4500-01)

The following plasmids were used in these experiments:

pTOPO, a plasmid used for sub-cloning of the various constructs
pTOPOcas1ko contains an integral fragment of cas1
pTOPOcas4ko contains an integral fragment of cas4
pTOPOS1S2 contains the S1S2 spacer construct
pTOPO RT contains the RT terminal repeat construct
pORI28 is a plasmid used for integration of the various constructs in the chromosome of *S. thermophilus* strains.
pORIcas1ko contains an integral fragment of cas1
pORIcas4ko contains an integral fragment of cas4
pORIS1S2 contains the S1S2 spacer construct
purist contains the RT terminal repeat construct The following primers were used in these experiments:

```
Cas1
                                    (SEQ ID NO: 670)
5'-caaatggatagagaaacgc-3'
and
                                    (SEQ ID NO: 671)
5'-ctgataaggtgttcgttgtcc-3'

Cas4
                                    (SEQ ID NO: 672)
5'-ggagcagatggaatacaagaaagg-3'
and
                                    (SEQ ID NO: 673)
5'-gagagactaggttgtctcagca-3'

S1S2 and RT
P1
                                    (SEQ ID NO: 666)
5'-acaaacaacagagaagtatctcattg-3'

P2
                                    (SEQ ID NO: 667)
5'-aacgagtacactcactatttgtacg-3'

P3
                                    (SEQ ID NO: 668)
5'-tccactcacgtacaaatagtgagtgtactcgtttttgtattctcaag

atttaagtaactgtacagtttgattcaacataaaaag-3'

P4
                                    (SEQ ID NO: 669)
5'-ctttccttcatcctcgctttggtt-3'
```

Strains and phages were obtained from the Danisco Culture Collection, or from referenced material (Russell and Klaenhammer, Appl. Environ. Microbiol., 67:43691-4364 [2001]; and Levesque et al., Appl. Environ. Microbiol., 71:4057-4068 [2005]).

Phage preparation, purification and tests were carried out using methods known in the art (See e.g., Duplessis et al., Virol., 340:192-208 [2005]; and Levesque et al., Appl. Environ. Microbiol., 71:4057-4068 [2005]).

*S. thermophilus* strains were grown at 37° C. or 42° C. in M17 (Difco) supplemented with 0.5% lactose or sucrose. For phage infection, 10 mM $CaCl_2$ were added to the medium prior to phage infection, as known in the art (See e.g., Duplessis et al., supra; and Levesque et al., supra).

Enzymes used to carry out restriction digests and PCR were purchased from Invitrogen and used according to the manufacturer's instructions. PCRs were carried out on an Eppendorf Mastercycler Gradient thermocycler as known in the art (See e.g., Barrangou et al., Appl. Environ. Microbiol., 68:2877-2884 [2002]).

Gene inactivation and site-specific plasmid insertion via homologous recombination in the *S. thermophilus* chromosome were carried out by sub-cloning into the Invitrogen pCR2.1TOPO system, subsequent cloning in the pORI system using *E. coli* as a host and the constructs were ultimately purified and transformed into *S. thermophilus* as previously described (Russell and Klaenhammer, supra).

RT Construct Integration

Figure 3:
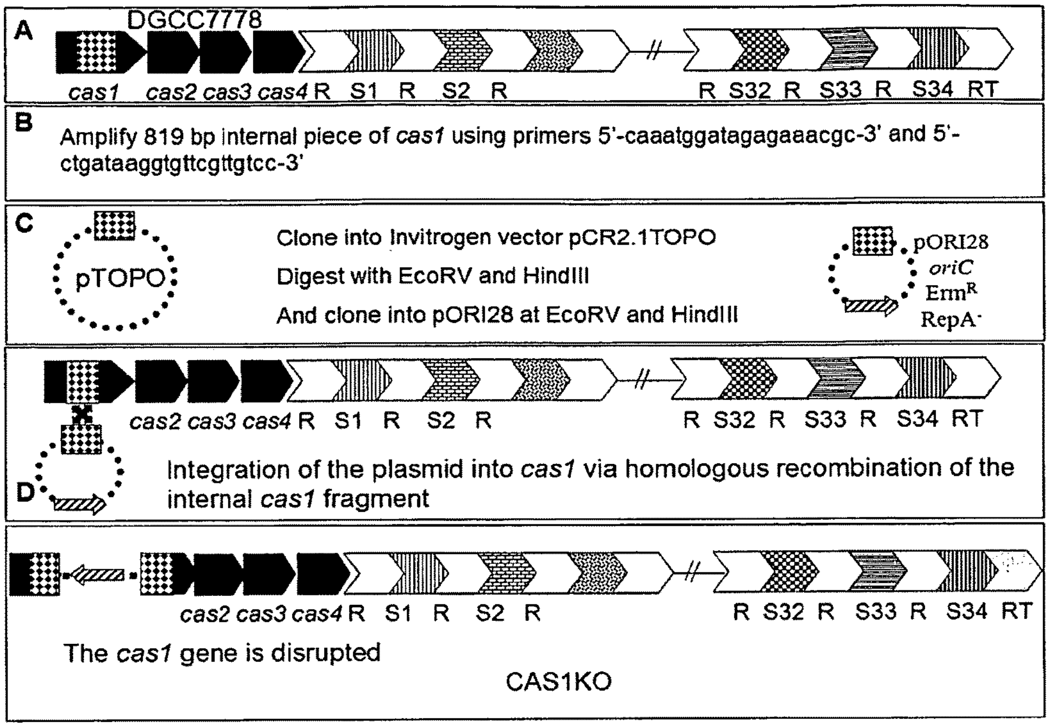
FIG. 3 provides a graphical representation illustrating the preparation of the CAS1KO construct in which the cas1 gene is disrupted by homologous recombination.
Figure 4:
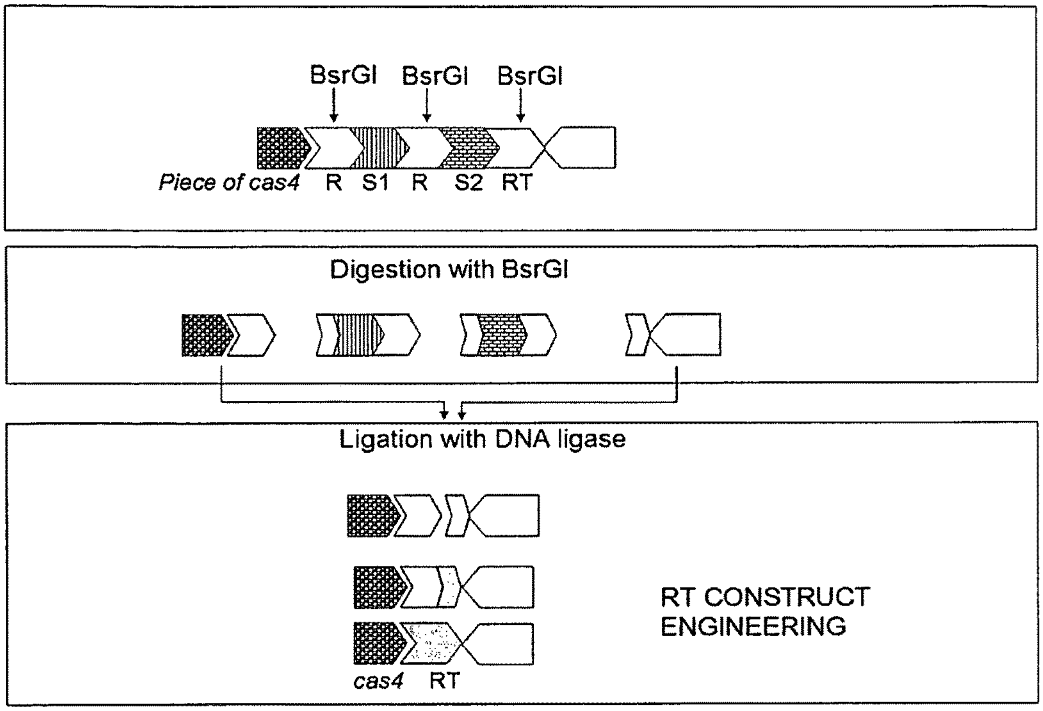
FIG. 4 provides a graphical representation of the preparation of the RT construct using a restriction enzyme to generate the RT construct from the S1S2 construct. There are BglI restriction sites within the repeats that allow the "middle" part of the construct to be cut. Following enzymatic digestion, a ligase was used to patch together the two end pieces, thus generating a new construct that has RT, but no spacers.
Figure 5:
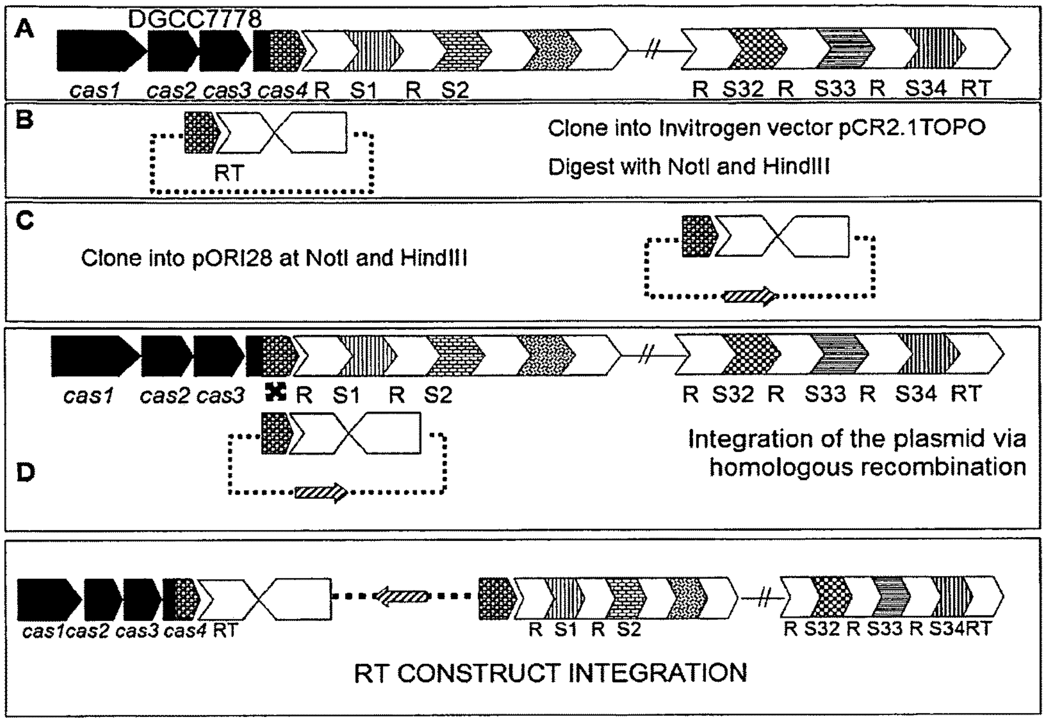
FIG. 5 provides a graphical representation of the integration of the RT construct.
Figure 6:
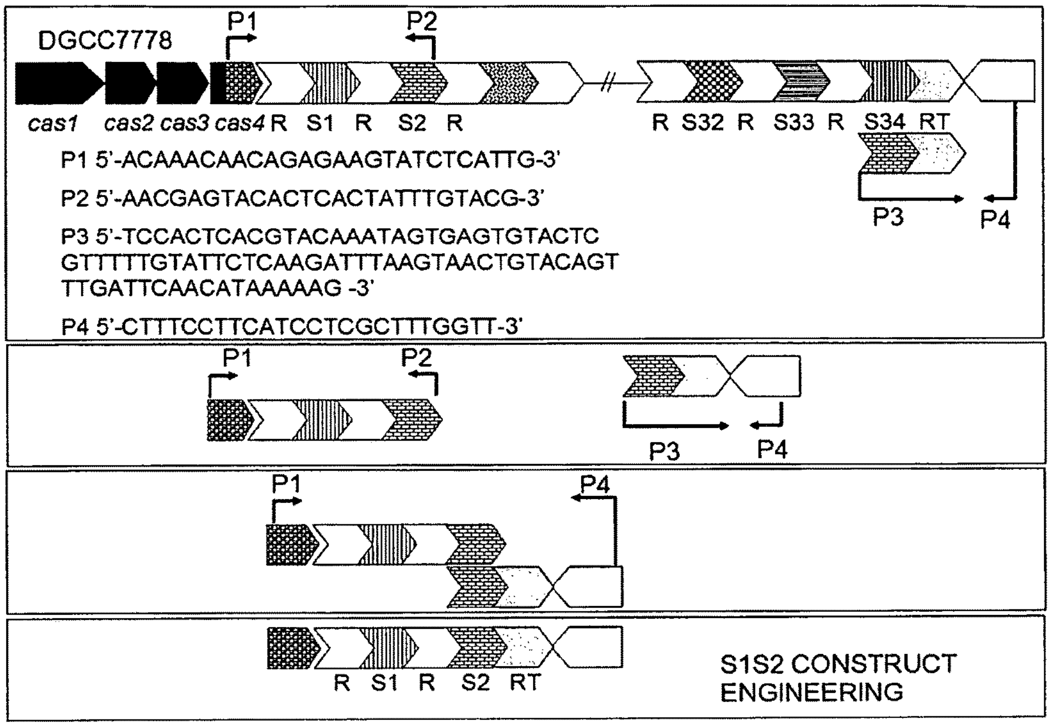
FIG. 6 provides a graphical representation illustrating the S1 S2 construct engineering using specific primers and iterative PCR reactions. The first panel illustrates all primers used and the set up for the first two PCR reactions (reaction #1 with primers P1 (SEQ ID NO: 666) and P2 (SEQ ID NO: 667) and reaction #2 with primers P2 (SEQ ID NO: 667) and P3 (SEQ ID NO: 668)). The second panel shows the PCR products obtained from the first two PCR reactions, with the product from reaction #1 on the left and the product from reaction #2 on the right. The third panel shows the third PCR reaction, using a combination of the products from the first two PCRs as the template for the third PCR reaction, and primer P1 (SEQ ID NO: 666) from the first reaction along with primer P4 (SEQ ID NO: 669) from the second reaction. The fourth panel shows the product of PCR#3, which technically generates the S1S2 construct.
Figure 7:
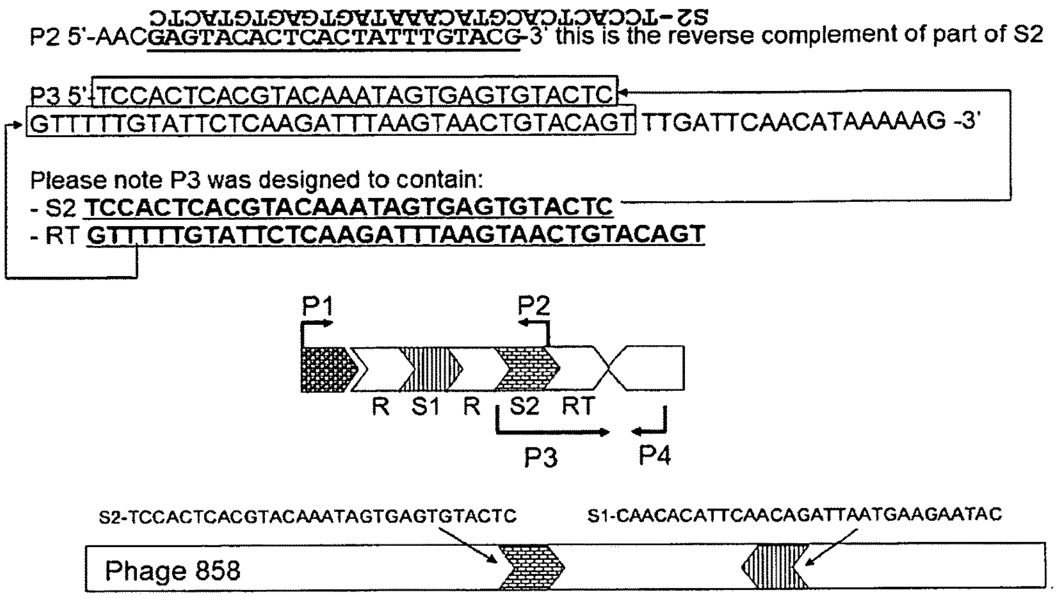
FIG. 7 provides a graphical representation of the details for primer design for primers 2 (SEQ ID NO: 667) and 3 (SEQ ID NO: 668), which contain key sequences for the experiment, derived from spacers identical to phage sequences (the PCR products derived from these PCR primers will generate the spacers that will ultimately provide resistance to the phages).
Figure 8:
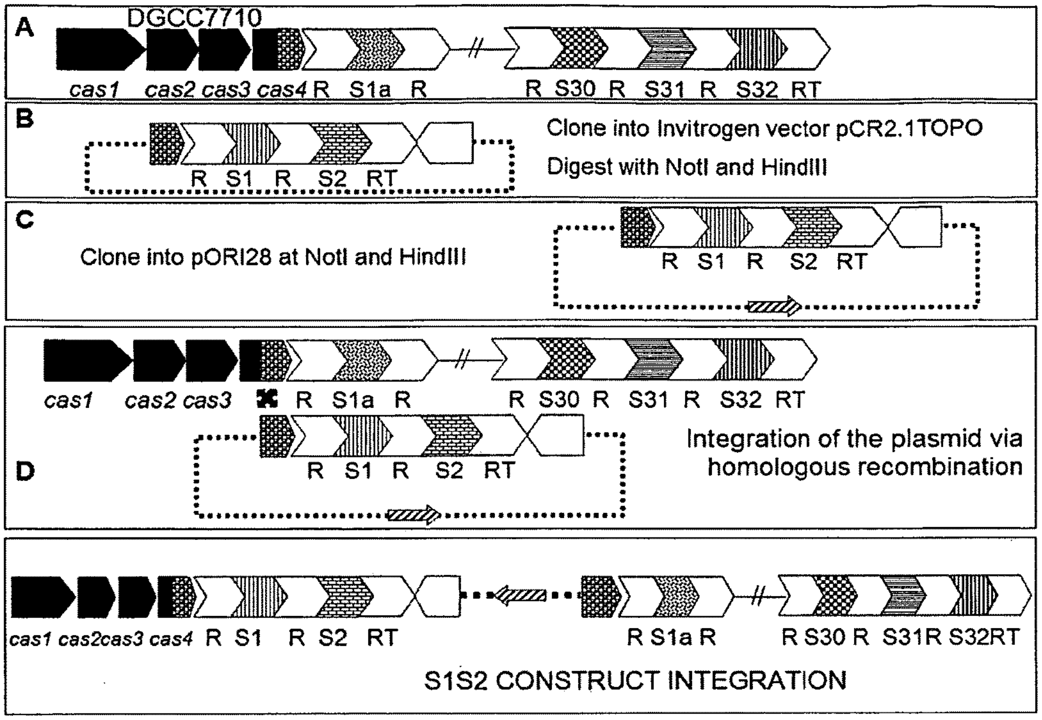
FIG. 8 provides a graphical representation of the integration of the S1S2 construct.

Using the RT construct engineered as shown in FIG. 4, the construct was inserted just after cas4, as shown in FIG. 5. The parent DGCC7778 is resistant to phage 858. The parent has two spacers (S1 and D2) which are identical to phage 858 DNA. The resulting strain (RT) lost resistance to phage 858. This result indicates that cas genes need to be in the immediate vicinity of the spacer(s) to confer resistance. As shown in FIG. 3, the parent DGCC7778 was engineered such that the cas1 gene is disrupted, resulting in a loss of resistance, meaning that cas1 is needed to confer resistance. As shown in FIG. 3, the parent DGCC7778 was engineered such that the cas4 gene is disrupted. In addition, the S1S2 construct was integrated into the parent DGCC7710, as shown in FIGS. 6-8.

Example 4

Isolation of Phage-Resistant Mutants and Confirmation of CRISPR Sequences

In this Example, methods used in the isolation of phage-resistant mutants and confirmation of CRISPR sequences are described. *S. thermophilus* phage-resistant mutants were obtained by challenging the wild-type host strain DGCC7710 (also called "RD534") with phage 2972 and/or phage 858 (Levesque et al., Appl. Environ. Microbiol., 71:4057 [2005]). The host strain was grown at 42° C. in 10 ml of M17 broth supplemented with 0.5% lactose (LM17). When the optical density (600 nm) reached 0.3, phages and calcium chloride 10 mM were added at a final concentration of $10^7$ pfu/ml and 50 mM, respectively. The phage-containing culture was incubated at 42° C. for 24 hours and monitored for lysis. Then, 100 μl of the lysate were inoculated into 10 ml of fresh LM17. The remaining lysate was centrifuged and the pellet was inoculated into another tube containing 10 ml of fresh LM17. These two cultures were incubated at 42° C. for 16 hours. Finally, these cultures were diluted and plated on LM17. Isolated colonies were tested for phage sensitivity as known in the art (See. Moineau et al., Can. J. Microbiol., 38:875 [1992]). The CRISPR loci of the resistant isolates were verified by sequencing PCR products, and using relevant phage genome information known in the art (See, Levesque et al., Appl. Environ. Microbiol., 71:4057 [2005]).

Example 5

CRISPR Spacer Engineering

In this Example, methods used in some embodiments for CRISPR spacer engineering are described. Enzymes used to carry out restriction digests and PCR were purchased from Invitrogen and used according to the manufacturer's instructions. PCRs were carried out on an Eppendorf Mastercycler Gradient thermocycler, using methods known in the art.

Gene inactivation and site-specific plasmid insertion via homologous recombination in the *S. thermophilus* chromosome were carried out by sub-cloning into the pCR2.1-TOPO system (Invitrogen), by subsequent cloning in the pORI system using *E. coli* as a host, and the constructs were ultimately purified and transformed into *S. thermophilus* as known in the art (See, Russell and Klaenhammer, Appl. Environ. Microbiol., 67:4361 [2001]).

DNA from mutant $WT_{\Phi858}{}^{+S1S2}$ was used as a template to amplify two distinct PCR fragments using P1 (5'-acaaacaacagagaagtatctcattg-3'; SEQ ID NO:666) and P2 (5'-aacgagtacactcactatttgtacg-3'; SEQ ID NO:667) in one reaction, and P3 (5'-tccactcacgtacaaatagtgagtgtactcgtttttgtattctcaagatttaagtaactgtacagtttgattcaacataaaaag-3'; SEQ ID NO:668) and P4 (5'-ctttccttcatcctcgctttggtt-3'; SEQ ID NO:669) in another reaction. Both PCR products were subsequently used as templates in another PCR reaction using primers P1 and P4 to generate the S1S2 construct according to FIG. 11.

The S1S2 construct was sub-cloned into the Invitrogen pCR2.1-TOPO system. This construct was digested with NotI and HindIII and subsequently cloned into pORI at the NotI and HindIII sites, providing the pS1S2 construct. Integration of pS1S2 into the CRISPR1 locus of $WT_{\Phi2972}^{+S4}$ occurred via homologous recombination at the 3' end of cas7, to generate $WT_{\Phi2972}^{+S4}$::pS1S2.

The pR construct was generated using the pS1S2 construct as a template. Specifically, the S1S2 construct sub-cloned into pCR2.1-TOPO was digested using BsrGI, which cuts within the CRISPR repeat. Then, the digest was religated and a plasmid containing a single repeat and no spacer was used subsequently for cloning into pORI using NotI and HindIII, generating pR. Integration of pR into the chromosome of $WT_{\Phi858}^{+S1S2}$ at the 3' end of cas7 via homologous recombination generated $WT_{\Phi858}^{+S1S2}$::pR, a mutant where the CRISPR1 locus is displaced and a unique repeat is inserted in its place.

The mutant $WT_{\Phi858}^{+S1S2}$::pR was subsequently grown in the absence of erythromycin, and antibiotic-sensitive variants were analyzed to find a mutant that had a complete deletion of the CRISPR1 locus. The deletion was derived from homologous recombination occurring at the 3' end of ORF (as opposed to a recombination event occurring at the 3' end of cas7, which would have resulted in restoration of the $WT_{\Phi858}^{+S1S2}$ strain), generating $WT_{\Phi858}^{+S1S2}\Delta$CRISPR1 (See, FIG. 12), a mutant where the CRISPR1 locus is deleted (See also, FIG. 10)

Example 6

Inactivation of cas Genes

For cas5 inactivation, a 801-bp internal piece of cas5 was amplified by PCR using primers 5'-caaatggatagagaaacgc-3' (SEQ ID NO:670) and 5'-ctgataaggtgttcgttgtcc-3' (SEQ ID NO:671) and subcloned into *E. coli* pCR2.1-TOPO (Invitrogen). This construct was digested with EcoRV and HindIII and subsequently cloned into pORI at the EcoRV and HindIII sites. Integration of this construct into the cas5 gene of $WT_{\Phi858}^{+S1S2}$ occurred via homologous recombination of the internal piece of the gene, resulting into $WT_{\Phi858}^{+S1S2}$::pcas5-.

Similarly, a 672-bp internal piece of cas7 was amplified by PCR using primers 5'-ggagcagatggaatacaagaaagg-3' (SEQ ID NO:672) and 5'-gagagactaggttgtctcagca-3' (SEQ ID NO:673) and subcloned into *E. coli* pCR2.1-TOPO (Invitrogen). This construct was digested with EcoRV and HindIII and subsequently cloned into pORI at the EcoRV and HindIII sites. Integration of this construct into the cas7 gene of $WT_{\Phi858}^{+S1S2}$ occurred via homologous recombination of the internal piece of the gene, resulting into $WT_{\Phi858}^{+S1S2}$::pcas7- (See, FIGS. 10-12).

Example 7

Natural Methods for Inserting an Additional Sequence in a CRISPR Locus

In this Example, methods used to naturally provoke the insertion of an additional sequence within a CRISPR locus of a bacterial strain are described. "Additional sequence" as used herein is defined as a spacer sequence associated with CRISPR repeat sequence. More particularly, the "additional sequence" originates partly from a donor phage able to infect the targeted bacterium and partly from the duplication of the CRISPR repeat sequence. The introduction of the donor phage DNA into the bacterial cell results from the infection of the cell by the donor phage. The selection of cells that contain additional sequence is made through selection pressure with the donor phage such that the selected modified cells are resistant to the phage.

In these experiments, a parental strain was exposed to a donor phage and a phage resistant variant of the parental strain (i.e., a variant strain) selected. The variant strain was analyzed (e.g., by PCR and/or DNA sequencing) to confirm the presence of an additional sequence within a CRISPR locus. The nucleotide sequence of the additional sequence was determined. Typically, the additional sequence is a fragment of approximately 30 nucleotides in size from the donor phage associated (fused) to a CRISPR repeat sequence, and confers resistance to the donor phage.

In some experiments, the parental strain was pre-cultivated overnight in a milk based medium at 42° C. A milk-based medium was then inoculated at 0.1% (v/v) with the pre-culture of the parental strain and with a suspension of the donor phage at an MOI of 10. After 6 h of incubation at 42° C., dilutions of the culture were plated on a nutritional medium, in order to obtain isolated colonies. Isolates were then tested for their resistance to the donor phage (any suitable method known in the art find use in these experiments). Variant strains were then analyzed for the presence of an additional sequence within one of their CRISPR loci.

CRISPR loci were amplified by PCR and the nucleotide sequences of the resulting PCR products were determined by DNA sequencing using standard PCR and sequencing methods known in the art. These sequence were then compared to that of the parental strain using standard methods known in the art.

In some experiments, DGCC7710 was used as the parental strain and D2972 was used as a donor phage. The parental *S. thermophilus* strain DGCC7710 was exposed to the donor phage D2972 as described above. A variant strain named $WT_{phi2972}^{+S6}$ was obtained (See, Table 7-1). Table 7-1 also includes results for variant strains described in other Examples. In Table 7-1, the EOP is expressed relatively to phage D2972. Positioning of the additional sequence in the phage genome is given relatively to phage D2972, unless specified otherwise.

TABLE 7.1

Description of CRISPR-Modified Variant Strains of DGCC7710

| Variant Strain | Parental Strain | Donor Phage | Additional Sequence | Sequence | EOP |
|---|---|---|---|---|---|
| — | DGCC7710 | — | — | | 1 |
| $WT_{phi2972}^{+S6}$ | DGCC7710 | D2972 | 34521-34492 | GCCCTTCTAATTGGAT TACCTTCCGAGGTG (SEQ ID NO: 524) | $10^{-4}$ |

TABLE 7.1-continued

Description of CRISPR-Modified Variant Strains of DGCC7710

| Variant Strain | Parental Strain | Donor Phage | Additional Sequence | Sequence | EOP |
|---|---|---|---|---|---|
| $WT_{phi858}{}^{+S1S2}$: : $pcas5_{phi858}{}^{+S19}$ | $WT_{phi858}{}^{+S1S2}$: : pcas5 | D858 | 33824-33853 | TGTAGATAGCGTGGG TGCAGAGATGCACGG (SEQ ID NO: 702) | 10-5 |
| $WT_{phi2972}{}^{+S4}$ | DGCC7710 | D2972 | 31582-31611 | CTCAGTCGTTACTGGT GAACCAGTTTCAAT (SEQ ID NO: 525) | $10^{-5}$ |
| $WT_{phi2972}{}^{+S20}$ | DGCC7710 | D2972 | 25693-25722 | TCTAATCCCACTAGGA ATAGTGGGTAGTAA (SEQ ID NO: 703) | $10^{-5}$ |
| $WT_{phi2972}{}^{+S21}$ | DGCC7710 | D2972 | 27560-27589 | TCGATAAATCAGCCAA AGTATTAAGTGGTT (SEQ ID NO: 704) | $10^{-5}$ |
| $WT_{phi2972}{}^{+S22}$ | DGCC7710 | D2972 | 24624-24653 | CAGCTTGAAATGTTTA TTGAAGCAGCAGTG (SEQ ID NO: 705) | $10^{-4}$ |
| $WT_{phi2972}{}^{+S6}{}_{phi4724}{}^{+S15}$ | $WT_{phi2972}{}^{+S6}$ | D4724 | 1113-1142 | TTATATCGAAGAACGA CTGAAAGAGCTTGA (SEQ ID NO: 706) | $<10^{-8}$ |
| $WT_{phi2972}{}^{+S6}{}_{phi4724}{}^{+S17}$ | $WT_{phi2972}{}^{+S6}$ | D4724 | 33968-33997 | TCCAAGTTATTTGAGGA GTTATTAAGACAT (SEQ ID NO: 707) | $<10^{-8}$ |
| $WT_{phi2972}{}^{+S6}{}_{phi4724}{}^{+S24}$ | $WT_{phi2972}{}^{+S6}$ | D4724 | 30803-30832 | TACCGAAACGACTGGT TTGAAAAATTCAAG (SEQ ID NO: 708) | $<10^{-8}$ |
| $WT_{phi2972}{}^{+S6}{}_{phi4724}{}^{+S15}{}_{phi4733}{}^{+S16}$ | $WT_{phi2972}{}^{+S6}{}_{phi4724}{}^{+S15}$ | D4733 | 29923-29894 | AGTTGATTGCGTAATC AACCATCTCCATAA (SEQ ID NO: 709) | $<10^{-8}$ |
| $WT_{phi2972}{}^{+S4}{}_{phi4720}{}^{+S17}$ | $WT_{phi2972}{}^{+S4}$ | D4720 | 33968-33997 | TCCAAGTTATTTGAGG AGTTATTAAGACAT (SEQ ID NO: 707) | $10^{-6}$ |
| $WT_{phi2972}{}^{+S4}{}_{phi858}{}^{+S18}$ | $WT_{phi2972}{}^{+S4}$ | D858 | 30338-30367 (relatively to D858) | CTTCAAATGTACTGCA AGGCTGCAAAAGTA (SEQ ID NO: 710) | $<10^{-8}$ |
| $WT_{phi2972}{}^{+S4}{}_{phi858}{}^{+S25}$ | $WT_{phi2972}{}^{+S4}$ | D858 | 33886-33915 (relatively to D858) | ATTGTCTATTACGACA ACATGGAAGATGAT (SEQ ID NO: 526) | $<10^{-7}$ |
| $WT_{phi858phi2972}{}^{+S9S10S11S12}$ | DGCC7710 | D2972 + D858 | 7874-7903 20650-20621 8360-8389 18998-19027 | TTACTAGAGCGTGTCG TTAACCACTTTAAA (SEQ ID NO: 528) TTCGTTAAAGTCACCTC GTGCTAGCGTTGC (SEQ ID NO: 529) ATAACGGTAGCAAATA TAAACCTGTTACTG (SEQ ID NO: 530) GAAGTAGCCATACAAG AAGATGGATCAGCA (SEQ ID NO: 531) | $<10^{-7}$ |
| $WT_{phi858phi2972}{}^{+}$ S13S14 | DGCC7710 | D2972 + D858 | 33602-33631 4830-4801 | GATGTCACTGAGTGTC TAAGCATTGCGTAC (SEQ ID NO: 776) TGAATAAGCAGTTCTT GACGACCAACCGAC (SEQ ID NO: 533) | $10^{-8}$ |
| $WT_{phi2972}{}^{+S26S27}$ | DGCC7710 | D2972 | 29647-29-618 16681-16652 | TTTTCCGTCTTCTTTT TTAGCAAAGATACG (SEQ ID NO: 711) TGTTTCAAGGTTTCGGGT CCAAGTATCATT (SEQ ID NO: 712) | $<10^{-8}$ |

TABLE 7.1-continued

| Description of CRISPR-Modified Variant Strains of DGCC7710 | | | | | |
|---|---|---|---|---|---|
| Variant Strain | Parental Strain | Donor Phage | Additional Sequence | Sequence | EOP |
| DGCC9705 | DGCC7710 | D2972 | 25582-25611<br>18079-18108 | AAATCAGTTTTTTGTTC AGAAACTTGTTCT (SEQ ID NO: 713) TAGAGGTAATGACGGC TTACCGGGTAAAGA (SEQ ID NO: 714) | $<10^{-8}$ |
| DGCC9726 | DGCC9705 | D3821 | 26530-26559 | GAAGTATTAGGTCTCT CAAAAGATGATATT (SEQ ID NO: 715) | $<10^{-8}$ |
| DGCC9733 | DGCC9726 | D3288 | 5339-5363 (relatively to 7201) | TAAACTATGAAATTTT ATAATTTTTGAACA (SEQ ID NO: 716) | $<10^{-8}$ |
| DGCC9836 | DGCC9733 | D4753 | 15562-15590 (relatively to D858)<br>362-333<br>24083-24112 (relatively to D858)<br>30059-30088 (relatively to D858) | AACCCAATAATTACAG TGAAGCACAATAG (SEQ ID NO: 717) AATTGTGTCGGTCTTT TTTATTGTTTTTACC (SEQ ID NO: 718) CTCGTTAATTGCAAGTT TGGTCGGCACGTT (SEQ ID NO: 719) TTGTGGCACAAACAAA ATGAATTAAAGATT (SEQ ID NO: 720) | $<10^{-8}$ |

Figure 14:
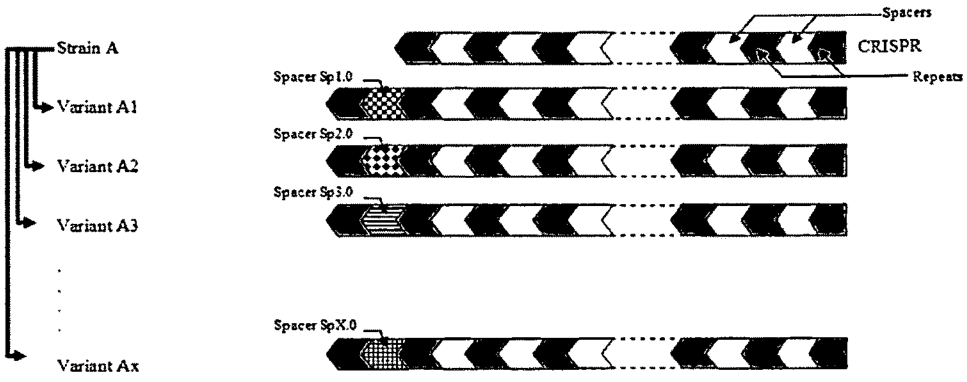
FIG. 14 provides a schematic representation of the construction of a first level phage resistant variant. Each variant has a single additional spacer within its CRISPR. Additional spacers are unrelated to each of the others (e.g., each has a different sequence). All spacers originate from phage P.

This variant exhibited resistance to D2972, as the efficiency of plaquing (EOP) of D2972 on $WT_{phi2972}^{+S6}$ was reduced by 4 logs. DNA was extracted from $WT_{phi2972}^{+S6}$ and the CRISPR1 locus was analyzed by PCR as known in the art (See e.g., Bolotin et al. [2005], supra) using combination of one forward primer (either YC70 and/or SPIDR-ups (5'-gTCTTTAgAAACTgTgACACC-3'; SEQ ID NO:674) and one reverse primer (either YC31 and/or SPIDR-dws (5'-TAAACAgAgCCTCCCTATCC; SEQ ID NO:675). The sequence of the PCR product was determined and compared to that of the CRISPR1 locus of DGCC7710. Compared to DGCC7710, $WT_{phi2972}^{+S6}$ was found to differ by the addition of a single spacer sequence of 30 bp at the 5' end of its CRISPR1 region and by the duplication of the repeat sequence, as shown in FIG. 14. Comparison of the additional sequence with the sequence of D2972 genome shows that the new spacer sequence is 100% identical to that of the D2972 genome from nucleotide 34521 to nucleotide 34492.

In some additional experiments, $WT_{phi858}^{+S1S2}$::pcas5 was used as the parental strain and D858 was used as a donor phage. The resulting variant strain named $WT_{phi858}^{+S1S2}$::pcas5$_{phi858}^{+S19}$ (See, Table 7-1) was resistant to D858, with an EOP reduced by 5 logs. DNA was extracted from $WT_{phi858}^{+S1S2}$::pcas5$_{phi858}^{+S19}$ and its CRISPR3 locus was analyzed by PCR using one forward primer (CR3_leadF1, 5'-CTGAGATTAATAGTGCGATTACG; SEQ ID NO:676) and one reverse primer (CR3_trailR2, 5'-GCTGGATATTCGTATAACATGTC; SEQ ID NO:677). The sequence of the PCR product was determined and compared to that of the CRISPR3 locus of $WT_{phi858}^{+S1S2}$::pcas5. Compared to $WT_{phi858}^{-S1S2}$::pcas5, $WT_{phi858}^{+S1S2}$::pcas5$_{phi858}^{+S19}$ differs by the addition of a single spacer sequence of 30 bp at the 5' end of its CRISPR3 region and by the duplication of the repeat sequence. Comparison of the additional sequence with the sequence of D858 genome showed that the new spacer sequence is 100% identical to that of the D858 genome from nucleotide 33824 to nucleotide 33853.

In other additional experiments, DGCC7809 was used as the parental strain and D3743 was used as the donor phage. The resulting variant strain named DGCC7809$_{phiD3743}^{+S28}$ (See, Table 7-2) was resistant to D3743 with an EOP reduced by 8 logs. DNA was extracted from DGCC7809$_{phiD3743}^{+S28}$ and its CRISPR3 locus was analyzed by PCR using one forward primer (CR3_leadF1, 5'-CTGAGATTAATAGTGCGATTACG; SEQ ID NO:676) and one reverse primer (CR3_trailR2, 5'-GCTGGATATTCGTATAACATGTC; SEQ ID NO:677). The sequence of the PCR product was determined and compared to that of the CRISPR3 locus of ST0189. Compared to DGCC7809, DGCC7809$_{phiD3743}^{+S28}$ differs by the addition of a single spacer sequence of 29 bp at the 5' end of its CRISPR3 region and by the duplication of the repeat sequence. The sequence of the phage D3743 is unknown; however comparison of the additional sequence with the sequence of other streptococcal phage genome shows that the new spacer sequence is 100% identical to that of the phage DT1 genome from nucleotide 6967 to nucleotide 6996.

In other additional experiments, DGCC3198 was used as the parental strain and D4241 was used as the donor phage. The resulting variant strain named DGCC3198$_{phi4241}^{+S29}$ (See, Table 7-2) was resistant to D4241 with an EOP reduced by 8 logs. DNA was extracted from DGCC3198$_{phi4241}^{+S1}$ and its CRISPR1 locus was analyzed by PCR using one forward primer (either YC70 and/or SPIDR-ups (5'-gTCTTTAgAAACTgTgACACC-3'; SEQ ID NO:674) and of one reverse primer (either YC31 and/or SPIDR-dws (5'-TAAACAgAgCCTCCCTATCC; SEQ ID NO:675). The sequence of the PCR product was determined and compared to that of the CRISPR1 locus of DGCC3198. Compared to DGCC3198, DGCC3198$_{phi4241}^{+S29}$ differs by the addition of a single spacer sequence of 30 bp at the 5' end of its CRISPR1 region and by the duplication of the repeat sequence. The sequence of the phage D4241 is unknown; however comparison of the additional sequence with the sequence of other streptococcal phage genome shows that the new spacer sequence is 100% identical to that of the DT1 phage genome from nucleotide 3484 to nucleotide 3455.

Table 7-2 below provides a description of CRISPR-modified variant strains from DGCC7809 and from DGCC3198. In this Table, EOP is expressed relatively to the donor phages. Positioning of the additional sequence in the phage genome is given relatively to the phage DT1.

TABLE 7-2

Description of CRISPR-Modified Variant Strains from DGCC7809 and DGCC3198

| Variant Strain | Parental Strain | Donor Phage | Additional sequence | Sequence | EOP |
|---|---|---|---|---|---|
| — | DGCC7809 | — | — | — | 1 |
| $DGCC7809_{phi3743}^{S28}$ | DGCC7809 | D3743 | 6967-6996 (relative to DT1) | ACAAGCAAAGATTACAACCG CTGGTGCTA (SEQ ID NO: 721) | $<10^{-8}$ |
| — | DGCC3198 | — | — | — | 1 |
| $DGCC3198_{phi4241}^{S29}$ | DGCC3198 | D4241 | 3484-3455 (relative to DT1) | ACCAAGTAGCATTTGAGCAAA GATAGATTG (SEQ ID NO: 722) | $<10^{-8}$ |

Example 8

Selection of a Set of CRISPR-Modified Variant Strains from the Same Parental Strain In this Example, methods used for the selection of a set of variant strains from the same parental strain differing by their additional sequence originating from the same phage are described. As various portions of a donor phage find use as sources for additional sequences, multiple different variant strains can be generated from given donor phage. Furthermore, each variant strain has a different additional sequence. Consequently, multiple strains were developed from the same parental strain in addition to the variant strain described in Example 7. In some experiments, these additional strains were generated by exposing the recipient strain to the same donor phage. The various resulting variant strains were contemplated to present different spectrum of phage sensitivity.

In independent cultures, the parental strain was submitted to the same donor phage. For each culture, a single phage resistant variant was isolated as described in Example 7 and then analyzed. Additional sequences in each of the variant strains were compared to each other. The spectrum of sensitivity of the variant strains to donor phage and other phages was determined using classical microbiological methods known in the art. The sensitivity spectra of the various strains were then compared. The selected variant strains were those presenting different additional sequence(s) and different spectra of phage sensitivity.

In some experiments, the selection of various variant strains of DGCC7710 using D2972 as a single donor phage was conducted. The parental strain DGCC7710 was exposed to the donor phage D2972 in four independent cultures as described in Example 7. From each of the cultures, a variant strain was isolated and was respectively named $WT_{phi2972}^{+S4}$, $WT_{phi2972}^{+S20}$, $WT_{phi2972}^{+S21}$ and $WT_{plu2972}^{+S22}$ (See, Table 7-1).

Figure 17:
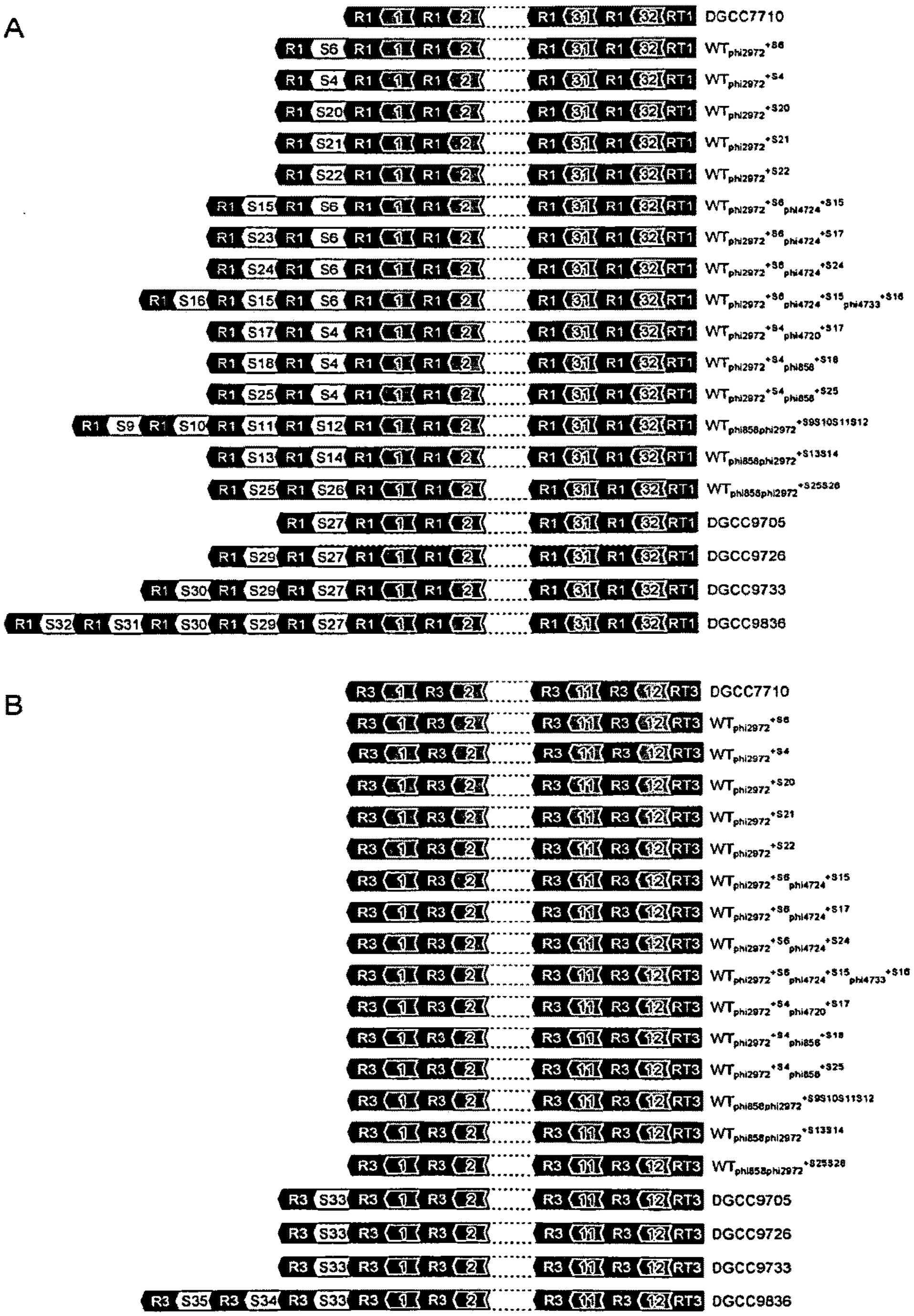
FIG. 17 provides a schematic representation of the CRISPR1 locus (Panel A) and of the CRISPR3 locus (Panel B) of *S. thermophilus* strains described in Examples 7 to Example 16. Strain names are given on the left side of the Figure. Black arrows represent CRISPR repeats, "R" stands for Repeat and "RT" stands for Terminal Repeat. Grey arrows numbered from 1 to 32 in part A and from 1 to 12 in part B represent CRISPR1 spacers and CRISPR3 spacers, respectively, as they are in DGCC7710. White arrows numbered from S4 to S35 represent CRISPR additional spacers specific to the described strains.

These variant strains exhibited resistance to D2972, as the efficiency of plaquing (EOP) of D2972 on the four phage resistant variants was reduced by 3 to 5 logs. DNA was extracted from $WT_{phi2972}^{+S4}$, $WT_{phi2972}^{+S20}$, $WT_{phi2972}^{+S21}$ and $WT_{phi2972}^{+S22}$ and was analyzed by PCR using methods known in the art (See e.g., Bolotin at a1. [2005], supra), using combination of one forward primer (either YC70 and/or SPIDR-ups (5'-gTCTTTAgAAACTgTgACACC; SEQ ID NO:674) and of one reverse primer (either YC31 and/or SPIDR-dws (5'-TAAACAgAgCCTCCCTATCC; SEQ ID NO:675). The sequence of the PCR products were determined and compared to that of the CRISPR1 locus of DGCC7710. Compared to DGCC7710, $WT_{phi2972}^{+S4}$, $WT_{phi2972}^{+S20}$, $WT_{phi2972}^{+S21}$ and $WT_{phi2972}^{+S22}$ differ by the addition of a spacer sequence of 30 bp at the 5' end of its CRISPR1 region and by the duplication of the repeat sequence, as shown in FIG. 17). Comparison of these new spacer sequences with the sequence of the D2972 genome shows that the new spacer sequences are 100% identical to that of the D2972 genome from nucleotide 31582 to nucleotide 31611, from nucleotide 25693 to nucleotide 25722, from nucleotide 27560 to nucleotide 27589, and from nucleotide 24624 to nucleotide 24653, respectively. All four additional spacers were found to be different from each other and different from the spacers described in Example 7.

Example 9

Natural Methods Used for the Insertion of a Second Additional Sequence in a CRISPR Locus In this Example, natural methods used to provoke the insertion of a second additional sequence in CRISPR locus are described. Upon insertion of an additional sequence from a given donor phage in a bacterial CRISPR locus, the variant strain becomes resistant or at least less sensitive to this phage. Therefore, the method described in Example 7 is no more efficient for the insertion of additional sequences in the CRISPR locus of this variant strain. For example, the method cannot be applied to variant strain $WT_{phi2972}^{+S6}$ (as a parental strain) using D2972 as a donor phage, because $WT_{phi2972}^{+S6}$ has significantly decreased sensitivity to D2972 (See, Example 7).

In some experiments, this problem was overcome by the use of a mutated donor phage derived from D2972 that includes at least one specific modification within its genome (i.e., a "mutated phage"). This mutated phage was selected by exposing the donor phage to the variant strain, such that the modification (i.e., mutation) of the parental phage rendered it virulent for the variant strain.

In some experiments, the mutated phage had a mutation in its genome within the region containing the sequence of the additional spacer that is part of the additional sequence in the variant strain. The variant strain was sensitive to this mutated phage. The variant strain was exposed to the mutated phage and a new phage resistant variant ($2^{nd}$ generation variant) of the variant strain was s selected. The $2^{nd}$ generation variant was analyzed using suitable methods known in the art (e.g., PCR and sequencing), to confirm the presence of an additional sequence within a CRISPR locus. The nucleotide sequence of the additional sequence was determined. In some experiments, the additional sequence was found to contain a fragment of approximately 30 nucleotides in size from the mutated phage which gives resistance to the mutated phage.

In some experiments, the variant strain was pre-cultivated overnight in an appropriate milk-based medium at 42° C. A suitable milk-based medium was then inoculated with the pre-culture of the variant strain at a concentration of about $10^6$ cfu/ml and with a suspension of the donor phage at an MOI greater than 100. The culture was incubated over night at 42° C., and then centrifuged. The supernatant was harvested and filtered using a 0.45 μm filter. Dilutions of the filtrated supernatant were used to inoculate a nutritive agar media seeded with the variant strain in order to obtain isolated phage plaques, using any suitable method known in the art. Isolated plaques were cultivated on the variant strain in liquid nutritive media, using any suitable method known in the art. A suspension of the mutated phage was obtained by filtering the culture through a 0.45 μm filter. The mutated phage was then used as described above (See, Example 7) to provoke the insertion of a second additional spacer sequence in the CRISPR locus of the variant strain.

In some experiments, $WT_{phi2972}^{+S6}$ (See, Example 7, and Table 7-1) was used as the parental strain and D4724 was used as the donor phage. The variant strain $WT_{phi2972}^{+S6}$ was cultivated in the presence of high concentration of phage D2972. A mutated phage named D4724 was isolated by plaquing the supernatant from this culture on strain $WT_{phi2972}^{+S6}$ using the methods described above. The virulence of the mutated phage D4724 on $WT_{phi2972}^{-S6}$ as verified. The variant strain $WT_{phi2972}^{+S6}$ was exposed to the mutated phage D4724 in a culture as described in Example 7. A phage resistant variant strain named $WT_{phi2972}^{+S6}{}_{phi4724}^{+S15}$ (See. Table 7-1) was obtained.

Compared to $WT_{phi2972}^{+S6}$, this variant strain exhibited an increased resistance to D2972, as the efficiency of plaquing (EOP) of D2972 on $WT_{phi2972}^{+S6}{}_{phi4724}^{+S15}$ was reduced by more than 8 logs (instead of 4 logs); in addition, its resistance was also enlarged compare to $WT_{phi2972}^{-S6}$ as its displays some resistance to D4724 (See, Table 9-1). DNA was extracted from $WT_{phi2972}^{+S6}{}_{phi4724}^{+S15}$ and its CRISPR1 locus was analyzed by PCR as described above using the same combinations of primers as described above. The sequence of the PCR product was determined and compared to that of the CRISPR1 locus of $WT_{phi2972}^{+S6}$. Compared to $WT_{phi2972}^{+S6}$, $WT_{phi2972}^{-S6}{}_{phi4724}^{-S15}$ differs by the addition of a spacer sequence of 30 bp at the 5' end of its CRISPR1 region and by the duplication of the repeat sequence, as shown in FIG. 17. Comparison of this additional spacer sequence with the sequence of D2972 genome showed that the second additional spacer sequence is 100% identical to that of the D2972 genome from nucleotide 1113 to nucleotide 1142.

From independent cultures using identical experimental conditions, $WT_{phi2972}^{+S6}{}_{phi4724}^{+S17}$ and $WT_{phi2972}^{+S6}{}_{phi4724}^{+S24}$ variant strains were isolated and analyzed (See, Table 7-1). As compared to $WT_{phi2972}^{+S6}$, these variant strains exhibited an increased resistance to D2972, as the efficiency of plaquing (EOP) of D2972 on $WT_{phi2972}^{+S6}{}_{phi4724}^{+S17}$ and $WT_{phi2972}^{+S6}{}_{phi4724}^{+S24}$ was reduced by more than 8 logs for both variant strains; and their resistance was also enlarged, as compared to $WT_{phi2972}^{+S6}$ as they displayed some resistance to D4724 (See Table 9-1). In addition, these variant strains display additional spacer sequences in CRISPR1 that are 100% identical to that of the genome of D2972 from nucleotide 33968 to nucleotide 33997 and nucleotide 30803 to nucleotide 30832, respectively.

In additional experiments, $WT_{phi2972}^{+S6}{}_{phi4724}^{+S15}$ was used as the parental strain and D4733 was used as the donor phage. The methods described above were used to generate the mutated phage D4733 from phage D4724. Then, phage D4733 was used to obtain a phage resistant variant strain from $WT_{phi2972}^{+S6}{}_{phi4724}^{+S15}$. The resulting variant strain was named $WT_{phi2972}^{+S6}{}_{phi4724}^{+S15}{}_{phi4733}^{+S16}$ (See, Table 7-1). This variant strain contains one additional sequence including a spacer sequence that is 100% identical to a sequence from D2972 genome, nucleotide 29923 to nucleotide 29894. It exhibited an increased resistance to D2972, as the efficiency of plaquing (EOP) of D2972 on $WT_{phi2972}^{+S6}{}_{phi4724}^{+S15}{}_{phi4733}^{+S16}$ was reduced by more than 8 logs and it resistance was expanded to phage D4733 (See Table 9-1). Table 9-1 provides a description of the phage resistance of some CRISPR-modified variant strains from DGCC7710. In this Table, "nd" indicates that results were not determined.

TABLE 9-1

Description of the Phage Resistance of Some CRISPR-Modified Variant Strains from DGCC7710

| Variant Strain | Parental Strain | Donor Phage | EOP D2972 | EOP D4724 | EOP D4733 | EOP D4720 | EOP D858 |
|---|---|---|---|---|---|---|---|
| — | DGCC7710 | — | 1 | 1 | 1 | 1 | 1 |
| $WT_{phi2972}^{+S6}$ | DGCC7710 | D2972 | $10^{-4}$ | 1 | 1 | nd | nd |
| $WT_{phi2972}^{+S6}{}_{phi4724}^{+S15}$ | $WT_{phi2972}^{+S6}$ | D4724 | $<10^{-8}$ | $<10^{-7}$ | 1 | nd | nd |
| $WT_{phi2972}^{+S6}{}_{phi4724}^{+S17}$ | $WT_{phi2972}^{+S6}$ | D4724 | $<10^{-8}$ | $<10^{-7}$ | nd | nd | nd |
| $WT_{phi2972}^{+S6}{}_{phi4724}^{+S24}$ | $WT_{phi2972}^{+S6}$ | D4724 | $<10^{-8}$ | $<10^{-7}$ | nd | nd | nd |
| $WT_{phi2972}^{+S6}{}_{phi4724}^{+S15}{}_{phi4733}^{+S16}$ | $WT_{phi2972}^{+S6}{}_{phi4724}^{+S15}$ | D4733 | $<10^{-8}$ | $<10^{-7}$ | $<10^{-6}$ | nd | nd |
| $WT_{phi2972}^{+S4}$ | DGCC7710 | D2972 | $10^{-5}$ | nd | nd | 1 | nd |
| $WT_{phi2972}^{+S4}{}_{phi4724}^{+S17}$ | $WT_{phi2972}^{+S4}$ | D4720 | $10^{-6}$ | nd | nd | $10^{-5}$ | nd |
| $WT_{phi2972}^{+S4}{}_{phi858}^{+S18}$ | $WT_{phi2972}^{+S4}$ | D858 | $<10^{-8}$ | nd | nd | nd | $10^{-5}$ |
| $WT_{phi2972}^{+S4}{}_{phi858}^{+S25}$ | $WT_{phi2972}^{+S4}$ | D858 | $<10^{-7}$ | nd | nd | nd | $10^{-3}$ |

In still further experiments, $WT_{phi2972}^{+S4}$ was used as the parental strain and D4720 was used as the donor phage. Using the same methods as described above, mutated phage D4720 was generated from phage D2972. Phage D4720 was used to obtain a phage resistant variant from $WT_{phi2972}^{+S4}$. The resulting variant strain was named $WT_{phi2972}^{+S4}{}_{phi4720}^{+S17}$ (See Table 7-1). This variant strain contains one additional sequence including a spacer sequence that is 100% identical to a sequence from D2972 genome from nucleotide 33968 to 33997. It exhibits an increased resistance to D2972, as the efficiency of plaquing (EOP) of D2972 on $WT_{phi2972}^{+S4}{}_{phi4724}^{+S17}$ was reduced by 6 logs (compared to 5 logs); and its resistance was enlarged to the phage D4720 (See, Table 9-1).

Example 10

Alternative Natural Methods to Insert Second Additional Sequence(s) in CRISPR Loci In this Example, alternative natural methods useful for inserting a second additional sequence in a CRISPR locus are described. It is known that a given parental strain may be sensitive to more than one family of phages. This diversity of sensitivity was advantageously used to insert additional sequences in a CRISPR locus of a variant strain, as described herein. In these experiments, the second donor phage was selected by testing the virulence of a selection of phages on the parental strain and on the variant strain(s). Second donor phages of interest were those that were virulent to both strains. It was contemplated that these phages would be likely to represent a different family of phages than those represented by the initial donor phage. Following its selection, the second donor phage was used to infect the variant strain. As described in the methods above, a second generation phage resistant variant strain was isolated and tested for an additional sequence within the CRISPR locus.

In these experiments, a collection of phages (or phage-containing samples) was tested against the parental strain using classical microbiological methods known in the art. Phages (or samples) that are virulent to the parental strain were then tested against the variant strain using the same methods. One phage (or sample) that was virulent to the variant strain was selected as a second donor phage. In the case of phage containing samples, the one virulent phage was purified to homogeneity on the variant strain using classical microbiological methods known in the art. In some experiments, the sequence of the second donor phage was determined. In some experiments, the second donor phage was then used as described above (See, Example 7) to provoke the insertion of a second additional sequence in the CRISPR locus of the variant strain.

In some experiments, $WT_{phi2972}^{+S4}$ (See, Example 8 and Table 7-1) was used as the parental strain and D858 was used as the donor phage. Upon testing of various phages, strain DGCC7710 was found to be sensitive to both phage D2972 and phage D858. In addition, D858 was found to be virulent against variant strain $WT_{phi2972}^{+S4}$. Phage D858 was therefore chosen as a second donor phage in some experiments.

The variant strain $WT_{phi2972}^{+S4}$ was exposed to the second donor phage D858, as described in Example 7. A phage resistant variant strain named $WT_{phi2972}^{-S4}{}_{phi8588}^{+S18}$ (See, Table 7-1) was obtained that is resistant to D858 (See Table 9-1). This strain exhibits an increased resistance to D2972, as the efficiency of plaquing of D2972 on $WT_{phi2972}^{+S4}{}_{phi858}^{+S18}$ was reduced by more than 8 logs (compared to 5 logs for $WT_{phi2972}^{-S4}$; See Table 9-1). DNA was extracted from $WT_{phi2972}^{+S4}{}_{phi858}^{+S18}$ and its CRISPR1 locus was analyzed by PCR using the same methods and primers as described above. The sequence of the PCR product was determined and compared to that of the CRISPR locus of $WT_{phi2972}^{+S4}$. Compared to $WT_{phi2972}^{+S4}$, $WT_{phi2972}^{-S4}{}_{phi858}^{+S18}$ differs by the addition of a spacer sequence of 30 bp at the 5' end of its CRISPR1 region and by the duplication of the repeat sequence, as shown in FIG. 17. Comparison of this additional spacer sequence with the sequence of D858 genome showed that the second additional spacer sequence is 100% identical to that of the D858 genome from nucleotide 30338 to nucleotide 30367.

Another variant strain named $WT_{phi2972}^{+S4}{}_{phi4720}^{+S25}$ (See, Table 7-1) was also obtained using this method in independent experimental work. This variant strain contains one additional sequence including a spacer sequence that is 100% identical to a sequence from D858 genome from nucleotide 33886 to 33915. It exhibits an increased resistance to D2972, as the efficiency of plaquing of D2972 on $WT_{phi2972}^{+S4}{}_{phi4724}^{+S25}$ was reduced by more than 7 logs (See. Table 9-1).

Example 11

Genesis of a CRISPR-Modified Variant Strain Resistant to Multiple Phages by Multiple Insertions of Additional Sequences in CRISPR Loci In this Example, the development of a multi-phage resistant strain is described through the iterative addition of phage sequences in CRISPR loci, as addition of 2 phage sequences in the CRISPR loci is not enough to confer resistance to all phages to a given strain. For example, strain $WT_{phi2972}^{+S4}{}_{phi858}^{+S18}$ (described in Example 10) was found to be sensitive to multiple other phages. In the process of developing a multi-phage resistant strain, the parental strain was submitted to a first phage to select a variant strain, then the variant strain was submitted to a second phage to select a second generation variant strain that is resistant to both phages. Then, the last variant strain was submitted iteratively to the phages to which it was still sensitive, until a final variant strain was obtained that was resistant to all available phages.

Using methods known in the art, a set of 10 reference phages were identified that are representative of the diversity of phages that are able to develop on strain DGCC7710, namely phages D858, D1126, D2766, D2972, D3288, D3821, D4083, D4752, D4753, and N1495. As described in Example 7, DGCC7710 was exposed to phage D2972 to generate the variant strain DGCC9705. DGCC9705 was found to be resistant to phage D2766 and D4752 in addition to phage D2972, but was still sensitive to the other phages as shown in Table 11-1. DGCC9705 is described in Table 11-1 and in FIG. 17. DGCC9705 presents 1 additional sequence in CRISPR1 and 1 additional sequence in CRISPR3. Analysis of the sequence of the CRISPR1 locus and of the CRISPR3 locus was done accordingly to the methods described in Example 7. The sequence of the PCR products were determined and compared to that of the CRISPR1 and 3 loci of DGCC7710. DGCC9705 presents 1 additional spacer in its CRISPR1 locus and one additional spacer in its CRISPR3 locus. The spacer sequences are identical to sequences from phage D2972. Using the same methods, DGCC9705 was then exposed to phage D3821 and variant strain DGCC9726 was then isolated. In addition to being resistant to D2972, DGCC9726 has resistance to phages D858, D3821, D4083 and N1495 (See. Table 11-1). DGCC9726 has 1 additional spacer sequence in its CRISPR1 locus as compared to DGCC9705 (See, Table 7-1 and FIG. 17). The additional spacer sequence is identical to a sequence from D2972. Through the exposure of strain DGCC9726 to phage D3288, DGCC9733 was isolated. Strain DGCC9733 is additionally resistant to phage D3288 and D1126 (See, Table 11-1). DGCC9733 has 1 additional spacer sequence in its CRISPR1 locus comparatively to DGCC9726 (See, Table 7-1 and FIG. 17). This spacer sequence has some identity (25/30 base pair identity) to a sequence of the streptococcal phage 7201. Finally, by a last iterative exposure to phage D4753, DGCC9836 was isolated that is resistant to all phages (See, Table 11-1). DGCC9836 has 2 additional spacer sequences in its CRISPR1 locus and 2 additional spacer sequences in its CRISPR3 locus (See, Table 7-1 and FIG. 17). One spacer sequence is identical to a sequence in phage D2972 and the 3 other spacer sequences are identical to sequences in phage D858.

Table 11-1 provides data regarding the phage sensitivity of the CRISPR-modified variant strain DGCC9836 and intermediate CRISPR-modified variant strains. In this Table, "S" indicates sensitivity and "R" indicates resistance.

reduced by more than 7 logs. DNA was extracted from $WT_{phi858phi2972}^{+S9S10S11S12}$ and its CRISPR loci were analyzed by PCR using the same methods and primers as described above. The sequence of the PCR products were determined and compared to that of the CRISPR1 locus and of the CRISPR3 locus of DGCC7710. Compared to DGCC7710, $WT_{phi858phi2972}^{+S9S10S11S12}$ differs by the addition of 4 spacer sequences of 30 bp at the 5' end of its CRISPR1 region and by duplication of the repeat sequences, as shown in FIG. 17. Comparison of the additional spacer sequences with the sequence of the D2972 genome showed that the additional spacer sequences are 100% identical to that of the D2972 from nucleotide 7874 to nucleotide 7903, from nucleotide 20650 to nucleotide 20621, from nucleotide 8360 to nucleotide 8389, and from nucleotide 18998 to nucleotide 19027.

In further experiments, strain $WT_{phi858phi2972}^{+S13S14}$ (See, Table 7-1) was also obtained following these methods. It exhibits resistance to D858, as the efficiency of plaquing of D858 on $WT_{phi858phi2972}^{-S13S14}$ was reduced by 7 logs, and

TABLE 11-1

Phage Sensitivity of the CRISPR-modified Variant Strain DGCC9836 and Intermediate CRISPR-Modified Variant Strains.

| | Parental | Donor | Phage | | | | | | | | | |
|---|---|---|---|---|---|---|---|---|---|---|---|---|
| Strain | Strain | Phage | D2972 | D2766 | D4752 | D3821 | D858 | D4083 | N1495 | D3288 | D1126 | D4753 |
| DGCC7710 | — | — | S | S | S | S | S | S | S | S | S | S |
| DGCC9705 | DGCC7710 | D2972 | R | R | R | S | S | S | S | S | S | S |
| DGCC9726 | DGCC9705 | D3821 | R | R | R | R | R | R | R | S | S | S |
| DGCC9733 | DGCC7710 | D3288 | R | R | R | R | R | R | R | R | R | S |
| DGCC9836 | DGCC7710 | D4753 | R | R | R | R | R | R | R | R | R | R |

Example 12

Natural Method to Insert Multiple Additional Sequence(s) in a CRISPR Locus

In this Example, methods are described to insert multiple additional sequences in CRISPR loci. In these methods, rather than using the various phages iteratively, the parental strain was exposed to a mix containing multiple phages. A collection of phages was tested against multiple strains using classical microbiological methods, in order to determine their host spectrum. Phages that were virulent to the parental strain but that have different host spectrum were selected. The selected phages were mixed and used in the methods provided above (See, Example 7) to provoke the insertion of additional sequences in the CRISPR loci of the variant strain.

In some experiments, DGCC7710 was used as the parental strain and D858 and D2972 were used as the donor phages. Upon testing of various phages, strain DGCC7710 was found to be sensitive to both phage D2972 and phage D858. However, D2972 and D858 presented different host spectra when tested on strain DGCC7778, suggesting that the two phages were different.

The parental strain DGCC7710 was exposed to a mix of phage D858 and D2972 as described in Example 7. A phage resistant variant strain named $WT_{phi858phi2972}^{+S9S10S11S12}$ (See, Table 7-1) was obtained. It exhibits resistance to D858, as the efficiency of plaquing of D858 on $WT_{phi858phi2972}^{-S9S10S11S12}$ was reduced by more than 7 logs, as well as resistance to D2972, as the efficiency of plaquing of D2972 on $WT_{phi858phi2972}^{+S9S10S11S12}$ was resistance to D2972, as the efficiency of plaquing of D2972 on $WT_{phi858phi2972}^{+S13S14}$ was reduced by 8 logs. Comparison of the additional spacer sequences with the sequence of D2972 genome showed that the additional spacer sequences are 100% identical to that of the D2972 from nucleotide 33602 to nucleotide 33631, and from nucleotide 4830 to nucleotide 4801.

Example 13

Fighting Phages in Fermentation Using a CRISPR-Modified Variant Strain

In this Example methods of fighting phages in fermentation by the use of a variant strain rather than a parental (i.e., wild-type, recipient) strain are described. Thus, this Example provides yet another description of the benefits provided by variant strains.

In some experiments, comparison of strain DGCC7710 to strain $WT_{phi2972}^{+S20}$ and to strain $WT_{phi2972}^{+S26S27}$ in milk fermentation in the presence of phage D2972 was performed. DGCC7710 is an industrial strain used in milk fermentation. Strain $WT_{phi2972}^{+S20}$ is described in Table 7-1 and in Example 8 and displays in its CRISPR1 locus an additional spacer, as compared to strain DGCC7710. Strain $WT_{phi2972}^{+S20}$ exhibits improved resistance to D2972, as compared to DGCC7710. $WT_{phi2972}^{+S26S27}$ is another variant exhibiting some resistance to D2972 (described in Table 7-1) and displays 2 additional spacers in its CRISPR1 locus.

Serial fermentations were performed with each strain. First, 10% milk powder medium (w/v) was seeded with 1% (v/v) of a pre-culture of the tested strain and with $10^4$ pfu/ml of phage D2972. The culture was incubated at 42° C. for 6 h. Following the first fermentation, a second fermentation was set up. The exact same fermentation conditions were used except that 0.1% volume of the fermentate of the preceding fermentation was added (before addition, the fermentate was filtrated using a 0.45 μm filter). Then, successive fermentations were performed with the same experimental conditions as those used for the second fermentation. All fermentations were recorded by impedimetry. At the end of each of the fermentation, the clotting of the milk was tested and titration of phages was performed using methods known in the art.

In the case of milk fermentation in the absence of phage, variation of impedance with DGCC7710 was above 2500 μS within 6 hours. In the presence of D2972, (DGCC7710 being very sensitive to phages), D2972 phages reached high level of population during first culture and fermentation failed to clot the milk. Variation of impedance at 6 hours was always below 500 μS. On the contrary, milk fermentation with $WT_{phi2972}^{+S20}$ in the presence of D2972 allowed clotting of milk at least until the 3rd sub-culture and slow evolution of phage level was noted. Variation of impedance increased to more than 2500 μS also until the 3rd sub-culture. This demonstrates that the variant strain $WT_{phi2972}^{+S20}$ is more appropriate than the parental strain DGCC7710 for milk acidification in the presence of phages. Furthermore, fermentation of milk with $WT_{phi2972}^{+S26S27}$ in the presence of D2972 allowed clotting of milk until the last sub-culture without phage development. In addition, variation of impedance increased to more than 2500 μS also until the last sub-culture. This demonstrates that the variant strain $WT_{phi2972}^{-S26S27}$ is more appropriate than the parental strain DGCC7710 and even more appropriate than $WT_{phi2972}^{+S20}$ for milk acidification in the presence of phages. The experiments were duplicated; the results are presented in Table 13-1.

TABLE 13-1

Comparison of Milk Fermentation with DGCC7710 or with Variant Strains in the Presence of phage D2972

| Strain | Subcultures | Clotting of Milk Within 6 h | Phage Level on Fermenting Strain | Variation of Impedance Within 6 h (in μS) |
|---|---|---|---|---|
| DGCC7710 | Control | Yes | No | 3246 |
| DGCC7710 | 1 | No | High | 319 |
| First trial | 2 | No | High | 23 |
| DGCC7710 | 1 | No | High | 287 |
| Second trial | 2 | No | High | 16 |
| $WT_{phi2972}^{+S20}$ | 1 | Yes | No | 3281 |
| First trial | 2 | Yes | Low | 3148 |
| | 3 | Yes | Low | 3251 |
| | 4 | Yes | High | 3101 |
| $WT_{phi2972}^{+S20}$ | 1 | Yes | Low | 3371 |
| Second trial | 2 | Yes | Medium | 3265 |
| | 3 | Yes | High | 2780 |
| | 4 | No | High | 223 |
| $WT_{phi2972}^{+S26S27}$ | 1 | Yes | No | 3322 |
| First trial | 2 | Yes | No | 3208 |
| | 3 | Yes | No | 3467 |
| | 4 | Yes | No | 3182 |
| $WT_{phi2972}^{+S26S27}$ | 1 | Yes | No | 3260 |
| Second trial | 2 | Yes | No | 3021 |
| | 3 | Yes | No | 3377 |
| | 4 | Yes | No | 3246 |

In a second set of experiments, comparison of strain DGCC7710 to strain $WT_{phi2972}^{+S20}$ and to strain $WT_{phi2972}^{-S26S27}$ in milk fermentation in the presence of phage D2972 was reproduced. In addition, strain DGCC9836 was studied. Strain DGCC9836 is an even more evolved variant strain of DGCC7710 that is the result of multiple phage challenge. This strain presents 5 additional spacers in its CRISPR1 locus and 3 additional spacers in its CRISPR3 locus (See, Example 11 and FIG. 17). DGCC9836 is resistant to all tested phages.

Experiments were conducted as described above. The results are displayed in Table 13-2. As for the first set of experiments, fermentation of milk with $WT_{phi2972}^{+S20}$ in the presence of D2972 allowed clotting of milk until the 5th sub-culture and slow evolution of phage level was measured. Variation of impedance increased to more than 2500 μS during the 5 first sub-cultures, demonstrating that milk acidification is unaffected by phages. At the 6th sub-culture, phage level increased significantly and the milk fermentation was impaired. For the 2 other variant strains, milk fermentation was unaffected all along the 6 sub-cultures, phages never developed and the recorded variation of impedance was always above 2500 μS.

These experiments demonstrate that strains containing at least one additional spacer sequence in its CRISPR1 locus allow milk fermentation even in the presence of phages. Milk fermentation is even more secured when strains have more than one additional spacer sequence in its CRISPR loci.

TABLE 13-2

Comparison of Milk Fermentation with Variant Strains of DGCC7710 in the Presence of Phage D2972

| Strain | Subcultures | Clotting of Milk Within 6 h | Phage Level on Fermenting Strain | Variation of Impedance Within 6 h (in μS) |
|---|---|---|---|---|
| $WT_{phi2972}^{+S20}$ | 1 | Yes | No | 3171 |
| | 2 | Yes | No | 2991 |
| | 3 | Yes | Low | 2871 |
| | 4 | Yes | Medium | 2934 |
| | 5 | Yes | Medium | 2906 |
| | 6 | No | High | 661 |
| $WT_{phi2972}^{+S26S27}$ | 1 | Yes | No | 2970 |
| | 2 | Yes | No | 2945 |
| | 3 | Yes | No | 2617 |
| | 4 | Yes | No | 2721 |
| | 5 | Yes | No | 2660 |
| | 6 | Yes | No | 2605 |
| DGCC9836 | 1 | Yes | No | 3028 |
| | 2 | Yes | No | 3115 |
| | 3 | Yes | No | 2708 |
| | 4 | Yes | No | 2817 |
| | 5 | Yes | No | 2845 |
| | 6 | Yes | No | 2813 |

Example 14

Fighting Phages in Fermentation Using a Combination of CRISPR-Modified Variant Strains In this Example, methods for fighting phages in fermentation through the use of a combination of variant strains instead of using a single strain are described. Thus, this Example illustrates the simultaneous use of more than one variant strains (i.e., a combination of variant strains). Indeed, mixtures of strains exhibiting the same functionalities, yet different phage sensitivity patterns find use in such applications. For example, 2 or 3 or even more variant strains as described herein find use in such applications. Using a combination of variant strains with different added spacer sequences in their CRISPR loci allows the fermentation to more easily resist any emerging mutant phages.

In some experiments, comparisons were made between strain $WT_{phi2972}^{+S21}$ alone and a combination of 3 strains (namely $WT_{phi2972}^{+S20}$, $WT_{phi2972}^{+S21}$ and $WT_{phi2972}^{-S22}$) used in milk fermentation in the presence of phage D2972. Strains $WT_{phi2972}^{+S20}$, $WT_{phi2972}^{+S21}$ and $WT_{phi2972}^{+S22}$ are described in Table 7-1 and in Example 8. They are independent variant strains of DGCC7710. Each variant strain displays in its CRISPR1 locus a distinct additional spacer sequence (which originated from phage D2972) as compared to strain DGCC7710.

Serial fermentations were performed either with strain $WT_{phi2972}^{+S21}$ alone or in the threes strain combination. First, 10% milk powder medium (w/v) was seeded with 1% (v/v) of a pre-culture of the strain alone or the combination of strains and with $10^4$ pfu/ml of phage D2972. The culture was incubated at 42° C. for 6 h. Following the first fermentation, a second fermentation was set up. The exact same fermentation conditions were used except that 0.1% volume of the fermentate of the preceding fermentation was added (before addition, the fermentate was filtrated using a 0.45 μm filter). Then successive fermentations were performed using the same experimental conditions as those used for the second fermentation. All fermentations were recorded by impedimetry. At the end of each of the fermentation the clotting of the milk was tested and titration of phages was performed using methods known in the art. The experiments were duplicated; the results are provided in Table 14-1.

TABLE 14-1

Comparison of Milk Fermentation with $WT_{phi2972}^{+S21}$ or with a Three Strain Combination in the Presence of Phage D2972

| Strain | Subcultures | Clotting of Milk Within 6 h | Phage Level on Fermenting Strain | Variation of Impedance Within 6 h (in μS) |
|---|---|---|---|---|
| DGCC7710 | Control | No | High | 46 |
| $WT_{phi2972}^{+S21}$ | 1 | Yes | Low | 3367 |
| First trial | 2 | Yes | High | 3312 |
| | 3 | No | High | 555 |
| | 4 | No | High | 33 |
| | 5 | No | High | 25 |
| $WT_{phi2972}^{+S21}$ | 1 | Yes | Low | 3450 |
| Second trial | 2 | Yes | High | 3293 |
| | 3 | No | High | 1071 |
| | 4 | No | High | 29 |
| | 5 | No | High | 26 |
| $WT_{phi2972}^{+S20}$ | 1 | Yes | Very low | 3242 |
| $WT_{phi2972}^{+S21}$ | 2 | Yes | Low | 3233 |

TABLE 14-1-continued

Comparison of Milk Fermentation with $WT_{phi2972}^{+S21}$ or with a Three Strain Combination in the Presence of Phage D2972

| Strain | Subcultures | Clotting of Milk Within 6 h | Phage Level on Fermenting Strain | Variation of Impedance Within 6 h (in μS) |
|---|---|---|---|---|
| $WT_{phi2972}^{+S22}$ | 3 | Yes | High | 3319 |
| First trial | 4 | Yes | High | 3169 |
| | 5 | Yes | High | 3261 |
| $WT_{phi2972}^{+S20}$ | 1 | Yes | Very low | 3384 |
| $WT_{phi2972}^{+S21}$ | 2 | Yes | Low | 3178 |
| $WT_{phi2972}^{+S22}$ | 3 | Yes | High | 3206 |
| Second trial | 4 | Yes | High | 3295 |
| | 5 | Yes | High | 3209 |

Milk fermentation done with $WT_{phi2972}^{-S21}$ in the presence of phages failed at the third subculture in both trials. This was shown by an absence of clotting of the milk and by a highly reduced variation of impedance following 6 hours of fermentation. On the contrary, despite some development of phage D2972, the fermentations were successfully conducted until the fifth subculture when the mix of the three strains was used. Clotting of milk was recorded in all cultures and variation of impedance within 6 hours of incubation was never below 3000 μS.

These experiments demonstrate that the use of combination of variant strains having at least one additional distinct spacer sequence in its CRISPR1 locus allows milk fermentation in the presence of phages, as compared to the use of single variant strain.

Example 15

Fighting Phages in Fermentation Using a Rotation of CRISPR-Modified Variant Strains In additional experiments, the variant strains were used in rotation. In some experiments, the strains had the same functionalities, but different phage sensitivity patterns. Thus, in this Example, experiments conducted on the iterative/subsequent use of several different strains (i.e., CRISPR-modified variant strains) sequentially in a rotation scheme are described.

In some experiments, comparisons were made between strain $WT_{phi2972}^{+S21}$ alone and strains $WT_{phi2972}^{+S20}$, $WT_{phi2972}^{+S21}$ and $WT_{phi2972}^{+S22}$ used successively (in rotation) in milk fermentation in the presence of phage D2972. The first milk fermentation was conducted with strain $WT_{phi2972}^{+S20}$. Then, strain $WT_{phi2972}^{-S22}$ was used for the second fermentation, and strain $WT_{phi2972}^{+S21}$ was used for the third fermentation. The fourth fermentation was then again done using strain $WT_{phi2972}^{-S20}$; followed by a fermentation with strain $WT_{phi2972}^{+S22}$, then strain $WT_{phi2972}^{-S21}$, and so on. Strains $WT_{phi2972}^{+S20}$ $WT_{phi2972}^{+S21}$ and $WT_{phi2972}^{-S22}$ are described above in Table 7-1. They are independent variant strains of strain DGCC7710. Each variant strain displays a distinct additional spacer sequence in its CRISPR1 locus, as compared to strain DGCC7710, which originated from phage D2972.

Serial fermentations were performed using the same experimental methods as described in Example 14. Experiments were done in triplicate; the results are displayed in Table 15-1. Serial fermentations inoculated with $WT_{phi2972}^{+S20}$ alone were successful until the 3rd subculture, as shown by values of variation of impedance above 3000 μS and by milk clotting. The next subcultures failed to clot the milk and high phage values were recorded. In contrast, serial fermentations made by inoculating the milk in rotation with 3 different variant strains ($WT_{phi2972}^{-S20}$, $WT_{phi2972}^{-S21}$ and $WT_{phi2972}^{+S22}$) were successful up to the tenth subculture. Under these experimental conditions, phages failed to propagate and remained at low levels. The results indicate that using a rotation of variant strains provides improved phage resistance during fermentation, as compared to the use of a single variant strain.

TABLE 15-1

Successive Milk Fermentation with Rotation of Strains in the Presence of Phage D2972

| Trial | Fermentation | Clotting of Milk Within 6 h | Phage Level on Fermenting Strain | Variation of Impedance Within 6 h (in μS) |
|---|---|---|---|---|
| Control | 1st fermentation $WT_{phi2972}^{+S20}$ | Yes | No | 3464 |
| | 2nd fermentation $WT_{phi2972}^{+S20}$ | Yes | Low | 3203 |
| | 3rd fermentation $WT_{phi2972}^{+S20}$ | Yes | Medium | 3300 |
| | 4th fermentation $WT_{phi2972}^{+S20}$ | No | High | 235 |
| | 5th fermentation $WT_{phi2972}^{+S20}$ | No | High | 249 |
| First trial | 1st fermentation $WT_{phi2972}^{+S20}$ | Yes | No | 3134 |
| | 2nd fermentation $WT_{phi2972}^{+S22}$ | Yes | No | 3253 |
| | 3rd fermentation $WT_{phi2972}^{+S21}$ | Yes | No | 3076 |
| | 4th fermentation $WT_{phi2972}^{+S20}$ | Yes | No | 3103 |
| | 5th fermentation $WT_{phi2972}^{+S22}$ | Yes | No | 2930 |
| | 6th fermentation $WT_{phi2972}^{+S21}$ | Yes | Low | 3127 |
| | 7th fermentation $WT_{phi2972}^{+S20}$ | Yes | No | 3160 |
| | 8th fermentation $WT_{phi2972}^{+S22}$ | Yes | Low | 2969 |
| | 9th fermentation $WT_{phi2972}^{+S21}$ | Yes | Low | 2967 |
| | 10th fermentation $WT_{phi2972}^{+S20}$ | Yes | Low | 3051 |

TABLE 15-1-continued

Successive Milk Fermentation with Rotation of Strains in the Presence of Phage D2972

| Trial | Fermentation | Clotting of Milk Within 6 h | Phage Level on Fermenting Strain | Variation of Impedance Within 6 h (in μS) |
|---|---|---|---|---|
| Second trial | 1$^{st}$ fermentation $WT_{phi2972}^{+S20}$ | Yes | No | 3168 |
| | 2$^{nd}$ fermentation $WT_{phi2972}^{+S22}$ | Yes | No | 3063 |
| | 3$^{rd}$ fermentation $WT_{phi2972}^{+S21}$ | Yes | No | 2992 |
| | 4$^{th}$ fermentation $WT_{phi2972}^{+S20}$ | Yes | No | 3186 |
| | 5$^{th}$ fermentation $WT_{phi2972}^{+S22}$ | Yes | Low | 3070 |
| | 6$^{th}$ fermentation $WT_{phi2972}^{+S21}$ | Yes | Low | 2932 |
| | 7$^{th}$ fermentation $WT_{phi2972}^{+S20}$ | Yes | Low | 3181 |
| | 8$^{th}$ fermentation $WT_{phi2972}^{+S22}$ | Yes | Low | 2920 |
| | 9$^{th}$ fermentation $WT_{phi2972}^{+S21}$ | Yes | Low | 2863 |
| | 10$^{th}$ fermentation $WT_{phi2972}^{+S20}$ | Yes | Low | 2995 |
| Third trial | 1$^{st}$ fermentation $WT_{phi2972}^{+S20}$ | Yes | No | 3308 |
| | 2$^{nd}$ fermentation $WT_{phi2972}^{+S22}$ | Yes | No | 3290 |
| | 3$^{rd}$ fermentation $WT_{phi2972}^{+S21}$ | Yes | No | 3023 |
| | 4$^{th}$ fermentation $WT_{phi2972}^{+S20}$ | Yes | No | 3039 |
| | 5$^{th}$ fermentation $WT_{phi2972}^{+S22}$ | Yes | Low | 2994 |
| | 6$^{th}$ fermentation $WT_{phi2972}^{+S21}$ | Yes | Low | 2945 |
| | 7$^{th}$ fermentation $WT_{phi2972}^{+S20}$ | Yes | Low | 3184 |
| | 8$^{th}$ fermentation $WT_{phi2972}^{+S22}$ | Yes | Low | 3048 |
| | 9$^{th}$ fermentation $WT_{phi2972}^{+S21}$ | Yes | Low | 3063 |
| | 10$^{th}$ fermentation $WT_{phi2972}^{+S20}$ | Yes | No | 3016 |

Example 16

Reduction and Control of Phage Population Using CRISPR-Modified Variant Strains In this Example, experiments conducted to determine the ability of a CRISPR-modified strain to destroy phages that it has been made resistant to are described. In particular, experiments were designed to determine whether a phage population will be decreased to an undetectable level during fermentation of a CRISPR-modified strain.

Figure 20:
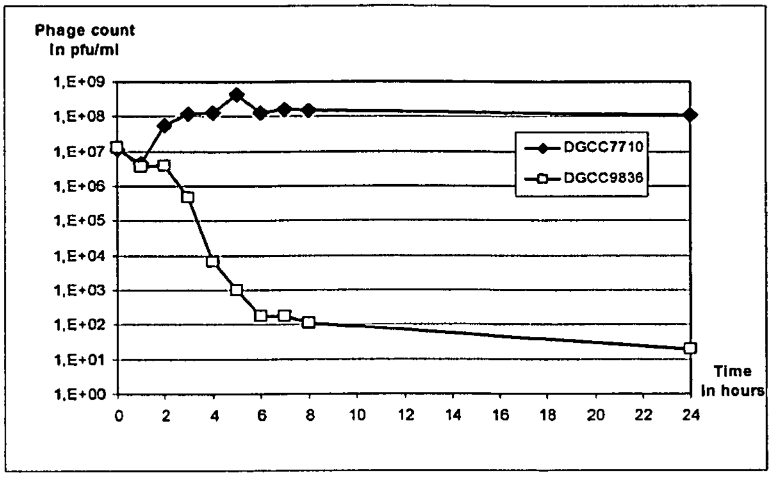
FIG. 20 provides a graph showing the evolution of phage count in milk containing $10^7$ pfu/ml of D2972 during fermentation with DGCC7710 (black diamonds) or with DGCC9836 (open squares). Milk was 10% (w/v) milk powder in water. The incubation temperature was 42° C.

In some experiments, DGCC9836 (described in Example 11 and in FIG. 17) was used to perform milk fermentation in the presence of phage D2972, in comparison to fermentations made with its parental strain DGCC7710 in the presence of D2972. Ten-percent milk powder medium (w/v) was seeded with about $10^6$ cfu/ml of a pre-culture of the tested strain and with $10^7$ pfu/ml of phage D2972. The culture was incubated at 42° C. for 24 h. At various time points, an aliquot was taken and the phage population was measured using double-layer agar plate seeded with DGCC7710 using standard methods known in the art. The results are presented in FIG. 20. In fermentation of milk by DGCC7710, phage D2972 developed to reach a population of above $10^8$ pfu/ml. In contrast, during the fermentation with DGCC9836, the D2972 phage population gradually decreased to very low level (120 pfu/ml) after 6 hours of incubation, and was almost undetectable after 24 hours of incubation. This last result suggests that phages were destroyed during the process of fermentation with the variant strain DGCC9836.

The property of a variant strain to destroy phages, as well as not being sensitive to the phages represents an additional benefit, as compared to the traditional starter culture rotation program for which the strains are not sensitive, but are harmless to phages. Indeed, by using variant strains, eradication of dormant phages will occur through the combination of washing out the phages (as for rotation using traditional starter culture) and of destroying the phages.

Figure 21:
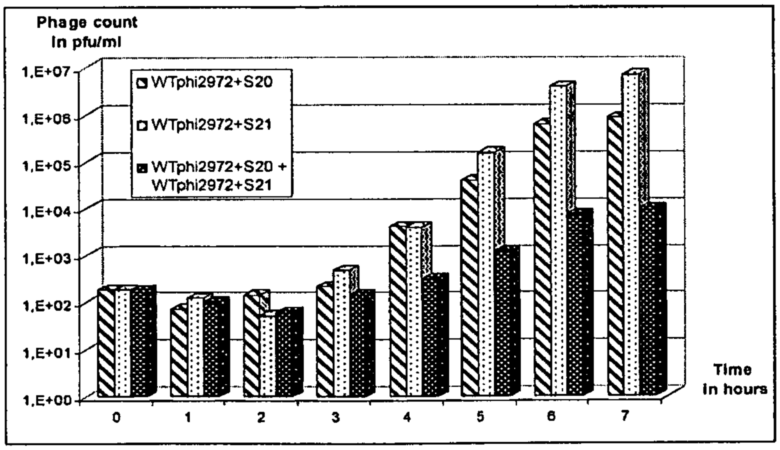
FIG. 21 provides a graph showing the evolution of the cumulated phage count on $WT_{phi2972}^{+S20}$ and $WT_{phi2972}^{+S21}$ in milk containing $10^7$ pfu/ml of D2972 during fermentation inoculated with $WT_{phi2972}^{+S20}$ (dashed) or with $WT_{phi2972}^{+S21}$ (light grey) or with both $WT_{phi2972}^{+S20}$ and $WT_{phi2972}^{+S21}$ (dark grey). Milk was 10% (w/v) milk powder in water. The incubation temperature was 42° C.

In other experiments, variant strains presenting some but incomplete resistance to phage D2972 were associated in milk fermentation in the presence of D2972. Selected variant strains included $WT_{phi2972}^{+S20}$ and $WT_{phi2972}^{+S21}$, as described in Example 8 and in Table 7-1. These strains display EOP reductions for the phage D2972 of about 5 logs. Milk fermentations were performed as described above (bacterial inoculation rate of $10^6$ cfu/ml; phage inoculation rate of $10^7$ pfu/ml). Milk fermentations were made either with $WT_{phi2972}^{+S20}$ or with $WT_{phi2972}^{+S21}$ or a mix of the two strains. At various time points, the population of phages was recorded. For this purpose, an aliquot was taken and phage population was measured using double-layer agar plate seeded either with $WT_{phi2972}^{+S20}$ or with $WT_{phi2972}^{+S21}$, using standard methods known in the art. The results are presented in FIG. 21, which indicates the sum of phages detected on $WT_{phi2972}^{+S20}$ and on $WT_{phi2972}^{+S21}$ for each of the milk fermentations. When a single strain was used for the fermentation ($WT_{phi2972}^{+S20}$ or $WT_{phi2972}^{-S21}$), the number of detected phages at inoculation time was about 100 pfu/ml (due to the 5 logs of EOP reduction). Upon cultivation, this number of phages rose to $10^6$ or $10^7$ (respectively), corresponding to a multiplication of the phages by 4 to 5 logs. The multiplication factor of the phages was much lower (2 logs) for the milk fermentation inoculated with the 2 strains. Indeed, the number of phages rose from 100 pfu/ml to a maximum of about $10^4$ pfu/ml. These results conclusively show that during a co-culture of 2 variant strains the propagation rate of the phages is significantly reduced compare to the propagation rate of the phages in a culture made with a single variant strains.

Example 17

Insertion of Spacers

Figure 18:
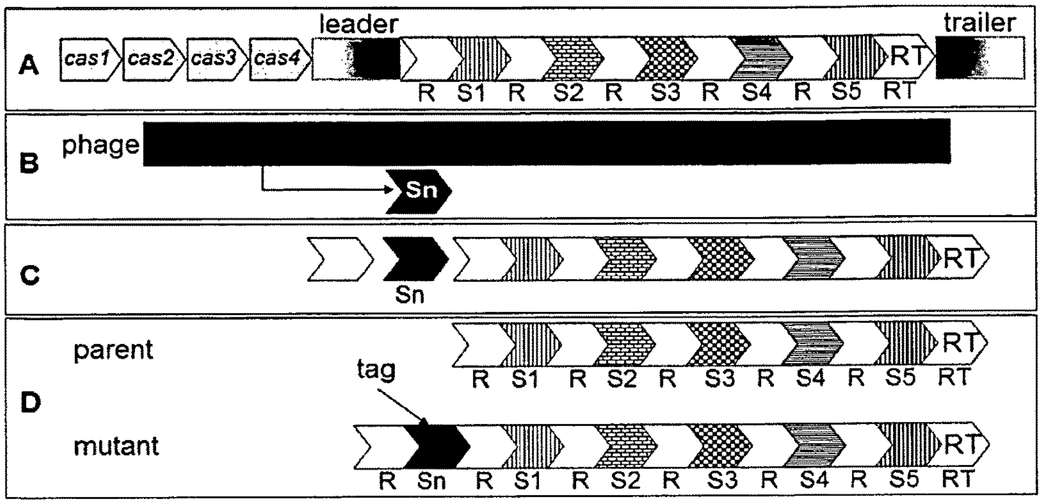
FIG. 18 provides a schematic showing an embodiment of the present invention, in which a tagging sequence and a CRISPR repeat are integrated at one end of the CRISPR locus. In Panel A, the CRISPR locus and elements, including repeats (R), spacers (S), the upstream leader and downstream trailer, with the terminal repeat (RT) adjacent to the trailer, and cas genes in the vicinity (4 cas genes named cas1 to cas4 herein, not drawn to scale) are indicated. The cas genes can be on either end, or split and present on both ends. In addition, cas genes may be located on any of the two DNA strands. Panel B shows the phage sequence, with a fragment of the sequence (Sn) being used as an additional spacer (i.e., tagging sequence). Panel C shows insertion of a new spacer (Sn) (i.e., tagging sequence) at one end of the CRISPR locus (close to the leader in this example at the 5' end of the CRISPR locus), between two repeats. Panel D provides a comparison of the CRISPR locus content between the parent and the mutant bacterium (i.e., labelled bacterium), with a new spacer (Sn) (i.e., tagging sequence) integrated at one end of the CRISPR locus (close to the leader in this example), between repeats. The new spacer (Sn) constitutes the tagging sequence which is specific for the mutant bacterium (i.e., labelled bacterium). In some embodiments, use of this method results in the addition of one or more spacers from the phage sequence.
Figure 19:
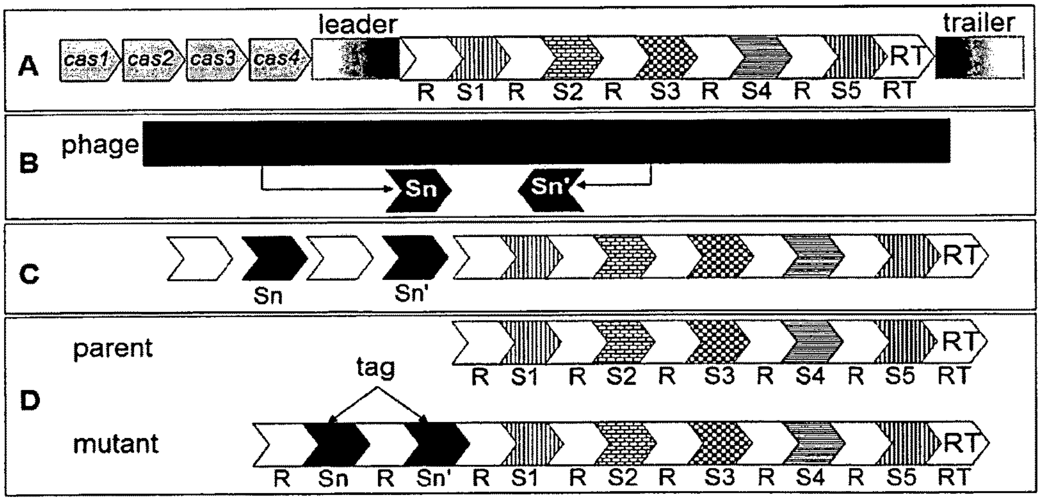
FIG. 19 provides a schematic showing an embodiment of the present invention, in which two tagging sequences and two CRISPR repeats are integrated at one end of the CRISPR locus. In Panel A, (A) CRISPR locus and elements, including repeats (R), spacers (S), the upstream leader and downstream trailer, with the terminal repeat (RT) adjacent to the trailer, and cas genes in the vicinity (4 cas genes named cas1 to cas4 herein, not drawn to scale) are indicated. The cas genes can be on either end, or split and present on both ends. cas genes may be located on any of the two DNA strands. Panel B shows the phage sequence in black, with two fragments of the sequence (Sn and Sn') being used as additional spacers (i.e., tagging sequences). Panel C shows the insertion of the new spacers (i.e., tagging sequences) (Sn and Sn') at the same end of the CRISPR locus (close to the leader in this example at the 5' end), each of which is in between two repeats. Panel B provides a comparison of the CRISPR locus content between the parent and the mutant bacterium (i.e., labelled bacterium), with two new spacers (Sn and Sn') integrated at the same end of the CRISPR locus (close to the leader in this example at the 5' end), with each located in between repeats. The new spacers Sn and Sn' constitute the tagging sequence which is specific of the mutant. In some embodiments, this method results in the addition of one or more spacers from the phage sequence.

In this Example, methods and compositions used to insert two spacers in *S. thermophilus* DGC7710 are described. *S. thermophilus* strain DGCC7710 (deposited at the French "Collection Nationale de Cultures de Microorganismes" under number CNCM 1-2423) possesses at least 3 CRISPR loci: CRISPR1, CRISPR2, and CRISPR3. In strains CNRZ1066 and LMG18311, for which the complete genome sequence is known (See, Bolotin et al., [2004], supra), CRISPR1 is located at the same chromosomal locus:

between str0660 (or stu0660) and str0661 (or stu0661) (See, FIG. 18). In strain DGCC7710, CRISPR1 is also located at the same chromosomal locus, between highly similar genes. CRISPR1 of strain DGCC7710 contains 33 repeats (including the terminal repeat), and thus 32 spacers (See, FIG. 19). All of these spacers are different from each other. Most of these spacers have not previously been described as being within CRISPR loci, but four spacers close to the CRISPR1 trailer are identical to known CRISPR1 spacers. For example, the 28$^{th}$ spacer of DGCC7710 is 100% identical to the 31$^{st}$ CRISPR1 spacer of strain CNRZ1575 (Genbank accession number DQ072991); the 30$^{th}$ spacer of DGCC7710 is 100% identical to the 27$^{th}$ CRISPR1 spacer of strain CNRZ703 (Genbank accession number DQ072990); the 31$^{st}$ spacer of DGCC7710 is 100% identical to the 28$^{th}$ CRISPR1 spacer of strain CNRZ703 (Genbank accession number DQ072990); and the 32$^{nd}$ spacer of DGCC7710 is 100% identical to the 30$^{th}$ CRISPR1 spacer of strain CNRZ703 (Genbank accession number DQ072990). The CRISPR1 sequence (5'-3') of strain DGCC7710 is shown in SEQ ID NO:678, below:

```
                                                  (SEQ ID NO: 678)
caaggacagttattgattttataatcactatgtgggtataaaaacgtcaaaatttcatttgag

GTTTTTGTACTCTCAAGATTTAAGTAACTGTACAACtgtttgacagcaaatcaagattcgaattgt

GTTTTTGTACTCTCAAGATTTAAGTAACTGTACAACaatgacgaggagctattggcacaacttaca

GTTTTTGTACTCTCAAGATTTAAGTAACTGTACAACcgatttgacaatctgctgaccactgttatc

GTTTTTGTACTCTCAAGATTTAAGTAACTGTACAACacacttggcaggcttattactcaacagcga

GTTTTTGTACTCTCAAGATTTAAGTAACTGTACAACctgttccttgttcttttgttgtatcttttc

GTTTTTGTACTCTCAAGATTTAAGTAACTGTACAACttcattcttccgtttttgtttgcgaatcct

GTTTTTGTACTCTCAAGATTTAAGTAACTGTACAACgctggcgaggaaacgaacaaggcctcaaca

GTTTTTGTACTCTCAAGATTTAAGTAACTGTACAACcatagagtggaaaactagaaacagattcaa

GTTTTTGTACTCTCAAGATTTAAGTAACTGTACAACataatgccgttgaattacacggcaaggtca

GTTTTTGTACTCTCAAGATTTAAGTAACTGTACAACgagcgagctcgaaataatcttaattacaag

GTTTTTGTACTCTCAAGATTTAAGTAACTGTACAACgttcgctagcgtcatgtggtaacgtattta

GTTTTTGTACTCTCAAGATTTAAGTAACTGTACAACggcgtcccaatcctgattaatacttactcg

GTTTTTGTACTCTCAAGATTTAAGTAACTGTACAACaacacagcaagacaagaggatgatgctatg

GTTTTTGTACTCTCAAGATTTAAGTAACTGTACAACcgacacaagaacgtatgcaagagttcaag

GTTTTTGTACTCTCAAGATTTAAGTAACTGTACAACacaattcttcatccggtaactgctcaagtg

GTTTTTGTACTCTCAAGATTTAAGTAACTGTACAACaattaagggcatagaaagggagacaacatg

GTTTTTGTACTCTCAAGATTTAAGTAACTGTACAACcgatatttaaaatcattttcataacttcat

GTTTTTGTACTCTCAAGATTTAAGTAACTGTACAACgcagtatcagcaagcaagctgttagttact

GTTTTTGTACTCTCAAGATTTAAGTAACTGTACAACataaactatgaaattttataattttaaga

GTTTTTGTACTCTCAAGATTTAAGTAACTGTACAACaataatttatggtatagcttaatatcattg

GTTTTTGTACTCTCAAGATTTAAGTAACTGTACAACtgcatcgagcacgttcgagtttaccgtttc

GTTTTTGTACTCTCAAGATTTAAGTAACTGTACAACtctatatcgaggtcaactaacaattatgct

GTTTTTGTACTCTCAAGATTTAAGTAACTGTACAACaatcgttcaaattctgttttaggtacattt

GTTTTTGTACTCTCAAGATTTAAGTAACTGTACAACaatcaatacgacaagagttaaaatggtctt

GTTTTTGTACTCTCAAGATTTAAGTAACTGTACAACgcttagctgtccaatccacgaacgtggatg

GTTTTTGTACTCTCAAGATTTAAGTAACTGTACAACcaaccaacggtaacagctactttttacagt

GTTTTTGTACTCTCAAGATTTAAGTAACTGTACAACataactgaaggataggagcttgtaaagtct

GTTTTTGTACTCTCAAGATTTAAGTAACTGTACAACtaatgctacatctcaaaggatgatcccaga

GTTTTTGTACTCTCAAGATTTAAGTAACTGTACAACaagtagttgatgacctctacaatggtttat

GTTTTTGTACTCTCAAGATTTAAGTAACTGTACAACacctagaagcatttgagcgtatattgattg

GTTTTTGTACTCTCAAGATTTAAGTAACTGTACAACaattttgccccttctttgccccttgactag

GTTTTTGTACTCTCAAGATTTAAGTAACTGTACAACaccattagcaatcatttgtgcccattgagt
```

-continued

GTTTTTGTACTCTCAAGATTTAAGTAACTGTACAGT

Ttgattcaacataaaaagccagttcaattgaacttggcttt

D858, the phage used in these experiments is a bacteriophage belonging to the Siphoviridae family of viruses. Its genome sequence has been completely determined, it apparently remains to be published. This phage is virulent to *S. thermophilus* strain DGCC7710. *S. thermophilus* strain DGCC7778 was isolated as a natural phage resistant mutant using DGCC7710 as the parental strain, and phage D858 as the virulent phage. The CRISPR1 of strain DGCC7778 contains 35 repeats (including the terminal repeat), and thus 34 spacers. When compared to the CRISPR1 sequence of DGCC7710, the CRISPR1 sequence of DGCC7778 possesses two additional, adjacent, new spacers (and of course two additional repeats which flank the new spacers) at one end of the CRISPR locus (i.e., close to the leader). All the other spacers of the CRISPR1 locus are unchanged. The CRISPR1 sequence (5'-3') of strain DGCC7778 is shown in SEQ ID NO:679, below:

(SEQ ID NO: 679)

caaggacagttattgattttataatcactatgtgggtataaaaacgtcaaaatttcatttgag

GTTTTTGTACTCTCAAGATTTAAGTAACTGTACAACcaacacattcaacagattaatgaagaatac

GTTTTTGTACTCTCAAGATTTAAGTAACTGTACAACtccactcacgtacaaatagtgagtgtactc

GTTTTTGTACTCTCAAGATTTAAGTAACTGTACAACtgtttgacagcaaatcaagattcgaattgt

GTTTTTGTACTCTCAAGATTTAAGTAACTGTACAACaatgacgaggagctattggcacaacttaca

GTTTTTGTACTCTCAAGATTTAAGTAACTGTACAACcgatttgacaatctgctgaccactgttatc

GTTTTTGTACTCTCAAGATTTAAGTAACTGTACAACacacttggcaggcttattactcaacagcga

GTTTTTGTACTCTCAAGATTTAAGTAACTGTACAACctgttccttgttcttttgttgtatcttttc

GTTTTTGTACTCTCAAGATTTAAGTAACTGTACAACttcattcttccgtttttgtttgcgaatcct

GTTTTTGTACTCTCAAGATTTAAGTAACTGTACAACgctggcgaggaaacgaacaaggcctcaaca

GTTTTTGTACTCTCAAGATTTAAGTAACTGTACAACcatagagtggaaaactagaaacagattcaa

GTTTTTGTACTCTCAAGATTTAAGTAACTGTACAACataatgccgttgaattacacggcaaggtca

GTTTTTGTACTCTCAAGATTTAAGTAACTGTACAACgagcgagctcgaaataatcttaattacaag

GTTTTTGTACTCTCAAGATTTAAGTAACTGTACAACgttcgctagcgtcatgtggtaacgtattta

GTTTTTGTACTCTCAAGATTTAAGTAACTGTACAACggcgtcccaatcctgattaatacttactcg

GTTTTTGTACTCTCAAGATTTAAGTAACTGTACAACaacacagcaagacaagaggatgatgctatg

GTTTTTGTACTCTCAAGATTTAAGTAACTGTACAACcgacacaagaacgtatgcaagagttcaag

GTTTTTGTACTCTCAAGATTTAAGTAACTGTACAACacaattcttcatccggtaactgctcaagtg

GTTTTTGTACTCTCAAGATTTAAGTAACTGTACAACaattaagggcatagaaagggagacaacatg

GTTTTTGTACTCTCAAGATTTAAGTAACTGTACAACcgatatttaaaatcattttcataacttcat

GTTTTTGTACTCTCAAGATTTAAGTAACTGTACAACgcagtatcagcaagcaagctgttagttact

GTTTTTGTACTCTCAAGATTTAAGTAACTGTACAACataaactatgaaattttataattttaaga

GTTTTTGTACTCTCAAGATTTAAGTAACTGTACAACaataatttatggtatagcttaatatcattg

GTTTTTGTACTCTCAAGATTTAAGTAACTGTACAACtgcatcgagcacgttcgagtttaccgtttc

GTTTTTGTACTCTCAAGATTTAAGTAACTGTACAACtctatatcgaggtcaactaacaattatgct

GTTTTTGTACTCTCAAGATTTAAGTAACTGTACAACaatcgttcaaattctgttttaggtacattt

GTTTTTGTACTCTCAAGATTTAAGTAACTGTACAACaatcaatacgacaagagttaaaatggtctt

GTTTTTGTACTCTCAAGATTTAAGTAACTGTACAACgcttagctgtccaatccacgaacgtggatg

GTTTTTGTACTCTCAAGATTTAAGTAACTGTACAACcaaccaacggtaacagctactttttacagt

GTTTTTGTACTCTCAAGATTTAAGTAACTGTACAACataactgaaggataggagcttgtaaagtct

GTTTTTGTACTCTCAAGATTTAAGTAACTGTACAACtaatgctacatctcaaaggatgatcccaga

-continued

```
GTTTTTGTACTCTCAAGATTTAAGTAACTGTACAACaagtagttgatgacctctacaatggtttat

GTTTTTGTACTCTCAAGATTTAAGTAACTGTACAACacctagaagcatttgagcgtatattgattg

GTTTTTGTACTCTCAAGATTTAAGTAACTGTACAACaattttgccccttctttgccccttgactag

GTTTTTGTACTCTCAAGATTTAAGTAACTGTACAACaccattagcaatcatttgtgcccattgagt

GTTTTTGTACTCTCAAGATTTAAGTAACTGTACAGT

Ttgattcaacataaaaagccagttcaattgaacttggcttt
```

In the case of DGCC7778, the first spacer (5'-caacacattcaacagattaatgaagaatac-3'; SEQ ID NO:680) and the second spacer (5'-tccactcacgtacaaatagtgagtgtactc-3'; SEQ ID NO:681) constitute the strain-specific tag which identifies this labelled strain. It was determined that the sequence of both new spacers exists within the D858 phage genome. The sequence of the second new spacer is found between positions 25471 and 25442 bp (i.e., on the minus strand) of D858's genome, with one mismatch (96.7% of identical nucleotides over 30 nucleotides):

```
spacer 2     1 tccactcacgtacaaatagtgagtgtactc    30 (SEQ ID NO: 681)
               |||||||||||||||||||||||| ||||||
D858     25471 tccactcacgtacaaatagtgagcgtactc 25442 (SEQ ID NO: 686)
```

The sequence of the first spacer is found between positions 31481 and 31410 bp (i.e., on the plus strand) of D858's genome (100% of identical nucleotides over 30 nucleotides):

```
spacer 1     1 caacacattcaacagattaatgaagaatac    30   (SEQ ID NO: 3)
               ||||||||||||||||||||||||||||||
D858     31481 caacacattcaacagattaatgaagaatac 31410 (SEQ ID NO: 687)
```

Although it is not intended that the present invention be limited to any particular mechanism nor theory, it is contemplated that two new spacers present in the CRISPR1 locus of DGCC7778 was needed to confer to strain DGCC7778 a new resistance to phage D858). Spacer "2" (as found in DGCC7778) was first inserted into the CRISPR1 locus of DGCC7710 (33 repeats and 32 spacers), at one end of this CRISPR locus, together with one repeat. This insertion gave rise to a bacteriophage insensitive mutant (intermediate strain), tagged by this additional new spacer (thus bearing 34 repeats and 33 spacers). This spacer was derived from the D858 genome, but a replication error or reverse transcription error likely occurred during the insertion process, leading to a point mutation. Due to the imperfect match (i.e., the 1 mismatch) between this newly acquired spacer and the targeted phage sequence, the efficiency of resistance of this intermediate strain to phage D858 was low. A second event of spacer insertion occurred in this intermediate strain (more resistant to phage D858 than parental strain DGCC7710, but not "fully" resistant because of the mismatch), leading to the insertion of a second new spacer (i.e., spacer "1" as found in DGCC7778) at the same end of CRISPR1 locus, together with one repeat. This second insertion gave rise to a new bacteriophage insensitive mutant, which was isolated and named DGCC7778. DGCC7778 is more resistant to D858 than the intermediate strain, and of course much more resistant than parental strain DGCC7710, due to the presence of spacer "1," which is 100% identical to the targeted phage sequence.

Example 18

Method for Tagging DGCC7710 and Selection of Labelled Strain DGCC7778

In this Example, methods used to tag DGCC7710 and selection of the labelled DGCC7778 strain are described. Strain DGCC7710 was infected/challenged by phage D858 by inoculating pasteurised milk with strain DGCC7710 at about $2.10^6$ cfu/ml and with phage D858 at about $1.10^5$ pfu/ml. The inoculated milk was cultivated for 12 hours at 35° C. After incubation, viable bacteria (i.e., those that are likely to be bacteriophage insensitive mutants) were isolated on non-selective medium (milk agar plates) at 35° C., using an appropriate dilution of the infected culture. One isolate, named DGCC7778, was propagated in M17-glucose liquid medium at 35° C. and its DNA was extracted using a classical DNA extraction protocol, as known in the art.

The DNA extract was amplified using PCR as known in the art (See e.g., Bolotin et al. [2005], supra) using combination of one forward primer (either yc70 and/or SPIDR-ups [5'-gTCTTTAgAAACTgTgACACC]; SEQ ID NO:674) and of one reverse primer (either yc31 and/or SPIDR-dws [5'-TAAACAgAgCCTCCCTATCC]; SEQ ID NO:675). The sequence of the PCR products was determined and compared to that of the CRISPR locus of DGCC7710.

Example 19

Production of a Second Tagged Strain

In this Example, methods used to produce a second tagged strain are described. *S. thermophilus* strain DGCC7710-RH1 was isolated as a natural phage resistant mutant using DGCC7710 as the parent strain and phage D858 as the virulent phage.

The CRISPR1 of strain DGCC7710-RH1 contains 34 repeats (including the terminal repeat), and thus 33 spacers. When compared to the CRISPR1 sequence of *S. thermophilus* strain DGCC7710, the CRISPR1 sequence of *S. thermophilus* strain DGCC7710-RH1 possesses one additional new spacer (i.e., tagging sequence) (and of course one additional repeat which flanks the new spacer) at one end of the CRISPR locus (i.e., close to the leader, at the 5' end of the CRISPR locus). All of the other spacers of CRISPR1 locus are unchanged. The CRISPR1 sequence (5'-3') of strain DGCC7710-RH1 is:

(SEQ ID NO: 682)

caaggacagttattgattttataatcactatgtgggtataaaaacgtcaaaatttcatttgag

GTTTTTGTACTCTCAAGATTTAAGTAACTGTACAACtcaacaattgcaacatcttataacccactt

GTTTTTGTACTCTCAAGATTTAAGTAACTGTACAACtgtttgacagcaaatcaagattcgaattgt

GTTTTTGTACTCTCAAGATTTAAGTAACTGTACAACaatgacgaggagctattggcacaacttaca

GTTTTTGTACTCTCAAGATTTAAGTAACTGTACAACcgatttgacaatctgctgaccactgttatc

GTTTTTGTACTCTCAAGATTTAAGTAACTGTACAACacacttggcaggcttattactcaacagcga

GTTTTTGTACTCTCAAGATTTAAGTAACTGTACAACctgttccttgttcttttgttgtatcttttc

GTTTTTGTACTCTCAAGATTTAAGTAACTGTACAACttcattcttccgtttttgtttgcgaatcct

GTTTTTGTACTCTCAAGATTTAAGTAACTGTACAACgctggcgaggaaacgaacaaggcctcaaca

GTTTTTGTACTCTCAAGATTTAAGTAACTGTACAACcatagagtggaaaactagaaacagattcaa

GTTTTTGTACTCTCAAGATTTAAGTAACTGTACAACataatgccgttgaattacacggcaaggtca

GTTTTTGTACTCTCAAGATTTAAGTAACTGTACAACgagcgagctcgaaataatcttaattacaag

GTTTTTGTACTCTCAAGATTTAAGTAACTGTACAACgttcgctagcgtcatgtggtaacgtattta

GTTTTTGTACTCTCAAGATTTAAGTAACTGTACAACggcgtcccaatcctgattaatacttactcg

GTTTTTGTACTCTCAAGATTTAAGTAACTGTACAACaacacagcaagacaagaggatgatgctatg

GTTTTTGTACTCTCAAGATTTAAGTAACTGTACAACcgacacaagaacgtatgcaagagttcaag

GTTTTTGTACTCTCAAGATTTAAGTAACTGTACAACacaattcttcatccggtaactgctcaagtg

GTTTTTGTACTCTCAAGATTTAAGTAACTGTACAACaattaagggcatagaaagggagacaacatg

GTTTTTGTACTCTCAAGATTTAAGTAACTGTACAACcgatatttaaaatcattttcataacttcat

GTTTTTGTACTCTCAAGATTTAAGTAACTGTACAACgcagtatcagcaagcaagctgttagttact

GTTTTTGTACTCTCAAGATTTAAGTAACTGTACAACataaactatgaaattttataatttttaaga

GTTTTTGTACTCTCAAGATTTAAGTAACTGTACAACaataatttatggtatagcttaatatcattg

GTTTTTGTACTCTCAAGATTTAAGTAACTGTACAACtgcatcgagcacgttcgagtttaccgtttc

GTTTTTGTACTCTCAAGATTTAAGTAACTGTACAACtctatatcgaggtcaactaacaattatgct

GTTTTTGTACTCTCAAGATTTAAGTAACTGTACAACaatcgttcaaattctgttttaggtacattt

GTTTTTGTACTCTCAAGATTTAAGTAACTGTACAACaatcaatacgacaagagttaaaatggtctt

GTTTTTGTACTCTCAAGATTTAAGTAACTGTACAACgcttagctgtccaatccacgaacgtggatg

GTTTTTGTACTCTCAAGATTTAAGTAACTGTACAACcaaccaacggtaacagctactttttacagt

GTTTTTGTACTCTCAAGATTTAAGTAACTGTACAACataactgaaggataggagcttgtaaagtct

GTTTTTGTACTCTCAAGATTTAAGTAACTGTACAACtaatgctacatctcaaaggatgatcccaga

GTTTTTGTACTCTCAAGATTTAAGTAACTGTACAACaagtagttgatgacctctacaatggtttat

GTTTTTGTACTCTCAAGATTTAAGTAACTGTACAACacctagaagcatttgagcgtatattgattg

GTTTTTGTACTCTCAAGATTTAAGTAACTGTACAACaattttgccccttctttgccccttgactag

GTTTTTGTACTCTCAAGATTTAAGTAACTGTACAACaccattagcaatcatttgtgcccattgagt

GTTTTTGTACTCTCAAGATTTAAGTAACTGTACAGT

Ttgattcaacataaaaagccagttcaattgaacttggcttt

The leader sequence is 5' caaggacagttattgattttataatcactatgtgggtataaaaacgtcaaaatttcatttgag 3' (SEQ ID NO:688). The integrated sequence (GTTTTTGTACTCTCAAGATTTAAGTAACTGTACAACtcaacaattgcaacatcttataacccactt; SEQ ID NO:689) is shown comprising a CRISPR Repeat (upper case) and a CRISPR spacer (i.e., tagging sequence), which is shown in lower case. The terminal repeat (5' gtttttgtactctcaagatttaagtaactgtacagt 3' (SEQ ID NO:3)) trailer sequence: 5' ttgattcaacataaaaagccagttcaattgaacttggcttt3' (SEQ ID NO:691) are shown.

Accordingly, in the case of *S. thermophilus* strain DGCC7710-RH1, the spacer (5'-tcaacaattgcaacatcttataacccactt-3'; SEQ ID NO:534) constitutes the strain-specific tagging sequence which identifies this mutant strain (i.e., the labelled bacterium). The sequence of the new spacer (i.e., tagging sequence) exists within the D858 phage genome. The sequence of the spacer is found between positions 31921 and 31950 bp (i.e., on the plus strand) of the D858 genome (and has 100% identity to the D858 genomic sequence over 30 nucleotides):

```
spacer     1 tcaacaattgcaacatcttataacccactt    30 (SEQ ID NO: 534)
             ||||||||||||||||||||||||||||||
D858   31921 tcaacaattgcaacatcttataacccactt 31950 (SEQ ID NO: 534)
```

1. The new spacer (i.e., tagging sequence) that is integrated into the CRISPR1 locus of *Streptococcus thermophilus* strain DGCC7710-RH1 confers to this strain a new resistance to phage D858.

Example 20

Production of a Third Tagged Strain

In this Example, methods used to produce a third tagged strain are described. *S. thermophilus* strain DGCC7710-RH2 was isolated as a natural phage resistant mutant using *S. thermophilus* strain DGCC7710 as the parental strain, and phage D858 as the virulent phage. The CRISPR1 of *S. thermophilus* strain DGCC7710-RH2 contains 34 repeats (including the terminal repeat), and thus 33 spacers. When compared to the CRISPR1 sequence of *S. thermophilus* strain DGCC7710, the CRISPR1 sequence of *S. thermophilus* strain DGCC7710-RH2 possesses one additional new spacer (i.e., tagging sequence) (and of course one additional repeat which flanks the new spacer) at one end of the CRISPR locus (i.e., close to the leader, at the 5' end of the CRISPR locus). All the other spacers of CRISPR1 locus are unchanged.

2. The CRISPR1 sequence (5'-3') of strain DGCC7710-RH2 is:

```
                                                          (SEQ ID NO: 684)
caaggacagttattgattttataatcactatgtgggtataaaaacgtcaaaatttcatttgag

GTTTTTGTACTCTCAAGATTTAAGTAACTGTACAACttacgtttgaaaagaatatcaaatcaatga

GTTTTTGTACTCTCAAGATTTAAGTAACTGTACAACtgtttgacagcaaatcaagattcgaattgt

GTTTTTGTACTCTCAAGATTTAAGTAACTGTACAACaatgacgaggagctattggcacaacttaca

GTTTTTGTACTCTCAAGATTTAAGTAACTGTACAACcgatttgacaatctgctgaccactgttatc

GTTTTTGTACTCTCAAGATTTAAGTAACTGTACAACacacttggcaggcttattactcaacagcga

GTTTTTGTACTCTCAAGATTTAAGTAACTGTACAACctgttccttgttcttttgttgtatcttttc

GTTTTTGTACTCTCAAGATTTAAGTAACTGTACAACttcattcttccgtttttgtttgcgaatcct

GTTTTTGTACTCTCAAGATTTAAGTAACTGTACAACgctggcgaggaaacgaacaaggcctcaaca

GTTTTTGTACTCTCAAGATTTAAGTAACTGTACAACcatagagtggaaaactagaaacagattcaa

GTTTTTGTACTCTCAAGATTTAAGTAACTGTACAACataatgccgttgaattacacggcaaggtca

GTTTTTGTACTCTCAAGATTTAAGTAACTGTACAACgagcgagctcgaaataatcttaattacaag

GTTTTTGTACTCTCAAGATTTAAGTAACTGTACAACgttcgctagcgtcatgtggtaacgtattta

GTTTTTGTACTCTCAAGATTTAAGTAACTGTACAACggcgtcccaatcctgattaatacttactcg
```

-continued

```
GTTTTTGTACTCTCAAGATTTAAGTAACTGTACAACaacacagcaagacaagaggatgatgctatg
GTTTTTGTACTCTCAAGATTTAAGTAACTGTACAACcgacacaagaacgtatgcaagagttcaag
GTTTTTGTACTCTCAAGATTTAAGTAACTGTACAACacaattcttcatccggtaactgctcaagtg
GTTTTTGTACTCTCAAGATTTAAGTAACTGTACAACaattaagggcatagaaagggagacaacatg
GTTTTTGTACTCTCAAGATTTAAGTAACTGTACAACcgatatttaaaatcattttcataacttcat
GTTTTTGTACTCTCAAGATTTAAGTAACTGTACAACgcagtatcagcaagcaagctgttagttact
GTTTTTGTACTCTCAAGATTTAAGTAACTGTACAACataaactatgaaattttataattttaaga
GTTTTTGTACTCTCAAGATTTAAGTAACTGTACAACaataatttatggtatagcttaatatcattg
GTTTTTGTACTCTCAAGATTTAAGTAACTGTACAACtgcatcgagcacgttcgagtttaccgtttc
GTTTTTGTACTCTCAAGATTTAAGTAACTGTACAACtctatatcgaggtcaactaacaattatgct
GTTTTTGTACTCTCAAGATTTAAGTAACTGTACAACaatcgttcaaattctgttttaggtacattt
GTTTTTGTACTCTCAAGATTTAAGTAACTGTACAACaatcaatacgacaagagttaaaatggtctt
GTTTTTGTACTCTCAAGATTTAAGTAACTGTACAACgcttagctgtccaatccacgaacgtggatg
GTTTTTGTACTCTCAAGATTTAAGTAACTGTACAACcaaccaacggtaacagctactttttacagt
GTTTTTGTACTCTCAAGATTTAAGTAACTGTACAACataactgaaggataggagcttgtaaagtct
GTTTTTGTACTCTCAAGATTTAAGTAACTGTACAACtaatgctacatctcaaaggatgatcccaga
GTTTTTGTACTCTCAAGATTTAAGTAACTGTACAACaagtagttgatgacctctacaatggtttat
GTTTTTGTACTCTCAAGATTTAAGTAACTGTACAACacctagaagcatttgagcgtatattgattg
GTTTTTGTACTCTCAAGATTTAAGTAACTGTACAACaatttgccccttctttgccccttgactag
GTTTTTGTACTCTCAAGATTTAAGTAACTGTACAACaccattagcaatcatttgtgcccattgagt
GTTTTTGTACTCTCAAGATTTAAGTAACTGTACAGT
Ttgattcaacataaaaagccagttcaattgaacttggcttt
```

The leader sequence is 5' caaggacagttattgattttataatcactatgtgggtataaaaacgtcaaaatttcatttgag 3' (SEQ ID NO:688).

The integrated sequence (GTTTTTGTACTCTCAAGATTTAAGTAACTGTACAACttacgtttgaaaagaatatcaaatcaatga; SEQ ID NO:694) is shown comprising a CRISPR Repeat (upper case) and a CRISPR spacer (i.e., tagging sequence), which is shown in lower case. The terminal repeat (5' gtttttgtactctcaagatttaagtaactgtacagt (SEQ ID NO:3)) trailer sequence: 5' ttgattcaacataaaaagccagttcaattgaacttggcttt3' (SEQ ID NO:691) are shown.

Thus, in the case of *Streptococcus thermophilus* strain DGCC7710-RH2, the spacer (5'-ttacgtttgaaaagaatatcaaatcaatga-3'; SEQ ID NO:697) constitutes the strain-specific tag which identifies this mutant strain (i.e., labelled bacterium). The sequence of the new spacer was shown to exist within D858 phage genome. The sequence of the spacer is found between positions 17215 and 17244 bp (i.e., on the plus strand) of D858's genome (and has 100% identity to the D858 genomic sequence over 30 nucleotides):

The new spacer integrated into the CRISPR1 locus of *S. thermophilus* strain DGCC7710-RH2 confers a new resistance to phage D858 to *S. thermophilus* strain DGCC7710-RH2.

Example 21

Construction of "CRISPR-Escape" Phage from Phage-Resistant Bacterial Variants In this Example, methods for construction of CRISPR-escape phages are described. Phage resistant host variants are first constructed as described in the Examples above. In these experiments, a parental strain "A" is exposed to phage "P" and a phage resistant variant (Variant "A1.0") selected. Variant A1.0 is analyzed (for example by PCR, and/or DNA sequencing) to confirm the presence of an additional inserted spacer within a CRISPR locus. The nucleotide sequence of the additional spacer (Spacer Sp1.0) is then determined. Typically, spacer Sp1.0 is a fragment of approximately 30 nucleotides in size from the phage P, and gives resistance to

```
spacer     1 ttacgtttgaaaagaatatcaaatcaatga    30 (SEQ ID NO: 697)
             ||||||||||||||||||||||||||||||
D858   17215 ttacgtttgaaaagaatatcaaatcaatga 17244 (SEQ ID NO: 698)
```

phage P and related phages ("related phages" are those containing the sequence of the spacer in their genomes, and define a family of phages).

Independently from the first phage exposure, the same parental strain A is exposed to the same phage P and a second phage resistant variant (Variant A2.0) is selected. Variant A2.0 is selected in order to also have an additional spacer inserted (Spacer Sp2.0) within a CRISPR locus but with the sequence of spacer Sp2.0 being different from that of spacer Sp1.0. Typically, spacer Sp2.0 is a fragment of approximately 30 nucleotides in size from the phage P, and gives resistance to phage P and related phages. Similarly, in some embodiments, variant A3.0 to variant Ax.0 are generated through the exposure of the same strain A to the same phage P. All the "A" variants are selected in order to also have an additional spacer inserted (Spacer Sp3.0 to Spx.0) within a CRISPR locus but with the sequence of all the "Sp" spacers being different from each of the others. Typically, "Sp" spacers are fragments of approximately 30 nucleotides in size from the phage P, and all give resistance to phage P and related phages.

Typically, it can be estimated that the level of resistance will be approximately that of a single mutation occurring within the phage genome within the sequence corresponding to the spacer (i.e., roughly $10^{-4}$ to $10^{-6}$). Thus, phage that escape the CRISPR-mediated resistance are easy to isolate. The mutated phage are generated through exposure of variant A1.0 to phage P. Typically, the mutated "CRISPR-escape" phage (P1.0) harbors at least one mutation within its genome corresponding to the sequence of spacer Sp1.0 (e.g., deletion(s), point mutation(s), etc.), or in some preferred embodiments, the region flanking Sp1.0, plus or minus 20 bp corresponding to the CRISPR motif Variant A1.0 would be sensitive to phage P1.0. Similarly, independently generated phage P resistant variants (Variant A2.0, A3.0, to Ax.0) that harbor unique spacers (Sp2.0, Sp3.0, to Spx.0, respectively) are likewise challenged with phage P to generate the corresponding mutant phages (P2.0, P3.0, to Px.0, respectively). Subsequently, a pool of mutant virulent phage, whose genomes have been specifically mutated to a sequence anticipated to be a CRISPR spacer, can be generated.

Indeed, phage D2792 represents a fully virulent biocontrol phage against *S. thermophilus* strain DGCC7710 (WT). In contrast, analysis of the CRISPR locus of related strains $WT_{phi2972}^{-S6}$, $WT_{phi2972}^{+S4}$, $WT_{phi2972}^{+S20}$, $WT_{phi2972}^{+S21}$, and $WT_{phi2972}^{-S22}$, indicate the presence of a spacer sequence that is similar to sequences found in phage D2972 which indicate that phage D2972 has reduced virulence upon these strains. Plaquing data (See, Table 7-1) confirms the reduced virulence of phage D2972 on these strains. In regards to strain $WT_{phi2972}^{+S6}$, which has been characterized to be resistant to phage D2972 due to the presence of a corresponding CRISPR spacer, screening of D2972-related phages for full increased virulence identify phages D4724 and D4733 as candidate agents as biocontrol agents (See, Table 7-1).

In additional experiments, strain DGCC7710 was exposed to phage D2972 to generate resistant variant $WT_{phi2972}^{+S6}$. When strain $WT_{phi2972}^{+S6}$ was exposed to phage D2972, it was possible to isolate mutant phage, such as D4724. This D4724 phage was found to be fully virulent upon DGCC7710 and $WT_{phi2972}^{+S6}$. In a second iteration, $WT_{phi2972}^{+S6}$ was exposed to phage D4724, to generate resistant variant $WT_{phi2972}^{+S6}{}_{phi4724}^{+S15}$. Upon exposure of this strain to D4724, mutant phages were identified such as D4733, that are fully virulent towards DGCC7710 and $WT_{phi2972}^{+S6}$. In some embodiments successive iterations are used to generate phage with the desired level of virulence.

Additional phage mutant examples are provided in FIG. 13. In this Figure, mutant phage 858-A and 858-B derived from parent phage D858 are shown. The mutations correspond to spacer S1 from WTΦ858+S1S2 challenged with phage D858.

In yet further examples, fully virulent phage mutants where the mutation is identified in the CRISPR motif (AGAAW) are shown in Table 20-1. In this Table, nucleotide sequences in wild-type and mutant phages that correspond to the newly acquired spacers by the *S. thermophilus* strains are shown. Each mutation is in bold and underlined. *, indicates a deletion. This Table provides sequences for phage resistant CRISPR variant and virulent phage mutant pairs: $DGCC7710_{\Phi858}^{+S3}$/phage 2972.S3C, $DGCC7710_{\Phi2972}^{+S4}$/phage 2972.S4A or phage 2972.S4C, $DGCC7710_{\Phi2972}^{+S6}$/phage 2972.S6A, and $DGCC7710_{\Phi2972}^{+S4}{}_{\Phi858}^{+S32}$/phage 858.S32A or phage 858.S32D. In this Table, the new spacer corresponds to SEQ ID NO:535 ($DGCC7710_{\Phi858}^{+S3}$).

TABLE 20-1

Nucleotide Sequences in Wild-Type and Mutant Phages That Correspond to Newly Acquired Spacers by *S. thermophilus* Strains

| Source | Sequence | SEQ ID NO: |
|---|---|---|
| $DGCC7710_{\phi858}^{+S3}$ | TTACGTTTGAAAAGAATATCAAATCAATGA | SEQ ID NO: 535 |
| Phage 2972 | TTACGTTTGAAAAGAATATCAAATCAATGACGAGAAAGA | SEQ ID NO: 725 |
| Phage 2972, S3A | TTACGTTTGAAAAGAATATCAAAT**T**AATGACGAGAAAGA | SEQ ID NO: 726 |
| Phage 2972, S3B | TTACGTTTGAAAAGAATATCAAATCAA**C**GACGAGAAAGA | SEQ ID NO: 727 |
| Phage 2972, S3C | TTACGTTTGAAAAGAATATCAAATCAATGACGAGA**G**AGA | SEQ ID NO: 728 |
| Phage 2972, S3D | TTACGTTTGAAAAGAATATCAAATC**T**ATGACGAGAAAGA | SEQ ID NO: 729 |
| Phage 2972, S3E | TTACGTTTGAAAAGAATATCAA**T**TCAATGACGAGAAAGA | SEQ ID NO: 730 |
| Phage 2972, S3F | TTACGTTTGAAAAGAATATCAAAT**T**AATG**G**CGAGAAAGA<br>TTACGTTTGAAAAGAATATCAAAT**T**AATG**G**CGAGAAAGA | SEQ ID NO: 731 |
| Phage 2972, S3G | TTACGTTTGAAAAGAA**C**ATCAAAT**T**AATGACGAGAAAGA<br>TTACGTTTGAAAAGAA**C**ATCAAAT**T**AATGACGAGAAAGA | SEQ ID NO: 732 |

TABLE 20-1-continued

Nucleotide Sequences in Wild-Type and Mutant Phages That Correspond to Newly Acquired Spacers by *S. thermophilus* Strains

| Source | Sequence | SEQ ID NO: |
|---|---|---|
| DGCC7710$_{\phi2972}^{+S4}$ | CTCAGTCGTTACTGGTGAACCAGTTTCAAT | SEQ ID NO: 525 |
| Phage 2972 | CTCAGTCGTTACTGGTGAACCAGTTTCAATTGAGAAAAA | SEQ ID NO: 733 |
| Phage 2972, S4A | CTCAGTCGTTACTGGTGAACCAGTTTCAATTGA**A**AAAAA | SEQ ID NO: 734 |
| Phage 2972, S4B | CTCAGTCGTTACTGGTGAACCAGTTTC**G**ATTGAGAAAAA | SEQ ID NO: 735 |
| Phage 2972, S4C | CTCAGTCGTTACTGGTGAACCAGTTTCAATTGAGA**G**AAA | SEQ ID NO: 736 |
| Phage 2972, S4D | CTCAGTCGTTACTGGTGAACC**G**GTTTCAATTGA**A**AAAAA<br>CTCAGTCGTTACTGGTGAACC**G**GTTTCAATTGA**A**AAAAA | SEQ ID NO: 737 |
| DGCC7710$_{\phi2972}^{+S6}$ | GCCCTTCTAATTGGATTACCTTCCGAGGTG | SEQ ID NO: 524 |
| Phage 2972 | GCCCTTCTAATTGGATTACCTTCCGAGGTGTTAGAATTC | SEQ ID NO: 738 |
| Phage 2972, S6A | GCCCTTCTAATTGGATTACCTTCCGAGGTGTTAGA**G**TTC | SEQ ID NO: 739 |
| Phage 2972, S6B | GCCCTTCTAATTGGATTACCTTCCGA**T**GTGTTAGAATTC | SEQ ID NO: 740 |
| Phage 2972, S6C | GCCCTTCTAATTGGATTACCTTCCGAG**T**TGTTAGAATTC | SEQ ID NO: 741 |
| Phage 2972, S6D | GCCCTTCTAATTGGATTACCTTCCGA*GTGTTAGAATTC | SEQ ID NO: 742 |
| DGCC7710$_{\phi2972}^{+S4}$ $_{\phi858}^{+S32}$ | ATTGTCTATTACGACAACATGGAAGATGAT | SEQ ID NO: 526 |
| Phage 858 | ATTGTCTATTACGACAACATGGAAGATGATGTAGAAATT | SEQ ID NO: 743 |
| Phage 858.S32A | ATTGTCTATTACGACAACATGGAAGATGATGTA**T**AAATT | SEQ ID NO: 744 |
| Phage 858.S32B | ATTGTCTATTACGACAACATGGAAGATTATGTAGAAATT | SEQ ID NO: 745 |
| Phage 858.S32C | ************************************ATT | SEQ ID NO: 746 |
| Phage 858.S32D | ATTGTCTATTACGACAACATGGAAGATGATGTA**A**AAATT | SEQ ID NO: 747 |
| DGCC7710$_{\phi2972}^{+S6}$ $_{\phi2972.S6B}^{+S20}$ | TTATATCGAAGAACGACTGAAAGAGCTTGA | SEQ ID NO: 706 |
| Phage 2972 | TTATATCGAAGAACGACTGAAAGAGCTTGAGAAGAAAAA | SEQ ID NO: 748 |
| Phage 2972.S20A | TTATATCGAAGAACGACTGAAAGAGCTTGAGAA**T**AAAAA | SEQ ID NO: 749 |

Example 22

Second Level "CRISPR-Escape" Phage

In this Example, experiments for construction of second-level (i.e., with multiple mutations directed at multiple spacers) CRISPR-escape phages are described.

Through an iterative process of creating CRISPR-mediated phage resistant variants followed by isolation of mutated ("CRISPR-escape") phage capable of overcoming the cas-CRISPR mechanism, it is possible to create phage that have "pre-adapted" with multiple mutations against potential CRISPR-mediated resistance.

In some embodiments, the second level variants are produced by isolating a mutated phage through exposure of variant A1.0 to phage P. Typically, this mutated phage (phage P1.0) has a mutation (deletion, point mutation, etc.) in its genome within the region containing the sequence of spacer Sp1.0 or within the region flanking Sp1.0, plus or minus 20 bp corresponding to the CRISPR motif. Variant A1.0 is sensitive to phage P1.0. Then, variant A1.0 is exposed to phage P1.0 and a phage resistant variant (Variant A1.1) selected (See, FIG. 15). Variant A1.1 is also selected such that it has an additional spacer inserted (Spacer Sp1.1) within a CRISPR locus but with the sequence of spacer Sp1.1 being different from that of spacers Sp1.0, Sp2.0 to Spx.0. Typically, spacer Sp1.1 is a fragment of approximately 30 nucleotides in size from the phage P1.0, and will give resistance to phage P1.0 and related phages. Variant A1.1 is resistant to phage P1.0 and preferably, has an increased resistance to phage P because of the accumulation of spacer Sp1.0 and Sp1.1.

In additional embodiments, a newly mutated phage (phage P1.1) is generated through exposure of variant A1.1 to phage P1.0. Then, upon exposure of variant A1.1 to phage P1.1 a new variant A1.2 is obtained that contains one new additional spacer (Sp1.2). This spacer gives resistance to phage P1.1 and preferably increases the resistance to phage P1.0 and P (i.e., due to the accumulation of spacers Sp1.0, Sp1.1, Sp1.2). Phage P1.1 is fully infective towards parental strain A, as well as variants A1.0 and A1.1.

In yet additional embodiments, different spacers (e.g., 2, 3 or 4) are iteratively accumulated within strain A through variant A1, then variant A1.1, then variant A1.2, etc to obtain a variant highly resistant to phages (variant A1.n). In still further embodiments, additional different spacers can be accumulated in the same strain through variant A2, then variant A2.1, then variant A2.2, etc to generate another variant of strain A highly resistant to phages (variant A2.n) in parallel. The same strategy finds use with variants A3.0 to Ax.0.

Following an iterative process of creating CRISPR phage resistant variants and isolation of mutant "CRISPR-escape" phage (e.g., exposure of variant A1.1 to phage P1.1 creating new variant A1.2 that contains one new additional spacer (Sp1.2) from which a mutant phage is isolated (P1.2) that is fully virulent on variant A1.2, A1.1, A1.0 and parent strain A.

In some embodiments, combinatorial mutations are accumulated by iterative construction of bacterial variants combining different spacers (e.g., Sp2.0. Sp3.0 to Spx.0), exposure to the corresponding first level mutant phage (P2.0, P3.0 to Px.0), and isolation of second level mutant phages.

An example of iterative combinatorial mutations creating CRISPR phage resistant variants and mutant "CRISPR-escape" phage is shown in Table 22-1. This table provides a list of new spacers found in CRISPR1 and the corresponding region in phages 2972, 858, or DT1. In this Table, the "a" indicates DNA regions that are 100% identical between phages 858 and 2972. The "5' Position" refers to the 5' position of the proto-spacer in the phage genome. Underlined and shaded nucleotides in the proto-spacer sequence indicate mismatches between the phage and the spacer. An asterisk (*) indicates a deletion. In the "3' Flanking Region" indicates the 3' flanking sequence in the phage genome. Mismatches in the AGAAW motif are underlined and shaded in grey. In the column designated "Strand/Module," the transcription modules are "E" (early expressed genes); "M" (middle expressed genes); and "L" (late expressed genes).

TABLE 20-2

List of New Spacers Found in CRISPR1 and the Corresponding Region in Phages 2972, 858, and DT1.

| Spacer Name | Phage | 5' Position | Spacer Length (pb) | Proto-Spacer Sequence | 3' Flanking Region | Strand/ Module | orf/Function in the Genome of the Phage Used in the Challenge |
|---|---|---|---|---|---|---|---|
| S1 | 858 | 31378 | 30 | CAACACATTCAACAGATTAATGAAGAATAC (SEQ ID NO: 680) | AAAGAAAAAA (SEQ ID NO: 750) | (+)/E | orf40/Primase |
| S2 | 2972[a] | 25432 | 30 | TCCACTCACGTACAAATAGTGAGCGTACTC (SEQ ID NO: 686) | CTAAAAGGAT (SEQ ID NO: 751) | (-)/L | orf27/Unknown |
| S3 | 2972[a] | 17202 | 30 | TTACGTTTGAAAAGAATATCAAATCAATGA (SEQ ID NO: 697) | CGAGAAAGAT (SEQ ID NO: 752) | (+)/L | orf20/Receptor-binding protein |
| S4 | 2972 | 31582 | 30 | CTCAGTCGTTACTGGTGAACCAGTTTCAAT (SEQ ID NO: 525) | TGAGAAAAAA (SEQ ID NO: 753) | (+)/E | orf38/Primase |
| S5 | 2972 | 22075 | 30 | AGTTTCTTTGTCAGACTCTAACACAGCCGC (SEQ ID NO: 754) | TCAGAAAGTT (SEQ ID NO: 755) | (+)/L | orf21/Tail protein |
| S6 | 2972[a] | 34521 | 30 | GCCCTTCTAATTGGATTACCTTCCGAGGTG (SEQ ID NO: 524) | TTAGAATTCC (SEQ ID NO: 756) | (-)/E | orf44/Unknown |
| S7 | 2972[a] | 10299 | 30 | AAGCAAGTTGATATATTTCTCTTTCTTTAT (SEQ ID NO: 757) | TAAGAAAACG (SEQ ID NO: 758) | (-)/L | orf17/Unknown |
| S8 | 2972 | 30016 | 29 | CGTTTTCAGTCATTGGTGGTTTGTCAGCG (SEQ ID NO: 759) | AAAGAAATAA (SEQ ID NO: 760) | (-)/E | orf37/Replication |
| S9 | 2972[a] | 7874 | 30 | TTACTAGAGCGTGTCGTTAACCACTTTAAA (SEQ ID NO: 528) | TCAGAATATG (SEQ ID NO: 761) | (+)/M | orf11/Unknown |
| S10 | 2972[a] | 20650 | 30 | TTCGTTAAAGTCACCTCGTGCTAGCGTTGC (SEQ ID NO: 529) | ATAGAAAGTT (SEQ ID NO: 772) | (-)/L | orf20/Receptor-binding protein |
| S11 | 2972[a] | 8360 | 30 | ATAACGGTAGCAAATATAAACCTGTTACTG (SEQ ID NO: 530) | TCAGAAGCTA (SEQ ID NO: 773) | (+)/M | orf12/Unknown |
| S12 | 2972[a] | 18998 | 30 | GAAGTAGCCATACAAGAAGATGGATCAGCA (SEQ ID NO: 531) | CCAGAAATTG (SEQ ID NO: 774) | (+)/L | orf20/Receptor-binding protein |
| S13 | 2972[a] | 33602 | 30 | GATGTCACTGAGTGTCTAAGCATTGCGTAC (SEQ ID NO: 776) | GAGGAAATCA (SEQ ID NO: 775) | (+)/E | orf42/DNA binding |
| S14 | 2972[a] | 4830 | 30 | TGAATAAGCAGTTCTTGACGACCAACCGAC (SEQ ID NO: 533) | ATAGAAAAGT (SEQ ID NO: 778) | (-)/M | orf6/Capsid protein |
| S15 | 2972[a] | 34444 | 29 | CAATTAACACAGCAATTAACACAGTATAT (SEQ ID NO: 779) | ACAGAAATTG (SEQ ID NO: 780) | (+)/E | orf44/Unknown |
| S16 | 2972[a] | 6799 | 30 | ATGCCATTCTTTAAAGAGGCTTTACTCGTT (SEQ ID NO: 781) | AAAGAAAACG (SEQ ID NO: 782) | (+)/M | orf9/Capsid protein |
| S17 | 2972 | 30547 | 30 | GTTGGCGGACTACTCCTTCGAGGGGTTGAT (SEQ ID NO: 783) | CCAGAAATTA (SEQ ID NO: 784) | (+)/E | orf37/Replication |

TABLE 20-2-continued

List of New Spacers Found in CRISPR1 and the Corresponding Region in Phages 2972, 858, and DT1.

| Spacer Name | Phage | 5' Position | Spacer Length (pb) | Proto-Spacer Sequence | 3' Flanking Region | Strand/Module | orf/Function in the Genome of the Phage Used in the Challenge |
|---|---|---|---|---|---|---|---|
| S18 | 2972 | 30370 | 29 | GAAGCACCTCTTGCGTTGATAAAAGTATT (SEQ ID NO: 785) | GC**AGAAAA**TG (SEQ ID NO: 786) | (+)/E | orf37/Replication |
| S19 | 2972 | 31709 | 29 | ACATATCGACGTATCGTGATTATCCCATT (SEQ ID NO: 787) | CA**AGAAAA**CA (SEQ ID NO: 788) | (+)/E | orf38/Primase |
| S20 | 2972[a] | 1113 | 30 | TTATATCGAAGAACGACTGAAAGAGCTTGA (SEQ ID NO: 706) | GA**AGAAAA**AA (SEQ ID NO: 789) | (+)/M | orf2/Small terminase |
| S21 | 2972[a] | 19188 | 30 | AAATCAACGTACATCCCGATATAGGCACGA (SEQ ID NO: 780) | TT**AGAAT**CAG (SEQ ID NO: 781) | (−)/L | orf20/Receptor-binding protein |
| S22 | 2972 | 31708 | 30 | GACATATCGACGTATCGTGATTATCCCATT (SEQ ID NO: 782) | CA**AGAAAA**CA (SEQ ID NO: 783) | (+)/E | orf38/Primase |
| S23 | 2972 | 26529 | 31 | TGAAGTATTAGGTCTCTCAAAAGATGATATT (SEQ ID NO: 784) | GT**AGAAT**ACT (SEQ ID NO: 785) | (+)/E | orf31/Cro-like repressor |
| S24 | 2972 | 29923 | 30 | AGTTGATTGCGTAATCAACCATCTCCATAA (SEQ ID NO: 709) | TT**AGAAT**GGA (SEQ ID NO: 786) | (−)/E | orf37/Replication |
| S25 | 2972[a] | 441 | 30 | GCAACACTCAAACGTTGCAAACGCAAGCTT (SEQ ID NO: 787) | CG**AGAAT**ATC (SEQ ID NO: 788) | (+)/E | orf1/Unknown |
| S26 | 2972 | 31606 | 31 | CTCAGTCGTTACTGGTGAACCAGTT*TCAAT (SEQ ID NO: 789) | TG**AGAAAA**AA (SEQ ID NO: 753) | (+)/E | orf38/Primase |
| S27 | 2972[a] | 27032 | 30 | TTTCATCGTCAATTTCCATGTTATAAATCT (SEQ ID NO: 790) | CT**AGAAA**CTG (SEQ ID NO: 791) | (−)/E | orf33/Unknown |
| S28 | 2972 | 26530 | 30 | GAAGTATTAGGTCTCTCAAAAGATGATATT (SEQ ID NO: 715) | GT**AGAAT**ACT (SEQ ID NO: 792) | (+)/E | orf31/Cro-like repressor |
| S29 | 2972 | 32136 | 29 | ATTGGCATGATTTCAATTTTAATTGGGAT (SEQ ID NO: 793) | GT**AGAAAA**AG (SEQ ID NO: 794) | (+)/E | orf38/Primase |
| S30 | 2972[a] | 33968 | 30 | TCCAAGTTATTTGAGGAGTTATTAAGACAT (SEQ ID NO: 707) | GA**AGAAA**TAT (SEQ ID NO: 795) | (+)/E | orf43/Unknown |
| S31 | 2972 | 30803 | 30 | TACCGAAACGACTGGTTTGAAAAATTCAAG (SEQ ID NO: 708) | GA**AGAAAA**TC (SEQ ID NO: 796) | (+)/E | orf38/Primase |
| S32 | 2972[a] | 33044 | 30 | ATTGTCTATTACGACAACATGGAAGATGAT (SEQ ID NO: 526) | GT**AGAAA**TTT (SEQ ID NO: 797) | (+)/E | orf41/Unknown |
| S33 | 858 | 30335 | 30 | CTTCAAATGTACTGCAAGGCTGCAAAAGTA (SEQ ID NO: 710) | CC**AGAAAA**TA (SEQ ID NO: 798) | (+)/E | orf38/Unknown |

DGCC7710 was exposed to phage 2972 to create CRISPR phage resistant variant DGCC7710$_{\Phi 2972}{}^{+S6}$ from which CRISPR-escape mutant phage 2972.S6B was generated. Exposure of DGCC7710$_{\Phi 2972}{}^{+S6}$ to phage 2972.S6B created CRISPR phage resistant variant DGCC7710$_{\Phi 2972}{}^{+S6}{}_{\Phi 2972.S6B}{}^{+S20}$ from which CRISPR-escape mutant phage 2972.S20A was isolated.

In some embodiments, strains that are resistant to more than one family of phages are provided. As a given strain can be sensitive to more than one family of phages, in some embodiments, it is desired to enlarge the strain resistance to multiple phage families by introducing additional spacer(s) within a CRISPR locus originating from the other families of phages (See, FIG. 16). For example, phages P, Q, and R are representative phages from three families of phages able to infect strain A. Using the method outlined above and herein, variants resistant to all three phage families are produced. In some embodiments, phage P is used to generate variant A1$^{p}$ (containing spacer Sp1) that is resistant to phage P. Then, variant A1$^{p}$ is exposed to phage Q and a phage resistant variant (Variant A1$^{pq}$) is selected. Variant A1$^{pq}$ has one additional spacer (Sq1) inserted within a CRISPR locus. Typically, spacer Sq1 is a fragment of approximately 30 nucleotides in size from the phage Q, and gives resistance to phage Q and related phages. Variant A1$^{pq}$ is resistant to both P and Q phages. Next, variant A1$^{pq}$ is exposed to phage R and a phage resistant variant (Variant A1$^{pqr}$) is selected. Variant A1$^{pqr}$ has a third additional spacer (Sr1) inserted within a CRISPR locus. Typically, Sr1 is a fragment of approximately 30 nucleotides in size from the phage R, and also gives resistance to phage R and related phages. Variant A1$^{pqr}$ is resistant to all three phages. In some particularly preferred embodiments, the variant is also resistant to related phages.

These CRISPR-escape phages find use as biocontrol/therapeutic phages. As described above, through the process of creating CRISPR-mediated phage resistant variants, exposure to phage and isolation of virulent "CRISPR-escape" phage, a mixture of phage species that harbor single and/or multiple mutations targeted against single and/or multiple phage genome sequences that are potential CRISPR spacer targets is generated. As target host bacteria can become resistant to phage through the incorporation of a single or multiple spacers and that the Cas-CRISPR mechanism can be overcome through a mutation within the phage genome corresponding to such spacers, the use of a mixture of phage harboring various mutations reduces the rate of an individual bacterium to successfully acquire new spacers and proliferate.

Figure 22:
FIG. 22 provides a Web Logo for the CRISPR1 motif NNAGAAW (SEQ ID NO:696).

In an additional embodiment, analysis of the protospacer and flanking regions, as determined from the spacers in the corresponding CRISPR phage resistant variants, facilitates identification of the CRISPR motif for a specific CRISPR. In the example of DGCC7710 CRISPR 1 phage-resistant variants containing spacers S1-S33, were generated following challenge with phage 2972 or 858. Alignment of the protospacer and flanking regions, from the genome of phages 2972 or 858 that correspond to spacers S1-S33, using the software program Clustal X, identified the CRISPR 1 motif as NNAGAAW (SEQ ID NO:696), and is visualized using WebLogo (FIG. 22).

Figure 23:
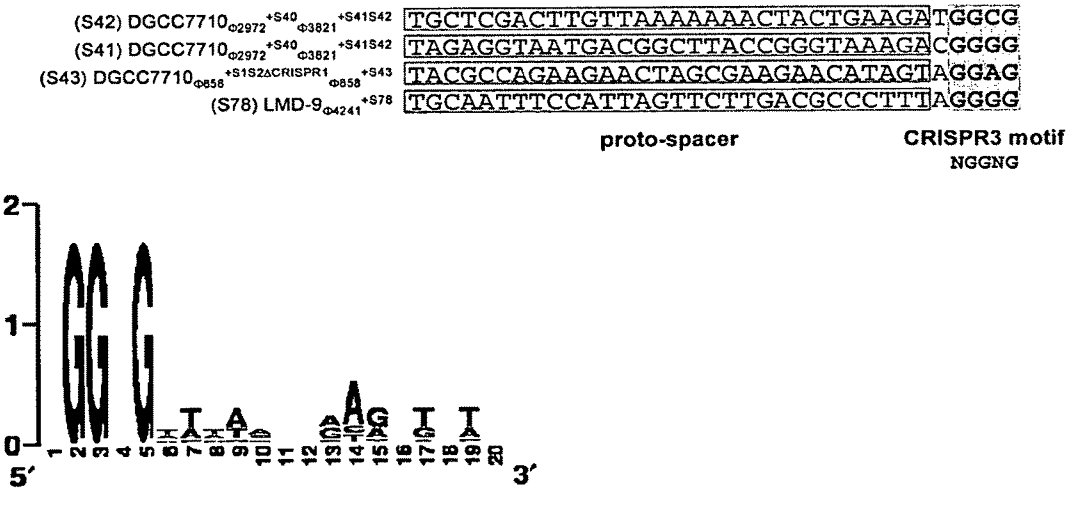
FIG. 23 provides an alignment of selected CRISPR3 protospacers and flanking regions and the web logo for the CRISPR3 motif NGGNG (SEQ ID NO:723). In this Figure, S42 $DGCC7710_{phi2972}^{+S40}{}_{phi3821}^{+S41S42}$ (SEQ ID NO:724), S41 $DGCC7710_{phi2972}^{+S40}{}_{phi3821}^{+S41S42}$, (SEQ ID NO:699) S41 $DGCC7710_{phi858}^{+S1S2deltaCRISPR1}{}_{phi848}^{+S43}$ (SEQ ID NO:700), and S78 $LMD\text{-}9_{phi4241}^{+S78}$ (SEQ ID NO:701) are provided.

In a further example, CRISPR 3 phage resistant variants were derived from DGCC7710 following challenge with phages 858 and 3821, and LMD-9 following challenge with phage 4241. Alignment of the protospacers and flanking region from the respective phage genomes with the corresponding spacers of the respective CRISPR 3 phage resistant variants, identified the CRISPR 3 motif as NGGNG (SEQ ID NO:723) (FIG. 23).

Analysis for the presence of a specific CRISPR motif provides means to identify the location of putative protospacers within a genome or other specified sequence (e.g., a plasmid or another mobile genetic element). In the example of sequenced phages 858, 2972, and DT1, analysis for the distribution of the AGAAW CRISPR 1 motif identified the location of potential protospacers within the respective genomes. Utilizing the degeneracy of the genetic code and/or the use of conservative amino acid substitutions, each AGAAW motif was eliminated in the process of chemically synthesizing a genome as described for phage ØX174, as known in the art. Thus, the phage became insensitive to the Cas-CRISPR 1 resistance system. Thus, a DNA molecule, devoid of specific CRISPR motifs is insensitive to the corresponding Cas-CRISPR system.

These phages and "cocktails" of multiple phage types find use in rotation strategies (e.g., defined sequential administration of phage). As an extension to the use of a single cocktail, composed of phage harboring different spacer mutations, in some embodiments, multiple virulent phage, each harboring a different spacer mutation in a defined sequential manner are used. For example, using a set of "CRISPR-escape" phages (P1.0, P2.0, and P3.0, or P1.0, P1.1, P1.2, or some combination thereof), each phage is applied individually and in a defined sequence and rotation (P.10>P2.0>P3.0>P1.0, P2.0> etc) so as to minimize the probability of the target bacteria developing CRISPR-mediated resistance to the phage. Likewise, a set of phage cocktails (i.e., each phage within the cocktail as well as each cocktail possesses a unique combination of mutations) finds use in sequence and rotation. In some embodiments, the phage and/or cocktail is comprised of a single phage family, while in other embodiments, the phage and/or cocktail is comprised of multiple phage families.

Example 23

Functional Combinations

This Example provides various functional combinations that find use in the present invention. By way of example only, the following functional combinations may be used in accordance with the present invention.

Functional Combination #1:

cas sequences: SEQ ID NO:461 to SEQ ID NO:465 and SEQ ID NO:473 to SEQ ID NO:477 (all of which are *S. thermophilus* sequences), as set forth below:

```
SEQ ID NO: 461:
ATGAGTGACTTAGTTTTAGGACTTGATATCGGTATAGGTTCTGTTGGTGTAGGTATCCTTAAC
AAAGTGACAGGAGAAATTATCCATAAAAACTCACGCATCTTCCCAGCAGCTCAAGCAGAAA
ATAACCTAGTACGTAGAACGAATCGTCAAGGAAGACGCTTGACACGACGTAAAAAACATCG
TATAGTTCGTTTAAATCGTCTATTTGAGGAAAGTGGATTAATCACCGATTTTACGAAGATTT
CAATTAATCTTAACCCATATCAATTACGAGTTAAGGGCTTGACCGATGAATTGTCTAATGAA
GAACTGTTTATCGCTCTTAAAAATATGGTGAAACACCGTGGGATTAGTTACCTCGATGATGC
TAGTGATGACGGAAATTCATCAGTAGGAGACTATGCACAAATTGTTAAGGAAAATAGTAAA
CAATTAGAAACTAAGACACCGGGACAGATACAGTTGGAACGCTACCAAACATATGGTCAAT
TACGTGGTGATTTTACTGTTGAGAAAGATGGCAAAAAACATCGCTTGATTAATGTCTTTCCA
ACATCAGCTTATCGTTCAGAAGCCTTAAGGATACTGCAAACTCAACAAGAATTTAATCCACA
GATTACAGATGAATTTATTAATCGTTATCTCGAAATTTTAACTGGAAAACGGAAATATTATC
ATGGACCCGGAAATGAAAAGTCACGGACTGATTATGGTCGTTACAGAACGAGTGGAGAAAC
TTTAGACAATATTTTTGGAATTCTAATTGGGAAATGTACATTTTATCCAGAAGAGTTTAGAG
CAGCAAAAGCTTCCTACACGGCTCAAGAATTCAATTTGCTAAATGATTTGAACAATCTAACA
GTTCCTACTGAAACCAAAAAGTTGAGCAAAGAACAGAAGAATCAAATCATTAATTATGTCA
AAAATGAAAAGGCAATGGGGCCAGCGAAACTTTTTAAATATATCGCTAAGTTACTTTCTTGT
GATGTTGCAGATATCAAGGGATACCGTATCGACAAATCAGGTAAGGCTGAGATTCATACTTT
CGAAGCCTATCGAAAAATGAAAACGCTTGAAACCTTAGATATTGAACAAATGGATAGAGAA
ACGCTTGATAAATTAGCCTATGTCTTAACATTAAACACTGAGAGGGAAGGTATTCAAGAAG
CCTTAGAACATGAATTTGCTGATGGTAGCTTTAGCCAGAAGCAAGTTGACGAATTGGTTCAA
TTCCGCAAAGCAAATAGTTCCATTTTTGGAAAAGGATGGCATAATTTTTCTGTCAAACTGAT
GATGGAGTTAATTCCAGAATTGTATGAGACGTCAGAAGAGCAAATGACTATCCTGACACGA
CTTGGAAAACAAAAACGACTTCGTCTTCAAATAAAACAAAATATTTCAAATAAAACAAAAT
ATATAGATGAGAAACTATTAACTGAAGAAATCTATAATCCTGTTGTTGCTAAGTCTGTTCGC
CAGGCTATAAAAATCGTAAATGCGGCGATTAAAGAATACGGAGACTTTGACAATATTGTCA
TCGAAATGGCTCGTGAAACAAATGAAGATGATGAAAAGAAAGCTATTCAAAAGATTCAAAA
AGCCAACAAAGATGAAAAAGATGCAGCAATGCTTAAGGCTGCTAACCAATATAATGGAAA
GGCTGAATTACCACATAGTGTTTTCCACGGTCATAAGCAATTAGCGACTAAAATCCGCCTTT
GGCATCAGCAAGGAGAACGTTGCCTTTATACTGGTAAGACAATCTCAATCCATGATTTGATA
AATAATCCTAATCAGTTTGAAGTAGATCATATTTTACCTCTTTCTATCACATTCGATGATAGC
CTTGCAAATAAGGTTTTGGTTTATGCAACTGCTAACCAAGAAAAAGGACAACGAACACCTT
```

-continued

ATCAGGCTTTAGATAGTATGGATGATGCGTGGTCTTTCCGTGAATTAAAAGCTTTTGTACGT
GAGTCAAAAACACTTTCAAACAAGAAAAAAGAATACCTCCTTACAGAAGAAGATATTTCAA
AGTTTGATGTTCGAAAGAAATTTATTGAACGAAATCTTGTAGATACAAGATACGCTTCAAGA
GTTGTCCTCAATGCCCTTCAAGAACACTTTAGAGCTCACAAGATTGATACAAAAGTTTCCGT
GGTTCGTGGCCAATTTACATCTCAATTGAGACGCCATTGGGGAATTGAGAAGACTCGTGATA
CTTATCATCACCATGCTGTCGATGCATTGATTATTGCCGCCTCAAGTCAGTTGAATTTGTGGA
AAAAACAAAAGAATACCCTTGTAAGTTATTCAGAAGAACAACTCCTTGATATTGAAACAGG
TGAACTTATTAGTGATGATGAGTACAAGGAATCTGTGTTCAAAGCCCCTTATCAACATTTTG
TTGATACATTGAAGAGTAAAGAATTTGAAGACAGTATCTTATTCTCATATCAAGTGGATTCT
AAGTTTAATCGTAAAATATCAGATGCCACTATTTATGCGACAAGACAGGCTAAAGTGGGAA
AAGATAAGAAGGATGAAACTTATGTCTTAGGGAAAATCAAAGATATCTATACTCAGGATGG
TTATGATGCCTTTATGAAGATTTATAAGAAGGATAAGTCAAAATTCCTCATGTATCGTCACG
ACCCACAAACCTTTGAGAAAGTTATCGAGCCAATTTTAGAGAACTATCCTAATAAGCAAAT
GAATGAAAAAGGAAAAGAGGTACCATGTAATCCTTTCCTAAAATATAAAGAAGAACATGGC
TATATTCGTAAATATAGTAAAAAAGGCAATGGTCCTGAAATCAAGAGTCTTAAATACTATG
ATAGTAAGCTTTTAGGTAATCCTATTGATATTACTCCAGAGAATAGTAAAAATAAAGTTGTC
TTACAGTCATTAAAACCTTGGAGAACAGATGTCTATTTCAATAAGGCTACTGGAAAATACGA
AATCCTTGGATTAAAATATGCTGATCTACAATTTGAGAAAGGGACAGGAACATATAAGATT
TCCCAGGAAAAATACAATGACATTAAGAAAAAAGAGGGTGTAGATTCTGATTCAGAATTCA
AGTTTACACTTTATAAAAATGATTTGTTACTCGTTAAAGATACAGAAACAAAAGAACAACA
GCTTTTCCGTTTTCTTTCTCGAACTTTACCTAAACAAAAGCATTATGTTGAATTAAAACCTTA
TGATAAACAGAAATTTGAAGGAGGTGAGGCGTTAATTAAAGTGTTGGGTAACGTTGCTAAT
GGTGGTCAATGCATAAAAGGACTAGCAAAATCAAATATTTCTATTTATAAAGTAAGAACAG
ATGTCCTAGGAAATCAGCATATCATCAAAAATGAGGGTGATAAGCCTAAGCTAGATTTTTA
ATATTAATTGTTAGAAAGTGTTGCAATTATAGTTATCATATGCTATAATAATCGTGTAAGGG
ACGCCTTACACAGTTACTTAAATCTTGCAGAAGCTACAAAGATAAGGCTTCATGCCGAAATC
AACACCCTGTCATTTTATGGCAGGGTGTTTTCGTTATTTAAAGAGGAGAAGAAATGACTTGG
AGAGTTGTACATGTCAGTCAAAGTGAGAAGATGCGCTTAAAGCTTGATAACTTATTAGTGCA
AAAAATGGGACAAGAGTTTACGGTGCCACTAAGTGATATTTCGATAATCGTTGCAGAAGGT
GGGGATACAGTTGTTACCCTTCGTCTATTAAGTGCCTTAAGTAAATATAATATTGCCTTGGTC
GTTTGTGATAACGAACATTTACCAACAGGAATTTATCACTCACAAAATGGGCACTTTAGAGC
GTACAAGCGCTTGAAAGAACAGCTGGATTGGTCTCAGAAACAAAAGGACAAGGCATGGCA
GATTGTAACTTATTATAAAATCAATAACCAAGAGGATGTTCTAGCCATGTTTGAAAAAAGTC
TGGACAACATTAGATTACTTTCAGACTATAAAGAGCAGATAGAACCTGGTGATAGAACGAA
TAGAGAGGGACATGCTGCCAAGGTCTACTTTAATGAGCTCTTTGGTAAACAATTTGTCAGAG
TAACTCAGCAAGAAGCTGATGTCATCAATGCTGGTTTAAACTATGGCTATGCTATCATGAGG
GCTCAGATGGCTAGAATAGTGGCGGGTTATGGTTTAAATGGCCTATTAGGAATCTTCCATAA
AAATGAATACAATCAGTTTAATTTGGTTGACGATTTGATGGAGCCATTTAGACAGATTGTAG
ATGTTTGGGTATATGATAATCTACGAGATCAGGAATTCCTTAAGTATGAGTATAGGTTGGGA
TTGACAGATTTACTCAATGCTAAAATCAAATATGGCAAAGAGACTTGCTCAGTGACAGTTGC
TATGGACAAATATGTCAAAGGCTTTATCAAATATATTTCGGAAAAAGATAGTAGTAAATTTC
ACTGCCCAGTGGTATCAAGTTTAGAGTGGAGAAAATAAGATGAGGTATGAAGCATTGAGAT
TATTATGTTTTTTTGATTTACCAATGGAATCCAAGGATGAAAAAAGAATATATCGTAATTTT
CGTAAAGAATTAATTTCAAATGGGTTTGAAATGTTACAATTTTCGGTCTACTATCGCACTTGT
CCTAATAGAAGCTTTGCAAATAAATTTTATAAGAAGTTAAAGATTAGCAATCTTCCTGCTGG
GAATGTGAGACTTTTGGCAGTTACTGAAAAACAATTTTCAGAGATGACATTAATTATAGGTG
GTAAAACTAAGCAAGAAGAAATCGTCAGTGATAATAAGTTGGTGGTTATATGAAATATTTT
GTACAACATCCTTACAAAGAACGTATTGAATTAAATATTGGTGCAATCACACAAATTGTTGG
TCAGAATAAAGAACTCAAATATTATATTTGGCAAATTTTGAGCTGGTATTTTGGCGGAAAAA
AATACTCAAGTGAGGACTTAAGTATTTTTGATTATGAGGAACCTACTATACTTGATGAGTCT
GGAGAAATAGTGAAGCGAAGTAGCTATCACTATATCGACATTTCAAGTTTTAAGGATTTACT
GGAGCAGATGGAATACAAGAAAGGAACACTTGCTCAGGGTTACCTTAGTAAAATTCTCAAT
CAGGTTGATATTGTAGGCCATTTGGAGAAAATTAATGAACAAGTAGAGCTTATAGAAGGAG
CAATGAATCAGCATATAAACTTAAACTGTGGTCAGGTGGAGTACCATTTGGAGAATCACCCT
CTAACACTAGACCAATTACTTTCAAAAAATTTTAGTCCCTTTTTTGCTATCGAGAATAAGAA
TTTATCTTTTGAATGGGTTTCAAATACTGATAAACTTTCTCTCTTTCTAGAAATGTTAGACCG
CCTTCTGTCACAAACAACAGAGAAGTATCTCATTGTGCTAAAAAATATTGATGGCTTTATCT
CAGAAGAATCTTATACTATTTTTTATAGGCAAATCTGTCATCTGGTCAAGAAGTATCCAAAT
CTAACCTTTATTTTGTTTCCTAGTGACCAAGGCTATTTAAAAATTGATGAAGAAAATAGTAG
GTTCGTCAATATTTTATCTGACCAGGTGGAGCATTTGTATGATGTTGAGTTTATGTATGAAA
GAGTAATGAAATATTATCCAAGTAATGATTTTCCGACGAGAGAAGGTTTTAGGATGTCTTTA
GAAACTGTGACACCTTATTTATTGACAAAAATGCTGAGACAACCTAGTCTCTCACTTGTTGA
TTCAGTAATATTGAATATCCTAAATCAGTTGTTTCATTTTAGTTACCGTATAAGATATTCTCA
GACACCTGATAAGGAACTATTACATAAATTTTTAGAAAGTAAGGATTGA (SEQ ID NO: 461)

SEQ ID NO: 462:
ATGAGTGACTTAGTTTTAGGACTTGATATCGGTATAGGTTCTGTTGGTGTAGGTATCCTTAAC
AAAGTGACAGGAGAAATTATCCATAAAAACTCACGCATCTTCCCAGCAGCTCAAGCAGAAA
ATAACCTAGTACGTAGAACGAATCGTCAAGGAAGACGCTTGACACGACGTAAAAAACATCG
TATAGTTCGTTTAAATCGTCTATTTGAGGAAAGTGGATTAATCACCGATTTTACGAAGATTT
CAATTAATCTTAACCCATATCAATTACGAGTTAAGGGCTTGACCGATGAATTGTCTAATGAA
GAACTGTTTATCGCTCTTAAAAATATGGTGAAACACCGTGGGATTAGTTACCTCGATGATGC
TAGTGATGACGGAAATTCATCAGTAGGAGACTATGCACAAATTGTTAAGGAAAATAGTAAA
CAATTAGAAACTAAGACACCGGGACAGATACAGTTGGAACGCTACCAAACATATGGTCAAT
TACGTGGTGATTTTACTGTTGAGAAAGATGGCAAAAAACATCGCTTGATTAATGTCTTTCCA
ACATCAGCTTATCGTTCAGAAGCCTTAAGGATACTGCAAACTCAACAAGAATTTAATCCACA
GATTACAGATGAATTTATTAATCGTTATCTCGAAATTTTAACTGGAAAACGGAAATATTATC
ATGGACCCGGAAATGAAAAGTCACGGACTGATTATGGTCGTTACAGAACGAGTGGAGAAAC
TTTAGACAATATTTTTGGAATTCTAATTGGGAAATGTACATTTTATCCAGAAGAGTTTAGAG
CAGCAAAAGCTTCCTACACGGCTCAAGAATTCAATTTGCTAAATGATTTGAACAATCTAACA
GTTCCTACTGAAACCAAAAAGTTGAGCAAAGAACAGAAGAATCAAATCATTAATTATGTCA

-continued

AAAATGAAAAGGCAATGGGGCCAGCGAAACTTTTTAAATATATCGCTAAGTTACTTTCTTGT
GATGTTGCAGATATCAAGGGATACCGTATCGACAAATCAGGTAAGGCTGAGATTCATACTTT
CGAAGCCTATCGAAAAATGAAAACGCTTGAAACCTTAGATATTGAACAAATGGATAGAGAA
ACGCTTGATAAATTAGCCTATGTCTTAACATTAAACACTGAGAGGGAAGGTATTCAAGAAG
CCTTAGAACATGAATTTGCTGATGGTAGCTTTAGCCAGAAGCAAGTTGACGAATTGGTTCAA
TTCCGCAAAGCAAATAGTTCCATTTTTGGAAAAGGATGGCATAATTTTTCTGTCAAACTGAT
GATGGAGTTAATTCCAGAATTGTATGAGACGTCAGAAGAGCAAATGACTATCCTGACACGA
CTTGGAAAACAAAAACGACTTCGTCTTCAAATAAAACAAAATATTTCAAATAAAACAAAAT
ATATAGATGAGAAACTATTAACTGAAGAAATCTATAATCCTGTTGTTGCTAAGTCTGTTCGC
CAGGCTATAAAAATCGTAAATGCGGCGATTAAAGAATACGGAGACTTTGACAATATTGTCA
TCGAAATGGCTCGTGAAACAAATGAAGATGATGAAAAGAAAGCTATTCAAAAGATTCAAAA
AGCCAACAAAGATGAAAAAGATGCAGCAATGCTTAAGGCTGCTAACCAATATAATGGAAA
GGCTGAATTACCACATAGTGTTTTCCACGGTCATAAGCAATTAGCGACTAAAATCCGCCTTT
GGCATCAGCAAGGAGAACGTTGCCTTTATACTGGTAAGACAATCTCAATCCATGATTTGATA
AATAATCCTAATCAGTTTGAAGTAGATCATATTTTACCTCTTTCTATCACATTCGATGATAGC
CTTGCAAATAAGGTTTTGGTTTATGCAACTGCTAACCAAGAAAAAGGACAACGAACACCTT
ATCAGGCTTTAGATAGTATGGATGATGCGTGGTCTTTCCGTGAATTAAAAGCTTTTGTACGT
GAGTCAAAAACACTTTCAAACAAGAAAAAAGAATACCTCCTTACAGAAGAAGATATTTCAA
AGTTTGATGTTCGAAAGAAATTTATTGAACGAAATCTTGTAGATACAAGATACGCTTCAAGA
GTTGTCCTCAATGCCCTTCAAGAACACTTTAGAGCTCACAAGATTGATACAAAAGTTTCCGT
GGTTCGTGGCCAATTTACATCTCAATTGAGACGCCATTGGGGAATTGAGAAGACTCGTGATA
CTTATCATCACCATGCTGTCGATGCATTGATTATTGCCGCCTCAAGTCAGTTGAATTTGTGGA
AAAAACAAAAGAATACCCTTGTAAGTTATTCAGAAGAACAACTCCTTGATATTGAAACAGG
TGAACTTATTAGTGATGATGAGTACAAGGAATCTGTGTTCAAAGCCCCTTATCAACATTTTG
TTGATACATTGAAGAGTAAAGAATTTGAAGACAGTATCTTATTCTCATATCAAGTGGATTCT
AAGTTTAATCGTAAAATATCAGATGCCACTATTTATGCGACAAGACAGGCTAAAGTGGGAA
AAGATAAGAAGGATGAAACTTATGTCTTAGGGAAAATCAAAGATATCTATACTCAGGATGG
TTATGATGCCTTTATGAAGATTTATAAGAAGGATAAGTCAAAATTCCTCATGTATCGTCACG
ACCCACAAACCTTTGAGAAAGTTATCGAGCCAATTTTAGAGAACTATCCTAATAAGCAAAT
GAATGAAAAAGGAAAAGAGGTACCATGTAATCCTTTCCTAAAATATAAAGAAGAACATGGC
TATATTCGTAAATATAGTAAAAAGGCAATGGTCCTGAAATCAAGAGTCTTAAATACTATG
ATAGTAAGCTTTTAGGTAATCCTATTGATATTACTCCAGAGAATAGTAAAAATAAAGTTGTC
TTACAGTCATTAAAACCTTGGAGAACAGATGTCTATTTCAATAAGGCTACTGGAAAATACGA
AATCCTTGGATTAAAATATGCTGATCTACAATTTGAGAAAGGGACAGGAACATATAAGATT
TCCCAGGAAAAATACAATGACATTAAGAAAAAAGAGGGTGTAGATTCTGATTCAGAATTCA
AGTTTACACTTTATAAAAATGATTTGTTACTCGTTAAAGATACAGAAACAAAAGAACAACA
GCTTTTCCGTTTTCTTTCTCGAACTTTACCTAAACAAAAGCATTATGTTGAATTAAAACCTTA
TGATAAACAGAAATTTGAAGGAGGTGAGGCGTTAATTAAAGTGTTGGGTAACGTTGCTAAT
GGTGGTCAATGCATAAAAGGACTAGCAAAATCAAATATTTCTATTTATAAAGTAAGAACAG
ATGTCCTAGGAAATCAGCATATCATCAAAAATGAGGGTGATAAGCCTAAGCTAGATTTTTA
A (SEQ ID NO: 462)

SEQ ID NO: 463:
ATGACTTGGAGAGTTGTACATGTCAGTCAAAGTGAGAAGATGCGCTTAAAGCTTGATAACTT
ATTAGTGCAAAAAATGGGACAAGAGTTTACGGTGCCACTAAGTGATATTTCGATAATCGTTG
CAGAAGGTGGGGATACAGTTGTTACCCTTCGTCTATTAAGTGCCTTAAGTAAATATAATATT
GCCTTGGTCGTTTGTGATAACGAACATTTACCAACAGGAATTTATCACTCACAAAATGGGCA
CTTTAGAGCGTACAAGCGCTTGAAAGAACAGCTGGATTGGTCTCAGAAACAAAAGGACAAG
GCATGGCAGATTGTAACTTATTATAAAATCAATAACCAAGAGGATGTTCTAGCCATGTTTGA
AAAAAGTCTGGACAACATTAGATTACTTTCAGACTATAAAGAGCAGATAGAACCTGGTGAT
AGAACGAATAGAGAGGGACATGCTGCCAAGGTCTACTTTAATGAGCTCTTTGGTAAACAAT
TTGTCAGAGTAACTCAGCAAGAAGCTGATGTCATCAATGCTGGTTTAAACTATGGCTATGCT
ATCATGAGGGCTCAGATGGCTAGAATAGTGGCGGGTTATGGTTTAAATGGCCTATTAGGAA
TCTTCCATAAAAAATGAATACAATCAGTTTAATTTGGTTGACGATTTGATGGAGCCATTTAGA
CAGATTGTAGATGTTTGGGTATATGATAATCTACGAGATCAGGAATTCCTTAAGTATGAGTA
TAGGTTGGGATTGACAGATTTACTCAATGCTAAAATCAAATATGGCAAAGAGACTTGCTCA
GTGACAGTTGCTATGGACAAATATGTCAAAGGCTTTATCAAATATATTTCGGAAAAAGATA
GTAGTAAATTTCACTGCCCAGTGGTATCAAGTTTAGAGTGGAGAAAATAA (SEQ ID NO: 463)

SEQ ID NO: 464:
ATGAGGTATGAAGCATTGAGATTATTATGTTTTTTTGATTTACCAATGGAATCCAAGGATGA
AAAAAGAATATATCGTAATTTTCGTAAAGAATTAATTTCAAATGGGTTTGAAATGTTACAAT
TTTCGGTCTACTATCGCACTTGTCCTAATAGAAGCTTTGCAAATAAATTTTATAAGAAGTTA
AAGATTAGCAATCTTCCTGCTGGGAATGTGAGACTTTTGGCAGTTACTGAAAAACAATTTTC
AGAGATGACATTAATTATAGGTGGTAAAACTAAGCAAGAAGAAATCGTCAGTGATAATAAG
TTGGTGGTTATATGA (SEQ ID NO: 464)

SEQ ID NO: 465:
ATGAAATATTTTGTACAACATCCTTACAAAGAACGTATTGAATTAAATATTGGTGCAATCAC
ACAAATTGTTGGTCAGAATAAAGAACTCAAATATTATATTTGGCAAATTTTGAGCTGGTATT
TTGGCGGAAAAAAATACTCAAGTGAGGACTTAAGTATTTTTGATTATGAGGAACCTACTATA
CTTGATGAGTCTGGAGAAATAGTGAAGCGAAGTAGCTATCACTATATCGACATTTCAAGTTT
TAAGGATTTACTGGAGCAGATGGAATACAAGAAAGGAACACTTGCTCAGGGTTACCTTAGT
AAAATTCTCAATCAGGTTGATATTGTAGGCCATTTGGAGAAAATTAATGAACAAGTAGAGC
TTATAGAAGGAGCAATGAATCAGCATATAAACTTAAACTGTGGTCAGGTGGAGTACCATTT
GGAGAATCACCCTCTAACACTAGACCAATTACTTTCAAAAAATTTAGTCCCTTTTTTGCTAT
CGAGAATAAGAATTTATCTTTTGAATGGGTTTCAAATACTGATAAACTTTCTCTCTTTCTAGA
AATGTTAGACCGCCTTCTGTCACAAACAACAGAGAAGTATCTCATTGTGCTAAAAAAATATTG
ATGGCTTTATCTCAGAAGAATCTTATACTATTTTTTATAGGCAAATCTGTCATCTGGTCAAGA
AGTATCCAAATCTAACCTTTATTTTGTTTCCTAGTGACCAAGGCTATTTAAAAATTGATGAA
GAAAATAGTAGGTTCGTCAATATTTTATCTGACCAGGTGGAGCATTTGTATGATGTTGAGTT

-continued

TATGTATGAAAGAGTAATGAAATATTATCCAAGTAATGATTTTCCGACGAGAGAAGGTTTTA
GGATGTCTTTAGAAACTGTGACACCTTATTTATTGACAAAAATGCTGAGACAACCTAGTCTC
TCACTTGTTGATTCAGTAATATTGAATATCCTAAATCAGTTGTTTCATTTTAGTTACCGTATA
AGATATTCTCAGACACCTGATAAGGAACTATTACATAAATTTTTAGAAAGTAAGGATTGA
(SEQ ID NO: 465)

SEQ ID NO: 473:
ATGAGTGACTTAGTTTTAGGACTTGATATCGGTATAGGTTCTGTTGGTGTAGGTATCCTTAAC
AAAGTGACAGGAGAAATTATCCATAAAAACTCACGCATCTTCCCAGCAGCTCAAGCAGAAA
ATAACCTAGTACGTAGAACGAATCGTCAAGGAAGACGCTTGACACGACGTAAAAAACATCG
TATAGTTCGTTTAAATCGTCTATTTGAGGAAAGTGGATTAATCACCGATTTTACGAAGATTT
CAATTAATCTTAACCCATATCAATTACGAGTTAAGGGCTTGACCGATGAATTGTCTAATGAA
GAACTGTTTATCGCTCTTAAAAATATGGTGAAACACCGTGGGATTAGTTACCTCGATGATGC
TAGTGATGACGGAAATTCATCAGTAGGAGACTATGCACAAATTGTTAAGGAAAATAGTAAA
CAATTAGAAACTAAGACACCGGGACAGATACAGTTGGAACGCTACCAAACATATGGTCAAT
TACGTGGTGATTTTACTGTTGAGAAAGATGGCAAAAAACATCGCTTGATTAATGTCTTTCCA
ACATCAGCTTATCGTTCAGAAGCCTTAAGGATACTGCAAACTCAACAAGAATTTAATTCACA
GATTACAGATGAATTTATTAATCGTTATCTCGAAATTTTAACTGGAAAACGGAAATATTATC
ATGGACCCGGAAATGAAAAGTCACGGACTGATTATGGTCGTTACAGAACGAATGGAGAAAC
TTTAGACAATATTTTTGGAATTCTAATTGGGAAATGTACATTTTATCCAGACGAGTTTAGAG
CAGCAAAAGCTTCCTACACGGCTCAAGAATTCAATTTGCTAAATGATTTGAACAATCTAACA
GTTCCTACTGAAACCAAAAAGTTGAGCAAAGAACAGAAGAATCAAATCATTAATTATGTCA
AAAATGAAAAGGTAATGGGGCCAGCGAAACTTTTTAAATATATCGCTAAATTACTTTCTTGT
GATGTTGCAGATATCAAGGGACACCGTATCGACAAATCAGGTAAGGCTGAGATTCATACTT
TCGAAGCCTATCGAAAAATGAAAACGCTTGAAACCTTAGATATTGAGCAAATGGATAGAGA
AACGCTTGATAAATTAGCCTATGTCTTAACATTAAACACTGAGAGGGAAGGTATTCAAGAA
GCTTTAGAACATGAATTTGCTGATGGTAGCTTTAGCCAGAAGCAAGTTGACGAATTGGTTCA
ATTCCGCAAAGCAAATAGTTCCATTTTTGGAAAAGGATGGCATAATTTTTCTGTCAAACTGA
TGATGGAGTTAATTCCAGAATTGTATGAGACGTCAGAAGAGCAAATGACTATCCTGACACG
ACTTGGAAAACAAAAAACAACTTCGTCTTCAAATAAAACAAAATATATAGATGAGAAACTA
TTAACTGAAGAAATCTATAATCCTGTTGTTGCTAAGTCTGTTCGCCAGGCTATAAAAATCGT
AAATGCGGCGATTAAAGAATACGGAGACTTTGACAATATTGTCATCGAAATGGCTCGTGAA
ACAAATGAAGATGATGAAAAGAAAGCTATTCAAAAGATTCAAAAAGCCAACAAAGATGAA
AAAGATGCAGCAATGCTTAAGGCTGCTAACCAATATAATGGAAAGGCTGAATTACCACATA
GTGTTTTCCACGGTCATAAGCAATTAGCGACTAAAATCCGCCTTTGGCATCAGCAAGGAGAA
CGTTGCCTTTATACTGGTAAGACAATCTCAATCCATGATTTGATAAATAATCCTAATCAGTTT
GAAGTAGATCATATTTTACCTCTTTCTATCACATTCGATGATAGCCTTGCAAATAAGGTTTTG
GTTTATGCAACTGCTAACCAAGAAAAAGGACAACGAACACCTTATCAGGCTTTAGATAGTA
TGGATGATGCGTGGTCTTTCCGTGAATTAAAAGCTTTTGTACGTGAGTCAAAAACACTTTCA
AACAAGAAAAAAGAATACCTCCTTACAGAAGAAGATATTTCAAAGTTTGATGTTCGAAAGA
AATTTATTGAACGAAATCTTGTAGATACAAGATACGCTTCAAGAGTTGTCCTCAATGCCCTT
CAAGAACACTTTAGAGCTCACAAGATTGATACAAAAGTTTCCGTGGTTCGTGGCCAATTTAC
ATCTCAATTGAGACGCCATTGGGGAATTGAGAAGACTCGTGATACTTATCATCACCATGCTG
TCGATGCATTGATTATTGCCGCCTCAAGTCAGTTGAATTTGTGGAAAAAACAAAAGAATACC
CTTGTAAGTTATTCAGAAGAACAACTCCTTGATATTGAAACAGGTGAACTTATTAGTGATGA
TGAGTACAAGGAATCTGTGTTCAAAGCCCCTTATCAACATTTTGTTGATACATTGAAGAGTA
AAGAATTTGAAGACAGTATCTTATTCTCATATCAAGTGGATTCTAAGTTTAATCGTAAAATA
TCAGATGCCACTATTTATGCGACAAGACAGGCTAAAGTGGGAAAAGATAAGAAGGATGAA
ACTTATGTCTTAGGGAAAATCAAAGATATCTATACTCAGGATGGTTATGATGCCTTTATGAA
GATTTATAAGAAGGATAAGTCAAAATTCCTCATGTATCGTCACGACCCACAAACCTTTGAGA
AAGTTATCGAGCCAATTTTAGAGAACTATCCTAATAAGGAAATGAATGAAAAAGGGAAAGA
AGTACCATGTAATCCTTTCCTAAAATATAAAGAAGAACATGGCTATATTCGTAAATATAGTA
AAAAAGGCAATGGTCCTGAAATCAAGAGTCTTAAATACTATGATAGTAAGCTTTTAGGTAA
TCCTATTGATATTACTCCAGAGAATAGTAAAAATAAAGTTGTCTTACAGTCATTAAAACCTT
GGAGAACAGATGTCTATTTCAATAAAAATACTGGTAAATATGAAATTTTAGGACTGAAATA
TGCTGATTTACAATTTGAAAAGAAGACAGGAACATATAAGATTTCCCAGGAAAAATACAAT
GGCATTATGAAAGAAGAGGGTGTAGATTCTGATTCAGAATTCAAGTTTACACTTTATAAAAA
TGATTTGTTACTCGTTAAAGATACAGAAACAAAAGAACAACAGCTTTTCCGTTTTCTTTCTC
GAACTATGCCTAATGTGAAATATTATGTAGAGTTAAAGCCTTATTCAAAAGATAAATTTGAG
AAGAATGAGTCACTTATTGAAATTTTAGGTTCTGCAGATAAGTCAGGACGATGTATAAAAG
GGCTAGGAAAATCAAATATTTCTATTTATAAGGTAAGAACAGATGTCCTAGGAAATCAGCA
TATCATCAAAAATGAGGGTGATAAGCCTAAGCTAGATTTTTAATATTAATTGTTAAAAAAGT
GTTGCAATTATAGTTATCATATGCTATAATAATCGTGTAAGGGACGCCTTACACAGTTACTT
AAATCTTGCAGAAGCTACAAAGATAAGGCTTCATGCCGAAATCAACACCCTGTCATTTTATG
GCAGGGTGTTTTCGTTATTTAAAGAGGAGAAGAAATGACTTGGAGAGTTGTACATGTCAGTC
AAAGTGAGAAGATGCGCTTAAAGCTTGATAACTTATTAGTGCAAAAGATGGGACAAGAGTT
TACGGTGCCACTAAGTGATATTTCGATAATCGTTGCAGAAGGTGGGGATACAGTTGTTACCC
TTCGTCTATTAAGTGCCTTAAGTAAATATAATATTGCCTTGGTCGTTTGTGATAACGAACATT
TACCAACAGGAATTTATCACTCACAAAATGGGCACTTTAGAGCGTACAAGCGCTTGAAAGA
ACAGCTGGATTGGTCTCAGAAACAAAAGGAAAAGGCATGGCAGATTGTAACTTATTATAAA
ATCAATAACCAAGAGGATGTCCTAGCCATGTTTGAAAAAAGTCTGGACAACATTAGATTAC
TTTCAGACTATAAAGAGCAGATAGAACCTGGTGATAGAACGAATAGAGAGGGACATGCTGC
CAAGGTCTACTTTAATGAGCTCTTTGGTAAACAATTTGTCAGAGTAACTCAGCAAGAAGCTG
ATGTCATCAATGCTGGTTTAAACTATGGCTATGCTATCATGAGGGCTCAGATGGCTAGAATA
GTGGCGGGTTATGGTTTAAATGGCCTATTAGGAATCTTCCATAAAAATGAATACAATCAGTT
TAATTTGGTTGACGATTTGATGGAGCCATTTAGACAGATTGTAGATGTTTGGGTATATGATA
ATCTACGAGATCAGGAATTCCTTAAGTATGAGTATAGGTTGGGATTGACAGATTTACTCAAT
GCTAAAATCAAATATGGCAAAGAGACTTGCTCAGTGACAGTTGCTATGGACAAATATGTCA
AAGGCTTTATCAAATATATTTCGGAAAAAGATAGTAGTAAATTTCACTGCCCAGTGGTATCA
AGTTTAGAGTGGAGAAAATAAGATGAGGTATGAAGCATTGAGATTATTATGTTTTTTTGATT
TACCAATGGAATCCAAGGATGAAAAAAGAATATATCGTAATTTTCGTAAAGAATTAATTTC

-continued

AAATGGGTTTGAAATGTTACAATTTTCGGTCTACTATCGCACTTGTCCTAATAGAAGCTTTGC
AAATAAATTTTATAAGAAGTTAAAGATGAGCAATCTTCCTGCTGGGAATGTGAGACTTTTGG
CAGTTACTGAAAAACAATTTTCAGAGATGACATTAATTATAGGTGGTAAAACTAAGCAAGA
AGAAATCGTCAGTGATAATAAGTTGGTGATCATATGAAATTTTTTGTACAACATCCTTACAA
AGAACGTATTGAATTAAATATTGGTGCAATCACACAAATTGTTGGTCAGAATAATGAACTCA
AATATTATACTTGGCAGATTTTGAGCTGGTATTTTGGTGGAAAAAAATACTCAAGTGAGGAC
TTAAGTATTTTTGATTATGAGGAGCCTACCATACTTGATGAGGCCAGAGAAATAGTGAAACG
AAGTAGCTATCACTATATCGACATTTCAAGTTTTAAGGATTTACTGGAGCAGATGGAATACA
AGAAAGGAACACTTGCTCAGGGTTACCTTCGTAAAATTGTCAATCAAGTTGATATTGTAGGC
CATTTGGAGAAAATTAATGAACAAGTAGAGCTTATTGAAGAAGCTATGAATCGGCATATAA
ACTTAAACTGTGGACAGGTAGAATACCATTTGGAGAATCTCCCTCTAACACTAGACCAACTA
CTCACAAAAAATTTTAGCCCATTTTTTGCCATTGAGAACAAGAATCTATCTTTTGAATGGGTT
TCTAATATTGATAAACTATCCCTCTTTTTTAGAAATGTTAGACCATCTTCTTTCACAAACAACA
GAGAAGTATCTCATTGTGCTAAAAAATATTGATGGCTTTATCTCAGAAGAATCTTATACTAT
TTTTTATAGGCAAATCTGTCATCTGGTCAAGAAGTATCCAAATCTAACCTTTATTTTGTTTCC
TAGTGACCAAGGCTATTTAAAAATTGATGAAGAAAATAGTAGGTTCGTCAATATTTTATCTG
ACCAGGTGGAACATTTGTATGATGTTGAGTTTATGTATGAAAGGGTAATGAAATATTATCCA
AGTAATGATTTTCCGACGAGAGAAGGTTTTAGGATGTCTTTAGAAACTGTGACACCTTATTT
ATTGACAAAAATGCTGAGACAACCTAGTCTCTCACTTGTTGATTCAGTAATATTGAATATCC
TAAATCAGCTGTTTCATTTTAGTTACCGTATAAGATGTTCTCAGACACCTGATAAGGAACTA
TTACAGAAATTTTTAGAAAGTAAGGATTGA (SEQ ID NO: 473)

SEQ ID NO: 474:
ATGAGTGACTTAGTTTTAGGACTTGATATCGGTATAGGTTCTGTTGGTGTAGGTATCCTTAAC
AAAGTGACAGGAGAAATTATCCATAAAAACTCACGCATCTTCCCAGCAGCTCAAGCAGAAA
ATAACCTAGTACGTAGAACGAATCGTCAAGGAAGACGCTTGACACGACGTAAAAAACATCG
TATAGTTCGTTTAAATCGTCTATTTGAGGAAAGTGGATTAATCACCGATTTTACGAAGATTT
CAATTAATCTTAACCCATATCAATTACGAGTTAAGGGCTTGACCGATGAATTGTCTAATGAA
GAACTGTTTATCGCTCTTAAAAATATGGTGAAACACCGTGGGATTAGTTACCTCGATGATGC
TAGTGATGACGGAAATTCATCAGTAGGAGACTATGCACAAATTGTTAAGGAAAATAGTAAA
CAATTAGAAACTAAGACACCGGGACAGATACAGTTGGAACGCTACCAAACATATGGTCAAT
TACGTGGTGATTTTACTGTTGAGAAAGATGGCAAAAAACATCGCTTGATTAATGTCTTTCCA
ACATCAGCTTATCGTTCAGAAGCCTTAAGGATACTGCAAACTCAACAAGAATTTAATTCACA
GATTACAGATGAATTTATTAATCGTTATCTCGAAATTTTAACTGGAAAACGGAAATATTATC
ATGGACCCGGAAATGAAAAGTCACGGACTGATTATGGTCGTTACAGAACGAATGGAGAAAC
TTTAGACAATATTTTTGGAATTCTAATTGGGAAATGTACATTTTTATCCAGACGAGTTTAGAG
CAGCAAAAGCTTCCTACACGGCTCAAGAATTCAATTTGCTAAATGATTTGAACAATCTAACA
GTTCCTACTGAAACCAAAAAGTTGAGCAAAGAACAGAAGAATCAAATCATTAATTATGTCA
AAAATGAAAAGGTAATGGGGCCAGCGAAACTTTTTAAATATATCGCTAAATTACTTTCTTGT
GATGTTGCAGATATCAAGGGACACCGTATCGACAAATCAGGTAAGGCTGAGATTCATACTT
TCGAAGCCTATCGAAAAATGAAAACGCTTGAAACCTTAGATATTGAGCAAATGGATAGAGA
AACGCTTGATAAATTAGCCTATGTCTTAACATTAAACACTGAGAGGGAAGGTATTCAAGAA
GCTTTAGAACATGAATTTGCTGATGGTAGCTTTAGCCAGAAGCAAGTTGACGAATTGGTTCA
ATTCCGCAAAGCAAATAGTTCCATTTTTGGAAAAGGATGGCATAATTTTTCTGTCAAACTGA
TGATGGAGTTAATTCCAGAATTGTATGAGACGTCAGAAGAGCAAATGACTATCCTGACACG
ACTTGGAAAACAAAAAACAACTTCGTCTTCAAATAAAACAAAATATATAGATGAGAAACTA
TTAACTGAAGAAATCTATAATCCTGTTGTTGCTAAGTCTGTTCGCCAGGCTATAAAAATCGT
AAATGCGGCGATTAAAGAATACGGAGACTTTGACAATATTGTCATCGAAATGGCTCGTGAA
ACAAATGAAGATGATGAAAAGAAAGCTATTCAAAAGATTCAAAAAGCCAACAAAGATGAA
AAAGATGCAGCAATGCTTAAGGCTGCTAACCAATATAATGGAAAGGCTGAATTACCACATA
GTGTTTTCCACGGTCATAAGCAATTAGCGACTAAAATCCGCCTTTGGCATCAGCAAGGAGAA
CGTTGCCTTTATACTGGTAAGACAATCTCAATCCATGATTTGATAAATAATCCTAATCAGTTT
GAAGTAGATCATATTTTACCTCTTTCTATCACATTCGATGATAGCCTTGCAAATAAGGTTTTG
GTTTATGCAACTGCTAACCAAGAAAAAGGACAACGAACACCTTATCAGGCTTTAGATAGTA
TGGATGATGCGTGGTCTTTCCGTGAATTAAAAGCTTTTGTACGTGAGTCAAAAACACTTTCA
AACAAGAAAAAAGAATACCTCCTTACAGAAGAAGATATTTCAAAGTTTGATGTTCGAAAGA
AATTTATTGAACGAAATCTTGTAGATACAAGATACGCTTCAAGAGTTGTCCTCAATGCCCTT
CAAGAACACTTTAGAGCTCACAAGATTGATACAAAAGTTTCCGTGGTTCGTGGCCAATTTAC
ATCTCAATTGAGACGCCATTGGGGAATTGAGAAGACTCGTGATACTTATCATCACCATGCTG
TCGATGCATTGATTATTGCCGCCTCAAGTCAGTTGAATTTGTGGAAAAAACAAAAGAATACC
CTTGTAAGTTATTCAGAAGAACAACTCCTTGATATTGAAACAGGTGAACTTATTAGTGATGA
TGAGTACAAGGAATCTGTGTTCAAAGCCCCTTATCAACATTTTGTTGATACATTGAAGAGTA
AAGAATTTGAAGACAGTATCTTATTCTCATATCAAGTGGATTCTAAGTTTAATCGTAAAATA
TCAGATGCCACTATTTATGCGACAAGACAGGCTAAAGTGGGAAAAGATAAGAAGGATGAA
ACTTATGTCTTAGGGAAAATCAAAGATATCTATACTCAGGATGGTTATGATGCCTTTATGAA
GATTTATAAGAAGGATAAGTCAAAATTCCTCATGTATCGTCACGACCCACAAACCTTTGAGA
AAGTTATCGAGCCAATTTTAGAGAACTATCCTAATAAGGAAATGAATGAAAAAGGGAAAGA
AGTACCATGTAATCCTTTCCTAAAATATAAAGAAGAACATGGCTATATTCGTAAATATAGTA
AAAAAGGCAATGGTCCTGAAATCAAGAGTCTTAAATACTATGATAGTAAGCTTTTAGGTAA
TCCTATTGATATTACTCCAGAGAATAGTAAAAATAAAGTTGTCTTACAGTCATTAAAACCTT
GGAGAACAGATGTCTATTTCAATAAAAATACTGGTAAATATGAAATTTTAGGACTGAAATA
TGCTGATTTACAATTTGAAAAGAAGACAGGAACATATAAGATTTCCCAGGAAAAATACAAT
GGCATTATGAAAGAAGAGGGTGTAGATTCTGATTCAGAATTCAAGTTTACACTTTATAAAAA
TGATTTGTTACTCGTTAAAGATACAGAAACAAAAGAACAACAGCTTTTCCGTTTTCTTTCTC
GAACTATGCCTAATGTGAAATATTATGTAGAGTTAAAGCCTTATTCAAAAGATAAATTTGAG
AAGAATGAGTCACTTATTGAAATTTTAGGTTCTGCAGATAAGTCAGGACGATGTATAAAAG
GGCTAGGAAAATCAAATATTTCTATTTATAAGGTAAGAACAGATGTCCTAGGAAATCAGCA
TATCATCAAAAATGAGGGTGATAAGCCTAAGCTAGATTTTTAA (SEQ ID NO: 474)

-continued

SEQ ID NO: 475:
ATGACTTGGAGAGTTGTACATGTCAGTCAAAGTGAGAAGATGCGCTTAAAGCTTGATAACTT
ATTAGTGCAAAAGATGGGACAAGAGTTTACGGTGCCACTAAGTGATATTTCGATAATCGTTG
CAGAAGGTGGGGATACAGTTGTTACCCTTCGTCTATTAAGTGCCTTAAGTAAATATAATATT
GCCTTGGTCGTTTGTGATAACGAACATTTACCAACAGGAATTTATCACTCACAAAATGGGCA
CTTTAGAGCGTACAAGCGCTTGAAAGAACAGCTGGATTGGTCTCAGAAACAAAAGGAAAAG
GCATGGCAGATTGTAACTTATTATAAAATCAATAACCAAGAGGATGTCCTAGCCATGTTTGA
AAAAAGTCTGGACAACATTAGATTACTTTCAGACTATAAAGAGCAGATAGAACCTGGTGAT
AGAACGAATAGAGAGGGACATGCTGCCAAGGTCTACTTTAATGAGCTCTTTGGTAAACAAT
TTGTCAGAGTAACTCAGCAAGAAGCTGATGTCATCAATGCTGGTTTAAACTATGGCTATGCT
ATCATGAGGGCTCAGATGGCTAGAATAGTGGCGGGTTATGGTTTAAATGGCCTATTAGGAA
TCTTCCATAAAAATGAATACAATCAGTTTAATTTGGTTGACGATTTGATGGAGCCATTTAGA
CAGATTGTAGATGTTTGGGTATATGATAATCTACGAGATCAGGAATTCCTTAAGTATGAGTA
TAGGTTGGGATTGACAGATTTACTCAATGCTAAAATCAAATATGGCAAAGAGACTTGCTCA
GTGACAGTTGCTATGGACAAATATGTCAAAGGCTTTATCAAATATATTTCGGAAAAAGATA
GTAGTAAATTTCACTGCCCAGTGGTATCAAGTTTAGAGTGGAGAAAATAA (SEQ ID NO: 475)

SEQ ID NO: 476:
ATGAGGTATGAAGCATTGAGATTATTATGTTTTTTTGATTTACCAATGGAATCCAAGGATGA
AAAAAGAATATATCGTAATTTTCGTAAAGAATTAATTTCAAATGGGTTTGAAATGTTACAAT
TTTCGGTCTACTATCGCACTTGTCCTAATAGAAGCTTTGCAAATAAATTTTATAAGAAGTTA
AAGATGAGCAATCTTCCTGCTGGGAATGTGAGACTTTTGGCAGTTACTGAAAAACAATTTTC
AGAGATGACATTAATTATAGGTGGTAAAACTAAGCAAGAAGAAATCGTCAGTGATAATAAG
TTGGTGATCATATGA (SEQ ID NO: 476)

SEQ ID NO: 477:
ATGAAATTTTTTGTACAACATCCTTACAAAGAACGTATTGAATTAAATATTGGTGCAATCAC
ACAAATTGTTGGTCAGAATAATGAACTCAAATATTATACTTGGCAGATTTTGAGCTGGTATT
TTGGTGGAAAAAAATACTCAAGTGAGGACTTAAGTATTTTTGATTATGAGGAGCCTACCATA
CTTGATGAGGCCAGAGAAATAGTGAAACGAAGTAGCTATCACTATATCGACATTTCAAGTTT
TAAGGATTTACTGGAGCAGATGGAATACAAGAAAGGAACACTTGCTCAGGGTTACCTTCGT
AAAATTGTCAATCAAGTTGATATTGTAGGCCATTTGGAGAAAATTAATGAACAAGTAGAGC
TTATTGAAGAAGCTATGAATCGGCATATAAACTTAAACTGTGGACAGGTAGAATACCATTTG
GAGAATCTCCCTCTAACACTAGACCAACTACTCACAAAAAATTTTAGCCCATTTTTTGCCAT
TGAGAACAAGAATCTATCTTTTGAATGGGTTTCTAATATTGATAAACTATCCCTCTTTTTAGA
AATGTTAGACCATCTTCTTTCACAAACAACAGAGAAGTATCTCATTGTGCTAAAAAATATTG
ATGGCTTTATCTCAGAAGAATCTTATACTATTTTTTATAGGCAAATCTGTCATCTGGTCAAGA
AGTATCCAAATCTAACCTTTATTTTGTTTCCTAGTGACCAAGGCTATTTAAAAATTGATGAA
GAAAATAGTAGGTTCGTCAATATTTTATCTGACCAGGTGGAACATTTGTATGATGTTGAGTT
TATGTATGAAAGGGTAATGAAATATTATCCAAGTAATGATTTTCCGACGAGAGAAGGTTTTA
GGATGTCTTTAGAAACTGTGACACCTTATTTATTGACAAAAATGCTGAGACAACCTAGTCTC
TCACTTGTTGATTCAGTAATATTGAATATCCTAAATCAGCTGTTTCATTTTAGTTACCGTATA
AGATGTTCTCAGACACCTGATAAGGAACTATTACAGAAATTTTTAGAAAGTAAGGATTGA
(SEQ ID NO: 477)

with repeat sequences: SEQ ID NO:1 to SEQ ID NO:10
Functional Combination #2:

cas sequences: SEQ ID NO:466 to SEQ ID NO:472, and SEQ ID NO:478 to SEQ ID NO:487 (all of which are *S. thermophilus* sequences), as shown below:

SEQ ID NO: 466:
ATGAGCGATTTATATAGTCAAAGGTCCAATTATTACCTGTCCTTATCTGAACAAAGAATTAT
CATTAAAAATGATAATAAAGAGATTGTCAAAGAAGTGTCCATTTCACTCGTTGATAATGTAT
TACTTTTTGGTAATGCACAACTGACCACCCAACTCATCAAAGCCTTGTCAAAGAACAAGGTG
AATGTTTACTATTTCTCAAATGTTGGTCAATTTATTTCTAGTATTGAAACCCACAGGCAGGAC
GAATTCCAAAAGCAAGAGTTGCAAGCAAAGGCTTATTTTGAAGAGGATTTCCGTTTAGAGG
TTGCGAGGAGTATTGCTACGACCAAGGTGAGGCACCCAATTGCCTTACTTAGAGAGTTTGAT
ACGGATGGTCTACTAGATACCTCAGATTATTCTAGGTTTGAAGATAGTGTCAATGATATTCA
GAAAGCTTATTCCATTACAGAAATTATGGGTTACGAAGGTCGCCTTGCGAAATCCTATTTTT
ACTATCTGAATTTACTCGTTCCTAATGACTTTCATTTTAATGGTAGGAGTAGACGGCCTGGG
GAGGATTGTTTTAACAGTGCCCTCAATTTTGGCTATAGTATCTTATATTCTTGCTTAATGGGC
TGATTAAGAAAAACGGGCTAAGCTTGGGATTTGGGGTAATTCACAAGCATCATCAGCATCA
TGCGACCTTGGCCAGTGATTTAATGGAAGAATGGAGACCTATCATCGTCGATAATACGCTTA
TGGAGTTGGTACGAAATGGTAAACTTCTTTTAAGTCATTTTGAAAATAAGGATCAAGACTTC
ATACTCACCCATGAAGGCAGAGAAATCTTTGCACGGGCTTTACGTTCAAGAATATTAGAAGT
CCATCAGTATATTGAGTTAGATAAAAAACGCTATTCTTTTCTTTATACAGCAGATAGGCAAA
TCAAGAGTTTGATTAGGGCTTTTAGAGAACTTGACCCTAGTCTCTATGAGACAAGTTACACA
GGAGGGCATTAATGGGACTTTACTTTAACCTCAGCGAAGAAGAGCGTGAGTTTGCCAAACA
AAAAAACCATGTTTTGTCTGATTATTTATGATATTCGAAGTAACAAACGTAGACTTAAACTC
TCGAAATTACTTGAGGGTTATGGCGTGAGGGTGCAAAAATCCTGTTTCGAAGTCGACCTGTC
AAGAAATGATTATCAGTCTCTCCTTAAGGATATCGAGGGCTTCTCCAAGGCTGATGAAGAA
GACAGCATAATAGTGTATGTGCCAACCAAAGAAGAGGTGACTAGTTTTAGCCCCTACCATA
GTGCTGAAAAATTAGATGACATTCTCTTCCCCTAAGCCTTTATAGACCTTTAATCATATGGTA
CACTATAGATAGTGTTTCCAGAGGCTCTTAAGGAAATCAAAGATAGAGAGACACTTCAAAG
ATTTGTAGATATATGGAAGCATTAGTAGCCTATTTCAAGTTTTATGGAGGTAAAGATTAAT
GACATTCGCTAAGATTAAATTTTCAGCTCAAATTCGTTTAGAGACAGGCCTCCATATTGGTG

-continued

GAAGCGATGCTTTTGCAGCCATTGGTGCAATCGATTCGCCTGTTATTAAAGATCCTATTACC
AACCTACCGATCATTCCTGGTTCAAGTCTCAAAGGAAAAATGAGAACGCTTCTTGCCAAGGT
TTATAATGAAAAGGTAGCTGAGAAACCAAGCGATGACAGTGATATTCTTAGCCGTTTATTTG
GGAATAGTAAAGATAAACGATTCAAAATGGGACGCTTGATTTTTCGTGATGCCTTCTTGTCA
AACGCTGATGAGCTAGACTCTCTTGGGGTAAGAAGTTATACAGAAGTAAAATTTGAAAATA
CAATTGACCGTATCACTGCCGAAGCTAATCCAAGACAAATTGAACGTGCTATTCGTACCAGT
ACTTTTGATTTCGAGTTGATTTATGAAATTACAGATGAGAATGAAAATCAAGTCGAAGAAG
ATTCCAAAGTGATTCGAGATGGTTTAAAACTGCTTGAACTTGATTATCTTGGTGGTTCTGGA
TCTCGAGGTTACGGTAAGGTTGCTTTTGAAAACCTCAAAGCTACTACCGTATTTGGTAATTA
TGATGTTAAAACATTAAATGAACTTTTAACTGCGGAGGTCTAATATGACCTATAAACTGTAT
ATTATGACCTTTCAGAATGCTCATTTTGGTTCGGGCACTCTTGATAGCTCAAAATTAACATTC
TCAGCAGACCGTATCTTCTCAGCACTAGTGCTAGAATCCCTAAAAATGGGAAAACTCGATGC
ATTTCTTGCGGAAGCTAACCAAGACAAGTTCACGCTCACAGATGCCTTTCCATTTCAATTTG
GTCCCTTTTTGCCGAAACCTATTGGTTATCCCAAACATGACCAAATAGATCAATCAGTTGAT
GTCAAAGAGGTTCGCCGTCAAGCAAAATTGTCTAAGAAACTGCAATTTCTTGCTCTAGAAAA
TGTTGACGATTATATCAATGGAGAGTTATTTGAAAATGAAGAGCATGCAGTCATCGATACTG
TGACAAAAAATCAACCACATAAGGACGGCAATCTTTATCAGGTAGCTACAACCAGATTTTC
AAATGATACGTCGCTTTACGTCATCGCAAACGAATCTGATTTGCTTAATGAGTTGATGTCTA
GTCTTCAGTATTCAGGTCTTGGTGGAAAGCGTTCAAGTGGTTTTGGTCGTTTTGAGTTAGATA
TTCAAAATATCCCACTAGAATTGTCAGATAGACTGACTAAGAATCATTCAGATAAAGTGATG
AGTCTTACGACAGCACTTCCTGTAGATGCTGACCTTGAAGAAGCAATGGAAGATGGACATT
ACTTATTAACTAAATCAAGTGGTTTTGCATTTAGTCATGCCACCAATGAGAATTATCGTAAG
CAGGATCTTTACAAATTTGCTTCTGGTTCAACTTTTAGTAAAACATTTGAAGGTCAGATTGTT
GATGTGAGACCACTTGATTTCCCTCATGCTGTTTTAAATTATGCTAAACCACTCTTCTTTAAA
TTGGAGGTATAAAAATGAAAAATGACTATAGAACATTTAAATTAAGCCTCCTGACACTTGCT
CCAATTCATATTGGTAATGGAGAGAAGTATACCTCTAGAGAATTTATCTATGAAAATAAAA
AGTTTTACTTTCCTGACATGGGGAAATTCTATAATAAAATGGTGGAGAAGAGGCTTGCTGAA
AAGTTTGAAGCATTTCTAATTCAAACTCGTCCAAATGCACGTAATAATCGTCTTATTTCCTTC
TTAAATGATAACCGAATTGCAGAGCGTTCTTTTGGAGGTTATAGTATCTCTGAAACAGGTTT
AGAATCGGACAAAAATCCTGATTCAACCGGAGCTATTAACGAAGTTAATAAATTTATTCGA
GATGCTTTTGGAAATCCCTACATTCCTGGTAGCTCACTAAAAGGTGCTATTCGTACCATTTTA
ATGAATACTACCCCTAAGTGGAATAATGAAAATGCTGTAAATGACTTTGGAAGATTTCCGA
AAGAGAATAAGAACCTTATCCCTTGGGGACCAAAAAAGGGAAAAGAATACGATGATTTGTT
TAACGCAATTCGTGTGAGTGATAGTAAGCCTTTTGATAATAAGAGTCTTATCTTAGTGCAGA
AATGGGATTATTCAGCGAAAACAAATAAAGCTAAACCACTTCCCTTGTATAGAGAATCAAT
CTCTCCATTAACAAAAATTGAATTTGAGATTACAACAACCACTGATGAAGCTGGAAGATTG
ATTGAAGAATTAGGTAAGAGAGCACAAGCGTTTTATAAAGACTATAAGGCATTTTTCCTATC
TGAATTTCCTGATGATAAGATTCAAGCCAATCTACAATACCCAATTTATTTAGGTGCGGGGA
GCGGTGCTTGGACAAAGACTCTATTTAAGCAAGCTGATGGTATTTTACAAAGACGATACAGT
CGAATGAAAACTAAAATGGTTAAAAAAGGAGTTCTTAAGCTCACAAAAGCACCTCTTAAAA
CAGTTAAGATTCCATCTGGTAATCATTCATTAGTCAAGAACCACGAGTCCTTTTATGAAATG
GGAAAAGCTAATTTCATGATTAAGGAGATTGATAAATGA (SEQ ID NO: 466)

SEQ ID NO: 467:
ATGAGCGATTTATATAGTCAAAGGTCCAATTATTACCTGTCCTTATCTGAACAAAGAATTAT
CATTAAAAATGATAATAAAGAGATTGTCAAAGAAGTGTCCATTTCACTCGTTGATAATGTAT
TACTTTTTGGTAATGCACAACTGACCACCCAACTCATCAAAGCCTTGTCAAAGAACAAGGTG
AATGTTTACTATTTCTCAAATGTTGGTCAATTTATTTCTAGTATTGAAACCCACAGGCAGGAC
GAATTCCAAAAGCAAGAGTTGCAAGCAAAGGCTTATTTTGAAGAGGATTTCCGTTTAGAGG
TTGCGAGGAGTATTGCTACGACCAAGGTGAGGCACCCAATTGCCTTACTTAGAGAGTTTGAT
ACGGATGGTCTACTAGATACCTCAGATTATTCTAGGTTTGAAGATAGTGTCAATGATATTCA
GAAAGCTTATTCCATTACAGAAATTATGGGTTACGAAGGTCGCCTTGCGAAATCCTATTTTT
ACTATCTGAATTTACTCGTTCCTAATGACTTTCATTTTAATGGTAGGAGTAGACGGCCTGGG
GAGGATTGTTTTAACAGTGCCCTCAATTTTGGCTATAGTATCTTATATTCTTGCTTAATGGGC
TGA (SEQ ID NO: 467)

SEQ ID NO: 468:
TTGCTTAATGGGCTGATTAAGAAAAACGGGCTAAGCTTGGGATTTGGGGTAATTCACAAGC
ATCATCAGCATCATGCGACCTTGGCCAGTGATTTAATGGAAGAATGGAGACCTATCATCGTC
GATAATACGCTTATGGAGTTGGTACGAAATGGTAAACTTCTTTTAAGTCATTTTGAAAATAA
GGATCAAGACTTCATACTCACCCATGAAGGCAGAGAAATCTTTGCACGGGCTTTACGTTCAA
GAATATTAGAAGTCCATCAGTATATTGAGTTAGATAAAAAACGCTATTCTTTTCTTTATACA
GCAGATAGGCAAATCAAGAGTTTGATTAGGGCTTTTAGAGAACTTGACCCTAGTCTCTATGA
GACAAGTTACACAGGAGGGCATTAA (SEQ ID NO: 468)

SEQ ID NO: 469:
ATGTTTTGTCTGATTATTTATGATATTCGAAGTAACAAACGTAGACTTAAACTCTCGAAATT
ACTTGAGGGTTATGGCGTGAGGGTGCAAAAATCCTGTTTCGAAGTCGACCTGTCAAGAAAT
GATTATCAGTCTCTCCTTAAGGATATCGAGGGCTTCTCCAAGGCTGATGAAGAAGACAGCAT
AATAGTGTATGTGCCAACCAAAGAAGAGGTGACTAGTTTTAGCCCCTACCATAGTGCTGAA
AAATTAGATGACATTCTCTTCCCCTAA (SEQ ID NO: 469)

SEQ ID NO: 470:
ATGACATTCGCTAAGATTAAATTTTCAGCTCAAATTCGTTTAGAGACAGGCCTCCATATTGG
TGGAAGCGATGCTTTTGCAGCCATTGGTGCAATCGATTCGCCTGTTATTAAAGATCCTATTA
CCAACCTACCGATCATTCCTGGTTCAAGTCTCAAAGGAAAAATGAGAACGCTTCTTGCCAAG
GTTTATAATGAAAAGGTAGCTGAGAAACCAAGCGATGACAGTGATATTCTTAGCCGTTTATT
TGGGAATAGTAAAGATAAACGATTCAAAATGGGACGCTTGATTTTTCGTGATGCCTTCTTGT
CAAACGCTGATGAGCTAGACTCTCTTGGGGTAAGAAGTTATACAGAAGTAAAATTTGAAAA
TACAATTGACCGTATCACTGCCGAAGCTAATCCAAGACAAATTGAACGTGCTATTCGTACCA
GTACTTTTGATTTCGAGTTGATTTATGAAATTACAGATGAGAATGAAAATCAAGTCGAAGAA

-continued

GATTCCAAAGTGATTCGAGATGGTTTAAAACTGCTTGAACTTGATTATCTTGGTGGTTCTGG
ATCTCGAGGTTACGGTAAGGTTGCTTTTGAAAACCTCAAAGCTACTACCGTATTTGGTAATT
ATGATGTTAAAACATTAAATGAACTTTTAACTGCGGAGGTCTAA (SEQ ID NO: 470)

SEQ ID NO: 471:
ATGACCTATAAACTGTATATTATGACCTTTCAGAATGCTCATTTTGGTTCGGGCACTCTTGAT
AGCTCAAAATTAACATTCTCAGCAGACCGTATCTTCTCAGCACTAGTGCTAGAATCCCTAAA
AATGGGAAAACTCGATGCATTTCTTGCGGAAGCTAACCAAGACAAGTTCACGCTCACAGAT
GCCTTTCCATTTCAATTTGGTCCCTTTTTGCCGAAACCTATTGGTTATCCCAAACATGACCAA
ATAGATCAATCAGTTGATGTCAAAGAGGTTCGCCGTCAAGCAAAATTGTCTAAGAAACTGC
AATTTCTTGCTCTAGAAAATGTTGACGATTATATCAATGGAGAGTTATTTGAAAATGAAGAG
CATGCAGTCATCGATACTGTGACAAAAAATCAACCACATAAGGACGGCAATCTTTATCAGG
TAGCTACAACCAGATTTTCAAATGATACGTCGCTTTACGTCATCGCAAACGAATCTGATTTG
CTTAATGAGTTGATGTCTAGTCTTCAGTATTCAGGTCTTGGTGGAAAGCGTTCAAGTGGTTTT
GGTCGTTTTGAGTTAGATATTCAAAATATCCCACTAGAATTGTCAGATAGACTGACTAAGAA
TCATTCAGATAAAGTGATGAGTCTTACGACAGCACTTCCTGTAGATGCTGACCTTGAAGAAG
CAATGGAAGATGGACATTACTTATTAACTAAATCAAGTGGTTTTGCATTTAGTCATGCCACC
AATGAGAATTATCGTAAGCAGGATCTTTACAAATTTGCTTCTGGTTCAACTTTTAGTAAAAC
ATTTGAAGGTCAGATTGTTGATGTGAGACCACTTGATTTCCCTCATGCTGTTTTAAATTATGC
TAAACCACTCTTCTTTAAATTGGAGGTATAA (SEQ ID NO: 471)

SEQ ID NO: 472:
ATGAAAAATGACTATAGAACATTTAAATTAAGCCTCCTGACACTTGCTCCAATTCATATTGG
TAATGGAGAGAAGTATACCTCTAGAGAATTTATCTATGAAAATAAAAAGTTTTACTTTCCTG
ACATGGGGAAATTCTATAATAAAATGGTGGAGAAGAGGCTTGCTGAAAAGTTTGAAGCATT
TCTAATTCAAACTCGTCCAAATGCACGTAATAATCGTCTTATTTCCTTCTTAAATGATAACCG
AATTGCAGAGCGTTCTTTTGGAGGTTATAGTATCTCTGAAACAGGTTTAGAATCGGACAAAA
ATCCTGATTCAACCGGAGCTATTAACGAAGTTAATAAATTTATTCGAGATGCTTTTGGAAAT
CCCTACATTCCTGGTAGCTCACTAAAAGGTGCTATTCGTACCATTTTAATGAATACTACCCCT
AAGTGGAATAATGAAAATGCTGTAAATGACTTTGGAAGATTTCCGAAAGAGAATAAGAACC
TTATCCCTTGGGGACCAAAAAAGGGAAAAGAATACGATGATTTGTTTAACGCAATTCGTGT
GAGTGATAGTAAGCCTTTTGATAATAAGAGTCTTATCTTAGTGCAGAAATGGGATTATTCAG
CGAAAACAAATAAAGCTAAACCACTTCCCTTGTATAGAGAATCAATCTCTCCATTAACAAA
AATTGAATTTGAGATTACAACAACCACTGATGAAGCTGGAAGATTGATTGAAGAATTAGGT
AAGAGAGCACAAGCGTTTTATAAAGACTATAAGGCATTTTTCCTATCTGAATTTCCTGATGA
TAAGATTCAAGCCAATCTACAATACCCAATTTATTTAGGTGCGGGGAGCGGTGCTTGGACAA
AGACTCTATTTAAGCAAGCTGATGGTATTTTACAAAGACGATACAGTCGAATGAAAACTAA
AATGGTTAAAAAAGGAGTTCTTAAGCTCACAAAAGCACCTCTTAAAACAGTTAAGATTCCA
TCTGGTAATCATTCATTAGTCAAGAACCACGAGTCCTTTTATGAAATGGGAAAAGCTAATTT
CATGATTAAGGAGATTGATAAATGA (SEQ ID NO: 472)

SEQ ID NO: 478:
ATGAGCGATTTATATAGTCAAAGGTCCAATTATTACCTGTCCTTATCTGAACAAAGAATTAT
CATTAAAAATGATAATAAAGAGATTGTCAAAGAAGTGTCCATTTCACTCGTTGATAATGTAT
TACTTTTTGGTAATGCACAACTGACCACCCAACTCATCAAAGCCTTGTCAAAGAACAAGGTG
AATGTTTACTATTTCTCAAATGTTGGTCAATTTATTTCTAGTATTGAAACCCACAGGCAGGAC
GAATTCCAAAAGCAAGAGTTGCAAGCAAAGGCTTATTTTGAAGAGGATTTCCGTTTAGAGG
TTGCGAGGAGTATTGCTACGACCAAGGTGAGGCACCCAATTGCCTTACTTAGAGAGTTTGAT
ACGGATGGTCTACTAGATACCTCAGATTATTCTAGGTTTGAAGATAGTGTCAATGATATTCA
GAAAGCTTATTCCATTACAGAAATTATGGGTTACGAAGGTCGCCTTGCGAAATCCTATTTTT
ACTATCTGAATTTACTCGTTCCTAATGACTTTCATTTTAATGGTAGGAGTAGACGGCCTGGG
GAGGATTGTTTTAACAGTGCCCTCAATTTTGGCTATAGTATCTTATATTCTTGCTTAATGGGC
TGATTAAGAAAAACGGGCTAAGCTTGGGATTTGGGGTAATTCACAAGCATCATCAGCATCA
TGCGACCTTGGCCAGTGATTTAATGGAAGAATGGAGACCTATCATCGTCGATAATACGCTTA
TGGAGTTGGTACGAAATGGTAAACTTCTTTTAAGTCATTTTGAAAATAAGGATCAAGACTTC
ATACTCACCCATGAAGGCAGAGAAATCTTTGCACGGGCTTTACGTTCAAGAATATTAGAAGT
CCATCAGTATATTGAGTTAGATAAAAAACGCTATTCTTTTCTTTATACAGCAGATAGGCAAA
TCAAGAGTTTGATTAGGGCTTTTAGAGAACTTGACCCTAGTCTCTATGAGACAAGTTACACA
GGAGGGCATTAATGGGACTTTACTTTAACCTCAGCGAAGAAGAGCGTGAGTTTGCCAAACA
AAAAACCATGTTTTGTCTGATTATTTTATGATATTCGAAGTAACAAACGTAGACTTAAACTCT
CGAAATTACTTGAGGGTTATGGCGTGAGGGTGCAAAAATCCTGTTTCGAAGTCAACCTGTCA
AGAAATGATTATCAGTCTCTCCTTAAGGATATCGAGGGCTTCTACAAGGCTGATGAAGAAG
ACAGCATAATAGTGTATGTGACAACCAAAGAAGAGGTGACTAGTTTAGCCCCTACCATAG
TGCTGAAAAAATTAGATGACATTCTCTTCTTCTAAGCCTTTATAGACCTTTAATCATATGGTAC
ACTATAGATAGTGTTTCCAGTAGGTCCTACATCTTGTGCCTCTAGCAACTGCCTAGAGCACA
AGATATGGGGATATAAACCTAATTACCTCGAGAGGGGACGGAAACGCTTTCTAGCTCGCTA
TAATTACCCATTCCTAGAAAGATATAAACCTAATTACCTCGAGAGGGGACGGAAACTTTGA
ATAGTCTTTGAATCGCATTTGAACCATATAGATATAAACCTAATTACCTCGAGAGGGGACGG
AAACAGGTTTTTTGCCATAGATTTTCCAAGACCTTCCCAACTGATATAAACCTAATTACCTC
GAGAGGGGACGGAAACGCTTTCTAGCTCGCTATAATTACCCATTCCTAGAAAGATATAAAC
CTAATTACCTCGAGAGGGGACTTTTTTGAAAATTTTGAAAACAGTATTGATACCGCTTCCAG
AAAGTGTTAGACTAAAAGCACATTAAGGGCGCCCCAATGAGTTGAAAAGTACTTTCAGCTT
TTGGGGTTTTTTCATACAAAGATGAAGGAGTCGAATGAAAAAATTAGTATTTACTTTTAAAA
GGATCGACCATCCTGCACAAGATTTGGCTGTTAAATTTCATGGCTTCTTGATGGAGCAGTTG
GATAGTGACTATGTTGATTATCTGCATCAGCAGCAAACAAATCCCTATGCGACCAAGGTAAT
CCAAGGGAAAGAAAACACGCAGTGGGTTGTACATCTGCTCACAGACGACATCGAGGATAAG
GTTTTTATGACCTTATTACAGATTAAAGAGGTGTCCTTAAACGATCTGCCTAAACTCAGTGT
CGAAAAAGTTGAGATTCAGGAGTTGGGGGCAGATAAACTGTTAGAGATTTTCAATAGTGAG
GAAAATCAAACCTATTTTTCAATTATTTTTGAGACTCCAACAGGTTTTAAATCTCAAGGTTCC
TACGTCATCTTCCCGTCTATGCGTTTGATTTTTCAAAGTTTGATGCAAAAGTATGGAAGGTTG
GTTGAAAATCAACCTGAAATTGAAGAGGATACCTTAGATTACCTATCTGAACACAGCACTAT

-continued

CACGAATTATCGCTTGGAGACGAGTTATTTCAGGGTGCACAGGCAACGAATTCCTGCCTTTA
GAGGAAAGTTAACCTTTAAAGTACAAGGCGCCCAAACTCTAAAAGCTTATGTCAAAATGCT
TCTAACATTCGGTGAATATTCAGGTCTTGGCATGAAAACGAGTCTCGGTATGGGAGGGATA
AAGCTTGAAGAAAGAAAAGATTGATTTATTTTACGGAGCTCTTTTGCATGATATCGGTAAGG
TCATTCAAAGGGCGACAGGAGAACGAAAAAAACACGCCTTGGTAGGCGCGGATTGGTTTGA
TGAGATTGCTGATAATCAAGTTATTTCCGATCAAATTAGATATCACATGGCTAACTACCAGA
GTGATAAACTTGGAAATGACCATCTTGCTTACATAACTTATATCGCTGATAACATTGCCTCT
GGTGTCGACAGAAGACAGTCAAATGAGGAGAGTGACGAGGATACATCAGCTAAGATTTGG
GATACCTATACAAACCAGGCTGATATTTTTAACGTTTTTGGGGCACAAACGGATAAACGCTA
CTTTAAACCGACGGTTCTAAACTTGAAATCTAAACCTAACTTTGCGTCGGCAACATATGAAC
CTTTCTCAAAAGGTGATTATGCGGCAATTGCGACTCGTATCAAAAATGAATTGGCAGAATTT
GAGTTTAATCAAGTACAAATTGACTCTTTGTTAAATCTGTTCGAAGCAACCCTCTCTTTTGTG
CCTTCTTCGACTAATACTAAAGAAATCGCTGATATTTCACTTGCTGATCATAGTCGTCTGACA
GCAGCTTTTGCTCTAGCCATCTATGATTACTTGGAAGACAAAGGTCGTCATAACTATAAGGA
GGACTTGTTTACTAAAGCATCAGCCTTTTATGAGGAAGAAGCTTTTCTCCTAGCTAGCTTTG
ACTTATCAGGGATTCAAGACTTTATCTATAATATTAATATTGCGACGAATGGTGCTGCTAAA
CAATTGAAGGCTAGATCTTTATATCTTGACTTTATGAGCGAGTATATAGCAGACAGTTTACT
TGATAAACTAGGCCTCAATCGGGCTAATATGCTCTATGTCGGTGGGGGACATGCTTACTTTG
TCCTAGCCAATACTGAAAAAACGGTAGAAACACTCGTTCAATTTGAAAAAGATTTCAATCA
ATTTTTATTGGCAAATTTCCAAACCAGATTATATGTTGCCTTTGGTTGGGGAAGCTTTGCGGC
TAAGGATATCATGAGCGAACTGAACTCACCTGAAAGCTATAGACAGGTCTATCAAAAGGCT
AGTCGCATGATTTCTGAGAAAAAAATCTCAAGGTATGATTATCAAACCCTTATGTTGTTGAA
CAGGGGCGGTAAATCTTCTGAAAGAGAGTGCGAGATTTGTCATTCCGTTGAGAATTTAGTTG
CTTATCATGACCAAAAAGTGTGTGACATTTGTCGAGGCTTGTATCAATTTTCTAAAGAGATT
GCCCATGACCATTTCATTATCACTGAAAATGAAGGGCTTCCTATTGGTCCGAACGCATGTCT
TAAGGGTGTTGCATTTGAAAAGCTGAGCCAAGAAGCTTTTTCCCGTGTCTATGTCAAAAATG
ACTATAAGGCTGGTACAGTTAAGGCAACCCATGTTTTTGTTGGAGATTACCAGTATGATGAA
ATATACAATTATGCTGCCTTATCTAAAAACGAAAATGGGTTAGGTATTAAACGTTTAGCTGT
TGTACGTCTTGACGTGGATGATTTGGGAGCAGCCTTTATGGCTGGCTTCTCCCAACAAGGAA
ATGGGCAATATAGTACTCTATCACGCTCAGCCACTTTCTCTCGAAGCATGAGTCTTTTCTTCA
AGGTTTATATTAACCAGTTTGCTAGTGATAAGAAGCTCTCTATCATCTATGCCGGTGGGGAT
GATGTTTTTGCTATTGGCTCTTGGCAAGATATTATTGCCTTTACTGTTGAACTTCGTGAGAAC
TTCATTAAATGGACAAATGGAAAACTAACACTATCAGCTGGTATCGGTCTGTTTGCTGATAA
GACCCCTATTAGCTTAATGGCACATCAAACAGGGGAGCTAGAAGAAACAGCTAAAGGCAAT
GAGAAAGATAGTATTTCACTCTTTAGTTCCGACTATACCTTTAAATTTGATCGGTTTATCACT
AATGTTTACGACGATAAGTTAGAGCAGATTCGCTATTTCTTTAATCACCAAGATGAACGAGG
CAAGAATTTCATTTATAAATTGATTGAATTGCTTCGAAATTATGATCGTATGAATATGGCAC
GTTTAGCTTATTATTTAACACGACTTGAAGAATTGACGCGTGAAACAGACAGGGATAAATTT
AAAACATTTAAAAATTTATTCTATTCTTGGTACACAAATAAGGATGATAAGGATAGAAAAG
AAGCAGAGTTAGCCTTGCTTCTCTATATCTATGAGATTAGAAAGGATTAGGATATGACAATC
TTGACTGATGAGAATTACGTTGATATTGCAGAAAAAGCAATTCTAAAACTAGAAAGAAATA
CTAGGAACAGAAAGAATCCTGATGCCTTCTTTCTTACAACAAGTAAGCTCAGAAACTTGCTG
AGCTTAACTAGTACACTTTTTGATGAGAGTAAGGTCAAAGAATATGATGCTCTCCTTGATCG
TATTGCTTATTTAAGAGTACAATTTGTCTACCAAGCAGGTAGAGAGATTGCAGTAAAAGATC
TGATAGAAAAGGCTCAAATTCTTGAGGCTCTTAAGGAAATCAAAGATAGAGAGACACTTCA
AAGATTTTGTAGATATATGGAAGCATTAGTAGCCTATTTCAAGTTTTATGGAGGTAAAGATT
AATGACATTCGCTAAGATTAAATTTTCAGCTCAAATTCGTTTAGAGACAGGCCTCCATATTG
GTGGAAGCGATGCTTTTGCAGCCATTGGTGCAATCGATTCGCCTGTTATTAAAGATCCTATT
ACCAACCTACCGATCATTCCTGGTTCAAGTCTCAAAGGAAAAATGAGAACGCTTCTTGCCAA
GGTTTATAATGAAAAGGTAGCTGAGAAACCAAGCGATGACAGTGATATTCTTAGCCGTTTAT
TTGGGAATAGTAAAGATAAACGATTCAAAATGGGACGCTTGATTTTTCGTGATGCCTTCTTG
TCAAACGCTGATGAGCTAGACTCTCTTGGGGTAAGAAGTTATACAGAAGTAAAATTTGAAA
ATACAATTGACCGTATCACTGCCGAAGCTAATCCAAGACAAATTGAACGTGCTATTCGTACC
AGTACTTTTGATTTCGAGTTGATTTATGAAATTACAGATGAGAATGAAAATCAAGTCGAAGA
AGATTTCAAAGTGATTCGAGATGGTTTAAAACTGCTTGAACTTGATTATCTTGGTGGTTCTG
GATCTCGAGGTTACGGTAAGGTTGCTTTTGAAAAACTCAAAGCTACTACCGTATTTGGTAAT
TATGATGTTAAAACATTAAATGAACTTTTAACTGCGGAGGTCTAATATGACCTATAAACTGT
ATATTATGACCTTTCAGAATGCTCATTTTGGTTCGGGCACTCTTGATAGCTCAAAATTAACAT
TCTCAGCAGACCGTATCTTCTCAGCACTAGTGCTAGAATCCCTAAAAATGGGAAAACTCGAT
GCATTTCTTGCGGAAGCTAACCAAGACAAGTTCACGCTCACAGATGCCTTTCCATTTCAATT
TGGTCCCTTTTTGCCGAAACCGATTGGTTATCCCAAACATGACCAAATAGATCAATCAGTTG
ATGTCAAAGAGGTTCGCCGTCAAGCAAAATTGTCTAAGAAACTGCAATTTCTTGCTCTAGAA
AATGTTGACGATTATCTCAATGGAGAGTTATTTGAAAATGAAGAGCATGCAGTCATCGATAC
TGTGACAAAAAATCAACCACATAAGGACGGCAATCTTTATCAGGTAGCTACAACCAGATTT
TCAAATGATACGTCGCTTTACGTCATCGCAAACGAATCTGATTTGCTTAATGAGTTGATGTC
TAGTCTTCAGTATTCAGGTCTTGGTGGAAAGCGTTCAAGTGGTTTTGGTCGTTTTGAGTTAGA
TATTCAAAATATCCCACTAGAATTGTCAGATAGACTGACTAAGAATCATTCAGATAAAGTGA
TGAGTCTTACGACAGCACTTCCTGTAGATGCTGACCTTGAAGAAGCAATGGAAGATGGACA
TTACTTATTAACTAAATCAAGTGGTTTTGCATTTAGTCATGCTACCAATGAGAATTATCGTAA
GCAGGATCTTTACAAATTTGCTTCTGGTTCAACTTTTAGTAAAACATTTGAAGGTCAGATTGT
TGATGTGAGACCACTTGATTTCCCTCATGCTGTTTTAAATTATGCTAAACCACTCTTCTTTAA
ATTGGAGGTATAAAAATGAAAAATGACTATAGAACATTTAAATTAAGCCTCCTGACACTTG
CTCCAATTCATATTGGTAATGGAGAGAAGTATACCTCTAGAGAATTTATCTATGAAAATAAG
AAGTTTTACTTTCCTGACATGGGGAAATTCTATAATAAAATGGTGGAGAAGAGGCTTGCTGA
AAAGTTTGAAGCATTTCTAATTCAAACTCGTCCAAATGCACGTAATAATCGTCTTATTTCCTT
CTTAAATGATAACCGAATTGCAGAGCGTTCTTTTGGAGGTTATAGTATCTCTGAAACAGGTT
TAGAATCGGACAAAAATCCTGATTCAGCCGGAGCTATTAACGAAGTTAATAAATTTATTCGA
GATGCTTTTGGAAATCCCTACATTCCTGGTAGCTCACTAAAAGGTGCTATTCGTACCATTTTA
ATGAATACTACCCCTAAGTGGAATAATGAAAATGCTGTAAATGACTTTGGAAGATTTCCGA
AAGAGAATAAGAACCTTATCCCTTGGGGACCAAAAAAGGGAAAAGAATACGATGATTTGTT
TAACGCAATTCGTGTGAGTGATAGTAAGCCTTTTGATAATAAGAGTCTTATCTTAGTGCAGA

-continued

AATGGGATTATTCAGCGAAAACAAATAAAGCTAAACCACTTCCCTTGTATAGAGAATCAAT
CTCTCCATTAACAAAAATTGAATTTGAGATTACAACAACCACTGATGAAGCTGGAAGATTG
ATTGAAGAATTAGGTAAGAGAGCACAAGCGTTTTATAAAGACTATAAGGCATTTTTCCTATC
TGAATTTCCTGATGATAAGATTCAAGCCAATCTACAATACCCAATTTATTTAGGTGCGGGGA
GCGGTGCTTGGACAAAGACTCTATTTAAGCAAGCTGATGGTATTTTACAAAGACGATACAGT
CGAATGAAAACTAAAATGGTTAAAAAAGGAGTTCTTAAGCTCACAAAAGCACCTCTTAAAA
CAGTTAAGATTCCATCTGGTAATCATTCATTAGTCAAGAACCACGAGTCCTTTTATGAAATG
GGAAAAGCTAATTTCATGATTAAGGAGATTGATAAATGA (SEQ ID NO: 478)

SEQ ID NO: 479:
ATGAGCGATTTATATAGTCAAAGGTCCAATTATTACCTGTCCTTATCTGAACAAAGAATTAT
CATTAAAAATGATAATAAAGAGATTGTCAAAGAAGTGTCCATTTCACTCGTTGATAATGTAT
TACTTTTTGGTAATGCACAACTGACCACCCAACTCATCAAAGCCTTGTCAAAGAACAAGGTG
AATGTTTACTATTTCTCAAATGTTGGTCAATTTATTTCTAGTATTGAAACCCACAGGCAGGAC
GAATTCCAAAAGCAAGAGTTGCAAGCAAAGGCTTATTTTGAAGAGGATTTCCGTTTAGAGG
TTGCGAGGAGTATTGCTACGACCAAGGTGAGGCACCCAATTGCCTTACTTAGAGAGTTTGAT
ACGGATGGTCTACTAGATACCTCAGATTATTCTAGGTTTGAAGATAGTGTCAATGATATTCA
GAAAGCTTATTCCATTACAGAAATTATGGGTTACGAAGGTCGCCTTGCGAAATCCTATTTTT
ACTATCTGAATTTACTCGTTCCTAATGACTTTCATTTTAATGGTAGGAGTAGACGGCCTGGG
GAGGATTGTTTTAACAGTGCCCTCAATTTTGGCTATAGTATCTTATATTCTTGCTTAATGGGC
TGA (SEQ ID NO: 479)

SEQ ID NO: 480:
TTGCTTAATGGGCTGATTAAGAAAAACGGGCTAAGCTTGGGATTTGGGGTAATTCACAAGC
ATCATCAGCATCATGCGACCTTGGCCAGTGATTTAATGGAAGAATGGAGACCTATCATCGTC
GATAATACGCTTATGGAGTTGGTACGAAATGGTAAACTTCTTTTAAGTCATTTTGAAAATAA
GGATCAAGACTTCATACTCACCCATGAAGGCAGAGAAATCTTTGCACGGGCTTTACGTTCAA
GAATATTAGAAGTCCATCAGTATATTGAGTTAGATAAAAAACGCTATTCTTTTCTTTATACA
GCAGATAGGCAAATCAAGAGTTTGATTAGGGCTTTTAGAGAACTTGACCCTAGTCTCTATGA
GACAAGTTACACAGGAGGGCATTAA (SEQ ID NO: 480)

SEQ ID NO: 481:
ATGGGACTTTACTTTAACCTCAGCGAAGAAGAGCGTGAGTTTGCCAAACAAAAAACCATGT
TTTGTCTGATTATTTATGATATTCGAAGTAACAAACGTAGACTTAAACTCTCGAAATTACTTG
AGGGTTATGGCGTGAGGGTGCAAAAATCCTGTTTCGAAGTCAACCTGTCAAGAAATGATTA
TCAGTCTCTCCTTAAGGATATCGAGGGCTTCTACAAGGCTGATGAAGAAGACAGCATAATA
GTGTATGTGACAACCAAAGAAGAGGTGACTAGTTTTAGCCCCTACCATAGTGCTGAAAAAT
TAGATGACATTCTCTTCTTCTAA (SEQ ID NO: 481)

SEQ ID NO: 482:
ATGAAAAAATTAGTATTTACTTTTAAAAGGATCGACCATCCTGCACAAGATTTGGCTGTTAA
ATTTCATGGCTTCTTGATGGAGCAGTTGGATAGTGACTATGTTGATTATCTGCATCAGCAGC
AAACAAATCCCTATGCGACCAAGGTAATCCAAGGGAAAGAAAACACGCAGTGGGTTGTACA
TCTGCTCACAGACGACATCGAGGATAAGGTTTTTATGACCTTATTACAGATTAAAGAGGTGT
CCTTAAACGATCTGCCTAAACTCAGTGTCGAAAAAGTTGAGATTCAGGAGTTGGGGGCAGA
TAAACTGTTAGAGATTTTCAATAGTGAGGAAAATCAAACCTATTTTTCAATTATTTTTGAGA
CTCCAACAGGTTTTAAATCTCAAGGTTCCTACGTCATCTTCCCGTCTATGCGTTTGATTTTTC
AAAGTTTGATGCAAAAGTATGGAAGGTTGGTTGAAAATCAACCTGAAATTGAAGAGGATAC
CTTAGATTACCTATCTGAACACAGCACTATCACGAATTATCGCTTGGAGACGAGTTATTTCA
GGGTGCACAGGCAACGAATTCCTGCCTTTAGAGGAAAGTTAACCTTTAAAGTACAAGGCGC
CCAAACTCTAAAAGCTTATGTCAAAATGCTTCTAACATTCGGTGAATATTCAGGTCTTGGCA
TGAAAACGAGTCTCGGTATGGGAGGGATAAAGCTTGAAGAAAGAAAAGATTGA (SEQ ID
NO: 482)

SEQ ID NO: 483:
TTGAAGAAAGAAAAGATTGATTTATTTTACGGAGCTCTTTTGCATGATATCGGTAAGGTCAT
TCAAAGGGCGACAGGAGAACGAAAAAAACACGCCTTGGTAGGCGCGGATTGGTTTGATGA
GATTGCTGATAATCAAGTTATTTCCGATCAAATTAGATATCACATGGCTAACTACCAGAGTG
ATAAACTTGGAAATGACCATCTTGCTTACATAACTTATATCGCTGATAACATTGCCTCTGGT
GTCGACAGAAGACAGTCAAATGAGGAGAGTGACGAGGATACATCAGCTAAGATTTGGGAT
ACCTATACAAACCAGGCTGATATTTTTAACGTTTTTGGGGCACAAACGGATAAACGCTACTT
TAAACCGACGGTTCTAAACTTGAAATCTAAACCTAACTTTGCGTCGGCAACATATGAACCTT
TCTCAAAAGGTGATTATGCGGCAATTGCGACTCGTATCAAAAATGAATTGGCAGAATTTGA
GTTTAATCAAGTACAAATTGACTCTTTGTTAAATCTGTTCGAAGCAACCCTCTCTTTTGTGCC
TTCTTCGACTAATACTAAAGAAATCGCTGATATTTCACTTGCTGATCATAGTCGTCTGACAG
CAGCTTTTGCTCTAGCCATCTATGATTACTTGGAAGACAAAGGTCGTCATAACTATAAGGAG
GACTTGTTTACTAAAGCATCAGCCTTTTATGAGGAAGAAGCTTTTCTCCTAGCTAGCTTTGAC
TTATCAGGGATTCAAGACTTTATCTATAATATTAATATTGCGACGAATGGTGCTGCTAAACA
ATTGAAGGCTAGATCTTTATATCTTGACTTTATGAGCGAGTATATAGCAGACAGTTTACTTG
ATAAACTAGGCCTCAATCGGGCTAATATGCTCTATGTCGGTGGGGGACATGCTTACTTTGTC
CTAGCCAATACTGAAAAAACGGTAGAAACACTCGTTCAATTTGAAAAAGATTTCAATCAAT
TTTTATTGGCAAATTTCCAAACCAGATTATATGTTGCCTTTGGTTGGGGAAGCTTTGCGGCTA
AGGATATCATGAGCGAACTGAACTCACCTGAAAGCTATAGACAGGTCTATCAAAAGGCTAG
TCGCATGATTTCTGAGAAAAAAATCTCAAGGTATGATTATCAAACCCTTATGTTGTTGAACA
GGGGCGGTAAATCTTCTGAAAGAGAGTGCGAGATTTGTCATTCCGTTGAGAATTTAGTTGCT
TATCATGACCAAAAAGTGTGTGACATTTGTCGAGGCTTGTATCAATTTTCTAAAGAGATTGC
CCATGACCATTTCATTATCACTGAAAATGAAGGGCTTCCTATTGGTCCGAACGCATGTCTTA
AGGGTGTTGCATTTGAAAAGCTGAGCCAAGAAGCTTTTTCCCGTGTCTATGTCAAAAATGAC
TATAAGGCTGGTACAGTTAAGGCAACCCATGTTTTTGTTGGAGATTACCAGTATGATGAAAT
ATACAATTATGCTGCCTTATCTAAAAACGAAAATGGGTTAGGTATTAAACGTTTAGCTGTTG
TACGTCTTGACGTGGATGATTTGGGAGCAGCCTTTATGGCTGGCTTCTCCCAACAAGGAAAT

-continued

GGGCAATATAGTACTCTATCACGCTCAGCCACTTTCTCTCGAAGCATGAGTCTTTTCTTCAAG
GTTTATATTAACCAGTTTGCTAGTGATAAGAAGCTCTCTATCATCTATGCCGGTGGGGATGA
TGTTTTTGCTATTGGCTCTTGGCAAGATATTATTGCCTTTACTGTTGAACTTCGTGAGAACTT
CATTAAATGGACAAATGGAAAACTAACACTATCAGCTGGTATCGGTCTGTTTGCTGATAAGA
CCCCTATTAGCTTAATGGCACATCAAACAGGGGAGCTAGAAGAAACAGCTAAAGGCAATGA
GAAAGATAGTATTTCACTCTTTAGTTCCGACTATACCTTTAAATTTGATCGGTTTATCACTAA
TGTTTACGACGATAAGTTAGAGCAGATTCGCTATTTCTTTAATCACCAAGATGAACGAGGCA
AGAATTTCATTTATAAATTGATTGAATTGCTTCGAAATTATGATCGTATGAATATGGCACGT
TTAGCTTATTATTTAACACGACTTGAAGAATTGACGCGTGAAACAGACAGGGATAAATTTAA
AACATTTAAAAATTTATTCTATTCTTGGTACACAAATAAGGATGATAAGGATAGAAAAGAA
GCAGAGTTAGCCTTGCTTCTCTATATCTATGAGATTAGAAAGGATTAG (SEQ ID NO: 483)

SEQ ID NO: 484:
ATGACAATCTTGACTGATGAGAATTACGTTGATATTGCAGAAAAAGCAATTCTAAAACTAG
AAAGAAATACTAGGAACAGAAAGAATCCTGATGCCTTCTTTCTTACAACAAGTAAGCTCAG
AAACTTGCTGAGCTTAACTAGTACACTTTTTGATGAGAGTAAGGTCAAAGAATATGATGCTC
TCCTTGATCGTATTGCTTATTTAAGAGTACAATTTGTCTACCAAGCAGGTAGAGAGATTGCA
GTAAAAGATCTGATAGAAAAGGCTCAAATTCTTGAGGCTCTTAAGGAAATCAAAGATAGAG
AGACACTTCAAAGATTTTGTAGATATATGGAAGCATTAGTAGCCTATTTCAAGTTTTATGGA
GGTAAAGATTAA (SEQ ID NO: 484)

SEQ ID NO: 485:
ATGACATTCGCTAAGATTAAATTTTCAGCTCAAATTCGTTTAGAGACAGGCCTCCATATTGG
TGGAAGCGATGCTTTTGCAGCCATTGGTGCAATCGATTCGCCTGTTATTAAAGATCCTATTA
CCAACCTACCGATCATTCCTGGTTCAAGTCTCAAAGGAAAAATGAGAACGCTTCTTGCCAAG
GTTTATAATGAAAAGGTAGCTGAGAAACCAAGCGATGACAGTGATATTCTTAGCCGTTTATT
TGGGAATAGTAAAGATAAACGATTCAAAATGGGACGCTTGATTTTTCGTGATGCCTTCTTGT
CAAACGCTGATGAGCTAGACTCTCTTGGGGTAAGAAGTTATACAGAAGTAAAATTTGAAAA
TACAATTGACCGTATCACTGCCGAAGCTAATCCAAGACAAATTGAACGTGCTATTCGTACCA
GTACTTTTGATTTCGAGTTGATTTATGAAATTACAGATGAGAATGAAAATCAAGTCGAAGAA
GATTTCAAAGTGATTCGAGATGGTTTAAAACTGCTTGAACTTGATTATCTTGGTGGTTCTGG
ATCTCGAGGTTACGGTAAGGTTGCTTTTGAAAAACTCAAAGCTACTACCGTATTTGGTAATT
ATGATGTTAAAACATTAAATGAACTTTTAACTGCGGAGGTCTAA (SEQ ID NO: 485)

SEQ ID NO: 486:
ATGACCTATAAACTGTATATTATGACCTTTCAGAATGCTCATTTTGGTTCGGGCACTCTTGAT
AGCTCAAAATTAACATTCTCAGCAGACCGTATCTTCTCAGCACTAGTGCTAGAATCCCTAAA
AATGGGAAAACTCGATGCATTTCTTGCGGAAGCTAACCAAGACAAGTTCACGCTCACAGAT
GCCTTTCCATTTCAATTTGGTCCCTTTTTGCCGAAACCGATTGGTTATCCCAAACATGACCAA
ATAGATCAATCAGTTGATGTCAAAGAGGTTCGCCGTCAAGCAAAATTGTCTAAGAAACTGC
AATTTCTTGCTCTAGAAAATGTTGACGATTATCTCAATGGAGAGTTATTTGAAAATGAAGAG
CATGCAGTCATCGATACTGTGACAAAAAATCAACCACATAAGGACGGCAATCTTTTATCAGG
TAGCTACAACCAGATTTTCAAATGATACGTCGCTTTACGTCATCGCAAACGAATCTGATTTG
CTTAATGAGTTGATGTCTAGTCTTCAGTATTCAGGTCTTGGTGGAAAGCGTTCAAGTGGTTTT
GGTCGTTTTGAGTTAGATATTCAAAATATCCCACTAGAATTGTCAGATAGACTGACTAAGAA
TCATTCAGATAAAGTGATGAGTCTTACGACAGCACTTCCTGTAGATGCTGACCTTGAAGAAG
CAATGGAAGATGGACATTACTTATTAACTAAATCAAGTGGTTTTGCATTTAGTCATGCTACC
AATGAGAATTATCGTAAGCAGGATCTTTACAAATTTGCTTCTGGTTCAACTTTTAGTAAAAC
ATTTGAAGGTCAGATTGTTGATGTGAGACCACTTGATTTCCCTCATGCTGTTTTAAATTATGC
TAAACCACTCTTCTTTAAATTGGAGGTATAA (SEQ ID NO: 486)

SEQ ID NO: 487
ATGAAAAATGACTATAGAACATTTAAATTAAGCCTCCTGACACTTGCTCCAATTCATATTGG
TAATGGAGAGAAGTATACCTCTAGAGAATTTATCTATGAAAATAAGAAGTTTTACTTTCCTG
ACATGGGGAAATTCTATAATAAAATGGTGGAGAAGAGGCTTGCTGAAAAGTTTGAAGCATT
TCTAATTCAAACTCGTCCAAATGCACGTAATAATCGTCTTATTTCCTTCTTAAATGATAACCG
AATTGCAGAGCGTTCTTTTGGAGGTTATAGTATCTCTGAAACAGGTTTAGAATCGGACAAAA
ATCCTGATTCAGCCGGAGCTATTAACGAAGTTAATAAATTTATTCGAGATGCTTTTGGAAAT
CCCTACATTCCTGGTAGCTCACTAAAAGGTGCTATTCGTACCATTTTAATGAATACTACCCCT
AAGTGGAATAATGAAAATGCTGTAAATGACTTTGGAAGATTTCCGAAAGAGAATAAGAACC
TTATCCCTTGGGGACCAAAAAAAGGGAAAAGAATACGATGATTTGTTTAACGCAATTCGTGT
GAGTGATAGTAAGCCTTTTGATAATAAGAGTCTTATCTTAGTGCAGAAATGGGATTATTCAG
CGAAAACAAATAAAGCTAAACCACTTCCCTTGTATAGAGAATCAATCTCTCCATTAACAAA
AATTGAATTTGAGATTACAACAACCACTGATGAAGCTGGAAGATTGATTGAAGAATTAGGT
AAGAGAGCACAAGCGTTTTATAAAGACTATAAGGCATTTTTCCTATCTGAATTTCCTGATGA
TAAGATTCAAGCCAATCTACAATACCCAATTTATTTAGGTGCGGGGAGCGGTGCTTGGACAA
AGACTCTATTTAAGCAAGCTGATGGTATTTTACAAAGACGATACAGTCGAATGAAAACTAA

-continued
AATGGTTAAAAAAGGAGTTCTTAAGCTCACAAAAGCACCTCTTAAAACAGTTAAGATTCCA
TCTGGTAATCATTCATTAGTCAAGAACCACGAGTCCTTTTATGAAATGGGAAAAGCTAATTT
CATGATTAAGGAGATTGATAAATGA (SEQ ID NO: 487)

with repeat sequences: SEQ ID NO:11 and/or SEQ ID NO:12

Functional Combination #13:

cas sequences: SEQ ID NO:488 to SEQ ID NO:508, and SEQ ID NO:517 to SEQ ID NO:521, as shown below. SEQ ID NOS:488-497 are from *S. agalactiae*, while SEQ ID NOS:498-503 are from *S. mutans*, and SEQ ID NOS:504-508, 517-521 are from *S. pyogenes*.

SEQ ID NO: 488:
ATGAATAAGCCATATTCAATAGGCCTTGACATCGGTACTAATTCCGTCGGATGGAGCATTAT
TACAGATGATTATAAAGTACCTGCTAAGAAGATGAGAGTTTTAGGGAACACTGATAAAGAA
TATATTAAGAAGAATCTCATAGGTGCTCTGCTTTTTGATGGCGGGAATACTGCTGCAGATAG
ACGCTTGAAGCGAACTGCTCGTCGTCGTTATACACGTCGTAGAAATCGTATTCTATATTTAC
AAGAAATTTTTGCAGAGGAAATGAGTAAAGTTGATGATAGTTTCTTTCATCGATTAGAGGAT
TCTTTTCTAGTTGAGGAAGATAAGAGAGGGAGCAAGTATCCTATCTTTGCAACATTGCAGGA
AGAGAAAGATTATCATGAAAAATTTTCGACAATCTATCATTTGAGAAAAGAATTAGCTGAC
AAGAAAGAAAAAGCAGACCTTCGTCTTATTTATATTGCTCTAGCTCATATCATTAAATTTAG
AGGGCATTTCCTAATTGAGGATGATAGCTTTGATGTCAGGAATACAGACATTTCAAAACAAT
ATCAAGATTTTTTAGAAATCTTTAATACAACTTTTGAAAATAATGATTTGTTATCTCAAAACG
TTGACGTAGAGGCAATACTAACAGATAAGATTAGCAAGTCTGCGAAGAAAGATCGTATTTT
AGCGCAGTATCCTAACCAAAAATCTACTGGCATTTTTGCAGAATTTTTGAAATTGATTGTCG
GAAATCAAGCTGACTTCAAGAAATATTTCAATTTGGAGGATAAAACGCCGCTTCAATTCGCT
AAGGATAGCTACGATGAAGATTTAGAAAATCTTCTTGGACAGATTGGTGATGAATTTGCAG
ACTTATTCTCAGCAGCGAAAAAGTTATATGATAGTGTCCTTTTGTCTGGCATTCTTACAGTAA
TCGACCTCAGTACCAAGGCGCCACTTTCAGCTTCTATGATTCAGCGTTATGATGAACATAGA
GAGGACTTGAAACAGTTAAAACAATTCGTAAAAGCTTCATTGCCGGAAAAATATCAAGAAA
TATTTGCTGATTCATCAAAAGATGGCTACGCTGGTTATATTGAAGGTAAAACTAATCAAGAA
GCTTTTTATAAATACCTGTCAAAATTGTTGACCAAGCAAGAAGATAGCGAGAATTTTCTTGA
AAAAATCAAGAATGAAGATTTCTTGAGAAAACAAAGGACCTTTGATAATGGCTCAATTCCA
CACCAAGTCCATTTGACAGAGCTGAAAGCTATTATCCGCCGTCAATCAGAATACTATCCCTT
CTTGAAAGAGAATCAAGATAGGATTGAAAAAATCCTTACCTTTAGAATTCCTTATTATATCG
GGCCACTAGCACGTGAGAAGAGTGATTTTGCATGGATGACTCGCAAAACAGATGACAGTAT
TCGACCTTGGAATTTTGAAGACTTGGTTGATAAAGAAAAATCTGCGGAAGCTTTTATCCATC
GTATGACCAACAATGATTTTTATCTTCCTGAAGAAAAAGTTTTACCAAAGCATAGTCTTATT
TATGAAAAATTTACGGTCTATAATGAGTTGACTAAGGTTAGATATAAAAATGAGCAAGGTG
AGACTTATTTTTTTGATAGCAATATTAAACAAGAAATCTTTGATGGAGTATTCAAGGAACAT
CGTAAGGTATCCAAGAAGAAGTTGCTAGATTTTCTGGCTAAAGAATATGAGGAGTTTAGGA
TAGTAGATGTTATTGGTCTAGATAAAGAAAATAAAGCTTTCAACGCCTCATTGGGAACTTAC
CACGATCTCGAAAAAATACTAGACAAAGATTTTCTAGATAATCCAGATAATGAGTCTATTCT
GGAAGATATCGTCCAAACTCTAACATTATTTGAAGACAGAGAAATGATTAAGAAGCGTCTT
GAAAACTATAAAGATCTTTTTACAGAGTCACAACTAAAAAAACTCTATCGTCGTCACTATAC
TGGCTGGGGACGATTGTCTGCTAAGTTAATCAATGGTATTCGAGATAAAGAGAGTCAAAAA
ACAATCTTGGACTATCTTATTGATGATGGTAGATCTAATCGCAACTTTATGCAGTTGATAAA
TGATGATGGTCTATCTTTCAAATCAATTATCAGTAAGGCACAGGCTGGTAGTCATTCAGATA
ATCTAAAAGAAGTTGTAGGTGAGCTTGCAGGTAGCCCTGCTATTAAAAAGGGAATTCTACA
AAGTTTGAAAATTGTTGATGAGCTTGTTAAAGTCATGGGATACGAACCTGAACAAATTGTGG
TTGAGATGGCGCGTGAGAATCAAACAACAAATCAAGGTCGTCGTAACTCTCGACAACGCTA
TAAACTTCTTGATGATGGCGTTAAGAATCTAGCTAGTGACTTGAATGGCAATATTTTGAAAG
AATATCCTACGGATAATCAAGCGTTGCAAAATGAAAGACTTTTCCTTTACTACTTACAAAAC
GGAAGAGATATGTATACAGGGGAAGCTCTAGATATTGACAATTTAAGTCAATATGATATTG
ACCACATTATTCCTCAAGCTTTCATAAAAGATGATTCTATTGATAATCGTGTTTTGGTATCAT
CTGCTAAAAATCGTGGAAAGTCAGATGATGTTCCTAGCCTTGAAATTGTAAAAGATTGTAAA
GTTTCTGGAAAAAATTACTTGATGCTAAGTTAATGAGTCAGCGTAAGTATGATAATTTGAC
TAAGGCAGAGCGCGGAGGCCTAACTTCCGATGATAAGGCAAGATTTATCCAACGTCAGTTG
GTTGAGACACGACAAATTACCAAGCATGTTGCCCGTATCTTGGATGAACGCTTTAATAATGA
GCTTGATAGTAAAGGTAGAAGGATCCGCAAAGTTAAAATTGTAACCTTGAAGTCAAATTTG
GTTTCAAATTTCCGAAAAGAATTTGGATTCTATAAAATTCGTGAAGTTAACAATTATCACCA
TGCACATGATGCCTATCTTAATGCAGTAGTTGCTAAAGCTATTCTAACCAAATATCCTCAGT
TAGAGCCAGAATTTGTCTACGGCGACTATCCAAAATATAATAGTTACAAAACGCGTAAATC
CGCTACAGAAAAGCTATTTTTCTATTCAAATATTATGAACTTCTTTAAAACTAAGGTAACTTT
AGCGGATGGAACCGTTGTTGTAAAAGATGATATTGAAGTTAATAATGATACGGGTGAAATT
GTTTGGGATAAAAAGAAACACTTTGCGACAGTTAGAAAAGTCTTGTCATACCCTCAGAACA
ATATCGTGAAGAAGACAGAGATTCAGACAGGTGGTTTCTCTAAGGAATCAATCTTGGCGCA
TGGTAACTCAGATAAGTTGATTCCAAGAAAAACGAAGGATATTTATTTAGATCCTAAGAAA
TATGGAGGTTTTGATAGTCCGATAGTAGCTTACTCTGTTTTAGTTGTAGCTGATATCAAAAA
GGGTAAAGCACAAAAACTAAAAACAGTTACGGAACTTTTAGGAATTACCATCATGGAGAGG
TCCAGATTTGAGAAAAATCCATCAGCTTTCCTTGAATCAAAAGGCTATTTAAATATTAGGGC
TGATAAACTAATTATTTTGCCCAAGTATAGTCTGTTCGAATTAGAAAATGGGCGTCGTCGAT
TACTTGCTAGTGCTGGTGAATTACAAAAAGGTAATGAGCTAGCCTTACCAACACAATTTATG
AAGTTCTTATACCTTGCAAGTCGTTATAATGAGTCAAAAGGTAAACCAGAGGAGATTGAGA
AGAAACAAGAATTTGTAAATCAACATGTCTCTTATTTTGATGACATCCTTCAATTAATTAAT
GATTTTTCAAAACGAGTTATTCTAGCAGATGCTAATTTAGAGAAAATCAATAAGCTTTACCA

-continued

AGATAATAAGGAAAATATATCAGTAGATGAACTTGCTAATAATATTATCAATCTATTTACTT
TTACCAGTCTAGGAGCTCCAGCAGCTTTTAAATTTTTTGATAAAATAGTTGATAGAAAACGC
TATACATCAACTAAAGAAGTACTTAATTCTACCCTAATTCATCAATCTATTACTGGACTTTAT
GAAACACGTATTGATTTGGGTAAGTTAGGAGAAGATTGATATGGCAGGTTGGCGAACCGTT
GTTGTAAATACACATTCTAAGCTCTCTTATAAAAATAATCATCTGATTTTTAAAGATTCTTAT
CAGACGGAAATGATTCATCTATCAGAGATTGACATTCTAATCATGGAAACAACAGATATCG
TTTTGTCGACCATGCTGATTAAACGTTTGGTTGATGAAAATATTTTAGTTATATTTTGTGACG
ATAAACGCTTGCCAACAGCTATGTTAATGCCGTACTATGCCAGACATGATTCGAGTTTACAA
TTATCTAGGCAGATGTCATGGATTGAAGATGTCAAAGCAGATGTTTGGACATCAATTATTGC
ACAAAAAATTTTGAATCAGTCTTTTTATCTCGGTGAGTGTTCTTTCTTTGAAAAATCCCAGTC
TATTATGAATCTCTACCATGACTTAGAACCTTTTGATCCTTCTAATCGTGAGGGGCATGCTGC
TAGGATTTATTTCAATACACTTTTTGGAAATGATTTTTCAAGAGAGCAGGATAATCCAATAA
ATGCTGGTTTAGACTACGGATATTCATTGCTTTTGAGTATGTTTGCGCGTGAAGTTGTTAAGT
GTGGTTGCATGACACAATTTGGCTTGAAGCATGCTAATCAATTTAATCAGTTCAACCTAGCA
AGCGATATTATGGAACCATTTCGCCCAATCGTTGATAGGATTATTTATGAAAATAGGCAGAG
TGATTTTGTCAAAATGAAAAGAGAACTCTTTTCTATGTTTTCAGAGACATACAGCTACAATG
GTAAAGAAATGTATCTCTCAAATATTGTCAGCGACTATACCAAAAAAGTTATTAAGTCGCTA
AATAGTGATGGGAATGGAATTCCGGAGTTTAGGATATGAGTTATCGGTATATGCGAATGATT
TTAATGTTTGATATGCCTACTGAAACAGCAGAAGAACGGAAGGCGTATCGTAAGTTTAGAA
AGTTTCTCTTGAGCGAAGGCTTTATCATGCATCAGTTTTCTGTTTATAGTAAATTATTACTCA
ATAATACAGCTAATAATGCTATGATAGGTCGGCTTAAAGTGAATAATCCTAAAAAGGGTAA
TATCACACTCTTAACAGTTACGGAAAAACAATTTGCGAGAATGGTTTACCTCCATGGAGAAC
GCAACACAAGTGTTGCCAACTCTGATAGTCGCTTGGTTTTCCTAGGAGATTCTTATGATCAA
GATTAATTTTCCAATTTTAGATGAACCATTAGTGTTAAGTAATGCTACGATTTTAACGATAG
AAGATGTTTCAGTTTATTCTTCATTGGTGAAACATTTTTATCAATATGACGTAGATGAACATT
TGAAATTATTTGATGATAAGCAGAAAAGTCTGAAGGCAACAGAGTTAATGCTGGTTACAGA
TATCTTAGGATACGATGTCAACTCAGCACCTATTCTAAAGTTGATACATGGTGACTTAGAAA
ATCAATTCAACGAAAAGCCAGAAGTGAAATCAATGGTAGAAAAATTAGCAGCTACTATTAC
AGAACTTATCGCATTTGAGTGTCTAGAGAATGAGCTTGATTTAGAATACGATGAAATTAAGA
TTTTAGAACTCATTAAGGCACTGGGAGTCAAAATTGAGACACAGAGCGACACTATCTTTGA
AAAATGTTTTGAAATTATACAAGTTTACCATTATTTAACGAAAAAGAATCTCTTGGTTTTTGT
TAATAGCGGAGCTTATCTTACCAAAGATGAAGTTATAAAATTATGTGAATACATCAATTTAA
TGCAAAAGTCAGTACTCTTTCTAGAACCTAGAAGACTCTATGATTTACCGCAATATGTTATT
GATAAGGATTATTTCTTGATAGGCGAAAATATGGTATAA (SEQ ID NO: 488)

SEQ ID NO: 489:
ATGAATAAGCCATATTCAATAGGCCTTGACATCGGTACTAATTCCGTCGGATGGAGCATTAT
TACAGATGATTATAAAGTACCTGCTAAGAAGATGAGAGTTTTAGGGAACACTGATAAAGAA
TATATTAAGAAGAATCTCATAGGTGCTCTGCTTTTTGATGGCGGGAATACTGCTGCAGATAG
ACGCTTGAAGCGAACTGCTCGTCGTCGTTATACACGTCGTAGAAATCGTATTCTATATTTAC
AAGAAATTTTTGCAGAGGAAATGAGTAAAGTTGATGATAGTTTCTTTCATCGATTAGAGGAT
TCTTTTCTAGTTGAGGAAGATAAGAGAGGGAGCAAGTATCCTATCTTTGCAACATTGCAGGA
AGAGAAAGATTATCATGAAAAATTTTCGACAATCTATCATTTGAGAAAAGAATTAGCTGAC
AAGAAAGAAAAAGCAGACCTTCGTCTTATTTATATTGCTCTAGCTCATATCATTAAATTTAG
AGGGCATTTCCTAATTGAGGATGATAGCTTTGATGTCAGGAATACAGACATTTCAAAACAAT
ATCAAGATTTTTTAGAAATCTTTAATACAACTTTTGAAAATAATGATTTGTTATCTCAAAACG
TTGACGTAGAGGCAATACTAACAGATAAGATTAGCAAGTCTGCGAAGAAAGATCGTATTTT
AGCGCAGTATCCTAACCAAAAATCTACTGGCATTTTTGCAGAATTTTTGAAATTGATTGTCG
GAAATCAAGCTGACTTCAAGAAATATTTCAATTTGGAGGATAAAACGCCGCTTCAATTCGCT
AAGGATAGCTACGATGAAGATTTAGAAAATCTTCTTGGACAGATTGGTGATGAATTTGCAG
ACTTATTCTCAGCAGCGAAAAAGTTATATGATAGTGTCCTTTTGTCTGGCATTCTTACAGTAA
TCGACCTCAGTACCAAGGCGCCACTTTCAGCTTCTATGATTCAGCGTTATGATGAACATAGA
GAGGACTTGAAACAGTTAAAACAATTCGTAAAAGCTTCATTGCCGGAAAAATATCAAGAAA
TATTTGCTGATTCATCAAAAGATGGCTACGCTGGTTATATTGAAGGTAAAACTAATCAAGAA
GCTTTTTATAAATACCTGTCAAAATTGTTGACCAAGCAAGAAGATAGCGAGAATTTTCTTGA
AAAAATCAAGAATGAAGATTTCTTGAGAAAACAAAGGACCTTTGATAATGGCTCAATTCCA
CACCAAGTCCATTTGACAGAGCTGAAAGCTATTATCCGCCGTCAATCAGAATACTATCCCTT
CTTGAAAGAGAATCAAGATAGGATTGAAAAAATCCTTACCTTTAGAATTCCTTATTATATCG
GGCCACTAGCACGTGAGAAGAGTGATTTTGCATGGATGACTCGCAAAACAGATGACAGTAT
TCGACCTTGGAATTTTGAAGACTTGGTTGATAAAGAAAAATCTGCGGAAGCTTTTATCCATC
GTATGACCAACAATGATTTTTATCTTCCTGAAGAAAAAGTTTTACCAAAGCATAGTCTTATT
TATGAAAAATTTACGGTCTATAATGAGTTGACTAAGGTTAGATATAAAAATGAGCAAGGTG
AGACTTATTTTTTTGATAGCAATATTAAACAAGAAATCTTTGATGGAGTATTCAAGGAACAT
CGTAAGGTATCCAAGAAGAAGTTGCTAGATTTTCTGGCTAAAGAATATGAGGAGTTTAGGA
TAGTAGATGTTATTGGTCTAGATAAAGAAAATAAAGCTTTCAACGCCTCATTGGGAACTTAC
CACGATCTCGAAAAAATACTAGACAAAGATTTTCTAGATAATCCAGATAATGAGTCTATTCT
GGAAGATATCGTCCAAACTCTAACATTATTTGAAGACAGAGAAATGATTAAGAAGCGTCTT
GAAAACTATAAAGATCTTTTTACAGAGTCACAACTAAAAAAACTCTATCGTCGTCACTATAC
TGGCTGGGGACGATTGTCTGCTAAGTTAATCAATGGTATTCGAGATAAAGAGAGTCAAAAA
ACAATCTTGGACTATCTTATTGATGATGGTAGATCTAATCGCAACTTTATGCAGTTGATAAA
TGATGATGGTCTATCTTTCAAATCAATTATCAGTAAGGCACAGGCTGGTAGTCATTCAGATA
ATCTAAAAGAAGTTGTAGGTGAGCTTGCAGGTAGCCCTGCTATTAAAAAGGGAATTCTACA
AAGTTTGAAAATTGTTGATGAGCTTGTTAAAGTCATGGGATACGAACCTGAACAAATTGTGG
TTGAGATGGCGCGTGAGAATCAAACAACAAATCAAGGTCGTCGTAACTCTCGACAACGCTA
TAAACTTCTTGATGATGGCGTTAAGAATCTAGCTAGTGACTTGAATGGCAATATTTTGAAAG
AATATCCTACGGATAATCAAGCGTTGCAAAATGAAAGACTTTTCCTTTACTACTTACAAAAC
GGAAGAGATATGTATACAGGGGAAGCTCTAGATATTGACAATTTAAGTCAATATGATATTG
ACCACATTATTCCTCAAGCTTTCATAAAAGATGATTCTATTGATAATCGTGTTTTGGTATCAT
CTGCTAAAAATCGTGGAAAGTCAGATGATGTTCCTAGCCTTGAAATTGTAAAAGATTGTAAA
GTTTTCTGGAAAAAATTACTTGATGCTAAGTTAATGAGTCAGCGTAAGTATGATAATTTGAC
TAAGGCAGAGCGCGGAGGCCTAACTTCCGATGATAAGGCAAGATTTATCCAACGTCAGTTG

-continued

GTTGAGACACGACAAATTACCAAGCATGTTGCCCGTATCTTGGATGAACGCTTTAATAATGA
GCTTGATAGTAAAGGTAGAAGGATCCGCAAAGTTAAAATTGTAACCTTGAAGTCAAATTTG
GTTTCAAATTTCCGAAAAGAATTTGGATTCTATAAAATTCGTGAAGTTAACAATTATCACCA
TGCACATGATGCCTATCTTAATGCAGTAGTTGCTAAAGCTATTCTAACCAAATATCCTCAGT
TAGAGCCAGAATTTGTCTACGGCGACTATCCAAAATATAATAGTTACAAAACGCGTAAATC
CGCTACAGAAAAGCTATTTTTCTATTCAAATATTATGAACTTCTTTAAAACTAAGGTAACTTT
AGCGGATGGAACCGTTGTTGTAAAAGATGATATTGAAGTTAATAATGATACGGGTGAAATT
GTTTGGGATAAAAAGAAACACTTTGCGACAGTTAGAAAAGTCTTGTCATACCCTCAGAACA
ATATCGTGAAGAAGACAGAGATTCAGACAGGTGGTTTCTCTAAGGAATCAATCTTGGCGCA
TGGTAACTCAGATAAGTTGATTCCAAGAAAAACGAAGGATATTTATTTAGATCCTAAGAAA
TATGGAGGTTTTGATAGTCCGATAGTAGCTTACTCTGTTTTAGTTGTAGCTGATATCAAAAA
GGGTAAAGCACAAAAACTAAAAACAGTTACGGAACTTTTAGGAATTACCATCATGGAGAGG
TCCAGATTTGAGAAAAATCCATCAGCTTTCCTTGAATCAAAAGGCTATTTAAATATTAGGGC
TGATAAACTAATTATTTTGCCCAAGTATAGTCTGTTCGAATTAGAAAATGGGCGTCGTCGAT
TACTTGCTAGTGCTGGTGAATTACAAAAAGGTAATGAGCTAGCCTTACCAACACAATTTATG
AAGTTCTTATACCTTGCAAGTCGTTATAATGAGTCAAAAGGTAAACCAGAGGAGATTGAGA
AGAAACAAGAATTTGTAAATCAACATGTCTCTTATTTTGATGACATCCTTCAATTAATTAAT
GATTTTTCAAAACGAGTTATTCTAGCAGATGCTAATTTAGAGAAAATCAATAAGCTTTACCA
AGATAATAAGGAAAATATATCAGTAGATGAACTTGCTAATAATATTATCAATCTATTTACTT
TTACCAGTCTAGGAGCTCCAGCAGCTTTTAAATTTTTTGATAAAATAGTTGATAGAAAACGC
TATACATCAACTAAAGAAGTACTTAATTCTACCCTAATTCATCAATCTATTACTGGACTTTAT
GAAACACGTATTGATTTGGGTAAGTTAGGAGAAGATTGA (SEQ ID NO: 489)

SEQ ID NO: 490:
ATGGCAGGTTGGCGAACCGTTGTTGTAAATACACATTCTAAGCTCTCTTATAAAAATAATCA
TCTGATTTTTAAAGATTCTTATCAGACGGAAATGATTCATCTATCAGAGATTGACATTCTAAT
CATGGAAACAACAGATATCGTTTTGTCGACCATGCTGATTAAACGTTTGGTTGATGAAAATA
TTTTAGTTATATTTTGTGACGATAAACGCTTGCCAACAGCTATGTTAATGCCGTACTATGCCA
GACATGATTCGAGTTTACAATTATCTAGGCAGATGTCATGGATTGAAGATGTCAAAGCAGAT
GTTTGGACATCAATTATTGCACAAAAAATTTTGAATCAGTCTTTTTATCTCGGTGAGTGTTCT
TTCTTTGAAAAATCCCAGTCTATTATGAATCTCTACCATGACTTAGAACCTTTTGATCCTTCT
AATCGTGAGGGGCATGCTGCTAGGATTTATTTCAATACACTTTTTGGAAATGATTTTTCAAG
AGAGCAGGATAATCCAATAAATGCTGGTTTAGACTACGGATATTCATTGCTTTTGAGTATGT
TTGCGCGTGAAGTTGTTAAGTGTGGTTGCATGACACAATTTGGCTTGAAGCATGCTAATCAA
TTTAATCAGTTCAACCTAGCAAGCGATATTATGGAACCATTTCGCCCAATCGTTGATAGGAT
TATTTATGAAAATAGGCAGAGTGATTTTGTCAAAATGAAAAGAGAACTCTTTTCTATGTTTT
CAGAGACATACAGCTACAATGGTAAAGAAATGTATCTCTCAAATATTGTCAGCGACTATAC
CAAAAAAGTTATTAAGTCGCTAAATAGTGATGGGAATGGAATTCCGGAGTTTAGGATATGA
(SEQ ID NO: 490)

SEQ ID NO: 491:
ATGCGAATGATTTTAATGTTTGATATGCCTACTGAAACAGCAGAAGAACGGAAGGCGTATC
GTAAGTTTAGAAAGTTTCTCTTGAGCGAAGGCTTTATCATGCATCAGTTTTCTGTTTATAGTA
AATTATTACTCAATAATACAGCTAATAATGCTATGATAGGTCGGCTTAAAGTGAATAATCCT
AAAAAGGGTAATATCACACTCTTAACAGTTACGGAAAAACAATTTGCGAGAATGGTTTACC
TCCATGGAGAACGCAACACAAGTGTTGCCAACTCTGATAGTCGCTTGGTTTTCCTAGGAGAT
TCTTATGATCAAGATTAA (SEQ ID NO: 491)

SEQ ID NO: 492:
ATGATCAAGATTAATTTTCCAATTTTAGATGAACCATTAGTGTTAAGTAATGCTACGATTTTA
ACGATAGAAGATGTTTCAGTTTATTCTTCATTGGTGAAACATTTTTATCAATATGACGTAGAT
GAACATTTGAAATTATTTGATGATAAGCAGAAAAGTCTGAAGGCAACAGAGTTAATGCTGG
TTACAGATATCTTAGGATACGATGTCAACTCAGCACCTATTCTAAAGTTGATACATGGTGAC
TTAGAAAATCAATTCAACGAAAAGCCAGAAGTGAAATCAATGGTAGAAAAATTAGCAGCTA
CTATTACAGAACTTATCGCATTTGAGTGTCTAGAGAATGAGCTTGATTTAGAATACGATGAA
ATTAAGATTTTAGAACTCATTAAGGCACTGGGAGTCAAAATTGAGACACAGAGCGACACTA
TCTTTGAAAAAATGTTTTGAAATTATACAAGTTTACCATTATTTAACGAAAAAGAATCTCTTG
GTTTTTGTTAATAGCGGAGCTTATCTTACCAAAGATGAAGTTATAAAATTATGTGAATACAT
CAATTTAATGCAAAAGTCAGTACTCTTTCTAGAACCTAGAAGACTCTATGATTTACCGCAAT
ATGTTATTGATAAGGATTATTTCTTGATAGGCGAAAATATGGTATAA (SEQ ID NO: 492)

SEQ ID NO: 493:
ATGAATAAGCCATATTCAATAGGCCTTGACATCGGTACTAATTCCGTCGGATGGAGCATTAT
TACAGATGATTATAAAGTACCTGCTAAGAAGATGAGAGTTTTAGGGAACACTGATAAAGAA
TATATTAAGAAGAATCTCATAGGTGCTCTGCTTTTTGATGGCGGGAATACTGCTGCAGATAG
ACGCTTGAAGCGAACTGCTCGTCGTCGTTATACACGTCGTAGAAATCGTATTCTATATTTAC
AAGAAATTTTTGCAGAGGAAATGAGTAAAGTTGATGATAGTTTCTTTCATCGATTAGAGGAT
TCTTTTCTAGTTGAGGAAGATAAGAGAGGTAGCAAGTATCCTATCTTTGCAACAATGCAGGA
GGAGAAATATTATCATGAAAAATTTCCGACAATCTATCATTTGAGAAAAGAATTGGCTGAC
AAGAAAGAAAAAGCAGACCTTCGTCTTGTTTATCTGGCTCTAGCTCATATCATTAAATTCAG
AGGGCATTTCCTAATTGAGGATGATAGATTTGATGTGAGGAATACCGATATTCAAAAACAA
TATCAAGCCTTTTTAGAAATTTTTGATACTACCTTTGAAAATAATCATTTGTTATCTCAAAAT
GTAGATGTAGAAGCAATTCTAACAGATAAGATTAGCAAGTCTGCGAAGAAGGATCGCATCT
TAGCGCAGTATCCTAACCAAAAATCTACTGGTATTTTTGCAGAATTTTTGAAATTGATTGTC
GGAAATCAAGCTGACTTCAAGAAACATTTCAATTTGGAGGATAAAACACCGCTTCAATTCG
CTAAGGATAGCTACGATGAAGATTTAGAAAATCTTCTTGGACAGATTGGTGATGAATTTGCA
GACTTATTCTCAGTAGCGAAAAAGCTATATGATAGTGTTCTTTTATCTGGCATTCTTACAGTA
ACTGATCTCAGTACCAAGGCGCCACTTTCTGCCTCTATGATTCAGCGTTATGATGAACATCA
TGAGGACTTAAAGCATCTAAAACAATTCGTAAAAGCTTCATTACCTGAAAATTATCGGGAA
GTATTTGCTGATTCATCAAAAGATGGCTACGCTGGCTATATTGAAGGCAAAACTAATCAAGA
AGCTTTTTATAAATATCTGTTAAAATTGTTGACCAAACAAGAAGGTAGCGAGTATTTTCTTG

-continued

AGAAAATTAAGAATGAAGATTTTTTGAGAAAACAGAGAACCTTTGATAATGGCTCAATCCC
GCATCAAGTCCATTTGACAGAATTGAGGGCTATTATTCGACGTCAATCAGAATACTATCCAT
TCTTGAAAGAGAATCAAGATAGGATTGAAAAAATCCTTACCTTTAGAATTCCTTATTATGTC
GGGCCACTAGCACGTGAGAAGAGTGATTTTGCATGGATGACTCGCAAAACAGATGACAGTA
TTCGACCTTGGAATTTTGAAGACTTGGTTGATAAAGAAAAATCTGCGGAAGCTTTTATCCAT
CGCATGACCAACAATGACCTCTATCTTCCAGAAGAAAAAGTTTTACCAAAGCATAGTCTTAT
TTATGAAAAATTTACTGTTTACAATGAATTAACGAAGGTTAGATTTTTGGCAGAAGGCTTTA
AAGATTTTCAATTTTTAAATAGGAAGCAAAAAGAAACTATCTTTAACAGCTTGTTTAAGGAA
AAACGTAAAGTAACTGAAAAGGATATTATTAGTTTTTTGAATAAAGTTGATGGATATGAAG
GAATTGCAATCAAAGGAATTGAGAAACAGTTTAACGCTAGCCTTTCAACCTATCATGATCTT
AAAAAAATACTTGGCAAGGATTTCCTTGATAATACAGATAACGAGCTTATTTTGGAAGATAT
CGTCCAAACTCTAACCTTATTTGAAGATAGAGAAATGATTAAGAAGTGTCTTGACATCTATA
AAGATTTTTTTACAGAGTCACAGCTTAAAAAGCTCTATCGCCGTCACTATACTGGCTGGGGA
CGATTGTCTGCTAAGCTAATAAATGGCATCCGAAATAAAGAGAATCAAAAAACAATCTTGG
ACTATCTTATTGATGATGGAAGTGCAAACCGAAACTTCATGCAGTTGATAAATGATGATGAT
CTATCATTTAAACCAATTATTGACAAGGCACGAACTGGTAGTCATTCGGATAATCTGAAAGA
AGTTGTAGGTGAACTTGCTGGTAGCCCTGCTATTAAAAAAGGGATTCTACAAAGTTTGAAAA
TAGTTGATGAGCTGGTTAAAGTCATGGGCTATGAACCTGAACAAATCGTGGTTGAAATGGC
ACGTGAGAACCAAACGACAGCAAAAGGATTAAGTCGTTCACGACAACGCTTGACAACCTTG
AGAGAATCTCTTGCTAATTTGAAGAGTAATATTTTGGAAGAGAAAAAGCCTAAGTATGTGA
AAGATCAAGTTGAAAATCATCATTTATCTGATGACCGTCTTTTCCTTTACTACTTACAAAACG
GAAGAGATATGTATACAAAAAAGGCTCTGGATATTGATAATTTAAGTCAATATGATATTGA
CCACATTATTCCTCAAGCTTTCATAAAAGATGATTCTATTGATAATCGTGTTTTGGTATCATC
TGCTAAAAATCGTGGAAAATCAGATGATGTTCCTAGCATTGAAATTGTAAAAGCTCGCAAA
ATGTTCTGGAAAAATTTACTGGATGCTAAGTTAATGAGTCAGCGTAAGTATGATAATTTGAC
TAAGGCAGAGCGCGGAGGCCTAACTTCCGATGATAAGGCAAGATTTATCCAACGTCAGTTG
GTTGAGACTCGACAAATTACCAAGCATGTAGCTCGTATCTTGGATGAACGCTTCAATAATGA
AGTTGATAATGGTAAAAAGATTTGCAAGGTTAAAATTGTAACCTTGAAGTCAAATTTGGTTT
CAAATTTCCGAAAAGAATTTGGATTCTATAAAATTCGTGAAGTTAATGATTATCACCATGCA
CACGATGCTTATCTTAATGCAGTAGTTGCCAAAGCTATTCTAACCAAATATCCACAGTTAGA
GCCAGAGTTTGTCTACGGAATGTATAGACAGAAAAAACTTTCGAAAATCGTTCATGAGGAT
AAGGAAGAAAAATATAGTGAAGCAACCAGGAAAATGTTTTTCTACTCCAACTTGATGAATA
TGTTCAAAAGAGTTGTGAGGTTAGCAGATGGTTCTATTGTTGTAAGACCAGTAATAGAAACT
GGTAGATATATGAGAAAAACTGCATGGGATAAAAAGAAACACTTTGCGACAGTTAGAAAA
GTCTTGTCATACCCTCAGAACAATATCGTGAAGAAGACAGAGATTCAGACAGGTGGTTTCTC
TAAGGAATCAATCTTGGCGCATGGTAACTCAGATAAGTTGATTCCAAGAAAAACGAAGGAT
ATTTATTTAGATCCTAAGAAATATGGAGGTTTTGATAGTCCGATAGTAGCTTACTCTGTTTTA
GTTGTAGCTGATATCAAAAAAGGTAAAGCACAAAAACTAAAAACAGTTACGGAACTTTTAG
GAATTACCATCATGGAGAGGTCCAGATTTGAGAAAAATCCATCAGCTTTCCTTGAATCAAAA
GGTTATTTAAATATTAGGGACGATAAATTAATGATTTTACCGAAGTATAGTCTGTTCGAATT
AGAAAATGGGCGTCGTCGATTACTTGCTAGTGCTGGTGAATTACAAAAAGGTAACGAGCTA
GCCTTACCAACACAATTTATGAAGTTCTTATACCTTGCAAGTCGTTATAATGAGTCAAAAGG
TAAACCAGAGGAGATTGAGAAGAAACAAGAATTTGTAAATCAACATGTCTCTTATTTTGAT
GACATCCTTCAATTAATTAATGATTTTTCAAAACGAGTTATTCTAGCAGATGCTAATTTAGA
GAAAATCAATAAGCTTTACCAGGATAATAAGGAAAATATACCAGTAGATGAACTTGCTAAT
AATATTATCAATCTATTTACTTTTACCAGTCTAGGAGCTCCAGCAGCTTTTAAATTTTTTGAT
AAAATAGTTGATAGAAAACGCTATACATCAACTAAAGAAGTACTTAATTCTACTCTAATCCA
TCAATCTATTACTGGACTTTATGAAACACGTATTGATTTGGGTAAATTAGGAGAAGATTGAT
ATGGCAGGTTGGCGAACTGTTGTTGTAAATACACATTCTAAGCTCTCTTATAAAAATAATCA
TCTGATTTTTAAAGATTCTTATCAGACGGAAATGATTCATCTTTCAGAGATTGATATTCTAAT
CATGGAAACGACAGATATTGTTTTGTCGACTATGCTGATTAAACGTTTGGTTGATGAAAATA
TTTTAGTCATATTTTGTGATGATAAACGCTTGCCAACAGCTATGTTAATGCCGTACTATGCTA
GACATGATTCGAGTTTACAATTATCTAGGCAGATGTCATGGATTGAGGATGTCAAAGCGGAT
GTTTGGACATCAATTATTGCACAAAAAATTTTGAATCAGTCCTTTTATCTCGGTGAGTGTTCT
TTCTTTGAAAAATCCCAGTCTATTATGAATCTCTATCATGATTTAGAATCTTTTGACCCTTCC
AATCGTGAAGGTCATGCAGCTAGGATTTATTTCAATACACTTTTTGGAAATGATTTTTCAAG
AGAGCAGGATAATCCAATAAATGCTGGTTTAGACTATGGATATTCTCTGATTTTGAGTATGT
TTGCGCGTGAAGTTGTTAAGTGTGGTTGCATGACACAATTTGGCTTAAAGCATGCTAATCAA
TTTAATCAGTTCAACCTAGCAAGCGATATTATGGAACCATTTCGCCCAATCGTTGATAGGAT
TATTTATGAAAATAGGCAGAGTGATTTTGTCAAAATGAAAAGAGAACTCTTTTCTATGTTTT
CAGAGACATACAGCTACAACGGTAAAGAAATGTATCTTTCAAATATTGTCAGCGATTACAC
CAAAAAAGTTATTAAGTCGCTAAATAGTGATGGGAATGGAATTCCGGAGTTTAGGATATGA
GTTATCGGTATATGAGAATGATTTTAATGTTTGATATGCCTACTGAAACAGTAGAAGAACGT
AAGGCGTATCGTAAGTTTAGAAAGTTTCTGTTGAGCGAAGGTTTTATTATGCATCAGTTCTC
TGTTTATAGTAAATTATTGCTCAATAATACAGCTAATAATGCCATGATAGGTCGGCTTAAAG
TGAATAATCCTAAGAAAGGGAGTATAACTCTTTTGACAGTTACCGAGAAGCAGTTTGCAAG
GATGGTTTATCTACATGGTGAACATAATATGAGTGTTGCCAACTCTGATAGTCGCTTGGTTTT
CCTAGGAGATTCTTATGATCAAGATTAATTTTCCAATTTTAGATGAACCATTAGTGTTAAGT
AATGCTACGATTTTAACGATAGAAGATGTTTCAGTTTATTCTTCATTGGTGAAACATTTTTAT
CAATATGACGTAGATGAACATTTGAAATTATTTGATGATAAGCAGAAAAGTCTGAAGGCAA
CGGAGTTAATGTTAGTTACAGATATCTTAGGATACGATGTCAACTCAGCACCTATTCTAAAG
TTGATACATGGTGACTTAGAAAATCAATTCAACGAAAAGCCAGAAGTGAAATCAATGGTAG
AAAAATTAGCAGCTACTATTACAGAACTTATCGCATTTGAGTGTCTAGAGAATGAGCTTGAT
TTAGAATACGATGAAATTACGATTTTAGAACTCATTAAGGCACTGGGAGTCAAAATTGAGA
CACAGAGCGACACTATCTTTGAAAAATGTTTTGAAATTATACAAGTTTACCATTATTTAACG
AAAAAGAATCTCTTAGTTTTTGTTAATAGCGGAGCTTATCTTACCAAAGATGAAGTTATAAA
ATTATGTGAATACATCAATTTAATGCAAAAGTCAGTACTCTTTCTAGAACCTAGAAGACTCT
ATGATTTACCGCAATATGTTATTGATAAGGATTATTTCTTGATAGGCGAAAATATGGTATAA
(SEQ ID NO: 493)

-continued

SEQ ID NO: 494:
ATGAATAAGCCATATTCAATAGGCCTTGACATCGGTACTAATTCCGTCGGATGGAGCATTAT
TACAGATGATTATAAAGTACCTGCTAAGAAGATGAGAGTTTTAGGGAACACTGATAAAGAA
TATATTAAGAAGAATCTCATAGGTGCTCTGCTTTTTGATGGCGGGAATACTGCTGCAGATAG
ACGCTTGAAGCGAACTGCTCGTCGTCGTTATACACGTCGTAGAAATCGTATTCTATATTTAC
AAGAAATTTTTGCAGAGGAAATGAGTAAAGTTGATGATAGTTTCTTTCATCGATTAGAGGAT
TCTTTTCTAGTTGAGGAAGATAAGAGAGGTAGCAAGTATCCTATCTTTGCAACAATGCAGGA
GGAGAAATATTATCATGAAAAATTTCCGACAATCTATCATTTGAGAAAAGAATTGGCTGAC
AAGAAAGAAAAAGCAGACCTTCGTCTTGTTTATCTGGCTCTAGCTCATATCATTAAATTCAG
AGGGCATTTCCTAATTGAGGATGATAGATTTGATGTGAGGAATACCGATATTCAAAAACAA
TATCAAGCCTTTTTAGAAATTTTTGATACTACCTTTGAAAATAATCATTTGTTATCTCAAAAT
GTAGATGTAGAAGCAATTCTAACAGATAAGATTAGCAAGTCTGCGAAGAAGGATCGCATCT
TAGCGCAGTATCCTAACCAAAAATCTACTGGTATTTTTGCAGAATTTTTGAAATTGATTGTC
GGAAATCAAGCTGACTTCAAGAAACATTTCAATTTGGAGGATAAAACACCGCTTCAATTCG
CTAAGGATAGCTACGATGAAGATTTAGAAAATCTTCTTGGACAGATTGGTGATGAATTTGCA
GACTTATTCTCAGTAGCGAAAAAGCTATATGATAGTGTTCTTTTATCTGGCATTCTTACAGTA
ACTGATCTCAGTACCAAGGCGCCACTTTCTGCCTCTATGATTCAGCGTTATGATGAACATCA
TGAGGACTTAAAGCATCTAAAACAATTCGTAAAAGCTTCATTACCTGAAAATTATCGGGAA
GTATTTGCTGATTCATCAAAAGATGGCTACGCTGGCTATATTGAAGGCAAAACTAATCAAGA
AGCTTTTTATAAATATCTGTTAAAATTGTTGACCAAACAAGAAGGTAGCGAGTATTTTCTTG
AGAAAATTAAGAATGAAGATTTTTTGAGAAAACAGAGAACCTTTGATAATGGCTCAATCCC
GCATCAAGTCCATTTGACAGAATTGAGGGCTATTATTCGACGTCAATCAGAATACTATCCAT
TCTTGAAAGAGAATCAAGATAGGATTGAAAAAATCCTTACCTTTAGAATTCCTTATTATGTC
GGGCCACTAGCACGTGAGAAGAGTGATTTTGCATGGATGACTCGCAAAACAGATGACAGTA
TTCGACCTTGGAATTTTGAAGACTTGGTTGATAAAGAAAAATCTGCGGAAGCTTTTATCCAT
CGCATGACCAACAATGACCTCTATCTTCCAGAAGAAAAAGTTTTACCAAAGCATAGTCTTAT
TTATGAAAAATTTACTGTTTACAATGAATTAACGAAGGTTAGATTTTTGGCAGAAGGCTTTA
AAGATTTTCAATTTTTAAATAGGAAGCAAAAAGAAACTATCTTTAACAGCTTGTTTAAGGAA
AAACGTAAAGTAACTGAAAAGGATATTATTAGTTTTTTGAATAAAGTTGATGGATATGAAG
GAATTGCAATCAAAGGAATTGAGAAACAGTTTAACGCTAGCCTTTCAACCTATCATGATCTT
AAAAAAATACTTGGCAAGGATTTCCTTGATAATACAGATAACGAGCTTATTTTGGAAGATAT
CGTCCAAACTCTAACCTTATTTGAAGATAGAGAAATGATTAAGAAGTGTCTTGACATCTATA
AAGATTTTTTTACAGAGTCACAGCTTAAAAAGCTCTATCGCCGTCACTATACTGGCTGGGGA
CGATTGTCTGCTAAGCTAATAAATGGCATCCGAAATAAAGAGAATCAAAAAACAATCTTGG
ACTATCTTATTGATGATGGAAGTGCAAACCGAAACTTCATGCAGTTGATAAATGATGATGAT
CTATCATTTAAACCAATTATTGACAAGGCACGAACTGGTAGTCATTCGGATAATCTGAAAGA
AGTTGTAGGTGAACTTGCTGGTAGCCCTGCTATTAAAAAAGGGATTCTACAAAGTTTGAAAA
TAGTTGATGAGCTGGTTAAAGTCATGGGCTATGAACCTGAACAAATCGTGGTTGAAATGGC
ACGTGAGAACCAAACGACAGCAAAAGGATTAAGTCGTTCACGACAACGCTTGACAACCTTG
AGAGAATCTCTTGCTAATTTGAAGAGTAATATTTTGGAAGAGAAAAAGCCTAAGTATGTGA
AAGATCAAGTTGAAAATCATCATTTATCTGATGACCGTCTTTTCCTTTACTACTTACAAAACG
GAAGAGATATGTATACAAAAAAGGCTCTGGATATTGATAATTTAAGTCAATATGATATTGA
CCACATTATTCCTCAAGCTTTCATAAAAGATGATTCTATTGATAATCGTGTTTTGGTATCATC
TGCTAAAAATCGTGGAAAATCAGATGATGTTCCTAGCATTGAAATTGTAAAAGCTCGCAAA
ATGTTCTGGAAAAATTTACTGGATGCTAAGTTAATGAGTCAGCGTAAGTATGATAATTTGAC
TAAGGCAGAGCGCGGAGGCCTAACTTCCGATGATAAGGCAAGATTTATCCAACGTCAGTTG
GTTGAGACTCGACAAATTACCAAGCATGTAGCTCGTATCTTGGATGAACGCTTCAATAATGA
AGTTGATAATGGTAAAAAGATTTGCAAGGTTAAAATTGTAACCTTGAAGTCAAATTTGGTTT
CAAATTTCCGAAAAGAATTTGGATTCTATAAAATTCGTGAAGTTAATGATTATCACCATGCA
CACGATGCTTATCTTAATGCAGTAGTTGCCAAAGCTATTCTAACCAAATATCCACAGTTAGA
GCCAGAGTTTGTCTACGGAATGTATAGACAGAAAAAACTTTCGAAAATCGTTCATGAGGAT
AAGGAAGAAAAATATAGTGAAGCAACCAGGAAAATGTTTTTCTACTCCAACTTGATGAATA
TGTTCAAAAGAGTTGTGAGGTTAGCAGATGGTTCTATTGTTGTAAGACCAGTAATAGAAACT
GGTAGATATATGAGAAAAACTGCATGGGATAAAAAGAAACACTTTGCGACAGTTAGAAAA
GTCTTGTCATACCCTCAGAACAATATCGTGAAGAAGACAGAGATTCAGACAGGTGGTTTCTC
TAAGGAATCAATCTTGGCGCATGGTAACTCAGATAAGTTGATTCCAAGAAAAACGAAGGAT
ATTTATTTAGATCCTAAGAAATATGGAGGTTTTGATAGTCCGATAGTAGCTTACTCTGTTTTA
GTTGTAGCTGATATCAAAAAAGGTAAAGCACAAAAACTAAAAACAGTTACGGAACTTTTAG
GAATTACCATCATGGAGAGGTCCAGATTTGAGAAAAATCCATCAGCTTTCCTTGAATCAAAA
GGTTATTTAAATATTAGGGACGATAAATTAATGATTTTACCGAAGTATAGTCTGTTCGAATT
AGAAAATGGGCGTCGTCGATTACTTGCTAGTGCTGGTGAATTACAAAAAGGTAACGAGCTA
GCCTTACCAACACAATTTATGAAGTTCTTATACCTTGCAAGTCGTTATAATGAGTCAAAAGG
TAAACCAGAGGAGATTGAGAAGAAACAAGAATTTGTAAATCAACATGTCTCTTATTTTGAT
GACATCCTTCAATTAATTAATGATTTTTCAAAACGAGTTATTCTAGCAGATGCTAATTTAGA
GAAAATCAATAAGCTTTACCAGGATAATAAGGAAAATATACCAGTAGATGAACTTGCTAAT
AATATTATCAATCTATTTACTTTTACCAGTCTAGGAGCTCCAGCAGCTTTTAAATTTTTTGAT
AAAATAGTTGATAGAAAACGCTATACATCAACTAAAGAAGTACTTAATTCTACTCTAATCCA
TCAATCTATTACTGGACTTTATGAAACACGTATTGATTTGGGTAAATTAGGAGAAGATTGA
(SEQ ID NO: 494)

SEQ ID NO: 495:
ATGGCAGGTTGGCGAACTGTTGTTGTAAATACACATTCTAAGCTCTCTTATAAAAATAATCA
TCTGATTTTTAAAGATTCTTATCAGACGGAAATGATTCATCTTTCAGAGATTGATATTCTAAT
CATGGAAACGACAGATATTGTTTTGTCGACTATGCTGATTAAACGTTTGGTTGATGAAAATA
TTTTAGTCATATTTTGTGATGATAAACGCTTGCCAACAGCTATGTTAATGCCGTACTATGCTA
GACATGATTCGAGTTTACAATTATCTAGGCAGATGTCATGGATTGAGGATGTCAAAGCGGAT
GTTTGGACATCAATTATTGCACAAAAAATTTTGAATCAGTCCTTTTATCTCGGTGAGTGTTCT
TTCTTTGAAAAATCCCAGTCTATTATGAATCTCTATCATGATTTAGAATCTTTTGACCCTTCC
AATCGTGAAGGTCATGCAGCTAGGATTTATTTCAATACACTTTTTGGAAATGATTTTTCAAG
AGAGCAGGATAATCCAATAAATGCTGGTTTAGACTATGGATATTCTCTGATTTTGAGTATGT

-continued
TTGCGCGTGAAGTTGTTAAGTGTGGTTGCATGACACAATTTGGCTTAAAGCATGCTAATCAA
TTTAATCAGTTCAACCTAGCAAGCGATATTATGGAACCATTTCGCCCAATCGTTGATAGGAT
TATTTATGAAAATAGGCAGAGTGATTTTGTCAAAATGAAAAGAGAACTCTTTTCTATGTTTT
CAGAGACATACAGCTACAACGGTAAAGAAATGTATCTTTCAAATATTGTCAGCGATTACAC
CAAAAAAGTTATTAAGTCGCTAAATAGTGATGGGAATGGAATTCCGGAGTTTAGGATATGA
(SEQ ID NO: 495)

SEQ ID NO: 496:
ATGAGTTATCGGTATATGAGAATGATTTTAATGTTTGATATGCCTACTGAAACAGTAGAAGA
ACGTAAGGCGTATCGTAAGTTTAGAAAGTTTCTGTTGAGCGAAGGTTTTATTATGCATCAGT
TCTCTGTTTATAGTAAATTATTGCTCAATAATACAGCTAATAATGCCATGATAGGTCGGCTT
AAAGTGAATAATCCTAAGAAAGGGAGTATAACTCTTTTGACAGTTACCGAGAAGCAGTTTG
CAAGGATGGTTTATCTACATGGTGAACATAATATGAGTGTTGCCAACTCTGATAGTCGCTTG
GTTTTCCTAGGAGATTCTTATGATCAAGATTAA (SEQ ID NO: 496)

SEQ ID NO: 497:
ATGATCAAGATTAATTTTCCAATTTTAGATGAACCATTAGTGTTAAGTAATGCTACGATTTTA
ACGATAGAAGATGTTTCAGTTTATTCTTCATTGGTGAAACATTTTTATCAATATGACGTAGAT
GAACATTTGAAATTATTTGATGATAAGCAGAAAAGTCTGAAGGCAACGGAGTTAATGTTAG
TTACAGATATCTTAGGATACGATGTCAACTCAGCACCTATTCTAAAGTTGATACATGGTGAC
TTAGAAAATCAATTCAACGAAAAGCCAGAAGTGAAATCAATGGTAGAAAAAATTAGCAGCTA
CTATTACAGAACTTATCGCATTTGAGTGTCTAGAGAATGAGCTTGATTTAGAATACGATGAA
ATTACGATTTTAGAACTCATTAAGGCACTGGGAGTCAAAATTGAGACACAGAGCGACACTA
TCTTTGAAAAATGTTTTGAAATTATACAAGTTTACCATTATTTAACGAAAAAGAATCTCTTA
GTTTTTGTTAATAGCGGAGCTTATCTTACCAAAGATGAAGTTATAAAATTATGTGAATACAT
CAATTTAATGCAAAAGTCAGTACTCTTTCTAGAACCTAGAAGACTCTATGATTTACCGCAAT
ATGTTATTGATAAGGATTATTTCTTGATAGGCGAAAATATGGTATAA (SEQ ID NO: 497)

SEQ ID NO: 498:
ATGAAAAAACCTTACTCTATTGGACTTGATATTGGAACCAATTCTGTTGGTTGGGCTGTTGT
GACAGATGACTACAAAGTTCCTGCTAAGAAGATGAAGGTTCTGGGAAATACAGATAAAAGT
CATATCGAGAAAAATTTGCTTGGCGCTTTATTATTTGATAGCGGGAATACTGCAGAAGACAG
ACGGTTAAAGAGAACTGCTCGCCGTCGTTACACACGTCGCAGAAATCGTATTTTATATTTGC
AAGAGATTTTTTCAGAAGAAATGGGCAAGGTAGATGATAGTTTCTTTCATCGTTTAGAGGAT
TCTTTTCTTGTTACTGAGGATAAACGAGGAGAGCGCCATCCCATTTTTGGGAATCTTGAAGA
AGAAGTTAAGTATCATGAAAATTTTCCAACCATTTATCATTTGCGGCAATATCTTGCGGATA
ATCCAGAAAAAGTTGATTTGCGTTTAGTTTATTTGGCTTTGGCACATATAATTAAGTTTAGA
GGTCATTTTTTAATTGAAGGAAAGTTTGATACACGCAATAATGATGTACAAAGACTGTTTCA
AGAATTTTTAGCAGTCTATGATAATACTTTTGAGAATAGTTCGCTTCAGGAGCAAAATGTTC
AAGTTGAAGAAATTCTGACTGATAAAATCAGTAAATCTGCTAAGAAAGATAGAGTTTTGAA
ACTTTTTCCTAATGAAAAGTCTAATGGCCGCTTTGCAGAATTTCTAAAACTAATTGTTGGTA
ATCAAGCTGATTTTAAAAAGCATTTTGAATTAGAAGAGAAAGCACCATTGCAATTTTCTAAA
GATACTTATGAAGAAGAGTTAGAAGTACTATTAGCTCAAATTGGAGATAATTACGCAGAGC
TCTTTTTATCAGCAAAGAAACTGTATGATAGTATCCTTTTATCAGGGATTTTAACAGTTACTG
ATGTTGGTACCAAAGCGCCTTTATCTGCTTCGATGATTCAGCGATATAATGAACATCAGATG
GATTTAGCTCAGCTTAAACAATTCATTCGTCAGAAATTATCAGATAAATATAACGAAGTTTT
TTCTGATGTTTCAAAAGACGGCTATGCGGGTTATATTGATGGGAAAACAAATCAAGAAGCTT
TTTATAAATACCTTAAAGGTCTATTAAATAAGATTGAGGGAAGTGGCTATTTCCTTGATAAA
ATTGAGCGTGAAGATTTTCTAAGAAAGCAACGTACCTTTGACAATGGCTCTATTCCACATCA
GATTCATCTTCAAGAAATGCGTGCTATCATTCGTAGACAGGCTGAATTTTATCCGTTTTTAGC
AGACAATCAAGATAGGATTGAGAAATTATTGACTTTCCGTATTCCCTACTATGTTGGTCCAT
TAGCGCGCGGAAAAAGTGATTTTGCTTGGTTAAGTCGGAAATCGGCTGATAAAATTACACC
ATGGAATTTTGATGAAATCGTTGATAAAGAATCCTCTGCAGAAGCTTTTATCAATCGTATGA
CAAATTATGATTTGTACTTGCCAAATCAAAAAGTTCTTCCTAAACATAGTTTATTATATACGAA
AAATTTACTGTTTACAATGAATTAACAAAGGTTAAATATAAAACAGAGCAAGGAAAAACAG
CATTTTTTGATGCCAATATGAAGCAAGAAATCTTTGATGGCGTATTTAAGGTTTATCGAAAA
GTAACTAAAGATAAATTAATGGATTTCCTTGAAAAAGAATTTGATGAATTTCGTATTGTTGA
TTTAACAGGTCTGGATAAAGAAAATAAAGTATTTAACGCTTCTTATGGAACTTATCATGATT
TGTGTAAAATTTTAGATAAAGATTTTCTCGATAATTCAAAGAATGAAAAGATTTTAGAAGAT
ATTGTGTTGACCTTAACGTTATTTGAAGATAGAGAAATGATTAGAAAACGTCTAGAAAATTA
CAGTGATTTATTGACCAAAGAACAAGTGAAAAAGCTGGAAAGACGTCATTATACTGGTTGG
GGAAGATTATCAGCTGAGTTAATTCATGGTATTCGCAATAAAGAAAGCAGAAAAACAATTC
TTGATTATCTCATTGATGATGGCAATAGCAATCGGAACTTTATGCAACTGATTAACGATGAT
GCTCTTTCTTTCAAAGAAGAGATTGCTAAGGCACAAGTTATTGGAGAAACAGACAATCTAA
ATCAAGTTGTTAGTGATATTGCTGGCAGCCCTGCTATTAAAAAAGGAATTTTACAAAGCTTG
AAGATTGTTGATGAGCTTGTCAAAATTATGGGACATCAACCTGAAAATATCGTCGTGGAGAT
GGCGCGTGAAAACCAGTTTACCAATCAGGGACGACGAAATTCACAGCAACGTTTGAAAGGT
TTGACAGATTCTATTAAAGAATTTGGAAGTCAAATTCTTAAAGAACATCCGGTTGAGAATTC
ACAGTTACAAAATGATAGATTGTTTCTATATTATTTACAAAACGGCAGAGATATGTATACTG
GAGAAGAATTGGATATTGATTATCTAAGCCAGTATGATATAGACCATATTATCCCGCAAGCT
TTTATAAAGGATAATTCTATTGATAATAGAGTATTGACTAGCTCAAAGGAAAATCGTGGAA
AATCGGATGATGTACCAAGTAAAGATGTTGTTCGTAAAATGAAATCCTATTGGAGTAAGCT
ACTTTCGGCAAAGCTTATTACACAACGTAAATTTGATAATTTGACAAAAGCTGAACGAGGTG
GATTGACCGACGATGATAAAGCTGGATTCATCAAGCGTCAATTAGTAGAAACACGACAAAT
TACCAAACATGTAGCACGTATTCTGGACGAACGATTTAATACAGAAACAGATGAAAACAAC
AAGAAAATTCGTCAAGTAAAAATTGTGACCTTGAAATCAAATCTTGTTTCCAATTTCCGTAA
AGAGTTTGAACTCTACAAAGTGCGTGAAATTAATGACTATCATCATGCACATGATGCCTATC
TCAATGCTGTAATTGGAAAGGCTTTACTAGGTGTTTACCCACAATTGGAACCTGAATTTGTT
TATGGTGATTATCCTCATTTTCATGGACATAAAGAAAATAAAGCAACTGCTAAGAAATTTTT
CTATTCAAATATTATGAACTTCTTTAAAAAAGATGATGTCCGTACTGATAAAAATGGTGAAA
TTATCTGGAAAAAAGATGAGCATATTTCTAATATTAAAAAAGTGCTTTCTTATCCACAAGTT

-continued

AATATTGTTAAGAAAGTAGAGGAGCAAACGGGAGGATTTTCTAAAGAATCTATCTTGCCGA
AAGGTAATTCTGACAAGCTTATTCCTCGAAAAACGAAGAAATTTTATTGGGATACCAAGAA
ATATGGAGGATTTGATAGCCCGATTGTTGCTTATTCTATTTTAGTTATTGCTGATATTGAAAA
AGGTAAATCTAAAAAATTGAAAACAGTCAAAGCCTTAGTTGGTGTCACTATTATGGAAAAG
ATGACTTTTGAAAGGGATCCAGTTGCTTTTCTTGAGCGAAAAGGCTATCGAAATGTTCAAGA
AGAAAATATTATAAAGTTACCAAAATATAGTTTATTTAAACTAGAAAACGGACGAAAAAGG
CTATTGGCAAGTGCTAGGGAACTTCAAAAGGGAAATGAAATCGTTTTGCCAAATCATTTAG
GAACCTTGCTTTATCACGCTAAAAATATTCATAAAGTTGATGAACCAAAGCATTTGGACTAT
GTTGATAAACATAAAGATGAATTTAAGGAGTTGCTAGATGTTGTGTCAAACTTTTCTAAAAA
ATATACTTTAGCAGAAGGAAATTTAGAAAAAATCAAAGAATTATATGCACAAAATAATGGT
GAAGATCTTAAAGAATTAGCAAGTTCATTTATCAACTTATTAACATTTACTGCTATAGGAGC
ACCGGCTACTTTTAAATTCTTTGATAAAAATATTGATCGAAAACGATATACTTCAACTACTG
AAATTCTCAACGCTACCCTCATCCACCAATCCATCACCGGTCTTTATGAAACGCGGATTGAT
CTCAATAAGTTAGGAGGAGACTAATGGGCTGGCGGACAGTGGTTGTTAATACGCATTCCAA
GTTGTCTTATAAGAACAACCACTTGATTTTTAAAGATGCTTATCAGACAGAGATGATTCATC
TGTCTGAGATTGACATCTTATTACTTGAGACAACAGATATTGTTTTGTCAACTATGCTAATCA
AACGCTTGGTTGATGAGAATATTTTGGTCATTTTTTGTGATGACAAACGTCTGCCAACAGCC
ATGCTCATGCCTTACTATGCGCGTCACGATTCCAGCTTGCAGCTGAGTCATCAGATTTCTTGG
ACAGAAGAAGTGAAATGCGATGTCTGGACAACAATCATCGCTCAAAAGATTTTGAATCAGT
CATGTTATTTGGGAGAATGTTTTTATTTTGAAAAATCTCAGTCAATTATGGATTTATATCATG
ACTTAGAGCCTTTTGACCCTAGTAATCGAGAAGGACATTCTGCGCGGATTTATTTCAATACC
TTATTTGGAAATGTTTTTTCCAGAGAACAAGATAATGATATTAATGCAGGTCTTGACTATGG
TTATACGCTGCTGTTAAGTATGTTTGCGCGTGAAGTGGTTGTATCTGGCTGTATGACACAATT
TGGTCTCAAGCATGCCAACCAATTCAATCAGTTTAACTTTGCCAGTGATATTATGGAGCCTT
TTCGTCCAATTGTTGACCGTATTGTTTATGAAAATCGAAATAACTCTTTTATTAAAATAAAAC
GTGAGCTATTCAGCATGTTTTCAGACACCTATCTTTATAATAATAAGGAGATGTATTTGACA
AATATTGTCAGCGATTATACCAAAAAGGTAATCAAGGCGCTGAATAATGATGGGAAAGGAG
TTCCTGAGTTTAGGATATGAGTTACCGATATATGCGAATGATTTTAATGTTTGATATGCCAA
CAGATACTGCTGAGGAACGCAAAGCTTATCGTAAATTTCGGAAATTTTTACTGAGCGAAGGT
TTCATCATGCATCAGTTTTCAGTATACAGCAAGCTGCTTTTGAATAACTCTGCCAATACAGC
CATGATTGCCCGCTTGAAGGAGAATAATCCAAAGAAGGGCAATATCACCTTGTTGACCGTG
ACTGAAAAGCAGTTTGCCCGTATGATTTACCTGAATGGTGAGCGTGATACTAGCATTGCTAA
TTCGGATTCACGACTGGTCTTTCTAGGGGAGGCTTTTCCTGATGAAACTTAATTTTCCTATAT
TGGATGAACCAATAACTCTTGAAAAATCTACGATTTTGGTATTAGAAGATGTGCAAGTTTTT
GCTCAAATGGTGAGAAATCTTTATCAATATGATGAAGATAGTGAACTTAAATTTTTTAATAG
AAAATTTAAGAGTCTGAAACCATCTGAGTTAATGCTTGTGACAGATATTTTAGGTTATGATG
TCAATGCCCCGTCCTTGCTGAAGTTGGTTCACGCTGATTTAGAAAATCAGTTTAATGAAAAA
CCAGAGGTTAAGTCTATGGTTGAAAAACTGGCAAATACCATTACGGAATTAATTGCTTATGA
ATGTTTAGAAAATGAATTGGACTTAGAATATGATGAGATTACTATTTTAGAGTTAATCAAAG
CTTTAGGCGTCAAAATTGAAACACAAAGTGATACCATTTTTGAAAAAATGTTTGAAGTCCTT
CAAGTTTATAAGTATCTAAATAAAAAGAAGCTTCTCGTTTTTATCAATACTTTATCCTATTTT
AAAAGAGAAGAAATCGCGCAAATTCTAGAATATATTCACTTATCCGATATGGTTGTTTTATT
TCTTGAACCCCGTAAAATTGATGGTTTTGCTCAATATATTTTAGATGAAGATTATTTCTTGAT
AACAGAAAGCAACAACTAAATACGAATAATAAGATAGTTTCTAAATCAGGGGCTGTCTTTT
ATTATGGATTGACAAATGCGTATAATGCGTATAAAATAAAAAGAGAAATGTTATTTGCCATT
AACAGGGAAAGAATTAGCTAAATTAGCGATAAACAATGGATGGGAAGAAGTTCGGGTGAG
AGGAAGTCATCATCATTTCAAGAAAGATGGAGTATCTTATATTGTGACGATTCCTATTCATG
GAAATAAAGTGCTTAAAATTGGTCTTGAAAAGAAACTCTTAAGGGATTTAAATTTATTATGA
TAGAGGAGGAAGTCGTCATGTTAAAATCATATCCTGTAATTTTTCATAAGGAAGAGGAAGG
GTATTGGGTTGAATTTCCTGAATTTGGCGGTGGTACGCAAGGGGAAGATTTGGAAGAAGCC
ATGAAGAACGCTCGTCAGATGTTAGAAAGTGTGTTGGCATCTTATCTTGATGAAGGGTTGGT
TCTACCCATTTCAAGCGATATTCAGAAAATATCTGTTGAAGATGGTTTTGCGACCATGATTC
AAGCTGATCCTAGTCCTTATCTCAAAAATAACAAAGCTATTCGGAAAAATGTTACCGTGCCT
GAGTGGTTGATACGATTAGCAGACCGTGACCGAGTAAATTATTCTGAAGTATTAACAAAGG
CTTTGGAAAAGAAACTACAATTATAA (SEQ ID NO: 498)

SEQ ID NO: 499:
ATGAAAAAACCTTACTCTATTGGACTTGATATTGGAACCAATTCTGTTGGTTGGGCTGTTGT
GACAGATGACTACAAAGTTCCTGCTAAGAAGATGAAGGTTCTGGGAAATACAGATAAAAGT
CATATCGAGAAAAATTTGCTTGGCGCTTTATTATTTGATAGCGGGAATACTGCAGAAGACAG
ACGGTTAAAGAGAACTGCTCGCCGTCGTTACACACGTCGCAGAAATCGTATTTTATATTTGC
AAGAGATTTTTTCAGAAGAAATGGGCAAGGTAGATGATAGTTTCTTTCATCGTTTAGAGGAT
TCTTTTCTTGTTACTGAGGATAAACGAGGAGAGCGCCATCCCATTTTTGGGAATCTTGAAGA
AGAAGTTAAGTATCATGAAAATTTTCCAACCATTTATCATTTGCGGCAATATCTTGCGGATA
ATCCAGAAAAAGTTGATTTGCGTTTAGTTTATTTGGCTTTGGCACATATAATTAAGTTTAGA
GGTCATTTTTTAATTGAAGGAAAGTTTGATACACGCAATAATGATGTACAAAGACTGTTTCA
AGAATTTTTAGCAGTCTATGATAATACTTTTGAGAATAGTTCGCTTCAGGAGCAAAATGTTC
AAGTTGAAGAAATTCTGACTGATAAAATCAGTAAATCTGCTAAGAAAGATAGAGTTTTGAA
ACTTTTTCCTAATGAAAAGTCTAATGGCCGCTTTGCAGAATTTCTAAAACTAATTGTTGGTA
ATCAAGCTGATTTTAAAAAGCATTTTGAATTAGAAGAGAAAGCACCATTGCAATTTTCTAAA
GATACTTATGAAGAAGAGTTAGAAGTACTATTAGCTCAAATTGGAGATAATTACGCAGAGC
TCTTTTTATCAGCAAAGAAACTGTATGATAGTATCCTTTTATCAGGGATTTTAACAGTTACTG
ATGTTGGTACCAAAGCGCCTTTATCTGCTTCGATGATTCAGCGATATAATGAACATCAGATG
GATTTAGCTCAGCTTAAACAATTCATTCGTCAGAAATTATCAGATAAATATAACGAAGTTTT
TTCTGATGTTTCAAAAGACGGCTATGCGGGTTATATTGATGGGAAAACAAATCAAGAAGCTT
TTTATAAATACCTTAAAGGTCTATTAAATAAGATTGAGGGAAGTGGCTATTTCCTTGATAAA
ATTGAGCGTGAAGATTTTCTAAGAAAGCAACGTACCTTTGACAATGGCTCTATTCCACATCA
GATTCATCTTCAAGAAATGCGTGCTATCATTCGTAGACAGGCTGAATTTTATCCGTTTTTAGC
AGACAATCAAGATAGGATTGAGAAATTATTGACTTTCCGTATTCCCTACTATGTTGGTCCAT
TAGCGCGCGGAAAAAGTGATTTTGCTTGGTTAAGTCGGAAATCGGCTGATAAAATTACACC
ATGGAATTTTGATGAAATCGTTGATAAAGAATCCTCTGCAGAAGCTTTTATCAATCGTATGA

-continued

CAAATTATGATTTGTACTTGCCAAATCAAAAAGTTCTTCCTAAACATAGTTTATTATACGAA
AAATTTACTGTTTACAATGAATTAACAAAGGTTAAATATAAAACAGAGCAAGGAAAAACAG
CATTTTTTGATGCCAATATGAAGCAAGAAATCTTTGATGGCGTATTTAAGGTTTATCGAAAA
GTAACTAAAGATAAATTAATGGATTTCCTTGAAAAAGAATTTGATGAATTTCGTATTGTTGA
TTTAACAGGTCTGGATAAAGAAAATAAAGTATTTAACGCTTCTTATGGAACTTATCATGATT
TGTGTAAAATTTTAGATAAAGATTTTCTCGATAATTCAAAGAATGAAAAGATTTTAGAAGAT
ATTGTGTTGACCTTAACGTTATTTGAAGATAGAGAAATGATTAGAAAACGTCTAGAAAATTA
CAGTGATTTATTGACCAAAGAACAAGTGAAAAAGCTGGAAAGACGTCATTATACTGGTTGG
GGAAGATTATCAGCTGAGTTAATTCATGGTATTCGCAATAAAGAAAGCAGAAAAACAATTC
TTGATTATCTCATTGATGATGGCAATAGCAATCGGAACTTTATGCAACTGATTAACGATGAT
GCTCTTTCTTTCAAAGAAGAGATTGCTAAGGCACAAGTTATTGGAGAAACAGACAATCTAA
ATCAAGTTGTTAGTGATATTGCTGGCAGCCCTGCTATTAAAAAAGGAATTTTACAAAGCTTG
AAGATTGTTGATGAGCTTGTCAAAATTATGGGACATCAACCTGAAAATATCGTCGTGGAGAT
GGCGCGTGAAAACCAGTTTACCAATCAGGGACGACGAAATTCACAGCAACGTTTGAAAGGT
TTGACAGATTCTATTAAAGAATTTGGAAGTCAAATTCTTAAAGAACATCCGGTTGAGAATTC
ACAGTTACAAAATGATAGATTGTTTCTATATTATTTACAAAACGGCAGAGATATGTATACTG
GAGAAGAATTGGATATTGATTATCTAAGCCAGTATGATATAGACCATATTATCCCGCAAGCT
TTTATAAAGGATAATTCTATTGATAATAGAGTATTGACTAGCTCAAAGGAAAATCGTGGAA
AATCGGATGATGTACCAAGTAAAGATGTTGTTCGTAAAATGAAATCCTATTGGAGTAAGCT
ACTTTCGGCAAAGCTTATTACACAACGTAAATTTGATAATTTGACAAAAGCTGAACGAGGTG
GATTGACCGACGATGATAAAGCTGGATTCATCAAGCGTCAATTAGTAGAAACACGACAAAT
TACCAAACATGTAGCACGTATTCTGGACGAACGATTTAATACAGAAACAGATGAAAACAAC
AAGAAAATTCGTCAAGTAAAAATTGTGACCTTGAAATCAAATCTTGTTTCCAATTTCCGTAA
AGAGTTTGAACTCTACAAAGTGCGTGAAATTAATGACTATCATCATGCACATGATGCCTATC
TCAATGCTGTAATTGGAAAGGCTTTACTAGGTGTTTACCCACAATTGGAACCTGAATTTGTT
TATGGTGATTATCCTCATTTTCATGGACATAAAGAAAATAAAGCAACTGCTAAGAAATTTTT
CTATTCAAATATTATGAACTTCTTTAAAAAAGATGATGTCCGTACTGATAAAAATGGTGAAA
TTATCTGGAAAAAAGATGAGCATATTTCTAATATTAAAAAAGTGCTTTCTTATCCACAAGTT
AATATTGTTAAGAAAGTAGAGGAGCAAACGGGAGGATTTTCTAAAGAATCTATCTTGCCGA
AAGGTAATTCTGACAAGCTTATTCCTCGAAAAACGAAGAAATTTTATTGGGATACCAAGAA
ATATGGAGGATTTGATAGCCCGATTGTTGCTTATTCTATTTTAGTTATTGCTGATATTGAAAA
AGGTAAATCTAAAAAATTGAAAACAGTCAAAGCCTTAGTTGGTGTCACTATTATGGAAAAG
ATGACTTTTGAAAGGGATCCAGTTGCTTTTCTTGAGCGAAAAGGCTATCGAAATGTTCAAGA
AGAAAATATTATAAAGTTACCAAAATATAGTTTATTTAAACTAGAAAACGGACGAAAAAGG
CTATTGGCAAGTGCTAGGGAACTTCAAAAGGGAAATGAAATCGTTTTGCCAAATCATTTAG
GAACCTTGCTTTATCACGCTAAAAATATTCATAAAGTTGATGAACCAAAGCATTTGGACTAT
GTTGATAAACATAAAGATGAATTTAAGGAGTTGCTAGATGTTGTGTCAAACTTTTCTAAAAA
ATATACTTTAGCAGAAGGAAATTTAGAAAAAATCAAAGAATTATATGCACAAAATAATGGT
GAAGATCTTAAAGAATTAGCAAGTTCATTTATCAACTTATTAACATTTACTGCTATAGGAGC
ACCGGCTACTTTTAAATTCTTTGATAAAAATATTGATCGAAAACGATATACTTCAACTACTG
AAATTCTCAACGCTACCCTCATCCACCAATCCATCACCGGTCTTTATGAAACGCGGATTGAT
CTCAATAAGTTAGGAGGAGACTAA (SEQ ID NO: 499)

SEQ ID NO: 500:
ATGGGCTGGCGGACAGTGGTTGTTAATACGCATTCCAAGTTGTCTTATAAGAACAACCACTT
GATTTTTAAAGATGCTTATCAGACAGAGATGATTCATCTGTCTGAGATTGACATCTTATTACT
TGAGACAACAGATATTGTTTTGTCAACTATGCTAATCAAACGCTTGGTTGATGAGAATATTT
TGGTCATTTTTTGTGATGACAAACGTCTGCCAACAGCCATGCTCATGCCTTACTATGCGCGTC
ACGATTCCAGCTTGCAGCTGAGTCATCAGATTTCTTGGACAGAAGAAGTGAAATGCGATGTC
TGGACAACAATCATCGCTCAAAAGATTTTGAATCAGTCATGTTATTTGGGAGAATGTTTTTA
TTTTGAAAAATCTCAGTCAATTATGGATTTATATCATGACTTAGAGCCTTTTGACCCTAGTAA
TCGAGAAGGACATTCTGCGCGGATTTATTTCAATACCTTATTTGGAAATGTTTTTTTCCAGAG
AACAAGATAATGATATTAATGCAGGTCTTGACTATGGTTATACGCTGCTGTTAAGTATGTTT
GCGCGTGAAGTGGTTGTATCTGGCTGTATGACACAATTTGGTCTCAAGCATGCCAACCAATT
CAATCAGTTTAACTTTGCCAGTGATATTATGGAGCCTTTTCGTCCAATTGTTGACCGTATTGT
TTATGAAAATCGAAATAACTCTTTTATTAAAATAAAACGTGAGCTATTCAGCATGTTTTCAG
ACACCTATCTTTATAATAATAAGGAGATGTATTTGACAAATATTGTCAGCGATTATACCAAA
AAGGTAATCAAGGCGCTGAATAATGATGGGAAAGGAGTTCCTGAGTTTAGGATATGA (SEQ
ID NO: 500)

SEQ ID NO: 501:
ATGCGAATGATTTTAATGTTTGATATGCCAACAGATACTGCTGAGGAACGCAAAGCTTATCG
TAAATTTCGGAAATTTTTACTGAGCGAAGGTTTCATCATGCATCAGTTTTCAGTATACAGCA
AGCTGCTTTTGAATAACTCTGCCAATACAGCCATGATTGCCCGCTTGAAGGAGAATAATCCA
AAGAAGGGCAATATCACCTTGTTGACCGTGACTGAAAAGCAGTTTGCCCGTATGATTTACCT
GAATGGTGAGCGTGATACTAGCATTGCTAATTCGGATTCACGACTGGTCTTTCTAGGGGAGG
CTTTTCCTGATGAAACTTAA (SEQ ID NO: 501)

SEQ ID NO: 502:
ATGGTGAGAAATCTTTATCAATATGATGAAGATAGTGAACTTAAATTTTTTAATAGAAAATT
TAAGAGTCTGAAACCATCTGAGTTAATGCTTGTGACAGATATTTTAGGTTATGATGTCAATG
CCCCGTCCTTGCTGAAGTTGGTTCACGCTGATTTAGAAAATCAGTTTAATGAAAAACCAGAG
GTTAAGTCTATGGTTGAAAAACTGGCAAATACCATTACGGAATTAATTGCTTATGAATGTTT
AGAAAATGAATTGGACTTAGAATATGATGAGATTACTATTTTAGAGTTAATCAAAGCTTTAG
GCGTCAAAATTGAAACACAAAGTGATACCATTTTTGAAAAAATGTTTGAAGTCCTTCAAGTT
TATAAGTATCTAAATAAAAAGAAGCTTCTCGTTTTTATCAATACTTTATCCTATTTTAAAAGA
GAAGAAATCGCGCAAATTCTAGAATATATTCACTTATCCGATATGGTTGTTTTATTTCTTGAA
CCCCGTAAAATTGATGGTTTTGCTCAATATATTTAGATGAAGATTATTTCTTGATAACAGA
AAGCAACAACTAA (SEQ ID NO: 502)

-continued

SEQ ID NO: 503:
ATGTTAAAATCATATCCTGTAATTTTTCATAAGGAAGAGGAAGGGTATTGGGTTGAATTTCC
TGAATTTGGCGGTGGTACGCAAGGGGAAGATTTGGAAGAAGCCATGAAGAACGCTCGTCAG
ATGTTAGAAAGTGTGTTGGCATCTTATCTTGATGAAGGGTTGGTTCTACCCATTTCAAGCGA
TATTCAGAAAATATCTGTTGAAGATGGTTTTGCGACCATGATTCAAGCTGATCCTAGTCCTT
ATCTCAAAAATAACAAAGCTATTCGGAAAAATGTTACCGTGCCTGAGTGGTTGATACGATTA
GCAGACCGTGACCGAGTAAATTATTCTGAAGTATTAACAAAGGCTTTGGAAAAGAAACTAC
AATTATAA (SEQ ID NO: 503)

SEQ ID NO: 504:
ATGGATAAGAAATACTCAATAGGCTTAGATATCGGCACAAATAGCGTCGGATGGGCGGTGA
TCACTGATGAATATAAGGTTCCGTCTAAAAAGTTCAAGGTTCTGGGAAATACAGACCGCCA
CAGTATCAAAAAAAATCTTATAGGGGCTCTTTTATTTGACAGTGGAGAGACAGCGGAAGCG
ACTCGTCTCAAACGGACAGCTCGTAGAAGGTATACACGTCGGAAGAATCGTATTTGTTATCT
ACAGGAGATTTTTTCAAATGAGATGGCGAAAGTAGATGATAGTTTCTTTCATCGACTTGAAG
AGTCTTTTTTGGTGGAAGAAGACAAGAAGCATGAACGTCATCCTATTTTTGGAAATATAGTA
GATGAAGTTGCTTATCATGAGAAATATCCAACTATCTATCATCTGCGAAAAAAATTGGTAGA
TTCTACTGATAAAGCGGATTTGCGCTTAATCTATTTGGCCTTAGCGCATATGATTAAGTTTCG
TGGTCATTTTTTGATTGAGGGAGATTTAAATCCTGATAATAGTGATGTGGACAAACTATTTA
TCCAGTTGGTACAAACCTACAATCAATTATTTGAAGAAAACCCTATTAACGCAAGTGGAGTA
GATGCTAAAGCGATTCTTTCTGCACGATTGAGTAAATCAAGACGATTAGAAAATCTCATTGC
TCAGCTCCCCGGTGAGAAGAAAAATGGCTTATTTGGGAATCTCATTGCTTTGTCATTGGGTT
TGACCCCTAATTTTAAATCAAATTTTGATTTGGCAGAAGATGCTAAATTACAGCTTTCAAAA
GATACTTACGATGATGATTTAGATAATTTATTGGCGCAAATTGGAGATCAATATGCTGATTT
GTTTTTGGCAGCTAAGAATTTATCAGATGCTATTTTACTTTCAGATATCCTAAGAGTAAATAC
TGAAATAACTAAGGCTCCCCTATCAGCTTCAATGATTAAACGCTACGATGAACATCATCAAG
ACTTGACTCTTTTAAAAGCTTTAGTTCGACAACAACTTCCAGAAAAGTATAAAGAAATCTTT
TTTGATCAATCAAAAAACGGATATGCAGGTTATATTGATGGGGGAGCTAGCCAAGAAGAAT
TTTATAAATTTATCAAACCAATTTTAGAAAAAATGGATGGTACTGAGGAATTATTGGTGAAA
CTAAATCGTGAAGATTTGCTGCGCAAGCAACGGACCTTTGACAACGGCTCTATTCCCCATCA
AATTCACTTGGGTGAGCTGCATGCTATTTTGAGAAGACAAGAAGACTTTTATCCATTTTTAA
AAGACAATCGTGAGAAGATTGAAAAAATCTTGACTTTTCGAATTCCTTATTATGTTGGTCCA
TTGGCGCGTGGCAATAGTCGTTTTGCATGGATGACTCGGAAGTCTGAAGAAACAATTACCCC
ATGGAATTTTGAAGAAGTTGTCGATAAAGGTGCTTCAGCTCAATCATTTATTGAACGCATGA
CAAACTTTGATAAAAATCTTCCAAATGAAAAAGTACTACCAAAACATAGTTTGCTTTATGAG
TATTTTACGGTTTATAACGAATTGACAAAGGTCAAATATGTTACTGAAGGAATGCGAAAACC
AGCATTTCTTTCAGGTGAACAGAAGAAAGCCATTGTTGATTTACTCTTCAAAACAAATCGAA
AAGTAACCGTTAAGCAATTAAAAGAAGATTATTTCAAAAAAATAGAATGTTTTGATAGTGTT
GAAATTTCAGGAGTTGAAGATAGATTTAATGCTTCATTAGGTACCTACCATGATTTGCTAAA
AATTATTAAAGATAAAGATTTTTTGGATAATGAAGAAAATGAAGATATCTTAGAGGATATT
GTTTTAACATTGACCTTATTTGAAGATAGGGAGATGATTGAGGAAAGACTTAAAACATATGC
TCACCTCTTTGATGATAAGGTGATGAAACAGCTTAAACGTCGCCGTTATACTGGTTGGGGAC
GTTTGTCTCGAAAATTGATTAATGGTATTAGGGATAAGCAATCTGGCAAAACAATATTAGAT
TTTTTGAAATCAGATGGTTTTGCCAATCGCAATTTTATGCAGCTGATCCATGATGATAGTTTG
ACATTTAAAGAAGACATTCAAAAAGCACAAGTGTCTGGACAAGGCGATAGTTTACATGAAC
ATATTGCAAATTTAGCTGGTAGCCCTGCTATTAAAAAAGGTATTTTACAGACTGTAAAAGTT
GTTGATGAATTGGTCAAAGTAATGGGGCGGCATAAGCCAGAAAATATCGTTATTGAAATGG
CACGTGAAAATCAGACAACTCAAAAGGGCCAGAAAAATTCGCGAGAGCGTATGAAACGAA
TCGAAGAAGGTATCAAAGAATTAGGAAGTCAGATTCTTAAAGAGCATCCTGTTGAAAATAC
TCAATTGCAAAATGAAAAGCTCTATCTCTATTATCTCCAAAATGGAAGAGACATGTATGTGG
ACCAAGAATTAGATATTAATCGTTTAAGTGATTATGATGTCGATCACATTGTTCCACAAAGT
TTCCTTAAAGACGATTCAATAGACAATAAGGTCTTAACGCGTTCTGATAAAAATCGTGGTAA
ATCGGATAACGTTCCAAGTGAAGAAGTAGTCAAAAAGATGAAAAACTATTGGAGACAACTT
CTAAACGCCAAGTTAATCACTCAACGTAAGTTTGATAATTTAACGAAAGCTGAACGTGGAG
GTTTGAGTGAACTTGATAAAGCTGGTTTTATCAAACGCCAATTGGTTGAAACTCGCCAAATC
ACTAAGCATGTGGCACAAATTTTGGATAGTCGCATGAATACTAAATACGATGAAAATGATA
AACTTATTCGAGAGGTTAAAGTGATTACCTTAAAATCTAAATTAGTTTCTGACTTCCGAAAA
GATTTCCAATTCTATAAAGTACGTGAGATTAACAATTACCATCATGCCCATGATGCGTATCT
AAATGCCGTCGTTGGAACTGCTTTGATTAAGAAATATCCAAAACTTGAATCGGAGTTTGTCT
ATGGTGATTATAAAGTTTATGATGTTCGTAAAATGATTGCTAAGTCTGAGCAAGAAATAGGC
AAAGCAACCGCAAAATATTTCTTTTACTCTAATATCATGAACTTCTTCAAAACAGAAATTAC
ACTTGCAAATGGAGAGATTCGCAAACGCCCTCTAATCGAAACTAATGGGGAAACTGGAGAA
ATTGTCTGGGATAAAGGGCGAGATTTTGCCACAGTGCGCAAAGTATTGTCCATGCCCCAAGT
CAATATTGTCAAGAAAACAGAAGTACAGACAGGCGGATTCTCCAAGGAGTCAATTTTACCA
AAAAGAAATTCGGACAAGCTTATTGCTCGTAAAAAAGACTGGGATCCAAAAAAATATGGTG
GTTTTGATAGTCCAACGGTAGCTTATTCAGTCCTAGTGGTTGCTAAGGTGGAAAAAGGGAAA
TCGAAGAAGTTAAAATCCGTTAAAGAGTTACTAGGGATCACAATTATGGAAAGAAGTTCCT
TTGAAAAAAATCCGATTGACTTTTTAGAAGCTAAAGGATATAAGGAAGTTAAAAAAGACTT
AATCATTAAACTACCTAAATATAGTCTTTTTGAGTTAGAAAACGGTCGTAAACGGATGCTGG
CTAGTGCCGGAGAATTACAAAAAGGAAATGAGCTGGCTCTGCCAAGCAAATATGTGAATTT
TTTATATTTAGCTAGTCATTATGAAAAGTTGAAGGGTAGTCCAGAAGATAACGAACAAAAA
CAATTGTTTGTGGAGCAGCATAAGCATTATTTAGATGAGATTATTGAGCAAATCAGTGAATT
TTCTAAGCGTGTTATTTTAGCAGATGCCAATTTAGATAAAGTTCTTAGTGCATATAACAAAC
ATAGAGACAAACCAATACGTGAACAAGCAGAAAATATTATTCATTTATTTACGTTGACGAA
TCTTGGAGCTCCCGCTGCTTTTAAATATTTTGATACAACAATTGATCGTAAACGATATACGTC
TACAAAAGAAGTTTTAGATGCCACTCTTATCCATCAATCCATCACTGGTCTTTATGAAACAC
GCATTGATTTGAGTCAGCTAGGAGGTGACTGATGGCTGGTTGGCGTACTGTTGTGGTAAATA
CCCACTCGAAATTATCCTATAAGAATAATCATCTGATTTTTAAGGATGCCTATAAAACGGAG
CTGATCCATTTATCAGAAATTGATATTTTGTTATTAGAAACGACCGATATTGTCTTGTCCACT
ATGCTGGTAAAACGGCTAGTGGATGAGAATGTCCTTGTCATATTCTGTGATGATAAACGATT

-continued

ACCAACAGCTATGCTGATGCCTTTTTATGGTCGTCATGATTCGAGTTTACAGCTTGGGAAAC
AAATGTCCTGGTCAGAAACAGTCAAATCGCAGGTTTGGACGACGATTATTGCTCAAAAGAT
TTTGAATCAATCTTGCTATCTAGGAGCATGCTCCTATTTTGAAAAATCCCAATCTATTATGGA
TTTATATCATGGTTTGGAAAATTTTGATCCGAGTAATCGAGAAGGGCATGCAGCGAGAATTT
ATTTTAATACACTTTTTGGGAACGATTTCTCAAGAGATTTGGAGCATCCAATCAATGCAGGT
CTGGATTATGGTTATACTTTATTATTGAGTATGTTTGCGCGTGAAGTGGTTGTGTCTGGATGT
ATGACTCAGTTTGGGCTTAAACACGCTAATCAGTTTAATCAGTTCAATTTTGCTAGCGATATT
ATGGAACCATTTAGGCCTTTAGTGGATAAGATTGTTTATGAAAATCGAAATCAGCCTTTTCC
CAAAATAAAGAGAGAGTTATTTACTTTGTTTTCAGATACATTTTCATATAATGGTAAAGAGA
TGTATCTCACGAATATTATTAGCGATTATACTAAAAAAGTTGTCAAAGCTCTGAATAATGAA
GGGAAAGGAGTTCCTGAATTTAGGATATGAGTTATAGATATATGAGAATGATACTTATGTTT
GATATGCCGACGGACACCGCTGAGGAACGAAAAGCCTATCGAAAATTTCGGAAATTTTTAC
TTAGTGAAGGGTTTATCATGCATCAATTTTCTATTTATAGTAAGTTGCTGTTGAATAATACAG
CTAACAATGCCATGATTGGTCGGCTGAGGGAGCATAATCCTAATAAAGGAAATATTACATT
ACTAACGGTCACGGAAAAACAGTTTGCACGAATGATTTATTTACATGGTGAAAGAAATAAT
TGTATTGCAAACTCCGATGAAAGACTTGTATTTCTTGGGGAGGCTTTTGATGAATCTTAATTT
TTCCTTACTAGATGAACCGATTCCATTAAGAGGCGGTACAATTCTTGTGCTCGAAGATGTCT
GTGTATTTTCAAAAATAGTGCAATATTGTTACCAATATGAGGAAGATTCTGAACTTAAATTT
TTTGATCACAAGATGAAAACAATCAAAGAATCAGAAATCATGCTTGTAACAGATATTTTAG
GATTTGATGTTAACTCCTCAACCATTTTAAAATTGATTCATGCAGATTTAGAATCTCAATTTA
ATGAGAAACCCGAAGTGAAATCGATGATTGACAAATTGGTTGCTACGATTACAGAACTGAT
TGTCTTTGAATGCTTAGAAAATGAATTAGATTTAGAGTATGATGAAATCACAATCCTGGAAT
TGATTAAGTCCTTAGGAGTAAAAGTAGAAACGCAAAGTGATACTATTTTTGAAAAATGTCTA
GAGATACTTCAAATTTTCAAATATCTCACTAAGAAAAAGTTGCTTATTTTTGTCAATAGCGG
AGCTTTTCTAACAAAGGATGAAGTGGCTAGTTTACAAGAGTATATATCATTGACAAATTTAA
CAGTTCTCTTTTTAGAACCACGTGAACTATATGATTTTCCGCAGTATATTTTAGATGAAGATT
ATTTCTTAATAACTAAAAATATGGTATAA (SEQ ID NO: 504)

SEQ ID NO: 505:
ATGGATAAGAAATACTCAATAGGCTTAGATATCGGCACAAATAGCGTCGGATGGGCGGTGA
TCACTGATGAATATAAGGTTCCGTCTAAAAAGTTCAAGGTTCTGGGAAATACAGACCGCCA
CAGTATCAAAAAAAATCTTATAGGGGCTCTTTTATTTGACAGTGGAGAGACAGCGGAAGCG
ACTCGTCTCAAACGGACAGCTCGTAGAAGGTATACACGTCGGAAGAATCGTATTTGTTATCT
ACAGGAGATTTTTTCAAATGAGATGGCGAAAGTAGATGATAGTTTCTTTCATCGACTTGAAG
AGTCTTTTTTGGTGGAAGAAGACAAGAAGCATGAACGTCATCCTATTTTTGGAAATATAGTA
GATGAAGTTGCTTATCATGAGAAATATCCAACTATCTATCATCTGCGAAAAAAATTGGTAGA
TTCTACTGATAAAGCGGATTTGCGCTTAATCTATTTGGCCTTAGCGCATATGATTAAGTTTCG
TGGTCATTTTTTGATTGAGGGAGATTTAAATCCTGATAATAGTGATGTGGACAAACTATTTA
TCCAGTTGGTACAAACCTACAATCAATTATTTGAAGAAAACCCTATTAACGCAAGTGGAGTA
GATGCTAAAGCGATTCTTTCTGCACGATTGAGTAAATCAAGACGATTAGAAAATCTCATTGC
TCAGCTCCCCGGTGAGAAGAAAAATGGCTTATTTGGGAATCTCATTGCTTTGTCATTGGGTT
TGACCCCTAATTTTAAATCAAATTTTGATTTGGCAGAAGATGCTAAATTACAGCTTTCAAAA
GATACTTACGATGATGATTTAGATAATTTATTGGCGCAAATTGGAGATCAATATGCTGATTT
GTTTTTGGCAGCTAAGAATTTATCAGATGCTATTTTACTTTCAGATATCCTAAGAGTAAATAC
TGAAATAACTAAGGCTCCCCTATCAGCTTCAATGATTAAACGCTACGATGAACATCATCAAG
ACTTGACTCTTTTAAAAGCTTTAGTTCGACAACAACTTCCAGAAAAGTATAAAGAAATCTTT
TTTGATCAATCAAAAAACGGATATGCAGGTTATATTGATGGGGGAGCTAGCCAAGAAGAAT
TTTATAAATTTATCAAACCAATTTTAGAAAAAATGGATGGTACTGAGGAATTATTGGTGAAA
CTAAATCGTGAAGATTTGCTGCGCAAGCAACGGACCTTTGACAACGGCTCTATTCCCCATCA
AATTCACTTGGGTGAGCTGCATGCTATTTTGAGAAGACAAGAAGACTTTTATCCATTTTTAA
AAGACAATCGTGAGAAGATTGAAAAAATCTTGACTTTTCGAATTCCTTATTATGTTGGTCCA
TTGGCGCGTGGCAATAGTCGTTTTGCATGGATGACTCGGAAGTCTGAAGAAACAATTACCCC
ATGGAATTTTGAAGAAGTTGTCGATAAAGGTGCTTCAGCTCAATCATTTATTGAACGCATGA
CAAACTTTGATAAAAATCTTCCAAATGAAAAAGTACTACCAAAACATAGTTTGCTTTATGAG
TATTTTACGGTTTATAACGAATTGACAAAGGTCAAATATGTTACTGAAGGAATGCGAAAACC
AGCATTTCTTTCAGGTGAACAGAAGAAAGCCATTGTTGATTTACTCTTCAAAACAAATCGAA
AAGTAACCGTTAAGCAATTAAAAGAAGATTATTTCAAAAAAATAGAATGTTTTGATAGTGTT
GAAATTTCAGGAGTTGAAGATAGATTTAATGCTTCATTAGGTACCTACCATGATTTGCTAAA
AATTATTAAAGATAAAGATTTTTTGGATAATGAAGAAAATGAAGATATCTTAGAGGATATT
GTTTTAACATTGACCTTATTTGAAGATAGGGAGATGATTGAGGAAAGACTTAAAACATATGC
TCACCTCTTTGATGATAAGGTGATGAAACAGCTTAAACGTCGCCGTTATACTGGTTGGGGAC
GTTTGTCTCGAAAATTGATTAATGGTATTAGGGATAAGCAATCTGGCAAAACAATATTAGAT
TTTTTGAAATCAGATGGTTTTGCCAATCGCAATTTTATGCAGCTGATCCATGATGATAGTTTG
ACATTTAAAGAAGACATTCAAAAAGCACAAGTGTCTGGACAAGGCGATAGTTTACATGAAC
ATATTGCAAATTTAGCTGGTAGCCCTGCTATTAAAAAAGGTATTTTACAGACTGTAAAAGTT
GTTGATGAATTGGTCAAAGTAATGGGGCGGCATAAGCCAGAAAATATCGTTATTGAAATGG
CACGTGAAAATCAGACAACTCAAAAGGGCCAGAAAAATTCGCGAGAGCGTATGAAACGAA
TCGAAGAAGGTATCAAAGAATTAGGAAGTCAGATTCTTAAAGAGCATCCTGTTGAAAATAC
TCAATTGCAAAATGAAAAGCTCTATCTCTATTATCTCCAAAATGGAAGAGACATGTATGTGG
ACCAAGAATTAGATATTAATCGTTTAAGTGATTATGATGTCGATCACATTGTTCCACAAAGT
TTCCTTAAAGACGATTCAATAGACAATAAGGTCTTAACGCGTTCTGATAAAAATCGTGGTAA
ATCGGATAACGTTCCAAGTGAAGAAGTAGTCAAAAAGATGAAAAACTATTGGAGACAACTT
CTAAACGCCAAGTTAATCACTCAACGTAAGTTTGATAATTTAACGAAAGCTGAACGTGGAG
GTTTGAGTGAACTTGATAAAGCTGGTTTTATCAAACGCCAATTGGTTGAAACTCGCCAAATC
ACTAAGCATGTGGCACAAATTTTGGATAGTCGCATGAATACTAAATACGATGAAAATGATA
AACTTATTCGAGAGGTTAAAGTGATTACCTTAAAATCTAAATTAGTTTCTGACTTCCGAAAA
GATTTCCAATTCTATAAAGTACGTGAGATTAACAATTACCATCATGCCCATGATGCGTATCT
AAATGCCGTCGTTGGAACTGCTTTGATTAAGAAATATCCAAAACTTGAATCGGAGTTTGTCT
ATGGTGATTATAAAGTTTATGATGTTCGTAAAATGATTGCTAAGTCTGAGCAAGAAATAGGC
AAAGCAACCGCAAAATATTTCTTTTACTCTAATATCATGAACTTCTTCAAAACAGAAATTAC
ACTTGCAAATGGAGAGATTCGCAAACGCCCTCTAATCGAAACTAATGGGGAAACTGGAGAA

-continued

ATTGTCTGGGATAAAGGGCGAGATTTTGCCACAGTGCGCAAAGTATTGTCCATGCCCCAAGT
CAATATTGTCAAGAAAACAGAAGTACAGACAGGCGGATTCTCCAAGGAGTCAATTTTACCA
AAAAGAAATTCGGACAAGCTTATTGCTCGTAAAAAAGACTGGGATCCAAAAAAATATGGTG
GTTTTGATAGTCCAACGGTAGCTTATTCAGTCCTAGTGGTTGCTAAGGTGGAAAAAGGGAAA
TCGAAGAAGTTAAAATCCGTTAAAGAGTTACTAGGGATCACAATTATGGAAAGAAGTTCCT
TTGAAAAAAATCCGATTGACTTTTTAGAAGCTAAAGGATATAAGGAAGTTAAAAAAGACTT
AATCATTAAACTACCTAAATATAGTCTTTTTGAGTTAGAAAACGGTCGTAAACGGATGCTGG
CTAGTGCCGGAGAATTACAAAAAGGAAATGAGCTGGCTCTGCCAAGCAAATATGTGAATTT
TTTATATTTAGCTAGTCATTATGAAAAGTTGAAGGGTAGTCCAGAAGATAACGAACAAAAA
CAATTGTTTGTGGAGCAGCATAAGCATTATTTAGATGAGATTATTGAGCAAATCAGTGAATT
TTCTAAGCGTGTTATTTTAGCAGATGCCAATTTAGATAAAGTTCTTAGTGCATATAACAAAC
ATAGAGACAAACCAATACGTGAACAAGCAGAAAATATTATTCATTTATTTACGTTGACGAA
TCTTGGAGCTCCCGCTGCTTTTAAATATTTTGATACAACAATTGATCGTAAACGATATACGTC
TACAAAAGAAGTTTTAGATGCCACTCTTATCCATCAATCCATCACTGGTCTTTATGAAACAC
GCATTGATTTGAGTCAGCTAGGAGGTGACTGA (SEQ ID NO: 505)

SEQ ID NO: 506:
ATGGCTGGTTGGCGTACTGTTGTGGTAAATACCCACTCGAAATTATCCTATAAGAATAATCA
TCTGATTTTTAAGGATGCCTATAAAACGGAGCTGATCCATTTATCAGAAATTGATATTTTGTT
ATTAGAAACGACCGATATTGTCTTGTCCACTATGCTGGTAAAACGGCTAGTGGATGAGAATG
TCCTTGTCATATTCTGTGATGATAAACGATTACCAACAGCTATGCTGATGCCTTTTTATGGTC
GTCATGATTCGAGTTTACAGCTTGGGAAACAAATGTCCTGGTCAGAAACAGTCAAATCGCA
GGTTTGGACGACGATTATTGCTCAAAAGATTTTGAATCAATCTTGCTATCTAGGAGCATGCT
CCTATTTTGAAAAATCCCAATCTATTATGGATTTATATCATGGTTTGGAAAATTTTGATCCGA
GTAATCGAGAAGGGCATGCAGCGAGAATTTATTTTAATACACTTTTTGGGAACGATTTCTCA
AGAGATTTGGAGCATCCAATCAATGCAGGTCTGGATTATGGTTATACTTTATTATTGAGTAT
GTTTGCGCGTGAAGTGGTTGTGTCTGGATGTATGACTCAGTTTGGGCTTAAACACGCTAATC
AGTTTAATCAGTTCAATTTTGCTAGCGATATTATGGAACCATTTAGGCCTTTAGTGGATAAG
ATTGTTTATGAAAATCGAAATCAGCCTTTTCCCAAAATAAAGAGAGAGTTATTTACTTTGTT
TTCAGATACATTTTCATATAATGGTAAAGAGATGTATCTCACGAATATTATTAGCGATTATA
CTAAAAAAGTTGTCAAAGCTCTGAATAATGAAGGGAAAGGAGTTCCTGAATTTAGGATATG
A (SEQ ID NO: 506)

SEQ ID NO: 507:
ATGAGTTATAGATATATGAGAATGATACTTATGTTTGATATGCCGACGGACACCGCTGAGGA
ACGAAAAGCCTATCGAAAATTTCGGAAATTTTTACTTAGTGAAGGGTTTATCATGCATCAAT
TTTCTATTTATAGTAAGTTGCTGTTGAATAATACAGCTAACAATGCCATGATTGGTCGGCTG
AGGGAGCATAATCCTAATAAAGGAAATATTACATTACTAACGGTCACGGAAAAACAGTTTG
CACGAATGATTTATTTACATGGTGAAAGAAATAATTGTATTGCAAACTCCGATGAAAGACTT
GTATTTCTTGGGGAGGCTTTTGATGAATCTTAA (SEQ ID NO: 507)

SEQ ID NO: 508:
ATGAATCTTAATTTTTCCTTACTAGATGAACCGATTCCATTAAGAGGCGGTACAATTCTTGTG
CTCGAAGATGTCTGTGTATTTTCAAAAATAGTGCAATATTGTTACCAATATGAGGAAGATTC
TGAACTTAAATTTTTTGATCACAAGATGAAAACAATCAAAGAATCAGAAATCATGCTTGTAA
CAGATATTTTAGGATTTGATGTTAACTCCTCAACCATTTTAAAATTGATTCATGCAGATTTAG
AATCTCAATTTAATGAGAAACCCGAAGTGAAATCGATGATTGACAAATTGGTTGCTACGATT
ACAGAACTGATTGTCTTTGAATGCTTAGAAAATGAATTAGATTTAGAGTATGATGAAATCAC
AATCCTGGAATTGATTAAGTCCTTAGGAGTAAAAGTAGAAACGCAAAGTGATACTATTTTTG
AAAAATGTCTAGAGATACTTCAAATTTTCAAATATCTCACTAAGAAAAAGTTGCTTATTTTT
GTCAATAGCGGAGCTTTTCTAACAAAGGATGAAGTGGCTAGTTTACAAGAGTATATATCATT
GACAAATTTAACAGTTCTCTTTTTAGAACCACGTGAACTATATGATTTTCCGCAGTATATTTT
AGATGAAGATTATTTCTTAATAACTAAAAATATGGTATAA (SEQ ID NO: 508)

SEQ ID NO: 517:
ATGGATAAGAAATACTCAATAGGCTTAGATATCGGCACAAATAGCGTCGGATGGGCGGTGA
TCACTGATGATTATAAGGTTCCGTCTAAAAAGCTCAAGGGTCTGGGAAATACAGACCGCCA
CGGTATCAAAAAAAATCTTATAGGGGCTCTTTTATTTGACAGTGGAGAGACAGCGGAAGCG
ACTCGTCTCAAACGGACAGCTCGTAGAAGGTATACACGTCGGAAGAATCGTATTTGTTATCT
ACAGGAGATTTTTTCAAATGAGATGGCGAAAGTAGATGATAGTTTCTTTCATCGACTTGAAG
AGTCTTTTTTGGTGGAAGAAGACAAGAAGCATGAACGTCATCCTATTTTTGGAAATATAGTA
GATGAAGTTGCTTATCATGAGAAATATCCAACTATCTATCATCTGCGAAAAAAATTGGCAGA
TTCTACTGATAAAGTGGATTTGCGCTTAATCTATTTGGCCTTAGCGCATATGATTAAGTTTCG
TGGTCATTTTTTGATTGAGGGAGATTTAAATCCTGATAATAGTGATGTGGACAAACTATTTA
TCCAGTTGGTACAAACCTACAATCAATTATTTGAAGAAAACCCTATTAACGCAAGTAGAGTA
GATGCTAAAGCGATTCTTTCTGCACGATTGAGTAAATCAAGACGATTAGAAAATCTCATTGC
TCAGCTCCCCGGTGAGAAGAAAAATGGATTGTTTGGGAATCTCATTGCTTTGTCATTGGGAT
TGACCCCTAATTTTAAATCAAATTTTGATTTGGCAGAAGATGCTAAATTACAGCTTTCAAAA
GATACTTACGATGATGATTTAGATAATTTATTGGCGCAAATTGGAGATCAATATGCTGATTT
GTTTTTGGCAGCTAAGAATTTATCAGATGCTACTTTACTTTCAGATATCCTAAGAGTAAATA
GTGAAATAACTAAGGCTCCCCTATCAGCTTCAATGATTAAGCGCTACGATGAACATCATCAA
GACTTGACTCTTTTAAAAGCTTTAGTTCGACAACAACTTCCAGAAAAGTATAAAGAAATCTT
TTTTGATCAATCAAAAAACGGATATGCAGGTTATATTGATGGGGGAGCTAGCCAAGAAGAA
TTTTATAAATTTATCAAACCAATTTTAGAAAAAATGGATGGTACTGAGGAATTATTGGCGAA
ACTAAATCGTGAAGATTTGCTGCGCAAGCAACGGACCTTTGACAACGGCTCTATTCCCTATC
AAATTCACTTGGGTGAGCTGCATGCTATTTTGAGAAGACAAGAAGACTTTTATCCATTTTTA
AAAGACAATCGTGAGAAGATTGAAAAAATCTTGACTTTTCGAATTCCTTATTATGTTGGTCC
ATTGGCGCGTGGCAATAGTCGTTTTGCATGGATGACTCGGAAGTCTGAAGAAACAATTACCC
CATGGAATTTTGAAGAAGTTGTCGATAAAGGTGCTTCAGCTCAATCATTTATTGAACGCATG
ACAAACTTTGATAAAAATCTTCCAAATGAAAAAGTACTACCAAAACATAGTTTGCTTTATGA
GTATTTTACGGTTTATAACGAATTGACAAAAGTCAAATATGTTACTGAGGGAATGCGAAAA

-continued

CCAGCATTTCTTTCAGGTGAACAGAAGAAAGCCATTGTTGATTTACTCTTCAAAACAAATCG
AAAAGTAACCGTTAAGCAATTAAAAGAAGATTATTTCAAAAAAATAGAATGTTTTGATAGT
GTTGAAATTTCAGGAGTTGAAGATAGATTTAATGCTTCATTAGGTACCTACCATGATTTGCT
AAAAATTATTAAAGATAAAGATTTTTTGGATAATGAAGAAAACGAAGATATCTTAGAGGAT
ATTGTTTTAACATTGACCTTATTTGAAGATAGGGAGATGATTGAGGAAAGACTTAAAACATA
TGCTCACCTCTTTGATGATAAGGTGATGAAACAGCTTAAACGTCGCCGTTATACTGGTTGGG
GACGTTTGTCTCGAAAATTGATTAATGGTATTAGGGATAAGCAATCTGGCAAAACAATATTA
GATTTTTTGAAATCAGATGGTTTTGCCAATCGCAATTTTATGCAGCTGATCCATGATGATAGT
TTGACATTTAAAGAAGACATTCAAAAAGCACAAGTGTCTGGACAAGGCGATAGTTTACATG
AACATATTGCAAATTTAGCTGGTAGCCCTGCTATTAAAAAAGGTATTTTACAGACTGTAAAA
GTTGTTGATGAATTGGTCAAAGTAATGGGGCGGCATAAGCCAGAAAATATCGTTATTGAAA
TGGCACGTGAAAATCAGACAACTCAAAAGGGCCAGAAAAATTCGCGTGAGCGTATGAAAC
GTATTGAAGAAGGAATAAAAGAACTAGGAAGTGATATTCTAAAGGAGTATCCTGTTGAAAA
CACTCAATTACAAAATGAAAAGCTCTATCTCTATTATCTCCAAAATGGAAGAGACATGTATG
TGGACCAAGAATTAGATATTAATCGTTTAAGTGATTATGATGTCGATCACATTGTTCCACAA
AGTTTCCTTAAAGACGATTCAATAGACAATAAGGTCTTAACGCGTTCTGATAAAAATCGTGG
TAAATCGGATAACGTTCCAAGTGAAGAAGTAGTCAAAAAGATGAAAAACTATTGGAGACAA
CTTCTAAACGCCAAGTTAATCACTCAACGTAAGTTTGATAATTTAACAAAAGCTGAACGTGG
AGGTTTGAGTGAACTTGATAAAGTTGGTTTTATCAAACGCCAATTGGTTGAAACTCGCCAAA
TCACTAAGCATGTGGCACAAATTTTGGATAGTCGCATGAATACTAAATACGATGAAAATGA
TAAACTTATTCGAGAGGTTAGAGTGATTACCTTAAAATCTAAATTAGTTTCTGACTTCCGAA
AAGATTTCCAATTCTATAAAGTACGTGAGATTAACAATTACCATCATGCCCATGATGCGTAT
CTTAATGCCGTCGTTGGAACTGCTTTGATTAAGAAATATCCAAAACTTGAATCGGAGTTTGT
CTATGGTGATTATAAAGTTTATGATGTTCGTAAAATGATTGCTAAGTCTGAGCAGGAAATAG
GCAAAGCAACCGCAAAATATTTCTTTTACTCTAATATCATGAACTTCTTCAAAACAGAAATT
ACACTTGCAAATGGAGAGATTCGCAAACGCCCTCTAATCGAAACTAATGGGGAAACTGGAG
AAATTGTCTGGGATAAAGGGCGAGATTTTGCCACAGTGCGCAAAGTATTGTCCATGCCCCA
AGTCAATATTGTCAAGAAAACAGAAGTACAGACAGGCGGATTCTCCAAGGAGTCAATTTTA
CCAAAAAGAAATTCGGACAAGCTTATTGCTCGTAAAAAAGACTGGGATCCAAAAAAATATG
GTGGTTTTGATAGTCCAACGGTAGCTTATTCAGTCCTAGTGGTTGCTAAGGTGGAAAAAGGG
AAATCGAAGAAGTTAAAATCCGTTAAAGAGTTACTAGGGATCACAATAATGGAAAGAAGCT
CTTTTGAAAAAGATCCGATTGACTTTTTAGAAGCTAAAGGATATAAGGAAGTTAGAAAAGA
CTTAATCATTAAACTACCTAAATATAGTCTTTTTGAGTTAGAAAACGGTCGTAAACGGATGC
TGGCTAGTGCCGGAGAATTGCAAAAAGGAAATGAGCTAGCTCTGCCAAGCAAATATGTGAA
TTTTTTATATTTAGCTAGTCATTATGAAAAGTTGAAGGGTAGTCCAGAAGATAACGAACAAA
AACAATTGTTTGTGGAGCAGCATAAGCATTATTTAGATGAGATTATTGAGCAAATCAGTGAA
TTTTCTAAGCGTGTTATTTTAGCAGATGCCAATTTAGATAAAGTTCTTAGTGCATATAACAA
ACATAGAGACAAACCAATACGTGAACAAGCAGAAAATATTATTCATTTATTTACGTTGACG
AATCTTGGAGCTCCCGCTGCTTTTAAATATTTTGATACAACAATTGATCGTAAACGATATAC
GTCTACAAAAGAAGTTTTAGATGCCACTCTTATCCATCAATCCATCACTGGTCTTTATGAAA
CACGCATTGATTTGAGTCAGCTAGGAGGTGACTGATGGCTGGTTGGCGTACTGTTGTGGTAA
ATACCCACTCGAAATTATCCTATAAGAATAATCATCTGATTTTTAAGGATGCCTATAAAACG
GAGCTGATCCATTTATCAGAAATTGATATTTTGTTATTAGAAACGACCGATATTGTCTTGTCC
ACTATGCTGGTAAAACGGCTAGTGGATGAGAATGTCCTTGTCATATTCTGTGATGATAAACG
ATTACCAACAGCTATGCTGATGCCTTTTTATGGTCGTCATGATTCGAGTTTACAGCTTGGGA
AACAAATGTCCTGGTCAGAAACAGTCAAATCGCAGGTTTGGACGACGATTATTGCTCAAAA
GATTTTGAATCAATCTTGCTATCTAGGAGCATGCTCCTATTTTGAAAAATCCCAATCTATTAT
GGATTTATATCATGGTTTGGAAAATTTTGATCCGAGTAATCGAGAAGGGCATGCAGCGAGA
ATTTATTTTAATACACTTTTTGGGAACGATTTCTCAAGAGATTTGGAGCATCCAATCAATGC
AGGTCTGGATTATGGTTATACTTTATTATTGAGTATGTTTGCGCGTGAAGTGGTTGTGTCTGG
ATGTATGACTCAATTTGGACTCAAACACGCCAATCAGTTTAATCAGTTCAATTTTGCTAGCG
ATATTATGGAACCATTTAGGCCTTTGGTGGATAAGATTGTTTATGAAAATCGAAATCAGCCT
TTTCCCAAAATAAAGAGAGAGTTATTTACTTTGTTTTCAGATACATTTTCATATAATGGTAAA
GAGATGTATCTCACGAATATTATTAGCGATTATACTAAAAAAGTTGTCAAAGCTCTGAATAA
TGAAGGGAAAGGAGTTCCTGAATTTAGGATATGAGTTATAGATATATGAGAATGATACTTA
TGTTTGATATGCCGACGGACACTGCTGAGGAACGAAAAGCTTATCGAAAATTTCGGAAATTT
TTACTTAGTGAAGGGTTTATCATGCATCAATTTTCTATTTATAGTAAGTTACTGTTGAATAAT
ACAGCTAACAACGCCATGATTGGTCGGCTGAGGGAGCATAATCCTCATAAAGGAAATATTA
CATTACTAACAGTCACAGAAAAACAGTTTGCACGAATGATTTATTTACATGGTGAAAGAAA
TAATTGTATTGCAAACTCCGATGAGAGACTTGTATTTCTTGGGGAGGCTTTTGATGAATCTT
AATTTTCCCTTATTAGATGAACCGATTCCATTAAGAGGCGGTACAATTCTTGTGCTCGAAGA
TGTCTGTGTATTTTCAAAAATAGTGCAATATTGTTACAAATATGAGGAAGATTCTGAACTTA
AATTTTTTGATCACAAGATGAAAACCATCAAAGAATCAGAAATCATGCTTGTAACAGATATT
TTAGGATTTGATGTTAACTCCTCAACCATTTTAAAATTGATTCATGCAGATTTAGAATCTCAA
TTTAATGAGAAACCCGAAGTGAAATCGATGATTGACAAATTGGTTGCTACGATTACAGAAC
TGATTGTCTTTGAATGCTTAGAAAATGAATTAGATTTAGAGTATGATGAAATCACAATCCTG
GAATTGATTAAGTCCTTAGGAGTAAAAGTAGAAACGCAAAGTGATACTATTTTTGAAAAAT
GTCTAGAGATACTTCAAATTTTCAAATATCTCACTAAGAAAAAGTTGCTTATTTTTGTCAATA
GCGGAGCTTTTCTAACAAAGGATGAAGTGGCTAGTTTACAAGAGTATATATCATTGACAAAT
TTAACAGTTCTCTTTTTAGAACCACGTGAACTATATGATTTTCCGCAGTATATTTTAGATGAA
GATTATTTCTTAATAACTAAAAATATGGTATAA (SEQ ID NO: 517)

SEQ ID NO: 518:
ATGGATAAGAAATACTCAATAGGCTTAGATATCGGCACAAATAGCGTCGGATGGGCGGTGA
TCACTGATGATTATAAGGTTCCGTCTAAAAAGCTCAAGGGTCTGGGAAATACAGACCGCCA
CGGTATCAAAAAAAATCTTATAGGGGCTCTTTTATTTGACAGTGGAGAGACAGCGGAAGCG
ACTCGTCTCAAACGGACAGCTCGTAGAAGGTATACACGTCGGAAGAATCGTATTTGTTATCT
ACAGGAGATTTTTTCAAATGAGATGGCGAAAGTAGATGATAGTTTCTTTCATCGACTTGAAG
AGTCTTTTTTGGTGGAAGAAGACAAGAAGCATGAACGTCATCCTATTTTTGGAAATATAGTA
GATGAAGTTGCTTATCATGAGAAATATCCAACTATCTATCATCTGCGAAAAAAATTGGCAGA
TTCTACTGATAAAGTGGATTTGCGCTTAATCTATTTGGCCTTAGCGCATATGATTAAGTTTCG

-continued

TGGTCATTTTTTGATTGAGGGAGATTTAAATCCTGATAATAGTGATGTGGACAAACTATTTA
TCCAGTTGGTACAAACCTACAATCAATTATTTGAAGAAAACCCTATTAACGCAAGTAGAGTA
GATGCTAAAGCGATTCTTTCTGCACGATTGAGTAAATCAAGACGATTAGAAAATCTCATTGC
TCAGCTCCCCGGTGAGAAGAAAAATGGATTGTTTGGGAATCTCATTGCTTTGTCATTGGGAT
TGACCCCTAATTTTAAATCAAATTTTGATTTGGCAGAAGATGCTAAATTACAGCTTTCAAAA
GATACTTACGATGATGATTTAGATAATTTATTGGCGCAAATTGGAGATCAATATGCTGATTT
GTTTTTGGCAGCTAAGAATTTATCAGATGCTACTTTACTTTCAGATATCCTAAGAGTAAATA
GTGAAATAACTAAGGCTCCCCTATCAGCTTCAATGATTAAGCGCTACGATGAACATCATCAA
GACTTGACTCTTTTAAAAGCTTTAGTTCGACAACAACTTCCAGAAAAGTATAAAGAAATCTT
TTTTGATCAATCAAAAAACGGATATGCAGGTTATATTGATGGGGGAGCTAGCCAAGAAGAA
TTTTATAAATTTATCAAACCAATTTTAGAAAAAATGGATGGTACTGAGGAATTATTGGCGAA
ACTAAATCGTGAAGATTTGCTGCGCAAGCAACGGACCTTTGACAACGGCTCTATTCCCTATC
AAATTCACTTGGGTGAGCTGCATGCTATTTTGAGAAGACAAGAAGACTTTTATCCATTTTTA
AAAGACAATCGTGAGAAGATTGAAAAAATCTTGACTTTTCGAATTCCTTATTATGTTGGTCC
ATTGGCGCGTGGCAATAGTCGTTTTGCATGGATGACTCGGAAGTCTGAAGAAACAATTACCC
CATGGAATTTTGAAGAAGTTGTCGATAAAGGTGCTTCAGCTCAATCATTTATTGAACGCATG
ACAAACTTTGATAAAAATCTTCCAAATGAAAAAGTACTACCAAAACATAGTTTGCTTTATGA
GTATTTTACGGTTTATAACGAATTGACAAAAGTCAAATATGTTACTGAGGGAATGCGAAAA
CCAGCATTTCTTTCAGGTGAACAGAAGAAAGCCATTGTTGATTTACTCTTCAAAACAAATCG
AAAAGTAACCGTTAAGCAATTAAAAGAAGATTATTTCAAAAAAATAGAATGTTTTGATAGT
GTTGAAATTTCAGGAGTTGAAGATAGATTTAATGCTTCATTAGGTACCTACCATGATTTGCT
AAAAATTATTAAAGATAAAGATTTTTTGGATAATGAAGAAAACGAAGATATCTTAGAGGAT
ATTGTTTTAACATTGACCTTATTTGAAGATAGGGAGATGATTGAGGAAAGACTTAAAACATA
TGCTCACCTCTTTGATGATAAGGTGATGAAACAGCTTAAACGTCGCCGTTATACTGGTTGGG
GACGTTTGTCTCGAAAATTGATTAATGGTATTAGGGATAAGCAATCTGGCAAAACAATATTA
GATTTTTTGAAATCAGATGGTTTTGCCAATCGCAATTTTATGCAGCTGATCCATGATGATAGT
TTGACATTTAAAGAAGACATTCAAAAAGCACAAGTGTCTGGACAAGGCGATAGTTTACATG
AACATATTGCAAATTTAGCTGGTAGCCCTGCTATTAAAAAAGGTATTTTACAGACTGTAAAA
GTTGTTGATGAATTGGTCAAAGTAATGGGGCGGCATAAGCCAGAAAATATCGTTATTGAAA
TGGCACGTGAAAATCAGACAACTCAAAAGGGCCAGAAAAATTCGCGTGAGCGTATGAAAC
GTATTGAAGAAGGAATAAAAGAACTAGGAAGTGATATTCTAAAGGAGTATCCTGTTGAAAA
CACTCAATTACAAAATGAAAAGCTCTATCTCTATTATCTCCAAAATGGAAGAGACATGTATG
TGGACCAAGAATTAGATATTAATCGTTTAAGTGATTATGATGTCGATCACATTGTTCCACAA
AGTTTCCTTAAAGACGATTCAATAGACAATAAGGTCTTAACGCGTTCTGATAAAAATCGTGG
TAAATCGGATAACGTTCCAAGTGAAGAAGTAGTCAAAAAGATGAAAAACTATTGGAGACAA
CTTCTAAACGCCAAGTTAATCACTCAACGTAAGTTTGATAATTTAACAAAAGCTGAACGTGG
AGGTTTGAGTGAACTTGATAAAGTTGGTTTTATCAAACGCCAATTGGTTGAAACTCGCCAAA
TCACTAAGCATGTGGCACAAATTTTGGATAGTCGCATGAATACTAAATACGATGAAAATGA
TAAACTTATTCGAGAGGTTAGAGTGATTACCTTAAAATCTAAATTAGTTTCTGACTTCCGAA
AAGATTTCCAATTCTATAAAGTACGTGAGATTAACAATTACCATCATGCCCATGATGCGTAT
CTTAATGCCGTCGTTGGAACTGCTTTGATTAAGAAATATCCAAAACTTGAATCGGAGTTTGT
CTATGGTGATTATAAAGTTTATGATGTTCGTAAAATGATTGCTAAGTCTGAGCAGGAAATAG
GCAAAGCAACCGCAAAATATTTCTTTTACTCTAATATCATGAACTTCTTCAAAACAGAAATT
ACACTTGCAAATGGAGAGATTCGCAAACGCCCTCTAATCGAAACTAATGGGGAAACTGGAG
AAATTGTCTGGGATAAAGGGCGAGATTTTGCCACAGTGCGCAAAGTATTGTCCATGCCCCA
AGTCAATATTGTCAAGAAAACAGAAGTACAGACAGGCGGATTCTCCAAGGAGTCAATTTTA
CCAAAAAGAAATTCGGACAAGCTTATTGCTCGTAAAAAAGACTGGGATCCAAAAAAATATG
GTGGTTTTGATAGTCCAACGGTAGCTTATTCAGTCCTAGTGGTTGCTAAGGTGGAAAAAGGG
AAATCGAAGAAGTTAAAATCCGTTAAAGAGTTACTAGGGATCACAATAATGGAAAGAAGCT
CTTTTGAAAAAGATCCGATTGACTTTTTAGAAGCTAAAGGATATAAGGAAGTTAGAAAAGA
CTTAATCATTAAACTACCTAAATATAGTCTTTTTGAGTTAGAAAACGGTCGTAAACGGATGC
TGGCTAGTGCCGGAGAATTGCAAAAAGGAAATGAGCTAGCTCTGCCAAGCAAATATGTGAA
TTTTTTATATTTAGCTAGTCATTATGAAAAGTTGAAGGGTAGTCCAGAAGATAACGAACAAA
AACAATTGTTTGTGGAGCAGCATAAGCATTATTTAGATGAGATTATTGAGCAAATCAGTGAA
TTTTCTAAGCGTGTTATTTTAGCAGATGCCAATTTAGATAAAGTTCTTAGTGCATATAACAA
ACATAGAGACAAACCAATACGTGAACAAGCAGAAAATATTATTCATTTATTTACGTTGACG
AATCTTGGAGCTCCCGCTGCTTTTAAATATTTTGATACAACAATTGATCGTAAACGATATAC
GTCTACAAAAGAAGTTTTAGATGCCACTCTTATCCATCAATCCATCACTGGTCTTTATGAAA
CACGCATTGATTTGAGTCAGCTAGGAGGTGACTGA (SEQ ID NO: 518)

SEQ ID NO: 519:
ATGGCTGGTTGGCGTACTGTTGTGGTAAATACCCACTCGAAATTATCCTATAAGAATAATCA
TCTGATTTTTAAGGATGCCTATAAAACGGAGCTGATCCATTTATCAGAAATTGATATTTTGTT
ATTAGAAACGACCGATATTGTCTTGTCCACTATGCTGGTAAAACGGCTAGTGGATGAGAATG
TCCTTGTCATATTCTGTGATGATAAACGATTACCAACAGCTATGCTGATGCCTTTTTATGGTC
GTCATGATTCGAGTTTACAGCTTGGGAAACAAATGTCCTGGTCAGAAACAGTCAAATCGCA
GGTTTGGACGACGATTATTGCTCAAAAGATTTTGAATCAATCTTGCTATCTAGGAGCATGCT
CCTATTTTGAAAAATCCCAATCTATTATGGATTTATATCATGGTTTGGAAAATTTTGATCCGA
GTAATCGAGAAGGGCATGCAGCGAGAATTTATTTTAATACACTTTTTGGGAACGATTTCTCA
AGAGATTTGGAGCATCCAATCAATGCAGGTCTGGATTATGGTTATACTTTATTATTGAGTAT
GTTTGCGCGTGAAGTGGTTGTGTCTGGATGTATGACTCAATTTGGACTCAAACACGCCAATC
AGTTTAATCAGTTCAATTTTGCTAGCGATATTATGGAACCATTTAGGCCTTTGGTGGATAAG
ATTGTTTATGAAAATCGAAATCAGCCTTTTCCCAAAATAAAGAGAGAGTTATTTACTTTGTT
TTCAGATACATTTTCATATAATGGTAAAGAGATGTATCTCACGAATATTATTAGCGATTATA
CTAAAAAAGTTGTCAAAGCTCTGAATAATGAAGGGAAAGGAGTTCCTGAATTTAGGATATG
A (SEQ ID NO: 519)

SEQ ID NO: 520:
ATGAGAATGATACTTATGTTTGATATGCCGACGGACACTGCTGAGGAACGAAAAGCTTATC
GAAAATTTCGGAAATTTTTACTTAGTGAAGGGTTTATCATGCATCAATTTTCTATTTATAGTA
AGTTACTGTTGAATAATACAGCTAACAACGCCATGATTGGTCGGCTGAGGGAGCATAATCCT

-continued

CATAAAGGAAATATTACATTACTAACAGTCACAGAAAAACAGTTTGCACGAATGATTTATTT
ACATGGTGAAAGAAATAATTGTATTGCAAACTCCGATGAGAGACTTGTATTTCTTGGGGAG
GCTTTTGATGAATCTTAA (SEQ ID NO: 520)

SEQ ID NO: 521:
ATGAATCTTAATTTTCCCTTATTAGATGAACCGATTCCATTAAGAGGCGGTACAATTCTTGTG
CTCGAAGATGTCTGTGTATTTTCAAAAATAGTGCAATATTGTTACAAATATGAGGAAGATTC
TGAACTTAAATTTTTTGATCACAAGATGAAAACCATCAAAGAATCAGAAATCATGCTTGTAA
CAGATATTTTAGGATTTGATGTTAACTCCTCAACCATTTTAAAATTGATTCATGCAGATTTAG
AATCTCAATTTAATGAGAAACCCGAAGTGAAATCGATGATTGACAAATTGGTTGCTACGATT
ACAGAACTGATTGTCTTTGAATGCTTAGAAAATGAATTAGATTTAGAGTATGATGAAATCAC
AATCCTGGAATTGATTAAGTCCTTAGGAGTAAAAGTAGAAACGCAAAGTGATACTATTTTTG
AAAAATGTCTAGAGATACTTCAAATTTTCAAATATCTCACTAAGAAAAAGTTGCTTATTTTT
GTCAATAGCGGAGCTTTTCTAACAAAGGATGAAGTGGCTAGTTTACAAGAGTATATATCATT
GACAAATTTAACAGTTCTCTTTTTAGAACCACGTGAACTATATGATTTTCCGCAGTATATTTT
AGATGAAGATTATTTCTTAATAACTAAAAATATGGTATAA (SEQ ID NO: 521)

with repeat sequences SEQ ID NO:13 to SEQ ID NO:19 cas sequences: SEQ ID NO:509 to SEQ ID NO:516 (all of which are from *S. pyogenes*), as shown below:

Functional Combination #4:

SEQ ID NO: 509:
ATGAGAATGATTTTAGCACACTATGACTGTAAAAAAGATAAAAAGCAATCTTTAGATGAGC
ATTTATGGCATGTGGCCTGTTCTAGTCGACAGGAAGCATCTATAATTGGTCAAGGAGATGTG
CTTTTTTTAATTGGTCTTTACCACGACCTGGGCAAAGCTGATCGAACCTTTCAAGATAAATTA
TTAAATAATCCAAATCGGCATGTTGATCACTCTTATGCAGGGGCAAAATACTTATGTTCTAT
TATTGGGCCTCATCTAAAAAACCGAGGGGTTGATAAAAATGAGAGAATGACATTCAACGAA
ATGGTGGGGTATGTCATCTCTGCTCATCATGGGATGTATGATTTATGCTACTATTTTGACGAT
GCTGAATATTATGGCTTTAATAAGTTTAAAAATCGTATCAATAGAGACTTAGATGGTTATCA
CTATCATGAAGATATTAAAGGGTACGCTCTAAAATTAGAAAAAAAATTATGTGATTATGGCT
ACAAAGATTTAAGGGAGCTTATTGATAAAGCTTTTGATAATTACCAACAAGCCATGTCTTCC
TTAAACTGGCAAGATAAGAGTGAGTGGGATTATTATCAGTCTTGTATGGTGAGACTTTACTT
GTCACTCTTAAAAAACGCTGATATTTTGGACACAGTAAATGCCTATGGCCTTAAGATAAGTC
CTATGGATAAAACAGAGCGATCCTTTCTAAAACACTCCTATTTAGCGGCCATTGAACAAAAA
TATGCTAGCTTTGGACAGCCAAACAATCAGTTGAACACTATTCGGACAGAAATCGCTGAGC
GTGTTAAAGAAAGAGGTAAACGAGATTCCAAGGGGATTTATCGCTTAGATTTACCGACAGG
AGCTGGCAAGACTAATCTTAGTATGCGTTATGCGTTTCACCAATTAGTTCATCACGACAAAT
CAAGGTTTTTTTACATAACTCCCTTTCTTTCGGTTCTTGAGCAAAATGCTTCCGAAATTAGAA
AAGTTACAGGTGACCTTGGCGTTCTAGAACACCATTCCAATGTGGTGAAACAGGCTAATGA
AGATGATGATGATAAGGACAGTTTATTGTCAGCTTATCTTAGTGATAGCTGGGACAGTCAAG
TAGTCTTGACTTCTATGGTTCAATTTTTCCAAACACTTTTCAAAACAAAATCAGCTAATCTGA
GACGTTTTTCAAGTTTGATTAATAGTGTTGTGATTCTAGATGAAGTTCAATCCCTGCCTATTG
AAGTCACCACTTTGTTTAATTTAACGATGAATTTTTTAAATAAAGTTATGGATACAACCATC
GTTCTTTGCACAGCGACACAACCTGCTTATGATTCTTCAGAGATTGACCATCGTATCTGTTAT
GGAGGGAACTTGGGAGAATTAGCTGAAATAGTTGAGTTAACGATTGAAGAAAAACAGATTT
TTTCAAGGACAGAGCTTAGAAAATTTGATGATAGTGATCAGAAAGTTCACTTGACTGATGTT
ATTAACCTTATTCTAGGTGAGGAAAACTCAGTTCTTGCTATTTTTAATACGAAAAAAACGGT
TCATAACTGCTATACTATGCTAAAAGACATGACTGATAGACCGGTCTATCAGCTTTCGACAA
ATATGTGTGCGCAGCATAGACTTGACTTGATTGCTAAGATCAAAACGGAGTTACAAAATAA
TATCCCTATTATTTGTATTAGCACGCAATTAATTGAAGCAGGTGTAGATGTTGATTTTCATCG
CGTCATTCGTTCCTACTCAGGGATTGATTCTATTGTTCAGGCTGCTGGACGGTGTAACCGAG
AAGGCAAACGAGATAAAGGGCAAGTCACTCTTGTCAATCTGACCAATGAAGAGGAAAATAT
TTCTAGGCTGACAGAAATAAAAACTAAAAAAGAAGCCACAGAATCTATTCTTCATAAGATT
GGGTCTCCAATTGATATCTCAACTTTAAACCGTGACTTTTTTGAGTATTATTATGCCAATAAT
CAGGGACTGATGGATTATCCTTTGGAAGACAACCTATCAATCTACGACTATTTAAGCCTTAA
TATTTATCAGACGGCAAATAAAAAGTTCAAAGGTAAGTTAAAACAAGCTTTTAAAACAGCA
GGAGCCAAAATGAACCTCATCAATAATGATATGATAGGAATTCTCGTACCTTATGGCGAAG
CTGAGAAAAAATTGGCTTATTTAGAAGAATTAGGTGTGTCACATTTTTTATCAGCAAAAGAT
TATCAAACGATAAAATCATTACTAAAAGAGTTACAACCTTTTACGGTTAATGTCCGCGAGAA
CGATCCTCTCTTTGAGACAACAAAATCTTATCTAAATGGTCAGATTCTGGTTTTGACGTCGG
AGTATTATGACACGGAAAGAGGAGTTAAATACGATTCAGCTAGCTTTTACTTCTAACTCAAA
ACGAAAGAAGATTAACAAAAGGTTGTTAGAGGACCTTGTTAACCTGCCAATCATCATTAGT
AATTATTATCAATTTAGACTATTTAATAAAATTAGATTACAAAAAAACAGAAGGAGGAAAG
TAGCTTGTACAGATCTAGAGACTTCTACGTGAGAGTAAGTGGTCAGCGAGCTCTTTTTACAA
ATCCAGCCACAAAAGGGGGATCGGAACGCTCATCCTATTCGGTTCCGACTAGACAGGCACT
GAATGGTATCGTTGATGCCATCTATTATAAGCCGACCTTTACTAATATCGTCACAGAGGTTA
AGGTTATTAACCAGATTCAAACCGAATTACAGGGTGTCAGGGCTCTGTTACATGATTATAGT
GCAGATTTAAGTTATGTATCCTATTTGAGTGATGTTGTTTATCTGATCAAGTTTCATTTTGTTT
GGAATGAAGATAGAAAAGATTTGAACTCAGATAGACTTCCAGCTAAACATGAAGCCATTAT
GGAGCGTTCTATTCGTAAAGGGGGACGTCGAGATGTGTTTTTGGGTACAAGAGAATGTTTAG
GGCTTGTAGATGATATCAGCCAAGAAGAGTATGAGACTACTGTGTCGTATTATAATGGTGTC
AATATCGACTTGGGAATCATGTTCCATTCCTTTGCCTATCCGAAGGACAAAAAGACACCATT
AAAATCATACTTTACAAAGACTGTGATGAAAAATGGAGTCATTACGTTTAAAGCACAGTCT
GAATGCGATATTGTTAACACGCTTTCTAGTTATGCTTTTAAAGCACCAGAGGAGATAAAATC
GGTTAACGATGAATGCATGGAGTATGATGCCATGGAGAAAGGAGAAAACTGATGGATTTTT
TTACTTCTCTCTTGAAGACTTATGAAAAAGCAGAGCTAGCAGACTTGGTTGATCATCAAAAA
AGAAATAATGAGCCGGTTTTACTGCCGATTTATCATACGAGTTTAAAGTCAAATGGTAAAAA
TATCATTTCAGTGAAACTTGACAAAGATGGCCAGTTTCACAAGGCAGAATTTATGGCAGATA
AGCAAATGATTATTTTTCCTGTAACGGCTGATTCTGTTGCTAGGTCAGGTAGTCATCCTGCAC

-continued

CGCATCCCCTAGTCGATAAATTTGCTTATTATAGTGCTGAAATGGGGCAGATTCAGTATGAT
TCTTTTCATAAGCAACTGAATAACTGGATTGATTATTGTGAGGAGGGTGATGTCAAGAAATT
TTTAACCTTTGTTCAGCAGTTCATTTTGAAGCCAGAATTTCTAACATTGATTCTTGATTCTTT
AATTGGTCCTGATTATCAACATAATCAATTAAAAGTCACATTTTGTGATGCCACTGGAAAAG
AAAAATTAATTGATTTATCAGCTTGCTTTTTAGAATTTTCAATTGATCAGTTCCAGGGCTTTA
AAAATGAATCGGTTTCGACATTTAAAGCCTTACACCAATCCTATATTTCTTTTGTTGAAGCCA
ATCGTGAAAATCTCGGTATTTGTAATATTAGTGGACGAGAGGAACAGCTTACCGATAAGCA
TAGAGGTTTGATGGGGAATGCTAAAATCATCTCTGTTAGTAATAAAAGAGAAGCTTATAAA
GGACGTTTTAGAGAACGCGAAGACGTTTTTAGTGTTGGCTATGAAACTTCCGAAAAGATTCA
TTTAATGCTCAAGTACCTTTTAGAAAATAAAAATACCAGTACTTGGTTAGGGTCTTCTCAAT
ATTTAATCAACTGGTTCAGCGATGATTTAACAAATGATAGTCGGTTGGATATTGTATCACCA
ATCTTTGATGATGGACTTGAAGAAGATGATGATGACGATACGCCTCCTGTTATAACATTAGC
AACTGAAGACAATAAAAGAATTGGTAAATCATTCATCAAGGGACAAAAATTATTTGCTAAT
GATGCCACTTACTACGTTGCTATTTTGAATAAAACCAGCAATGGGCGGATTGCTTTAAAATA
TTTTCGTCAGCTTCAAGCGTCCCAATTACTCACCAATCTTAACAAGTGGCAGGAAACATACA
GTTGGGAGTCGCGATCTAAGTTTGGGAAAAGTCGCTTAAGAACCCCTACTTTTCATGACATC
CTTAATGTGTCCTACGGGGTTGATAGGGATCGCTTCCTTGAATTAGATAATGATAACTTCAA
AAGTGATCAAATTCAAAGTTAGTGGCAAGTTTGATTGATGGTAAACCGATGCCACAGTCC
ATTGTCAAAAGTTAGGTAACAATGTTAAAGAACGACATCGTTACCGTAAGCACTGGTATC
AAGTTGAGCAGGTCTGCTTAGCAATTTTACACAAACAAAATGGGGAGGAATTTTCACCGAT
GCTAGATCATACCAATCAAAATCGTTCCTATCTTTTTGGACGATTATTAGCAATTTTTGAATT
AATCGAGACCTTGCGTTATGGCTTGGATGGAAACAATAACGACCGTATTACCAATGCTGAA
CGTTATTGGACAGCCTATACTGGACAACCAACAAAATTGATGATGTTATTGGAAAATAAAA
TTAAGCCTTACGAAGAACCATTGAAATTAAATCGTCGTGGCAGTTGGATGAAATTAGAAAA
AGAAAAAGAAGAGATTTTAGAACTGTTAAATCCTCTGTTAGAAACAGAAACAATGGAAAAA
CCCTTAGATTACCGCTTTATTTTTGGGTATTATGCTGAGAAAAACTATTACTATACAAAACA
AAACACGGAAGTAACAGAAAGTGAGGAGTAAAAAGATGTTGGAACACAAAATTGATTTTAT
GGTAACTCTTGAAGTGAAAGAAGCAAATGCAAATGGTGATCCCTTAAATGGAAACATGCCT
CGTACAGATGCCAAAGGATATGGTGTGATGAGTGATGTCTCCATTAAACGTAAGATTCGTA
ATCGTTTGCAAGATATGGGGAAGTCTATTTTTGTGCAAGCTAATGAGCGTATTGAAGATGAT
TTTCGTTCACTGGAAAAACGCTTTTCGCAACATTTTACAGCTAAGACACCTGACAAAGAAAT
TGAAGAAAAAGCAAATGCATTATGGTTTGATGTTCGTGCTTTTGGACAAGTTTTTACTTATCT
GAAAAAATCAATTGGGGTGCGTGGACCAGTTTCCATCAGTATGGCTAAGTCCTTGGAGCCA
ATTGTCATTTCCAGCCTTCAAATTACGCGTAGTACCAATGGTATGGAAGCTAAGAATAATAG
TGGCCGCTCTTCTGATACGATGGGGACAAAACATTTTGTAGATTATGGTGTGTATGTACTTA
AAGGTTCTATCAATGCTTATTTTGCTGAAAAGACTGGTTTTTCTCAGGAAGATGCTGAGGCT
ATTAAAGAAGTTTTGGTTAGCTTGTTTGAAAATGATGCGTCGTCTGCACGTCCGGAAGGCTC
TATGCGAGTTTGTGAAGTCTTTTGGTTTACGCATTCAAGCAAATTGGGAAATGTTTCAAGTG
CGCGTGTCTTTGACTTGTTAGAGTATCATCAATCAATAGAAGAAAAAAGCACTTATGACGCT
TATCAGATTCATCTAAATCAAGAAAAATTGGCTAAATATGAAGCGAAAGGGTTAACGCTTG
AAATCCTAGAAGGACTCTAGTATGGTCTATGCCGAAGATGATTATTTAATGCTGTCAGGTAT
TCAGCATTTCCAATTTTGTAAACGTCAATGGGCGTTGATCCATATTGAGCAACAATGGCTTG
ATAATGAAGCGACAGCGCATGGACAGGTTTTACATACTAAAGCAGATAACCCTTACATTAA
AGAAAAACGAAAAGAGCTTTTGGTCTCACGTGCTATGCCCATTTCTTCTGCAGAACTTGGAC
TTTCAGGAATTATGGATGTTGTGGAATTTTATAAAGATGATCAAGGTGTGTCTTTGAGGGGA
AAACGTGGGAAATGGTTACCAAAAGTTGTGGAATACAAGCGCGGAAAACCTAAAAAAGAT
ACCAGAGATATTGTCCAGTTGGTGGCTCAGACCATGTGTTTAGAAGAAACGCTAGACTGCG
ACATTAACGAAGGTTGTCTTTATTACCATAGTGTCAATCAAAGAGTGATTGTTCCTATGACA
TCAGCTTTGCGTCAAGAAGTGAAGGAATTAGCCGCAGAGATGCATGAGGTTTATCAGAGTC
AAATGCTACCTAAAGCAGCTTATTTTAAAAACTGTCAGCTTTGTTCTTTAGTCGATATTTGTA
AGCCCAGGTTGAGTAAAAAAACAAGGAGTGTGTCGCGTTACATCAATGAGGCTATGACCAG
TGAGGAGATGGACCTATGAAGAAGTTGCTAAATACCTTGTATTTGACGCAAGAAGATTTTTA
TGTCACTAAAGAGGGCGATAACATTGTTATCAAGCAAGAAGGTAAGGTTCTCAAACGGTTT
CCGTTTCGGATTATTGACGGTATTGTCTGTTTTTCTTATTTGGGTGTGTCGTCTGCTTTGGTGA
AGTTATGTACGGAGAATCAGATTAATTTATCGTTTCATACACCACAAGGGCGTTTTTGTGGT
CGCTATATTGGTTCAACCAATGGGAATGTGTTGTTGCGTAGAGAACATTATCGTTTATCTGA
TCGTGAGGAATCTTTGGAATACGCAAAGCGGTTTATTTTGGCTAAAATTTCCAACTCAAGGA
AATACTTGCTACGCTTTAAACGAGATCATCGTCAACAGATTGATACCAAGCTTTTTGAGGCT
GTTAATGACGAATTGATATGGGCTTTAGAGATGGTTCAGGCAGCAGATAATAAAGACTCTTT
AAGAGGGATTGAAGGCCAAGCTGCTAATCAGTATTTTCGCATATTTAATGACCTGGTGTTGA
CGGACAAAAAAACGTTTTACTTCCAAGGTCGGAGTAAACGACCACCCTTAGATTGTGTTAAT
GCCCTCTTGTCTTTTGGTTACAGTTTACTGACCTTTGAATGTCAATCTGCCTTGGAAGCTGTC
GGATTAGACAGTTACGTTGGTTTCTTTCACACGGATCGTCCTGGGCGTGCTAGTTTAGCGCTT
GATTTAGTTGAAGAGTTCCGCTCATATATTGTAGATCGTTTTGTCTTTTCATTAATTAATAAA
GGACAACTTCAGAAAAAACACTTTGAGGTTAAAGAAAATGGTAGTATTTTATTGACGGAAA
ATGGCAGAGCTATTTTTATTGATTTGTGGCAGAAGCGTAAGCATACTGAGGTAGAACATCCT
TTTACAAAAGAGAAAGTAAAACTTATGTTATTACCCTATGTACAAGCGCAGCTTTTAGCTAA
GGCTATACGAGGAGATTTAGAAAGCTATCCACCTTTTATGGTTTAGGAGATGTTATATGATG
GTTTTAGTCACTTATGATGTAAATACGGAAACACCTGCTGGTAGAAAAAGATTGCGTCATGT
TGCCAAACTCTGTGTGGACTATGGGCAACGTGTTCAAAATTCTGTTTTTGAATGTTCTGTGAC
ACCCGCAGAATTTGTGGATATAAAGCACCGCTTAACACAAATCATTGATGAGAAAACTGAT
AGTATTCGCTTTTATTTATTGGGGAAAAATTGGCAGAGGCGTGTGGAAACACTTGGTCGCTC
AGACAGCTATGACCCAGATAAAGGTGTCTTATTATTGTAA (SEQ ID NO: 509)

SEQ ID NO: 510:
ATGAGAATGATTTTAGCACACTATGACTGTAAAAAAGATAAAAAGCAATCTTTAGATGAGC
ATTTATGGCATGTGGCCTGTTCTAGTCGACAGGAAGCATCTATAATTGGTCAAGGAGATGTG
CTTTTTTTAATTGGTCTTTACCACGACCTGGGCAAAGCTGATCGAACCTTTCAAGATAAATTA
TTAAATAATCCAAATCGGCATGTTGATCACTCTTATGCAGGGGCAAAATACTTATGTTCTAT
TATTGGGCCTCATCTAAAAAACCGAGGGGTTGATAAAAATGAGAGAATGACATTCAACGAA
ATGGTGGGGTATGTCATCTCTGCTCATCATGGGATGTATGATTTATGCTACTATTTTGACGAT

-continued

GCTGAATATTATGGCTTTAATAAGTTTAAAAATCGTATCAATAGAGACTTAGATGGTTATCA
CTATCATGAAGATATTAAAGGGTACGCTCTAAAATTAGAAAAAAAATTATGTGATTATGGCT
ACAAAGATTTAAGGGAGCTTATTGATAAAGCTTTTGATAATTACCAACAAGCCATGTCTTCC
TTAAACTGGCAAGATAAGAGTGAGTGGGATTATTATCAGTCTTGTATGGTGAGACTTTACTT
GTCACTCTTAAAAAACGCTGATATTTTGGACACAGTAAATGCCTATGGCCTTAAGATAAGTC
CTATGGATAAAACAGAGCGATCCTTTCTAAAACACTCCTATTTAGCGGCCATTGAACAAAAA
TATGCTAGCTTTGGACAGCCAAACAATCAGTTGAACACTATTCGGACAGAAATCGCTGAGC
GTGTTAAAGAAAGAGGTAAACGAGATTCCAAGGGGATTTATCGCTTAGATTTACCGACAGG
AGCTGGCAAGACTAATCTTAGTATGCGTTATGCGTTTCACCAATTAGTTCATCACGACAAAT
CAAGGTTTTTTTACATAACTCCCTTTCTTTCGGTTCTTGAGCAAAATGCTTCCGAAATTAGAA
AAGTTACAGGTGACCTTGGCGTTCTAGAACACCATTCCAATGTGGTGAAACAGGCTAATGA
AGATGATGATGATAAGGACAGTTTATTGTCAGCTTATCTTAGTGATAGCTGGGACAGTCAAG
TAGTCTTGACTTCTATGGTTCAATTTTTCCAAACACTTTTCAAAACAAAATCAGCTAATCTGA
GACGTTTTTCAAGTTTGATTAATAGTGTTGTGATTCTAGATGAAGTTCAATCCCTGCCTATTG
AAGTCACCACTTTGTTTAATTTAACGATGAATTTTTTAAATAAAGTTATGGATACAACCATC
GTTCTTTGCACAGCGACACAACCTGCTTATGATTCTTCAGAGATTGACCATCGTATCTGTTAT
GGAGGGAACTTGGGAGAATTAGCTGAAATAGTTGAGTTAACGATTGAAGAAAAACAGATTT
TTTCAAGGACAGAGCTTAGAAAATTTGATGATAGTGATCAGAAAGTTCACTTGACTGATGTT
ATTAACCTTATTCTAGGTGAGGAAAACTCAGTTCTTGCTATTTTTAATACGAAAAAAACGGT
TCATAACTGCTATACTATGCTAAAAGACATGACTGATAGACCGGTCTATCAGCTTTCGACAA
ATATGTGTGCGCAGCATAGACTTGACTTGATTGCTAAGATCAAAACGGAGTTACAAAATAA
TATCCCTATTATTTGTATTAGCACGCAATTAATTGAAGCAGGTGTAGATGTTGATTTTCATCG
CGTCATTCGTTCCTACTCAGGGATTGATTCTATTGTTCAGGCTGCTGGACGGTGTAACCGAG
AAGGCAAACGAGATAAAGGGCAAGTCACTCTTGTCAATCTGACCAATGAAGAGGAAAATAT
TTCTAGGCTGACAGAAATAAAAACTAAAAAAGAAGCCACAGAATCTATTCTTCATAAGATT
GGGTCTCCAATTGATATCTCAACTTTAAACCGTGACTTTTTTGAGTATTATTATGCCAATAAT
CAGGGACTGATGGATTATCCTTTGGAAGACAACCTATCAATCTACGACTATTTAAGCCTTAA
TATTTATCAGACGGCAAATAAAAAGTTCAAAGGTAAGTTAAAACAAGCTTTTAAAACAGCA
GGAGCCAAAATGAACCTCATCAATAATGATATGATAGGAATTCTCGTACCTTATGGCGAAG
CTGAGAAAAAATTGGCTTATTTAGAAGAATTAGGTGTGTCACATTTTTTATCAGCAAAAGAT
TATCAAACGATAAAATCATTACTAAAAGAGTTACAACCTTTTACGGTTAATGTCCGCGAGAA
CGATCCTCTCTTTGAGACAACAAAATCTTATCTAAATGGTCAGATTCTGGTTTTGACGTCGG
AGTATTATGACACGGAAAGAGGAGTTAAATACGATTCAGCTAGCTTTTACTTCTAA (SEQ ID NO: 510)

SEQ ID NO: 511
TTGTACAGATCTAGAGACTTCTACGTGAGAGTAAGTGGTCAGCGAGCTCTTTTTACAAATCC
AGCCACAAAAGGGGGATCGGAACGCTCATCCTATTCGGTTCCGACTAGACAGGCACTGAAT
GGTATCGTTGATGCCATCTATTATAAGCCGACCTTTACTAATATCGTCACAGAGGTTAAGGT
TATTAACCAGATTCAAACCGAATTACAGGGTGTCAGGGCTCTGTTACATGATTATAGTGCAG
ATTTAAGTTATGTATCCTATTTGAGTGATGTTGTTTATCTGATCAAGTTTCATTTTGTTTGGA
ATGAAGATAGAAAAGATTTGAACTCAGATAGACTTCCAGCTAAACATGAAGCCATTATGGA
GCGTTCTATTCGTAAAGGGGGACGTCGAGATGTGTTTTTGGGTACAAGAGAATGTTTAGGGC
TTGTAGATGATGATATCAGCCAAGAAGAGTATGAGACTACTGTGTCGTATTATAATGGTGTCAAT
ATCGACTTGGGAATCATGTTCCATTCCTTTGCCTATCCGAAGGACAAAAAGACACCATTAAA
ATCATACTTTACAAAGACTGTGATGAAAAATGGAGTCATTACGTTTAAAGCACAGTCTGAAT
GCGATATTGTTAACACGCTTTCTAGTTATGCTTTTAAAGCACCAGAGGAGATAAAATCGGTT
AACGATGAATGCATGGAGTATGATGCCATGGAGAAAGGAGAAAACTGA (SEQ ID NO: 511)

SEQ ID NO: 512:
ATGGATTTTTTACTTCTCTCTTGAAGACTTATGAAAAAGCAGAGCTAGCAGACTTGGTTGA
TCATCAAAAAAGAAATAATGAGCCGGTTTTACTGCCGATTTATCATACGAGTTTAAAGTCAA
ATGGTAAAAATATCATTTCAGTGAAACTTGACAAAGATGGCCAGTTTCACAAGGCAGAATT
TATGGCAGATAAGCAAATGATTATTTTTCCTGTAACGGCTGATTCTGTTGCTAGGTCAGGTA
GTCATCCTGCACCGCATCCCCTAGTCGATAAATTTGCTTATTATAGTGCTGAAATGGGGCAG
ATTCAGTATGATTCTTTTCATAAGCAACTGAATAACTGGATTGATTATTGTGAGGAGGGTGA
TGTCAAGAAATTTTTAACCTTTGTTCAGCAGTTCATTTTGAAGCCAGAATTTCTAACATTGAT
TCTTGATTCTTTAATTGGTCCTGATTATCAACATAATCAATTAAAAGTCACATTTTGTGATGC
CACTGGAAAAGAAAAATTAATTGATTTATCAGCTTGCTTTTTAGAATTTTCAATTGATCAGTT
CCAGGGCTTTAAAAATGAATCGGTTTCGACATTTAAAGCCTTACACCAATCCTATATTTCTTT
TGTTGAAGCCAATCGTGAAAATCTCGGTATTTGTAATATTAGTGGACGAGAGGAACAGCTTA
CCGATAAGCATAGAGGTTTGATGGGGAATGCTAAAATCATCTCTGTTAGTAATAAAAGAGA
AGCTTATAAAGGACGTTTTAGAGAACGCGAAGACGTTTTTAGTGTTGGCTATGAAACTTCCG
AAAAGATTCATTTAATGCTCAAGTACCTTTTAGAAAATAAAAATACCAGTACTTGGTTAGGG
TCTTCTCAATATTTAATCAACTGGTTCAGCGATGATTTAACAAATGATAGTCGGTTGGATATT
GTATCACCAATCTTTGATGATGGACTTGAAGAAGATGATGATGACGATACGCCTCCTGTTAT
AACATTAGCAACTGAAGACAATAAAAGAATTGGTAAATCATTCATCAAGGGACAAAAATTA
TTTGCTAATGATGCCACTTACTACGTTGCTATTTTGAATAAAACCAGCAATGGGCGGATTGC
TTTAAAATATTTTCGTCAGCTTCAAGCGTCCCAATTACTCACCAATCTTAACAAGTGGCAGG
AAACATACAGTTGGGAGTCGCGATCTAAGTTTGGGAAAAGTCGCTTAAGAACCCCTACTTTT
CATGACATCCTTAATGTGTCCTACGGGGTTGATAGGGATCGCTTCCTTGAATTAGATAATGA
TAACTTCAAAAGTGATCAAATTCAAAAGTTAGTGGCAAGTTTGATTGATGGTAAACCGATGC
CACAGTCCATTGTCAAAAGTTAGGTAACAATGTTAAAGAACGACATCGTTACCGTAAGCA
CTGGTATCAAGTTGAGCAGGTCTGCTTAGCAATTTTACACAAACAAAATGGGGAGGAATTTT
CACCGATGCTAGATCATACCAATCAAAATCGTTCCTATCTTTTTGGACGATTATTAGCAATTT
TTGAATTAATCGAGACCTTGCGTTATGGCTTGGATGGAAACAATAACGACCGTATTACCAAT
GCTGAACGTTATTGGACAGCCTATACTGGACAACCAACAAAATTGATGATGTTATTGGAAA
ATAAAATTAAGCCTTACGAAGAACCATTGAAATTAAATCGTCGTGGCAGTTGGATGAAATT
AGAAAAAGAAAAAGAAGAGATTTTAGAACTGTTAAATCCTCTGTTAGAAACAGAAACAATG
GAAAAACCCTTAGATTACCGCTTTATTTTTGGGTATTATGCTGAGAAAAACTATTACTATAC
AAAACAAAACACGGAAGTAACAGAAAGTGAGGAGTAA (SEQ ID NO: 512)

-continued

SEQ ID NO: 513:
ATGTTGGAACACAAAATTGATTTTATGGTAACTCTTGAAGTGAAAGAAGCAAATGCAAATG
GTGATCCCTTAAATGGAAACATGCCTCGTACAGATGCCAAAGGATATGGTGTGATGAGTGA
TGTCTCCATTAAACGTAAGATTCGTAATCGTTTGCAAGATATGGGGAAGTCTATTTTTGTGC
AAGCTAATGAGCGTATTGAAGATGATTTTCGTTCACTGGAAAAACGCTTTTCGCAACATTTT
ACAGCTAAGACACCTGACAAAGAAATTGAAGAAAAAGCAAATGCATTATGGTTTGATGTTC
GTGCTTTTGGACAAGTTTTTACTTATCTGAAAAAATCAATTGGGGTGCGTGGACCAGTTTCC
ATCAGTATGGCTAAGTCCTTGGAGCCAATTGTCATTTCCAGCCTTCAAATTACGCGTAGTAC
CAATGGTATGGAAGCTAAGAATAATAGTGGCCGCTCTTCTGATACGATGGGGACAAAACAT
TTTGTAGATTATGGTGTGTATGTACTTAAAGGTTCTATCAATGCTTATTTTGCTGAAAAGACT
GGTTTTTCTCAGGAAGATGCTGAGGCTATTAAAGAAGTTTTGGTTAGCTTGTTTGAAAATGA
TGCGTCGTCTGCACGTCCGGAAGGCTCTATGCGAGTTTGTGAAGTCTTTTGGTTTACGCATTC
AAGCAAATTGGGAAATGTTTCAAGTGCGCGTGTCTTTGACTTGTTAGAGTATCATCAATCAA
TAGAAGAAAAAAGCACTTATGACGCTTATCAGATTCATCTAAATCAAGAAAAATTGGCTAA
ATATGAAGCGAAAGGGTTAACGCTTGAAATCCTAGAAGGACTCTAG (SEQ ID NO: 513)

SEQ ID NO: 514:
ATGGTCTATGCCGAAGATGATTATTTAATGCTGTCAGGTATTCAGCATTTCCAATTTTGTAAA
CGTCAATGGGCGTTGATCCATATTGAGCAACAATGGCTTGATAATGAAGCGACAGCGCATG
GACAGGTTTTACATACTAAAGCAGATAACCCTTACATTAAAGAAAAACGAAAAGAGCTTTT
GGTCTCACGTGCTATGCCCATTTCTTCTGCAGAACTTGGACTTTCAGGAATTATGGATGTTGT
GGAATTTTATAAAGATGATCAAGGTGTGTCTTTGAGGGGAAAACGTGGGAAATGGTTACCA
AAAGTTGTGGAATACAAGCGCGGAAAACCTAAAAAAGATACCAGAGATATTGTCCAGTTGG
TGGCTCAGACCATGTGTTTAGAAGAAACGCTAGACTGCGACATTAACGAAGGTTGTCTTTAT
TACCATAGTGTCAATCAAAGAGTGATTGTTCCTATGACATCAGCTTTGCGTCAAGAAGTGAA
GGAATTAGCCGCAGAGATGCATGAGGTTTATCAGAGTCAAATGCTACCTAAAGCAGCTTAT
TTTAAAAACTGTCAGCTTTGTTCTTTAGTCGATATTTGTAAGCCCAGGTTGAGTAAAAAAAC
AAGGAGTGTGTCGCGTTACATCAATGAGGCTATGACCAGTGAGGAGATGGACCTATGA
(SEQ ID NO: 514)

SEQ ID NO: 515:
ATGAAGAAGTTGCTAAATACCTTGTATTTGACGCAAGAAGATTTTTATGTCACTAAAGAGGG
CGATAACATTGTTATCAAGCAAGAAGGTAAGGTTCTCAAACGGTTTCCGTTTCGGATTATTG
ACGGTATTGTCTGTTTTTCTTATTTGGGTGTGTCGTCTGCTTTGGTGAAGTTATGTACGGAGA
ATCAGATTAATTTATCGTTTCATACACCACAAGGGCGTTTTTGTGGTCGCTATATTGGTTCAA
CCAATGGGAATGTGTTGTTGCGTAGAGAACATTATCGTTTATCTGATCGTGAGGAATCTTTG
GAATACGCAAAGCGGTTTATTTTGGCTAAAATTTCCAACTCAAGGAAATACTTGCTACGCTT
TAAACGAGATCATCGTCAACAGATTGATACCAAGCTTTTTGAGGCTGTTAATGACGAATTGA
TATGGGCTTTAGAGATGGTTCAGGCAGCAGATAATAAAGACTCTTTAAGAGGGATTGAAGG
CCAAGCTGCTAATCAGTATTTTCGCATATTTAATGACCTGGTGTTGACGGACAAAAAAACGT
TTTACTTCCAAGGTCGGAGTAAACGACCACCCTTAGATTGTGTTAATGCCCTCTTGTCTTTTG
GTTACAGTTTACTGACCTTTGAATGTCAATCTGCCTTGGAAGCTGTCGGATTAGACAGTTAC
GTTGGTTTCTTTCACACGGATCGTCCTGGGCGTGCTAGTTTAGCGCTTGATTTAGTTGAAGAG
TTCCGCTCATATATTGTAGATCGTTTTGTCTTTTCATTAATTAATAAAGGACAACTTCAGAAA
AAACACTTTGAGGTTAAAGAAAATGGTAGTATTTTATTGACGGAAAATGGCAGAGCTATTTT
TATTGATTTGTGGCAGAAGCGTAAGCATACTGAGGTAGAACATCCTTTTACAAAAGAGAAA
GTAAAACTTATGTTATTACCCTATGTACAAGCGCAGCTTTTAGCTAAGGCTATACGAGGAGA
TTTAGAAAGCTATCCACCTTTTATGGTTTAG (SEQ ID NO: 515)

SEQ ID NO: 516:
ATGATGGTTTTAGTCACTTATGATGTAAATACGGAAACACCTGCTGGTAGAAAAAGATTGCG
TCATGTTGCCAAACTCTGTGTGGACTATGGGCAACGTGTTCAAAATTCTGTTTTTGAATGTTC
TGTGACACCCGCAGAATTTGTGGATATAAAGCACCGCTTAACACAAATCATTGATGAGAAA
ACTGATAGTATTCGCTTTTATTTATTGGGGAAAAATTGGCAGAGGCGTGTGGAAACACTTGG
TCGCTCAGACAGCTATGACCCAGATAAAGGTGTCTTATTATTGTAA (SEQ ID NO: 516)

with repeat sequences: SEQ ID NO:20 and SEQ ID NO:22

All patents and publications mentioned in the specification are indicative of the levels of those skilled in the art to which the invention pertains. All patents and publications are herein incorporated by reference to the same extent as if each individual publication was specifically and individually indicated to be incorporated by reference.

Those of skill in the art readily appreciate that the present invention is well adapted to carry out the objects and obtain the ends and advantages mentioned, as well as those inherent therein. The compositions and methods described herein are representative of preferred embodiments, are exemplary, and are not intended as limitations on the scope of the invention. It is readily apparent to one skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

We claim:

1. A method for generating a mixed bacterial starter culture comprising at least two different bacteriophage resistant variant strains, comprising the steps of:

(a) exposing a parent bacterial strain comprising a CRISPR locus to at least one bacteriophage to produce a mixture of bacteria comprising at least one bacteriophage resistant variant strain;

(a)(1) selecting said bacteriophage resistant variant strains from the mixture of stop (a);

(a)(2) selecting, from said bacteriophage resistant strains selected in step (a1) bacteriophage resistant variant strains comprising in a CRISPR locus an additional repeat-spacer unit that is absent from the CRISPR locus in the parent bacteria, wherein the nucleotide sequence of the repeat of the additional unit is 100% identical to a repeat of the CRISPR locus of the parent bacteria and wherein the nucleotide sequence of spacer of the additional unit has at least 95% identity to the genome of the bacteriophage used for the selection of the bacteriophage resistant variant strains;

(a)(3) isolating said bacteriophage resistant variant strains selected in step (a2); and (b) exposing a parent bacterial strain comprising a CRISPR locus, different to the parent bacterial strain of step (a), to a different at least one bacteriophage to that of step (a) to produce a mixture of bacteria comprising at least another bacteriophage resistant variant strain;

(b1) selecting said bacteriophage resistant variant strains from the mixture of step (b);

(b2) selecting, from said bacteriophage resistant strains selected in step (b1) bacteriophage resistant variant strains comprising in a CRISPR locus an additional repeat-spacer unit that is absent from the CRISPR locus in the parent bacteria, wherein the nucleotide sequence of the repeat of the additional unit is 100% identical to a repeat of the CRISPR locus of the parent bacteria and wherein the nucleotide sequence of spacer of the additional unit has at least 95% identity to the genome of the bacteriophage used for the selection of the bacteriophage resistant variant strains; and (b3) isolating said bacteriophage resistant variant strains selected in step (b2); and (c) combining at least one isolated bacteriophage resistant variant strain from step (a3) and at least one isolated bacteriophage resistant variant strain from step (b3).

2. The method of claim 1, wherein said method further comprises the step of comparing said CRISPR locus or a portion thereof of said parent bacterial bacteriophage resistant variant strain selected in step (a1) and the step of comparing said CRISPR locus or a portion thereof of said parent bacterial strain exposed in step (b) and said CRISPR locus or a portion thereof of said bacteriophage resistant variant strain selected in step (b1) to identify bacteriophage resistant variant strains comprising at least one additional repeat-spacer unit in their CRISPR locus that is absent from said CRISPR locus of said parent bacterial strain.

3. The method of claim 1, wherein said parent bacterial strain is exposed to two or more bacteriophages.

4. The method of claim 1, wherein said parent bacterial strain is simultaneously exposed to two or more bacteriophages.

5. The method of claim 1, wherein said parent bacterial strain is sequentially exposed to two or more bacteriophages.

6. The method of claim 1, wherein said parent bacterial strain is infected by the bacteriophage.

7. The method of claim 6, wherein said at least one bacteriophage is selected from the group of virus families consisting of: Corticoviridae, Cystoviridae, Inoviridae, Leviviridae, Microviridae, Myoviridae, Podoviridae, Siphoviridae, and Tectiviridae.

8. The method of claim 6, wherein said at least one bacteriophage is a naturally occurring bacteriophage.

9. The method of claim 6, wherein said at least one bacteriophage is a mutated bacteriophage obtained through selective pressure using a bacteriophage resistant bacterium.

10. The method of claim 2, wherein the 5' end and/or the 3' end of said CRISPR loci are compared.

11. The method of claim 2, wherein the 5' and/or the 3' end of the first CRISPR spacer of said CRISPR loci are compared.

12. The method of claim 2, wherein comparing said at least a portion of said CRISPR locus of said parent bacterial strain and at least a portion of said CRISPR locus of said bacteriophage resistant variant strain includes amplifying said at least a portion of said CRISPR locus of said parent bacterial strain and said and least a portion of said CRISPR locus of said bacteriophage resistant variant strain.

13. The method of claim 12, wherein said amplifying is conducted using the polymerase chain reaction.

14. The method of claim 1, wherein said at least a portion of said CRISPR locus of said parent bacterial strain and at least a portion of said CRISPR locus of said bacteriophage resistant variant strain are compared by sequencing.

15. The method of claim 12, further comprising the step of sequencing said amplified CRISPR locus sequence of said parent bacterial strain and said amplified CRISPR sequence locus of said bacteriophage resistant variant strain.

16. The method of claim 1, wherein said additional repeat-spacer unit comprises at least about 44 nucleotides.

17. The method of claim 1, wherein said additional repeat-spacer unit comprises between about 44 and about 119 nucleotides.

18. The method of claim 1, wherein said parent bacterial strain is an industrially useful strain.

19. The method of claim 18, wherein said parent bacterial strain is susceptible to infection by at least one bacteriophage.

20. The method of claim 18, wherein said parent bacterial strain is suitable for use as a starter culture, a probiotic culture, and/or a dietary supplement culture.

21. The method of claim 1, wherein said parent bacterial strain is selected from *Escherichia, Shigella, Salmonella, Erwinia, Yersinia, Bacillus, Vibrio, Legionella, Pseudomonas, Neisseria, Bordetella, Helicobacter, Listeria, Agrobacterium, Staphylococcus, Streptococcus, Enterococcus, Clostridium, Corynebacterium, Mycobacterium, Treponema, Borrelia, Francisella, Brucella, Campylobacter, Klebsiella, Frankia, Bartonella, Rickettsia, Shewanella, Serratia, Enterobacter, Proteus, Providencia, Brochothrix, Bifidobacterium, Brevibacterium, Propionibacterium, Lactococcus, Lactobacillus, Pediococcus, Leuconostoc*, and *Oenococcus*.

22. The method of claim 1, wherein the parental bacterial strain is sensitive to each of the bacteriophages that it is exposed to in the mixture.

23. The method of claim 1, wherein the parental bacterial strain is sensitive to some of the bacteriophages that it is exposed to in the mixture.

24. The method of claim 1, wherein two or more different repeat-spacer units, each integrate into two or more different CRISPR loci.

25. The method of claim 1, wherein two or more different repeat-spacer units integrate into one CRISPR locus.

* * * * *

SEQUENCE LISTING

<160> NUMBER OF SEQ ID NOS: 798

<210> SEQ ID NO 1
<211> LENGTH: 36
<212> TYPE: DNA
<213> ORGANISM: Streptococcus thermophilus

<400> SEQUENCE: 1
gtttttgtac tctcaagatt taagtaactg tacaac 36

<210> SEQ ID NO 2
<211> LENGTH: 36
<212> TYPE: DNA
<213> ORGANISM: Streptococcus thermophilus

<400> SEQUENCE: 2
gtttttgtat tctcaagatt taagtaactg tacagt 36

<210> SEQ ID NO 3
<211> LENGTH: 36
<212> TYPE: DNA
<213> ORGANISM: Streptococcus thermophilus

<400> SEQUENCE: 3
gtttttgtac tctcaagatt taagtaactg tacagt 36

<210> SEQ ID NO 4
<211> LENGTH: 36
<212> TYPE: DNA
<213> ORGANISM: Streptococcus thermophilus

<400> SEQUENCE: 4
gtttttgtac tctcaagatt taagtaaccg tacaac 36

<210> SEQ ID NO 5
<211> LENGTH: 36
<212> TYPE: DNA
<213> ORGANISM: Streptococcus thermophilus

<400> SEQUENCE: 5
gtttttgtac tctcaagatt taagtaactg tgcaac 36

<210> SEQ ID NO 6
<211> LENGTH: 36
<212> TYPE: DNA
<213> ORGANISM: Streptococcus thermophilus

<400> SEQUENCE: 6
gtttttgtac tctcaagatt taagtagctg tacagt 36

<210> SEQ ID NO 7
<211> LENGTH: 36
<212> TYPE: DNA
<213> ORGANISM: Streptococcus thermophilus

<400> SEQUENCE: 7
gtttttgtac tctcaagata taagtaactg tacaac 36

<210> SEQ ID NO 8
<211> LENGTH: 36
<212> TYPE: DNA

<213> ORGANISM: Streptococcus thermophilus

<400> SEQUENCE: 8
gtttttgtac tctcaagatc taagtaactg tacaac 36

<210> SEQ ID NO 9
<211> LENGTH: 36
<212> TYPE: DNA
<213> ORGANISM: Streptococcus thermophilus

<400> SEQUENCE: 9
gtttttgtac tctcaagatg taagtaactg tacaac 36

<210> SEQ ID NO 10
<211> LENGTH: 36
<212> TYPE: DNA
<213> ORGANISM: Streptococcus thermophilus

<400> SEQUENCE: 10
gtctttgtac tctcaagatt taagtaactg tacaac 36

<210> SEQ ID NO 11
<211> LENGTH: 36
<212> TYPE: DNA
<213> ORGANISM: Streptococcus thermophilus

<400> SEQUENCE: 11
aaaaaagtcc cctctcgagg taattaggtt tatatc 36

<210> SEQ ID NO 12
<211> LENGTH: 36
<212> TYPE: DNA
<213> ORGANISM: Streptococcus thermophilus

<400> SEQUENCE: 12
gtttccgtcc cctctcgagg taattaggtt tatatc 36

<210> SEQ ID NO 13
<211> LENGTH: 36
<212> TYPE: DNA
<213> ORGANISM: Streptococcus agalactiae

<400> SEQUENCE: 13
gttttagagc tgtgttgttt cgaatggttc caaaac 36

<210> SEQ ID NO 14
<211> LENGTH: 36
<212> TYPE: DNA
<213> ORGANISM: Streptococcus agalactiae

<400> SEQUENCE: 14
gttttaaagc tgtgctgtta ttatgctagg gcacca 36

<210> SEQ ID NO 15
<211> LENGTH: 36
<212> TYPE: DNA
<213> ORGANISM: Streptococcus agalactiae

<400> SEQUENCE: 15
gttttagagc tgtgctgttt cgaatggttc caaaac 36

<210> SEQ ID NO 16
<211> LENGTH: 36

-continued

<212> TYPE: DNA
<213> ORGANISM: Streptococcus agalactiae

<400> SEQUENCE: 16
gttttagagc tgtgctgtta ttatgctagg acatca 36

<210> SEQ ID NO 17
<211> LENGTH: 36
<212> TYPE: DNA
<213> ORGANISM: Streptococcus mutans

<400> SEQUENCE: 17
gttttagagc catgttagtt actgatttac taaaat 36

<210> SEQ ID NO 18
<211> LENGTH: 36
<212> TYPE: DNA
<213> ORGANISM: Streptococcus pyogenes

<400> SEQUENCE: 18
gttttagagc tatgctgttt tgaatggtcc caaaac 36

<210> SEQ ID NO 19
<211> LENGTH: 36
<212> TYPE: DNA
<213> ORGANISM: Streptococcus pyogenes

<400> SEQUENCE: 19
gttttagagc tatgctgttt tgaatggtct ccattc 36

<210> SEQ ID NO 20
<211> LENGTH: 33
<212> TYPE: DNA
<213> ORGANISM: Streptococcus pyogenes

<400> SEQUENCE: 20
ctttcaatcc actcacccat gaagggtgag acg 33

<210> SEQ ID NO 21
<211> LENGTH: 33
<212> TYPE: DNA
<213> ORGANISM: Streptococcus pyogenes

<400> SEQUENCE: 21
atttcaatcc actcacccat gaagggtgag act 33

<210> SEQ ID NO 22
<211> LENGTH: 33
<212> TYPE: DNA
<213> ORGANISM: Streptococcus pyogenes

<400> SEQUENCE: 22
atttcaatcc actcacccat gaagggtgag acc 33

<210> SEQ ID NO 23
<211> LENGTH: 30
<212> TYPE: DNA
<213> ORGANISM: Streptococcus thermophilus

<400> SEQUENCE: 23
agaacgtatt ccaaaacctc tttacgatta 30

<210> SEQ ID NO 24

<211> LENGTH: 30
<212> TYPE: DNA
<213> ORGANISM: Streptococcus thermophilus

<400> SEQUENCE: 24
ttaactgtta tcaaaatgat aagatagtct 30

<210> SEQ ID NO 25
<211> LENGTH: 30
<212> TYPE: DNA
<213> ORGANISM: Streptococcus thermophilus

<400> SEQUENCE: 25
cgttgatgtt tattcaagta aaataattaa 30

<210> SEQ ID NO 26
<211> LENGTH: 30
<212> TYPE: DNA
<213> ORGANISM: Streptococcus thermophilus

<400> SEQUENCE: 26
tcctttcacg ggtagcacac taacatacac 30

<210> SEQ ID NO 27
<211> LENGTH: 30
<212> TYPE: DNA
<213> ORGANISM: Streptococcus thermophilus

<400> SEQUENCE: 27
gttggcaatg caaacaacct ttatgaaccg 30

<210> SEQ ID NO 28
<211> LENGTH: 30
<212> TYPE: DNA
<213> ORGANISM: Streptococcus thermophilus

<400> SEQUENCE: 28
tttatttcct tgcgataacg ttccaccttt 30

<210> SEQ ID NO 29
<211> LENGTH: 30
<212> TYPE: DNA
<213> ORGANISM: Streptococcus thermophilus

<400> SEQUENCE: 29
agattataag gaacacaacc aactatatag 30

<210> SEQ ID NO 30
<211> LENGTH: 30
<212> TYPE: DNA
<213> ORGANISM: Streptococcus thermophilus

<400> SEQUENCE: 30
acgacatcaa gctgattgtc ttctacataa 30

<210> SEQ ID NO 31
<211> LENGTH: 30
<212> TYPE: DNA
<213> ORGANISM: Streptococcus thermophilus

<400> SEQUENCE: 31
tttggaatac tgaatgtttt actgaaaatc 30

<210> SEQ ID NO 32
<211> LENGTH: 30
<212> TYPE: DNA
<213> ORGANISM: Streptococcus thermophilus

<400> SEQUENCE: 32
acaccactat cttttcctcc tgaaaatgaa 30

<210> SEQ ID NO 33
<211> LENGTH: 30
<212> TYPE: DNA
<213> ORGANISM: Streptococcus thermophilus

<400> SEQUENCE: 33
gtaattccac gaaattatca accttatgca 30

<210> SEQ ID NO 34
<211> LENGTH: 29
<212> TYPE: DNA
<213> ORGANISM: Streptococcus thermophilus

<400> SEQUENCE: 34
ttggaggatt gccccatatt cccaagagt 29

<210> SEQ ID NO 35
<211> LENGTH: 30
<212> TYPE: DNA
<213> ORGANISM: Streptococcus thermophilus

<400> SEQUENCE: 35
gagaggcgtt aaatatagaa atgcaagatt 30

<210> SEQ ID NO 36
<211> LENGTH: 30
<212> TYPE: DNA
<213> ORGANISM: Streptococcus thermophilus

<400> SEQUENCE: 36
ttttaacgtc atcagtccac cgccttaaat 30

<210> SEQ ID NO 37
<211> LENGTH: 30
<212> TYPE: DNA
<213> ORGANISM: Streptococcus thermophilus

<400> SEQUENCE: 37
cacctctttc gatggaaagg tatccttcta 30

<210> SEQ ID NO 38
<211> LENGTH: 30
<212> TYPE: DNA
<213> ORGANISM: Streptococcus thermophilus

<400> SEQUENCE: 38
gaccaaagtt tgattataga gctatacacc 30

<210> SEQ ID NO 39
<211> LENGTH: 30
<212> TYPE: DNA
<213> ORGANISM: Streptococcus thermophilus

<400> SEQUENCE: 39
accatcattc ttaccattac aactgtaatg 30

<210> SEQ ID NO 40
<211> LENGTH: 30
<212> TYPE: DNA
<213> ORGANISM: Streptococcus thermophilus

<400> SEQUENCE: 40
atacgaattc ggttcgcaca attacaattc 30

<210> SEQ ID NO 41
<211> LENGTH: 32
<212> TYPE: DNA
<213> ORGANISM: Streptococcus thermophilus

<400> SEQUENCE: 41
tatcaacgca atcattacaa caacttcaaa ca 32

<210> SEQ ID NO 42
<211> LENGTH: 30
<212> TYPE: DNA
<213> ORGANISM: Streptococcus thermophilus

<400> SEQUENCE: 42
atctacgtgt caatacatat cacaaaacag 30

<210> SEQ ID NO 43
<211> LENGTH: 29
<212> TYPE: DNA
<213> ORGANISM: Streptococcus thermophilus

<400> SEQUENCE: 43
atttttagaa atttctgata taataatga 29

<210> SEQ ID NO 44
<211> LENGTH: 30
<212> TYPE: DNA
<213> ORGANISM: Streptococcus thermophilus

<400> SEQUENCE: 44
ttgttggaac aaggacgact tggtaaacta 30

<210> SEQ ID NO 45
<211> LENGTH: 30
<212> TYPE: DNA
<213> ORGANISM: Streptococcus thermophilus

<400> SEQUENCE: 45
catattaagc tgactgggcc taatgctttt 30

<210> SEQ ID NO 46
<211> LENGTH: 30
<212> TYPE: DNA
<213> ORGANISM: Streptococcus thermophilus

<400> SEQUENCE: 46
ttcatagcat accgtagttg taaaatctat 30

<210> SEQ ID NO 47
<211> LENGTH: 30
<212> TYPE: DNA
<213> ORGANISM: Streptococcus thermophilus

<400> SEQUENCE: 47
aacatttagg gaatgaaatt gataagactg 30

<210> SEQ ID NO 48
<211> LENGTH: 30
<212> TYPE: DNA
<213> ORGANISM: Streptococcus thermophilus

<400> SEQUENCE: 48
aacatgagaa actgtagaaa acaagcaata 30

<210> SEQ ID NO 49
<211> LENGTH: 31
<212> TYPE: DNA
<213> ORGANISM: Streptococcus thermophilus

<400> SEQUENCE: 49
tggtgaagat ggcagtcata aatggcacat t 31

<210> SEQ ID NO 50
<211> LENGTH: 30
<212> TYPE: DNA
<213> ORGANISM: Streptococcus thermophilus

<400> SEQUENCE: 50
aagggttgaa aaatgttggt atatcaaacg 30

<210> SEQ ID NO 51
<211> LENGTH: 30
<212> TYPE: DNA
<213> ORGANISM: Streptococcus thermophilus

<400> SEQUENCE: 51
ttctggtagt ggatttagtc aaacagatgt 30

<210> SEQ ID NO 52
<211> LENGTH: 30
<212> TYPE: DNA
<213> ORGANISM: Streptococcus thermophilus

<400> SEQUENCE: 52
tccatagagc gtcttaaaca aagaatagtc 30

<210> SEQ ID NO 53
<211> LENGTH: 30
<212> TYPE: DNA
<213> ORGANISM: Streptococcus thermophilus

<400> SEQUENCE: 53
ttatgattga atgacatggt tgtataagta 30

<210> SEQ ID NO 54
<211> LENGTH: 30
<212> TYPE: DNA
<213> ORGANISM: Streptococcus thermophilus

<400> SEQUENCE: 54
tttctttagg aataccaggg agttcagctt 30

<210> SEQ ID NO 55
<211> LENGTH: 30
<212> TYPE: DNA
<213> ORGANISM: Streptococcus thermophilus

<400> SEQUENCE: 55

```
tggcagagat tacacagcaa cggaaacagc                                  30


<210> SEQ ID NO 56
<211> LENGTH: 30
<212> TYPE: DNA
<213> ORGANISM: Streptococcus thermophilus

<400> SEQUENCE: 56

gggtatcatt gtatctagtg atggacctga                                  30


<210> SEQ ID NO 57
<211> LENGTH: 30
<212> TYPE: DNA
<213> ORGANISM: Streptococcus thermophilus

<400> SEQUENCE: 57

atttgaaaaa tgcacaacag cgtttgatag                                  30


<210> SEQ ID NO 58
<211> LENGTH: 30
<212> TYPE: DNA
<213> ORGANISM: Streptococcus thermophilus

<400> SEQUENCE: 58

gagctaccag ctaccccgta tgtcagagag                                  30


<210> SEQ ID NO 59
<211> LENGTH: 30
<212> TYPE: DNA
<213> ORGANISM: Streptococcus thermophilus

<400> SEQUENCE: 59

cgttcctttt ttcaaggtaa tctttgaaag                                  30


<210> SEQ ID NO 60
<211> LENGTH: 30
<212> TYPE: DNA
<213> ORGANISM: Streptococcus thermophilus

<400> SEQUENCE: 60

aagtccgtaa gcaccagttc caatcgtcat                                  30


<210> SEQ ID NO 61
<211> LENGTH: 30
<212> TYPE: DNA
<213> ORGANISM: Streptococcus thermophilus

<400> SEQUENCE: 61

ttgaatacca atgccagctt cttttaaggc                                  30


<210> SEQ ID NO 62
<211> LENGTH: 30
<212> TYPE: DNA
<213> ORGANISM: Streptococcus thermophilus

<400> SEQUENCE: 62

aacctcatac atggggaaaa ttggtaagta                                  30


<210> SEQ ID NO 63
<211> LENGTH: 30
<212> TYPE: DNA
<213> ORGANISM: Streptococcus thermophilus

<400> SEQUENCE: 63
```

taacttcatt agtgtagttg taattagcat 30

<210> SEQ ID NO 64
<211> LENGTH: 30
<212> TYPE: DNA
<213> ORGANISM: Streptococcus thermophilus

<400> SEQUENCE: 64
ttagctaccc aaatatcttc tgttttccaa 30

<210> SEQ ID NO 65
<211> LENGTH: 30
<212> TYPE: DNA
<213> ORGANISM: Streptococcus thermophilus

<400> SEQUENCE: 65
gagttttcaa tattggcaca ggagacaatt 30

<210> SEQ ID NO 66
<211> LENGTH: 30
<212> TYPE: DNA
<213> ORGANISM: Streptococcus thermophilus

<400> SEQUENCE: 66
tgatactatt ttagtcagat atgaaatatc 30

<210> SEQ ID NO 67
<211> LENGTH: 31
<212> TYPE: DNA
<213> ORGANISM: Streptococcus thermophilus

<400> SEQUENCE: 67
tcatcaatgt ttaaagccca acaatacatg a 31

<210> SEQ ID NO 68
<211> LENGTH: 30
<212> TYPE: DNA
<213> ORGANISM: Streptococcus thermophilus

<400> SEQUENCE: 68
tagatttaat cagtaatgag ttaggcataa 30

<210> SEQ ID NO 69
<211> LENGTH: 30
<212> TYPE: DNA
<213> ORGANISM: Streptococcus thermophilus

<400> SEQUENCE: 69
aggaaaatag catgagcgta caacaatcta 30

<210> SEQ ID NO 70
<211> LENGTH: 30
<212> TYPE: DNA
<213> ORGANISM: Streptococcus thermophilus

<400> SEQUENCE: 70
tgtctatcac gcttcctaag tgcatgaaaa 30

<210> SEQ ID NO 71
<211> LENGTH: 30
<212> TYPE: DNA
<213> ORGANISM: Streptococcus thermophilus -continued

<400> SEQUENCE: 71
atgtcaccaa tcactaaaga acctacgctg 30

<210> SEQ ID NO 72
<211> LENGTH: 30
<212> TYPE: DNA
<213> ORGANISM: Streptococcus thermophilus

<400> SEQUENCE: 72
aacatcttcc tctccgattg caaatagtgc 30

<210> SEQ ID NO 73
<211> LENGTH: 29
<212> TYPE: DNA
<213> ORGANISM: Streptococcus thermophilus

<400> SEQUENCE: 73
catatttggt gcccgttcga taaagagta 29

<210> SEQ ID NO 74
<211> LENGTH: 30
<212> TYPE: DNA
<213> ORGANISM: Streptococcus thermophilus

<400> SEQUENCE: 74
cattaaatcg cttgaagcag acattgaagc 30

<210> SEQ ID NO 75
<211> LENGTH: 30
<212> TYPE: DNA
<213> ORGANISM: Streptococcus thermophilus

<400> SEQUENCE: 75
gacttatctt ggaaggtagt gaaggcactt 30

<210> SEQ ID NO 76
<211> LENGTH: 30
<212> TYPE: DNA
<213> ORGANISM: Streptococcus thermophilus

<400> SEQUENCE: 76
tccttgccat ctgcactgta agcccaagca 30

<210> SEQ ID NO 77
<211> LENGTH: 30
<212> TYPE: DNA
<213> ORGANISM: Streptococcus thermophilus

<400> SEQUENCE: 77
tagtacgcat aatcaattca tcaagcttga 30

<210> SEQ ID NO 78
<211> LENGTH: 30
<212> TYPE: DNA
<213> ORGANISM: Streptococcus thermophilus

<400> SEQUENCE: 78
gtagtgaccc aaaattctat gaccttgaaa 30

<210> SEQ ID NO 79
<211> LENGTH: 30
<212> TYPE: DNA
<213> ORGANISM: Streptococcus thermophilus

<400> SEQUENCE: 79
agattgtggt gcttacggaa aattccttgt 30

<210> SEQ ID NO 80
<211> LENGTH: 30
<212> TYPE: DNA
<213> ORGANISM: Streptococcus thermophilus

<400> SEQUENCE: 80
tggcaagaag tgtaagagat gcaatggata 30

<210> SEQ ID NO 81
<211> LENGTH: 30
<212> TYPE: DNA
<213> ORGANISM: Streptococcus thermophilus

<400> SEQUENCE: 81
tttattatca ttattcttct tcccaagcgt 30

<210> SEQ ID NO 82
<211> LENGTH: 30
<212> TYPE: DNA
<213> ORGANISM: Streptococcus thermophilus

<400> SEQUENCE: 82
ttttatagaa tttggtggtg aactttttca 30

<210> SEQ ID NO 83
<211> LENGTH: 29
<212> TYPE: DNA
<213> ORGANISM: Streptococcus thermophilus

<400> SEQUENCE: 83
aatgggtcac agattgccat aataaggag 29

<210> SEQ ID NO 84
<211> LENGTH: 30
<212> TYPE: DNA
<213> ORGANISM: Streptococcus thermophilus

<400> SEQUENCE: 84
ccgaggtcac tttagaaccc acaaaataag 30

<210> SEQ ID NO 85
<211> LENGTH: 30
<212> TYPE: DNA
<213> ORGANISM: Streptococcus thermophilus

<400> SEQUENCE: 85
atgagagaac acagtataga ccctgataca 30

<210> SEQ ID NO 86
<211> LENGTH: 30
<212> TYPE: DNA
<213> ORGANISM: Streptococcus thermophilus

<400> SEQUENCE: 86
cagtattaat gaggtttggg tggtcattcc 30

<210> SEQ ID NO 87
<211> LENGTH: 31
<212> TYPE: DNA

<213> ORGANISM: Streptococcus thermophilus

<400> SEQUENCE: 87
ccatactctc tatcagttca tttaattctt c 31

<210> SEQ ID NO 88
<211> LENGTH: 30
<212> TYPE: DNA
<213> ORGANISM: Streptococcus thermophilus

<400> SEQUENCE: 88
taatatgtcg ctctactgat tccaaaacgg 30

<210> SEQ ID NO 89
<211> LENGTH: 30
<212> TYPE: DNA
<213> ORGANISM: Streptococcus thermophilus

<400> SEQUENCE: 89
atgaattaca ttcatgattt tatcgagttt 30

<210> SEQ ID NO 90
<211> LENGTH: 29
<212> TYPE: DNA
<213> ORGANISM: Streptococcus thermophilus

<400> SEQUENCE: 90
cgtgccattg tttcggtcgg acgtgggca 29

<210> SEQ ID NO 91
<211> LENGTH: 30
<212> TYPE: DNA
<213> ORGANISM: Streptococcus thermophilus

<400> SEQUENCE: 91
ctttctaagt tgaattaaat tcaagttttg 30

<210> SEQ ID NO 92
<211> LENGTH: 30
<212> TYPE: DNA
<213> ORGANISM: Streptococcus thermophilus

<400> SEQUENCE: 92
tcgctactat ggttaacgat gaggaactct 30

<210> SEQ ID NO 93
<211> LENGTH: 30
<212> TYPE: DNA
<213> ORGANISM: Streptococcus thermophilus

<400> SEQUENCE: 93
agcaacttta aaactaaaag agctacttga 30

<210> SEQ ID NO 94
<211> LENGTH: 30
<212> TYPE: DNA
<213> ORGANISM: Streptococcus thermophilus

<400> SEQUENCE: 94
aaaaccctac acagtgtgtg agatgtgtca 30

<210> SEQ ID NO 95
<211> LENGTH: 30

<212> TYPE: DNA
<213> ORGANISM: Streptococcus thermophilus

<400> SEQUENCE: 95
aatgggtcac agattgccat aataaggagg 30

<210> SEQ ID NO 96
<211> LENGTH: 30
<212> TYPE: DNA
<213> ORGANISM: Streptococcus thermophilus

<400> SEQUENCE: 96
ttttttaaaa tccgtcatgc tatactatat 30

<210> SEQ ID NO 97
<211> LENGTH: 30
<212> TYPE: DNA
<213> ORGANISM: Streptococcus thermophilus

<400> SEQUENCE: 97
aattcaaact ttctccaata ataccctcca 30

<210> SEQ ID NO 98
<211> LENGTH: 30
<212> TYPE: DNA
<213> ORGANISM: Streptococcus thermophilus

<400> SEQUENCE: 98
catgctttca gttaataaga cgtgggacta 30

<210> SEQ ID NO 99
<211> LENGTH: 30
<212> TYPE: DNA
<213> ORGANISM: Streptococcus thermophilus

<400> SEQUENCE: 99
tggaaggggt gtctagtgaa gaaattgtcg 30

<210> SEQ ID NO 100
<211> LENGTH: 30
<212> TYPE: DNA
<213> ORGANISM: Streptococcus thermophilus

<400> SEQUENCE: 100
ctcgaagcgc ttcattgccc tattcctttc 30

<210> SEQ ID NO 101
<211> LENGTH: 29
<212> TYPE: DNA
<213> ORGANISM: Streptococcus thermophilus

<400> SEQUENCE: 101
atgtctaagg tatccactcg tgaaatcat 29

<210> SEQ ID NO 102
<211> LENGTH: 30
<212> TYPE: DNA
<213> ORGANISM: Streptococcus thermophilus

<400> SEQUENCE: 102
atattaatgg aaatttcatt caaacgcagt 30

<210> SEQ ID NO 103

-continued

<211> LENGTH: 30
<212> TYPE: DNA
<213> ORGANISM: Streptococcus thermophilus

<400> SEQUENCE: 103
tagagagttt atatcctgat ggaatcgatg 30

<210> SEQ ID NO 104
<211> LENGTH: 30
<212> TYPE: DNA
<213> ORGANISM: Streptococcus thermophilus

<400> SEQUENCE: 104
tggcgaatta gagagccaat ggcaagcaag 30

<210> SEQ ID NO 105
<211> LENGTH: 30
<212> TYPE: DNA
<213> ORGANISM: Streptococcus thermophilus

<400> SEQUENCE: 105
agaagaccaa taaacttgag aaaaagcaag 30

<210> SEQ ID NO 106
<211> LENGTH: 30
<212> TYPE: DNA
<213> ORGANISM: Streptococcus thermophilus

<400> SEQUENCE: 106
aaatggtcgt ttaattgtta atgtcaaagc 30

<210> SEQ ID NO 107
<211> LENGTH: 30
<212> TYPE: DNA
<213> ORGANISM: Streptococcus thermophilus

<400> SEQUENCE: 107
caattgattc taaaatgctt ggtacacgta 30

<210> SEQ ID NO 108
<211> LENGTH: 30
<212> TYPE: DNA
<213> ORGANISM: Streptococcus thermophilus

<400> SEQUENCE: 108
tcttcgtgtt atcacagctt ctacacgttg 30

<210> SEQ ID NO 109
<211> LENGTH: 30
<212> TYPE: DNA
<213> ORGANISM: Streptococcus thermophilus

<400> SEQUENCE: 109
gaaatctcat tgaaaccaac ttcaagacca 30

<210> SEQ ID NO 110
<211> LENGTH: 30
<212> TYPE: DNA
<213> ORGANISM: Streptococcus thermophilus

<400> SEQUENCE: 110
tgcttggtag ttgatgcact gcattagtaa 30

-continued

<210> SEQ ID NO 111
<211> LENGTH: 30
<212> TYPE: DNA
<213> ORGANISM: Streptococcus thermophilus

<400> SEQUENCE: 111
aatgtaccgg aatagcgtta cattgcacat 30

<210> SEQ ID NO 112
<211> LENGTH: 30
<212> TYPE: DNA
<213> ORGANISM: Streptococcus thermophilus

<400> SEQUENCE: 112
ttcataaatt ctcacttttc cttgctattc 30

<210> SEQ ID NO 113
<211> LENGTH: 30
<212> TYPE: DNA
<213> ORGANISM: Streptococcus thermophilus

<400> SEQUENCE: 113
tgtcgaaaaa attacctagt cacgacagac 30

<210> SEQ ID NO 114
<211> LENGTH: 30
<212> TYPE: DNA
<213> ORGANISM: Streptococcus thermophilus

<400> SEQUENCE: 114
caacaattac ttatgcatta ggaacatctg 30

<210> SEQ ID NO 115
<211> LENGTH: 30
<212> TYPE: DNA
<213> ORGANISM: Streptococcus thermophilus

<400> SEQUENCE: 115
aattcgtgaa aaacaataaa aacaaaaaaa 30

<210> SEQ ID NO 116
<211> LENGTH: 30
<212> TYPE: DNA
<213> ORGANISM: Streptococcus thermophilus

<400> SEQUENCE: 116
taacatttct gtccatttct tccttgatgc 30

<210> SEQ ID NO 117
<211> LENGTH: 28
<212> TYPE: DNA
<213> ORGANISM: Streptococcus thermophilus

<400> SEQUENCE: 117
caaggcaact caaccaacca aattgacc 28

<210> SEQ ID NO 118
<211> LENGTH: 30
<212> TYPE: DNA
<213> ORGANISM: Streptococcus thermophilus

<400> SEQUENCE: 118
ctaaaatcgt aaatggtaag ttgcacgatg 30

<210> SEQ ID NO 119
<211> LENGTH: 30
<212> TYPE: DNA
<213> ORGANISM: Streptococcus thermophilus

<400> SEQUENCE: 119
aacgtaagga gtttttttat ttctttgtta 30

<210> SEQ ID NO 120
<211> LENGTH: 30
<212> TYPE: DNA
<213> ORGANISM: Streptococcus thermophilus

<400> SEQUENCE: 120
gtggaaaatt tcacacccta catatatcaa 30

<210> SEQ ID NO 121
<211> LENGTH: 30
<212> TYPE: DNA
<213> ORGANISM: Streptococcus thermophilus

<400> SEQUENCE: 121
cctctgctaa tgacttaaac ggctcgtttt 30

<210> SEQ ID NO 122
<211> LENGTH: 30
<212> TYPE: DNA
<213> ORGANISM: Streptococcus thermophilus

<400> SEQUENCE: 122
aaaatcaaag ttttgggttt gtctacgttg 30

<210> SEQ ID NO 123
<211> LENGTH: 30
<212> TYPE: DNA
<213> ORGANISM: Streptococcus thermophilus

<400> SEQUENCE: 123
atatgtacat acctaaagaa aacacgggca 30

<210> SEQ ID NO 124
<211> LENGTH: 30
<212> TYPE: DNA
<213> ORGANISM: Streptococcus thermophilus

<400> SEQUENCE: 124
cgttgtcaaa atatgtgatt actttgtatt 30

<210> SEQ ID NO 125
<211> LENGTH: 30
<212> TYPE: DNA
<213> ORGANISM: Streptococcus thermophilus

<400> SEQUENCE: 125
ccatagctgt aatgttgttt gtgactgctt 30

<210> SEQ ID NO 126
<211> LENGTH: 30
<212> TYPE: DNA
<213> ORGANISM: Streptococcus thermophilus

<400> SEQUENCE: 126
cgctaagttt ggctttaagt ataacaagct 30

<210> SEQ ID NO 127
<211> LENGTH: 30
<212> TYPE: DNA
<213> ORGANISM: Streptococcus thermophilus

<400> SEQUENCE: 127
aaagtacgct tcaaggcacg ttgaagacat 30

<210> SEQ ID NO 128
<211> LENGTH: 30
<212> TYPE: DNA
<213> ORGANISM: Streptococcus thermophilus

<400> SEQUENCE: 128
ctttttaacg tgttagcgtc tttagctttg 30

<210> SEQ ID NO 129
<211> LENGTH: 30
<212> TYPE: DNA
<213> ORGANISM: Streptococcus thermophilus

<400> SEQUENCE: 129
ttggcttcgt gaataatttt taaaacgcat 30

<210> SEQ ID NO 130
<211> LENGTH: 30
<212> TYPE: DNA
<213> ORGANISM: Streptococcus thermophilus

<400> SEQUENCE: 130
tgttgaatca atacgctgaa acacactccc 30

<210> SEQ ID NO 131
<211> LENGTH: 30
<212> TYPE: DNA
<213> ORGANISM: Streptococcus thermophilus

<400> SEQUENCE: 131
cgttatcagt tgaaagtttc aactcgtaag 30

<210> SEQ ID NO 132
<211> LENGTH: 30
<212> TYPE: DNA
<213> ORGANISM: Streptococcus thermophilus

<400> SEQUENCE: 132
taaactagtt ggcatctatg ctccaggaag 30

<210> SEQ ID NO 133
<211> LENGTH: 30
<212> TYPE: DNA
<213> ORGANISM: Streptococcus thermophilus

<400> SEQUENCE: 133
tagaccacca tagccgagtt gtctttttcg 30

<210> SEQ ID NO 134
<211> LENGTH: 30
<212> TYPE: DNA
<213> ORGANISM: Streptococcus thermophilus

<400> SEQUENCE: 134
acatcccact ttctgggttt tttagccatg 30

<210> SEQ ID NO 135
<211> LENGTH: 30
<212> TYPE: DNA
<213> ORGANISM: Streptococcus thermophilus

<400> SEQUENCE: 135
agtatggcta ttgtcctgat actcatccac 30

<210> SEQ ID NO 136
<211> LENGTH: 30
<212> TYPE: DNA
<213> ORGANISM: Streptococcus thermophilus

<400> SEQUENCE: 136
cgctcttgac gtggctggtg acatctacgc 30

<210> SEQ ID NO 137
<211> LENGTH: 30
<212> TYPE: DNA
<213> ORGANISM: Streptococcus thermophilus

<400> SEQUENCE: 137
gagtacatgg agtttctgct agatacacta 30

<210> SEQ ID NO 138
<211> LENGTH: 29
<212> TYPE: DNA
<213> ORGANISM: Streptococcus thermophilus

<400> SEQUENCE: 138
taagttatga aatataaagt tattgtcta 29

<210> SEQ ID NO 139
<211> LENGTH: 30
<212> TYPE: DNA
<213> ORGANISM: Streptococcus thermophilus

<400> SEQUENCE: 139
aacgttatga catttaggag cttccaaatt 30

<210> SEQ ID NO 140
<211> LENGTH: 29
<212> TYPE: DNA
<213> ORGANISM: Streptococcus thermophilus

<400> SEQUENCE: 140
aacacagcaa gacaaaagga tgacacttt 29

<210> SEQ ID NO 141
<211> LENGTH: 30
<212> TYPE: DNA
<213> ORGANISM: Streptococcus thermophilus

<400> SEQUENCE: 141
caaccataac ttacgcatca ggtacatctg 30

<210> SEQ ID NO 142
<211> LENGTH: 29
<212> TYPE: DNA
<213> ORGANISM: Streptococcus thermophilus

<400> SEQUENCE: 142
acacgcgctt acctcgtata tcaaattca 29

<210> SEQ ID NO 143
<211> LENGTH: 30
<212> TYPE: DNA
<213> ORGANISM: Streptococcus thermophilus

<400> SEQUENCE: 143
tgcccgcaaa ctagcgatac acaacagcat 30

<210> SEQ ID NO 144
<211> LENGTH: 31
<212> TYPE: DNA
<213> ORGANISM: Streptococcus thermophilus

<400> SEQUENCE: 144
ctcaagctct tcatctgtga taggtgtttt g 31

<210> SEQ ID NO 145
<211> LENGTH: 30
<212> TYPE: DNA
<213> ORGANISM: Streptococcus thermophilus

<400> SEQUENCE: 145
atcactcttt gatagtatct caaacgctgg 30

<210> SEQ ID NO 146
<211> LENGTH: 30
<212> TYPE: DNA
<213> ORGANISM: Streptococcus thermophilus

<400> SEQUENCE: 146
gaaacagtca gaccagctaa ttcgccaatt 30

<210> SEQ ID NO 147
<211> LENGTH: 30
<212> TYPE: DNA
<213> ORGANISM: Streptococcus thermophilus

<400> SEQUENCE: 147
atatttcgaa agatacaagg acacttacac 30

<210> SEQ ID NO 148
<211> LENGTH: 30
<212> TYPE: DNA
<213> ORGANISM: Streptococcus thermophilus

<400> SEQUENCE: 148
gcggatgaaa cacaacttca attgtattca 30

<210> SEQ ID NO 149
<211> LENGTH: 30
<212> TYPE: DNA
<213> ORGANISM: Streptococcus thermophilus

<400> SEQUENCE: 149
taatgctaca tctcaaagga tgatcccaga 30

<210> SEQ ID NO 150
<211> LENGTH: 31
<212> TYPE: DNA
<213> ORGANISM: Streptococcus thermophilus

<400> SEQUENCE: 150
acgtctgtct aactggaaag tacctgctaa t 31

<210> SEQ ID NO 151
<211> LENGTH: 30
<212> TYPE: DNA
<213> ORGANISM: Streptococcus thermophilus

<400> SEQUENCE: 151
ctgttctcta atcgagaggc gcgtgattga 30

<210> SEQ ID NO 152
<211> LENGTH: 30
<212> TYPE: DNA
<213> ORGANISM: Streptococcus thermophilus

<400> SEQUENCE: 152
aaacctcact agtcacttag tgcggttagg 30

<210> SEQ ID NO 153
<211> LENGTH: 30
<212> TYPE: DNA
<213> ORGANISM: Streptococcus thermophilus

<400> SEQUENCE: 153
tattaagttt agtcccaggt ttcttatcgt 30

<210> SEQ ID NO 154
<211> LENGTH: 30
<212> TYPE: DNA
<213> ORGANISM: Streptococcus thermophilus

<400> SEQUENCE: 154
aaaccaataa acataccgat tgctgccaat 30

<210> SEQ ID NO 155
<211> LENGTH: 30
<212> TYPE: DNA
<213> ORGANISM: Streptococcus thermophilus

<400> SEQUENCE: 155
gcaaacgtta gcccaggaaa gcatcatgaa 30

<210> SEQ ID NO 156
<211> LENGTH: 30
<212> TYPE: DNA
<213> ORGANISM: Streptococcus thermophilus

<400> SEQUENCE: 156
aagagcaaaa aataactcta gctctcgtcc 30

<210> SEQ ID NO 157
<211> LENGTH: 30
<212> TYPE: DNA
<213> ORGANISM: Streptococcus thermophilus

<400> SEQUENCE: 157
aagaaacctc taagttgagc atttaatgat 30

<210> SEQ ID NO 158
<211> LENGTH: 29
<212> TYPE: DNA
<213> ORGANISM: Streptococcus thermophilus

```
<400> SEQUENCE: 158

atatagtttt aaactttctt gaccttctg                                       29

<210> SEQ ID NO 159
<211> LENGTH: 29
<212> TYPE: DNA
<213> ORGANISM: Streptococcus thermophilus

<400> SEQUENCE: 159

acgttgatga atattgttga taaacttta                                       29

<210> SEQ ID NO 160
<211> LENGTH: 30
<212> TYPE: DNA
<213> ORGANISM: Streptococcus thermophilus

<400> SEQUENCE: 160

caagaagtga acaaagtaca cgctggaagt                                      30

<210> SEQ ID NO 161
<211> LENGTH: 30
<212> TYPE: DNA
<213> ORGANISM: Streptococcus thermophilus

<400> SEQUENCE: 161

gacagcaaga tacacgtagt tgatgaattg                                      30

<210> SEQ ID NO 162
<211> LENGTH: 30
<212> TYPE: DNA
<213> ORGANISM: Streptococcus thermophilus

<400> SEQUENCE: 162

taagaaatca acgcagattt ttagccaaca                                      30

<210> SEQ ID NO 163
<211> LENGTH: 30
<212> TYPE: DNA
<213> ORGANISM: Streptococcus thermophilus

<400> SEQUENCE: 163

taacccaata attacagtga agcacaatag                                      30

<210> SEQ ID NO 164
<211> LENGTH: 29
<212> TYPE: DNA
<213> ORGANISM: Streptococcus thermophilus

<400> SEQUENCE: 164

caggcgtaag gtatgctaat tataacgat                                       29

<210> SEQ ID NO 165
<211> LENGTH: 30
<212> TYPE: DNA
<213> ORGANISM: Streptococcus thermophilus

<400> SEQUENCE: 165

gctatcgaac taatagctta gaggaactca                                      30

<210> SEQ ID NO 166
<211> LENGTH: 30
<212> TYPE: DNA
```

<213> ORGANISM: Streptococcus thermophilus

<400> SEQUENCE: 166
gtggaatatt aagcccgaat tgttgcagca 30

<210> SEQ ID NO 167
<211> LENGTH: 30
<212> TYPE: DNA
<213> ORGANISM: Streptococcus thermophilus

<400> SEQUENCE: 167
tattgcaata tttgcgtttg ggaaaccttc 30

<210> SEQ ID NO 168
<211> LENGTH: 30
<212> TYPE: DNA
<213> ORGANISM: Streptococcus thermophilus

<400> SEQUENCE: 168
cgtctgtcta actggaaagt accggctaat 30

<210> SEQ ID NO 169
<211> LENGTH: 30
<212> TYPE: DNA
<213> ORGANISM: Streptococcus thermophilus

<400> SEQUENCE: 169
aaagagatgt acccatccat tctaacaggt 30

<210> SEQ ID NO 170
<211> LENGTH: 30
<212> TYPE: DNA
<213> ORGANISM: Streptococcus thermophilus

<400> SEQUENCE: 170
ggggagttga tttcttacat caaaacaatg 30

<210> SEQ ID NO 171
<211> LENGTH: 30
<212> TYPE: DNA
<213> ORGANISM: Streptococcus thermophilus

<400> SEQUENCE: 171
catcaaagtt gaaaaggact acaacagccc 30

<210> SEQ ID NO 172
<211> LENGTH: 30
<212> TYPE: DNA
<213> ORGANISM: Streptococcus thermophilus

<400> SEQUENCE: 172
cttaaattta gagcgtggga tcttgaatat 30

<210> SEQ ID NO 173
<211> LENGTH: 30
<212> TYPE: DNA
<213> ORGANISM: Streptococcus thermophilus

<400> SEQUENCE: 173
atataccgat ggcacatctg aaactggctg 30

<210> SEQ ID NO 174
<211> LENGTH: 30

-continued

<212> TYPE: DNA
<213> ORGANISM: Streptococcus thermophilus

<400> SEQUENCE: 174
taactcatat gtatcttgac caactatttt 30

<210> SEQ ID NO 175
<211> LENGTH: 30
<212> TYPE: DNA
<213> ORGANISM: Streptococcus thermophilus

<400> SEQUENCE: 175
aaatagcacc tctaagcgtt aatggtattc 30

<210> SEQ ID NO 176
<211> LENGTH: 30
<212> TYPE: DNA
<213> ORGANISM: Streptococcus thermophilus

<400> SEQUENCE: 176
aatatctaca ggtcactaca aagctacgct 30

<210> SEQ ID NO 177
<211> LENGTH: 30
<212> TYPE: DNA
<213> ORGANISM: Streptococcus thermophilus

<400> SEQUENCE: 177
gttggggtgt gtttgtaacg gcgtatgcta 30

<210> SEQ ID NO 178
<211> LENGTH: 30
<212> TYPE: DNA
<213> ORGANISM: Streptococcus thermophilus

<400> SEQUENCE: 178
tcaatcaggt gacggtgatg cttatattaa 30

<210> SEQ ID NO 179
<211> LENGTH: 30
<212> TYPE: DNA
<213> ORGANISM: Streptococcus thermophilus

<400> SEQUENCE: 179
catacatgat agtttgtcaa cacttttgat 30

<210> SEQ ID NO 180
<211> LENGTH: 30
<212> TYPE: DNA
<213> ORGANISM: Streptococcus thermophilus

<400> SEQUENCE: 180
tcagcatttg gtttacatga cccacgtctg 30

<210> SEQ ID NO 181
<211> LENGTH: 30
<212> TYPE: DNA
<213> ORGANISM: Streptococcus thermophilus

<400> SEQUENCE: 181
caatcaacag gtttgactga ttataacggt 30

<210> SEQ ID NO 182

<211> LENGTH: 30
<212> TYPE: DNA
<213> ORGANISM: Streptococcus thermophilus

<400> SEQUENCE: 182
tagctacaca tgaattttat tacaatggtg 30

<210> SEQ ID NO 183
<211> LENGTH: 30
<212> TYPE: DNA
<213> ORGANISM: Streptococcus thermophilus

<400> SEQUENCE: 183
cttacgtttg aaaagaatat caaatcaatg 30

<210> SEQ ID NO 184
<211> LENGTH: 30
<212> TYPE: DNA
<213> ORGANISM: Streptococcus thermophilus

<400> SEQUENCE: 184
ttaaaaaagg gcctttctct aaatcaagta 30

<210> SEQ ID NO 185
<211> LENGTH: 30
<212> TYPE: DNA
<213> ORGANISM: Streptococcus thermophilus

<400> SEQUENCE: 185
tgctgaacgt atctgtccac tgtgtggcca 30

<210> SEQ ID NO 186
<211> LENGTH: 30
<212> TYPE: DNA
<213> ORGANISM: Streptococcus thermophilus

<400> SEQUENCE: 186
ccgttcttca aacgttaaat tccaaggtgt 30

<210> SEQ ID NO 187
<211> LENGTH: 30
<212> TYPE: DNA
<213> ORGANISM: Streptococcus thermophilus

<400> SEQUENCE: 187
gctgcgatta tgacaatgct gtctgtaagg 30

<210> SEQ ID NO 188
<211> LENGTH: 30
<212> TYPE: DNA
<213> ORGANISM: Streptococcus thermophilus

<400> SEQUENCE: 188
gaagaattta ttaataaaga tggttctgct 30

<210> SEQ ID NO 189
<211> LENGTH: 30
<212> TYPE: DNA
<213> ORGANISM: Streptococcus thermophilus

<400> SEQUENCE: 189
aggcagaaaa gaagtatttt ggtaagtatg 30

-continued

<210> SEQ ID NO 190
<211> LENGTH: 29
<212> TYPE: DNA
<213> ORGANISM: Streptococcus thermophilus

<400> SEQUENCE: 190
aaatggttta tcgacaagaa aatgaagct 29

<210> SEQ ID NO 191
<211> LENGTH: 30
<212> TYPE: DNA
<213> ORGANISM: Streptococcus thermophilus

<400> SEQUENCE: 191
ccaaatttgc attatacaaa acgctccttc 30

<210> SEQ ID NO 192
<211> LENGTH: 30
<212> TYPE: DNA
<213> ORGANISM: Streptococcus thermophilus

<400> SEQUENCE: 192
atcctaactg ctttgctaac tacatcatgg 30

<210> SEQ ID NO 193
<211> LENGTH: 29
<212> TYPE: DNA
<213> ORGANISM: Streptococcus thermophilus

<400> SEQUENCE: 193
taacaagata agattagcgt cttcaacat 29

<210> SEQ ID NO 194
<211> LENGTH: 30
<212> TYPE: DNA
<213> ORGANISM: Streptococcus thermophilus

<400> SEQUENCE: 194
aaaagcctat gtttgcccac tttgtggaag 30

<210> SEQ ID NO 195
<211> LENGTH: 30
<212> TYPE: DNA
<213> ORGANISM: Streptococcus thermophilus

<400> SEQUENCE: 195
tgtcactttc tctttctggg ttgtgccaat 30

<210> SEQ ID NO 196
<211> LENGTH: 31
<212> TYPE: DNA
<213> ORGANISM: Streptococcus thermophilus

<400> SEQUENCE: 196
catacttttc catctgtttg ttgtttgaaa a 31

<210> SEQ ID NO 197
<211> LENGTH: 30
<212> TYPE: DNA
<213> ORGANISM: Streptococcus thermophilus

<400> SEQUENCE: 197
tgagagtgtc tgatggattt attggcagcc 30

-continued

<210> SEQ ID NO 198
<211> LENGTH: 30
<212> TYPE: DNA
<213> ORGANISM: Streptococcus thermophilus

<400> SEQUENCE: 198
ggggttattt tccattttac cgtctatcta 30

<210> SEQ ID NO 199
<211> LENGTH: 30
<212> TYPE: DNA
<213> ORGANISM: Streptococcus thermophilus

<400> SEQUENCE: 199
tatcacgccc attttcattt cgccatctgt 30

<210> SEQ ID NO 200
<211> LENGTH: 30
<212> TYPE: DNA
<213> ORGANISM: Streptococcus thermophilus

<400> SEQUENCE: 200
aacattttaa tataatttct aaatctattg 30

<210> SEQ ID NO 201
<211> LENGTH: 30
<212> TYPE: DNA
<213> ORGANISM: Streptococcus thermophilus

<400> SEQUENCE: 201
tacaaaattc cttcaaacgc tatttattga 30

<210> SEQ ID NO 202
<211> LENGTH: 29
<212> TYPE: DNA
<213> ORGANISM: Streptococcus thermophilus

<400> SEQUENCE: 202
agagtttgaa aattattttt cagtttcta 29

<210> SEQ ID NO 203
<211> LENGTH: 30
<212> TYPE: DNA
<213> ORGANISM: Streptococcus thermophilus

<400> SEQUENCE: 203
ttcctcatct ttctccgctt ttgctagctt 30

<210> SEQ ID NO 204
<211> LENGTH: 31
<212> TYPE: DNA
<213> ORGANISM: Streptococcus thermophilus

<400> SEQUENCE: 204
ttgagcgttc tagtgtgtgg cttgtaatga a 31

<210> SEQ ID NO 205
<211> LENGTH: 30
<212> TYPE: DNA
<213> ORGANISM: Streptococcus thermophilus

<400> SEQUENCE: 205
tgaaagaaat acaatacaac gataatgacc 30

<210> SEQ ID NO 206
<211> LENGTH: 30
<212> TYPE: DNA
<213> ORGANISM: Streptococcus thermophilus

<400> SEQUENCE: 206
ctagttttaa gagatagctc tctaagtagg 30

<210> SEQ ID NO 207
<211> LENGTH: 29
<212> TYPE: DNA
<213> ORGANISM: Streptococcus thermophilus

<400> SEQUENCE: 207
aaattcgaca taagcactac agttatatt 29

<210> SEQ ID NO 208
<211> LENGTH: 30
<212> TYPE: DNA
<213> ORGANISM: Streptococcus thermophilus

<400> SEQUENCE: 208
ctattttcga gagaacgtca gtcattttaa 30

<210> SEQ ID NO 209
<211> LENGTH: 30
<212> TYPE: DNA
<213> ORGANISM: Streptococcus thermophilus

<400> SEQUENCE: 209
gtgctaacta tatcagtcgc atcaataaca 30

<210> SEQ ID NO 210
<211> LENGTH: 30
<212> TYPE: DNA
<213> ORGANISM: Streptococcus thermophilus

<400> SEQUENCE: 210
ttagcggtga ttggaataga ataagcgaat 30

<210> SEQ ID NO 211
<211> LENGTH: 30
<212> TYPE: DNA
<213> ORGANISM: Streptococcus thermophilus

<400> SEQUENCE: 211
cttctacagc agtttaagac acattatcat 30

<210> SEQ ID NO 212
<211> LENGTH: 29
<212> TYPE: DNA
<213> ORGANISM: Streptococcus thermophilus

<400> SEQUENCE: 212
cgtatcgaaa acggcgataa tccaacagt 29

<210> SEQ ID NO 213
<211> LENGTH: 31
<212> TYPE: DNA
<213> ORGANISM: Streptococcus thermophilus

<400> SEQUENCE: 213
caataccttt ttttaattca tcttgataag t 31

<210> SEQ ID NO 214
<211> LENGTH: 30
<212> TYPE: DNA
<213> ORGANISM: Streptococcus thermophilus

<400> SEQUENCE: 214
ttaagaacaa tatcatcaat acgactttca 30

<210> SEQ ID NO 215
<211> LENGTH: 30
<212> TYPE: DNA
<213> ORGANISM: Streptococcus thermophilus

<400> SEQUENCE: 215
catctatcaa attcaaattc ggataaacta 30

<210> SEQ ID NO 216
<211> LENGTH: 30
<212> TYPE: DNA
<213> ORGANISM: Streptococcus thermophilus

<400> SEQUENCE: 216
tgagagtgtc tgatggattt attggtaacc 30

<210> SEQ ID NO 217
<211> LENGTH: 29
<212> TYPE: DNA
<213> ORGANISM: Streptococcus thermophilus

<400> SEQUENCE: 217
acctcataca tggggaaaac ttgtaagta 29

<210> SEQ ID NO 218
<211> LENGTH: 30
<212> TYPE: DNA
<213> ORGANISM: Streptococcus thermophilus

<400> SEQUENCE: 218
tatttcacga atttctacac ttttcaacct 30

<210> SEQ ID NO 219
<211> LENGTH: 30
<212> TYPE: DNA
<213> ORGANISM: Streptococcus thermophilus

<400> SEQUENCE: 219
ctgaaacctt gttttgaagc gcttggaagt 30

<210> SEQ ID NO 220
<211> LENGTH: 30
<212> TYPE: DNA
<213> ORGANISM: Streptococcus thermophilus

<400> SEQUENCE: 220
gtcaattgat actgcaatct ctttaacatt 30

<210> SEQ ID NO 221
<211> LENGTH: 31
<212> TYPE: DNA
<213> ORGANISM: Streptococcus thermophilus

<400> SEQUENCE: 221
acttcaatat ggtcaacatc ttgatcaccg a 31

<210> SEQ ID NO 222
<211> LENGTH: 30
<212> TYPE: DNA
<213> ORGANISM: Streptococcus thermophilus

<400> SEQUENCE: 222
taaactcgac aaaagcacta catgaatatt 30

<210> SEQ ID NO 223
<211> LENGTH: 30
<212> TYPE: DNA
<213> ORGANISM: Streptococcus thermophilus

<400> SEQUENCE: 223
attttttaag gaaaggagga aaataatata 30

<210> SEQ ID NO 224
<211> LENGTH: 30
<212> TYPE: DNA
<213> ORGANISM: Streptococcus thermophilus

<400> SEQUENCE: 224
cgttcaaaac agcgaaaact taaccctaac 30

<210> SEQ ID NO 225
<211> LENGTH: 30
<212> TYPE: DNA
<213> ORGANISM: Streptococcus thermophilus

<400> SEQUENCE: 225
cattaagtcg cttgaggcag acattgaagc 30

<210> SEQ ID NO 226
<211> LENGTH: 30
<212> TYPE: DNA
<213> ORGANISM: Streptococcus thermophilus

<400> SEQUENCE: 226
ccaaactcaa attgtctata ataataaccg 30

<210> SEQ ID NO 227
<211> LENGTH: 30
<212> TYPE: DNA
<213> ORGANISM: Streptococcus thermophilus

<400> SEQUENCE: 227
tatctctatt tcaggtggtt taaaacattc 30

<210> SEQ ID NO 228
<211> LENGTH: 30
<212> TYPE: DNA
<213> ORGANISM: Streptococcus thermophilus

<400> SEQUENCE: 228
aaacgaagat ggaagcgttg atgtttattc 30

<210> SEQ ID NO 229
<211> LENGTH: 30
<212> TYPE: DNA
<213> ORGANISM: Streptococcus thermophilus

<400> SEQUENCE: 229
gattgcattt gccagtattt cttttgatta 30

<210> SEQ ID NO 230
<211> LENGTH: 29
<212> TYPE: DNA
<213> ORGANISM: Streptococcus thermophilus

<400> SEQUENCE: 230
tgaagacaac ggaaacaatc aacctatta 29

<210> SEQ ID NO 231
<211> LENGTH: 30
<212> TYPE: DNA
<213> ORGANISM: Streptococcus thermophilus

<400> SEQUENCE: 231
acttcttttt taatgtcatc taagacaata 30

<210> SEQ ID NO 232
<211> LENGTH: 30
<212> TYPE: DNA
<213> ORGANISM: Streptococcus thermophilus

<400> SEQUENCE: 232
gccaatgatg ttcaattcgt taatggaatt 30

<210> SEQ ID NO 233
<211> LENGTH: 30
<212> TYPE: DNA
<213> ORGANISM: Streptococcus thermophilus

<400> SEQUENCE: 233
tcaacatggg atatttcgtt ggtcaggatg 30

<210> SEQ ID NO 234
<211> LENGTH: 30
<212> TYPE: DNA
<213> ORGANISM: Streptococcus thermophilus

<400> SEQUENCE: 234
tatggctctc ttgttggaat aaagatgatt 30

<210> SEQ ID NO 235
<211> LENGTH: 30
<212> TYPE: DNA
<213> ORGANISM: Streptococcus thermophilus

<400> SEQUENCE: 235
ataacatagc agtctatttc tttgctgatg 30

<210> SEQ ID NO 236
<211> LENGTH: 30
<212> TYPE: DNA
<213> ORGANISM: Streptococcus thermophilus

<400> SEQUENCE: 236
gttaccacgc gccctactgt attagtggag 30

<210> SEQ ID NO 237
<211> LENGTH: 30
<212> TYPE: DNA
<213> ORGANISM: Streptococcus thermophilus

<400> SEQUENCE: 237
tacataccca aggttgtaag tcgttaaatt 30

<210> SEQ ID NO 238
<211> LENGTH: 30
<212> TYPE: DNA
<213> ORGANISM: Streptococcus thermophilus

<400> SEQUENCE: 238
tgtaagtagt caatattcac ttctgataac 30

<210> SEQ ID NO 239
<211> LENGTH: 30
<212> TYPE: DNA
<213> ORGANISM: Streptococcus thermophilus

<400> SEQUENCE: 239
gatagcaata gctttcttga cctaaaagac 30

<210> SEQ ID NO 240
<211> LENGTH: 30
<212> TYPE: DNA
<213> ORGANISM: Streptococcus thermophilus

<400> SEQUENCE: 240
gaggtctgta atttcattcc ctcgtaatct 30

<210> SEQ ID NO 241
<211> LENGTH: 29
<212> TYPE: DNA
<213> ORGANISM: Streptococcus thermophilus

<400> SEQUENCE: 241
aaaggtttct ctaaacacat gcggaatat 29

<210> SEQ ID NO 242
<211> LENGTH: 30
<212> TYPE: DNA
<213> ORGANISM: Streptococcus thermophilus

<400> SEQUENCE: 242
gtcatagtac caagcacaaa taacgttagt 30

<210> SEQ ID NO 243
<211> LENGTH: 30
<212> TYPE: DNA
<213> ORGANISM: Streptococcus thermophilus

<400> SEQUENCE: 243
gtgtatttag taatggtgat tttttaaatt 30

<210> SEQ ID NO 244
<211> LENGTH: 30
<212> TYPE: DNA
<213> ORGANISM: Streptococcus thermophilus

<400> SEQUENCE: 244
cattcatttt ttatatatca ataaaacttt 30

<210> SEQ ID NO 245
<211> LENGTH: 30
<212> TYPE: DNA

<213> ORGANISM: Streptococcus thermophilus

<400> SEQUENCE: 245
ggggattctt atttcactgt agttacgatg 30

<210> SEQ ID NO 246
<211> LENGTH: 30
<212> TYPE: DNA
<213> ORGANISM: Streptococcus thermophilus

<400> SEQUENCE: 246
caaaaattga tgtcacaatt aataaaggtg 30

<210> SEQ ID NO 247
<211> LENGTH: 30
<212> TYPE: DNA
<213> ORGANISM: Streptococcus thermophilus

<400> SEQUENCE: 247
ctatttctga caatggttga aattgtgttc 30

<210> SEQ ID NO 248
<211> LENGTH: 29
<212> TYPE: DNA
<213> ORGANISM: Streptococcus thermophilus

<400> SEQUENCE: 248
ctttttttaa attaatttat cgtaagcaa 29

<210> SEQ ID NO 249
<211> LENGTH: 30
<212> TYPE: DNA
<213> ORGANISM: Streptococcus thermophilus

<400> SEQUENCE: 249
aacaaactta tgagaacggt tgaacggctt 30

<210> SEQ ID NO 250
<211> LENGTH: 30
<212> TYPE: DNA
<213> ORGANISM: Streptococcus thermophilus

<400> SEQUENCE: 250
agcccgctta ttgcttcagt tggtttatat 30

<210> SEQ ID NO 251
<211> LENGTH: 30
<212> TYPE: DNA
<213> ORGANISM: Streptococcus thermophilus

<400> SEQUENCE: 251
tggagcaaca agaatgatta actctaatgc 30

<210> SEQ ID NO 252
<211> LENGTH: 30
<212> TYPE: DNA
<213> ORGANISM: Streptococcus thermophilus

<400> SEQUENCE: 252
tttgatggat atcattgata aactatacga 30

<210> SEQ ID NO 253
<211> LENGTH: 30

-continued

<212> TYPE: DNA
<213> ORGANISM: Streptococcus thermophilus

<400> SEQUENCE: 253
taacgaaagc aataccaatc gtgctaaagc 30

<210> SEQ ID NO 254
<211> LENGTH: 30
<212> TYPE: DNA
<213> ORGANISM: Streptococcus thermophilus

<400> SEQUENCE: 254
tattcctatg gtcgatattc gaacagtcaa 30

<210> SEQ ID NO 255
<211> LENGTH: 30
<212> TYPE: DNA
<213> ORGANISM: Streptococcus thermophilus

<400> SEQUENCE: 255
caggggacaa ggactttgac ccaacagaag 30

<210> SEQ ID NO 256
<211> LENGTH: 30
<212> TYPE: DNA
<213> ORGANISM: Streptococcus thermophilus

<400> SEQUENCE: 256
agaaacacct aatggtctct tagaacccga 30

<210> SEQ ID NO 257
<211> LENGTH: 30
<212> TYPE: DNA
<213> ORGANISM: Streptococcus thermophilus

<400> SEQUENCE: 257
aagaagttaa agacaacttt gttaaagact 30

<210> SEQ ID NO 258
<211> LENGTH: 30
<212> TYPE: DNA
<213> ORGANISM: Streptococcus thermophilus

<400> SEQUENCE: 258
gaaaaagcat ccatgatagt gcttagacct 30

<210> SEQ ID NO 259
<211> LENGTH: 30
<212> TYPE: DNA
<213> ORGANISM: Streptococcus thermophilus

<400> SEQUENCE: 259
cggaatggta taaagaatac aaagaaaacg 30

<210> SEQ ID NO 260
<211> LENGTH: 29
<212> TYPE: DNA
<213> ORGANISM: Streptococcus thermophilus

<400> SEQUENCE: 260
ccaagtatca cgcaaagaaa tcaacgaga 29

<210> SEQ ID NO 261

<211> LENGTH: 31
<212> TYPE: DNA
<213> ORGANISM: Streptococcus thermophilus

<400> SEQUENCE: 261
ttgacctgtt tatccttgtt aactagaata g 31

<210> SEQ ID NO 262
<211> LENGTH: 30
<212> TYPE: DNA
<213> ORGANISM: Streptococcus thermophilus

<400> SEQUENCE: 262
agagcactag catactgttt agtccgaacg 30

<210> SEQ ID NO 263
<211> LENGTH: 30
<212> TYPE: DNA
<213> ORGANISM: Streptococcus thermophilus

<400> SEQUENCE: 263
aggcaaggta tttgatccaa cagaagccaa 30

<210> SEQ ID NO 264
<211> LENGTH: 29
<212> TYPE: DNA
<213> ORGANISM: Streptococcus thermophilus

<400> SEQUENCE: 264
catgatttac aaccacgcgc tagaccaag 29

<210> SEQ ID NO 265
<211> LENGTH: 30
<212> TYPE: DNA
<213> ORGANISM: Streptococcus thermophilus

<400> SEQUENCE: 265
acctagaagc atttgagcgt atattgattg 30

<210> SEQ ID NO 266
<211> LENGTH: 30
<212> TYPE: DNA
<213> ORGANISM: Streptococcus thermophilus

<400> SEQUENCE: 266
aattttgccc cttctttgcc ccttgactag 30

<210> SEQ ID NO 267
<211> LENGTH: 30
<212> TYPE: DNA
<213> ORGANISM: Streptococcus thermophilus

<400> SEQUENCE: 267
taatagttta ccaaatcgtc cttgttccaa 30

<210> SEQ ID NO 268
<211> LENGTH: 30
<212> TYPE: DNA
<213> ORGANISM: Streptococcus thermophilus

<400> SEQUENCE: 268
accattagca atcatttgtg cccattgagt 30

<210> SEQ ID NO 269
<211> LENGTH: 31
<212> TYPE: DNA
<213> ORGANISM: Streptococcus thermophilus

<400> SEQUENCE: 269
acgtctgtct aactggaaag tacctgttaa t 31

<210> SEQ ID NO 270
<211> LENGTH: 29
<212> TYPE: DNA
<213> ORGANISM: Streptococcus thermophilus

<400> SEQUENCE: 270
tttttatact ttgggtaatt acaaaatag 29

<210> SEQ ID NO 271
<211> LENGTH: 30
<212> TYPE: DNA
<213> ORGANISM: Streptococcus thermophilus

<400> SEQUENCE: 271
aagaaagaaa tattctagat atagatataa 30

<210> SEQ ID NO 272
<211> LENGTH: 30
<212> TYPE: DNA
<213> ORGANISM: Streptococcus thermophilus

<400> SEQUENCE: 272
caacgaccaa cacaacaact aaagttactg 30

<210> SEQ ID NO 273
<211> LENGTH: 30
<212> TYPE: DNA
<213> ORGANISM: Streptococcus thermophilus

<400> SEQUENCE: 273
tgattatggg tgttaaacaa ggagcttatg 30

<210> SEQ ID NO 274
<211> LENGTH: 30
<212> TYPE: DNA
<213> ORGANISM: Streptococcus thermophilus

<400> SEQUENCE: 274
tgagtggtaa gtacaaatac gcaggactga 30

<210> SEQ ID NO 275
<211> LENGTH: 30
<212> TYPE: DNA
<213> ORGANISM: Streptococcus thermophilus

<400> SEQUENCE: 275
ttatttcctc ctttccttaa aaaaattaga 30

<210> SEQ ID NO 276
<211> LENGTH: 30
<212> TYPE: DNA
<213> ORGANISM: Streptococcus thermophilus

<400> SEQUENCE: 276
ggatgtatct gttgaaagag gtgtgtatat 30

<210> SEQ ID NO 277
<211> LENGTH: 30
<212> TYPE: DNA
<213> ORGANISM: Streptococcus thermophilus

<400> SEQUENCE: 277
aataggtgaa aaatatgcaa gtcacacaaa 30

<210> SEQ ID NO 278
<211> LENGTH: 30
<212> TYPE: DNA
<213> ORGANISM: Streptococcus thermophilus

<400> SEQUENCE: 278
aaaatggcat taaaaattaa cataggaata 30

<210> SEQ ID NO 279
<211> LENGTH: 30
<212> TYPE: DNA
<213> ORGANISM: Streptococcus thermophilus

<400> SEQUENCE: 279
tatcagctcg taaatgttcg atagactctt 30

<210> SEQ ID NO 280
<211> LENGTH: 30
<212> TYPE: DNA
<213> ORGANISM: Streptococcus thermophilus

<400> SEQUENCE: 280
attccattaa cgtatttgac ttcactagct 30

<210> SEQ ID NO 281
<211> LENGTH: 30
<212> TYPE: DNA
<213> ORGANISM: Streptococcus thermophilus

<400> SEQUENCE: 281
ctgttaccga tccaagagca gacatcatac 30

<210> SEQ ID NO 282
<211> LENGTH: 30
<212> TYPE: DNA
<213> ORGANISM: Streptococcus thermophilus

<400> SEQUENCE: 282
aagaagcggt taaatgcttc aactgaatag 30

<210> SEQ ID NO 283
<211> LENGTH: 30
<212> TYPE: DNA
<213> ORGANISM: Streptococcus thermophilus

<400> SEQUENCE: 283
aattgctaaa catctaaaag acttaacggg 30

<210> SEQ ID NO 284
<211> LENGTH: 30
<212> TYPE: DNA
<213> ORGANISM: Streptococcus thermophilus

<400> SEQUENCE: 284
gatgaagatt tgactgatga taaagagaaa 30

<210> SEQ ID NO 285
<211> LENGTH: 30
<212> TYPE: DNA
<213> ORGANISM: Streptococcus thermophilus

<400> SEQUENCE: 285
gacatcagaa agcagtttat aaatatttta 30

<210> SEQ ID NO 286
<211> LENGTH: 30
<212> TYPE: DNA
<213> ORGANISM: Streptococcus thermophilus

<400> SEQUENCE: 286
tttgaattta acaaccttga ttttgatatc 30

<210> SEQ ID NO 287
<211> LENGTH: 31
<212> TYPE: DNA
<213> ORGANISM: Streptococcus thermophilus

<400> SEQUENCE: 287
tgatacggtc aaagtttttc cactaatagc g 31

<210> SEQ ID NO 288
<211> LENGTH: 30
<212> TYPE: DNA
<213> ORGANISM: Streptococcus thermophilus

<400> SEQUENCE: 288
atggttttca tttcctgaac ccctaagagg 30

<210> SEQ ID NO 289
<211> LENGTH: 30
<212> TYPE: DNA
<213> ORGANISM: Streptococcus thermophilus

<400> SEQUENCE: 289
aagttattga aaaacgccaa catgatgagt 30

<210> SEQ ID NO 290
<211> LENGTH: 30
<212> TYPE: DNA
<213> ORGANISM: Streptococcus thermophilus

<400> SEQUENCE: 290
atataagtcc tcctattaat atccacaata 30

<210> SEQ ID NO 291
<211> LENGTH: 30
<212> TYPE: DNA
<213> ORGANISM: Streptococcus thermophilus

<400> SEQUENCE: 291
ttgcctcaag agatcctgct tgttgccaag 30

<210> SEQ ID NO 292
<211> LENGTH: 30
<212> TYPE: DNA
<213> ORGANISM: Streptococcus thermophilus

<400> SEQUENCE: 292
tcccatagtt ttaatgagtc ggttaactta 30

<210> SEQ ID NO 293
<211> LENGTH: 30
<212> TYPE: DNA
<213> ORGANISM: Streptococcus thermophilus

<400> SEQUENCE: 293
gtgtactaaa agtgtgctaa gttcataagg 30

<210> SEQ ID NO 294
<211> LENGTH: 30
<212> TYPE: DNA
<213> ORGANISM: Streptococcus thermophilus

<400> SEQUENCE: 294
atatagtgat tgtatccagc tgcggcgtag 30

<210> SEQ ID NO 295
<211> LENGTH: 29
<212> TYPE: DNA
<213> ORGANISM: Streptococcus thermophilus

<400> SEQUENCE: 295
aaaagcaaat cgcgagtata aaggatata 29

<210> SEQ ID NO 296
<211> LENGTH: 30
<212> TYPE: DNA
<213> ORGANISM: Streptococcus thermophilus

<400> SEQUENCE: 296
ttttaattga tctagacacc ctatgaaata 30

<210> SEQ ID NO 297
<211> LENGTH: 30
<212> TYPE: DNA
<213> ORGANISM: Streptococcus thermophilus

<400> SEQUENCE: 297
acagaggaga gaaaccatgg ctattttaga 30

<210> SEQ ID NO 298
<211> LENGTH: 29
<212> TYPE: DNA
<213> ORGANISM: Streptococcus thermophilus

<400> SEQUENCE: 298
tggcagcagt gaattcgatg ccgagcaat 29

<210> SEQ ID NO 299
<211> LENGTH: 30
<212> TYPE: DNA
<213> ORGANISM: Streptococcus thermophilus

<400> SEQUENCE: 299
ccaaggaata ccaggtccta aaggtgccga 30

<210> SEQ ID NO 300
<211> LENGTH: 29
<212> TYPE: DNA
<213> ORGANISM: Streptococcus thermophilus

<400> SEQUENCE: 300
ctaaatgaac tacaacaaca gcttgatga 29

<210> SEQ ID NO 301
<211> LENGTH: 30
<212> TYPE: DNA
<213> ORGANISM: Streptococcus thermophilus

<400> SEQUENCE: 301
taccttaaca ttttcgatat ttttcaaatt 30

<210> SEQ ID NO 302
<211> LENGTH: 30
<212> TYPE: DNA
<213> ORGANISM: Streptococcus thermophilus

<400> SEQUENCE: 302
tttgactgct tttttatctg aattgtaatt 30

<210> SEQ ID NO 303
<211> LENGTH: 30
<212> TYPE: DNA
<213> ORGANISM: Streptococcus thermophilus

<400> SEQUENCE: 303
cagtaaccta aagctctatc aagcctattt 30

<210> SEQ ID NO 304
<211> LENGTH: 30
<212> TYPE: DNA
<213> ORGANISM: Streptococcus thermophilus

<400> SEQUENCE: 304
cgtcaagctg acagaccttg acaacaaatc 30

<210> SEQ ID NO 305
<211> LENGTH: 29
<212> TYPE: DNA
<213> ORGANISM: Streptococcus thermophilus

<400> SEQUENCE: 305
aggcataaat aacattgata accctaaca 29

<210> SEQ ID NO 306
<211> LENGTH: 30
<212> TYPE: DNA
<213> ORGANISM: Streptococcus thermophilus

<400> SEQUENCE: 306
gccaacgagg tcaaatatgt caacggcatt 30

<210> SEQ ID NO 307
<211> LENGTH: 30
<212> TYPE: DNA
<213> ORGANISM: Streptococcus thermophilus

<400> SEQUENCE: 307
gaaataggaa cttcaaaggt aatttcttta 30

<210> SEQ ID NO 308
<211> LENGTH: 30
<212> TYPE: DNA
<213> ORGANISM: Streptococcus thermophilus

<400> SEQUENCE: 308
atttagagca aggaaagcag tacatcatta 30

<210> SEQ ID NO 309
<211> LENGTH: 30
<212> TYPE: DNA
<213> ORGANISM: Streptococcus thermophilus

<400> SEQUENCE: 309
ctgtaatcat ttttaaatca ggattatcaa 30

<210> SEQ ID NO 310
<211> LENGTH: 30
<212> TYPE: DNA
<213> ORGANISM: Streptococcus thermophilus

<400> SEQUENCE: 310
ttaaatgtat cctagtattt ttgtactata 30

<210> SEQ ID NO 311
<211> LENGTH: 30
<212> TYPE: DNA
<213> ORGANISM: Streptococcus thermophilus

<400> SEQUENCE: 311
ccatcagcca actgtatcgg ctactttcta 30

<210> SEQ ID NO 312
<211> LENGTH: 30
<212> TYPE: DNA
<213> ORGANISM: Streptococcus thermophilus

<400> SEQUENCE: 312
atgctcttgg cgactatctc atggagcgtg 30

<210> SEQ ID NO 313
<211> LENGTH: 30
<212> TYPE: DNA
<213> ORGANISM: Streptococcus thermophilus

<400> SEQUENCE: 313
aggaaaaaac ccaaacaacc caaaatgtta 30

<210> SEQ ID NO 314
<211> LENGTH: 30
<212> TYPE: DNA
<213> ORGANISM: Streptococcus thermophilus

<400> SEQUENCE: 314
tctaattctg tcaccacgac tatatcgcca 30

<210> SEQ ID NO 315
<211> LENGTH: 30
<212> TYPE: DNA
<213> ORGANISM: Streptococcus thermophilus

<400> SEQUENCE: 315
aatctgtgtg ggaagtaaag attgaagatg 30

<210> SEQ ID NO 316
<211> LENGTH: 30
<212> TYPE: DNA
<213> ORGANISM: Streptococcus thermophilus

<400> SEQUENCE: 316
atagtttgtt aagtcatacc cattaaattg 30

<210> SEQ ID NO 317
<211> LENGTH: 30
<212> TYPE: DNA
<213> ORGANISM: Streptococcus thermophilus

<400> SEQUENCE: 317
tccacatgat tacaaagcca cgcaagacct 30

<210> SEQ ID NO 318
<211> LENGTH: 29
<212> TYPE: DNA
<213> ORGANISM: Streptococcus thermophilus

<400> SEQUENCE: 318
gaagaccaaa atttgacaat gagtcctgc 29

<210> SEQ ID NO 319
<211> LENGTH: 30
<212> TYPE: DNA
<213> ORGANISM: Streptococcus thermophilus

<400> SEQUENCE: 319
attatattta agttgtaaat gttgcttttc 30

<210> SEQ ID NO 320
<211> LENGTH: 30
<212> TYPE: DNA
<213> ORGANISM: Streptococcus thermophilus

<400> SEQUENCE: 320
gcagacattg gctcaacaag tgattatgaa 30

<210> SEQ ID NO 321
<211> LENGTH: 30
<212> TYPE: DNA
<213> ORGANISM: Streptococcus thermophilus

<400> SEQUENCE: 321
tgttctcata aattgccttt cctttttatg 30

<210> SEQ ID NO 322
<211> LENGTH: 30
<212> TYPE: DNA
<213> ORGANISM: Streptococcus thermophilus

<400> SEQUENCE: 322
cttatcaaac atcaaggatt gtagatgagg 30

<210> SEQ ID NO 323
<211> LENGTH: 30
<212> TYPE: DNA
<213> ORGANISM: Streptococcus thermophilus

<400> SEQUENCE: 323
atttcattag tagcttgata aatgtttcta 30

<210> SEQ ID NO 324
<211> LENGTH: 30
<212> TYPE: DNA

<213> ORGANISM: Streptococcus thermophilus

<400> SEQUENCE: 324
gaaaatacta tactttaaaa gaaattttaa 30

<210> SEQ ID NO 325
<211> LENGTH: 30
<212> TYPE: DNA
<213> ORGANISM: Streptococcus thermophilus

<400> SEQUENCE: 325
tctcctccga cataatcttt tgtctttccg 30

<210> SEQ ID NO 326
<211> LENGTH: 30
<212> TYPE: DNA
<213> ORGANISM: Streptococcus thermophilus

<400> SEQUENCE: 326
acaaaagcac tgccacctat agaagcattt 30

<210> SEQ ID NO 327
<211> LENGTH: 30
<212> TYPE: DNA
<213> ORGANISM: Streptococcus thermophilus

<400> SEQUENCE: 327
aaaaacttta tgctatccgt gtcagtatat 30

<210> SEQ ID NO 328
<211> LENGTH: 30
<212> TYPE: DNA
<213> ORGANISM: Streptococcus thermophilus

<400> SEQUENCE: 328
ttttcaatga ttgaaagccc ataactaaca 30

<210> SEQ ID NO 329
<211> LENGTH: 30
<212> TYPE: DNA
<213> ORGANISM: Streptococcus thermophilus

<400> SEQUENCE: 329
ctttcatagt tgttacgaaa tgtttggcat 30

<210> SEQ ID NO 330
<211> LENGTH: 30
<212> TYPE: DNA
<213> ORGANISM: Streptococcus thermophilus

<400> SEQUENCE: 330
cgatttgcaa tatgatgata ttgatgaatt 30

<210> SEQ ID NO 331
<211> LENGTH: 30
<212> TYPE: DNA
<213> ORGANISM: Streptococcus thermophilus

<400> SEQUENCE: 331
tttagatgct agtcctaaga ctgtagagac 30

<210> SEQ ID NO 332
<211> LENGTH: 30

<212> TYPE: DNA
<213> ORGANISM: Streptococcus thermophilus

<400> SEQUENCE: 332
gtaatcaagc gtatataagt caggactatc 30

<210> SEQ ID NO 333
<211> LENGTH: 30
<212> TYPE: DNA
<213> ORGANISM: Streptococcus thermophilus

<400> SEQUENCE: 333
ataacagaag gagtagggga cgtaggcgcg 30

<210> SEQ ID NO 334
<211> LENGTH: 30
<212> TYPE: DNA
<213> ORGANISM: Streptococcus thermophilus

<400> SEQUENCE: 334
ttatttgata ggaatgtcag taatttttga 30

<210> SEQ ID NO 335
<211> LENGTH: 30
<212> TYPE: DNA
<213> ORGANISM: Streptococcus thermophilus

<400> SEQUENCE: 335
aacatttcag cgcttactta tcaatctaat 30

<210> SEQ ID NO 336
<211> LENGTH: 29
<212> TYPE: DNA
<213> ORGANISM: Streptococcus thermophilus

<400> SEQUENCE: 336
gtattagtag gcatacgatt atggaagta 29

<210> SEQ ID NO 337
<211> LENGTH: 30
<212> TYPE: DNA
<213> ORGANISM: Streptococcus thermophilus

<400> SEQUENCE: 337
catatatata tatatattta ttttaaatat 30

<210> SEQ ID NO 338
<211> LENGTH: 30
<212> TYPE: DNA
<213> ORGANISM: Streptococcus thermophilus

<400> SEQUENCE: 338
ttgtcataat aattaaatcc aataggactt 30

<210> SEQ ID NO 339
<211> LENGTH: 30
<212> TYPE: DNA
<213> ORGANISM: Streptococcus thermophilus

<400> SEQUENCE: 339
gaaaatttct gttgtgttct taatattagc 30

<210> SEQ ID NO 340

<211> LENGTH: 30
<212> TYPE: DNA
<213> ORGANISM: Streptococcus vestibularis

<400> SEQUENCE: 340
gtacttcaaa ggttctaact acataacaca 30

<210> SEQ ID NO 341
<211> LENGTH: 30
<212> TYPE: DNA
<213> ORGANISM: Streptococcus vestibularis

<400> SEQUENCE: 341
taaaaccaga tggtggttct tctgatacta 30

<210> SEQ ID NO 342
<211> LENGTH: 30
<212> TYPE: DNA
<213> ORGANISM: Streptococcus vestibularis

<400> SEQUENCE: 342
cattttcttc agtcaattcg ttctcaagcg 30

<210> SEQ ID NO 343
<211> LENGTH: 30
<212> TYPE: DNA
<213> ORGANISM: Streptococcus vestibularis

<400> SEQUENCE: 343
aaaggacggg ggcaatgaac aaacgacaac 30

<210> SEQ ID NO 344
<211> LENGTH: 29
<212> TYPE: DNA
<213> ORGANISM: Streptococcus vestibularis

<400> SEQUENCE: 344
taatatcatt gatagcttca tcaaaggct 29

<210> SEQ ID NO 345
<211> LENGTH: 29
<212> TYPE: DNA
<213> ORGANISM: Streptococcus vestibularis

<400> SEQUENCE: 345
taaattgttc cttgactccg aactgccct 29

<210> SEQ ID NO 346
<211> LENGTH: 30
<212> TYPE: DNA
<213> ORGANISM: Streptococcus vestibularis

<400> SEQUENCE: 346
aaacaatcgt ttatctatcc tcaaaggatg 30

<210> SEQ ID NO 347
<211> LENGTH: 30
<212> TYPE: DNA
<213> ORGANISM: Streptococcus vestibularis

<400> SEQUENCE: 347
ataaaaaaac gcctcaaaaa ccgagacaac 30

<210> SEQ ID NO 348
<211> LENGTH: 30
<212> TYPE: DNA
<213> ORGANISM: Streptococcus vestibularis

<400> SEQUENCE: 348
tggaaatccc ttatatcgac aaatacgtta 30

<210> SEQ ID NO 349
<211> LENGTH: 30
<212> TYPE: DNA
<213> ORGANISM: Streptococcus vestibularis

<400> SEQUENCE: 349
ttcccagtcg ttgattttta ttgaataccc 30

<210> SEQ ID NO 350
<211> LENGTH: 30
<212> TYPE: DNA
<213> ORGANISM: Streptococcus vestibularis

<400> SEQUENCE: 350
ggacatcgaa caagtcaatg ccgtaagctt 30

<210> SEQ ID NO 351
<211> LENGTH: 30
<212> TYPE: DNA
<213> ORGANISM: Streptococcus vestibularis

<400> SEQUENCE: 351
aatctttaac cggattgtag aaccgttcgg 30

<210> SEQ ID NO 352
<211> LENGTH: 30
<212> TYPE: DNA
<213> ORGANISM: Streptococcus vestibularis

<400> SEQUENCE: 352
tgcctttaaa ataactagat tttaccatca 30

<210> SEQ ID NO 353
<211> LENGTH: 29
<212> TYPE: DNA
<213> ORGANISM: Streptococcus vestibularis

<400> SEQUENCE: 353
gagcaagcac aagcaagctt tactatcct 29

<210> SEQ ID NO 354
<211> LENGTH: 30
<212> TYPE: DNA
<213> ORGANISM: Streptococcus vestibularis

<400> SEQUENCE: 354
cagattggtt tatcgaacaa ggtcgcaagt 30

<210> SEQ ID NO 355
<211> LENGTH: 31
<212> TYPE: DNA
<213> ORGANISM: Streptococcus vestibularis

<400> SEQUENCE: 355
caaaagctgt tggttaacgg tgctttgggc a 31

<210> SEQ ID NO 356
<211> LENGTH: 30
<212> TYPE: DNA
<213> ORGANISM: Streptococcus vestibularis

<400> SEQUENCE: 356
cttgtttttc ctctggggtc tctgcgactt 30

<210> SEQ ID NO 357
<211> LENGTH: 30
<212> TYPE: DNA
<213> ORGANISM: Streptococcus vestibularis

<400> SEQUENCE: 357
gaaataaact gcccaaacat ttttattttc 30

<210> SEQ ID NO 358
<211> LENGTH: 30
<212> TYPE: DNA
<213> ORGANISM: Streptococcus vestibularis

<400> SEQUENCE: 358
tgagtaagcg acaagctaga aatcaagtca 30

<210> SEQ ID NO 359
<211> LENGTH: 30
<212> TYPE: DNA
<213> ORGANISM: Streptococcus thermophilus

<400> SEQUENCE: 359
atagctaaga tggaagaagc atcaagcacc 30

<210> SEQ ID NO 360
<211> LENGTH: 30
<212> TYPE: DNA
<213> ORGANISM: Streptococcus thermophilus

<400> SEQUENCE: 360
cagtatctca aacgctggat acaacaagat 30

<210> SEQ ID NO 361
<211> LENGTH: 30
<212> TYPE: DNA
<213> ORGANISM: Streptococcus thermophilus

<400> SEQUENCE: 361
cctactcagt ggacacctgc aattgaagac 30

<210> SEQ ID NO 362
<211> LENGTH: 29
<212> TYPE: DNA
<213> ORGANISM: Streptococcus thermophilus

<400> SEQUENCE: 362
cgattggaac gggtgcttat ggccttaac 29

<210> SEQ ID NO 363
<211> LENGTH: 30
<212> TYPE: DNA
<213> ORGANISM: Streptococcus thermophilus

<400> SEQUENCE: 363
gcgaacaatt gaatttgtta gaaaatgtcg 30

<210> SEQ ID NO 364
<211> LENGTH: 30
<212> TYPE: DNA
<213> ORGANISM: Streptococcus thermophilus

<400> SEQUENCE: 364
gaagcattta ttaatataga tggttctgct 30

<210> SEQ ID NO 365
<211> LENGTH: 28
<212> TYPE: DNA
<213> ORGANISM: Streptococcus thermophilus

<400> SEQUENCE: 365
tgctgacgta tctgtccact gtgtgcca 28

<210> SEQ ID NO 366
<211> LENGTH: 30
<212> TYPE: DNA
<213> ORGANISM: Streptococcus thermophilus

<400> SEQUENCE: 366
tttttatact ttgggtaaat tacaaaatag 30

<210> SEQ ID NO 367
<211> LENGTH: 31
<212> TYPE: DNA
<213> ORGANISM: Streptococcus thermophilus

<400> SEQUENCE: 367
tcaaggtgtc gccttatgga aaagatgctt g 31

<210> SEQ ID NO 368
<211> LENGTH: 31
<212> TYPE: DNA
<213> ORGANISM: Streptococcus thermophilus

<400> SEQUENCE: 368
tgtaaaaatt tctagacgtt tagacacttt a 31

<210> SEQ ID NO 369
<211> LENGTH: 30
<212> TYPE: DNA
<213> ORGANISM: Streptococcus thermophilus

<400> SEQUENCE: 369
aaatgatgat tgaatgcttg agatagcagt 30

<210> SEQ ID NO 370
<211> LENGTH: 30
<212> TYPE: DNA
<213> ORGANISM: Streptococcus thermophilus

<400> SEQUENCE: 370
aataagaagt tcttgacgac caaccgacat 30

<210> SEQ ID NO 371
<211> LENGTH: 30
<212> TYPE: DNA
<213> ORGANISM: Streptococcus thermophilus

<400> SEQUENCE: 371
tcgtcaacgt cgatacagaa caacgtgctt 30

<210> SEQ ID NO 372
<211> LENGTH: 30
<212> TYPE: DNA
<213> ORGANISM: Streptococcus thermophilus

<400> SEQUENCE: 372
tgattagcaa atttaaaaca ggatatttgg 30

<210> SEQ ID NO 373
<211> LENGTH: 30
<212> TYPE: DNA
<213> ORGANISM: Streptococcus thermophilus

<400> SEQUENCE: 373
aaagacaagc ccaagggatt gaactagcaa 30

<210> SEQ ID NO 374
<211> LENGTH: 30
<212> TYPE: DNA
<213> ORGANISM: Streptococcus thermophilus

<400> SEQUENCE: 374
cgaacagttg gcgagaaatc cgtctggcgt 30

<210> SEQ ID NO 375
<211> LENGTH: 30
<212> TYPE: DNA
<213> ORGANISM: Streptococcus thermophilus

<400> SEQUENCE: 375
ctacattatt gatcatgttt tttctcctgt 30

<210> SEQ ID NO 376
<211> LENGTH: 30
<212> TYPE: DNA
<213> ORGANISM: Streptococcus thermophilus

<400> SEQUENCE: 376
tagaaggctc tggaaataca aagcaattct 30

<210> SEQ ID NO 377
<211> LENGTH: 31
<212> TYPE: DNA
<213> ORGANISM: Streptococcus thermophilus

<400> SEQUENCE: 377
tagaaggctc tggtaaatac aaagcaattc t 31

<210> SEQ ID NO 378
<211> LENGTH: 30
<212> TYPE: DNA
<213> ORGANISM: Streptococcus thermophilus

<400> SEQUENCE: 378
tctgatggct cttggtaggg aactggatat 30

<210> SEQ ID NO 379
<211> LENGTH: 30
<212> TYPE: DNA
<213> ORGANISM: Streptococcus thermophilus

<400> SEQUENCE: 379
tttgatggct cttggtaggg aactggatat 30

<210> SEQ ID NO 380
<211> LENGTH: 31
<212> TYPE: DNA
<213> ORGANISM: Streptococcus thermophilus

<400> SEQUENCE: 380
ttttgatggc tcttggtagg gaactggata t 31

<210> SEQ ID NO 381
<211> LENGTH: 29
<212> TYPE: DNA
<213> ORGANISM: Streptococcus thermophilus

<400> SEQUENCE: 381
acagaacaaa atggtagaat atatcatct 29

<210> SEQ ID NO 382
<211> LENGTH: 30
<212> TYPE: DNA
<213> ORGANISM: Streptococcus thermophilus

<400> SEQUENCE: 382
ccctggacaa gctatcagca catatccttg 30

<210> SEQ ID NO 383
<211> LENGTH: 30
<212> TYPE: DNA
<213> ORGANISM: Streptococcus thermophilus

<400> SEQUENCE: 383
cgctgttgat gtaacccgct ttatatatat 30

<210> SEQ ID NO 384
<211> LENGTH: 30
<212> TYPE: DNA
<213> ORGANISM: Streptococcus thermophilus

<400> SEQUENCE: 384
gaatgaatgt attagagcaa gcacttgacc 30

<210> SEQ ID NO 385
<211> LENGTH: 30
<212> TYPE: DNA
<213> ORGANISM: Streptococcus thermophilus

<400> SEQUENCE: 385
tagacgaaaa ggaaggaaaa tagcatgagc 30

<210> SEQ ID NO 386
<211> LENGTH: 30
<212> TYPE: DNA
<213> ORGANISM: Streptococcus thermophilus

<400> SEQUENCE: 386
ataactcgat tgctaactta agcaagcagt 30

<210> SEQ ID NO 387
<211> LENGTH: 30
<212> TYPE: DNA
<213> ORGANISM: Streptococcus thermophilus

<400> SEQUENCE: 387
ctgcatgtgt aaccatgact tcttcgtcgt 30

<210> SEQ ID NO 388
<211> LENGTH: 30
<212> TYPE: DNA
<213> ORGANISM: Streptococcus thermophilus

<400> SEQUENCE: 388
cttcgctgga aacttcgtag tcatacatac 30

<210> SEQ ID NO 389
<211> LENGTH: 30
<212> TYPE: DNA
<213> ORGANISM: Streptococcus thermophilus

<400> SEQUENCE: 389
aagaccgctg tactggttgg tattcgtacc 30

<210> SEQ ID NO 390
<211> LENGTH: 30
<212> TYPE: DNA
<213> ORGANISM: Streptococcus thermophilus

<400> SEQUENCE: 390
caaccaagcg aacacagcag tagcaccgca 30

<210> SEQ ID NO 391
<211> LENGTH: 29
<212> TYPE: DNA
<213> ORGANISM: Streptococcus thermophilus

<400> SEQUENCE: 391
atgatgatga agtatcgtca tctactaac 29

<210> SEQ ID NO 392
<211> LENGTH: 30
<212> TYPE: DNA
<213> ORGANISM: Streptococcus thermophilus

<400> SEQUENCE: 392
cttcacctca aatcttagag atggactaaa 30

<210> SEQ ID NO 393
<211> LENGTH: 30
<212> TYPE: DNA
<213> ORGANISM: Streptococcus thermophilus

<400> SEQUENCE: 393
aaaaggtgcg tatgaaactc atcccagcgg 30

<210> SEQ ID NO 394
<211> LENGTH: 30
<212> TYPE: DNA
<213> ORGANISM: Streptococcus thermophilus

<400> SEQUENCE: 394
aagggtttaa gtccttcata gagtggaaaa 30

<210> SEQ ID NO 395
<211> LENGTH: 30
<212> TYPE: DNA
<213> ORGANISM: Streptococcus thermophilus

<400> SEQUENCE: 395
cctcaaagct taaaattggg ctgaagtaga 30

<210> SEQ ID NO 396
<211> LENGTH: 30
<212> TYPE: DNA
<213> ORGANISM: Streptococcus thermophilus

<400> SEQUENCE: 396
gcaatttatt cgcttgatgt actcacgttt 30

<210> SEQ ID NO 397
<211> LENGTH: 30
<212> TYPE: DNA
<213> ORGANISM: Streptococcus thermophilus

<400> SEQUENCE: 397
tatttattgc aaatggttac catattttta 30

<210> SEQ ID NO 398
<211> LENGTH: 30
<212> TYPE: DNA
<213> ORGANISM: Streptococcus thermophilus

<400> SEQUENCE: 398
tattttagca ctacggtatc agcgtatctc 30

<210> SEQ ID NO 399
<211> LENGTH: 30
<212> TYPE: DNA
<213> ORGANISM: Streptococcus thermophilus

<400> SEQUENCE: 399
tgctacgtgc tctggacggg cgctatcagc 30

<210> SEQ ID NO 400
<211> LENGTH: 30
<212> TYPE: DNA
<213> ORGANISM: Streptococcus thermophilus

<400> SEQUENCE: 400
aaatgaacag acaagaagca acagaaattg 30

<210> SEQ ID NO 401
<211> LENGTH: 30
<212> TYPE: DNA
<213> ORGANISM: Streptococcus thermophilus

<400> SEQUENCE: 401
aagttgatcg tatctattta gaatatcgca 30

<210> SEQ ID NO 402
<211> LENGTH: 30
<212> TYPE: DNA
<213> ORGANISM: Streptococcus thermophilus

<400> SEQUENCE: 402
attcactttg acagatacta atgctacatc 30

<210> SEQ ID NO 403
<211> LENGTH: 30
<212> TYPE: DNA

<213> ORGANISM: Streptococcus thermophilus

<400> SEQUENCE: 403
caagcagtgt aaaggtggtt tatatgttaa 30

<210> SEQ ID NO 404
<211> LENGTH: 30
<212> TYPE: DNA
<213> ORGANISM: Streptococcus thermophilus

<400> SEQUENCE: 404
catagtatag ccgtcttctt tgattgattg 30

<210> SEQ ID NO 405
<211> LENGTH: 30
<212> TYPE: DNA
<213> ORGANISM: Streptococcus thermophilus

<400> SEQUENCE: 405
ccatgggtgc taaaggtgat gactaccgct 30

<210> SEQ ID NO 406
<211> LENGTH: 36
<212> TYPE: DNA
<213> ORGANISM: Streptococcus thermophilus

<400> SEQUENCE: 406
tttctaggaa tgggtaatta tagcgagcta gaaagc 36

<210> SEQ ID NO 407
<211> LENGTH: 38
<212> TYPE: DNA
<213> ORGANISM: Streptococcus thermophilus

<400> SEQUENCE: 407
agttgggaag gtcttggaaa atctatggca aaaaacct 38

<210> SEQ ID NO 408
<211> LENGTH: 35
<212> TYPE: DNA
<213> ORGANISM: Streptococcus thermophilus

<400> SEQUENCE: 408
tatatggttc aaatgcgatt caaagactat tcaaa 35

<210> SEQ ID NO 409
<211> LENGTH: 30
<212> TYPE: DNA
<213> ORGANISM: Streptococcus agalactiae

<400> SEQUENCE: 409
taattgccaa tgcttacaat atcttcgtca 30

<210> SEQ ID NO 410
<211> LENGTH: 30
<212> TYPE: DNA
<213> ORGANISM: Streptococcus agalactiae

<400> SEQUENCE: 410
atgttctgaa ttacctttct cgacactccg 30

<210> SEQ ID NO 411
<211> LENGTH: 30

<212> TYPE: DNA
<213> ORGANISM: Streptococcus agalactiae

<400> SEQUENCE: 411
accatcaagg ctcttatctg cagattgtta 30

<210> SEQ ID NO 412
<211> LENGTH: 30
<212> TYPE: DNA
<213> ORGANISM: Streptococcus agalactiae

<400> SEQUENCE: 412
aaatggttgc caatgacttt ctagagtgat 30

<210> SEQ ID NO 413
<211> LENGTH: 30
<212> TYPE: DNA
<213> ORGANISM: Streptococcus agalactiae

<400> SEQUENCE: 413
acaaaatctt ttgttgctcc tggacgtatt 30

<210> SEQ ID NO 414
<211> LENGTH: 30
<212> TYPE: DNA
<213> ORGANISM: Streptococcus agalactiae

<400> SEQUENCE: 414
atgtaaggta ttgtaaaact tcttcttgcg 30

<210> SEQ ID NO 415
<211> LENGTH: 30
<212> TYPE: DNA
<213> ORGANISM: Streptococcus agalactiae

<400> SEQUENCE: 415
actgttccta taattaaaat aaaagaggta 30

<210> SEQ ID NO 416
<211> LENGTH: 30
<212> TYPE: DNA
<213> ORGANISM: Streptococcus agalactiae

<400> SEQUENCE: 416
tgttccagta aaaagtaatt ttaaagcatt 30

<210> SEQ ID NO 417
<211> LENGTH: 30
<212> TYPE: DNA
<213> ORGANISM: Streptococcus agalactiae

<400> SEQUENCE: 417
cgctcgattg atgctatcaa ctatattgaa 30

<210> SEQ ID NO 418
<211> LENGTH: 30
<212> TYPE: DNA
<213> ORGANISM: Streptococcus agalactiae

<400> SEQUENCE: 418
ttcttcaaga gaacttgtag aacagcttca 30

<210> SEQ ID NO 419

<211> LENGTH: 30
<212> TYPE: DNA
<213> ORGANISM: Streptococcus agalactiae

<400> SEQUENCE: 419
aaggtacttt tagcttgttc ttgtggtgtt 30

<210> SEQ ID NO 420
<211> LENGTH: 30
<212> TYPE: DNA
<213> ORGANISM: Streptococcus agalactiae

<400> SEQUENCE: 420
acagctactg taaattctgc ttttacggtt 30

<210> SEQ ID NO 421
<211> LENGTH: 30
<212> TYPE: DNA
<213> ORGANISM: Streptococcus agalactiae

<400> SEQUENCE: 421
tagtgcagtt gtcaaggaga ttgtgagcga 30

<210> SEQ ID NO 422
<211> LENGTH: 30
<212> TYPE: DNA
<213> ORGANISM: Streptococcus agalactiae

<400> SEQUENCE: 422
tttaaccttt gaaaatgtga aaggctcgta 30

<210> SEQ ID NO 423
<211> LENGTH: 30
<212> TYPE: DNA
<213> ORGANISM: Streptococcus agalactiae

<400> SEQUENCE: 423
gcgatgatgg taagtcatca tggacagcgt 30

<210> SEQ ID NO 424
<211> LENGTH: 30
<212> TYPE: DNA
<213> ORGANISM: Streptococcus agalactiae

<400> SEQUENCE: 424
ttttacacac gatgtcagat ataatgtcaa 30

<210> SEQ ID NO 425
<211> LENGTH: 30
<212> TYPE: DNA
<213> ORGANISM: Streptococcus agalactiae

<400> SEQUENCE: 425
agtactgcac taggaattgt agagatcaaa 30

<210> SEQ ID NO 426
<211> LENGTH: 30
<212> TYPE: DNA
<213> ORGANISM: Streptococcus agalactiae

<400> SEQUENCE: 426
cgtaccatct atcaatttac cgcaagctgt 30

<210> SEQ ID NO 427
<211> LENGTH: 30
<212> TYPE: DNA
<213> ORGANISM: Streptococcus agalactiae

<400> SEQUENCE: 427
ttaaaagatt taaactatca agcgtcaatt 30

<210> SEQ ID NO 428
<211> LENGTH: 30
<212> TYPE: DNA
<213> ORGANISM: Streptococcus agalactiae

<400> SEQUENCE: 428
ttctaaatgc tggtgactgc tttgcataaa 30

<210> SEQ ID NO 429
<211> LENGTH: 31
<212> TYPE: DNA
<213> ORGANISM: Streptococcus agalactiae

<400> SEQUENCE: 429
ttgctgctag acccaaacag tttattttta g 31

<210> SEQ ID NO 430
<211> LENGTH: 30
<212> TYPE: DNA
<213> ORGANISM: Streptococcus agalactiae

<400> SEQUENCE: 430
tcctttttta gataatgtgc gatcacggac 30

<210> SEQ ID NO 431
<211> LENGTH: 29
<212> TYPE: DNA
<213> ORGANISM: Streptococcus agalactiae

<400> SEQUENCE: 431
ttttaccaat gcttccatat cgcttatat 29

<210> SEQ ID NO 432
<211> LENGTH: 30
<212> TYPE: DNA
<213> ORGANISM: Streptococcus agalactiae

<400> SEQUENCE: 432
tggttataca tttactaatc catcagcatt 30

<210> SEQ ID NO 433
<211> LENGTH: 30
<212> TYPE: DNA
<213> ORGANISM: Streptococcus agalactiae

<400> SEQUENCE: 433
aagctaattc tcatctcacc gagatggata 30

<210> SEQ ID NO 434
<211> LENGTH: 30
<212> TYPE: DNA
<213> ORGANISM: Streptococcus agalactiae

<400> SEQUENCE: 434
aaaaactctt accacttaca tacatgtatg 30

<210> SEQ ID NO 435
<211> LENGTH: 30
<212> TYPE: DNA
<213> ORGANISM: Streptococcus agalactiae

<400> SEQUENCE: 435
gctggagatt ttacaagcag tttgaatttc 30

<210> SEQ ID NO 436
<211> LENGTH: 30
<212> TYPE: DNA
<213> ORGANISM: Streptococcus agalactiae

<400> SEQUENCE: 436
atcacaccag tcgttatgat ggatgactat 30

<210> SEQ ID NO 437
<211> LENGTH: 30
<212> TYPE: DNA
<213> ORGANISM: Streptococcus agalactiae

<400> SEQUENCE: 437
tgtcaacagt acgtgagacg agtgtgtagg 30

<210> SEQ ID NO 438
<211> LENGTH: 30
<212> TYPE: DNA
<213> ORGANISM: Streptococcus agalactiae

<400> SEQUENCE: 438
tgaagttgat ggatatgttg atttagagct 30

<210> SEQ ID NO 439
<211> LENGTH: 30
<212> TYPE: DNA
<213> ORGANISM: Streptococcus agalactiae

<400> SEQUENCE: 439
taatcatttt atgagagata ccgcctcaag 30

<210> SEQ ID NO 440
<211> LENGTH: 30
<212> TYPE: DNA
<213> ORGANISM: Streptococcus agalactiae

<400> SEQUENCE: 440
tttaaagaga tatctgtttc atcttgcgga 30

<210> SEQ ID NO 441
<211> LENGTH: 30
<212> TYPE: DNA
<213> ORGANISM: Streptococcus agalactiae

<400> SEQUENCE: 441
aatcacttct gcataaatat cttttacttc 30

<210> SEQ ID NO 442
<211> LENGTH: 30
<212> TYPE: DNA
<213> ORGANISM: Streptococcus agalactiae

<400> SEQUENCE: 442
aaacatccgc aacgggataa ataaagctag 30

<210> SEQ ID NO 443
<211> LENGTH: 30
<212> TYPE: DNA
<213> ORGANISM: Streptococcus agalactiae

<400> SEQUENCE: 443
agtttcttgt gggttagctt gtccaccgta 30

<210> SEQ ID NO 444
<211> LENGTH: 30
<212> TYPE: DNA
<213> ORGANISM: Streptococcus agalactiae

<400> SEQUENCE: 444
gaacatgaaa gattttaaaa aagaacattt 30

<210> SEQ ID NO 445
<211> LENGTH: 30
<212> TYPE: DNA
<213> ORGANISM: Streptococcus agalactiae

<400> SEQUENCE: 445
agaggggaaa atatcaatgc cgaatgctga 30

<210> SEQ ID NO 446
<211> LENGTH: 30
<212> TYPE: DNA
<213> ORGANISM: Streptococcus agalactiae

<400> SEQUENCE: 446
gatggtacaa aatcatttgt tggtactgat 30

<210> SEQ ID NO 447
<211> LENGTH: 30
<212> TYPE: DNA
<213> ORGANISM: Streptococcus mutans

<400> SEQUENCE: 447
aaaaggaaac gccattaatt aatatggtga 30

<210> SEQ ID NO 448
<211> LENGTH: 30
<212> TYPE: DNA
<213> ORGANISM: Streptococcus mutans

<400> SEQUENCE: 448
gattgaacca gctagcgcag ttagtgctct 30

<210> SEQ ID NO 449
<211> LENGTH: 30
<212> TYPE: DNA
<213> ORGANISM: Streptococcus mutans

<400> SEQUENCE: 449
cgctaaaagc tgttgtgtca tcatagttag 30

<210> SEQ ID NO 450
<211> LENGTH: 30
<212> TYPE: DNA
<213> ORGANISM: Streptococcus mutans

<400> SEQUENCE: 450
taaatatttt caattagaca atagacaaac 30

<210> SEQ ID NO 451
<211> LENGTH: 30
<212> TYPE: DNA
<213> ORGANISM: Streptococcus mutans

<400> SEQUENCE: 451
tgcctatgta ttcggacatg acttgccaca 30

<210> SEQ ID NO 452
<211> LENGTH: 30
<212> TYPE: DNA
<213> ORGANISM: Streptococcus mutans

<400> SEQUENCE: 452
atgtgaaaag aaagtaacta ctacatttga 30

<210> SEQ ID NO 453
<211> LENGTH: 30
<212> TYPE: DNA
<213> ORGANISM: Streptococcus pyogenes

<400> SEQUENCE: 453
tgcgctggtt gatttcttct tgcgcttttt 30

<210> SEQ ID NO 454
<211> LENGTH: 30
<212> TYPE: DNA
<213> ORGANISM: Streptococcus pyogenes

<400> SEQUENCE: 454
ttatatgaac ataactcaat ttgtaaaaaa 30

<210> SEQ ID NO 455
<211> LENGTH: 30
<212> TYPE: DNA
<213> ORGANISM: Streptococcus pyogenes

<400> SEQUENCE: 455
aggaatatcc gcaataatta attgcgctct 30

<210> SEQ ID NO 456
<211> LENGTH: 30
<212> TYPE: DNA
<213> ORGANISM: Streptococcus pyogenes

<400> SEQUENCE: 456
taaatttgtt tagcaggtaa accgtgcttt 30

<210> SEQ ID NO 457
<211> LENGTH: 30
<212> TYPE: DNA
<213> ORGANISM: Streptococcus pyogenes

<400> SEQUENCE: 457
ttcagcacac tgagacttgt tgagttccat 30

<210> SEQ ID NO 458
<211> LENGTH: 33
<212> TYPE: DNA
<213> ORGANISM: Streptococcus pyogenes

<400> SEQUENCE: 458
ctgtgacatt gcgggatgta atcaaagtaa aaa 33

<210> SEQ ID NO 459
<211> LENGTH: 32
<212> TYPE: DNA
<213> ORGANISM: Streptococcus pyogenes

<400> SEQUENCE: 459
aaagcaaacc tagcagaagc agaaaatgac tt 32

<210> SEQ ID NO 460
<211> LENGTH: 34
<212> TYPE: DNA
<213> ORGANISM: Streptococcus pyogenes

<400> SEQUENCE: 460
tgatgtaatt ggtgattttc gtgatatgct tttt 34

<210> SEQ ID NO 461
<211> LENGTH: 5849
<212> TYPE: DNA
<213> ORGANISM: Streptococcus thermophilus

<400> SEQUENCE: 461
atgagtgact tagttttagg acttgatatc ggtataggtt ctgttggtgt aggtatcctt 60
aacaaagtga caggagaaat tatccataaa aactcacgca tcttcccagc agctcaagca 120
gaaaataacc tagtacgtag aacgaatcgt caaggaagac gcttgacacg acgtaaaaaa 180
catcgtatag ttcgtttaaa tcgtctattt gaggaaagtg gattaatcac cgattttacg 240
aagatttcaa ttaatcttaa cccatatcaa ttacgagtta agggcttgac cgatgaattg 300
tctaatgaag aactgtttat cgctcttaaa aatatggtga aacaccgtgg gattagttac 360
ctcgatgatg ctagtgatga cggaaattca tcagtaggag actatgcaca aattgttaag 420
gaaaatagta aacaattaga aactaagaca ccgggacaga tacagttgga acgctaccaa 480
acatatggtc aattacgtgg tgattttact gttgagaaag atggcaaaaa acatcgcttg 540
attaatgtct ttccaacatc agcttatcgt tcagaagcct taaggatact gcaaactcaa 600
caagaattta atccacagat tacagatgaa tttattaatc gttatctcga aattttaact 660
ggaaaacgga aatattatca tggacccgga aatgaaaagt cacggactga ttatggtcgt 720
tacagaacga gtggagaaac tttagacaat atttttggaa ttctaattgg gaaatgtaca 780
ttttatccag aagagtttag agcagcaaaa gcttcctaca cggctcaaga attcaatttg 840
ctaaatgatt tgaacaatct aacagttcct actgaaacca aaaagttgag caaagaacag 900
aagaatcaaa tcattaatta tgtcaaaaat gaaaaggcaa tggggccagc gaaacttttt 960
aaatatatcg ctaagttact ttcttgtgat gttgcagata tcaagggata ccgtatcgac 1020
aaatcaggta aggctgagat tcatactttc gaagcctatc gaaaaatgaa aacgcttgaa 1080
accttagata ttgaacaaat ggatagagaa acgcttgata aattagccta tgtcttaaca 1140
ttaaacactg agagggaagg tattcaagaa gccttagaac atgaatttgc tgatggtagc 1200
tttagccaga agcaagttga cgaattggtt caattccgca aagcaaatag ttccattttt 1260
ggaaaaggat ggcataattt ttctgtcaaa ctgatgatgg agttaattcc agaattgtat 1320
gagacgtcag aagagcaaat gactatcctg acacgacttg gaaaacaaaa acgacttcgt 1380
cttcaaataa aacaaaatat ttcaaataaa acaaaatata tagatgagaa actattaact 1440

```
gaagaaatct ataatcctgt tgttgctaag tctgttcgcc aggctataaa aatcgtaaat   1500
gcggcgatta aagaatacgg agactttgac aatattgtca tcgaaatggc tcgtgaaaca   1560
aatgaagatg atgaaaagaa agctattcaa aagattcaaa aagccaacaa agatgaaaaa   1620
gatgcagcaa tgcttaaggc tgctaaccaa tataatggaa aggctgaatt accacatagt   1680
gttttccacg gtcataagca attagcgact aaaatccgcc tttggcatca gcaaggagaa   1740
cgttgccttt atactggtaa gacaatctca atccatgatt tgataaataa tcctaatcag   1800
tttgaagtag atcatatttt acctctttct atcacattcg atgatagcct tgcaaataag   1860
gttttggttt atgcaactgc taaccaagaa aaaggacaac gaacacctta tcaggcttta   1920
gatagtatgg atgatgcgtg gtctttccgt gaattaaaag cttttgtacg tgagtcaaaa   1980
acactttcaa acaagaaaaa agaatacctc cttacagaag aagatatttc aaagtttgat   2040
gttcgaaaga aatttattga acgaaatctt gtagatacaa gatacgcttc aagagttgtc   2100
ctcaatgccc ttcaagaaca ctttagagct cacaagattg atacaaaagt ttccgtggtt   2160
cgtggccaat ttacatctca attgagacgc cattggggaa ttgagaagac tcgtgatact   2220
tatcatcacc atgctgtcga tgcattgatt attgccgcct caagtcagtt gaatttgtgg   2280
aaaaaacaaa agaataccct tgtaagttat tcagaagaac aactccttga tattgaaaca   2340
ggtgaactta ttagtgatga tgagtacaag gaatctgtgt tcaaagcccc ttatcaacat   2400
tttgttgata cattgaagag taaagaattt gaagacagta tcttattctc atatcaagtg   2460
gattctaagt ttaatcgtaa aatatcagat gccactattt atgcgacaag acaggctaaa   2520
gtgggaaaag ataagaagga tgaaacttat gtcttaggga aatcaaaga tatctatact    2580
caggatggtt atgatgcctt tatgaagatt tataagaagg ataagtcaaa attcctcatg   2640
tatcgtcacg acccacaaac ctttgagaaa gttatcgagc caattttaga gaactatcct   2700
aataagcaaa tgaatgaaaa aggaaaagag gtaccatgta atcctttcct aaaatataaa   2760
gaagaacatg gctatattcg taaatatagt aaaaaaggca atggtcctga aatcaagagt   2820
cttaaatact atgatagtaa gcttttaggt aatcctattg atattactcc agagaatagt   2880
aaaaataaag ttgtcttaca gtcattaaaa ccttggagaa cagatgtcta tttcaataag   2940
gctactggaa aatacgaaat ccttggatta aaatatgctg atctacaatt tgagaaaggg   3000
acaggaacat ataagatttc ccaggaaaaa tacaatgaca ttaagaaaaa agagggtgta   3060
gattctgatt cagaattcaa gtttacactt tataaaaatg atttgttact cgttaaagat   3120
acagaaacaa aagaacaaca gcttttccgt tttctttctc gaactttacc taaacaaaag   3180
cattatgttg aattaaaacc ttatgataaa cagaaatttg aaggaggtga ggcgttaatt   3240
aaagtgttgg gtaacgttgc taatggtggt caatgcataa aaggactagc aaaatcaaat   3300
atttctattt ataaagtaag aacagatgtc ctaggaaatc agcatatcat caaaaatgag   3360
ggtgataagc ctaagctaga tttttaatat taattgttag aaagtgttgc aattatagtt   3420
atcatatgct ataataatcg tgtaagggac gccttacaca gttacttaaa tcttgcagaa   3480
gctacaaaga taaggcttca tgccgaaatc aacaccctgt cattttatgg cagggtgttt   3540
tcgttattta aagaggagaa gaaatgactt ggagagttgt acatgtcagt caaagtgaga   3600
agatgcgctt aaagcttgat aacttattag tgcaaaaaat gggacaagag tttacggtgc   3660
cactaagtga tatttcgata atcgttgcag aaggtgggga tacagttgtt acccttcgtc   3720
tattaagtgc cttaagtaaa tataatattg ccttggtcgt ttgtgataac gaacatttac   3780
caacaggaat ttatcactca caaaatgggc actttagagc gtacaagcgc ttgaaagaac   3840
```

agctggattg gtctcagaaa caaaaggaca aggcatggca gattgtaact tattataaaa 3900
tcaataacca agaggatgtt ctagccatgt ttgaaaaaag tctggacaac attagattac 3960
tttcagacta taaagagcag atagaacctg gtgatagaac gaatagagag ggacatgctg 4020
ccaaggtcta ctttaatgag ctctttggta aacaatttgt cagagtaact cagcaagaag 4080
ctgatgtcat caatgctggt ttaaactatg gctatgctat catgagggct cagatggcta 4140
gaatagtggc gggttatggt ttaaatggcc tattaggaat cttccataaa aatgaataca 4200
atcagtttaa tttggttgac gatttgatgg agccatttag acagattgta gatgtttggg 4260
tatatgataa tctacgagat caggaattcc ttaagtatga gtataggttg ggattgacag 4320
atttactcaa tgctaaaatc aaatatggca aagagacttg ctcagtgaca gttgctatgg 4380
acaaatatgt caaaggcttt atcaaatata tttcggaaaa agatagtagt aaatttcact 4440
gcccagtggt atcaagttta gagtggagaa aataagatga ggtatgaagc attgagatta 4500
ttatgttttt ttgatttacc aatggaatcc aaggatgaaa aaagaatata tcgtaatttt 4560
cgtaaagaat taatttcaaa tgggtttgaa atgttacaat tttcggtcta ctatcgcact 4620
tgtcctaata gaagctttgc aaataaattt tataagaagt taaagattag caatcttcct 4680
gctgggaatg tgagactttt ggcagttact gaaaaacaat tttcagagat gacattaatt 4740
ataggtggta aaactaagca agaagaaatc gtcagtgata ataagttggt ggttatatga 4800
aatattttgt acaacatcct tacaaagaac gtattgaatt aaatattggt gcaatcacac 4860
aaattgttgg tcagaataaa gaactcaaat attatatttg gcaaattttg agctggtatt 4920
ttggcggaaa aaaatactca agtgaggact taagtatttt tgattatgag gaacctacta 4980
tacttgatga gtctggagaa atagtgaagc gaagtagcta tcactatatc gacatttcaa 5040
gttttaagga tttactggag cagatggaat acaagaaagg aacacttgct cagggttacc 5100
ttagtaaaat tctcaatcag gttgatattg taggccattt ggagaaaatt aatgaacaag 5160
tagagcttat agaaggagca atgaatcagc atataaactt aaactgtggt caggtggagt 5220
accatttgga gaatcaccct ctaacactag accaattact ttcaaaaaat tttagtccct 5280
tttttgctat cgagaataag aatttatctt ttgaatgggt ttcaaatact gataaacttt 5340
ctctctttct agaaatgtta gaccgccttc tgtcacaaac aacagagaag tatctcattg 5400
tgctaaaaaa tattgatggc tttatctcag aagaatctta tactattttt tataggcaaa 5460
tctgtcatct ggtcaagaag tatccaaatc taacctttat tttgtttcct agtgaccaag 5520
gctatttaaa aattgatgaa gaaaatagta ggttcgtcaa tattttatct gaccaggtgg 5580
agcatttgta tgatgttgag tttatgtatg aaagagtaat gaaatattat ccaagtaatg 5640
attttccgac gagagaaggt tttaggatgt ctttagaaac tgtgacacct tatttattga 5700
caaaaatgct gagacaacct agtctctcac ttgttgattc agtaatattg aatatcctaa 5760
atcagttgtt tcattttagt taccgtataa gatattctca gacacctgat aaggaactat 5820
tacataaatt tttagaaagt aaggattga 5849

<210> SEQ ID NO 462
<211> LENGTH: 3387
<212> TYPE: DNA
<213> ORGANISM: Streptococcus thermophilus

<400> SEQUENCE: 462
atgagtgact tagttttagg acttgatatc ggtataggtt ctgttggtgt aggtatcctt 60

-continued

```
aacaaagtga caggagaaat tatccataaa aactcacgca tcttcccagc agctcaagca    120
gaaaataacc tagtacgtag aacgaatcgt caaggaagac gcttgacacg acgtaaaaaa    180
catcgtatag ttcgtttaaa tcgtctattt gaggaaagtg gattaatcac cgattttacg    240
aagatttcaa ttaatcttaa cccatatcaa ttacgagtta agggcttgac cgatgaattg    300
tctaatgaag aactgtttat cgctcttaaa aatatggtga aacaccgtgg gattagttac    360
ctcgatgatg ctagtgatga cggaaattca tcagtaggag actatgcaca aattgttaag    420
gaaaatagta aacaattaga aactaagaca ccgggacaga tacagttgga acgctaccaa    480
acatatggtc aattacgtgg tgattttact gttgagaaag atggcaaaaa acatcgcttg    540
attaatgtct ttccaacatc agcttatcgt tcagaagcct taaggatact gcaaactcaa    600
caagaattta atccacagat tacagatgaa tttattaatc gttatctcga aattttaact    660
ggaaaacgga aatattatca tggacccgga aatgaaaagt cacggactga ttatggtcgt    720
tacagaacga gtggagaaac tttagacaat atttttggaa ttctaattgg gaaatgtaca    780
ttttatccag aagagtttag agcagcaaaa gcttcctaca cggctcaaga attcaatttg    840
ctaaatgatt tgaacaatct aacagttcct actgaaacca aaaagttgag caaagaacag    900
aagaatcaaa tcattaatta tgtcaaaaat gaaaaggcaa tggggccagc gaaacttttt    960
aaatatatcg ctaagttact ttcttgtgat gttgcagata tcaagggata ccgtatcgac   1020
aaatcaggta aggctgagat tcatactttc gaagcctatc gaaaaatgaa aacgcttgaa   1080
accttagata ttgaacaaat ggatagagaa acgcttgata aattagccta tgtcttaaca   1140
ttaaacactg agagggaagg tattcaagaa gccttagaac atgaatttgc tgatggtagc   1200
tttagccaga agcaagttga cgaattggtt caattccgca aagcaaatag ttccattttt   1260
ggaaaaggat ggcataattt ttctgtcaaa ctgatgatgg agttaattcc agaattgtat   1320
gagacgtcag aagagcaaat gactatcctg acacgacttg gaaaacaaaa acgacttcgt   1380
cttcaaataa aacaaaatat ttcaaataaa acaaaatata tagatgagaa actattaact   1440
gaagaaatct ataatcctgt tgttgctaag tctgttcgcc aggctataaa aatcgtaaat   1500
gcggcgatta aagaatacgg agactttgac aatattgtca tcgaaatggc tcgtgaaaca   1560
aatgaagatg atgaaaagaa agctattcaa aagattcaaa aagccaacaa agatgaaaaa   1620
gatgcagcaa tgcttaaggc tgctaaccaa tataatggaa aggctgaatt accacatagt   1680
gttttccacg gtcataagca attagcgact aaaatccgcc tttggcatca gcaaggagaa   1740
cgttgccttt atactggtaa gacaatctca atccatgatt tgataaataa tcctaatcag   1800
tttgaagtag atcatatttt acctctttct atcacattcg atgatagcct tgcaaataag   1860
gttttggttt atgcaactgc taaccaagaa aaaggacaac gaacacctta tcaggcttta   1920
gatagtatgg atgatgcgtg gtctttccgt gaattaaaag cttttgtacg tgagtcaaaa   1980
acactttcaa acaagaaaaa agaatacctc cttacagaag aagatatttc aaagtttgat   2040
gttcgaaaga aatttattga acgaaatctt gtagatacaa gatacgcttc aagagttgtc   2100
ctcaatgccc ttcaagaaca ctttagagct cacaagattg atacaaaagt ttccgtggtt   2160
cgtggccaat ttacatctca attgagacgc cattggggaa ttgagaagac tcgtgatact   2220
tatcatcacc atgctgtcga tgcattgatt attgccgcct caagtcagtt gaatttgtgg   2280
aaaaaacaaa agaataccct tgtaagttat tcagaagaac aactccttga tattgaaaca   2340
ggtgaactta ttagtgatga tgagtacaag gaatctgtgt tcaaagcccc ttatcaacat   2400
tttgttgata cattgaagag taaagaattt gaagacagta tcttattctc atatcaagtg   2460
```

```
gattctaagt ttaatcgtaa aatatcagat gccactattt atgcgacaag acaggctaaa   2520

gtgggaaaag ataagaagga tgaaacttat gtcttaggga aaatcaaaga tatctatact   2580

caggatggtt atgatgcctt tatgaagatt tataagaagg ataagtcaaa attcctcatg   2640

tatcgtcacg acccacaaac ctttgagaaa gttatcgagc caattttaga gaactatcct   2700

aataagcaaa tgaatgaaaa aggaaaagag gtaccatgta atcctttcct aaaatataaa   2760

gaagaacatg gctatattcg taaatatagt aaaaaaggca atggtcctga aatcaagagt   2820

cttaaatact atgatagtaa gcttttaggt aatcctattg atattactcc agagaatagt   2880

aaaaataaag ttgtcttaca gtcattaaaa ccttggagaa cagatgtcta tttcaataag   2940

gctactggaa aatacgaaat ccttggatta aaatatgctg atctacaatt tgagaaaggg   3000

acaggaacat ataagatttc ccaggaaaaa tacaatgaca ttaagaaaaa agagggtgta   3060

gattctgatt cagaattcaa gtttacactt tataaaaatg atttgttact cgttaaagat   3120

acagaaacaa aagaacaaca gcttttccgt tttctttctc gaactttacc taaacaaaag   3180

cattatgttg aattaaaacc ttatgataaa cagaaatttg aaggaggtga ggcgttaatt   3240

aaagtgttgg gtaacgttgc taatggtggt caatgcataa aaggactagc aaaatcaaat   3300

atttctattt ataaagtaag aacagatgtc ctaggaaatc agcatatcat caaaaatgag   3360

ggtgataagc ctaagctaga tttttaa                                       3387
```

<210> SEQ ID NO 463
<211> LENGTH: 912
<212> TYPE: DNA
<213> ORGANISM: Streptococcus thermophilus

<400> SEQUENCE: 463

```
atgacttgga gagttgtaca tgtcagtcaa agtgagaaga tgcgcttaaa gcttgataac     60

ttattagtgc aaaaaatggg acaagagttt acggtgccac taagtgatat ttcgataatc    120

gttgcagaag gtggggatac agttgttacc cttcgtctat taagtgcctt aagtaaatat    180

aatattgcct tggtcgtttg tgataacgaa catttaccaa caggaattta tcactcacaa    240

aatgggcact ttagagcgta caagcgcttg aaagaacagc tggattggtc tcagaaacaa    300

aaggacaagg catggcagat tgtaacttat tataaaatca ataaccaaga ggatgttcta    360

gccatgtttg aaaaaagtct ggacaacatt agattacttt cagactataa agagcagata    420

gaacctggtg atagaacgaa tagagaggga catgctgcca aggtctactt taatgagctc    480

tttggtaaac aatttgtcag agtaactcag caagaagctg atgtcatcaa tgctggttta    540

aactatggct atgctatcat gagggctcag atggctagaa tagtggcggg ttatggttta    600

aatggcctat taggaatctt ccataaaaat gaatacaatc agtttaattt ggttgacgat    660

ttgatggagc catttagaca gattgtagat gtttgggtat atgataatct acgagatcag    720

gaattcctta agtatgagta taggttggga ttgacagatt tactcaatgc taaaatcaaa    780

tatggcaaag agacttgctc agtgacagtt gctatggaca aatatgtcaa aggctttatc    840

aaatatattt cggaaaaaga tagtagtaaa tttcactgcc cagtggtatc aagtttagag    900

tggagaaaat aa                                                        912
```

<210> SEQ ID NO 464
<211> LENGTH: 324
<212> TYPE: DNA
<213> ORGANISM: Streptococcus thermophilus

<400> SEQUENCE: 464
atgaggtatg aagcattgag attattatgt ttttttgatt taccaatgga atccaaggat 60
gaaaaaagaa tatatcgtaa ttttcgtaaa gaattaattt caaatgggtt tgaaatgtta 120
caattttcgg tctactatcg cacttgtcct aatagaagct ttgcaaataa attttataag 180
aagttaaaga ttagcaatct tcctgctggg aatgtgagac ttttggcagt tactgaaaaa 240
caattttcag agatgacatt aattataggt ggtaaaacta agcaagaaga aatcgtcagt 300
gataataagt tggtggttat atga 324

<210> SEQ ID NO 465
<211> LENGTH: 1053
<212> TYPE: DNA
<213> ORGANISM: Streptococcus thermophilus

<400> SEQUENCE: 465
atgaaatatt ttgtacaaca tccttacaaa gaacgtattg aattaaatat tggtgcaatc 60
acacaaattg ttggtcagaa taaagaactc aaatattata tttggcaaat tttgagctgg 120
tattttggcg gaaaaaaata ctcaagtgag gacttaagta tttttgatta tgaggaacct 180
actatacttg atgagtctgg agaaatagtg aagcgaagta gctatcacta tatcgacatt 240
tcaagtttta aggatttact ggagcagatg gaatacaaga aaggaacact tgctcagggt 300
taccttagta aaattctcaa tcaggttgat attgtaggcc atttggagaa aattaatgaa 360
caagtagagc ttatagaagg agcaatgaat cagcatataa acttaaactg tggtcaggtg 420
gagtaccatt tggagaatca ccctctaaca ctagaccaat tactttcaaa aaattttagt 480
ccctttttg ctatcgagaa taagaattta tcttttgaat gggtttcaaa tactgataaa 540
ctttctctct ttctagaaat gttagaccgc cttctgtcac aaacaacaga gaagtatctc 600
attgtgctaa aaaatattga tggctttatc tcagaagaat cttatactat tttttatagg 660
caaatctgtc atctggtcaa gaagtatcca aatctaacct ttattttgtt tcctagtgac 720
caaggctatt taaaaattga tgaagaaaat agtaggttcg tcaatatttt atctgaccag 780
gtggagcatt tgtatgatgt tgagtttatg tatgaaagag taatgaaata ttatccaagt 840
aatgattttc cgacgagaga aggttttagg atgtctttag aaactgtgac accttattta 900
ttgacaaaaa tgctgagaca acctagtctc tcacttgttg attcagtaat attgaatatc 960
ctaaatcagt tgtttcattt tagttaccgt ataagatatt ctcagacacc tgataaggaa 1020
ctattacata aatttttaga aagtaaggat tga 1053

<210> SEQ ID NO 466
<211> LENGTH: 4123
<212> TYPE: DNA
<213> ORGANISM: Streptococcus thermophilus

<400> SEQUENCE: 466
atgagcgatt tatatagtca aaggtccaat tattacctgt ccttatctga acaaagaatt 60
atcattaaaa atgataataa agagattgtc aaagaagtgt ccatttcact cgttgataat 120
gtattacttt ttggtaatgc acaactgacc acccaactca tcaaagcctt gtcaaagaac 180
aaggtgaatg tttactattt ctcaaatgtt ggtcaattta tttctagtat tgaaacccac 240
aggcaggacg aattccaaaa gcaagagttg caagcaaagg cttattttga agaggatttc 300
cgtttagagg ttgcgaggag tattgctacg accaaggtga ggcacccaat tgccttactt 360
agagagtttg atacggatgg tctactagat acctcagatt attctaggtt tgaagatagt 420
gtcaatgata ttcagaaagc ttattccatt acagaaatta tgggttacga aggtcgcctt 480
gcgaaatcct atttttacta tctgaattta ctcgttccta atgactttca ttttaatggt 540
aggagtagac ggcctgggga ggattgtttt aacagtgccc tcaattttgg ctatagtatc 600
ttatattctt gcttaatggg ctgattaaga aaaacgggct aagcttggga tttggggtaa 660
ttcacaagca tcatcagcat catgcgacct tggccagtga tttaatggaa gaatggagac 720
ctatcatcgt cgataatacg cttatggagt tggtacgaaa tggtaaactt cttttaagtc 780
attttgaaaa taaggatcaa gacttcatac tcacccatga aggcagagaa atctttgcac 840
gggctttacg ttcaagaata ttagaagtcc atcagtatat tgagttagat aaaaaacgct 900
attcttttct ttatacagca gataggcaaa tcaagagttt gattagggct tttagagaac 960
ttgaccctag tctctatgag acaagttaca caggagggca ttaatgggac tttactttaa 1020
cctcagcgaa gaagagcgtg agtttgccaa acaaaaaaac catgttttgt ctgattattt 1080
atgatattcg aagtaacaaa cgtagactta aactctcgaa attacttgag ggttatggcg 1140
tgagggtgca aaaatcctgt ttcgaagtcg acctgtcaag aaatgattat cagtctctcc 1200
ttaaggatat cgagggcttc tccaaggctg atgaagaaga cagcataata gtgtatgtgc 1260
caaccaaaga agaggtgact agttttagcc cctaccatag tgctgaaaaa ttagatgaca 1320
ttctcttccc ctaagccttt atagaccttt aatcatatgg tacactatag atagtgtttc 1380
cagaggctct taaggaaatc aaagatagag agacacttca aagattttgt agatatatgg 1440
aagcattagt agcctatttc aagttttatg gaggtaaaga ttaatgacat tcgctaagat 1500
taaattttca gctcaaattc gtttagagac aggcctccat attggtggaa gcgatgcttt 1560
tgcagccatt ggtgcaatcg attcgcctgt tattaaagat cctattacca acctaccgat 1620
cattcctggt tcaagtctca aaggaaaaat gagaacgctt cttgccaagg tttataatga 1680
aaaggtagct gagaaaccaa gcgatgacag tgatattctt agccgtttat ttgggaatag 1740
taaagataaa cgattcaaaa tgggacgctt gatttttcgt gatgccttct tgtcaaacgc 1800
tgatgagcta gactctcttg ggtaagaag ttatacagaa gtaaaatttg aaaatacaat 1860
tgaccgtatc actgccgaag ctaatccaag acaaattgaa cgtgctattc gtaccagtac 1920
ttttgatttc gagttgattt atgaaattac agatgagaat gaaaatcaag tcgaagaaga 1980
ttccaaagtg attcgagatg gtttaaaact gcttgaactt gattatcttg gtggttctgg 2040
atctcgaggt tacggtaagg ttgcttttga aaacctcaaa gctactaccg tatttggtaa 2100
ttatgatgtt aaaacattaa atgaactttt aactgcggag gtctaatatg acctataaac 2160
tgtatattat gacctttcag aatgctcatt ttggttcggg cactcttgat agctcaaaat 2220
taacattctc agcagaccgt atcttctcag cactagtgct agaatcccta aaaatgggaa 2280
aactcgatgc atttcttgcg gaagctaacc aagacaagtt cacgctcaca gatgcctttc 2340
catttcaatt tggtcccttt ttgccgaaac ctattggtta tcccaaacat gaccaaatag 2400
atcaatcagt tgatgtcaaa gaggttcgcc gtcaagcaaa attgtctaag aaactgcaat 2460
ttcttgctct agaaaatgtt gacgattata tcaatggaga gttatttgaa aatgaagagc 2520
atgcagtcat cgatactgtg acaaaaaatc aaccacataa ggacggcaat ctttatcagg 2580
tagctacaac cagattttca aatgatacgt cgctttacgt catcgcaaac gaatctgatt 2640
tgcttaatga gttgatgtct agtcttcagt attcaggtct tggtggaaag cgttcaagtg 2700
gttttggtcg ttttgagtta gatattcaaa atatcccact agaattgtca gatagactga 2760

-continued ctaagaatca ttcagataaa gtgatgagtc ttacgacagc acttcctgta gatgctgacc 2820
ttgaagaagc aatggaagat ggacattact tattaactaa atcaagtggt tttgcattta 2880
gtcatgccac caatgagaat tatcgtaagc aggatcttta caaatttgct tctggttcaa 2940
cttttagtaa aacatttgaa ggtcagattg ttgatgtgag accacttgat ttccctcatg 3000
ctgttttaaa ttatgctaaa ccactcttct ttaaattgga ggtataaaaa tgaaaaatga 3060
ctatagaaca tttaaattaa gcctcctgac acttgctcca attcatattg gtaatggaga 3120
gaagtatacc tctagagaat ttatctatga aaataaaaag ttttactttc ctgacatggg 3180
gaaattctat aataaaatgg tggagaagag gcttgctgaa aagtttgaag catttctaat 3240
tcaaactcgt ccaaatgcac gtaataatcg tcttatttcc ttcttaaatg ataaccgaat 3300
tgcagagcgt tcttttggag gttatagtat ctctgaaaca ggtttagaat cggacaaaaa 3360
tcctgattca accggagcta ttaacgaagt taataaattt attcgagatg cttttggaaa 3420
tccctacatt cctggtagct cactaaaagg tgctattcgt accattttaa tgaatactac 3480
ccctaagtgg aataatgaaa atgctgtaaa tgactttgga agatttccga aagagaataa 3540
gaaccttatc ccttggggac caaaaaaggg aaaagaatac gatgatttgt ttaacgcaat 3600
tcgtgtgagt gatagtaagc cttttgataa taagagtctt atcttagtgc agaaatggga 3660
ttattcagcg aaaacaaata aagctaaacc acttcccttg tatagagaat caatctctcc 3720
attaacaaaa attgaatttg agattacaac aaccactgat gaagctggaa gattgattga 3780
agaattaggt aagagagcac aagcgtttta taaagactat aaggcatttt tcctatctga 3840
atttcctgat gataagattc aagccaatct acaataccca atttatttag gtgcggggag 3900
cggtgcttgg acaaagactc tatttaagca agctgatggt attttacaaa gacgatacag 3960
tcgaatgaaa actaaaatgg ttaaaaaagg agttcttaag ctcacaaaag cacctcttaa 4020
aacagttaag attccatctg gtaatcattc attagtcaag aaccacgagt ccttttatga 4080
aatgggaaaa gctaatttca tgattaagga gattgataaa tga 4123

<210> SEQ ID NO 467
<211> LENGTH: 624
<212> TYPE: DNA
<213> ORGANISM: Streptococcus thermophilus

<400> SEQUENCE: 467
atgagcgatt tatatagtca aaggtccaat tattacctgt ccttatctga acaaagaatt 60
atcattaaaa atgataataa agagattgtc aaagaagtgt ccatttcact cgttgataat 120
gtattacttt ttggtaatgc acaactgacc acccaactca tcaaagcctt gtcaaagaac 180
aaggtgaatg tttactattt ctcaaatgtt ggtcaattta tttctagtat tgaaacccac 240
aggcaggacg aattccaaaa gcaagagttg caagcaaagg cttattttga agaggatttc 300
cgtttagagg ttgcgaggag tattgctacg accaaggtga ggcacccaat tgccttactt 360
agagagtttg atacggatgg tctactagat acctcagatt attctaggtt tgaagatagt 420
gtcaatgata ttcagaaagc ttattccatt acagaaatta tgggttacga aggtcgcctt 480
gcgaaatcct atttttacta tctgaattta ctcgttccta atgactttca ttttaatggt 540
aggagtagac ggcctgggga ggattgtttt aacagtgccc tcaattttgg ctatagtatc 600
ttatattctt gcttaatggg ctga 624

<210> SEQ ID NO 468
<211> LENGTH: 396

<212> TYPE: DNA
<213> ORGANISM: Streptococcus thermophilus

<400> SEQUENCE: 468
ttgcttaatg ggctgattaa gaaaaacggg ctaagcttgg gatttggggt aattcacaag 60
catcatcagc atcatgcgac cttggccagt gatttaatgg aagaatggag acctatcatc 120
gtcgataata cgcttatgga gttggtacga aatggtaaac ttcttttaag tcattttgaa 180
aataaggatc aagacttcat actcacccat gaaggcagag aaatctttgc acgggcttta 240
cgttcaagaa tattagaagt ccatcagtat attgagttag ataaaaaacg ctattctttt 300
ctttatacag cagataggca aatcaagagt ttgattaggg cttttagaga acttgaccct 360
agtctctatg agacaagtta cacaggaggg cattaa 396

<210> SEQ ID NO 469
<211> LENGTH: 273
<212> TYPE: DNA
<213> ORGANISM: Streptococcus thermophilus

<400> SEQUENCE: 469
atgttttgtc tgattattta tgatattcga agtaacaaac gtagacttaa actctcgaaa 60
ttacttgagg gttatggcgt gagggtgcaa aaatcctgtt tcgaagtcga cctgtcaaga 120
aatgattatc agtctctcct taaggatatc gagggcttct ccaaggctga tgaagaagac 180
agcataatag tgtatgtgcc aaccaaagaa gaggtgacta gttttagccc ctaccatagt 240
gctgaaaaat tagatgacat tctcttcccc taa 273

<210> SEQ ID NO 470
<211> LENGTH: 663
<212> TYPE: DNA
<213> ORGANISM: Streptococcus thermophilus

<400> SEQUENCE: 470
atgacattcg ctaagattaa attttcagct caaattcgtt tagagacagg cctccatatt 60
ggtggaagcg atgcttttgc agccattggt gcaatcgatt cgcctgttat taaagatcct 120
attaccaacc taccgatcat tcctggttca agtctcaaag gaaaaatgag aacgcttctt 180
gccaaggttt ataatgaaaa ggtagctgag aaaccaagcg atgacagtga tattcttagc 240
cgtttatttg ggaatagtaa agataaacga ttcaaaatgg gacgcttgat tttcgtgat 300 gccttcttgt caaacgctga tgagctagac tctcttgggg taagaagtta tacagaagta 360
aaatttgaaa atacaattga ccgtatcact gccgaagcta atccaagaca aattgaacgt 420
gctattcgta ccagtacttt tgatttcgag ttgatttatg aaattacaga tgagaatgaa 480
aatcaagtcg aagaagattc caaagtgatt cgagatggtt taaaactgct tgaacttgat 540
tatcttggtg gttctggatc tcgaggttac ggtaaggttg cttttgaaaa cctcaaagct 600
actaccgtat ttggtaatta tgatgttaaa acattaaatg aacttttaac tgcggaggtc 660
taa 663

<210> SEQ ID NO 471
<211> LENGTH: 900
<212> TYPE: DNA
<213> ORGANISM: Streptococcus thermophilus

<400> SEQUENCE: 471
atgacctata aactgtatat tatgaccttt cagaatgctc attttggttc gggcactctt 60

-continued

```
gatagctcaa aattaacatt ctcagcagac cgtatcttct cagcactagt gctagaatcc    120

ctaaaaatgg gaaaactcga tgcatttctt gcggaagcta accaagacaa gttcacgctc    180

acagatgcct ttccatttca atttggtccc tttttgccga aacctattgg ttatcccaaa    240

catgaccaaa tagatcaatc agttgatgtc aaagaggttc gccgtcaagc aaaattgtct    300

aagaaactgc aatttcttgc tctagaaaat gttgacgatt atatcaatgg agagttattt    360

gaaaatgaag agcatgcagt catcgatact gtgacaaaaa atcaaccaca taaggacggc    420

aatctttatc aggtagctac aaccagattt tcaaatgata cgtcgcttta cgtcatcgca    480

aacgaatctg atttgcttaa tgagttgatg tctagtcttc agtattcagg tcttggtgga    540

aagcgttcaa gtggttttgg tcgttttgag ttagatattc aaaatatccc actagaattg    600

tcagatagac tgactaagaa tcattcagat aaagtgatga gtcttacgac agcacttcct    660

gtagatgctg accttgaaga agcaatggaa gatggacatt acttattaac taaatcaagt    720

ggttttgcat ttagtcatgc caccaatgag aattatcgta agcaggatct ttacaaattt    780

gcttctggtt caacttttag taaaacattt gaaggtcaga ttgttgatgt gagaccactt    840

gatttccctc atgctgtttt aaattatgct aaaccactct tctttaaatt ggaggtataa    900
```

<210> SEQ ID NO 472
<211> LENGTH: 1074
<212> TYPE: DNA
<213> ORGANISM: Streptococcus thermophilus

<400> SEQUENCE: 472

```
atgaaaaatg actatagaac atttaaatta agcctcctga cacttgctcc aattcatatt     60

ggtaatggag agaagtatac ctctagagaa tttatctatg aaaataaaaa gttttacttt    120

cctgacatgg ggaaattcta taataaaatg gtggagaaga ggcttgctga aaagtttgaa    180

gcatttctaa ttcaaactcg tccaaatgca cgtaataatc gtcttatttc cttcttaaat    240

gataaccgaa ttgcagagcg ttcttttgga ggttatagta tctctgaaac aggtttagaa    300

tcggacaaaa atcctgattc aaccggagct attaacgaag ttaataaatt tattcgagat    360

gcttttggaa atccctacat tcctggtagc tcactaaaag gtgctattcg taccatttta    420

atgaatacta cccctaagtg gaataatgaa aatgctgtaa atgactttgg aagatttccg    480

aaagagaata agaaccttat cccttgggga ccaaaaaagg gaaaagaata cgatgatttg    540

tttaacgcaa ttcgtgtgag tgatagtaag ccttttgata ataagagtct tatcttagtg    600

cagaaatggg attattcagc gaaaacaaat aaagctaaac cacttccctt gtatagagaa    660

tcaatctctc cattaacaaa aattgaattt gagattacaa caaccactga tgaagctgga    720

agattgattg aagaattagg taagagagca caagcgtttt ataaagacta taaggcattt    780

ttcctatctg aatttcctga tgataagatt caagccaatc tacaataccc aatttattta    840

ggtgcgggga gcggtgcttg gacaaagact ctatttaagc aagctgatgg tattttacaa    900

agacgataca gtcgaatgaa aactaaaatg gttaaaaaag gagttcttaa gctcacaaaa    960

gcacctctta aaacagttaa gattccatct ggtaatcatt cattagtcaa gaaccacgag   1020

tccttttatg aaatgggaaa agctaatttc atgattaagg agattgataa atga         1074
```

<210> SEQ ID NO 473
<211> LENGTH: 5832
<212> TYPE: DNA
<213> ORGANISM: Streptococcus thermophilus

<400> SEQUENCE: 473

-continued

```
atgagtgact tagttttagg acttgatatc ggtataggtt ctgttggtgt aggtatcctt     60
aacaaagtga caggagaaat tatccataaa aactcacgca tcttcccagc agctcaagca    120
gaaaataacc tagtacgtag aacgaatcgt caaggaagac gcttgacacg acgtaaaaaa    180
catcgtatag ttcgtttaaa tcgtctattt gaggaaagtg gattaatcac cgattttacg    240
aagatttcaa ttaatcttaa cccatatcaa ttacgagtta agggcttgac cgatgaattg    300
tctaatgaag aactgtttat cgctcttaaa aatatggtga aacaccgtgg gattagttac    360
ctcgatgatg ctagtgatga cggaaattca tcagtaggag actatgcaca aattgttaag    420
gaaaatagta aacaattaga aactaagaca ccgggacaga tacagttgga acgctaccaa    480
acatatggtc aattacgtgg tgattttact gttgagaaag atggcaaaaa acatcgcttg    540
attaatgtct ttccaacatc agcttatcgt tcagaagcct taaggatact gcaaactcaa    600
caagaattta attcacagat tacagatgaa tttattaatc gttatctcga aattttaact    660
ggaaaacgga aatattatca tggacccgga aatgaaaagt cacggactga ttatggtcgt    720
tacagaacga atggagaaac tttagacaat atttttggaa ttctaattgg gaaatgtaca    780
ttttatccag acgagtttag agcagcaaaa gcttcctaca cggctcaaga attcaatttg    840
ctaaatgatt tgaacaatct aacagttcct actgaaacca aaaagttgag caaagaacag    900
aagaatcaaa tcattaatta tgtcaaaaat gaaaaggtaa tggggccagc gaaacttttt    960
aaatatatcg ctaaattact ttcttgtgat gttgcagata tcaagggaca ccgtatcgac   1020
aaatcaggta aggctgagat tcatactttc gaagcctatc gaaaaatgaa aacgcttgaa   1080
accttagata ttgagcaaat ggatagagaa acgcttgata aattagccta tgtcttaaca   1140
ttaaacactg agagggaagg tattcaagaa gctttagaac atgaatttgc tgatggtagc   1200
tttagccaga agcaagttga cgaattggtt caattccgca aagcaaatag ttccattttt   1260
ggaaaaggat ggcataattt ttctgtcaaa ctgatgatgg agttaattcc agaattgtat   1320
gagacgtcag aagagcaaat gactatcctg acacgacttg gaaaacaaaa aacaacttcg   1380
tcttcaaata aaacaaaata tatagatgag aaactattaa ctgaagaaat ctataatcct   1440
gttgttgcta agtctgttcg ccaggctata aaaatcgtaa atgcggcgat taaagaatac   1500
ggagactttg acaatattgt catcgaaatg gctcgtgaaa caaatgaaga tgatgaaaag   1560
aaagctattc aaaagattca aaaagccaac aaagatgaaa aagatgcagc aatgcttaag   1620
gctgctaacc aatataatgg aaaggctgaa ttaccacata gtgttttcca cggtcataag   1680
caattagcga ctaaaatccg cctttggcat cagcaaggag aacgttgcct ttatactggt   1740
aagacaatct caatccatga tttgataaat aatcctaatc agtttgaagt agatcatatt   1800
ttacctcttt ctatcacatt cgatgatagc cttgcaaata aggttttggt ttatgcaact   1860
gctaaccaag aaaaaggaca acgaacacct tatcaggctt tagatagtat ggatgatgcg   1920
tggtctttcc gtgaattaaa agcttttgta cgtgagtcaa aaacactttc aaacaagaaa   1980
aaagaatacc tccttacaga agaagatatt tcaaagtttg atgttcgaaa gaaatttatt   2040
gaacgaaatc ttgtagatac aagatacgct tcaagagttg tcctcaatgc ccttcaagaa   2100
cactttagag ctcacaagat tgatacaaaa gtttccgtgg ttcgtggcca atttacatct   2160
caattgagac gccattgggg aattgagaag actcgtgata cttatcatca ccatgctgtc   2220
gatgcattga ttattgccgc ctcaagtcag ttgaatttgt ggaaaaaaca aaagaatacc   2280
cttgtaagtt attcagaaga acaactcctt gatattgaaa caggtgaact tattagtgat   2340
```

-continued

```
gatgagtaca aggaatctgt gttcaaagcc ccttatcaac attttgttga tacattgaag   2400
agtaaagaat ttgaagacag tatcttattc tcatatcaag tggattctaa gtttaatcgt   2460
aaaatatcag atgccactat ttatgcgaca agacaggcta aagtgggaaa agataagaag   2520
gatgaaactt atgtcttagg gaaaatcaaa gatatctata ctcaggatgg ttatgatgcc   2580
tttatgaaga tttataagaa ggataagtca aaattcctca tgtatcgtca cgacccacaa   2640
acctttgaga aagttatcga gccaatttta gagaactatc ctaataagga aatgaatgaa   2700
aaagggaaag aagtaccatg taatcctttc ctaaaatata aagaagaaca tggctatatt   2760
cgtaaatata gtaaaaaagg caatggtcct gaaatcaaga gtcttaaata ctatgatagt   2820
aagcttttag gtaatcctat tgatattact ccagagaata gtaaaaataa agttgtctta   2880
cagtcattaa aaccttggag aacagatgtc tatttcaata aaaatactgg taaatatgaa   2940
attttaggac tgaaatatgc tgatttacaa tttgaaaaga agacaggaac atataagatt   3000
tcccaggaaa aatacaatgg cattatgaaa gaagagggtg tagattctga ttcagaattc   3060
aagtttacac tttataaaaa tgatttgtta ctcgttaaag atacagaaac aaaagaacaa   3120
cagcttttcc gttttctttc tcgaactatg cctaatgtga aatattatgt agagttaaag   3180
ccttattcaa aagataaatt tgagaagaat gagtcactta ttgaaatttt aggttctgca   3240
gataagtcag gacgatgtat aaaagggcta ggaaaatcaa atatttctat ttataaggta   3300
agaacagatg tcctaggaaa tcagcatatc atcaaaaatg agggtgataa gcctaagcta   3360
gatttttaat attaattgtt aaaaaagtgt tgcaattata gttatcatat gctataataa   3420
tcgtgtaagg gacgccttac acagttactt aaatcttgca gaagctacaa agataaggct   3480
tcatgccgaa atcaacaccc tgtcatttta tggcagggtg ttttcgttat ttaaagagga   3540
gaagaaatga cttggagagt tgtacatgtc agtcaaagtg agaagatgcg cttaaagctt   3600
gataacttat tagtgcaaaa gatgggacaa gagtttacgg tgccactaag tgatatttcg   3660
ataatcgttg cagaaggtgg ggatacagtt gttacccttc gtctattaag tgccttaagt   3720
aaatataata ttgccttggt cgtttgtgat aacgaacatt taccaacagg aatttatcac   3780
tcacaaaatg ggcactttag agcgtacaag cgcttgaaag aacagctgga ttggtctcag   3840
aaacaaaagg aaaaggcatg gcagattgta acttattata aaatcaataa ccaagaggat   3900
gtcctagcca tgtttgaaaa aagtctggac aacattagat tactttcaga ctataaagag   3960
cagatagaac ctggtgatag aacgaataga gagggacatg ctgccaaggt ctactttaat   4020
gagctctttg gtaaacaatt tgtcagagta actcagcaag aagctgatgt catcaatgct   4080
ggtttaaact atggctatgc tatcatgagg gctcagatgg ctagaatagt ggcgggttat   4140
ggtttaaatg gcctattagg aatcttccat aaaaatgaat acaatcagtt taatttggtt   4200
gacgatttga tggagccatt tagacagatt gtagatgttt gggtatatga taatctacga   4260
gatcaggaat tccttaagta tgagtatagg ttgggattga cagatttact caatgctaaa   4320
atcaaatatg gcaaagagac ttgctcagtg acagttgcta tggacaaata tgtcaaaggc   4380
tttatcaaat atatttcgga aaaagatagt agtaaatttc actgcccagt ggtatcaagt   4440
ttagagtgga gaaaataaga tgaggtatga agcattgaga ttattatgtt tttttgattt   4500
accaatggaa tccaaggatg aaaaaagaat atatcgtaat tttcgtaaag aattaatttc   4560
aaatgggttt gaaatgttac aattttcggt ctactatcgc acttgtccta atagaagctt   4620
tgcaaataaa ttttataaga agttaaagat gagcaatctt cctgctggga atgtgagact   4680
tttggcagtt actgaaaaac aattttcaga gatgacatta attataggtg gtaaaactaa   4740
```

gcaagaagaa atcgtcagtg ataataagtt ggtgatcata tgaaattttt tgtacaacat 4800
ccttacaaag aacgtattga attaaatatt ggtgcaatca cacaaattgt tggtcagaat 4860
aatgaactca aatattatac ttggcagatt ttgagctggt attttggtgg aaaaaaatac 4920
tcaagtgagg acttaagtat ttttgattat gaggagccta ccatacttga tgaggccaga 4980
gaaatagtga aacgaagtag ctatcactat atcgacattt caagttttaa ggatttactg 5040
gagcagatgg aatacaagaa aggaacactt gctcagggtt accttcgtaa aattgtcaat 5100
caagttgata ttgtaggcca tttggagaaa attaatgaac aagtagagct tattgaagaa 5160
gctatgaatc ggcatataaa cttaaactgt ggacaggtag aataccattt ggagaatctc 5220
cctctaacac tagaccaact actcacaaaa aattttagcc catttttgc cattgagaac 5280 aagaatctat cttttgaatg ggtttctaat attgataaac tatccctctt tttagaaatg 5340
ttagaccatc ttctttcaca aacaacagag aagtatctca ttgtgctaaa aaatattgat 5400
ggctttatct cagaagaatc ttatactatt ttttataggc aaatctgtca tctggtcaag 5460
aagtatccaa atctaacctt tattttgttt cctagtgacc aaggctattt aaaaattgat 5520
gaagaaaata gtaggttcgt caatatttta tctgaccagg tggaacattt gtatgatgtt 5580
gagtttatgt atgaaagggt aatgaaatat tatccaagta atgattttcc gacgagagaa 5640
ggttttagga tgtctttaga aactgtgaca ccttatttat tgacaaaaat gctgagacaa 5700
cctagtctct cacttgttga ttcagtaata ttgaatatcc taaatcagct gtttcatttt 5760
agttaccgta taagatgttc tcagacacct gataaggaac tattacagaa atttttagaa 5820
agtaaggatt ga 5832

<210> SEQ ID NO 474
<211> LENGTH: 3369
<212> TYPE: DNA
<213> ORGANISM: Streptococcus thermophilus

<400> SEQUENCE: 474
atgagtgact tagttttagg acttgatatc ggtataggtt ctgttggtgt aggtatcctt 60
aacaaagtga caggagaaat tatccataaa aactcacgca tcttcccagc agctcaagca 120
gaaaataacc tagtacgtag aacgaatcgt caaggaagac gcttgacacg acgtaaaaaa 180
catcgtatag ttcgtttaaa tcgtctattt gaggaaagtg gattaatcac cgattttacg 240
aagatttcaa ttaatcttaa cccatatcaa ttacgagtta agggcttgac cgatgaattg 300
tctaatgaag aactgtttat cgctcttaaa aatatggtga aacaccgtgg gattagttac 360
ctcgatgatg ctagtgatga cggaaattca tcagtaggag actatgcaca aattgttaag 420
gaaaatagta aacaattaga aactaagaca ccgggacaga tacagttgga acgctaccaa 480
acatatggtc aattacgtgg tgattttact gttgagaaag atggcaaaaa acatcgcttg 540
attaatgtct ttccaacatc agcttatcgt tcagaagcct taaggatact gcaaactcaa 600
caagaattta attcacagat tacagatgaa tttattaatc gttatctcga aattttaact 660
ggaaaacgga aatattatca tggacccgga aatgaaaagt cacggactga ttatggtcgt 720
tacagaacga atggagaaac tttagacaat atttttggaa ttctaattgg gaaatgtaca 780
ttttatccag acgagtttag agcagcaaaa gcttcctaca cggctcaaga attcaatttg 840
ctaaatgatt tgaacaatct aacagttcct actgaaacca aaaagttgag caaagaacag 900
aagaatcaaa tcattaatta tgtcaaaaat gaaaaggtaa tggggccagc gaaacttttt 960
aaatatatcg ctaaattact ttcttgtgat gttgcagata tcaagggaca ccgtatcgac 1020
aaatcaggta aggctgagat tcatactttc gaagcctatc gaaaaatgaa aacgcttgaa 1080
accttagata ttgagcaaat ggatagagaa acgcttgata aattagccta tgtcttaaca 1140
ttaaacactg agagggaagg tattcaagaa gctttagaac atgaatttgc tgatggtagc 1200
tttagccaga agcaagttga cgaattggtt caattccgca aagcaaatag ttccattttt 1260
ggaaaaggat ggcataattt ttctgtcaaa ctgatgatgg agttaattcc agaattgtat 1320
gagacgtcag aagagcaaat gactatcctg acacgacttg gaaaacaaaa aacaacttcg 1380
tcttcaaata aaacaaaata tatagatgag aaactattaa ctgaagaaat ctataatcct 1440
gttgttgcta agtctgttcg ccaggctata aaaatcgtaa atgcggcgat taaagaatac 1500
ggagactttg acaatattgt catcgaaatg gctcgtgaaa caaatgaaga tgatgaaaag 1560
aaagctattc aaaagattca aaaagccaac aaagatgaaa aagatgcagc aatgcttaag 1620
gctgctaacc aatataatgg aaaggctgaa ttaccacata gtgttttcca cggtcataag 1680
caattagcga ctaaaatccg cctttggcat cagcaaggag aacgttgcct ttatactggt 1740
aagacaatct caatccatga tttgataaat aatcctaatc agtttgaagt agatcatatt 1800
ttacctcttt ctatcacatt cgatgatagc cttgcaaata aggttttggt ttatgcaact 1860
gctaaccaag aaaaaggaca acgaacacct tatcaggctt tagatagtat ggatgatgcg 1920
tggtctttcc gtgaattaaa agcttttgta cgtgagtcaa aaacactttc aaacaagaaa 1980
aaagaatacc tccttacaga agaagatatt tcaaagtttg atgttcgaaa gaaatttatt 2040
gaacgaaatc ttgtagatac aagatacgct tcaagagttg tcctcaatgc ccttcaagaa 2100
cactttagag ctcacaagat tgatacaaaa gtttccgtgg ttcgtggcca atttacatct 2160
caattgagac gccattgggg aattgagaag actcgtgata cttatcatca ccatgctgtc 2220
gatgcattga ttattgccgc ctcaagtcag ttgaatttgt ggaaaaaaca aaagaatacc 2280
cttgtaagtt attcagaaga acaactcctt gatattgaaa caggtgaact tattagtgat 2340
gatgagtaca aggaatctgt gttcaaagcc ccttatcaac attttgttga tacattgaag 2400
agtaaagaat ttgaagacag tatcttattc tcatatcaag tggattctaa gtttaatcgt 2460
aaaatatcag atgccactat ttatgcgaca agacaggcta aagtgggaaa agataagaag 2520
gatgaaactt atgtcttagg gaaaatcaaa gatatctata ctcaggatgg ttatgatgcc 2580
tttatgaaga tttataagaa ggataagtca aaattcctca tgtatcgtca cgacccacaa 2640
acctttgaga aagttatcga gccaatttta gagaactatc ctaataagga aatgaatgaa 2700
aaagggaaag aagtaccatg taatcctttc ctaaaatata aagaagaaca tggctatatt 2760
cgtaaatata gtaaaaaagg caatggtcct gaaatcaaga gtcttaaata ctatgatagt 2820
aagcttttag gtaatcctat tgatattact ccagagaata gtaaaaataa agttgtctta 2880
cagtcattaa aaccttggag aacagatgtc tatttcaata aaaatactgg taaatatgaa 2940
attttaggac tgaaatatgc tgatttacaa tttgaaaaga agacaggaac atataagatt 3000
tcccaggaaa aatacaatgg cattatgaaa gaagagggtg tagattctga ttcagaattc 3060
aagtttacac tttataaaaa tgatttgtta ctcgttaaag atacagaaac aaaagaacaa 3120
cagcttttcc gttttctttc tcgaactatg cctaatgtga aatattatgt agagttaaag 3180
ccttattcaa aagataaatt tgagaagaat gagtcactta ttgaaatttt aggttctgca 3240
gataagtcag gacgatgtat aaaagggcta ggaaaatcaa atatttctat ttataaggta 3300
agaacagatg tcctaggaaa tcagcatatc atcaaaaatg agggtgataa gcctaagcta 3360
gatttttaa 3369

<210> SEQ ID NO 475
<211> LENGTH: 912
<212> TYPE: DNA
<213> ORGANISM: Streptococcus thermophilus

<400> SEQUENCE: 475
atgacttgga gagttgtaca tgtcagtcaa agtgagaaga tgcgcttaaa gcttgataac 60
ttattagtgc aaaagatggg acaagagttt acggtgccac taagtgatat ttcgataatc 120
gttgcagaag gtggggatac agttgttacc cttcgtctat taagtgcctt aagtaaatat 180
aatattgcct tggtcgtttg tgataacgaa catttaccaa caggaattta tcactcacaa 240
aatgggcact ttagagcgta caagcgcttg aaagaacagc tggattggtc tcagaaacaa 300
aaggaaaagg catggcagat tgtaacttat tataaaatca ataaccaaga ggatgtccta 360
gccatgtttg aaaaaagtct ggacaacatt agattacttt cagactataa agagcagata 420
gaacctggtg atagaacgaa tagagaggga catgctgcca aggtctactt taatgagctc 480
tttggtaaac aatttgtcag agtaactcag caagaagctg atgtcatcaa tgctggttta 540
aactatggct atgctatcat gagggctcag atggctagaa tagtggcggg ttatggttta 600
aatggcctat taggaatctt ccataaaaat gaatacaatc agtttaattt ggttgacgat 660
ttgatggagc catttagaca gattgtagat gtttgggtat atgataatct acgagatcag 720
gaattcctta agtatgagta taggttggga ttgacagatt tactcaatgc taaaatcaaa 780
tatggcaaag agacttgctc agtgacagtt gctatggaca aatatgtcaa aggctttatc 840
aaatatattt cggaaaaaga tagtagtaaa tttcactgcc cagtggtatc aagtttagag 900
tggagaaaat aa 912

<210> SEQ ID NO 476
<211> LENGTH: 324
<212> TYPE: DNA
<213> ORGANISM: Streptococcus thermophilus

<400> SEQUENCE: 476
atgaggtatg aagcattgag attattatgt ttttttgatt taccaatgga atccaaggat 60
gaaaaaagaa tatatcgtaa ttttcgtaaa gaattaattt caaatgggtt tgaaatgtta 120
caattttcgg tctactatcg cacttgtcct aatagaagct ttgcaaataa attttataag 180
aagttaaaga tgagcaatct tcctgctggg aatgtgagac ttttggcagt tactgaaaaa 240
caattttcag agatgacatt aattataggt ggtaaaacta agcaagaaga aatcgtcagt 300
gataataagt tggtgatcat atga 324

<210> SEQ ID NO 477
<211> LENGTH: 1053
<212> TYPE: DNA
<213> ORGANISM: Streptococcus thermophilus

<400> SEQUENCE: 477
atgaaatttt ttgtacaaca tccttacaaa gaacgtattg aattaaatat tggtgcaatc 60
acacaaattg ttggtcagaa taatgaactc aaatattata cttggcagat tttgagctgg 120
tattttggtg gaaaaaaata ctcaagtgag gacttaagta tttttgatta tgaggagcct 180
accatacttg atgaggccag agaaatagtg aaacgaagta gctatcacta tatcgacatt 240

-continued tcaagtttta aggatttact ggagcagatg gaatacaaga aaggaacact tgctcagggt 300
taccttcgta aaattgtcaa tcaagttgat attgtaggcc atttggagaa aattaatgaa 360
caagtagagc ttattgaaga agctatgaat cggcatataa acttaaactg tggacaggta 420
gaataccatt tggagaatct ccctctaaca ctagaccaac tactcacaaa aaattttagc 480
ccattttttg ccattgagaa caagaatcta tcttttgaat gggtttctaa tattgataaa 540
ctatccctct ttttagaaat gttagaccat cttctttcac aaacaacaga gaagtatctc 600
attgtgctaa aaaatattga tggctttatc tcagaagaat cttatactat tttttatagg 660
caaatctgtc atctggtcaa gaagtatcca aatctaacct ttattttgtt tcctagtgac 720
caaggctatt taaaaattga tgaagaaaat agtaggttcg tcaatatttt atctgaccag 780
gtggaacatt tgtatgatgt tgagtttatg tatgaaaggg taatgaaata ttatccaagt 840
aatgattttc cgacgagaga aggttttagg atgtctttag aaactgtgac accttattta 900
ttgacaaaaa tgctgagaca acctagtctc tcacttgttg attcagtaat attgaatatc 960
ctaaatcagc tgtttcattt tagttaccgt ataagatgtt ctcagacacc tgataaggaa 1020
ctattacaga aatttttaga aagtaaggat tga 1053

<210> SEQ ID NO 478
<211> LENGTH: 7900
<212> TYPE: DNA
<213> ORGANISM: Streptococcus thermophilus

<400> SEQUENCE: 478
atgagcgatt tatatagtca aaggtccaat tattacctgt ccttatctga acaaagaatt 60
atcattaaaa atgataataa agagattgtc aaagaagtgt ccatttcact cgttgataat 120
gtattacttt ttggtaatgc acaactgacc acccaactca tcaaagcctt gtcaaagaac 180
aaggtgaatg tttactattt ctcaaatgtt ggtcaattta tttctagtat tgaaacccac 240
aggcaggacg aattccaaaa gcaagagttg caagcaaagg cttattttga agaggatttc 300
cgtttagagg ttgcgaggag tattgctacg accaaggtga ggcacccaat tgccttactt 360
agagagtttg atacggatgg tctactagat acctcagatt attctaggtt tgaagatagt 420
gtcaatgata ttcagaaagc ttattccatt acagaaatta tgggttacga aggtcgcctt 480
gcgaaatcct atttttacta tctgaattta ctcgttccta atgactttca ttttaatggt 540
aggagtagac ggcctgggga ggattgtttt aacagtgccc tcaattttgg ctatagtatc 600
ttatattctt gcttaatggg ctgattaaga aaaacgggct aagcttggga tttggggtaa 660
ttcacaagca tcatcagcat catgcgacct tggccagtga tttaatggaa gaatggagac 720
ctatcatcgt cgataatacg cttatggagt tggtacgaaa tggtaaactt cttttaagtc 780
attttgaaaa taaggatcaa gacttcatac tcacccatga aggcagagaa atctttgcac 840
gggctttacg ttcaagaata ttagaagtcc atcagtatat tgagttagat aaaaaacgct 900
attcttttct ttatacagca gataggcaaa tcaagagttt gattagggct tttagagaac 960
ttgaccctag tctctatgag acaagttaca caggagggca ttaatgggac tttactttaa 1020
cctcagcgaa gaagagcgtg agtttgccaa acaaaaaacc atgttttgtc tgattattta 1080
tgatattcga agtaacaaac gtagacttaa actctcgaaa ttacttgagg gttatggcgt 1140
gagggtgcaa aaatcctgtt tcgaagtcaa cctgtcaaga aatgattatc agtctctcct 1200
taaggatatc gagggcttct acaaggctga tgaagaagac agcataatag tgtatgtgac 1260
aaccaaagaa gaggtgacta gttttagccc ctaccatagt gctgaaaaat tagatgacat 1320
tctcttcttc taagccttta tagaccttta atcatatggt acactataga tagtgtttcc 1380
agtaggtcct acatcttgtg cctctagcaa ctgcctagag cacaagatat ggggatataa 1440
acctaattac ctcgagaggg gacggaaacg ctttctagct cgctataatt acccattcct 1500
agaaagatat aaacctaatt acctcgagag gggacggaaa ctttgaatag tctttgaatc 1560
gcatttgaac catatagata taaacctaat tacctcgaga ggggacggaa acaggttttt 1620
tgccatagat tttccaagac cttcccaact gatataaacc taattacctc gagaggggac 1680
ggaaacgctt tctagctcgc tataattacc cattcctaga aagatataaa cctaattacc 1740
tcgagagggg actttttga aaattttgaa aacagtattg ataccgcttc cagaaagtgt 1800
tagactaaaa gcacattaag ggcgccccaa tgagttgaaa agtactttca gcttttgggg 1860 tttttcata caaagatgaa ggagtcgaat gaaaaaatta gtatttactt ttaaaaggat 1920
cgaccatcct gcacaagatt tggctgttaa atttcatggc ttcttgatgg agcagttgga 1980
tagtgactat gttgattatc tgcatcagca gcaaacaaat ccctatgcga ccaaggtaat 2040
ccaagggaaa gaaaacacgc agtgggttgt acatctgctc acagacgaca tcgaggataa 2100
ggtttttatg accttattac agattaaaga ggtgtcctta aacgatctgc ctaaactcag 2160
tgtcgaaaaa gttgagattc aggagttggg ggcagataaa ctgttagaga ttttcaatag 2220
tgaggaaaat caaacctatt tttcaattat ttttgagact ccaacaggtt ttaaatctca 2280
aggttcctac gtcatcttcc cgtctatgcg tttgattttt caaagtttga tgcaaaagta 2340
tggaaggttg gttgaaaatc aacctgaaat tgaagaggat accttagatt acctatctga 2400
acacagcact atcacgaatt atcgcttgga gacgagttat ttcagggtgc acaggcaacg 2460
aattcctgcc tttagaggaa agttaacctt taaagtacaa ggcgcccaaa ctctaaaagc 2520
ttatgtcaaa atgcttctaa cattcggtga atattcaggt cttggcatga aaacgagtct 2580
cggtatggga gggataaagc ttgaagaaag aaaagattga tttattttac ggagctcttt 2640
tgcatgatat cggtaaggtc attcaaaggg cgacaggaga acgaaaaaaa cacgccttgg 2700
taggcgcgga ttggtttgat gagattgctg ataatcaagt tatttccgat caaattagat 2760
atcacatggc taactaccag agtgataaac ttggaaatga ccatcttgct tacataactt 2820
atatcgctga taacattgcc tctggtgtcg acagaagaca gtcaaatgag gagagtgacg 2880
aggatacatc agctaagatt tgggatacct atacaaacca ggctgatatt tttaacgttt 2940
ttggggcaca aacggataaa cgctacttta aaccgacggt tctaaacttg aaatctaaac 3000
ctaactttgc gtcggcaaca tatgaacctt tctcaaaagg tgattatgcg gcaattgcga 3060
ctcgtatcaa aaatgaattg gcagaatttg agtttaatca agtacaaatt gactctttgt 3120
taaatctgtt cgaagcaacc ctctcttttg tgccttcttc gactaatact aaagaaatcg 3180
ctgatatttc acttgctgat catagtcgtc tgacagcagc ttttgctcta gccatctatg 3240
attacttgga agacaaaggt cgtcataact ataaggagga cttgtttact aaagcatcag 3300
ccttttatga ggaagaagct tttctcctag ctagctttga cttatcaggg attcaagact 3360
ttatctataa tattaatatt gcgacgaatg gtgctgctaa acaattgaag gctagatctt 3420
tatatcttga ctttatgagc gagtatatag cagacagttt acttgataaa ctaggcctca 3480
atcgggctaa tatgctctat gtcggtgggg gacatgctta ctttgtccta gccaatactg 3540
aaaaaacggt agaaacactc gttcaatttg aaaaagattt caatcaattt ttattggcaa 3600
atttccaaac cagattatat gttgcctttg gttggggaag ctttgcggct aaggatatca 3660

-continued

```
tgagcgaact gaactcacct gaaagctata gacaggtcta tcaaaaggct agtcgcatga   3720
tttctgagaa aaaaatctca aggtatgatt atcaaaccct tatgttgttg aacaggggcg   3780
gtaaatcttc tgaaagagag tgcgagattt gtcattccgt tgagaattta gttgcttatc   3840
atgaccaaaa agtgtgtgac atttgtcgag gcttgtatca attttctaaa gagattgccc   3900
atgaccattt cattatcact gaaaatgaag ggcttcctat tggtccgaac gcatgtctta   3960
agggtgttgc atttgaaaag ctgagccaag aagctttttc ccgtgtctat gtcaaaaatg   4020
actataaggc tggtacagtt aaggcaaccc atgtttttgt tggagattac cagtatgatg   4080
aaatatacaa ttatgctgcc ttatctaaaa acgaaaatgg gttaggtatt aaacgtttag   4140
ctgttgtacg tcttgacgtg gatgatttgg gagcagcctt tatggctggc ttctcccaac   4200
aaggaaatgg gcaatatagt actctatcac gctcagccac tttctctcga agcatgagtc   4260
ttttcttcaa ggtttatatt aaccagtttg ctagtgataa gaagctctct atcatctatg   4320
ccggtgggga tgatgttttt gctattggct cttggcaaga tattattgcc tttactgttg   4380
aacttcgtga gaacttcatt aaatggacaa atggaaaact aacactatca gctggtatcg   4440
gtctgtttgc tgataagacc cctattagct taatggcaca tcaaacaggg gagctagaag   4500
aaacagctaa aggcaatgag aaagatagta tttcactctt tagttccgac tatacctta   4560
aatttgatcg gtttatcact aatgtttacg acgataagtt agagcagatt cgctatttct   4620
ttaatcacca agatgaacga ggcaagaatt tcatttataa attgattgaa ttgcttcgaa   4680
attatgatcg tatgaatatg gcacgtttag cttattattt aacacgactt gaagaattga   4740
cgcgtgaaac agacagggat aaatttaaaa catttaaaaa tttattctat tcttggtaca   4800
caaataagga tgataaggat agaaaagaag cagagttagc cttgcttctc tatatctatg   4860
agattagaaa ggattaggat atgacaatct tgactgatga gaattacgtt gatattgcag   4920
aaaaagcaat tctaaaacta gaaagaaata ctaggaacag aaagaatcct gatgccttct   4980
ttcttacaac aagtaagctc agaaacttgc tgagcttaac tagtacactt tttgatgaga   5040
gtaaggtcaa agaatatgat gctctccttg atcgtattgc ttatttaaga gtacaatttg   5100
tctaccaagc aggtagagag attgcagtaa aagatctgat agaaaaggct caaattcttg   5160
aggctcttaa ggaaatcaaa gatagagaga cacttcaaag attttgtaga tatatggaag   5220
cattagtagc ctatttcaag ttttatggag gtaaagatta atgacattcg ctaagattaa   5280
attttcagct caaattcgtt tagagacagg cctccatatt ggtggaagcg atgcttttgc   5340
agccattggt gcaatcgatt cgcctgttat taaagatcct attaccaacc taccgatcat   5400
tcctggttca agtctcaaag gaaaaatgag aacgcttctt gccaaggttt ataatgaaaa   5460
ggtagctgag aaaccaagcg atgacagtga tattcttagc cgtttatttg ggaatagtaa   5520
agataaacga ttcaaaatgg gacgcttgat ttttcgtgat gccttcttgt caaacgctga   5580
tgagctagac tctcttgggg taagaagtta tacagaagta aaatttgaaa atacaattga   5640
ccgtatcact gccgaagcta atccaagaca aattgaacgt gctattcgta ccagtacttt   5700
tgatttcgag ttgatttatg aaattacaga tgagaatgaa aatcaagtcg aagaagattt   5760
caaagtgatt cgagatggtt taaaactgct tgaacttgat tatcttggtg gttctggatc   5820
tcgaggttac ggtaaggttg cttttgaaaa actcaaagct actaccgtat ttggtaatta   5880
tgatgttaaa acattaaatg aacttttaac tgcggaggtc taatatgacc tataaactgt   5940
atattatgac ctttcagaat gctcattttg gttcgggcac tcttgatagc tcaaaattaa   6000
cattctcagc agaccgtatc ttctcagcac tagtgctaga atccctaaaa atgggaaaac   6060
```

```
tcgatgcatt tcttgcggaa gctaaccaag acaagttcac gctcacagat gcctttccat   6120

ttcaatttgg tccctttttg ccgaaaccga ttggttatcc caaacatgac caaatagatc   6180

aatcagttga tgtcaaagag gttcgccgtc aagcaaaatt gtctaagaaa ctgcaatttc   6240

ttgctctaga aaatgttgac gattatctca atggagagtt atttgaaaat gaagagcatg   6300

cagtcatcga tactgtgaca aaaaatcaac cacataagga cggcaatctt tatcaggtag   6360

ctacaaccag attttcaaat gatacgtcgc tttacgtcat cgcaaacgaa tctgatttgc   6420

ttaatgagtt gatgtctagt cttcagtatt caggtcttgg tggaaagcgt tcaagtggtt   6480

ttggtcgttt tgagttagat attcaaaata tcccactaga attgtcagat agactgacta   6540

agaatcattc agataaagtg atgagtctta cgacagcact tcctgtagat gctgaccttg   6600

aagaagcaat ggaagatgga cattacttat taactaaatc aagtggtttt gcatttagtc   6660

atgctaccaa tgagaattat cgtaagcagg atctttacaa atttgcttct ggttcaactt   6720

ttagtaaaac atttgaaggt cagattgttg atgtgagacc acttgatttc cctcatgctg   6780

ttttaaatta tgctaaacca ctcttcttta aattggaggt ataaaaatga aaaatgacta   6840

tagaacattt aaattaagcc tcctgacact tgctccaatt catattggta atggagagaa   6900

gtatacctct agagaattta tctatgaaaa taagaagttt tactttcctg acatggggaa   6960

attctataat aaaatggtgg agaagaggct tgctgaaaag tttgaagcat ttctaattca   7020

aactcgtcca aatgcacgta ataatcgtct tatttccttc ttaaatgata accgaattgc   7080

agagcgttct tttggaggtt atagtatctc tgaaacaggt ttagaatcgg acaaaaatcc   7140

tgattcagcc ggagctatta acgaagttaa taaatttatt cgagatgctt ttggaaatcc   7200

ctacattcct ggtagctcac taaaaggtgc tattcgtacc attttaatga atactacccc   7260

taagtggaat aatgaaaatg ctgtaaatga ctttggaaga tttccgaaag agaataagaa   7320

ccttatccct tggggaccaa aaaagggaaa agaatacgat gatttgttta acgcaattcg   7380

tgtgagtgat agtaagcctt ttgataataa gagtcttatc ttagtgcaga aatgggatta   7440

ttcagcgaaa acaaataaag ctaaaccact tcccttgtat agagaatcaa tctctccatt   7500

aacaaaaatt gaatttgaga ttacaacaac cactgatgaa gctggaagat tgattgaaga   7560

attaggtaag agagcacaag cgttttataa agactataag gcatttttcc tatctgaatt   7620

tcctgatgat aagattcaag ccaatctaca atacccaatt tatttaggtg cggggagcgg   7680

tgcttggaca aagactctat ttaagcaagc tgatggtatt ttacaaagac gatacagtcg   7740

aatgaaaact aaaatggtta aaaaaggagt tcttaagctc acaaaagcac ctcttaaaac   7800

agttaagatt ccatctggta atcattcatt agtcaagaac cacgagtcct tttatgaaat   7860

gggaaaagct aatttcatga ttaaggagat tgataaatga                         7900
```

<210> SEQ ID NO 479
<211> LENGTH: 624
<212> TYPE: DNA
<213> ORGANISM: Streptococcus thermophilus

<400> SEQUENCE: 479

```
atgagcgatt tatatagtca aaggtccaat tattacctgt ccttatctga acaaagaatt     60

atcattaaaa atgataataa agagattgtc aaagaagtgt ccatttcact cgttgataat    120

gtattacttt ttggtaatgc acaactgacc acccaactca tcaaagcctt gtcaaagaac    180

aaggtgaatg tttactattt ctcaaatgtt ggtcaattta tttctagtat tgaaacccac    240
```

-continued aggcaggacg aattccaaaa gcaagagttg caagcaaagg cttattttga agaggatttc 300
cgtttagagg ttgcgaggag tattgctacg accaaggtga ggcacccaat tgccttactt 360
agagagtttg atacggatgg tctactagat acctcagatt attctaggtt tgaagatagt 420
gtcaatgata ttcagaaagc ttattccatt acagaaatta tgggttacga aggtcgcctt 480
gcgaaatcct atttttacta tctgaattta ctcgttccta atgactttca ttttaatggt 540
aggagtagac ggcctgggga ggattgtttt aacagtgccc tcaattttgg ctatagtatc 600
ttatattctt gcttaatggg ctga 624

<210> SEQ ID NO 480
<211> LENGTH: 396
<212> TYPE: DNA
<213> ORGANISM: Streptococcus thermophilus

<400> SEQUENCE: 480
ttgcttaatg ggctgattaa gaaaaacggg ctaagcttgg gatttggggt aattcacaag 60
catcatcagc atcatgcgac cttggccagt gatttaatgg aagaatggag acctatcatc 120
gtcgataata cgcttatgga gttggtacga aatggtaaac ttcttttaag tcattttgaa 180
aataaggatc aagacttcat actcacccat gaaggcagag aaatctttgc acgggcttta 240
cgttcaagaa tattagaagt ccatcagtat attgagttag ataaaaaacg ctattctttt 300
ctttatacag cagataggca aatcaagagt ttgattaggg cttttagaga acttgaccct 360
agtctctatg agacaagtta cacaggaggg cattaa 396

<210> SEQ ID NO 481
<211> LENGTH: 330
<212> TYPE: DNA
<213> ORGANISM: Streptococcus thermophilus

<400> SEQUENCE: 481
atgggacttt actttaacct cagcgaagaa gagcgtgagt ttgccaaaca aaaaaccatg 60
ttttgtctga ttatttatga tattcgaagt aacaaacgta gacttaaact ctcgaaatta 120
cttgagggtt atggcgtgag ggtgcaaaaa tcctgtttcg aagtcaacct gtcaagaaat 180
gattatcagt ctctccttaa ggatatcgag ggcttctaca aggctgatga agaagacagc 240
ataatagtgt atgtgacaac caaagaagag gtgactagtt ttagccccta ccatagtgct 300
gaaaaattag atgacattct cttcttctaa 330

<210> SEQ ID NO 482
<211> LENGTH: 732
<212> TYPE: DNA
<213> ORGANISM: Streptococcus thermophilus

<400> SEQUENCE: 482
atgaaaaaat tagtatttac ttttaaaagg atcgaccatc ctgcacaaga tttggctgtt 60
aaatttcatg gcttcttgat ggagcagttg gatagtgact atgttgatta tctgcatcag 120
cagcaaacaa atccctatgc gaccaaggta atccaaggga aagaaaacac gcagtgggtt 180
gtacatctgc tcacagacga catcgaggat aaggttttta tgaccttatt acagattaaa 240
gaggtgtcct taaacgatct gcctaaactc agtgtcgaaa aagttgagat tcaggagttg 300
ggggcagata aactgttaga gattttcaat agtgaggaaa atcaaaccta tttttcaatt 360
atttttgaga ctccaacagg ttttaaatct caaggttcct acgtcatctt cccgtctatg 420
cgtttgattt ttcaaagttt gatgcaaaag tatggaaggt tggttgaaaa tcaacctgaa 480
attgaagagg ataccttaga ttacctatct gaacacagca ctatcacgaa ttatcgcttg 540
gagacgagtt atttcagggt gcacaggcaa cgaattcctg cctttagagg aaagttaacc 600
tttaaagtac aaggcgccca aactctaaaa gcttatgtca aaatgcttct aacattcggt 660
gaatattcag gtcttggcat gaaaacgagt ctcggtatgg gagggataaa gcttgaagaa 720
agaaaagatt ga 732

<210> SEQ ID NO 483
<211> LENGTH: 2277
<212> TYPE: DNA
<213> ORGANISM: Streptococcus thermophilus

<400> SEQUENCE: 483
ttgaagaaag aaaagattga tttattttac ggagctcttt tgcatgatat cggtaaggtc 60
attcaaaggg cgacaggaga acgaaaaaaa cacgccttgg taggcgcgga ttggtttgat 120
gagattgctg ataatcaagt tatttccgat caaattagat atcacatggc taactaccag 180
agtgataaac ttggaaatga ccatcttgct tacataactt atatcgctga taacattgcc 240
tctggtgtcg acagaagaca gtcaaatgag gagagtgacg aggatacatc agctaagatt 300
tgggatacct atacaaacca ggctgatatt tttaacgttt ttggggcaca aacggataaa 360
cgctacttta aaccgacggt tctaaacttg aaatctaaac ctaactttgc gtcggcaaca 420
tatgaacctt tctcaaaagg tgattatgcg gcaattgcga ctcgtatcaa aaatgaattg 480
gcagaatttg agtttaatca agtacaaatt gactctttgt taaatctgtt cgaagcaacc 540
ctctcttttg tgccttcttc gactaatact aaagaaatcg ctgatatttc acttgctgat 600
catagtcgtc tgacagcagc ttttgctcta gccatctatg attacttgga agacaaaggt 660
cgtcataact ataaggagga cttgtttact aaagcatcag ccttttatga ggaagaagct 720
tttctcctag ctagctttga cttatcaggg attcaagact ttatctataa tattaatatt 780
gcgacgaatg gtgctgctaa acaattgaag gctagatctt tatatcttga ctttatgagc 840
gagtatatag cagacagttt acttgataaa ctaggcctca atcgggctaa tatgctctat 900
gtcggtgggg gacatgctta ctttgtccta gccaatactg aaaaaacggt agaaacactc 960
gttcaatttg aaaaagattt caatcaattt ttattggcaa atttccaaac cagattatat 1020
gttgcctttg gttggggaag ctttgcggct aaggatatca tgagcgaact gaactcacct 1080
gaaagctata gacaggtcta tcaaaaggct agtcgcatga tttctgagaa aaaaatctca 1140
aggtatgatt atcaaaccct tatgttgttg aacaggggcg gtaaatcttc tgaaagagag 1200
tgcgagattt gtcattccgt tgagaattta gttgcttatc atgaccaaaa agtgtgtgac 1260
atttgtcgag gcttgtatca attttctaaa gagattgccc atgaccattt cattatcact 1320
gaaaatgaag ggcttcctat tggtccgaac gcatgtctta agggtgttgc atttgaaaag 1380
ctgagccaag aagctttttc ccgtgtctat gtcaaaaatg actataaggc tggtacagtt 1440
aaggcaaccc atgtttttgt tggagattac cagtatgatg aaatatacaa ttatgctgcc 1500
ttatctaaaa acgaaaatgg gttaggtatt aaacgtttag ctgttgtacg tcttgacgtg 1560
gatgatttgg gagcagcctt tatggctggc ttctcccaac aaggaaatgg gcaatatagt 1620
actctatcac gctcagccac tttctctcga agcatgagtc ttttcttcaa ggtttatatt 1680
aaccagtttg ctagtgataa gaagctctct atcatctatg ccggtgggga tgatgttttt 1740
gctattggct cttggcaaga tattattgcc tttactgttg aacttcgtga gaacttcatt 1800
aaatggacaa atggaaaact aacactatca gctggtatcg gtctgtttgc tgataagacc 1860
cctattagct taatggcaca tcaaacaggg gagctagaag aaacagctaa aggcaatgag 1920
aaagatagta tttcactctt tagttccgac tataccttta aatttgatcg gtttatcact 1980
aatgtttacg acgataagtt agagcagatt cgctatttct ttaatcacca agatgaacga 2040
ggcaagaatt tcatttataa attgattgaa ttgcttcgaa attatgatcg tatgaatatg 2100
gcacgtttag cttattattt aacacgactt gaagaattga cgcgtgaaac agacagggat 2160
aaatttaaaa catttaaaaa tttattctat tcttggtaca caaataagga tgataaggat 2220
agaaaagaag cagagttagc cttgcttctc tatatctatg agattagaaa ggattag 2277

<210> SEQ ID NO 484
<211> LENGTH: 381
<212> TYPE: DNA
<213> ORGANISM: Streptococcus thermophilus

<400> SEQUENCE: 484
atgacaatct tgactgatga gaattacgtt gatattgcag aaaaagcaat tctaaaacta 60
gaaagaaata ctaggaacag aaagaatcct gatgccttct ttcttacaac aagtaagctc 120
agaaacttgc tgagcttaac tagtacactt tttgatgaga gtaaggtcaa agaatatgat 180
gctctccttg atcgtattgc ttatttaaga gtacaatttg tctaccaagc aggtagagag 240
attgcagtaa aagatctgat agaaaaggct caaattcttg aggctcttaa ggaaatcaaa 300
gatagagaga cacttcaaag attttgtaga tatatggaag cattagtagc ctatttcaag 360
ttttatggag gtaaagatta a 381

<210> SEQ ID NO 485
<211> LENGTH: 663
<212> TYPE: DNA
<213> ORGANISM: Streptococcus thermophilus

<400> SEQUENCE: 485
atgacattcg ctaagattaa attttcagct caaattcgtt tagagacagg cctccatatt 60
ggtggaagcg atgcttttgc agccattggt gcaatcgatt cgcctgttat taaagatcct 120
attaccaacc taccgatcat tcctggttca agtctcaaag gaaaaatgag aacgcttctt 180
gccaaggttt ataatgaaaa ggtagctgag aaaccaagcg atgacagtga tattcttagc 240
cgtttatttg ggaatagtaa agataaacga ttcaaaatgg gacgcttgat tttcgtgat 300 gccttcttgt caaacgctga tgagctagac tctcttgggg taagaagtta tacagaagta 360
aaatttgaaa atacaattga ccgtatcact gccgaagcta atccaagaca aattgaacgt 420
gctattcgta ccagtacttt tgatttcgag ttgatttatg aaattacaga tgagaatgaa 480
aatcaagtcg aagaagattt caaagtgatt cgagatggtt taaaactgct tgaacttgat 540
tatcttggtg gttctggatc tcgaggttac ggtaaggttg cttttgaaaa actcaaagct 600
actaccgtat ttggtaatta tgatgttaaa acattaaatg aacttttaac tgcggaggtc 660
taa 663

<210> SEQ ID NO 486
<211> LENGTH: 900
<212> TYPE: DNA
<213> ORGANISM: Streptococcus thermophilus

<400> SEQUENCE: 486
atgacctata aactgtatat tatgaccttt cagaatgctc attttggttc gggcactctt 60

```
gatagctcaa aattaacatt ctcagcagac cgtatcttct cagcactagt gctagaatcc    120
ctaaaaatgg gaaaactcga tgcatttctt gcggaagcta accaagacaa gttcacgctc    180
acagatgcct ttccatttca atttggtccc tttttgccga aaccgattgg ttatcccaaa    240
catgaccaaa tagatcaatc agttgatgtc aaagaggttc gccgtcaagc aaaattgtct    300
aagaaactgc aatttcttgc tctagaaaat gttgacgatt atctcaatgg agagttattt    360
gaaaatgaag agcatgcagt catcgatact gtgacaaaaa atcaaccaca taaggacggc    420
aatctttatc aggtagctac aaccagattt tcaaatgata cgtcgcttta cgtcatcgca    480
aacgaatctg atttgcttaa tgagttgatg tctagtcttc agtattcagg tcttggtgga    540
aagcgttcaa gtggttttgg tcgttttgag ttagatattc aaaatatccc actagaattg    600
tcagatagac tgactaagaa tcattcagat aaagtgatga gtcttacgac agcacttcct    660
gtagatgctg accttgaaga agcaatggaa gatggacatt acttattaac taaatcaagt    720
ggttttgcat ttagtcatgc taccaatgag aattatcgta agcaggatct ttacaaattt    780
gcttctggtt caacttttag taaaacattt gaaggtcaga ttgttgatgt gagaccactt    840
gatttccctc atgctgtttt aaattatgct aaaccactct tctttaaatt ggaggtataa    900
```

<210> SEQ ID NO 487
<211> LENGTH: 1074
<212> TYPE: DNA
<213> ORGANISM: Streptococcus thermophilus

<400> SEQUENCE: 487

```
atgaaaaatg actatagaac atttaaatta agcctcctga cacttgctcc aattcatatt     60
ggtaatggag agaagtatac ctctagagaa tttatctatg aaaataagaa gttttacttt    120
cctgacatgg ggaaattcta taataaaatg gtggagaaga ggcttgctga aaagtttgaa    180
gcatttctaa ttcaaactcg tccaaatgca cgtaataatc gtcttatttc cttcttaaat    240
gataaccgaa ttgcagagcg ttcttttgga ggttatagta tctctgaaac aggtttagaa    300
tcggacaaaa atcctgattc agccggagct attaacgaag ttaataaatt tattcgagat    360
gcttttggaa atccctacat tcctggtagc tcactaaaag gtgctattcg taccatttta    420
atgaatacta cccctaagtg gaataatgaa aatgctgtaa atgactttgg aagatttccg    480
aaagagaata agaaccttat cccttgggga ccaaaaaagg gaaaagaata cgatgatttg    540
tttaacgcaa ttcgtgtgag tgatagtaag ccttttgata ataagagtct tatcttagtg    600
cagaaatggg attattcagc gaaaacaaat aaagctaaac cacttccctt gtatagagaa    660
tcaatctctc cattaacaaa aattgaattt gagattacaa caaccactga tgaagctgga    720
agattgattg aagaattagg taagagagca caagcgtttt ataaagacta taaggcattt    780
ttcctatctg aatttcctga tgataagatt caagccaatc tacaataccc aatttattta    840
ggtgcgggga gcggtgcttg gacaaagact ctatttaagc aagctgatgg tattttacaa    900
agacgataca gtcgaatgaa aactaaaatg gttaaaaaag gagttcttaa gctcacaaaa    960
gcacctctta aaacagttaa gattccatct ggtaatcatt cattagtcaa gaaccacgag   1020
tccttttatg aaatgggaaa agctaatttc atgattaagg agattgataa atga         1074
```

<210> SEQ ID NO 488
<211> LENGTH: 5974
<212> TYPE: DNA
<213> ORGANISM: Streptococcus agalactiae

<400> SEQUENCE: 488

```
atgaataagc catattcaat aggccttgac atcggtacta attccgtcgg atggagcatt     60
attacagatg attataaagt acctgctaag aagatgagag ttttagggaa cactgataaa    120
gaatatatta agaagaatct cataggtgct ctgctttttg atggcgggaa tactgctgca    180
gatagacgct tgaagcgaac tgctcgtcgt cgttatacac gtcgtagaaa tcgtattcta    240
tatttacaag aaatttttgc agaggaaatg agtaaagttg atgatagttt ctttcatcga    300
ttagaggatt cttttctagt tgaggaagat aagagaggga gcaagtatcc tatctttgca    360
acattgcagg aagagaaaga ttatcatgaa aaattttcga caatctatca tttgagaaaa    420
gaattagctg acaagaaaga aaaagcagac cttcgtctta tttatattgc tctagctcat    480
atcattaaat ttagagggca tttcctaatt gaggatgata gctttgatgt caggaataca    540
gacatttcaa aacaatatca agattttttta gaaatcttta atacaacttt tgaaaataat    600
gatttgttat ctcaaaacgt tgacgtagag gcaatactaa cagataagat tagcaagtct    660
gcgaagaaag atcgtatttt agcgcagtat cctaaccaaa aatctactgg catttttgca    720
gaatttttga aattgattgt cggaaatcaa gctgacttca agaaatattt caatttggag    780
gataaaacgc cgcttcaatt cgctaaggat agctacgatg aagatttaga aaatcttctt    840
ggacagattg gtgatgaatt tgcagactta ttctcagcag cgaaaaagtt atatgatagt    900
gtccttttgt ctggcattct tacagtaatc gacctcagta ccaaggcgcc actttcagct    960
tctatgattc agcgttatga tgaacataga gaggacttga aacagttaaa acaattcgta   1020
aaagcttcat tgccggaaaa atatcaagaa atatttgctg attcatcaaa agatggctac   1080
gctggttata ttgaaggtaa aactaatcaa gaagcttttt ataaatacct gtcaaaattg   1140
ttgaccaagc aagaagatag cgagaatttt cttgaaaaaa tcaagaatga agatttcttg   1200
agaaaacaaa ggacctttga taatggctca attccacacc aagtccattt gacagagctg   1260
aaagctatta tccgccgtca atcagaatac tatcccttct tgaaagagaa tcaagatagg   1320
attgaaaaaa tccttacctt tagaattcct tattatatcg ggccactagc acgtgagaag   1380
agtgattttg catggatgac tcgcaaaaca gatgacagta ttcgaccttg gaattttgaa   1440
gacttggttg ataaagaaaa atctgcggaa gcttttatcc atcgtatgac caacaatgat   1500
ttttatcttc ctgaagaaaa agttttacca aagcatagtc ttatttatga aaaatttacg   1560
gtctataatg agttgactaa ggttagatat aaaaatgagc aaggtgagac ttattttttt   1620
gatagcaata ttaaacaaga aatctttgat ggagtattca aggaacatcg taaggtatcc   1680
aagaagaagt tgctagattt tctggctaaa gaatatgagg agtttaggat agtagatgtt   1740
attggtctag ataaagaaaa taaagctttc aacgcctcat tgggaactta ccacgatctc   1800
gaaaaaatac tagacaaaga ttttctagat aatccagata atgagtctat tctggaagat   1860
atcgtccaaa ctctaacatt atttgaagac agagaaatga ttaagaagcg tcttgaaaac   1920
tataaagatc tttttacaga gtcacaacta aaaaaactct atcgtcgtca ctatactggc   1980
tggggacgat tgtctgctaa gttaatcaat ggtattcgag ataaagagag tcaaaaaaca   2040
atcttggact atcttattga tgatggtaga tctaatcgca actttatgca gttgataaat   2100
gatgatggtc tatctttcaa atcaattatc agtaaggcac aggctggtag tcattcagat   2160
aatctaaaag aagttgtagg tgagcttgca ggtagccctg ctattaaaaa gggaattcta   2220
caaagtttga aaattgttga tgagcttgtt aaagtcatgg gatacgaacc tgaacaaatt   2280
gtggttgaga tggcgcgtga gaatcaaaca acaaatcaag gtcgtcgtaa ctctcgacaa   2340
```

-continued

```
cgctataaac ttcttgatga tggcgttaag aatctagcta gtgacttgaa tggcaatatt   2400
ttgaaagaat atcctacgga taatcaagcg ttgcaaaatg aaagactttt cctttactac   2460
ttacaaaacg gaagagatat gtatacaggg gaagctctag atattgacaa tttaagtcaa   2520
tatgatattg accacattat tcctcaagct ttcataaaag atgattctat tgataatcgt   2580
gttttggtat catctgctaa aaatcgtgga aagtcagatg atgttcctag ccttgaaatt   2640
gtaaaagatt gtaaagtttt ctggaaaaaa ttacttgatg ctaagttaat gagtcagcgt   2700
aagtatgata atttgactaa ggcagagcgc ggaggcctaa cttccgatga taaggcaaga   2760
tttatccaac gtcagttggt tgagacacga caaattacca agcatgttgc ccgtatcttg   2820
gatgaacgct ttaataatga gcttgatagt aaaggtagaa ggatccgcaa agttaaaatt   2880
gtaaccttga agtcaaattt ggtttcaaat ttccgaaaag aatttggatt ctataaaatt   2940
cgtgaagtta acaattatca ccatgcacat gatgcctatc ttaatgcagt agttgctaaa   3000
gctattctaa ccaaatatcc tcagttagag ccagaatttg tctacggcga ctatccaaaa   3060
tataatagtt acaaaacgcg taaatccgct acagaaaagc tatttttcta ttcaaatatt   3120
atgaacttct ttaaaactaa ggtaacttta gcggatggaa ccgttgttgt aaaagatgat   3180
attgaagtta ataatgatac gggtgaaatt gtttgggata aaaagaaaca ctttgcgaca   3240
gttagaaaag tcttgtcata ccctcagaac aatatcgtga agaagacaga gattcagaca   3300
ggtggtttct ctaaggaatc aatcttggcg catggtaact cagataagtt gattccaaga   3360
aaaacgaagg atatttattt agatcctaag aaatatggag gttttgatag tccgatagta   3420
gcttactctg ttttagttgt agctgatatc aaaaagggta aagcacaaaa actaaaaaca   3480
gttacggaac ttttaggaat taccatcatg gagaggtcca gatttgagaa aaatccatca   3540
gctttccttg aatcaaaagg ctatttaaat attagggctg ataaactaat tattttgccc   3600
aagtatagtc tgttcgaatt agaaaatggg cgtcgtcgat tacttgctag tgctggtgaa   3660
ttacaaaaag gtaatgagct agccttacca acacaattta tgaagttctt ataccttgca   3720
agtcgttata atgagtcaaa aggtaaacca gaggagattg agaagaaaca agaatttgta   3780
aatcaacatg tctcttattt tgatgacatc cttcaattaa ttaatgattt ttcaaaacga   3840
gttattctag cagatgctaa tttagagaaa atcaataagc tttaccaaga taataaggaa   3900
aatatatcag tagatgaact tgctaataat attatcaatc tatttacttt taccagtcta   3960
ggagctccag cagcttttaa attttttgat aaaatagttg atagaaaacg ctatacatca   4020
actaaagaag tacttaattc taccctaatt catcaatcta ttactggact ttatgaaaca   4080
cgtattgatt tgggtaagtt aggagaagat tgatatggca ggttggcgaa ccgttgttgt   4140
aaatacacat tctaagctct cttataaaaa taatcatctg atttttaaag attcttatca   4200
gacggaaatg attcatctat cagagattga cattctaatc atggaaacaa cagatatcgt   4260
tttgtcgacc atgctgatta aacgtttggt tgatgaaaat attttagtta tattttgtga   4320
cgataaacgc ttgccaacag ctatgttaat gccgtactat gccagacatg attcgagttt   4380
acaattatct aggcagatgt catggattga agatgtcaaa gcagatgttt ggacatcaat   4440
tattgcacaa aaaattttga atcagtcttt ttatctcggt gagtgttctt tctttgaaaa   4500
atcccagtct attatgaatc tctaccatga cttagaacct tttgatcctt ctaatcgtga   4560
ggggcatgct gctaggattt atttcaatac actttttgga aatgattttt caagagagca   4620
ggataatcca ataaatgctg gtttagacta cggatattca ttgcttttga gtatgtttgc   4680
```

gcgtgaagtt gttaagtgtg gttgcatgac acaatttggc ttgaagcatg ctaatcaatt 4740
taatcagttc aacctagcaa gcgatattat ggaaccattt cgcccaatcg ttgataggat 4800
tatttatgaa aataggcaga gtgattttgt caaaatgaaa agagaactct tttctatgtt 4860
ttcagagaca tacagctaca atggtaaaga aatgtatctc tcaaatattg tcagcgacta 4920
taccaaaaaa gttattaagt cgctaaatag tgatgggaat ggaattccgg agtttaggat 4980
atgagttatc ggtatatgcg aatgatttta atgtttgata tgcctactga aacagcagaa 5040
gaacggaagg cgtatcgtaa gtttagaaag tttctcttga gcgaaggctt tatcatgcat 5100
cagttttctg tttatagtaa attattactc aataatacag ctaataatgc tatgataggt 5160
cggcttaaag tgaataatcc taaaaagggt aatatcacac tcttaacagt tacggaaaaa 5220
caatttgcga gaatggttta cctccatgga gaacgcaaca caagtgttgc caactctgat 5280
agtcgcttgg ttttcctagg agattcttat gatcaagatt aattttccaa ttttagatga 5340
accattagtg ttaagtaatg ctacgatttt aacgatagaa gatgtttcag tttattcttc 5400
attggtgaaa catttttatc aatatgacgt agatgaacat ttgaaattat ttgatgataa 5460
gcagaaaagt ctgaaggcaa cagagttaat gctggttaca gatatcttag gatacgatgt 5520
caactcagca cctattctaa agttgataca tggtgactta gaaaatcaat tcaacgaaaa 5580
gccagaagtg aaatcaatgg tagaaaaatt agcagctact attacagaac ttatcgcatt 5640
tgagtgtcta gagaatgagc ttgatttaga atacgatgaa attaagattt tagaactcat 5700
taaggcactg ggagtcaaaa ttgagacaca gagcgacact atctttgaaa aatgttttga 5760
aattatacaa gtttaccatt atttaacgaa aaagaatctc ttggtttttg ttaatagcgg 5820
agcttatctt accaaagatg aagttataaa attatgtgaa tacatcaatt taatgcaaaa 5880
gtcagtactc tttctagaac ctagaagact ctatgattta ccgcaatatg ttattgataa 5940
ggattatttc ttgataggcg aaaatatggt ataa 5974

<210> SEQ ID NO 489
<211> LENGTH: 4113
<212> TYPE: DNA
<213> ORGANISM: Streptococcus agalactiae

<400> SEQUENCE: 489
atgaataagc catattcaat aggccttgac atcggtacta attccgtcgg atggagcatt 60
attacagatg attataaagt acctgctaag aagatgagag ttttagggaa cactgataaa 120
gaatatatta agaagaatct cataggtgct ctgctttttg atggcgggaa tactgctgca 180
gatagacgct tgaagcgaac tgctcgtcgt cgttatacac gtcgtagaaa tcgtattcta 240
tatttacaag aaatttttgc agaggaaatg agtaaagttg atgatagttt ctttcatcga 300
ttagaggatt cttttctagt tgaggaagat aagagaggga gcaagtatcc tatctttgca 360
acattgcagg aagagaaaga ttatcatgaa aaattttcga caatctatca tttgagaaaa 420
gaattagctg acaagaaaga aaaagcagac cttcgtctta tttatattgc tctagctcat 480
atcattaaat ttagagggca tttcctaatt gaggatgata gctttgatgt caggaataca 540
gacatttcaa aacaatatca agatttttta gaaatcttta atacaacttt tgaaaataat 600
gatttgttat ctcaaaacgt tgacgtagag gcaatactaa cagataagat tagcaagtct 660
gcgaagaaag atcgtatttt agcgcagtat cctaaccaaa aatctactgg catttttgca 720
gaatttttga aattgattgt cggaaatcaa gctgacttca agaaatattt caatttggag 780
gataaaacgc cgcttcaatt cgctaaggat agctacgatg aagatttaga aaatcttctt 840

-continued ggacagattg gtgatgaatt tgcagactta ttctcagcag cgaaaaagtt atatgatagt 900
gtccttttgt ctggcattct tacagtaatc gacctcagta ccaaggcgcc actttcagct 960
tctatgattc agcgttatga tgaacataga gaggacttga aacagttaaa acaattcgta 1020
aaagcttcat tgccggaaaa atatcaagaa atatttgctg attcatcaaa agatggctac 1080
gctggttata ttgaaggtaa aactaatcaa gaagcttttt ataaatacct gtcaaaattg 1140
ttgaccaagc aagaagatag cgagaatttt cttgaaaaaa tcaagaatga agatttcttg 1200
agaaaacaaa ggacctttga taatggctca attccacacc aagtccattt gacagagctg 1260
aaagctatta tccgccgtca atcagaatac tatcccttct tgaaagagaa tcaagatagg 1320
attgaaaaaa tccttacctt tagaattcct tattatatcg ggccactagc acgtgagaag 1380
agtgattttg catggatgac tcgcaaaaca gatgacagta ttcgaccttg gaattttgaa 1440
gacttggttg ataaagaaaa atctgcggaa gcttttatcc atcgtatgac caacaatgat 1500
ttttatcttc ctgaagaaaa agttttacca aagcatagtc ttatttatga aaaatttacg 1560
gtctataatg agttgactaa ggttagatat aaaaatgagc aaggtgagac ttattttttt 1620
gatagcaata ttaaacaaga aatctttgat ggagtattca aggaacatcg taaggtatcc 1680
aagaagaagt tgctagattt tctggctaaa gaatatgagg agtttaggat agtagatgtt 1740
attggtctag ataaagaaaa taaagctttc aacgcctcat tgggaactta ccacgatctc 1800
gaaaaaatac tagacaaaga ttttctagat aatccagata atgagtctat tctggaagat 1860
atcgtccaaa ctctaacatt atttgaagac agagaaatga ttaagaagcg tcttgaaaac 1920
tataaagatc tttttacaga gtcacaacta aaaaaactct atcgtcgtca ctatactggc 1980
tggggacgat tgtctgctaa gttaatcaat ggtattcgag ataaagagag tcaaaaaaca 2040
atcttggact atcttattga tgatggtaga tctaatcgca actttatgca gttgataaat 2100
gatgatggtc tatctttcaa atcaattatc agtaaggcac aggctggtag tcattcagat 2160
aatctaaaag aagttgtagg tgagcttgca ggtagccctg ctattaaaaa gggaattcta 2220
caaagtttga aaattgttga tgagcttgtt aaagtcatgg gatacgaacc tgaacaaatt 2280
gtggttgaga tggcgcgtga gaatcaaaca acaaatcaag gtcgtcgtaa ctctcgacaa 2340
cgctataaac ttcttgatga tggcgttaag aatctagcta gtgacttgaa tggcaatatt 2400
ttgaaagaat atcctacgga taatcaagcg ttgcaaaatg aaagactttt cctttactac 2460
ttacaaaacg gaagagatat gtatacaggg gaagctctag atattgacaa tttaagtcaa 2520
tatgatattg accacattat tcctcaagct ttcataaaag atgattctat tgataatcgt 2580
gttttggtat catctgctaa aaatcgtgga aagtcagatg atgttcctag ccttgaaatt 2640
gtaaaagatt gtaaagtttt ctggaaaaaa ttacttgatg ctaagttaat gagtcagcgt 2700
aagtatgata atttgactaa ggcagagcgc ggaggcctaa cttccgatga taaggcaaga 2760
tttatccaac gtcagttggt tgagacacga caaattacca agcatgttgc ccgtatcttg 2820
gatgaacgct ttaataatga gcttgatagt aaaggtagaa ggatccgcaa agttaaaatt 2880
gtaaccttga agtcaaattt ggtttcaaat ttccgaaaag aatttggatt ctataaaatt 2940
cgtgaagtta acaattatca ccatgcacat gatgcctatc ttaatgcagt agttgctaaa 3000
gctattctaa ccaaatatcc tcagttagag ccagaatttg tctacggcga ctatccaaaa 3060
tataatagtt acaaaacgcg taaatccgct acagaaaagc tatttttcta ttcaaatatt 3120
atgaacttct ttaaaactaa ggtaacttta gcggatggaa ccgttgttgt aaaagatgat 3180
attgaagtta ataatgatac gggtgaaatt gtttgggata aaaagaaaca ctttgcgaca 3240
gttagaaaag tcttgtcata ccctcagaac aatatcgtga agaagacaga gattcagaca 3300
ggtggtttct ctaaggaatc aatcttggcg catggtaact cagataagtt gattccaaga 3360
aaaacgaagg atatttattt agatcctaag aaatatggag gttttgatag tccgatagta 3420
gcttactctg ttttagttgt agctgatatc aaaaagggta aagcacaaaa actaaaaaca 3480
gttacggaac ttttaggaat taccatcatg gagaggtcca gatttgagaa aaatccatca 3540
gctttccttg aatcaaaagg ctatttaaat attagggctg ataaactaat tattttgccc 3600
aagtatagtc tgttcgaatt agaaaatggg cgtcgtcgat tacttgctag tgctggtgaa 3660
ttacaaaaag gtaatgagct agccttacca acacaattta tgaagttctt ataccttgca 3720
agtcgttata atgagtcaaa aggtaaacca gaggagattg agaagaaaca agaatttgta 3780
aatcaacatg tctcttattt tgatgacatc cttcaattaa ttaatgattt ttcaaaacga 3840
gttattctag cagatgctaa tttagagaaa atcaataagc tttaccaaga taataaggaa 3900
aatatatcag tagatgaact tgctaataat attatcaatc tatttacttt taccagtcta 3960
ggagctccag cagcttttaa attttttgat aaaatagttg atagaaaacg ctatacatca 4020
actaaagaag tacttaattc taccctaatt catcaatcta ttactggact ttatgaaaca 4080
cgtattgatt tgggtaagtt aggagaagat tga 4113

<210> SEQ ID NO 490
<211> LENGTH: 870
<212> TYPE: DNA
<213> ORGANISM: Streptococcus agalactiae

<400> SEQUENCE: 490
atggcaggtt ggcgaaccgt tgttgtaaat acacattcta agctctctta taaaaataat 60
catctgattt ttaaagattc ttatcagacg gaaatgattc atctatcaga gattgacatt 120
ctaatcatgg aaacaacaga tatcgttttg tcgaccatgc tgattaaacg tttggttgat 180
gaaaatattt tagttatatt ttgtgacgat aaacgcttgc caacagctat gttaatgccg 240
tactatgcca gacatgattc gagtttacaa ttatctaggc agatgtcatg gattgaagat 300
gtcaaagcag atgtttggac atcaattatt gcacaaaaaa ttttgaatca gtctttttat 360
ctcggtgagt gttctttctt tgaaaaatcc cagtctatta tgaatctcta ccatgactta 420
gaaccttttg atccttctaa tcgtgagggg catgctgcta ggatttattt caatacactt 480
tttggaaatg atttttcaag agagcaggat aatccaataa atgctggttt agactacgga 540
tattcattgc ttttgagtat gtttgcgcgt gaagttgtta agtgtggttg catgacacaa 600
tttggcttga agcatgctaa tcaatttaat cagttcaacc tagcaagcga tattatggaa 660
ccatttcgcc caatcgttga taggattatt tatgaaaata ggcagagtga ttttgtcaaa 720
atgaaaagag aactcttttc tatgttttca gagacataca gctacaatgg taaagaaatg 780
tatctctcaa atattgtcag cgactatacc aaaaaagtta ttaagtcgct aaatagtgat 840
gggaatggaa ttccggagtt taggatatga 870

<210> SEQ ID NO 491
<211> LENGTH: 327
<212> TYPE: DNA
<213> ORGANISM: Streptococcus agalactiae

<400> SEQUENCE: 491
atgcgaatga ttttaatgtt tgatatgcct actgaaacag cagaagaacg gaaggcgtat 60

-continued cgtaagttta gaaagtttct cttgagcgaa ggctttatca tgcatcagtt ttctgtttat 120
agtaaattat tactcaataa tacagctaat aatgctatga taggtcggct taaagtgaat 180
aatcctaaaa agggtaatat cacactctta acagttacgg aaaaacaatt tgcgagaatg 240
gtttacctcc atggagaacg caacacaagt gttgccaact ctgatagtcg cttggttttc 300
ctaggagatt cttatgatca agattaa 327

<210> SEQ ID NO 492
<211> LENGTH: 666
<212> TYPE: DNA
<213> ORGANISM: Streptococcus agalactiae

<400> SEQUENCE: 492
atgatcaaga ttaattttcc aattttagat gaaccattag tgttaagtaa tgctacgatt 60
ttaacgatag aagatgtttc agtttattct tcattggtga aacattttta tcaatatgac 120
gtagatgaac atttgaaatt atttgatgat aagcagaaaa gtctgaaggc aacagagtta 180
atgctggtta cagatatctt aggatacgat gtcaactcag cacctattct aaagttgata 240
catggtgact tagaaaatca attcaacgaa aagccagaag tgaaatcaat ggtagaaaaa 300
ttagcagcta ctattacaga acttatcgca tttgagtgtc tagagaatga gcttgattta 360
gaatacgatg aaattaagat tttagaactc attaaggcac tgggagtcaa aattgagaca 420
cagagcgaca ctatctttga aaaatgtttt gaaattatac aagtttacca ttatttaacg 480
aaaaagaatc tcttggtttt tgttaatagc ggagcttatc ttaccaaaga tgaagttata 540
aaattatgtg aatacatcaa tttaatgcaa aagtcagtac tctttctaga acctagaaga 600
ctctatgatt taccgcaata tgttattgat aaggattatt tcttgatagg cgaaaatatg 660
gtataa 666

<210> SEQ ID NO 493
<211> LENGTH: 5995
<212> TYPE: DNA
<213> ORGANISM: Streptococcus agalactiae

<400> SEQUENCE: 493
atgaataagc catattcaat aggccttgac atcggtacta attccgtcgg atggagcatt 60
attacagatg attataaagt acctgctaag aagatgagag ttttagggaa cactgataaa 120
gaatatatta agaagaatct catagggtgct ctgcttttttg atggcgggaa tactgctgca 180
gatagacgct tgaagcgaac tgctcgtcgt cgttatacac gtcgtagaaa tcgtattcta 240
tatttacaag aaatttttgc agaggaaatg agtaaagttg atgatagttt ctttcatcga 300
ttagaggatt cttttctagt tgaggaagat aagagaggta gcaagtatcc tatctttgca 360
acaatgcagg aggagaaata ttatcatgaa aaatttccga caatctatca tttgagaaaa 420
gaattggctg acaagaaaga aaaagcagac cttcgtcttg tttatctggc tctagctcat 480
atcattaaat tcagagggca tttcctaatt gaggatgata gatttgatgt gaggaatacc 540
gatattcaaa aacaatatca agcctttttta gaaatttttg atactacctt tgaaaataat 600
catttgttat ctcaaaatgt agatgtagaa gcaattctaa cagataagat tagcaagtct 660
gcgaagaagg atcgcatctt agcgcagtat cctaaccaaa aatctactgg tatttttgca 720
gaatttttga aattgattgt cggaaatcaa gctgacttca agaaacattt caatttggag 780
gataaaacac cgcttcaatt cgctaaggat agctacgatg aagatttaga aaatcttctt 840

-continued

```
ggacagattg gtgatgaatt tgcagactta ttctcagtag cgaaaaagct atatgatagt    900
gttcttttat ctggcattct tacagtaact gatctcagta ccaaggcgcc actttctgcc    960
tctatgattc agcgttatga tgaacatcat gaggacttaa agcatctaaa acaattcgta   1020
aaagcttcat tacctgaaaa ttatcgggaa gtatttgctg attcatcaaa agatggctac   1080
gctggctata ttgaaggcaa aactaatcaa gaagcttttt ataaatatct gttaaaattg   1140
ttgaccaaac aagaaggtag cgagtatttt cttgagaaaa ttaagaatga agatttttg    1200
agaaaacaga gaacctttga taatggctca atcccgcatc aagtccattt gacagaattg   1260
agggctatta ttcgacgtca atcagaatac tatccattct tgaaagagaa tcaagatagg   1320
attgaaaaaa tccttacctt tagaattcct tattatgtcg ggccactagc acgtgagaag   1380
agtgattttg catggatgac tcgcaaaaca gatgacagta ttcgaccttg gaattttgaa   1440
gacttggttg ataaagaaaa atctgcggaa gcttttatcc atcgcatgac caacaatgac   1500
ctctatcttc cagaagaaaa agttttacca aagcatagtc ttatttatga aaaatttact   1560
gtttacaatg aattaacgaa ggttagattt ttggcagaag gctttaaaga ttttcaattt   1620
ttaaatagga agcaaaaaga aactatcttt aacagcttgt ttaaggaaaa acgtaaagta   1680
actgaaaagg atattattag tttttgaat aaagttgatg gatatgaagg aattgcaatc    1740
aaaggaattg agaaacagtt taacgctagc ctttcaacct atcatgatct taaaaaaata   1800
cttggcaagg atttccttga taatacagat aacgagctta ttttggaaga tatcgtccaa   1860
actctaacct tatttgaaga tagagaaatg attaagaagt gtcttgacat ctataaagat   1920
tttttacag agtcacagct taaaaagctc tatcgccgtc actatactgg ctggggacga    1980
ttgtctgcta agctaataaa tggcatccga aataaagaga atcaaaaaac aatcttggac   2040
tatcttattg atgatggaag tgcaaaccga aacttcatgc agttgataaa tgatgatgat   2100
ctatcattta aaccaattat tgacaaggca cgaactggta gtcattcgga taatctgaaa   2160
gaagttgtag gtgaacttgc tggtagccct gctattaaaa aagggattct acaaagtttg   2220
aaaatagttg atgagctggt taaagtcatg ggctatgaac ctgaacaaat cgtggttgaa   2280
atggcacgtg agaaccaaac gacagcaaaa ggattaagtc gttcacgaca acgcttgaca   2340
accttgagag aatctcttgc taatttgaag agtaatattt tggaagagaa aaagcctaag   2400
tatgtgaaag atcaagttga aaatcatcat ttatctgatg accgtctttt cctttactac   2460
ttacaaaacg gaagagatat gtatacaaaa aaggctctgg atattgataa tttaagtcaa   2520
tatgatattg accacattat tcctcaagct ttcataaaag atgattctat tgataatcgt   2580
gttttggtat catctgctaa aaatcgtgga aaatcagatg atgttcctag cattgaaatt   2640
gtaaaagctc gcaaaatgtt ctggaaaaat ttactggatg ctaagttaat gagtcagcgt   2700
aagtatgata atttgactaa ggcagagcgc ggaggcctaa cttccgatga taaggcaaga   2760
tttatccaac gtcagttggt tgagactcga caaattacca agcatgtagc tcgtatcttg   2820
gatgaacgct tcaataatga agttgataat ggtaaaaaga tttgcaaggt taaaattgta   2880
accttgaagt caaatttggt ttcaaatttc cgaaaagaat ttggattcta taaaattcgt   2940
gaagttaatg attatcacca tgcacacgat gcttatctta atgcagtagt tgccaaagct   3000
attctaacca aatatccaca gttagagcca gagtttgtct acggaatgta tagacagaaa   3060
aaactttcga aaatcgttca tgaggataag gaagaaaaat atagtgaagc aaccaggaaa   3120
atgtttttct actccaactt gatgaatatg ttcaaaagag ttgtgaggtt agcagatggt   3180
tctattgttg taagaccagt aatagaaact ggtagatata tgagaaaaac tgcatgggat   3240
```

-continued aaaaagaaac actttgcgac agttagaaaa gtcttgtcat accctcagaa caatatcgtg 3300
aagaagacag agattcagac aggtggtttc tctaaggaat caatcttggc gcatggtaac 3360
tcagataagt tgattccaag aaaaacgaag gatatttatt tagatcctaa gaaatatgga 3420
ggttttgata gtccgatagt agcttactct gttttagttg tagctgatat caaaaaaggt 3480
aaagcacaaa aactaaaaac agttacggaa cttttaggaa ttaccatcat ggagaggtcc 3540
agatttgaga aaaatccatc agctttcctt gaatcaaaag gttatttaaa tattagggac 3600
gataaattaa tgattttacc gaagtatagt ctgttcgaat tagaaaatgg gcgtcgtcga 3660
ttacttgcta gtgctggtga attacaaaaa ggtaacgagc tagccttacc aacacaattt 3720
atgaagttct tataccttgc aagtcgttat aatgagtcaa aaggtaaacc agaggagatt 3780
gagaagaaac aagaatttgt aaatcaacat gtctcttatt ttgatgacat ccttcaatta 3840
attaatgatt tttcaaaacg agttattcta gcagatgcta atttagagaa aatcaataag 3900
ctttaccagg ataataagga aaatatacca gtagatgaac ttgctaataa tattatcaat 3960
ctatttactt ttaccagtct aggagctcca gcagctttta aatttttgga taaaatagtt 4020
gatagaaaac gctatacatc aactaaagaa gtacttaatt ctactctaat ccatcaatct 4080
attactggac tttatgaaac acgtattgat ttgggtaaat taggagaaga ttgatatggc 4140
aggttggcga actgttgttg taaatacaca ttctaagctc tcttataaaa ataatcatct 4200
gatttttaaa gattcttatc agacggaaat gattcatctt tcagagattg atattctaat 4260
catggaaacg acagatattg ttttgtcgac tatgctgatt aaacgtttgg ttgatgaaaa 4320
tattttagtc atattttgtg atgataaacg cttgccaaca gctatgttaa tgccgtacta 4380
tgctagacat gattcgagtt tacaattatc taggcagatg tcatggattg aggatgtcaa 4440
agcggatgtt tggacatcaa ttattgcaca aaaaattttg aatcagtcct tttatctcgg 4500
tgagtgttct ttctttgaaa aatcccagtc tattatgaat ctctatcatg atttagaatc 4560
ttttgaccct tccaatcgtg aaggtcatgc agctaggatt tatttcaata cactttttgg 4620
aaatgatttt tcaagagagc aggataatcc aataaatgct ggtttagact atggatattc 4680
tctgattttg agtatgtttg cgcgtgaagt tgttaagtgt ggttgcatga cacaatttgg 4740
cttaaagcat gctaatcaat ttaatcagtt caacctagca agcgatatta tggaaccatt 4800
tcgcccaatc gttgatagga ttatttatga aaataggcag agtgattttg tcaaaatgaa 4860
aagagaactc ttttctatgt tttcagagac atacagctac aacggtaaag aaatgtatct 4920
ttcaaatatt gtcagcgatt acaccaaaaa agttattaag tcgctaaata gtgatgggaa 4980
tggaattccg gagtttagga tatgagttat cggtatatga gaatgatttt aatgtttgat 5040
atgcctactg aaacagtaga agaacgtaag gcgtatcgta agtttagaaa gtttctgttg 5100
agcgaaggtt ttattatgca tcagttctct gtttatagta aattattgct caataataca 5160
gctaataatg ccatgatagg tcggcttaaa gtgaataatc ctaagaaagg gagtataact 5220
cttttgacag ttaccgagaa gcagtttgca aggatggttt atctacatgg tgaacataat 5280
atgagtgttg ccaactctga tagtcgcttg gttttcctag gagattctta tgatcaagat 5340
taattttcca attttagatg aaccattagt gttaagtaat gctacgattt taacgataga 5400
agatgtttca gtttattctt cattggtgaa acatttttat caatatgacg tagatgaaca 5460
tttgaaatta tttgatgata agcagaaaag tctgaaggca acggagttaa tgttagttac 5520
agatatctta ggatacgatg tcaactcagc acctattcta aagttgatac atggtgactt 5580
agaaaatcaa ttcaacgaaa agccagaagt gaaatcaatg gtagaaaaat tagcagctac 5640
tattacagaa cttatcgcat ttgagtgtct agagaatgag cttgatttag aatacgatga 5700
aattacgatt ttagaactca ttaaggcact gggagtcaaa attgagacac agagcgacac 5760
tatctttgaa aaatgttttg aaattataca agtttaccat tatttaacga aaaagaatct 5820
cttagttttt gttaatagcg gagcttatct taccaaagat gaagttataa aattatgtga 5880
atacatcaat ttaatgcaaa agtcagtact ctttctagaa cctagaagac tctatgattt 5940
accgcaatat gttattgata aggattattt cttgataggc gaaaatatgg tataa 5995

<210> SEQ ID NO 494
<211> LENGTH: 4134
<212> TYPE: DNA
<213> ORGANISM: Streptococcus agalactiae

<400> SEQUENCE: 494
atgaataagc catattcaat aggccttgac atcggtacta attccgtcgg atggagcatt 60
attacagatg attataaagt acctgctaag aagatgagag ttttagggaa cactgataaa 120
gaatatatta agaagaatct cataggtgct ctgctttttg atggcgggaa tactgctgca 180
gatagacgct tgaagcgaac tgctcgtcgt cgttatacac gtcgtagaaa tcgtattcta 240
tatttacaag aaatttttgc agaggaaatg agtaaagttg atgatagttt ctttcatcga 300
ttagaggatt cttttctagt tgaggaagat aagagaggta gcaagtatcc tatctttgca 360
acaatgcagg aggagaaata ttatcatgaa aaatttccga caatctatca tttgagaaaa 420
gaattggctg acaagaaaga aaaagcagac cttcgtcttg tttatctggc tctagctcat 480
atcattaaat tcagagggca tttcctaatt gaggatgata gatttgatgt gaggaatacc 540
gatattcaaa aacaatatca agccttttta gaaatttttg atactacctt tgaaaataat 600
catttgttat ctcaaaatgt agatgtagaa gcaattctaa cagataagat tagcaagtct 660
gcgaagaagg atcgcatctt agcgcagtat cctaaccaaa aatctactgg tatttttgca 720
gaatttttga aattgattgt cggaaatcaa gctgacttca agaaacattt caatttggag 780
gataaaacac cgcttcaatt cgctaaggat agctacgatg aagatttaga aaatcttctt 840
ggacagattg gtgatgaatt tgcagactta ttctcagtag cgaaaaagct atatgatagt 900
gttcttttat ctggcattct tacagtaact gatctcagta ccaaggcgcc actttctgcc 960
tctatgattc agcgttatga tgaacatcat gaggacttaa agcatctaaa acaattcgta 1020
aaagcttcat tacctgaaaa ttatcgggaa gtatttgctg attcatcaaa agatggctac 1080
gctggctata ttgaaggcaa aactaatcaa gaagcttttt ataaatatct gttaaaattg 1140
ttgaccaaac aagaaggtag cgagtatttt cttgagaaaa ttaagaatga agattttttg 1200
agaaaacaga gaacctttga taatggctca atcccgcatc aagtccattt gacagaattg 1260
agggctatta ttcgacgtca atcagaatac tatccattct tgaaagagaa tcaagatagg 1320
attgaaaaaa tccttacctt tagaattcct tattatgtcg ggccactagc acgtgagaag 1380
agtgattttg catggatgac tcgcaaaaca gatgacagta ttcgaccttg gaattttgaa 1440
gacttggttg ataaagaaaa atctgcggaa gcttttatcc atcgcatgac caacaatgac 1500
ctctatcttc cagaagaaaa agttttacca aagcatagtc ttatttatga aaaatttact 1560
gtttacaatg aattaacgaa ggttagattt ttggcagaag gctttaaaga ttttcaattt 1620
ttaaatagga agcaaaaaga aactatcttt aacagcttgt ttaaggaaaa acgtaaagta 1680
actgaaaagg atattattag ttttttgaat aaagttgatg gatatgaagg aattgcaatc 1740

-continued

```
aaaggaattg agaaacagtt taacgctagc ctttcaacct atcatgatct taaaaaaata   1800
cttggcaagg atttccttga taatacagat aacgagctta ttttggaaga tatcgtccaa   1860
actctaacct tatttgaaga tagagaaatg attaagaagt gtcttgacat ctataaagat   1920
tttttacag agtcacagct taaaaagctc tatcgccgtc actatactgg ctggggacga   1980
ttgtctgcta agctaataaa tggcatccga aataaagaga atcaaaaaac aatcttggac   2040
tatcttattg atgatggaag tgcaaaccga aacttcatgc agttgataaa tgatgatgat   2100
ctatcattta aaccaattat tgacaaggca cgaactggta gtcattcgga taatctgaaa   2160
gaagttgtag gtgaacttgc tggtagccct gctattaaaa aagggattct acaaagtttg   2220
aaaatagttg atgagctggt taaagtcatg ggctatgaac ctgaacaaat cgtggttgaa   2280
atggcacgtg agaaccaaac gacagcaaaa ggattaagtc gttcacgaca acgcttgaca   2340
accttgagag aatctcttgc taatttgaag agtaatattt tggaagagaa aaagcctaag   2400
tatgtgaaag atcaagttga aaatcatcat ttatctgatg accgtctttt cctttactac   2460
ttacaaaacg gaagagatat gtatacaaaa aaggctctgg atattgataa tttaagtcaa   2520
tatgatattg accacattat tcctcaagct ttcataaaag atgattctat tgataatcgt   2580
gttttggtat catctgctaa aaatcgtgga aaatcagatg atgttcctag cattgaaatt   2640
gtaaaagctc gcaaaatgtt ctggaaaaat ttactggatg ctaagttaat gagtcagcgt   2700
aagtatgata atttgactaa ggcagagcgc ggaggcctaa cttccgatga taaggcaaga   2760
tttatccaac gtcagttggt tgagactcga caaattacca agcatgtagc tcgtatcttg   2820
gatgaacgct tcaataatga agttgataat ggtaaaaaga tttgcaaggt taaaattgta   2880
accttgaagt caaatttggt ttcaaatttc cgaaaagaat ttggattcta taaaattcgt   2940
gaagttaatg attatcacca tgcacacgat gcttatctta atgcagtagt tgccaaagct   3000
attctaacca aatatccaca gttagagcca gagtttgtct acggaatgta tagacagaaa   3060
aaactttcga aaatcgttca tgaggataag gaagaaaaat atagtgaagc aaccaggaaa   3120
atgtttttct actccaactt gatgaatatg ttcaaaagag ttgtgaggtt agcagatggt   3180
tctattgttg taagaccagt aatagaaact ggtagatata tgagaaaaac tgcatgggat   3240
aaaaagaaac actttgcgac agttagaaaa gtcttgtcat accctcagaa caatatcgtg   3300
aagaagacag agattcagac aggtggtttc tctaaggaat caatcttggc gcatggtaac   3360
tcagataagt tgattccaag aaaaacgaag gatatttatt tagatcctaa gaaatatgga   3420
ggttttgata gtccgatagt agcttactct gttttagttg tagctgatat caaaaaaggt   3480
aaagcacaaa aactaaaaac agttacggaa cttttaggaa ttaccatcat ggagaggtcc   3540
agatttgaga aaaatccatc agctttcctt gaatcaaaag gttatttaaa tattagggac   3600
gataaattaa tgattttacc gaagtatagt ctgttcgaat tagaaaatgg gcgtcgtcga   3660
ttacttgcta gtgctggtga attacaaaaa ggtaacgagc tagccttacc aacacaattt   3720
atgaagttct tatacttgc aagtcgttat aatgagtcaa aaggtaaacc agaggagatt   3780
gagaagaaac aagaatttgt aaatcaacat gtctcttatt ttgatgacat ccttcaatta   3840
attaatgatt tttcaaaacg agttattcta gcagatgcta atttagagaa aatcaataag   3900
ctttaccagg ataataagga aaatatacca gtagatgaac ttgctaataa tattatcaat   3960
ctatttactt ttaccagtct aggagctcca gcagctttta aattttttga taaaatagtt   4020
gatagaaaac gctatacatc aactaaagaa gtacttaatt ctactctaat ccatcaatct   4080
```

attactggac tttatgaaac acgtattgat ttgggtaaat taggagaaga ttga 4134

<210> SEQ ID NO 495
<211> LENGTH: 870
<212> TYPE: DNA
<213> ORGANISM: Streptococcus agalactiae

<400> SEQUENCE: 495
atggcaggtt ggcgaactgt tgttgtaaat acacattcta agctctctta taaaaataat 60
catctgattt ttaaagattc ttatcagacg gaaatgattc atctttcaga gattgatatt 120
ctaatcatgg aaacgacaga tattgttttg tcgactatgc tgattaaacg tttggttgat 180
gaaaatattt tagtcatatt ttgtgatgat aaacgcttgc caacagctat gttaatgccg 240
tactatgcta gacatgattc gagtttacaa ttatctaggc agatgtcatg gattgaggat 300
gtcaaagcgg atgtttggac atcaattatt gcacaaaaaa ttttgaatca gtccttttat 360
ctcggtgagt gttctttctt tgaaaaatcc cagtctatta tgaatctcta tcatgattta 420
gaatcttttg acccttccaa tcgtgaaggt catgcagcta ggatttattt caatacactt 480
tttggaaatg atttttcaag agagcaggat aatccaataa atgctggttt agactatgga 540
tattctctga ttttgagtat gtttgcgcgt gaagttgtta agtgtggttg catgacacaa 600
tttggcttaa agcatgctaa tcaatttaat cagttcaacc tagcaagcga tattatggaa 660
ccatttcgcc caatcgttga taggattatt tatgaaaata ggcagagtga ttttgtcaaa 720
atgaaaagag aactcttttc tatgttttca gagacataca gctacaacgg taaagaaatg 780
tatctttcaa atattgtcag cgattacacc aaaaaagtta ttaagtcgct aaatagtgat 840
gggaatggaa ttccggagtt taggatatga 870

<210> SEQ ID NO 496
<211> LENGTH: 342
<212> TYPE: DNA
<213> ORGANISM: Streptococcus agalactiae

<400> SEQUENCE: 496
atgagttatc ggtatatgag aatgatttta atgtttgata tgcctactga aacagtagaa 60
gaacgtaagg cgtatcgtaa gtttagaaag tttctgttga gcgaaggttt tattatgcat 120
cagttctctg tttatagtaa attattgctc aataatacag ctaataatgc catgataggt 180
cggcttaaag tgaataatcc taagaaaggg agtataactc ttttgacagt taccgagaag 240
cagtttgcaa ggatggttta tctacatggt gaacataata tgagtgttgc caactctgat 300
agtcgcttgg ttttcctagg agattcttat gatcaagatt aa 342

<210> SEQ ID NO 497
<211> LENGTH: 666
<212> TYPE: DNA
<213> ORGANISM: Streptococcus agalactiae

<400> SEQUENCE: 497
atgatcaaga ttaattttcc aattttagat gaaccattag tgttaagtaa tgctacgatt 60
ttaacgatag aagatgtttc agtttattct tcattggtga aacattttta tcaatatgac 120
gtagatgaac atttgaaatt atttgatgat aagcagaaaa gtctgaaggc aacggagtta 180
atgttagtta cagatatctt aggatacgat gtcaactcag cacctattct aaagttgata 240
catggtgact tagaaaatca attcaacgaa aagccagaag tgaaatcaat ggtagaaaaa 300
ttagcagcta ctattacaga acttatcgca tttgagtgtc tagagaatga gcttgattta 360

```
gaatacgatg aaattacgat tttagaactc attaaggcac tgggagtcaa aattgagaca    420

cagagcgaca ctatctttga aaaatgtttt gaaattatac aagtttacca ttatttaacg    480

aaaaagaatc tcttagtttt tgttaatagc ggagcttatc ttaccaaaga tgaagttata    540

aaattatgtg aatacatcaa tttaatgcaa aagtcagtac tctttctaga acctagaaga    600

ctctatgatt taccgcaata tgttattgat aaggattatt tcttgatagg cgaaaatatg    660

gtataa                                                               666


<210> SEQ ID NO 498
<211> LENGTH: 6580
<212> TYPE: DNA
<213> ORGANISM: Streptococcus mutans

<400> SEQUENCE: 498

atgaaaaaac cttactctat tggacttgat attggaacca attctgttgg ttgggctgtt     60

gtgacagatg actacaaagt tcctgctaag aagatgaagg ttctgggaaa tacagataaa    120

agtcatatcg agaaaaattt gcttggcgct ttattatttg atagcgggaa tactgcagaa    180

gacagacggt taaagagaac tgctcgccgt cgttacacac gtcgcagaaa tcgtatttta    240

tatttgcaag agatttttc agaagaaatg ggcaaggtag atgatagttt ctttcatcgt    300

ttagaggatt cttttcttgt tactgaggat aaacgaggag agcgccatcc catttttggg    360

aatcttgaag aagaagttaa gtatcatgaa aattttccaa ccatttatca tttgcggcaa    420

tatcttgcgg ataatccaga aaaagttgat ttgcgtttag tttatttggc tttggcacat    480

ataattaagt ttagaggtca ttttttaatt gaaggaaagt ttgatacacg caataatgat    540

gtacaaagac tgtttcaaga atttttagca gtctatgata atacttttga gaatagttcg    600

cttcaggagc aaaatgttca agttgaagaa attctgactg ataaaaatcag taaatctgct    660

aagaaagata gagttttgaa actttttcct aatgaaaagt ctaatggccg ctttgcagaa    720

tttctaaaac taattgttgg taatcaagct gattttaaaa agcattttga attagaagag    780

aaagcaccat tgcaattttc taaagatact tatgaagaag agttagaagt actattagct    840

caaattggag ataattacgc agagctcttt ttatcagcaa agaaactgta tgatagtatc    900

cttttatcag ggattttaac agttactgat gttggtacca aagcgccttt atctgcttcg    960

atgattcagc gatataatga acatcagatg gatttagctc agcttaaaca attcattcgt   1020

cagaaattat cagataaata taacgaagtt ttttctgatg tttcaaaaga cggctatgcg   1080

ggttatattg atgggaaaac aaatcaagaa gctttttata aataccttaa aggtctatta   1140

aataagattg agggaagtgg ctatttcctt gataaaattg agcgtgaaga ttttctaaga   1200

aagcaacgta cctttgacaa tggctctatt ccacatcaga ttcatcttca agaaatgcgt   1260

gctatcattc gtagacaggc tgaattttat ccgtttttag cagacaatca agataggatt   1320

gagaaattat tgactttccg tattccctac tatgttggtc cattagcgcg cggaaaaagt   1380

gattttgctt ggttaagtcg gaaatcggct gataaaatta caccatggaa ttttgatgaa   1440

atcgttgata aagaatcctc tgcagaagct tttatcaatc gtatgacaaa ttatgatttg   1500

tacttgccaa atcaaaaagt tcttcctaaa catagtttat tatacgaaaa atttactgtt   1560

tacaatgaat taacaaaggt taaatataaa acagagcaag gaaaaacagc attttttgat   1620

gccaatatga agcaagaaat ctttgatggc gtatttaagg tttatcgaaa agtaactaaa   1680

gataaattaa tggatttcct tgaaaaagaa tttgatgaat ttcgtattgt tgatttaaca   1740
```

-continued

```
ggtctggata aagaaaataa agtatttaac gcttcttatg gaacttatca tgatttgtgt   1800
aaaattttag ataaagattt tctcgataat tcaaagaatg aaaagatttt agaagatatt   1860
gtgttgacct taacgttatt tgaagataga gaaatgatta gaaaacgtct agaaaattac   1920
agtgatttat tgaccaaaga acaagtgaaa aagctggaaa gacgtcatta tactggttgg   1980
ggaagattat cagctgagtt aattcatggt attcgcaata aagaaagcag aaaaacaatt   2040
cttgattatc tcattgatga tggcaatagc aatcggaact ttatgcaact gattaacgat   2100
gatgctcttt ctttcaaaga agagattgct aaggcacaag ttattggaga aacagacaat   2160
ctaaatcaag ttgttagtga tattgctggc agccctgcta ttaaaaaagg aattttacaa   2220
agcttgaaga ttgttgatga gcttgtcaaa attatgggac atcaacctga aaatatcgtc   2280
gtggagatgg cgcgtgaaaa ccagtttacc aatcagggac gacgaaattc acagcaacgt   2340
ttgaaaggtt tgacagattc tattaaagaa tttggaagtc aaattcttaa agaacatccg   2400
gttgagaatt cacagttaca aaatgataga ttgtttctat attatttaca aaacggcaga   2460
gatatgtata ctggagaaga attggatatt gattatctaa gccagtatga tatagaccat   2520
attatcccgc aagcttttat aaaggataat tctattgata atagagtatt gactagctca   2580
aaggaaaatc gtggaaaatc ggatgatgta ccaagtaaag atgttgttcg taaaatgaaa   2640
tcctattgga gtaagctact ttcggcaaag cttattacac aacgtaaatt tgataatttg   2700
acaaaagctg aacgaggtgg attgaccgac gatgataaag ctggattcat caagcgtcaa   2760
ttagtagaaa cacgacaaat taccaaacat gtagcacgta ttctggacga acgatttaat   2820
acagaaacag atgaaaacaa caagaaaatt cgtcaagtaa aaattgtgac cttgaaatca   2880
aatcttgttt ccaatttccg taaagagttt gaactctaca aagtgcgtga aattaatgac   2940
tatcatcatg cacatgatgc ctatctcaat gctgtaattg gaaaggcttt actaggtgtt   3000
tacccacaat tggaacctga atttgtttat ggtgattatc ctcattttca tggacataaa   3060
gaaaataaag caactgctaa gaaatttttc tattcaaata ttatgaactt ctttaaaaaa   3120
gatgatgtcc gtactgataa aaatggtgaa attatctgga aaaaagatga gcatatttct   3180
aatattaaaa aagtgctttc ttatccacaa gttaatattg ttaagaaagt agaggagcaa   3240
acgggaggat tttctaaaga atctatcttg ccgaaaggta attctgacaa gcttattcct   3300
cgaaaaacga agaaatttta ttgggatacc aagaaatatg gaggatttga tagcccgatt   3360
gttgcttatt ctattttagt tattgctgat attgaaaaag gtaaatctaa aaaattgaaa   3420
acagtcaaag ccttagttgg tgtcactatt atggaaaaga tgacttttga aagggatcca   3480
gttgcttttc ttgagcgaaa aggctatcga aatgttcaag aagaaaatat tataaagtta   3540
ccaaaatata gtttatttaa actagaaaac ggacgaaaaa ggctattggc aagtgctagg   3600
gaacttcaaa agggaaatga aatcgttttg ccaaatcatt taggaacctt gctttatcac   3660
gctaaaaata ttcataaagt tgatgaacca aagcatttgg actatgttga taaacataaa   3720
gatgaattta aggagttgct agatgttgtg tcaaactttt ctaaaaaata tactttagca   3780
gaaggaaatt tagaaaaaat caaagaatta tatgcacaaa ataatggtga agatcttaaa   3840
gaattagcaa gttcatttat caacttatta acatttactg ctataggagc accggctact   3900
tttaaattct ttgataaaaa tattgatcga aaacgatata cttcaactac tgaaattctc   3960
aacgctaccc tcatccacca atccatcacc ggtctttatg aaacgcggat tgatctcaat   4020
aagttaggag gagactaatg ggctggcgga cagtggttgt taatacgcat tccaagttgt   4080
cttataagaa caaccacttg atttttaaag atgcttatca gacagagatg attcatctgt   4140
```

-continued

```
ctgagattga catcttatta cttgagacaa cagatattgt tttgtcaact atgctaatca   4200
aacgcttggt tgatgagaat attttggtca ttttttgtga tgacaaacgt ctgccaacag   4260
ccatgctcat gccttactat gcgcgtcacg attccagctt gcagctgagt catcagattt   4320
cttggacaga agaagtgaaa tgcgatgtct ggacaacaat catcgctcaa aagattttga   4380
atcagtcatg ttatttggga gaatgttttt attttgaaaa atctcagtca attatggatt   4440
tatatcatga cttagagcct tttgacccta gtaatcgaga aggacattct gcgcggattt   4500
atttcaatac cttatttgga aatgtttttt ccagagaaca agataatgat attaatgcag   4560
gtcttgacta tggttatacg ctgctgttaa gtatgtttgc gcgtgaagtg gttgtatctg   4620
gctgtatgac acaatttggt ctcaagcatg ccaaccaatt caatcagttt aactttgcca   4680
gtgatattat ggagcctttt cgtccaattg ttgaccgtat tgtttatgaa aatcgaaata   4740
actcttttat taaaataaaa cgtgagctat tcagcatgtt ttcagacacc tatctttata   4800
ataataagga gatgtatttg acaaatattg tcagcgatta taccaaaaag gtaatcaagg   4860
cgctgaataa tgatgggaaa ggagttcctg agtttaggat atgagttacc gatatatgcg   4920
aatgatttta atgtttgata tgccaacaga tactgctgag gaacgcaaag cttatcgtaa   4980
atttcggaaa tttttactga gcgaaggttt catcatgcat cagttttcag tatacagcaa   5040
gctgcttttg aataactctg ccaatacagc catgattgcc cgcttgaagg agaataatcc   5100
aaagaagggc aatatcacct tgttgaccgt gactgaaaag cagtttgccc gtatgattta   5160
cctgaatggt gagcgtgata ctagcattgc taattcggat tcacgactgg tctttctagg   5220
ggaggctttt cctgatgaaa cttaattttc ctatattgga tgaaccaata actcttgaaa   5280
aatctacgat tttggtatta gaagatgtgc aagtttttgc tcaaatggtg agaaatcttt   5340
atcaatatga tgaagatagt gaacttaaat tttttaatag aaaatttaag agtctgaaac   5400
catctgagtt aatgcttgtg acagatattt taggttatga tgtcaatgcc ccgtccttgc   5460
tgaagttggt tcacgctgat ttagaaaatc agtttaatga aaaaccagag gttaagtcta   5520
tggttgaaaa actggcaaat accattacgg aattaattgc ttatgaatgt ttagaaaatg   5580
aattggactt agaatatgat gagattacta ttttagagtt aatcaaagct ttaggcgtca   5640
aaattgaaac acaaagtgat accatttttg aaaaaatgtt tgaagtcctt caagtttata   5700
agtatctaaa taaaaagaag cttctcgttt ttatcaatac tttatcctat tttaaaagag   5760
aagaaatcgc gcaaattcta gaatatattc acttatccga tatggttgtt ttatttcttg   5820
aaccccgtaa aattgatggt tttgctcaat atattttaga tgaagattat ttcttgataa   5880
cagaaagcaa caactaaata cgaataataa gatagtttct aaatcagggg ctgtctttta   5940
ttatggattg acaaatgcgt ataatgcgta taaaataaaa agagaaatgt tatttgccat   6000
taacagggaa agaattagct aaattagcga taaacaatgg atgggaagaa gttcgggtga   6060
gaggaagtca tcatcatttc aagaaaagatg gagtatctta tattgtgacg attcctattc   6120
atggaaataa agtgcttaaa attggtcttg aaaagaaact cttaagggat ttaaatttat   6180
tatgatagag gaggaagtcg tcatgttaaa atcatatcct gtaatttttc ataaggaaga   6240
ggaagggtat tgggttgaat ttcctgaatt tggcggtggt acgcaagggg aagatttgga   6300
agaagccatg aagaacgctc gtcagatgtt agaaagtgtg ttggcatctt atcttgatga   6360
agggttggtt ctacccattt caagcgatat tcagaaaata tctgttgaag atggttttgc   6420
gaccatgatt caagctgatc ctagtcctta tctcaaaaat aacaaagcta ttcggaaaaa   6480
```

-continued tgttaccgtg cctgagtggt tgatacgatt agcagaccgt gaccgagtaa attattctga 6540
agtattaaca aaggctttgg aaaagaaact acaattataa 6580

<210> SEQ ID NO 499
<211> LENGTH: 4038
<212> TYPE: DNA
<213> ORGANISM: Streptococcus mutans

<400> SEQUENCE: 499
atgaaaaaac cttactctat tggacttgat attggaacca attctgttgg ttgggctgtt 60
gtgacagatg actacaaagt tcctgctaag aagatgaagg ttctgggaaa tacagataaa 120
agtcatatcg agaaaaattt gcttggcgct ttattatttg atagcgggaa tactgcagaa 180
gacagacggt taaagagaac tgctcgccgt cgttacacac gtcgcagaaa tcgtatttta 240
tatttgcaag agatttttc agaagaaatg ggcaaggtag atgatagttt ctttcatcgt 300
ttagaggatt cttttcttgt tactgaggat aaacgaggag agcgccatcc catttttggg 360
aatcttgaag aagaagttaa gtatcatgaa aattttccaa ccatttatca tttgcggcaa 420
tatcttgcgg ataatccaga aaaagttgat ttgcgtttag tttatttggc tttggcacat 480
ataattaagt ttagaggtca ttttttaatt gaaggaaagt ttgatacacg caataatgat 540
gtacaaagac tgtttcaaga atttttagca gtctatgata atacttttga gaatagttcg 600
cttcaggagc aaaatgttca agttgaagaa attctgactg ataaaatcag taaatctgct 660
aagaaagata gagttttgaa actttttcct aatgaaaagt ctaatggccg ctttgcagaa 720
tttctaaaac taattgttgg taatcaagct gattttaaaa agcattttga attagaagag 780
aaagcaccat tgcaattttc taaagatact tatgaagaag agttagaagt actattagct 840
caaattggag ataattacgc agagctcttt ttatcagcaa agaaactgta tgatagtatc 900
cttttatcag ggattttaac agttactgat gttggtacca aagcgccttt atctgcttcg 960
atgattcagc gatataatga acatcagatg gatttagctc agcttaaaca attcattcgt 1020
cagaaattat cagataaata taacgaagtt ttttctgatg tttcaaaaga cggctatgcg 1080
ggttatattg atgggaaaac aaatcaagaa gctttttata aataccttaa aggtctatta 1140
aataagattg agggaagtgg ctatttcctt gataaaattg agcgtgaaga ttttctaaga 1200
aagcaacgta cctttgacaa tggctctatt ccacatcaga ttcatcttca agaaatgcgt 1260
gctatcattc gtagacaggc tgaattttat ccgtttttag cagacaatca agataggatt 1320
gagaaattat tgactttccg tattccctac tatgttggtc cattagcgcg cggaaaaagt 1380
gattttgctt ggttaagtcg gaaatcggct gataaaatta caccatggaa ttttgatgaa 1440
atcgttgata aagaatcctc tgcagaagct tttatcaatc gtatgacaaa ttatgatttg 1500
tacttgccaa atcaaaaagt tcttcctaaa catagtttat tatacgaaaa atttactgtt 1560
tacaatgaat taacaaaggt taaatataaa acagagcaag gaaaaacagc atttttttgat 1620 gccaatatga agcaagaaat ctttgatggc gtatttaagg tttatcgaaa agtaactaaa 1680
gataaattaa tggatttcct tgaaaaagaa tttgatgaat ttcgtattgt tgatttaaca 1740
ggtctggata aagaaaataa agtatttaac gcttcttatg gaacttatca tgatttgtgt 1800
aaaattttag ataaagattt tctcgataat tcaaagaatg aaaagatttt agaagatatt 1860
gtgttgacct taacgttatt tgaagataga gaaatgatta gaaaacgtct agaaaattac 1920
agtgatttat tgaccaaaga acaagtgaaa aagctggaaa gacgtcatta tactggttgg 1980
ggaagattat cagctgagtt aattcatggt attcgcaata aagaaagcag aaaaacaatt 2040

-continued

```
cttgattatc tcattgatga tggcaatagc aatcggaact ttatgcaact gattaacgat   2100

gatgctcttt ctttcaaaga agagattgct aaggcacaag ttattggaga aacagacaat   2160

ctaaatcaag ttgttagtga tattgctggc agccctgcta ttaaaaaagg aattttacaa   2220

agcttgaaga ttgttgatga gcttgtcaaa attatgggac atcaacctga aaatatcgtc   2280

gtggagatgg cgcgtgaaaa ccagtttacc aatcagggac gacgaaattc acagcaacgt   2340

ttgaaaggtt tgacagattc tattaaagaa tttggaagtc aaattcttaa agaacatccg   2400

gttgagaatt cacagttaca aaatgataga ttgtttctat attatttaca aaacggcaga   2460

gatatgtata ctggagaaga attggatatt gattatctaa gccagtatga tatagaccat   2520

attatcccgc aagcttttat aaaggataat tctattgata atagagtatt gactagctca   2580

aaggaaaatc gtggaaaatc ggatgatgta ccaagtaaag atgttgttcg taaaatgaaa   2640

tcctattgga gtaagctact ttcggcaaag cttattacac aacgtaaatt tgataatttg   2700

acaaaagctg aacgaggtgg attgaccgac gatgataaag ctggattcat caagcgtcaa   2760

ttagtagaaa cacgacaaat taccaaacat gtagcacgta ttctggacga acgatttaat   2820

acagaaacag atgaaaacaa caagaaaatt cgtcaagtaa aaattgtgac cttgaaatca   2880

aatcttgttt ccaatttccg taaagagttt gaactctaca aagtgcgtga aattaatgac   2940

tatcatcatg cacatgatgc ctatctcaat gctgtaattg gaaaggcttt actaggtgtt   3000

tacccacaat tggaacctga atttgtttat ggtgattatc ctcattttca tggacataaa   3060

gaaaataaag caactgctaa gaaatttttc tattcaaata ttatgaactt ctttaaaaaa   3120

gatgatgtcc gtactgataa aaatggtgaa attatctgga aaaaagatga gcatatttct   3180

aatattaaaa aagtgctttc ttatccacaa gttaatattg ttaagaaagt agaggagcaa   3240

acgggaggat tttctaaaga atctatcttg ccgaaaggta attctgacaa gcttattcct   3300

cgaaaaacga agaaatttta ttgggatacc aagaaatatg gaggatttga tagcccgatt   3360

gttgcttatt ctattttagt tattgctgat attgaaaaag gtaaatctaa aaaattgaaa   3420

acagtcaaag ccttagttgg tgtcactatt atggaaaaga tgacttttga aagggatcca   3480

gttgcttttc ttgagcgaaa aggctatcga aatgttcaag aagaaaatat tataaagtta   3540

ccaaaatata gtttatttaa actagaaaac ggacgaaaaa ggctattggc aagtgctagg   3600

gaacttcaaa agggaaatga aatcgttttg ccaaatcatt taggaacctt gctttatcac   3660

gctaaaaata ttcataaagt tgatgaacca aagcatttgg actatgttga taaacataaa   3720

gatgaattta aggagttgct agatgttgtg tcaaactttt ctaaaaaata tactttagca   3780

gaaggaaatt tagaaaaaat caaagaatta tatgcacaaa ataatggtga agatcttaaa   3840

gaattagcaa gttcatttat caacttatta acatttactg ctataggagc accggctact   3900

tttaaattct ttgataaaaa tattgatcga aaacgatata cttcaactac tgaaattctc   3960

aacgctaccc tcatccacca atccatcacc ggtctttatg aaacgcggat tgatctcaat   4020

aagttaggag gagactaa                                                 4038
```

<210> SEQ ID NO 500
<211> LENGTH: 867
<212> TYPE: DNA
<213> ORGANISM: Streptococcus mutans

<400> SEQUENCE: 500

```
atgggctggc ggacagtggt tgttaatacg cattccaagt tgtcttataa gaacaaccac     60
```

-continued

```
ttgattttta aagatgctta tcagacagag atgattcatc tgtctgagat tgacatctta    120

ttacttgaga caacagatat tgttttgtca actatgctaa tcaaacgctt ggttgatgag    180

aatattttgg tcatttttttg tgatgacaaa cgtctgccaa cagccatgct catgccttac    240

tatgcgcgtc acgattccag cttgcagctg agtcatcaga tttcttggac agaagaagtg    300

aaatgcgatg tctggacaac aatcatcgct caaaagattt tgaatcagtc atgttatttg    360

ggagaatgtt tttattttga aaaatctcag tcaattatgg atttatatca tgacttagag    420

ccttttgacc ctagtaatcg agaaggacat tctgcgcgga tttatttcaa taccttattt    480

ggaaatgttt tttccagaga acaagataat gatattaatg caggtcttga ctatggttat    540

acgctgctgt taagtatgtt tgcgcgtgaa gtggttgtat ctggctgtat gacacaattt    600

ggtctcaagc atgccaacca attcaatcag tttaactttg ccagtgatat tatggagcct    660

tttcgtccaa ttgttgaccg tattgtttat gaaaatcgaa ataactcttt tattaaaata    720

aaacgtgagc tattcagcat gttttcagac acctatcttt ataataataa ggagatgtat    780

ttgacaaata ttgtcagcga ttataccaaa aaggtaatca aggcgctgaa taatgatggg    840

aaaggagttc ctgagtttag gatatga                                        867
```

<210> SEQ ID NO 501
<211> LENGTH: 330
<212> TYPE: DNA
<213> ORGANISM: Streptococcus mutans

<400> SEQUENCE: 501

```
atgcgaatga ttttaatgtt tgatatgcca acagatactg ctgaggaacg caaagcttat     60

cgtaaatttc ggaaattttt actgagcgaa ggtttcatca tgcatcagtt ttcagtatac    120

agcaagctgc ttttgaataa ctctgccaat acagccatga ttgcccgctt gaaggagaat    180

aatccaaaga agggcaatat caccttgttg accgtgactg aaaagcagtt tgcccgtatg    240

atttacctga atggtgagcg tgatactagc attgctaatt cggattcacg actggtcttt    300

ctaggggagg cttttcctga tgaaacttaa                                     330
```

<210> SEQ ID NO 502
<211> LENGTH: 573
<212> TYPE: DNA
<213> ORGANISM: Streptococcus mutans

<400> SEQUENCE: 502

```
atggtgagaa atctttatca atatgatgaa gatagtgaac ttaaattttt taatagaaaa     60

tttaagagtc tgaaaccatc tgagttaatg cttgtgacag atattttagg ttatgatgtc    120

aatgccccgt ccttgctgaa gttggttcac gctgatttag aaaatcagtt taatgaaaaa    180

ccagaggtta agtctatggt tgaaaaactg gcaaatacca ttacggaatt aattgcttat    240

gaatgtttag aaaatgaatt ggacttagaa tatgatgaga ttactatttt agagttaatc    300

aaagctttag gcgtcaaaat tgaaacacaa agtgatacca tttttgaaaa aatgtttgaa    360

gtccttcaag tttataagta tctaaataaa aagaagcttc tcgtttttat caatacttta    420

tcctatttta aaagagaaga aatcgcgcaa attctagaat atattcactt atccgatatg    480

gttgttttat ttcttgaacc ccgtaaaatt gatggttttg ctcaatatat tttagatgaa    540

gattatttct tgataacaga aagcaacaac taa                                 573
```

<210> SEQ ID NO 503
<211> LENGTH: 378

<212> TYPE: DNA
<213> ORGANISM: Streptococcus mutans

<400> SEQUENCE: 503
atgttaaaat catatcctgt aatttttcat aaggaagagg aagggtattg ggttgaattt 60
cctgaatttg gcggtggtac gcaaggggaa gatttggaag aagccatgaa gaacgctcgt 120
cagatgttag aaagtgtgtt ggcatcttat cttgatgaag ggttggttct acccatttca 180
agcgatattc agaaaatatc tgttgaagat ggttttgcga ccatgattca agctgatcct 240
agtccttatc tcaaaaataa caaagctatt cggaaaaatg ttaccgtgcc tgagtggttg 300
atacgattag cagaccgtga ccgagtaaat tattctgaag tattaacaaa ggctttggaa 360
aagaaactac aattataa 378

<210> SEQ ID NO 504
<211> LENGTH: 5966
<212> TYPE: DNA
<213> ORGANISM: Streptococcus pyogenes

<400> SEQUENCE: 504
atggataaga aatactcaat aggcttagat atcggcacaa atagcgtcgg atgggcggtg 60
atcactgatg aatataaggt tccgtctaaa aagttcaagg ttctgggaaa tacagaccgc 120
cacagtatca aaaaaaatct tataggggct cttttatttg acagtggaga gacagcggaa 180
gcgactcgtc tcaaacggac agctcgtaga aggtatacac gtcggaagaa tcgtatttgt 240
tatctacagg agatttttc aaatgagatg gcgaaagtag atgatagttt ctttcatcga 300
cttgaagagt cttttttggt ggaagaagac aagaagcatg aacgtcatcc tatttttgga 360
aatatagtag atgaagttgc ttatcatgag aaatatccaa ctatctatca tctgcgaaaa 420
aaattggtag attctactga taaagcggat ttgcgcttaa tctatttggc cttagcgcat 480
atgattaagt ttcgtggtca tttttgatt gagggagatt taaatcctga taatagtgat 540
gtggacaaac tatttatcca gttggtacaa acctacaatc aattatttga agaaaaccct 600
attaacgcaa gtggagtaga tgctaaagcg attctttctg cacgattgag taaatcaaga 660
cgattagaaa atctcattgc tcagctcccc ggtgagaaga aaaatggctt atttgggaat 720
ctcattgctt tgtcattggg tttgacccct aattttaaat caaattttga tttggcagaa 780
gatgctaaat tacagctttc aaaagatact tacgatgatg atttagataa tttattggcg 840
caaattggag atcaatatgc tgatttgttt ttggcagcta agaatttatc agatgctatt 900
ttactttcag atatcctaag agtaaatact gaaataacta aggctcccct atcagcttca 960
atgattaaac gctacgatga acatcatcaa gacttgactc ttttaaaagc tttagttcga 1020
caacaacttc cagaaaagta taaagaaatc ttttttgatc aatcaaaaaa cggatatgca 1080
ggttatattg atgggggagc tagccaagaa gaattttata aatttatcaa accaatttta 1140
gaaaaaatgg atggtactga ggaattattg gtgaaactaa atcgtgaaga tttgctgcgc 1200
aagcaacgga cctttgacaa cggctctatt ccccatcaaa ttcacttggg tgagctgcat 1260
gctattttga gaagacaaga agacttttat ccatttttaa aagacaatcg tgagaagatt 1320
gaaaaaatct tgacttttcg aattccttat tatgttggtc cattggcgcg tggcaatagt 1380
cgttttgcat ggatgactcg gaagtctgaa gaaacaatta ccccatggaa ttttgaagaa 1440
gttgtcgata aaggtgcttc agctcaatca tttattgaac gcatgacaaa ctttgataaa 1500
aatcttccaa atgaaaaagt actaccaaaa catagtttgc tttatgagta ttttacggtt 1560

-continued tataacgaat tgacaaaggt caaatatgtt actgaaggaa tgcgaaaacc agcatttctt 1620
tcaggtgaac agaagaaagc cattgttgat ttactcttca aaacaaatcg aaaagtaacc 1680
gttaagcaat taaaagaaga ttatttcaaa aaaatagaat gttttgatag tgttgaaatt 1740
tcaggagttg aagatagatt taatgcttca ttaggtacct accatgattt gctaaaaatt 1800
attaaagata aagatttttt ggataatgaa gaaaatgaag atatcttaga ggatattgtt 1860
ttaacattga ccttatttga agatagggag atgattgagg aaagacttaa aacatatgct 1920
cacctctttg atgataaggt gatgaaacag cttaaacgtc gccgttatac tggttgggga 1980
cgtttgtctc gaaaattgat taatggtatt agggataagc aatctggcaa aacaatatta 2040 gatttttga aatcagatgg ttttgccaat cgcaatttta tgcagctgat ccatgatgat 2100
agtttgacat ttaaagaaga cattcaaaaa gcacaagtgt ctggacaagg cgatagttta 2160
catgaacata ttgcaaattt agctggtagc cctgctatta aaaaaggtat tttacagact 2220
gtaaaagttg ttgatgaatt ggtcaaagta atggggcggc ataagccaga aaatatcgtt 2280
attgaaatgg cacgtgaaaa tcagacaact caaaagggcc agaaaaattc gcgagagcgt 2340
atgaaacgaa tcgaagaagg tatcaaagaa ttaggaagtc agattcttaa agagcatcct 2400
gttgaaaata ctcaattgca aaatgaaaag ctctatctct attatctcca aaatggaaga 2460
gacatgtatg tggaccaaga attagatatt aatcgtttaa gtgattatga tgtcgatcac 2520
attgttccac aaagtttcct taaagacgat tcaatagaca ataaggtctt aacgcgttct 2580
gataaaaatc gtggtaaatc ggataacgtt ccaagtgaag aagtagtcaa aaagatgaaa 2640
aactattgga gacaacttct aaacgccaag ttaatcactc aacgtaagtt tgataattta 2700
acgaaagctg aacgtggagg tttgagtgaa cttgataaag ctggttttat caaacgccaa 2760
ttggttgaaa ctcgccaaat cactaagcat gtggcacaaa ttttggatag tcgcatgaat 2820
actaaatacg atgaaaatga taaacttatt cgagaggtta aagtgattac cttaaaatct 2880
aaattagttt ctgacttccg aaaagatttc caattctata aagtacgtga gattaacaat 2940
taccatcatg cccatgatgc gtatctaaat gccgtcgttg gaactgcttt gattaagaaa 3000
tatccaaaac ttgaatcgga gtttgtctat ggtgattata aagtttatga tgttcgtaaa 3060
atgattgcta agtctgagca agaaataggc aaagcaaccg caaaatattt cttttactct 3120
aatatcatga acttcttcaa aacagaaatt acacttgcaa atggagagat tcgcaaacgc 3180
cctctaatcg aaactaatgg ggaaactgga gaaattgtct gggataaagg gcgagatttt 3240
gccacagtgc gcaaagtatt gtccatgccc caagtcaata ttgtcaagaa aacagaagta 3300
cagacaggcg gattctccaa ggagtcaatt ttaccaaaaa gaaattcgga caagcttatt 3360
gctcgtaaaa aagactggga tccaaaaaaa tatggtggtt ttgatagtcc aacggtagct 3420
tattcagtcc tagtggttgc taaggtggaa aaagggaaat cgaagaagtt aaaatccgtt 3480
aaagagttac tagggatcac aattatggaa agaagttcct ttgaaaaaaa tccgattgac 3540
tttttagaag ctaaaggata taaggaagtt aaaaaagact taatcattaa actacctaaa 3600
tatagtcttt ttgagttaga aaacggtcgt aaacggatgc tggctagtgc cggagaatta 3660
caaaaaggaa atgagctggc tctgccaagc aaatatgtga atttttata tttagctagt 3720 cattatgaaa agttgaaggg tagtccagaa gataacgaac aaaaacaatt gtttgtggag 3780
cagcataagc attatttaga tgagattatt gagcaaatca gtgaattttc taagcgtgtt 3840
attttagcag atgccaattt agataaagtt cttagtgcat ataacaaaca tagagacaaa 3900
ccaatacgtg aacaagcaga aaatattatt catttattta cgttgacgaa tcttggagct 3960
cccgctgctt ttaaatattt tgatacaaca attgatcgta aacgatatac gtctacaaaa 4020
gaagttttag atgccactct tatccatcaa tccatcactg gtctttatga aacacgcatt 4080
gatttgagtc agctaggagg tgactgatgg ctggttggcg tactgttgtg gtaaataccc 4140
actcgaaatt atcctataag aataatcatc tgatttttaa ggatgcctat aaaacggagc 4200
tgatccattt atcagaaatt gatattttgt tattagaaac gaccgatatt gtcttgtcca 4260
ctatgctggt aaaacggcta gtggatgaga atgtccttgt catattctgt gatgataaac 4320
gattaccaac agctatgctg atgccttttt atggtcgtca tgattcgagt ttacagcttg 4380
ggaaacaaat gtcctggtca gaaacagtca aatcgcaggt ttggacgacg attattgctc 4440
aaaagatttt gaatcaatct tgctatctag gagcatgctc ctattttgaa aaatcccaat 4500
ctattatgga tttatatcat ggtttggaaa attttgatcc gagtaatcga gaagggcatg 4560
cagcgagaat ttattttaat acacttttttg ggaacgattt ctcaagagat ttggagcatc 4620
caatcaatgc aggtctggat tatggttata ctttattatt gagtatgttt gcgcgtgaag 4680
tggttgtgtc tggatgtatg actcagtttg ggcttaaaca cgctaatcag tttaatcagt 4740
tcaattttgc tagcgatatt atggaaccat ttaggccttt agtggataag attgtttatg 4800
aaaatcgaaa tcagcctttt cccaaaataa agagagagtt atttactttg ttttcagata 4860
cattttcata taatggtaaa gagatgtatc tcacgaatat tattagcgat tatactaaaa 4920
aagttgtcaa agctctgaat aatgaaggga aaggagttcc tgaatttagg atatgagtta 4980
tagatatatg agaatgatac ttatgtttga tatgccgacg gacaccgctg aggaacgaaa 5040
agcctatcga aaatttcgga aatttttact tagtgaaggg tttatcatgc atcaattttc 5100
tatttatagt aagttgctgt tgaataatac agctaacaat gccatgattg gtcggctgag 5160
ggagcataat cctaataaag gaaatattac attactaacg gtcacggaaa aacagtttgc 5220
acgaatgatt tatttacatg gtgaaagaaa taattgtatt gcaaactccg atgaaagact 5280
tgtatttctt ggggaggctt ttgatgaatc ttaattttc cttactagat gaaccgattc 5340
cattaagagg cggtacaatt cttgtgctcg aagatgtctg tgtattttca aaaatagtgc 5400
aatattgtta ccaatatgag gaagattctg aacttaaatt ttttgatcac aagatgaaaa 5460
caatcaaaga atcagaaatc atgcttgtaa cagatatttt aggatttgat gttaactcct 5520
caaccatttt aaaattgatt catgcagatt tagaatctca atttaatgag aaacccgaag 5580
tgaaatcgat gattgacaaa ttggttgcta cgattacaga actgattgtc tttgaatgct 5640
tagaaaatga attagattta gagtatgatg aaatcacaat cctggaattg attaagtcct 5700
taggagtaaa agtagaaacg caaagtgata ctatttttga aaaatgtcta gagatacttc 5760
aaattttcaa atatctcact aagaaaaagt tgcttatttt tgtcaatagc ggagcttttc 5820
taacaaagga tgaagtggct agtttacaag agtatatatc attgacaaat ttaacagttc 5880
tctttttaga accacgtgaa ctatatgatt ttccgcagta tattttagat gaagattatt 5940
tcttaataac taaaaatatg gtataa 5966

<210> SEQ ID NO 505
<211> LENGTH: 4107
<212> TYPE: DNA
<213> ORGANISM: Streptococcus pyogenes

<400> SEQUENCE: 505
atggataaga aatactcaat aggcttagat atcggcacaa atagcgtcgg atgggcggtg 60

-continued

```
atcactgatg aatataaggt tccgtctaaa aagttcaagg ttctgggaaa tacagaccgc    120
cacagtatca aaaaaaatct tatagggget cttttatttg acagtggaga gacagcggaa    180
gcgactcgtc tcaaacggac agctcgtaga aggtatacac gtcggaagaa tcgtatttgt    240
tatctacagg agatttttc aaatgagatg gcgaaagtag atgatagttt ctttcatcga    300
cttgaagagt ctttttggt ggaagaagac aagaagcatg aacgtcatcc tatttttgga    360
aatatagtag atgaagttgc ttatcatgag aaatatccaa ctatctatca tctgcgaaaa    420
aaattggtag attctactga taaagcggat ttgcgcttaa tctatttggc cttagcgcat    480
atgattaagt ttcgtggtca tttttgatt gagggagatt taaatcctga taatagtgat    540
gtggacaaac tatttatcca gttggtacaa acctacaatc aattatttga agaaaaccct    600
attaacgcaa gtggagtaga tgctaaagcg attctttctg cacgattgag taaatcaaga    660
cgattagaaa atctcattgc tcagctcccc ggtgagaaga aaaatggctt atttgggaat    720
ctcattgctt tgtcattggg tttgacccct aattttaaat caaattttga tttggcagaa    780
gatgctaaat tacagctttc aaaagatact tacgatgatg atttagataa tttattggcg    840
caaattggag atcaatatgc tgatttgttt ttggcagcta agaatttatc agatgctatt    900
ttactttcag atatcctaag agtaaatact gaaataacta aggctcccct atcagcttca    960
atgattaaac gctacgatga acatcatcaa gacttgactc ttttaaaagc tttagttcga   1020
caacaacttc cagaaaagta taaagaaatc tttttgatc aatcaaaaaa cggatatgca   1080
ggttatattg atgggggagc tagccaagaa gaattttata aatttatcaa accaatttta   1140
gaaaaaatgg atggtactga ggaattattg gtgaaactaa atcgtgaaga tttgctgcgc   1200
aagcaacgga cctttgacaa cggctctatt ccccatcaaa ttcacttggg tgagctgcat   1260
gctattttga gaagacaaga agacttttat ccattttaa aagacaatcg tgagaagatt   1320
gaaaaaatct tgacttttcg aattccttat tatgttggtc cattggcgcg tggcaatagt   1380
cgttttgcat ggatgactcg gaagtctgaa gaaacaatta ccccatggaa ttttgaagaa   1440
gttgtcgata aaggtgcttc agctcaatca tttattgaac gcatgacaaa ctttgataaa   1500
aatcttccaa atgaaaaagt actaccaaaa catagtttgc tttatgagta ttttacggtt   1560
tataacgaat tgacaaaggt caaatatgtt actgaaggaa tgcgaaaacc agcatttctt   1620
tcaggtgaac agaagaaagc cattgttgat ttactcttca aaacaaatcg aaaagtaacc   1680
gttaagcaat taaaagaaga ttatttcaaa aaaatagaat gttttgatag tgttgaaatt   1740
tcaggagttg aagatagatt taatgcttca ttaggtacct accatgattt gctaaaaatt   1800
attaaagata aagatttttt ggataatgaa gaaaatgaag atatcttaga ggatattgtt   1860
ttaacattga ccttatttga agatagggag atgattgagg aaagacttaa aacatatgct   1920
cacctctttg atgataaggt gatgaaacag cttaaacgtc gccgttatac tggttgggga   1980
cgtttgtctc gaaaattgat taatggtatt agggataagc aatctggcaa aacaatatta   2040
gatttttga aatcagatgg ttttgccaat cgcaatttta tgcagctgat ccatgatgat   2100
agtttgacat ttaaagaaga cattcaaaaa gcacaagtgt ctggacaagg cgatagttta   2160
catgaacata ttgcaaattt agctggtagc cctgctatta aaaaaggtat tttacagact   2220
gtaaaagttg ttgatgaatt ggtcaaagta atggggcggc ataagccaga aaatatcgtt   2280
attgaaatgg cacgtgaaaa tcagacaact caaaagggcc agaaaaattc gcgagagcgt   2340
atgaaacgaa tcgaagaagg tatcaaagaa ttaggaagtc agattcttaa agagcatcct   2400
gttgaaaata ctcaattgca aaatgaaaag ctctatctct attatctcca aaatggaaga   2460
```

```
gacatgtatg tggaccaaga attagatatt aatcgtttaa gtgattatga tgtcgatcac   2520
attgttccac aaagtttcct taaagacgat tcaatagaca ataaggtctt aacgcgttct   2580
gataaaaatc gtggtaaatc ggataacgtt ccaagtgaag aagtagtcaa aaagatgaaa   2640
aactattgga gacaacttct aaacgccaag ttaatcactc aacgtaagtt tgataattta   2700
acgaaagctg aacgtggagg tttgagtgaa cttgataaag ctggttttat caaacgccaa   2760
ttggttgaaa ctcgccaaat cactaagcat gtggcacaaa ttttggatag tcgcatgaat   2820
actaaatacg atgaaaatga taaacttatt cgagaggtta aagtgattac cttaaaatct   2880
aaattagttt ctgacttccg aaaagatttc caattctata aagtacgtga gattaacaat   2940
taccatcatg cccatgatgc gtatctaaat gccgtcgttg gaactgcttt gattaagaaa   3000
tatccaaaac ttgaatcgga gtttgtctat ggtgattata aagtttatga tgttcgtaaa   3060
atgattgcta agtctgagca agaaataggc aaagcaaccg caaaatattt cttttactct   3120
aatatcatga acttcttcaa aacagaaatt acacttgcaa atggagagat tcgcaaacgc   3180
cctctaatcg aaactaatgg ggaaactgga gaaattgtct gggataaagg gcgagatttt   3240
gccacagtgc gcaaagtatt gtccatgccc caagtcaata ttgtcaagaa aacagaagta   3300
cagacaggcg gattctccaa ggagtcaatt ttaccaaaaa gaaattcgga caagcttatt   3360
gctcgtaaaa aagactggga tccaaaaaaa tatggtggtt ttgatagtcc aacggtagct   3420
tattcagtcc tagtggttgc taaggtggaa aaagggaaat cgaagaagtt aaaatccgtt   3480
aaagagttac tagggatcac aattatggaa agaagttcct ttgaaaaaaa tccgattgac   3540
tttttagaag ctaaaggata taaggaagtt aaaaaagact taatcattaa actacctaaa   3600
tatagtcttt ttgagttaga aaacggtcgt aaacggatgc tggctagtgc cggagaatta   3660
caaaaaggaa atgagctggc tctgccaagc aaatatgtga atttttttata tttagctagt   3720
cattatgaaa agttgaaggg tagtccagaa gataacgaac aaaaacaatt gtttgtggag   3780
cagcataagc attatttaga tgagattatt gagcaaatca gtgaattttc taagcgtgtt   3840
attttagcag atgccaattt agataaagtt cttagtgcat ataacaaaca tagagacaaa   3900
ccaatacgtg aacaagcaga aaatattatt catttattta cgttgacgaa tcttggagct   3960
cccgctgctt ttaaatattt tgatacaaca attgatcgta aacgatatac gtctacaaaa   4020
gaagttttag atgccactct tatccatcaa tccatcactg gtctttatga aacacgcatt   4080
gatttgagtc agctaggagg tgactga                                     4107
```

<210> SEQ ID NO 506
<211> LENGTH: 870
<212> TYPE: DNA
<213> ORGANISM: Streptococcus pyogenes

<400> SEQUENCE: 506

```
atggctggtt ggcgtactgt tgtggtaaat acccactcga aattatccta taagaataat     60
catctgattt ttaaggatgc ctataaaacg gagctgatcc atttatcaga aattgatatt    120
ttgttattag aaacgaccga tattgtcttg tccactatgc tggtaaaacg gctagtggat    180
gagaatgtcc ttgtcatatt ctgtgatgat aaacgattac caacagctat gctgatgcct    240
ttttatggtc gtcatgattc gagtttacag cttgggaaac aaatgtcctg gtcagaaaca    300
gtcaaatcgc aggtttggac gacgattatt gctcaaaaga ttttgaatca atcttgctat    360
ctaggagcat gctcctattt tgaaaaatcc caatctatta tggatttata tcatggtttg    420
```

-continued

```
gaaaattttg atccgagtaa tcgagaaggg catgcagcga gaatttattt taatacactt    480

tttgggaacg atttctcaag agatttggag catccaatca atgcaggtct ggattatggt    540

tatactttat tattgagtat gtttgcgcgt gaagtggttg tgtctggatg tatgactcag    600

tttgggctta aacacgctaa tcagtttaat cagttcaatt ttgctagcga tattatggaa    660

ccatttaggc ctttagtgga taagattgtt tatgaaaatc gaaatcagcc ttttcccaaa    720

ataaagagag agttatttac tttgttttca gatacatttt catataatgg taaagagatg    780

tatctcacga atattattag cgattatact aaaaaagttg tcaaagctct gaataatgaa    840

gggaaaggag ttcctgaatt taggatatga                                     870
```

<210> SEQ ID NO 507
<211> LENGTH: 342
<212> TYPE: DNA
<213> ORGANISM: Streptococcus pyogenes

<400> SEQUENCE: 507

```
atgagttata gatatatgag aatgatactt atgtttgata tgccgacgga caccgctgag     60

gaacgaaaag cctatcgaaa atttcggaaa tttttactta gtgaagggtt tatcatgcat    120

caattttcta tttatagtaa gttgctgttg aataatacag ctaacaatgc catgattggt    180

cggctgaggg agcataatcc taataaagga aatattacat tactaacggt cacggaaaaa    240

cagtttgcac gaatgattta tttacatggt gaaagaaata attgtattgc aaactccgat    300

gaaagacttg tatttcttgg ggaggctttt gatgaatctt aa                       342
```

<210> SEQ ID NO 508
<211> LENGTH: 663
<212> TYPE: DNA
<213> ORGANISM: Streptococcus pyogenes

<400> SEQUENCE: 508

```
atgaatctta atttttcctt actagatgaa ccgattccat taagaggcgg tacaattctt     60

gtgctcgaag atgtctgtgt attttcaaaa atagtgcaat attgttacca atatgaggaa    120

gattctgaac ttaaattttt tgatcacaag atgaaaacaa tcaaagaatc agaaatcatg    180

cttgtaacag atattttagg atttgatgtt aactcctcaa ccattttaaa attgattcat    240

gcagatttag aatctcaatt taatgagaaa cccgaagtga aatcgatgat tgacaaattg    300

gttgctacga ttacagaact gattgtcttt gaatgcttag aaaatgaatt agatttagag    360

tatgatgaaa tcacaatcct ggaattgatt aagtccttag gagtaaaagt agaaacgcaa    420

agtgatacta tttttgaaaa atgtctagag atacttcaaa ttttcaaata tctcactaag    480

aaaaagttgc ttatttttgt caatagcgga gcttttctaa caaaggatga agtggctagt    540

ttacaagagt atatatcatt gacaaattta acagttctct ttttagaacc acgtgaacta    600

tatgattttc cgcagtatat tttagatgaa gattatttct taataactaa aaatatggta    660

taa                                                                  663
```

<210> SEQ ID NO 509
<211> LENGTH: 8020
<212> TYPE: DNA
<213> ORGANISM: Streptococcus pyogenes

<400> SEQUENCE: 509

```
atgagaatga ttttagcaca ctatgactgt aaaaaagata aaaagcaatc tttagatgag     60

catttatggc atgtggcctg ttctagtcga caggaagcat ctataattgg tcaaggagat    120
```

-continued

```
gtgctttttt taattggtct ttaccacgac ctgggcaaag ctgatcgaac ctttcaagat    180
aaattattaa ataatccaaa tcggcatgtt gatcactctt atgcaggggc aaaatactta    240
tgttctatta ttgggcctca tctaaaaaac cgaggggttg ataaaaatga gagaatgaca    300
ttcaacgaaa tggtggggta tgtcatctct gctcatcatg ggatgtatga tttatgctac    360
tattttgacg atgctgaata ttatggcttt aataagttta aaaatcgtat caatagagac    420
ttagatggtt atcactatca tgaagatatt aaagggtacg ctctaaaatt agaaaaaaaa    480
ttatgtgatt atggctacaa agatttaagg gagcttattg ataaagcttt tgataattac    540
caacaagcca tgtcttcctt aaactggcaa gataagagtg agtgggatta ttatcagtct    600
tgtatggtga gactttactt gtcactctta aaaaacgctg atattttgga cacagtaaat    660
gcctatggcc ttaagataag tcctatggat aaaacagagc gatcctttct aaaacactcc    720
tatttagcgg ccattgaaca aaaatatgct agctttggac agccaaacaa tcagttgaac    780
actattcgga cagaaatcgc tgagcgtgtt aaagaaagag gtaaacgaga ttccaagggg    840
atttatcgct tagatttacc gacaggagct ggcaagacta atcttagtat gcgttatgcg    900
tttcaccaat tagttcatca cgacaaatca aggttttttt acataactcc ctttctttcg    960
gttcttgagc aaaatgcttc cgaaattaga aaagttacag gtgaccttgg cgttctagaa   1020
caccattcca atgtggtgaa acaggctaat gaagatgatg atgataagga cagtttattg   1080
tcagcttatc ttagtgatag ctgggacagt caagtagtct tgacttctat ggttcaattt   1140
ttccaaacac ttttcaaaac aaaatcagct aatctgagac gtttttcaag tttgattaat   1200
agtgttgtga ttctagatga agttcaatcc ctgcctattg aagtcaccac tttgtttaat   1260
ttaacgatga attttttaaa taaagttatg gatacaacca tcgttctttg cacagcgaca   1320
caacctgctt atgattcttc agagattgac catcgtatct gttatggagg gaacttggga   1380
gaattagctg aaatagttga gttaacgatt gaagaaaaac agattttttc aaggacagag   1440
cttagaaaat ttgatgatag tgatcagaaa gttcacttga ctgatgttat taaccttatt   1500
ctaggtgagg aaaactcagt tcttgctatt tttaatacga aaaaaacggt tcataactgc   1560
tatactatgc taaaagacat gactgataga ccggtctatc agctttcgac aaatatgtgt   1620
gcgcagcata gacttgactt gattgctaag atcaaaacgg agttacaaaa taatatccct   1680
attatttgta ttagcacgca attaattgaa gcaggtgtag atgttgattt tcatcgcgtc   1740
attcgttcct actcagggat tgattctatt gttcaggctg ctggacggtg taaccgagaa   1800
ggcaaacgag ataaagggca agtcactctt gtcaatctga ccaatgaaga ggaaaatatt   1860
tctaggctga cagaaataaa aactaaaaaa gaagccacag aatctattct tcataagatt   1920
gggtctccaa ttgatatctc aactttaaac cgtgactttt ttgagtatta ttatgccaat   1980
aatcagggac tgatggatta tcctttggaa gacaacctat caatctacga ctatttaagc   2040
cttaatattt atcagacggc aaataaaaag ttcaaaggta agttaaaaca agcttttaaa   2100
acagcaggag ccaaaatgaa cctcatcaat aatgatatga taggaattct cgtaccttat   2160
ggcgaagctg agaaaaaatt ggcttattta gaagaattag gtgtgtcaca tttttatca    2220
gcaaaagatt atcaaacgat aaaatcatta ctaaaagagt tacaaccttt tacggttaat   2280
gtccgcgaga acgatcctct ctttgagaca acaaaatctt atctaaatgg tcagattctg   2340
gttttgacgt cggagtatta tgacacggaa agaggagtta aatacgattc agctagcttt   2400
tacttctaac tcaaaacgaa agaagattaa caaaaggttg ttagaggacc ttgttaacct   2460
```

```
gccaatcatc attagtaatt attatcaatt tagactattt aataaaatta gattacaaaa   2520
aaacagaagg aggaaagtag cttgtacaga tctagagact tctacgtgag agtaagtggt   2580
cagcgagctc tttttacaaa tccagccaca aaagggggat cggaacgctc atcctattcg   2640
gttccgacta gacaggcact gaatggtatc gttgatgcca tctattataa gccgaccttt   2700
actaatatcg tcacagaggt taaggttatt aaccagattc aaaccgaatt acagggtgtc   2760
agggctctgt tacatgatta tagtgcagat ttaagttatg tatcctattt gagtgatgtt   2820
gtttatctga tcaagtttca ttttgtttgg aatgaagata gaaaagattt gaactcagat   2880
agacttccag ctaaacatga agccattatg gagcgttcta ttcgtaaagg gggacgtcga   2940
gatgtgtttt tgggtacaag agaatgttta gggcttgtag atgatatcag ccaagaagag   3000
tatgagacta ctgtgtcgta ttataatggt gtcaatatcg acttgggaat catgttccat   3060
tcctttgcct atccgaagga caaaaagaca ccattaaaat catactttac aaagactgtg   3120
atgaaaaatg gagtcattac gtttaaagca cagtctgaat gcgatattgt taacacgctt   3180
tctagttatg cttttaaagc accagaggag ataaaatcgg ttaacgatga atgcatggag   3240
tatgatgcca tggagaaagg agaaaactga tggatttttt tacttctctc ttgaagactt   3300
atgaaaaagc agagctagca gacttggttg atcatcaaaa aagaaataat gagccggttt   3360
tactgccgat ttatcatacg agtttaaagt caaatggtaa aaatatcatt tcagtgaaac   3420
ttgacaaaga tggccagttt cacaaggcag aatttatggc agataagcaa atgattattt   3480
ttcctgtaac ggctgattct gttgctaggt caggtagtca tcctgcaccg catcccctag   3540
tcgataaatt tgcttattat agtgctgaaa tggggcagat tcagtatgat tcttttcata   3600
agcaactgaa taactggatt gattattgtg aggagggtga tgtcaagaaa tttttaacct   3660
ttgttcagca gttcattttg aagccagaat ttctaacatt gattcttgat tctttaattg   3720
gtcctgatta tcaacataat caattaaaag tcacattttg tgatgccact ggaaaagaaa   3780
aattaattga tttatcagct tgctttttag aattttcaat tgatcagttc cagggcttta   3840
aaaatgaatc ggtttcgaca tttaaagcct tacaccaatc ctatatttct tttgttgaag   3900
ccaatcgtga aaatctcggt atttgtaata ttagtggacg agaggaacag cttaccgata   3960
agcatagagg tttgatgggg aatgctaaaa tcatctctgt tagtaataaa agagaagctt   4020
ataaaggacg ttttagagaa cgcgaagacg tttttagtgt tggctatgaa acttccgaaa   4080
agattcattt aatgctcaag taccttttag aaaataaaaa taccagtact tggttagggt   4140
cttctcaata tttaatcaac tggttcagcg atgatttaac aaatgatagt cggttggata   4200
ttgtatcacc aatctttgat gatggacttg aagaagatga tgatgacgat acgcctcctg   4260
ttataacatt agcaactgaa gacaataaaa gaattggtaa atcattcatc aagggacaaa   4320
aattatttgc taatgatgcc acttactacg ttgctatttt gaataaaacc agcaatgggc   4380
ggattgcttt aaaatatttt cgtcagcttc aagcgtccca attactcacc aatcttaaca   4440
agtggcagga aacatacagt tgggagtcgc gatctaagtt tgggaaaagt cgcttaagaa   4500
cccctacttt tcatgacatc cttaatgtgt cctacggggt tgatagggat cgcttccttg   4560
aattagataa tgataacttc aaaagtgatc aaattcaaaa gttagtggca agtttgattg   4620
atggtaaacc gatgccacag tccattgtca aaaagttagg taacaatgtt aaagaacgac   4680
atcgttaccg taagcactgg tatcaagttg agcaggtctg cttagcaatt ttacacaaac   4740
aaaatgggga ggaattttca ccgatgctag atcataccaa tcaaaatcgt tcctatcttt   4800
ttggacgatt attagcaatt tttgaattaa tcgagacctt gcgttatggc ttggatggaa   4860
```

-continued

```
acaataacga ccgtattacc aatgctgaac gttattggac agcctatact ggacaaccaa   4920
caaaattgat gatgttattg gaaaataaaa ttaagcctta cgaagaacca ttgaaattaa   4980
atcgtcgtgg cagttggatg aaattagaaa aagaaaaaga agagatttta gaactgttaa   5040
atcctctgtt agaaacagaa acaatggaaa aaccccttaga ttaccgcttt atttttgggt   5100
attatgctga gaaaaactat tactatacaa aacaaaacac ggaagtaaca gaaagtgagg   5160
agtaaaaaga tgttggaaca caaaattgat tttatggtaa ctcttgaagt gaaagaagca   5220
aatgcaaatg gtgatccctt aaatggaaac atgcctcgta cagatgccaa aggatatggt   5280
gtgatgagtg atgtctccat taaacgtaag attcgtaatc gtttgcaaga tatggggaag   5340
tctattttg tgcaagctaa tgagcgtatt gaagatgatt ttcgttcact ggaaaaacgc   5400
ttttcgcaac attttacagc taagacacct gacaaagaaa ttgaagaaaa agcaaatgca   5460
ttatggtttg atgttcgtgc ttttggacaa gtttttactt atctgaaaaa atcaattggg   5520
gtgcgtggac cagtttccat cagtatggct aagtccttgg agccaattgt catttccagc   5580
cttcaaatta cgcgtagtac caatggtatg gaagctaaga ataatagtgg ccgctcttct   5640
gatacgatgg ggacaaaaca ttttgtagat tatggtgtgt atgtacttaa aggttctatc   5700
aatgcttatt ttgctgaaaa gactggtttt tctcaggaag atgctgaggc tattaaagaa   5760
gttttggtta gcttgtttga aaatgatgcg tcgtctgcac gtccggaagg ctctatgcga   5820
gtttgtgaag tcttttggtt tacgcattca agcaaattgg gaaatgtttc aagtgcgcgt   5880
gtctttgact tgttagagta tcatcaatca atagaagaaa aaagcactta tgacgcttat   5940
cagattcatc taaatcaaga aaaattggct aaatatgaag cgaaagggtt aacgcttgaa   6000
atcctagaag gactctagta tggtctatgc cgaagatgat tatttaatgc tgtcaggtat   6060
tcagcatttc caattttgta aacgtcaatg ggcgttgatc catattgagc aacaatggct   6120
tgataatgaa gcgacagcgc atggacaggt tttacatact aaagcagata acccttacat   6180
taaagaaaaa cgaaaagagc ttttggtctc acgtgctatg cccatttctt ctgcagaact   6240
tggactttca ggaattatgg atgttgtgga attttataaa gatgatcaag gtgtgtcttt   6300
gaggggaaaa cgtgggaaat ggttaccaaa agttgtggaa tacaagcgcg gaaaacctaa   6360
aaaagatacc agagatattg tccagttggt ggctcagacc atgtgtttag aagaaacgct   6420
agactgcgac attaacgaag gttgtcttta ttaccatagt gtcaatcaaa gagtgattgt   6480
tcctatgaca tcagctttgc gtcaagaagt gaaggaatta gccgcagaga tgcatgaggt   6540
ttatcagagt caaatgctac ctaaagcagc ttattttaaa aactgtcagc tttgttcttt   6600
agtcgatatt tgtaagccca ggttgagtaa aaaaacaagg agtgtgtcgc gttacatcaa   6660
tgaggctatg accagtgagg agatggacct atgaagaagt tgctaaatac cttgtatttg   6720
acgcaagaag atttttatgt cactaaagag ggcgataaca ttgttatcaa gcaagaaggt   6780
aaggttctca aacggtttcc gtttcggatt attgacggta ttgtctgttt ttcttatttg   6840
ggtgtgtcgt ctgctttggt gaagttatgt acggagaatc agattaattt atcgtttcat   6900
acaccacaag ggcgtttttg tggtcgctat attggttcaa ccaatgggaa tgtgttgttg   6960
cgtagagaac attatcgttt atctgatcgt gaggaatctt tggaatacgc aaagcggttt   7020
attttggcta aaatttccaa ctcaaggaaa tacttgctac gctttaaacg agatcatcgt   7080
caacagattg ataccaagct tttgaggct gttaatgacg aattgatatg ggctttagag   7140
atggttcagg cagcagataa taaagactct ttaagaggga ttgaaggcca agctgctaat   7200
```

-continued

```
cagtattttc gcatatttaa tgacctggtg ttgacggaca aaaaaacgtt ttacttccaa   7260

ggtcggagta aacgaccacc cttagattgt gttaatgccc tcttgtcttt tggttacagt   7320

ttactgacct ttgaatgtca atctgccttg gaagctgtcg gattagacag ttacgttggt   7380

ttctttcaca cggatcgtcc tgggcgtgct agtttagcgc ttgatttagt tgaagagttc   7440

cgctcatata ttgtagatcg ttttgtcttt tcattaatta ataaaggaca acttcagaaa   7500

aaacactttg aggttaaaga aaatggtagt attttattga cggaaaatgg cagagctatt   7560

tttattgatt tgtggcagaa gcgtaagcat actgaggtag aacatccttt tacaaaagag   7620

aaagtaaaac ttatgttatt accctatgta caagcgcagc ttttagctaa ggctatacga   7680

ggagatttag aaagctatcc accttttatg gtttaggaga tgttatatga tggttttagt   7740

cacttatgat gtaaatacgg aaacacctgc tggtagaaaa agattgcgtc atgttgccaa   7800

actctgtgtg gactatgggc aacgtgttca aaattctgtt tttgaatgtt ctgtgacacc   7860

cgcagaattt gtggatataa agcaccgctt aacacaaatc attgatgaga aaactgatag   7920

tattcgcttt tatttattgg ggaaaaattg gcagaggcgt gtggaaacac ttggtcgctc   7980

agacagctat gacccagata aaggtgtctt attattgtaa                         8020
```

<210> SEQ ID NO 510
<211> LENGTH: 2409
<212> TYPE: DNA
<213> ORGANISM: Streptococcus pyogenes

<400> SEQUENCE: 510

```
atgagaatga ttttagcaca ctatgactgt aaaaaagata aaaagcaatc tttagatgag     60

catttatggc atgtggcctg ttctagtcga caggaagcat ctataattgg tcaaggagat    120

gtgctttttt taattggtct ttaccacgac ctgggcaaag ctgatcgaac ctttcaagat    180

aaattattaa ataatccaaa tcggcatgtt gatcactctt atgcaggggc aaaatactta    240

tgttctatta ttgggcctca tctaaaaaac cgaggggttg ataaaaatga gagaatgaca    300

ttcaacgaaa tggtggggta tgtcatctct gctcatcatg ggatgtatga tttatgctac    360

tattttgacg atgctgaata ttatggcttt aataagttta aaaatcgtat caatagagac    420

ttagatggtt atcactatca tgaagatatt aaagggtacg ctctaaaatt agaaaaaaaa    480

ttatgtgatt atggctacaa agatttaagg gagcttattg ataaagcttt tgataattac    540

caacaagcca tgtcttcctt aaactggcaa gataagagtg agtgggatta ttatcagtct    600

tgtatggtga gactttactt gtcactctta aaaaacgctg atattttgga cacagtaaat    660

gcctatggcc ttaagataag tcctatggat aaaacagagc gatcctttct aaaacactcc    720

tatttagcgg ccattgaaca aaaatatgct agctttggac agccaaacaa tcagttgaac    780

actattcgga cagaaatcgc tgagcgtgtt aaagaaagag gtaaacgaga ttccaagggg    840

atttatcgct tagatttacc gacaggagct ggcaagacta atcttagtat gcgttatgcg    900

tttcaccaat tagttcatca cgacaaatca aggttttttt acataactcc ctttctttcg    960

gttcttgagc aaaatgcttc cgaaattaga aaagttacag gtgaccttgg cgttctagaa   1020

caccattcca atgtggtgaa acaggctaat gaagatgatg atgataagga cagtttattg   1080

tcagcttatc ttagtgatag ctgggacagt caagtagtct tgacttctat ggttcaattt   1140

ttccaaacac ttttcaaaac aaaatcagct aatctgagac gtttttcaag tttgattaat   1200

agtgttgtga ttctagatga agttcaatcc ctgcctattg aagtcaccac tttgtttaat   1260

ttaacgatga attttttaaa taaagttatg gatacaacca tcgttctttg cacagcgaca   1320
```

caacctgctt atgattcttc agagattgac catcgtatct gttatggagg gaacttggga 1380
gaattagctg aaatagttga gttaacgatt gaagaaaaac agatttttc aaggacagag 1440 cttagaaaat ttgatgatag tgatcagaaa gttcacttga ctgatgttat taaccttatt 1500
ctaggtgagg aaaactcagt tcttgctatt tttaatacga aaaaaacggt tcataactgc 1560
tatactatgc taaaagacat gactgataga ccggtctatc agctttcgac aaatatgtgt 1620
gcgcagcata gacttgactt gattgctaag atcaaaacgg agttacaaaa taatatccct 1680
attatttgta ttagcacgca attaattgaa gcaggtgtag atgttgattt tcatcgcgtc 1740
attcgttcct actcagggat tgattctatt gttcaggctg ctggacggtg taaccgagaa 1800
ggcaaacgag ataaagggca agtcactctt gtcaatctga ccaatgaaga ggaaaatatt 1860
tctaggctga cagaaataaa aactaaaaaa gaagccacag aatctattct tcataagatt 1920
gggtctccaa ttgatatctc aactttaaac cgtgactttt ttgagtatta ttatgccaat 1980
aatcagggac tgatggatta tcctttggaa gacaacctat caatctacga ctatttaagc 2040
cttaatattt atcagacggc aaataaaaag ttcaaaggta agttaaaaca agcttttaaa 2100
acagcaggag ccaaaatgaa cctcatcaat aatgatatga taggaattct cgtaccttat 2160
ggcgaagctg agaaaaaatt ggcttattta gaagaattag gtgtgtcaca ttttttatca 2220
gcaaaagatt atcaaacgat aaaatcatta ctaaaagagt tacaaccttt tacggttaat 2280
gtccgcgaga acgatcctct ctttgagaca acaaaatctt atctaaatgg tcagattctg 2340
gttttgacgt cggagtatta tgacacggaa agaggagtta aatacgattc agctagcttt 2400
tacttctaa 2409

<210> SEQ ID NO 511
<211> LENGTH: 729
<212> TYPE: DNA
<213> ORGANISM: Streptococcus pyogenes

<400> SEQUENCE: 511
ttgtacagat ctagagactt ctacgtgaga gtaagtggtc agcgagctct ttttacaaat 60
ccagccacaa aagggggatc ggaacgctca tcctattcgg ttccgactag acaggcactg 120
aatggtatcg ttgatgccat ctattataag ccgaccttta ctaatatcgt cacagaggtt 180
aaggttatta accagattca aaccgaatta cagggtgtca gggctctgtt acatgattat 240
agtgcagatt taagttatgt atcctatttg agtgatgttg tttatctgat caagtttcat 300
tttgtttgga atgaagatag aaaagatttg aactcagata gacttccagc taaacatgaa 360
gccattatgg agcgttctat tcgtaaaggg ggacgtcgag atgtgttttt gggtacaaga 420
gaatgtttag ggcttgtaga tgatatcagc caagaagagt atgagactac tgtgtcgtat 480
tataatggtg tcaatatcga cttgggaatc atgttccatt cctttgccta tccgaaggac 540
aaaaagacac cattaaaatc atactttaca aagactgtga tgaaaaatgg agtcattacg 600
tttaaagcac agtctgaatg cgatattgtt aacacgcttt ctagttatgc ttttaaagca 660
ccagaggaga taaaatcggt taacgatgaa tgcatggagt atgatgccat ggagaaagga 720
gaaaactga 729

<210> SEQ ID NO 512
<211> LENGTH: 1896
<212> TYPE: DNA
<213> ORGANISM: Streptococcus pyogenes -continued

<400> SEQUENCE: 512
atggattttt ttacttctct cttgaagact tatgaaaaag cagagctagc agacttggtt 60
gatcatcaaa aaagaaataa tgagccggtt ttactgccga tttatcatac gagtttaaag 120
tcaaatggta aaaatatcat ttcagtgaaa cttgacaaag atggccagtt tcacaaggca 180
gaatttatgg cagataagca aatgattatt tttcctgtaa cggctgattc tgttgctagg 240
tcaggtagtc atcctgcacc gcatccccta gtcgataaat ttgcttatta tagtgctgaa 300
atggggcaga ttcagtatga ttcttttcat aagcaactga ataactggat tgattattgt 360
gaggagggtg atgtcaagaa atttttaacc tttgttcagc agttcatttt gaagccagaa 420
tttctaacat tgattcttga ttctttaatt ggtcctgatt atcaacataa tcaattaaaa 480
gtcacatttt gtgatgccac tggaaaagaa aaattaattg atttatcagc ttgcttttta 540
gaattttcaa ttgatcagtt ccagggcttt aaaaatgaat cggtttcgac atttaaagcc 600
ttacaccaat cctatatttc ttttgttgaa gccaatcgtg aaaatctcgg tatttgtaat 660
attagtggac gagaggaaca gcttaccgat aagcatagag gtttgatggg gaatgctaaa 720
atcatctctg ttagtaataa aagagaagct tataaaggac gttttagaga acgcgaagac 780
gtttttagtg ttggctatga aacttccgaa aagattcatt taatgctcaa gtacctttta 840
gaaaataaaa ataccagtac ttggttaggg tcttctcaat atttaatcaa ctggttcagc 900
gatgatttaa caaatgatag tcggttggat attgtatcac caatctttga tgatggactt 960
gaagaagatg atgatgacga tacgcctcct gttataacat tagcaactga agacaataaa 1020
agaattggta aatcattcat caagggacaa aaattatttg ctaatgatgc cacttactac 1080
gttgctattt tgaataaaac cagcaatggg cggattgctt taaaatattt tcgtcagctt 1140
caagcgtccc aattactcac caatcttaac aagtggcagg aaacatacag ttgggagtcg 1200
cgatctaagt ttgggaaaag tcgcttaaga acccctactt ttcatgacat ccttaatgtg 1260
tcctacgggg ttgataggga tcgcttcctt gaattagata atgataactt caaaagtgat 1320
caaattcaaa agttagtggc aagtttgatt gatggtaaac cgatgccaca gtccattgtc 1380
aaaaagttag gtaacaatgt taaagaacga catcgttacc gtaagcactg gtatcaagtt 1440
gagcaggtct gcttagcaat tttacacaaa caaaatgggg aggaattttc accgatgcta 1500
gatcatacca atcaaaatcg ttcctatctt tttggacgat tattagcaat ttttgaatta 1560
atcgagacct tgcgttatgg cttggatgga aacaataacg accgtattac caatgctgaa 1620
cgttattgga cagcctatac tggacaacca acaaaattga tgatgttatt ggaaaataaa 1680
attaagcctt acgaagaacc attgaaatta aatcgtcgtg gcagttggat gaaattagaa 1740
aaagaaaaag aagagatttt agaactgtta aatcctctgt tagaaacaga aacaatggaa 1800
aaacccttag attaccgctt tatttttggg tattatgctg agaaaaacta ttactataca 1860
aaacaaaaca cggaagtaac agaaagtgag gagtaa 1896

<210> SEQ ID NO 513
<211> LENGTH: 849
<212> TYPE: DNA
<213> ORGANISM: Streptococcus pyogenes

<400> SEQUENCE: 513
atgttggaac acaaaattga ttttatggta actcttgaag tgaaagaagc aaatgcaaat 60
ggtgatccct taaatggaaa catgcctcgt acagatgcca aaggatatgg tgtgatgagt 120
gatgtctcca ttaaacgtaa gattcgtaat cgtttgcaag atatggggaa gtctattttt 180
gtgcaagcta atgagcgtat tgaagatgat tttcgttcac tggaaaaacg cttttcgcaa 240
cattttacag ctaagacacc tgacaaagaa attgaagaaa aagcaaatgc attatggttt 300
gatgttcgtg cttttggaca agtttttact tatctgaaaa aatcaattgg ggtgcgtgga 360
ccagtttcca tcagtatggc taagtccttg gagccaattg tcatttccag ccttcaaatt 420
acgcgtagta ccaatggtat ggaagctaag aataatagtg gccgctcttc tgatacgatg 480
gggacaaaac attttgtaga ttatggtgtg tatgtactta aaggttctat caatgcttat 540
tttgctgaaa agactggttt ttctcaggaa gatgctgagg ctattaaaga agttttggtt 600
agcttgtttg aaaatgatgc gtcgtctgca cgtccggaag gctctatgcg agtttgtgaa 660
gtcttttggt ttacgcattc aagcaaattg ggaaatgttt caagtgcgcg tgtctttgac 720
ttgttagagt atcatcaatc aatagaagaa aaaagcactt atgacgctta tcagattcat 780
ctaaatcaag aaaaattggc taaatatgaa gcgaaagggt taacgcttga aatcctagaa 840
ggactctag 849

<210> SEQ ID NO 514
<211> LENGTH: 675
<212> TYPE: DNA
<213> ORGANISM: Streptococcus pyogenes

<400> SEQUENCE: 514
atggtctatg ccgaagatga ttatttaatg ctgtcaggta ttcagcattt ccaattttgt 60
aaacgtcaat gggcgttgat ccatattgag caacaatggc ttgataatga agcgacagcg 120
catggacagg ttttacatac taaagcagat aacccttaca ttaaagaaaa acgaaaagag 180
cttttggtct cacgtgctat gcccatttct tctgcagaac ttggactttc aggaattatg 240
gatgttgtgg aattttataa agatgatcaa ggtgtgtctt tgaggggaaa acgtgggaaa 300
tggttaccaa aagttgtgga atacaagcgc ggaaaaccta aaaaagatac cagagatatt 360
gtccagttgg tggctcagac catgtgttta gaagaaacgc tagactgcga cattaacgaa 420
ggttgtcttt attaccatag tgtcaatcaa agagtgattg ttcctatgac atcagctttg 480
cgtcaagaag tgaaggaatt agccgcagag atgcatgagg tttatcagag tcaaatgcta 540
cctaaagcag cttattttaa aaactgtcag ctttgttctt tagtcgatat ttgtaagccc 600
aggttgagta aaaaaacaag gagtgtgtcg cgttacatca atgaggctat gaccagtgag 660
gagatggacc tatga 675

<210> SEQ ID NO 515
<211> LENGTH: 1026
<212> TYPE: DNA
<213> ORGANISM: Streptococcus pyogenes

<400> SEQUENCE: 515
atgaagaagt tgctaaatac cttgtatttg acgcaagaag atttttatgt cactaaagag 60
ggcgataaca ttgttatcaa gcaagaaggt aaggttctca aacggtttcc gtttcggatt 120
attgacggta ttgtctgttt ttcttatttg ggtgtgtcgt ctgctttggt gaagttatgt 180
acggagaatc agattaattt atcgtttcat acaccacaag ggcgtttttg tggtcgctat 240
attggttcaa ccaatgggaa tgtgttgttg cgtagagaac attatcgttt atctgatcgt 300
gaggaatctt tggaatacgc aaagcggttt attttggcta aaatttccaa ctcaaggaaa 360
tacttgctac gctttaaacg agatcatcgt caacagattg ataccaagct tttgaggct 420 gttaatgacg aattgatatg ggctttagag atggttcagg cagcagataa taaagactct 480
ttaagaggga ttgaaggcca agctgctaat cagtattttc gcatatttaa tgacctggtg 540
ttgacggaca aaaaaacgtt ttacttccaa ggtcggagta aacgaccacc cttagattgt 600
gttaatgccc tcttgtcttt tggttacagt ttactgacct ttgaatgtca atctgccttg 660
gaagctgtcg gattagacag ttacgttggt ttctttcaca cggatcgtcc tgggcgtgct 720
agtttagcgc ttgatttagt tgaagagttc cgctcatata ttgtagatcg ttttgtcttt 780
tcattaatta ataaaggaca acttcagaaa aaacactttg aggttaaaga aaatggtagt 840
attttattga cggaaaatgg cagagctatt tttattgatt tgtggcagaa gcgtaagcat 900
actgaggtag aacatccttt tacaaaagag aaagtaaaac ttatgttatt accctatgta 960
caagcgcagc ttttagctaa ggctatacga ggagatttag aaagctatcc accttttatg 1020
gtttag 1026

<210> SEQ ID NO 516
<211> LENGTH: 294
<212> TYPE: DNA
<213> ORGANISM: Streptococcus pyogenes

<400> SEQUENCE: 516
atgatggttt tagtcactta tgatgtaaat acggaaacac ctgctggtag aaaaagattg 60
cgtcatgttg ccaaactctg tgtggactat gggcaacgtg ttcaaaattc tgtttttgaa 120
tgttctgtga cacccgcaga atttgtggat ataaagcacc gcttaacaca aatcattgat 180
gagaaaactg atagtattcg cttttattta ttggggaaaa attggcagag gcgtgtggaa 240
acacttggtc gctcagacag ctatgaccca gataaaggtg tcttattatt gtaa 294

<210> SEQ ID NO 517
<211> LENGTH: 5966
<212> TYPE: DNA
<213> ORGANISM: Streptococcus pyogenes

<400> SEQUENCE: 517
atggataaga aatactcaat aggcttagat atcggcacaa atagcgtcgg atgggcggtg 60
atcactgatg attataaggt tccgtctaaa aagctcaagg gtctgggaaa tacagaccgc 120
cacggtatca aaaaaaatct tataggggct cttttatttg acagtggaga gacagcggaa 180
gcgactcgtc tcaaacggac agctcgtaga aggtatacac gtcggaagaa tcgtatttgt 240
tatctacagg agattttttc aaatgagatg gcgaaagtag atgatagttt ctttcatcga 300
cttgaagagt cttttttggt ggaagaagac aagaagcatg aacgtcatcc tatttttgga 360
aatatagtag atgaagttgc ttatcatgag aaatatccaa ctatctatca tctgcgaaaa 420
aaattggcag attctactga taaagtggat ttgcgcttaa tctatttggc cttagcgcat 480
atgattaagt ttcgtggtca tttttttgatt gagggagatt taaatcctga taatagtgat 540
gtggacaaac tatttatcca gttggtacaa acctacaatc aattatttga agaaaaccct 600
attaacgcaa gtagagtaga tgctaaagcg attctttctg cacgattgag taaatcaaga 660
cgattagaaa atctcattgc tcagctcccc ggtgagaaga aaaatggatt gtttgggaat 720
ctcattgctt tgtcattggg attgacccct aattttaaat caaattttga tttggcagaa 780
gatgctaaat tacagctttc aaaagatact tacgatgatg atttagataa tttattggcg 840
caaattggag atcaatatgc tgatttgttt ttggcagcta agaatttatc agatgctact 900
ttactttcag atatcctaag agtaaatagt gaaataacta aggctcccct atcagcttca 960

-continued

```
atgattaagc gctacgatga acatcatcaa gacttgactc ttttaaaagc tttagttcga   1020
caacaacttc cagaaaagta taaagaaatc ttttttgatc aatcaaaaaa cggatatgca   1080
ggttatattg atgggggagc tagccaagaa gaattttata aatttatcaa accaatttta   1140
gaaaaaatgg atggtactga ggaattattg gcgaaactaa atcgtgaaga tttgctgcgc   1200
aagcaacgga cctttgacaa cggctctatt ccctatcaaa ttcacttggg tgagctgcat   1260
gctattttga gaagacaaga agacttttat ccatttttaa aagacaatcg tgagaagatt   1320
gaaaaaatct tgacttttcg aattccttat tatgttggtc cattggcgcg tggcaatagt   1380
cgttttgcat ggatgactcg gaagtctgaa gaaacaatta ccccatggaa ttttgaagaa   1440
gttgtcgata aaggtgcttc agctcaatca tttattgaac gcatgacaaa ctttgataaa   1500
aatcttccaa atgaaaaagt actaccaaaa catagtttgc tttatgagta ttttacggtt   1560
tataacgaat tgacaaaagt caaatatgtt actgagggaa tgcgaaaacc agcatttctt   1620
tcaggtgaac agaagaaagc cattgttgat ttactcttca aaacaaatcg aaaagtaacc   1680
gttaagcaat taaaagaaga ttatttcaaa aaaatagaat gttttgatag tgttgaaatt   1740
tcaggagttg aagatagatt taatgcttca ttaggtacct accatgattt gctaaaaatt   1800
attaaagata aagatttttt ggataatgaa gaaaacgaag atatcttaga ggatattgtt   1860
ttaacattga ccttatttga agatagggag atgattgagg aaagacttaa aacatatgct   1920
cacctctttg atgataaggt gatgaaacag cttaaacgtc gccgttatac tggttgggga   1980
cgtttgtctc gaaaattgat taatggtatt agggataagc aatctggcaa aacaatatta   2040
gatttttga aatcagatgg ttttgccaat cgcaatttta tgcagctgat ccatgatgat   2100
agtttgacat ttaaagaaga cattcaaaaa gcacaagtgt ctggacaagg cgatagttta   2160
catgaacata ttgcaaattt agctggtagc cctgctatta aaaaaggtat tttacagact   2220
gtaaaagttg ttgatgaatt ggtcaaagta atggggcggc ataagccaga aaatatcgtt   2280
attgaaatgg cacgtgaaaa tcagacaact caaaagggcc agaaaaattc gcgtgagcgt   2340
atgaaacgta ttgaagaagg aataaaagaa ctaggaagtg atattctaaa ggagtatcct   2400
gttgaaaaca ctcaattaca aaatgaaaag ctctatctct attatctcca aaatggaaga   2460
gacatgtatg tggaccaaga attagatatt aatcgtttaa gtgattatga tgtcgatcac   2520
attgttccac aaagtttcct taaagacgat tcaatagaca ataaggtctt aacgcgttct   2580
gataaaaatc gtggtaaatc ggataacgtt ccaagtgaag aagtagtcaa aaagatgaaa   2640
aactattgga gacaacttct aaacgccaag ttaatcactc aacgtaagtt tgataattta   2700
acaaaagctg aacgtggagg tttgagtgaa cttgataaag ttggttttat caaacgccaa   2760
ttggttgaaa ctcgccaaat cactaagcat gtggcacaaa ttttggatag tcgcatgaat   2820
actaaatacg atgaaaatga taaacttatt cgagaggtta gagtgattac cttaaaatct   2880
aaattagttt ctgacttccg aaaagatttc caattctata aagtacgtga gattaacaat   2940
taccatcatg cccatgatgc gtatcttaat gccgtcgttg gaactgcttt gattaagaaa   3000
tatccaaaac ttgaatcgga gtttgtctat ggtgattata aagtttatga tgttcgtaaa   3060
atgattgcta agtctgagca ggaaataggc aaagcaaccg caaaatattt cttttactct   3120
aatatcatga acttcttcaa aacagaaatt acacttgcaa atggagagat tcgcaaacgc   3180
cctctaatcg aaactaatgg ggaaactgga gaaattgtct gggataaagg gcgagatttt   3240
gccacagtgc gcaaagtatt gtccatgccc caagtcaata ttgtcaagaa aacagaagta   3300
```

-continued

```
cagacaggcg gattctccaa ggagtcaatt ttaccaaaaa gaaattcgga caagcttatt   3360
gctcgtaaaa aagactggga tccaaaaaaa tatggtggtt ttgatagtcc aacggtagct   3420
tattcagtcc tagtggttgc taaggtggaa aaagggaaat cgaagaagtt aaaatccgtt   3480
aaagagttac tagggatcac aataatggaa agaagctctt ttgaaaaaga tccgattgac   3540
tttttagaag ctaaaggata taaggaagtt agaaaagact taatcattaa actacctaaa   3600
tatagtcttt ttgagttaga aaacggtcgt aaacggatgc tggctagtgc cggagaattg   3660
caaaaaggaa atgagctagc tctgccaagc aaatatgtga atttttata tttagctagt   3720
cattatgaaa agttgaaggg tagtccagaa gataacgaac aaaaacaatt gtttgtggag   3780
cagcataagc attatttaga tgagattatt gagcaaatca gtgaattttc taagcgtgtt   3840
attttagcag atgccaattt agataaagtt cttagtgcat ataacaaaca tagagacaaa   3900
ccaatacgtg aacaagcaga aaatattatt catttattta cgttgacgaa tcttggagct   3960
cccgctgctt ttaaatattt tgatacaaca attgatcgta aacgatatac gtctacaaaa   4020
gaagttttag atgccactct tatccatcaa tccatcactg gtctttatga aacacgcatt   4080
gatttgagtc agctaggagg tgactgatgg ctggttggcg tactgttgtg gtaaataccc   4140
actcgaaatt atcctataag aataatcatc tgatttttaa ggatgcctat aaaacggagc   4200
tgatccattt atcagaaatt gatattttgt tattagaaac gaccgatatt gtcttgtcca   4260
ctatgctggt aaaacggcta gtggatgaga atgtccttgt catattctgt gatgataaac   4320
gattaccaac agctatgctg atgccttttt atggtcgtca tgattcgagt ttacagcttg   4380
ggaaacaaat gtcctggtca gaaacagtca aatcgcaggt ttggacgacg attattgctc   4440
aaaagatttt gaatcaatct tgctatctag gagcatgctc ctatttgaa aaatcccaat   4500
ctattatgga tttatatcat ggtttggaaa attttgatcc gagtaatcga gaagggcatg   4560
cagcgagaat ttattttaat acacttttg ggaacgattt ctcaagagat ttggagcatc   4620
caatcaatgc aggtctggat tatggttata ctttattatt gagtatgttt gcgcgtgaag   4680
tggttgtgtc tggatgtatg actcaatttg gactcaaaca cgccaatcag tttaatcagt   4740
tcaattttgc tagcgatatt atggaaccat ttaggccttt ggtggataag attgtttatg   4800
aaaatcgaaa tcagcctttt cccaaaataa agagagagtt atttactttg ttttcagata   4860
cattttcata taatggtaaa gagatgtatc tcacgaatat tattagcgat tatactaaaa   4920
aagttgtcaa agctctgaat aatgaaggga aaggagttcc tgaatttagg atatgagtta   4980
tagatatatg agaatgatac ttatgtttga tatgccgacg gacactgctg aggaacgaaa   5040
agcttatcga aaatttcgga aatttttact tagtgaaggg tttatcatgc atcaattttc   5100
tatttatagt aagttactgt tgaataatac agctaacaac gccatgattg gtcggctgag   5160
ggagcataat cctcataaag gaaatattac attactaaca gtcacagaaa aacagtttgc   5220
acgaatgatt tatttacatg gtgaaagaaa taattgtatt gcaaactccg atgagagact   5280
tgtatttctt ggggaggctt ttgatgaatc ttaattttcc cttattagat gaaccgattc   5340
cattaagagg cggtacaatt cttgtgctcg aagatgtctg tgtattttca aaaatagtgc   5400
aatattgtta caaatatgag gaagattctg aacttaaatt ttttgatcac aagatgaaaa   5460
ccatcaaaga atcagaaatc atgcttgtaa cagatatttt aggatttgat gttaactcct   5520
caaccatttt aaaattgatt catgcagatt tagaatctca atttaatgag aaacccgaag   5580
tgaaatcgat gattgacaaa ttggttgcta cgattacaga actgattgtc tttgaatgct   5640
tagaaaatga attagattta gagtatgatg aaatcacaat cctggaattg attaagtcct   5700
```

taggagtaaa agtagaaacg caaagtgata ctatttttga aaaatgtcta gagatacttc 5760
aaattttcaa atatctcact aagaaaaagt tgcttatttt tgtcaatagc ggagcttttc 5820
taacaaagga tgaagtggct agtttacaag agtatatatc attgacaaat ttaacagttc 5880
tctttttaga accacgtgaa ctatatgatt ttccgcagta tattttagat gaagattatt 5940
tcttaataac taaaaatatg gtataa 5966

<210> SEQ ID NO 518
<211> LENGTH: 4107
<212> TYPE: DNA
<213> ORGANISM: Streptococcus pyogenes

<400> SEQUENCE: 518
atggataaga aatactcaat aggcttagat atcggcacaa atagcgtcgg atgggcggtg 60
atcactgatg attataaggt tccgtctaaa aagctcaagg gtctgggaaa tacagaccgc 120
cacggtatca aaaaaaatct tataggggct cttttatttg acagtggaga gacagcggaa 180
gcgactcgtc tcaaacggac agctcgtaga aggtatacac gtcggaagaa tcgtatttgt 240
tatctacagg agatttttc aaatgagatg gcgaaagtag atgatagttt ctttcatcga 300
cttgaagagt cttttttggt ggaagaagac aagaagcatg aacgtcatcc tatttttgga 360
aatatagtag atgaagttgc ttatcatgag aaatatccaa ctatctatca tctgcgaaaa 420
aaattggcag attctactga taaagtggat ttgcgcttaa tctatttggc cttagcgcat 480
atgattaagt ttcgtggtca tttttgatt gagggagatt taaatcctga taatagtgat 540
gtggacaaac tatttatcca gttggtacaa acctacaatc aattatttga agaaaaccct 600
attaacgcaa gtagagtaga tgctaaagcg attctttctg cacgattgag taaatcaaga 660
cgattagaaa atctcattgc tcagctcccc ggtgagaaga aaaatggatt gtttgggaat 720
ctcattgctt tgtcattggg attgacccct aattttaaat caaattttga tttggcagaa 780
gatgctaaat tacagctttc aaaagatact tacgatgatg atttagataa tttattggcg 840
caaattggag atcaatatgc tgatttgttt ttggcagcta agaatttatc agatgctact 900
ttactttcag atatcctaag agtaaatagt gaaataacta aggctcccct atcagcttca 960
atgattaagc gctacgatga acatcatcaa gacttgactc ttttaaaagc tttagttcga 1020
caacaacttc cagaaaagta taaagaaatc ttttttgatc aatcaaaaaa cggatatgca 1080
ggttatattg atgggggagc tagccaagaa gaattttata aatttatcaa accaatttta 1140
gaaaaaatgg atggtactga ggaattattg gcgaaactaa atcgtgaaga tttgctgcgc 1200
aagcaacgga cctttgacaa cggctctatt ccctatcaaa ttcacttggg tgagctgcat 1260
gctattttga gaagacaaga agacttttat ccattttaa aagacaatcg tgagaagatt 1320
gaaaaaatct tgacttttcg aattccttat tatgttggtc cattggcgcg tggcaatagt 1380
cgttttgcat ggatgactcg gaagtctgaa gaaacaatta ccccatggaa ttttgaagaa 1440
gttgtcgata aaggtgcttc agctcaatca tttattgaac gcatgacaaa ctttgataaa 1500
aatcttccaa atgaaaaagt actaccaaaa catagtttgc tttatgagta ttttacggtt 1560
tataacgaat tgacaaaagt caaatatgtt actgagggaa tgcgaaaacc agcatttctt 1620
tcaggtgaac agaagaaagc cattgttgat ttactcttca aaacaaatcg aaaagtaacc 1680
gttaagcaat taaaagaaga ttatttcaaa aaaatagaat gttttgatag tgttgaaatt 1740
tcaggagttg aagatagatt taatgcttca ttaggtacct accatgattt gctaaaaatt 1800

-continued

```
attaaagata aagatttttt ggataatgaa gaaaacgaag atatcttaga ggatattgtt   1860
ttaacattga ccttatttga agatagggag atgattgagg aaagacttaa aacatatgct   1920
cacctctttg atgataaggt gatgaaacag cttaaacgtc gccgttatac tggttgggga   1980
cgtttgtctc gaaaattgat taatggtatt agggataagc aatctggcaa aacaatatta   2040
gatttttga aatcagatgg ttttgccaat cgcaatttta tgcagctgat ccatgatgat    2100
agtttgacat ttaaagaaga cattcaaaaa gcacaagtgt ctggacaagg cgatagttta   2160
catgaacata ttgcaaattt agctggtagc cctgctatta aaaaaggtat tttacagact   2220
gtaaaagttg ttgatgaatt ggtcaaagta atggggcggc ataagccaga aaatatcgtt   2280
attgaaatgg cacgtgaaaa tcagacaact caaaagggcc agaaaaattc gcgtgagcgt   2340
atgaaacgta ttgaagaagg aataaaagaa ctaggaagtg atattctaaa ggagtatcct   2400
gttgaaaaca ctcaattaca aaatgaaaag ctctatctct attatctcca aaatggaaga   2460
gacatgtatg tggaccaaga attagatatt aatcgtttaa gtgattatga tgtcgatcac   2520
attgttccac aaagtttcct taaagacgat tcaatagaca ataaggtctt aacgcgttct   2580
gataaaaatc gtggtaaatc ggataacgtt ccaagtgaag aagtagtcaa aaagatgaaa   2640
aactattgga gacaacttct aaacgccaag ttaatcactc aacgtaagtt tgataattta   2700
acaaaagctg aacgtggagg tttgagtgaa cttgataaag ttggttttat caaacgccaa   2760
ttggttgaaa ctcgccaaat cactaagcat gtggcacaaa ttttggatag tcgcatgaat   2820
actaaatacg atgaaaatga taaacttatt cgagaggtta gagtgattac cttaaaatct   2880
aaattagttt ctgacttccg aaaagatttc caattctata aagtacgtga gattaacaat   2940
taccatcatg cccatgatgc gtatcttaat gccgtcgttg gaactgcttt gattaagaaa   3000
tatccaaaac ttgaatcgga gtttgtctat ggtgattata aagtttatga tgttcgtaaa   3060
atgattgcta agtctgagca ggaaataggc aaagcaaccg caaaatattt cttttactct   3120
aatatcatga acttcttcaa aacagaaatt acacttgcaa atggagagat tcgcaaacgc   3180
cctctaatcg aaactaatgg ggaaactgga gaaattgtct gggataaagg gcgagatttt   3240
gccacagtgc gcaaagtatt gtccatgccc caagtcaata ttgtcaagaa aacagaagta   3300
cagacaggcg gattctccaa ggagtcaatt ttaccaaaaa gaaattcgga caagcttatt   3360
gctcgtaaaa aagactggga tccaaaaaaa tatggtggtt ttgatagtcc aacggtagct   3420
tattcagtcc tagtggttgc taaggtggaa aaagggaaat cgaagaagtt aaaatccgtt   3480
aaagagttac tagggatcac aataatggaa agaagctctt ttgaaaaaga tccgattgac   3540
tttttagaag ctaaaggata taaggaagtt agaaaagact taatcattaa actacctaaa   3600
tatagtcttt ttgagttaga aaacggtcgt aaacggatgc tggctagtgc cggagaattg   3660
caaaaaggaa atgagctagc tctgccaagc aaatatgtga atttttata tttagctagt    3720
cattatgaaa agttgaaggg tagtccagaa gataacgaac aaaaacaatt gtttgtggag   3780
cagcataagc attatttaga tgagattatt gagcaaatca gtgaattttc taagcgtgtt   3840
attttagcag atgccaattt agataaagtt cttagtgcat ataacaaaca tagagacaaa   3900
ccaatacgtg aacaagcaga aaatattatt catttattta cgttgacgaa tcttggagct   3960
cccgctgctt ttaaatattt tgatacaaca attgatcgta aacgatatac gtctacaaaa   4020
gaagttttag atgccactct tatccatcaa tccatcactg gtctttatga aacacgcatt   4080
gatttgagtc agctaggagg tgactga                                       4107
```

<210> SEQ ID NO 519
<211> LENGTH: 870
<212> TYPE: DNA
<213> ORGANISM: Streptococcus pyogenes

<400> SEQUENCE: 519
atggctggtt ggcgtactgt tgtggtaaat acccactcga aattatccta taagaataat 60
catctgattt ttaaggatgc ctataaaacg gagctgatcc atttatcaga aattgatatt 120
ttgttattag aaacgaccga tattgtcttg tccactatgc tggtaaaacg gctagtggat 180
gagaatgtcc ttgtcatatt ctgtgatgat aaacgattac caacagctat gctgatgcct 240
ttttatggtc gtcatgattc gagtttacag cttgggaaac aaatgtcctg gtcagaaaca 300
gtcaaatcgc aggtttggac gacgattatt gctcaaaaga ttttgaatca atcttgctat 360
ctaggagcat gctcctattt tgaaaaatcc caatctatta tggatttata tcatggtttg 420
gaaaattttg atccgagtaa tcgagaaggg catgcagcga gaatttattt taatacactt 480
tttgggaacg atttctcaag agatttggag catccaatca atgcaggtct ggattatggt 540
tatactttat tattgagtat gtttgcgcgt gaagtggttg tgtctggatg tatgactcaa 600
tttggactca aacacgccaa tcagtttaat cagttcaatt ttgctagcga tattatggaa 660
ccatttaggc ctttggtgga taagattgtt tatgaaaatc gaaatcagcc ttttcccaaa 720
ataaagagag agttatttac tttgttttca gatacatttt catataatgg taaagagatg 780
tatctcacga atattattag cgattatact aaaaaagttg tcaaagctct gaataatgaa 840
gggaaaggag ttcctgaatt taggatatga 870

<210> SEQ ID NO 520
<211> LENGTH: 327
<212> TYPE: DNA
<213> ORGANISM: Streptococcus pyogenes

<400> SEQUENCE: 520
atgagaatga tacttatgtt tgatatgccg acggacactg ctgaggaacg aaaagcttat 60
cgaaaatttc ggaaattttt acttagtgaa gggtttatca tgcatcaatt ttctatttat 120
agtaagttac tgttgaataa tacagctaac aacgccatga ttggtcggct gagggagcat 180
aatcctcata aaggaaatat tacattacta acagtcacag aaaaacagtt tgcacgaatg 240
atttatttac atggtgaaag aaataattgt attgcaaact ccgatgagag acttgtattt 300
cttggggagg cttttgatga atcttaa 327

<210> SEQ ID NO 521
<211> LENGTH: 663
<212> TYPE: DNA
<213> ORGANISM: Streptococcus pyogenes

<400> SEQUENCE: 521
atgaatctta attttccctt attagatgaa ccgattccat taagaggcgg tacaattctt 60
gtgctcgaag atgtctgtgt attttcaaaa atagtgcaat attgttacaa atatgaggaa 120
gattctgaac ttaaattttt tgatcacaag atgaaaacca tcaaagaatc agaaatcatg 180
cttgtaacag atattttagg atttgatgtt aactcctcaa ccattttaaa attgattcat 240
gcagatttag aatctcaatt taatgagaaa cccgaagtga aatcgatgat tgacaaattg 300
gttgctacga ttacagaact gattgtcttt gaatgcttag aaaatgaatt agatttagag 360
tatgatgaaa tcacaatcct ggaattgatt aagtccttag gagtaaaagt agaaacgcaa 420
agtgatacta tttttgaaaa atgtctagag atacttcaaa ttttcaaata tctcactaag 480
aaaaagttgc ttatttttgt caatagcgga gcttttctaa caaaggatga agtggctagt 540
ttacaagagt atatatcatt gacaaattta acagttctct ttttagaacc acgtgaacta 600
tatgattttc cgcagtatat tttagatgaa gattatttct taataactaa aaatatggta 660
taa 663

<210> SEQ ID NO 522
<211> LENGTH: 30
<212> TYPE: DNA
<213> ORGANISM: Streptococcus thermophilus

<400> SEQUENCE: 522
caacacattc aacagattaa tgaagaatac 30

<210> SEQ ID NO 523
<211> LENGTH: 30
<212> TYPE: DNA
<213> ORGANISM: Streptococcus thermophilus

<400> SEQUENCE: 523
tccactcacg tacaaatagt gagtgtactc 30

<210> SEQ ID NO 524
<211> LENGTH: 30
<212> TYPE: DNA
<213> ORGANISM: Streptococcus thermophilus

<400> SEQUENCE: 524
gcccttctaa ttggattacc ttccgaggtg 30

<210> SEQ ID NO 525
<211> LENGTH: 30
<212> TYPE: DNA
<213> ORGANISM: Streptococcus thermophilus

<400> SEQUENCE: 525
ctcagtcgtt actggtgaac cagtttcaat 30

<210> SEQ ID NO 526
<211> LENGTH: 30
<212> TYPE: DNA
<213> ORGANISM: Streptococcus thermophilus

<400> SEQUENCE: 526
attgtctatt acgacaacat ggaagatgat 30

<210> SEQ ID NO 527
<211> LENGTH: 31
<212> TYPE: DNA
<213> ORGANISM: Streptococcus thermophilus

<400> SEQUENCE: 527
gagtttcttt gtcagactct aacacagccg c 31

<210> SEQ ID NO 528
<211> LENGTH: 30
<212> TYPE: DNA
<213> ORGANISM: Streptococcus thermophilus

<400> SEQUENCE: 528
ttactagagc gtgtcgttaa ccactttaaa 30

<210> SEQ ID NO 529
<211> LENGTH: 30
<212> TYPE: DNA
<213> ORGANISM: Streptococcus thermophilus

<400> SEQUENCE: 529
ttcgttaaag tcacctcgtg ctagcgttgc 30

<210> SEQ ID NO 530
<211> LENGTH: 30
<212> TYPE: DNA
<213> ORGANISM: Streptococcus thermophilus

<400> SEQUENCE: 530
ataacggtag caaatataaa cctgttactg 30

<210> SEQ ID NO 531
<211> LENGTH: 30
<212> TYPE: DNA
<213> ORGANISM: Streptococcus thermophilus

<400> SEQUENCE: 531
gaagtagcca tacaagaaga tggatcagca 30

<210> SEQ ID NO 532
<211> LENGTH: 29
<212> TYPE: DNA
<213> ORGANISM: Streptococcus thermophilus

<400> SEQUENCE: 532
atgtcactga gtgtctaagc attgcgtac 29

<210> SEQ ID NO 533
<211> LENGTH: 30
<212> TYPE: DNA
<213> ORGANISM: Streptococcus thermophilus

<400> SEQUENCE: 533
tgaataagca gttcttgacg accaaccgac 30

<210> SEQ ID NO 534
<211> LENGTH: 30
<212> TYPE: DNA
<213> ORGANISM: Streptococcus thermophilus

<400> SEQUENCE: 534
tcaacaattg caacatctta taacccactt 30

<210> SEQ ID NO 535
<211> LENGTH: 30
<212> TYPE: DNA
<213> ORGANISM: Streptococcus thermophilus

<400> SEQUENCE: 535
ttacgtttga aaagaatatc aaatcaatga 30

<210> SEQ ID NO 536
<211> LENGTH: 30
<212> TYPE: DNA
<213> ORGANISM: Streptococcus thermophilus

<400> SEQUENCE: 536
gctctacgac ttcttccacg agttcctgcc 30

<210> SEQ ID NO 537
<211> LENGTH: 30
<212> TYPE: DNA
<213> ORGANISM: Streptococcus thermophilus

<400> SEQUENCE: 537
aacacagcaa gacaagagga tgatgctatg 30

<210> SEQ ID NO 538
<211> LENGTH: 30
<212> TYPE: DNA
<213> ORGANISM: Streptococcus thermophilus

<400> SEQUENCE: 538
aagtagttga tgacctctac aatggtttat 30

<210> SEQ ID NO 539
<211> LENGTH: 30
<212> TYPE: DNA
<213> ORGANISM: Streptococcus thermophilus

<400> SEQUENCE: 539
aataatttat ggtatagctt aatatcattg 30

<210> SEQ ID NO 540
<211> LENGTH: 30
<212> TYPE: DNA
<213> ORGANISM: Streptococcus thermophilus

<400> SEQUENCE: 540
aatcaatacg acaagagtta aaatggtctt 30

<210> SEQ ID NO 541
<211> LENGTH: 30
<212> TYPE: DNA
<213> ORGANISM: Streptococcus thermophilus

<400> SEQUENCE: 541
aatcgttcaa attctgtttt aggtacattt 30

<210> SEQ ID NO 542
<211> LENGTH: 30
<212> TYPE: DNA
<213> ORGANISM: Streptococcus thermophilus

<400> SEQUENCE: 542
aatgacgagg agctattggc acaacttaca 30

<210> SEQ ID NO 543
<211> LENGTH: 30
<212> TYPE: DNA
<213> ORGANISM: Streptococcus thermophilus

<400> SEQUENCE: 543
aattaagggc atagaaaggg agacaacatg 30

<210> SEQ ID NO 544
<211> LENGTH: 30
<212> TYPE: DNA
<213> ORGANISM: Streptococcus thermophilus

<400> SEQUENCE: 544
acaattcttc atccggtaac tgctcaagtg 30

<210> SEQ ID NO 545
<211> LENGTH: 30
<212> TYPE: DNA
<213> ORGANISM: Streptococcus thermophilus

<400> SEQUENCE: 545
acacttggca ggcttattac tcaacagcga 30

<210> SEQ ID NO 546
<211> LENGTH: 30
<212> TYPE: DNA
<213> ORGANISM: Streptococcus thermophilus

<400> SEQUENCE: 546
ataaactatg aaattttata atttttaaga 30

<210> SEQ ID NO 547
<211> LENGTH: 30
<212> TYPE: DNA
<213> ORGANISM: Streptococcus thermophilus

<400> SEQUENCE: 547
ataactgaag gataggagct tgtaaagtct 30

<210> SEQ ID NO 548
<211> LENGTH: 29
<212> TYPE: DNA
<213> ORGANISM: Streptococcus thermophilus

<400> SEQUENCE: 548
ataatgccgt tgaattacac ggcaagtca 29

<210> SEQ ID NO 549
<211> LENGTH: 30
<212> TYPE: DNA
<213> ORGANISM: Streptococcus thermophilus

<400> SEQUENCE: 549
caaccaacgg taacagctac tttttacagt 30

<210> SEQ ID NO 550
<211> LENGTH: 30
<212> TYPE: DNA
<213> ORGANISM: Streptococcus thermophilus

<400> SEQUENCE: 550
catagagtgg aaaactagaa acagattcaa 30

<210> SEQ ID NO 551
<211> LENGTH: 29
<212> TYPE: DNA
<213> ORGANISM: Streptococcus thermophilus

<400> SEQUENCE: 551
cgacacaaga acgtatgcaa gagttcaag 29

<210> SEQ ID NO 552
<211> LENGTH: 30
<212> TYPE: DNA
<213> ORGANISM: Streptococcus thermophilus

<400> SEQUENCE: 552
cgatatttaa aatcattttc ataacttcat 30

<210> SEQ ID NO 553
<211> LENGTH: 30
<212> TYPE: DNA
<213> ORGANISM: Streptococcus thermophilus

<400> SEQUENCE: 553
cgatttgaca atctgctgac cactgttatc 30

<210> SEQ ID NO 554
<211> LENGTH: 30
<212> TYPE: DNA
<213> ORGANISM: Streptococcus thermophilus

<400> SEQUENCE: 554
ctgttccttg ttcttttgtt gtatcttttc 30

<210> SEQ ID NO 555
<211> LENGTH: 30
<212> TYPE: DNA
<213> ORGANISM: Streptococcus thermophilus

<400> SEQUENCE: 555
gagcgagctc gaaataatct taattacaag 30

<210> SEQ ID NO 556
<211> LENGTH: 30
<212> TYPE: DNA
<213> ORGANISM: Streptococcus thermophilus

<400> SEQUENCE: 556
gcagtatcag caagcaagct gttagttact 30

<210> SEQ ID NO 557
<211> LENGTH: 30
<212> TYPE: DNA
<213> ORGANISM: Streptococcus thermophilus

<400> SEQUENCE: 557
gctggcgagg aaacgaacaa ggcctcaaca 30

<210> SEQ ID NO 558
<211> LENGTH: 30
<212> TYPE: DNA
<213> ORGANISM: Streptococcus thermophilus

<400> SEQUENCE: 558
gcttagctgt ccaatccacg aacgtggatg 30

<210> SEQ ID NO 559
<211> LENGTH: 30
<212> TYPE: DNA
<213> ORGANISM: Streptococcus thermophilus

<400> SEQUENCE: 559
ggcgtcccaa tcctgattaa tacttactcg 30

<210> SEQ ID NO 560
<211> LENGTH: 30
<212> TYPE: DNA
<213> ORGANISM: Streptococcus thermophilus

<400> SEQUENCE: 560
gttcgctagc gtcatgtggt aacgtattta 30

<210> SEQ ID NO 561
<211> LENGTH: 30
<212> TYPE: DNA
<213> ORGANISM: Streptococcus thermophilus

<400> SEQUENCE: 561
tctatatcga ggtcaactaa caattatgct 30

<210> SEQ ID NO 562
<211> LENGTH: 30
<212> TYPE: DNA
<213> ORGANISM: Streptococcus thermophilus

<400> SEQUENCE: 562
tgcatcgagc acgttcgagt ttaccgtttc 30

<210> SEQ ID NO 563
<211> LENGTH: 30
<212> TYPE: DNA
<213> ORGANISM: Streptococcus thermophilus

<400> SEQUENCE: 563
tgtttgacag caaatcaaga ttcgaattgt 30

<210> SEQ ID NO 564
<211> LENGTH: 30
<212> TYPE: DNA
<213> ORGANISM: Streptococcus thermophilus

<400> SEQUENCE: 564
ttcattcttc cgtttttgtt tgcgaatcct 30

<210> SEQ ID NO 565
<211> LENGTH: 30
<212> TYPE: DNA
<213> ORGANISM: Streptococcus thermophilus

<400> SEQUENCE: 565
tgacttagcg aatttaatcg ctaagatatc 30

<210> SEQ ID NO 566
<211> LENGTH: 30
<212> TYPE: DNA
<213> ORGANISM: Streptococcus thermophilus

<400> SEQUENCE: 566
tttatacttt atctttttaa agaatgtatt 30

<210> SEQ ID NO 567
<211> LENGTH: 30
<212> TYPE: DNA
<213> ORGANISM: Streptococcus thermophilus

<400> SEQUENCE: 567
cctaaaatca ttttcaacga gttgcgatac 30

<210> SEQ ID NO 568
<211> LENGTH: 30
<212> TYPE: DNA

<213> ORGANISM: Streptococcus thermophilus

<400> SEQUENCE: 568
aataaattgc tatgatacag cgtaccgata 30

<210> SEQ ID NO 569
<211> LENGTH: 30
<212> TYPE: DNA
<213> ORGANISM: Streptococcus thermophilus

<400> SEQUENCE: 569
tgctctctat gcgattggac gtctgtctaa 30

<210> SEQ ID NO 570
<211> LENGTH: 30
<212> TYPE: DNA
<213> ORGANISM: Streptococcus thermophilus

<400> SEQUENCE: 570
aagaaagata agaaaaaagt aacactactt 30

<210> SEQ ID NO 571
<211> LENGTH: 30
<212> TYPE: DNA
<213> ORGANISM: Streptococcus thermophilus

<400> SEQUENCE: 571
tctctttcca tcggtactgg tatatctcat 30

<210> SEQ ID NO 572
<211> LENGTH: 30
<212> TYPE: DNA
<213> ORGANISM: Streptococcus thermophilus

<400> SEQUENCE: 572
attggtagcc aagtaaatat caccattgat 30

<210> SEQ ID NO 573
<211> LENGTH: 30
<212> TYPE: DNA
<213> ORGANISM: Streptococcus thermophilus

<400> SEQUENCE: 573
ttcttcaaat tcaccgactg caaaattaca 30

<210> SEQ ID NO 574
<211> LENGTH: 30
<212> TYPE: DNA
<213> ORGANISM: Streptococcus thermophilus

<400> SEQUENCE: 574
gcttcctaag tgcatgaaaa tcgcaaacgg 30

<210> SEQ ID NO 575
<211> LENGTH: 30
<212> TYPE: DNA
<213> ORGANISM: Streptococcus thermophilus

<400> SEQUENCE: 575
tatacctgtc tatgtaaggg aatttaactc 30

<210> SEQ ID NO 576
<211> LENGTH: 30

<212> TYPE: DNA
<213> ORGANISM: Streptococcus thermophilus

<400> SEQUENCE: 576
ggtgtaggtg ctgttggtaa gttgtttaat 30

<210> SEQ ID NO 577
<211> LENGTH: 30
<212> TYPE: DNA
<213> ORGANISM: Streptococcus thermophilus

<400> SEQUENCE: 577
gtgaaacagg ttatcaaaaa acgtatattg 30

<210> SEQ ID NO 578
<211> LENGTH: 30
<212> TYPE: DNA
<213> ORGANISM: Streptococcus thermophilus

<400> SEQUENCE: 578
ttattcttgg aattattaca gaccctacta 30

<210> SEQ ID NO 579
<211> LENGTH: 30
<212> TYPE: DNA
<213> ORGANISM: Streptococcus thermophilus

<400> SEQUENCE: 579
gctttcatta tatcacttac tcataaatct 30

<210> SEQ ID NO 580
<211> LENGTH: 30
<212> TYPE: DNA
<213> ORGANISM: Streptococcus thermophilus

<400> SEQUENCE: 580
taatcacccc tttttctagc tcttgattga 30

<210> SEQ ID NO 581
<211> LENGTH: 30
<212> TYPE: DNA
<213> ORGANISM: Streptococcus thermophilus

<400> SEQUENCE: 581
caagcagtgt aaaggtggtt taaatgttaa 30

<210> SEQ ID NO 582
<211> LENGTH: 30
<212> TYPE: DNA
<213> ORGANISM: Streptococcus thermophilus

<400> SEQUENCE: 582
aacccgcgtg gttatgggct tgaggagtgt 30

<210> SEQ ID NO 583
<211> LENGTH: 30
<212> TYPE: DNA
<213> ORGANISM: Streptococcus thermophilus

<400> SEQUENCE: 583
atattaatag cgattctatg ctacaacgtg 30

<210> SEQ ID NO 584

-continued

<211> LENGTH: 30
<212> TYPE: DNA
<213> ORGANISM: Streptococcus thermophilus

<400> SEQUENCE: 584
tcatcttcta agtaaatacc actgtcaggg 30

<210> SEQ ID NO 585
<211> LENGTH: 29
<212> TYPE: DNA
<213> ORGANISM: Streptococcus thermophilus

<400> SEQUENCE: 585
ttttcgcaaa gtaagcgaag ctctacgtg 29

<210> SEQ ID NO 586
<211> LENGTH: 30
<212> TYPE: DNA
<213> ORGANISM: Streptococcus thermophilus

<400> SEQUENCE: 586
ttctgtagcc actccgtgga tgccttcagc 30

<210> SEQ ID NO 587
<211> LENGTH: 30
<212> TYPE: DNA
<213> ORGANISM: Streptococcus thermophilus

<400> SEQUENCE: 587
ttctttagtt cggacaccct caacacctat 30

<210> SEQ ID NO 588
<211> LENGTH: 30
<212> TYPE: DNA
<213> ORGANISM: Streptococcus thermophilus

<400> SEQUENCE: 588
gctttgattg gacggaaaat ggtatccctg 30

<210> SEQ ID NO 589
<211> LENGTH: 31
<212> TYPE: DNA
<213> ORGANISM: Streptococcus thermophilus

<400> SEQUENCE: 589
ttcctcatct ttctccgctt ttgctagact t 31

<210> SEQ ID NO 590
<211> LENGTH: 30
<212> TYPE: DNA
<213> ORGANISM: Streptococcus thermophilus

<400> SEQUENCE: 590
ttagaccaga tggacagata ttcttcatcg 30

<210> SEQ ID NO 591
<211> LENGTH: 31
<212> TYPE: DNA
<213> ORGANISM: Streptococcus thermophilus

<400> SEQUENCE: 591
tcatcagagt caacaatcac gggaaagacc t 31

<210> SEQ ID NO 592
<211> LENGTH: 30
<212> TYPE: DNA
<213> ORGANISM: Streptococcus thermophilus

<400> SEQUENCE: 592
acactcatcc ttatcctgta gttcaaaaca 30

<210> SEQ ID NO 593
<211> LENGTH: 30
<212> TYPE: DNA
<213> ORGANISM: Streptococcus thermophilus

<400> SEQUENCE: 593
cagcactagc cgcaagccct tgtatattaa 30

<210> SEQ ID NO 594
<211> LENGTH: 30
<212> TYPE: DNA
<213> ORGANISM: Streptococcus thermophilus

<400> SEQUENCE: 594
tagaaatcaa ggaacttgga tgaaaagtaa 30

<210> SEQ ID NO 595
<211> LENGTH: 30
<212> TYPE: DNA
<213> ORGANISM: Streptococcus thermophilus

<400> SEQUENCE: 595
atatgaaagg gaaatgatat gaagaatgaa 30

<210> SEQ ID NO 596
<211> LENGTH: 31
<212> TYPE: DNA
<213> ORGANISM: Streptococcus thermophilus

<400> SEQUENCE: 596
ttttgggata caacacgcag tcgttgactt g 31

<210> SEQ ID NO 597
<211> LENGTH: 30
<212> TYPE: DNA
<213> ORGANISM: Streptococcus thermophilus

<400> SEQUENCE: 597
gtttgagatg ccaatgtttt tcaatccttg 30

<210> SEQ ID NO 598
<211> LENGTH: 30
<212> TYPE: DNA
<213> ORGANISM: Streptococcus thermophilus

<400> SEQUENCE: 598
gtatcaaaag acgcattcat gaagcgagct 30

<210> SEQ ID NO 599
<211> LENGTH: 30
<212> TYPE: DNA
<213> ORGANISM: Streptococcus thermophilus

<400> SEQUENCE: 599
aaaaacaatt gaaattcata atcagcgctt 30

<210> SEQ ID NO 600
<211> LENGTH: 29
<212> TYPE: DNA
<213> ORGANISM: Streptococcus thermophilus

<400> SEQUENCE: 600
gcttttaacg ttttaagaga ataccctct 29

<210> SEQ ID NO 601
<211> LENGTH: 30
<212> TYPE: DNA
<213> ORGANISM: Streptococcus thermophilus

<400> SEQUENCE: 601
gtgacgctgc aatgacttgc catagtaatt 30

<210> SEQ ID NO 602
<211> LENGTH: 30
<212> TYPE: DNA
<213> ORGANISM: Streptococcus thermophilus

<400> SEQUENCE: 602
atactggtat atagtaattc atacttcatc 30

<210> SEQ ID NO 603
<211> LENGTH: 30
<212> TYPE: DNA
<213> ORGANISM: Streptococcus thermophilus

<400> SEQUENCE: 603
ttggtttcat atttactcct ttgtgttttg 30

<210> SEQ ID NO 604
<211> LENGTH: 30
<212> TYPE: DNA
<213> ORGANISM: Streptococcus thermophilus

<400> SEQUENCE: 604
ctgatttggt cttgttcttt tgtccctttt 30

<210> SEQ ID NO 605
<211> LENGTH: 30
<212> TYPE: DNA
<213> ORGANISM: Streptococcus thermophilus

<400> SEQUENCE: 605
gcagcagttg agaactttag cgtccagtgg 30

<210> SEQ ID NO 606
<211> LENGTH: 30
<212> TYPE: DNA
<213> ORGANISM: Streptococcus thermophilus

<400> SEQUENCE: 606
tgctactatg aaggacgctg ttgatacttt 30

<210> SEQ ID NO 607
<211> LENGTH: 30
<212> TYPE: DNA
<213> ORGANISM: Streptococcus thermophilus

<400> SEQUENCE: 607
tcttctttaa tctttttaa cgtcaacgtt 30

<210> SEQ ID NO 608
<211> LENGTH: 30
<212> TYPE: DNA
<213> ORGANISM: Streptococcus thermophilus

<400> SEQUENCE: 608
gtatccatta atatagtagc atttctatca 30

<210> SEQ ID NO 609
<211> LENGTH: 30
<212> TYPE: DNA
<213> ORGANISM: Streptococcus thermophilus

<400> SEQUENCE: 609
attcattaat atctgcaagg atgtcttgtt 30

<210> SEQ ID NO 610
<211> LENGTH: 30
<212> TYPE: DNA
<213> ORGANISM: Streptococcus thermophilus

<400> SEQUENCE: 610
gagaaagtag cccattcggc ccattcgggg 30

<210> SEQ ID NO 611
<211> LENGTH: 30
<212> TYPE: DNA
<213> ORGANISM: Streptococcus thermophilus

<400> SEQUENCE: 611
tacttgagtt agctctggaa gtcatttatc 30

<210> SEQ ID NO 612
<211> LENGTH: 30
<212> TYPE: DNA
<213> ORGANISM: Streptococcus thermophilus

<400> SEQUENCE: 612
ctgcatttgt aaccatgact tcttcgtcgt 30

<210> SEQ ID NO 613
<211> LENGTH: 30
<212> TYPE: DNA
<213> ORGANISM: Streptococcus thermophilus

<400> SEQUENCE: 613
aatttgtcat cgacatctac caacgcccag 30

<210> SEQ ID NO 614
<211> LENGTH: 30
<212> TYPE: DNA
<213> ORGANISM: Streptococcus thermophilus

<400> SEQUENCE: 614
ataaaattat gccacgtttt ggcactagat 30

<210> SEQ ID NO 615
<211> LENGTH: 30
<212> TYPE: DNA
<213> ORGANISM: Streptococcus thermophilus

<400> SEQUENCE: 615
atgtctctga ggctgtagta atttacttgt 30

<210> SEQ ID NO 616
<211> LENGTH: 30
<212> TYPE: DNA
<213> ORGANISM: Streptococcus thermophilus

<400> SEQUENCE: 616
ctttaaagag ttgattaagt gcgttactgt 30

<210> SEQ ID NO 617
<211> LENGTH: 30
<212> TYPE: DNA
<213> ORGANISM: Streptococcus thermophilus

<400> SEQUENCE: 617
aaatgggtta tgctgttcaa tatgcgtccc 30

<210> SEQ ID NO 618
<211> LENGTH: 30
<212> TYPE: DNA
<213> ORGANISM: Streptococcus thermophilus

<400> SEQUENCE: 618
aaactgaaaa caacacagac aattcaacaa 30

<210> SEQ ID NO 619
<211> LENGTH: 30
<212> TYPE: DNA
<213> ORGANISM: Streptococcus thermophilus

<400> SEQUENCE: 619
gcccaaaatg ctagacgttt gaatgacggc 30

<210> SEQ ID NO 620
<211> LENGTH: 30
<212> TYPE: DNA
<213> ORGANISM: Streptococcus thermophilus

<400> SEQUENCE: 620
atgaagaacg tgattcacct acggtatgct 30

<210> SEQ ID NO 621
<211> LENGTH: 31
<212> TYPE: DNA
<213> ORGANISM: Streptococcus thermophilus

<400> SEQUENCE: 621
gcttttgcag aattgtctcc agtgccgatt t 31

<210> SEQ ID NO 622
<211> LENGTH: 30
<212> TYPE: DNA
<213> ORGANISM: Streptococcus thermophilus

<400> SEQUENCE: 622
tgtactctat tgattgcttc atctttatta 30

<210> SEQ ID NO 623
<211> LENGTH: 31
<212> TYPE: DNA
<213> ORGANISM: Streptococcus thermophilus

<400> SEQUENCE: 623
ctttcaagat actcatcaac cattgatgtc a 31

<210> SEQ ID NO 624
<211> LENGTH: 30
<212> TYPE: DNA
<213> ORGANISM: Streptococcus thermophilus

<400> SEQUENCE: 624
ctatgtcttt actgttcttc caaaaccacc 30

<210> SEQ ID NO 625
<211> LENGTH: 30
<212> TYPE: DNA
<213> ORGANISM: Streptococcus thermophilus

<400> SEQUENCE: 625
tgctacgtgc tctgtacggg cgctatcagc 30

<210> SEQ ID NO 626
<211> LENGTH: 30
<212> TYPE: DNA
<213> ORGANISM: Streptococcus thermophilus

<400> SEQUENCE: 626
cgtggcagcg tggtcgggtt taatagcccg 30

<210> SEQ ID NO 627
<211> LENGTH: 29
<212> TYPE: DNA
<213> ORGANISM: Streptococcus thermophilus

<400> SEQUENCE: 627
aagcccaagt cagagcatcc gtccaagcc 29

<210> SEQ ID NO 628
<211> LENGTH: 30
<212> TYPE: DNA
<213> ORGANISM: Streptococcus thermophilus

<400> SEQUENCE: 628
attgggtttc ggtaagaact aaacatacca 30

<210> SEQ ID NO 629
<211> LENGTH: 30
<212> TYPE: DNA
<213> ORGANISM: Streptococcus thermophilus

<400> SEQUENCE: 629
cacaaaataa ttcggtagtt tttactaact 30

<210> SEQ ID NO 630
<211> LENGTH: 29
<212> TYPE: DNA
<213> ORGANISM: Streptococcus thermophilus

<400> SEQUENCE: 630
tttgaccgtt tatttagacg tgctaaagt 29

<210> SEQ ID NO 631
<211> LENGTH: 30
<212> TYPE: DNA
<213> ORGANISM: Streptococcus thermophilus

<400> SEQUENCE: 631
cttcacctca aatcttagag ctggactaaa 30

<210> SEQ ID NO 632
<211> LENGTH: 30
<212> TYPE: DNA
<213> ORGANISM: Streptococcus thermophilus

<400> SEQUENCE: 632
atgtctgaaa aataaccgac catcattact 30

<210> SEQ ID NO 633
<211> LENGTH: 30
<212> TYPE: DNA
<213> ORGANISM: Streptococcus thermophilus

<400> SEQUENCE: 633
gaagctcatc atgttaaggc taaaacctat 30

<210> SEQ ID NO 634
<211> LENGTH: 30
<212> TYPE: DNA
<213> ORGANISM: Streptococcus thermophilus

<400> SEQUENCE: 634
tagtctaaat agatttcttg caccattgta 30

<210> SEQ ID NO 635
<211> LENGTH: 30
<212> TYPE: DNA
<213> ORGANISM: Streptococcus thermophilus

<400> SEQUENCE: 635
attcgtgaaa aaatatcgtg aaataggcaa 30

<210> SEQ ID NO 636
<211> LENGTH: 30
<212> TYPE: DNA
<213> ORGANISM: Streptococcus thermophilus

<400> SEQUENCE: 636
tctaggctca tctaaagata aatcagtagc 30

<210> SEQ ID NO 637
<211> LENGTH: 31
<212> TYPE: DNA
<213> ORGANISM: Streptococcus thermophilus

<400> SEQUENCE: 637
taaaaacatg gggcggcggt aatagtgtaa g 31

<210> SEQ ID NO 638
<211> LENGTH: 30
<212> TYPE: DNA
<213> ORGANISM: Streptococcus thermophilus

<400> SEQUENCE: 638
acaaccagca aagagagcgc cgacaacatt 30

<210> SEQ ID NO 639
<211> LENGTH: 30
<212> TYPE: DNA
<213> ORGANISM: Streptococcus thermophilus

<400> SEQUENCE: 639
tataacacag gtttagagga tgttatactt 30

<210> SEQ ID NO 640
<211> LENGTH: 31
<212> TYPE: DNA
<213> ORGANISM: Streptococcus thermophilus

<400> SEQUENCE: 640
ctagaagctc aagcggtaaa agttgatggc g 31

<210> SEQ ID NO 641
<211> LENGTH: 30
<212> TYPE: DNA
<213> ORGANISM: Streptococcus thermophilus

<400> SEQUENCE: 641
ctttgagggc aagccctcgc cgttccattt 30

<210> SEQ ID NO 642
<211> LENGTH: 30
<212> TYPE: DNA
<213> ORGANISM: Streptococcus thermophilus

<400> SEQUENCE: 642
aactaccaag caaatcagca atcaataagt 30

<210> SEQ ID NO 643
<211> LENGTH: 30
<212> TYPE: DNA
<213> ORGANISM: Streptococcus thermophilus

<400> SEQUENCE: 643
ctataagtga caatcagcgt agggaatacg 30

<210> SEQ ID NO 644
<211> LENGTH: 30
<212> TYPE: DNA
<213> ORGANISM: Streptococcus thermophilus

<400> SEQUENCE: 644
atcagtgcgg tatatttacc ctagacgcta 30

<210> SEQ ID NO 645
<211> LENGTH: 30
<212> TYPE: DNA
<213> ORGANISM: Streptococcus thermophilus

<400> SEQUENCE: 645
aacagttact attaatcacg attccaacgg 30

<210> SEQ ID NO 646
<211> LENGTH: 30
<212> TYPE: DNA
<213> ORGANISM: Streptococcus thermophilus

<400> SEQUENCE: 646
aattagggcg tcttccttta ttccgtggtt 30

<210> SEQ ID NO 647
<211> LENGTH: 30
<212> TYPE: DNA

<213> ORGANISM: Streptococcus thermophilus

<400> SEQUENCE: 647
atagcttcat tgcgcttttt aatttgacct 30

<210> SEQ ID NO 648
<211> LENGTH: 30
<212> TYPE: DNA
<213> ORGANISM: Streptococcus thermophilus

<400> SEQUENCE: 648
aacaacaaag caaatacaac agtaacaacc 30

<210> SEQ ID NO 649
<211> LENGTH: 30
<212> TYPE: DNA
<213> ORGANISM: Streptococcus thermophilus

<400> SEQUENCE: 649
ctaaactacg tttgaaggtc tcaactccgt 30

<210> SEQ ID NO 650
<211> LENGTH: 30
<212> TYPE: DNA
<213> ORGANISM: Streptococcus thermophilus

<400> SEQUENCE: 650
gaggttgaat agtgagtgca ccatgtttgt 30

<210> SEQ ID NO 651
<211> LENGTH: 30
<212> TYPE: DNA
<213> ORGANISM: Streptococcus thermophilus

<400> SEQUENCE: 651
agtagagaga ccagcacact actgtactac 30

<210> SEQ ID NO 652
<211> LENGTH: 30
<212> TYPE: DNA
<213> ORGANISM: Streptococcus thermophilus

<400> SEQUENCE: 652
cttcgcacga aagtttatta gacaactcgc 30

<210> SEQ ID NO 653
<211> LENGTH: 30
<212> TYPE: DNA
<213> ORGANISM: Streptococcus thermophilus

<400> SEQUENCE: 653
tgatagagct agaattgtct tttttaccga 30

<210> SEQ ID NO 654
<211> LENGTH: 30
<212> TYPE: DNA
<213> ORGANISM: Streptococcus thermophilus

<400> SEQUENCE: 654
agatactctt gctcgcctct gaacaaccag 30

<210> SEQ ID NO 655
<211> LENGTH: 30

<212> TYPE: DNA
<213> ORGANISM: Streptococcus thermophilus

<400> SEQUENCE: 655
ggtgaaaaag gttcactgta cgagtactta 30

<210> SEQ ID NO 656
<211> LENGTH: 30
<212> TYPE: DNA
<213> ORGANISM: Streptococcus thermophilus

<400> SEQUENCE: 656
tcaatgagtg gtatccaaga cgaaaactta 30

<210> SEQ ID NO 657
<211> LENGTH: 30
<212> TYPE: DNA
<213> ORGANISM: Streptococcus thermophilus

<400> SEQUENCE: 657
ccttgtcgtg gctctccata cgcccatata 30

<210> SEQ ID NO 658
<211> LENGTH: 30
<212> TYPE: DNA
<213> ORGANISM: Streptococcus thermophilus

<400> SEQUENCE: 658
tgtttgggaa accgcagtag ccatgattaa 30

<210> SEQ ID NO 659
<211> LENGTH: 32
<212> TYPE: DNA
<213> ORGANISM: Streptococcus thermophilus

<400> SEQUENCE: 659
acagagtaca atattgtcct cattggagac ac 32

<210> SEQ ID NO 660
<211> LENGTH: 30
<212> TYPE: DNA
<213> ORGANISM: Streptococcus thermophilus

<400> SEQUENCE: 660
ctcatattcg ttagttgctt ttgtcataaa 30

<210> SEQ ID NO 661
<211> LENGTH: 30
<212> TYPE: DNA
<213> ORGANISM: Streptococcus thermophilus

<400> SEQUENCE: 661
agaactttat caagataaaa ctactttaaa 30

<210> SEQ ID NO 662
<211> LENGTH: 30
<212> TYPE: DNA
<213> ORGANISM: Streptococcus thermophilus

<400> SEQUENCE: 662
atagtattaa tttcattgaa aaataattgt 30

<210> SEQ ID NO 663

<211> LENGTH: 36
<212> TYPE: DNA
<213> ORGANISM: Streptococcus thermophilus

<400> SEQUENCE: 663
gctttctagc tcgctataat tacccattcc tagaaa 36

<210> SEQ ID NO 664
<211> LENGTH: 40
<212> TYPE: DNA
<213> ORGANISM: Streptococcus thermophilus

<400> SEQUENCE: 664
tcaaaatatg ttattacctt gtatttcata attcaattaa 40

<210> SEQ ID NO 665
<211> LENGTH: 39
<212> TYPE: DNA
<213> ORGANISM: Streptococcus thermophilus

<400> SEQUENCE: 665
ccacttgctg tgtacatcct accagttccg cctatgatg 39

<210> SEQ ID NO 666
<211> LENGTH: 26
<212> TYPE: DNA
<213> ORGANISM: Artificial Sequence
<220> FEATURE:
<223> OTHER INFORMATION: synthetic primer

<400> SEQUENCE: 666
acaaacaaca gagaagtatc tcattg 26

<210> SEQ ID NO 667
<211> LENGTH: 25
<212> TYPE: DNA
<213> ORGANISM: Artificial Sequence
<220> FEATURE:
<223> OTHER INFORMATION: synthetic primer

<400> SEQUENCE: 667
aacgagtaca ctcactattt gtacg 25

<210> SEQ ID NO 668
<211> LENGTH: 84
<212> TYPE: DNA
<213> ORGANISM: Artificial Sequence
<220> FEATURE:
<223> OTHER INFORMATION: synthetic primer

<400> SEQUENCE: 668
tccactcacg tacaaatagt gagtgtactc gtttttgtat tctcaagatt taagtaactg 60
tacagtttga ttcaacataa aaag 84

<210> SEQ ID NO 669
<211> LENGTH: 24
<212> TYPE: DNA
<213> ORGANISM: Artificial Sequence
<220> FEATURE:
<223> OTHER INFORMATION: synthetic primer

<400> SEQUENCE: 669
ctttccttca tcctcgcttt ggtt 24

<210> SEQ ID NO 670
<211> LENGTH: 19
<212> TYPE: DNA
<213> ORGANISM: Artificial Sequence
<220> FEATURE:
<223> OTHER INFORMATION: synthetic primer

<400> SEQUENCE: 670
caaatggata gagaaacgc 19

<210> SEQ ID NO 671
<211> LENGTH: 21
<212> TYPE: DNA
<213> ORGANISM: Artificial Sequence
<220> FEATURE:
<223> OTHER INFORMATION: synthetic primer

<400> SEQUENCE: 671
ctgataaggt gttcgttgtc c 21

<210> SEQ ID NO 672
<211> LENGTH: 24
<212> TYPE: DNA
<213> ORGANISM: Artificial Sequence
<220> FEATURE:
<223> OTHER INFORMATION: synthetic primer

<400> SEQUENCE: 672
ggagcagatg gaatacaaga aagg 24

<210> SEQ ID NO 673
<211> LENGTH: 22
<212> TYPE: DNA
<213> ORGANISM: Artificial Sequence
<220> FEATURE:
<223> OTHER INFORMATION: synthetic primer

<400> SEQUENCE: 673
gagagactag gttgtctcag ca 22

<210> SEQ ID NO 674
<211> LENGTH: 21
<212> TYPE: DNA
<213> ORGANISM: Artificial Sequence
<220> FEATURE:
<223> OTHER INFORMATION: synthetic primer

<400> SEQUENCE: 674
gtctttagaa actgtgacac c 21

<210> SEQ ID NO 675
<211> LENGTH: 20
<212> TYPE: DNA
<213> ORGANISM: Artificial Sequence
<220> FEATURE:
<223> OTHER INFORMATION: synthetic primer

<400> SEQUENCE: 675
taaacagagc ctccctatcc 20

<210> SEQ ID NO 676
<211> LENGTH: 23
<212> TYPE: DNA
<213> ORGANISM: Artificial Sequence
<220> FEATURE:
<223> OTHER INFORMATION: synthetic primer

<400> SEQUENCE: 676
ctgagattaa tagtgcgatt acg 23

<210> SEQ ID NO 677
<211> LENGTH: 23
<212> TYPE: DNA
<213> ORGANISM: Artificial Sequence
<220> FEATURE:
<223> OTHER INFORMATION: synthetic primer

<400> SEQUENCE: 677
gctggatatt cgtataacat gtc 23

<210> SEQ ID NO 678
<211> LENGTH: 2251
<212> TYPE: DNA
<213> ORGANISM: Streptococcus thermophilus

<400> SEQUENCE: 678
caaggacagt tattgatttt ataatcacta tgtgggtata aaaacgtcaa aatttcattt 60
gaggtttttg tactctcaag atttaagtaa ctgtacaact gtttgacagc aaatcaagat 120
tcgaattgtg tttttgtact ctcaagattt aagtaactgt acaacaatga cgaggagcta 180
ttggcacaac ttacagtttt tgtactctca agatttaagt aactgtacaa ccgatttgac 240
aatctgctga ccactgttat cgtttttgta ctctcaagat ttaagtaact gtacaacaca 300
cttggcaggc ttattactca acagcgagtt tttgtactct caagatttaa gtaactgtac 360
aacctgttcc ttgttctttt gttgtatctt ttcgtttttg tactctcaag atttaagtaa 420
ctgtacaact tcattcttcc gtttttgttt gcgaatcctg tttttgtact ctcaagattt 480
aagtaactgt acaacgctgg cgaggaaacg aacaaggcct caacagtttt tgtactctca 540
agatttaagt aactgtacaa ccatagagtg gaaaactaga aacagattca agtttttgta 600
ctctcaagat ttaagtaact gtacaacata atgccgttga attacacggc aaggtcagtt 660
tttgtactct caagatttaa gtaactgtac aacgagcgag ctcgaaataa tcttaattac 720
aaggtttttg tactctcaag atttaagtaa ctgtacaacg ttcgctagcg tcatgtggta 780
acgtatttag tttttgtact ctcaagattt aagtaactgt acaacggcgt cccaatcctg 840
attaatactt actcggtttt tgtactctca agatttaagt aactgtacaa caacacagca 900
agacaagagg atgatgctat ggtttttgta ctctcaagat ttaagtaact gtacaaccga 960
cacaagaacg tatgcaagag ttcaaggttt ttgtactctc aagatttaag taactgtaca 1020
acacaattct tcatccggta actgctcaag tggtttttgt actctcaaga tttaagtaac 1080
tgtacaacaa ttaagggcat agaaagggag acaacatggt ttttgtactc tcaagattta 1140
agtaactgta caaccgatat ttaaaatcat tttcataact tcatgttttt gtactctcaa 1200
gatttaagta actgtacaac gcagtatcag caagcaagct gttagttact gtttttgtac 1260
tctcaagatt taagtaactg tacaacataa actatgaaat tttataattt ttaagagttt 1320
ttgtactctc aagatttaag taactgtaca acaataattt atggtatagc ttaatatcat 1380
tggtttttgt actctcaaga tttaagtaac tgtacaactg catcgagcac gttcgagttt 1440
accgtttcgt tttgtactc tcaagattta agtaactgta caactctata tcgaggtcaa 1500
ctaacaatta tgctgttttt gtactctcaa gatttaagta actgtacaac aatcgttcaa 1560
attctgtttt aggtacattt gtttttgtac tctcaagatt taagtaactg tacaacaatc 1620
aatacgacaa gagttaaaat ggtcttgttt ttgtactctc aagatttaag taactgtaca 1680

```
acgcttagct gtccaatcca cgaacgtgga tggtttttgt actctcaaga tttaagtaac   1740
tgtacaacca accaacggta acagctactt tttacagtgt ttttgtactc tcaagattta   1800
agtaactgta caacataact gaaggatagg agcttgtaaa gtctgttttt gtactctcaa   1860
gatttaagta actgtacaac taatgctaca tctcaaagga tgatcccaga gtttttgtac   1920
tctcaagatt taagtaactg tacaacaagt agttgatgac ctctacaatg gtttatgttt   1980
ttgtactctc aagatttaag taactgtaca acacctagaa gcatttgagc gtatattgat   2040
tggtttttgt actctcaaga tttaagtaac tgtacaacaa ttttgcccct tctttgcccc   2100
ttgactaggt ttttgtactc tcaagattta agtaactgta caacaccatt agcaatcatt   2160
tgtgcccatt gagtgttttt gtactctcaa gatttaagta actgtacagt ttgattcaac   2220
ataaaaagcc agttcaattg aacttggctt t                                 2251
```

<210> SEQ ID NO 679
<211> LENGTH: 2383
<212> TYPE: DNA
<213> ORGANISM: Streptococcus thermophilus

<400> SEQUENCE: 679

```
caaggacagt tattgatttt ataatcacta tgtgggtata aaaacgtcaa aatttcattt     60
gaggtttttg tactctcaag atttaagtaa ctgtacaacc aacacattca acagattaat    120
gaagaatacg tttttgtact ctcaagattt aagtaactgt acaactccac tcacgtacaa    180
atagtgagtg tactcgtttt tgtactctca agatttaagt aactgtacaa ctgtttgaca    240
gcaaatcaag attcgaattg tgtttttgta ctctcaagat ttaagtaact gtacaacaat    300
gacgaggagc tattggcaca acttacagtt tttgtactct caagatttaa gtaactgtac    360
aaccgatttg acaatctgct gaccactgtt atcgtttttg tactctcaag atttaagtaa    420
ctgtacaaca cacttggcag gcttattact caacagcgag tttttgtact ctcaagattt    480
aagtaactgt acaacctgtt ccttgttctt ttgttgtatc ttttcgtttt tgtactctca    540
agatttaagt aactgtacaa cttcattctt ccgtttttgt ttgcgaatcc tgtttttgta    600
ctctcaagat ttaagtaact gtacaacgct ggcgaggaaa cgaacaaggc ctcaacagtt    660
tttgtactct caagatttaa gtaactgtac aaccatagag tggaaaacta gaaacagatt    720
caagtttttg tactctcaag atttaagtaa ctgtacaaca taatgccgtt gaattacacg    780
gcaaggtcag tttttgtact ctcaagattt aagtaactgt acaacgagcg agctcgaaat    840
aatcttaatt acaaggtttt tgtactctca agatttaagt aactgtacaa cgttcgctag    900
cgtcatgtgg taacgtattt agtttttgta ctctcaagat ttaagtaact gtacaacggc    960
gtcccaatcc tgattaatac ttactcggtt tttgtactct caagatttaa gtaactgtac   1020
aacaacacag caagacaaga ggatgatgct atggtttttg tactctcaag atttaagtaa   1080
ctgtacaacc gacacaagaa cgtatgcaag agttcaaggt ttttgtactc tcaagattta   1140
agtaactgta caacacaatt cttcatccgg taactgctca agtggttttt gtactctcaa   1200
gatttaagta actgtacaac aattaagggc atagaaaggg agacaacatg gtttttgtac   1260
tctcaagatt taagtaactg tacaaccgat atttaaaatc attttcataa cttcatgttt   1320
ttgtactctc aagatttaag taactgtaca acgcagtatc agcaagcaag ctgttagtta   1380
ctgtttttgt actctcaaga tttaagtaac tgtacaacat aaactatgaa attttataat   1440
ttttaagagt ttttgtactc tcaagattta agtaactgta caacaataat ttatggtata   1500
```

```
gcttaatatc attggttttt gtactctcaa gatttaagta actgtacaac tgcatcgagc   1560
acgttcgagt ttaccgtttc gtttttgtac tctcaagatt taagtaactg tacaactcta   1620
tatcgaggtc aactaacaat tatgctgttt ttgtactctc aagatttaag taactgtaca   1680
acaatcgttc aaattctgtt ttaggtacat ttgtttttgt actctcaaga tttaagtaac   1740
tgtacaacaa tcaatacgac aagagttaaa atggtcttgt tttgtactc tcaagattta   1800
agtaactgta caacgcttag ctgtccaatc cacgaacgtg gatggttttt gtactctcaa   1860
gatttaagta actgtacaac caaccaacgg taacagctac tttttacagt gtttttgtac   1920
tctcaagatt taagtaactg tacaacataa ctgaaggata ggagcttgta aagtctgttt   1980
ttgtactctc aagatttaag taactgtaca actaatgcta catctcaaag gatgatccca   2040
gagtttttgt actctcaaga tttaagtaac tgtacaacaa gtagttgatg acctctacaa   2100
tggtttatgt tttgtactc tcaagattta agtaactgta caacacctag aagcatttga   2160
gcgtatattg attggttttt gtactctcaa gatttaagta actgtacaac aattttgccc   2220
cttctttgcc ccttgactag gtttttgtac tctcaagatt taagtaactg tacaacacca   2280
ttagcaatca tttgtgccca ttgagtgttt ttgtactctc aagatttaag taactgtaca   2340
gtttgattca acataaaaag ccagttcaat tgaacttggc ttt                     2383
```

<210> SEQ ID NO 680
<211> LENGTH: 30
<212> TYPE: DNA
<213> ORGANISM: Streptococcus thermophilus

<400> SEQUENCE: 680

```
caacacattc aacagattaa tgaagaatac                                      30
```

<210> SEQ ID NO 681
<211> LENGTH: 30
<212> TYPE: DNA
<213> ORGANISM: Streptococcus thermophilus

<400> SEQUENCE: 681

```
tccactcacg tacaaatagt gagtgtactc                                      30
```

<210> SEQ ID NO 682
<211> LENGTH: 2317
<212> TYPE: DNA
<213> ORGANISM: Streptococcus thermophilus

<400> SEQUENCE: 682

```
caaggacagt tattgatttt ataatcacta tgtgggtata aaaacgtcaa aatttcattt     60
gaggtttttg tactctcaag atttaagtaa ctgtacaact caacaattgc aacatcttat    120
aacccacttg tttttgtact ctcaagattt aagtaactgt acaactgttt gacagcaaat    180
caagattcga attgtgtttt tgtactctca agatttaagt aactgtacaa caatgacgag    240
gagctattgg cacaacttac agtttttgta ctctcaagat ttaagtaact gtacaaccga    300
tttgacaatc tgctgaccac tgttatcgtt tttgtactct caagatttaa gtaactgtac    360
aacacacttg gcaggcttat tactcaacag cgagtttttg tactctcaag atttaagtaa    420
ctgtacaacc tgttccttgt tcttttgttg tatcttttcg tttttgtact ctcaagattt    480
aagtaactgt acaacttcat tcttccgttt ttgtttgcga atcctgtttt tgtactctca    540
agatttaagt aactgtacaa cgctggcgag gaaacgaaca aggcctcaac agtttttgta    600
ctctcaagat ttaagtaact gtacaaccat agagtggaaa actagaaaca gattcaagtt    660
```

```
tttgtactct caagatttaa gtaactgtac aacataatgc cgttgaatta cacggcaagg    720
tcagtttttg tactctcaag atttaagtaa ctgtacaacg agcgagctcg aaataatctt    780
aattacaagg tttttgtact ctcaagattt aagtaactgt acaacgttcg ctagcgtcat    840
gtggtaacgt atttagtttt tgtactctca agatttaagt aactgtacaa cggcgtccca    900
atcctgatta atacttactc ggtttttgta ctctcaagat ttaagtaact gtacaacaac    960
acagcaagac aagaggatga tgctatggtt tttgtactct caagatttaa gtaactgtac   1020
aaccgacaca agaacgtatg caagagttca aggtttttgt actctcaaga tttaagtaac   1080
tgtacaacac aattcttcat ccggtaactg ctcaagtggt tttgtactc tcaagattta   1140
agtaactgta caacaattaa gggcatagaa agggagacaa catggttttt gtactctcaa   1200
gatttaagta actgtacaac cgatatttaa aatcattttc ataacttcat gtttttgtac   1260
tctcaagatt taagtaactg tacaacgcag tatcagcaag caagctgtta gttactgttt   1320
ttgtactctc aagatttaag taactgtaca acataaacta tgaaatttta taatttttaa   1380
gagtttttgt actctcaaga tttaagtaac tgtacaacaa taatttatgg tatagcttaa   1440
tatcattggt tttgtactc tcaagattta agtaactgta caactgcatc gagcacgttc   1500
gagtttaccg tttcgttttt gtactctcaa gatttaagta actgtacaac tctatatcga   1560
ggtcaactaa caattatgct gtttttgtac tctcaagatt taagtaactg tacaacaatc   1620
gttcaaattc tgttttaggt acatttgttt ttgtactctc aagatttaag taactgtaca   1680
acaatcaata cgacaagagt taaaatggtc ttgtttttgt actctcaaga tttaagtaac   1740
tgtacaacgc ttagctgtcc aatccacgaa cgtggatggt tttgtactc tcaagattta   1800
agtaactgta caaccaacca acggtaacag ctacttttta cagtgttttt gtactctcaa   1860
gatttaagta actgtacaac ataactgaag gataggagct tgtaaagtct gtttttgtac   1920
tctcaagatt taagtaactg tacaactaat gctacatctc aaaggatgat cccagagttt   1980
ttgtactctc aagatttaag taactgtaca acaagtagtt gatgacctct acaatggttt   2040
atgtttttgt actctcaaga tttaagtaac tgtacaacac ctagaagcat ttgagcgtat   2100
attgattggt tttgtactc tcaagattta agtaactgta caacaatttt gccccttctt   2160
tgccccttga ctaggttttt gtactctcaa gatttaagta actgtacaac accattagca   2220
atcatttgtg cccattgagt gtttttgtac tctcaagatt taagtaactg tacagtttga   2280
ttcaacataa aaagccagtt caattgaact tggcttt                            2317
```

<210> SEQ ID NO 683
<211> LENGTH: 2317
<212> TYPE: DNA
<213> ORGANISM: Streptococcus thermophilus

<400> SEQUENCE: 683

```
caaggacagt tattgatttt ataatcacta tgtgggtata aaaacgtcaa aatttcattt     60
gaggtttttg tactctcaag atttaagtaa ctgtacaact caacaattgc aacatcttat    120
aacccacttg tttttgtact ctcaagattt aagtaactgt acaactgttt gacagcaaat    180
caagattcga attgtgtttt tgtactctca agatttaagt aactgtacaa caatgacgag    240
gagctattgg cacaacttac agtttttgta ctctcaagat ttaagtaact gtacaaccga    300
tttgacaatc tgctgaccac tgttatcgtt tttgtactct caagatttaa gtaactgtac    360
aacacacttg gcaggcttat tactcaacag cgagtttttg tactctcaag atttaagtaa    420
```

```
ctgtacaacc tgttccttgt tcttttgttg tatcttttcg tttttgtact ctcaagattt    480

aagtaactgt acaacttcat tcttccgttt ttgtttgcga atcctgtttt tgtactctca    540

agatttaagt aactgtacaa cgctggcgag gaaacgaaca aggcctcaac agtttttgta    600

ctctcaagat ttaagtaact gtacaaccat agagtggaaa actagaaaca gattcaagtt    660

tttgtactct caagatttaa gtaactgtac aacataatgc cgttgaatta cacggcaagg    720

tcagtttttg tactctcaag atttaagtaa ctgtacaacg agcgagctcg aaataatctt    780

aattacaagg tttttgtact ctcaagattt aagtaactgt acaacgttcg ctagcgtcat    840

gtggtaacgt atttagtttt tgtactctca agatttaagt aactgtacaa cggcgtccca    900

atcctgatta atacttactc ggtttttgta ctctcaagat ttaagtaact gtacaacaac    960

acagcaagac aagaggatga tgctatggtt tttgtactct caagatttaa gtaactgtac   1020

aaccgacaca agaacgtatg caagagttca aggtttttgt actctcaaga tttaagtaac   1080

tgtacaacac aattcttcat ccggtaactg ctcaagtggt ttttgtactc tcaagattta   1140

agtaactgta caacaattaa gggcatagaa agggagacaa catggttttt gtactctcaa   1200

gatttaagta actgtacaac cgatatttaa aatcattttc ataacttcat gtttttgtac   1260

tctcaagatt taagtaactg tacaacgcag tatcagcaag caagctgtta gttactgttt   1320

ttgtactctc aagatttaag taactgtaca acataaacta tgaaatttta taatttttaa   1380

gagtttttgt actctcaaga tttaagtaac tgtacaacaa taatttatgg tatagcttaa   1440

tatcattggt ttttgtactc tcaagattta agtaactgta caactgcatc gagcacgttc   1500

gagtttaccg tttcgttttt gtactctcaa gatttaagta actgtacaac tctatatcga   1560

ggtcaactaa caattatgct gtttttgtac tctcaagatt taagtaactg tacaacaatc   1620

gttcaaattc tgttttaggt acatttgttt ttgtactctc aagatttaag taactgtaca   1680

acaatcaata cgacaagagt taaaatggtc ttgtttttgt actctcaaga tttaagtaac   1740

tgtacaacgc ttagctgtcc aatccacgaa cgtggatggt ttttgtactc tcaagattta   1800

agtaactgta caaccaacca acggtaacag ctacttttta cagtgttttt gtactctcaa   1860

gatttaagta actgtacaac ataactgaag gataggagct tgtaaagtct gtttttgtac   1920

tctcaagatt taagtaactg tacaactaat gctacatctc aaaggatgat cccagagttt   1980

ttgtactctc aagatttaag taactgtaca acaagtagtt gatgacctct acaatggttt   2040

atgtttttgt actctcaaga tttaagtaac tgtacaacac ctagaagcat ttgagcgtat   2100

attgattggt ttttgtactc tcaagattta agtaactgta caacaatttt gccccttctt   2160

tgccccttga ctaggttttt gtactctcaa gatttaagta actgtacaac accattagca   2220

atcatttgtg cccattgagt gtttttgtac tctcaagatt taagtaactg tacagtttga   2280

ttcaacataa aaagccagtt caattgaact tggcttt                            2317
```

<210> SEQ ID NO 684
<211> LENGTH: 2317
<212> TYPE: DNA
<213> ORGANISM: Streptococcus thermophilus

<400> SEQUENCE: 684

```
caaggacagt tattgatttt ataatcacta tgtgggtata aaaacgtcaa aatttcattt     60

gaggtttttg tactctcaag atttaagtaa ctgtacaact tacgtttgaa aagaatatca    120

aatcaatgag tttttgtact ctcaagattt aagtaactgt acaactgttt gacagcaaat    180

caagattcga attgtgtttt tgtactctca agatttaagt aactgtacaa caatgacgag    240
```

-continued

```
gagctattgg cacaacttac agtttttgta ctctcaagat ttaagtaact gtacaaccga    300
tttgacaatc tgctgaccac tgttatcgtt tttgtactct caagatttaa gtaactgtac    360
aacacacttg gcaggcttat tactcaacag cgagtttttg tactctcaag atttaagtaa    420
ctgtacaacc tgttccttgt tcttttgttg tatcttttcg tttttgtact ctcaagattt    480
aagtaactgt acaacttcat tcttccgttt ttgtttgcga atcctgtttt tgtactctca    540
agatttaagt aactgtacaa cgctggcgag gaaacgaaca aggcctcaac agtttttgta    600
ctctcaagat ttaagtaact gtacaaccat agagtggaaa actagaaaca gattcaagtt    660
tttgtactct caagatttaa gtaactgtac aacataatgc cgttgaatta cacggcaagg    720
tcagtttttg tactctcaag atttaagtaa ctgtacaacg agcgagctcg aaataatctt    780
aattacaagg tttttgtact ctcaagattt aagtaactgt acaacgttcg ctagcgtcat    840
gtggtaacgt atttagtttt tgtactctca agatttaagt aactgtacaa cggcgtccca    900
atcctgatta atacttactc ggtttttgta ctctcaagat ttaagtaact gtacaacaac    960
acagcaagac aagaggatga tgctatggtt tttgtactct caagatttaa gtaactgtac   1020
aaccgacaca agaacgtatg caagagttca aggtttttgt actctcaaga tttaagtaac   1080
tgtacaacac aattcttcat ccggtaactg ctcaagtggt tttgtactc tcaagattta   1140
agtaactgta caacaattaa gggcatagaa agggagacaa catggttttt gtactctcaa   1200
gatttaagta actgtacaac cgatatttaa aatcattttc ataacttcat gtttttgtac   1260
tctcaagatt taagtaactg tacaacgcag tatcagcaag caagctgtta gttactgttt   1320
ttgtactctc aagatttaag taactgtaca acataaacta tgaaatttta taatttttaa   1380
gagtttttgt actctcaaga tttaagtaac tgtacaacaa taatttatgg tatagcttaa   1440
tatcattggt tttgtactc tcaagattta agtaactgta caactgcatc gagcacgttc   1500
gagtttaccg tttcgttttt gtactctcaa gatttaagta actgtacaac tctatatcga   1560
ggtcaactaa caattatgct gtttttgtac tctcaagatt taagtaactg tacaacaatc   1620
gttcaaattc tgttttaggt acatttgttt ttgtactctc aagatttaag taactgtaca   1680
acaatcaata cgacaagagt taaaatggtc ttgtttttgt actctcaaga tttaagtaac   1740
tgtacaacgc ttagctgtcc aatccacgaa cgtggatggt tttgtactc tcaagattta   1800
agtaactgta caaccaacca acggtaacag ctacttttta cagtgttttt gtactctcaa   1860
gatttaagta actgtacaac ataactgaag gataggagct tgtaaagtct gtttttgtac   1920
tctcaagatt taagtaactg tacaactaat gctacatctc aaaggatgat cccagagttt   1980
ttgtactctc aagatttaag taactgtaca acaagtagtt gatgacctct acaatggttt   2040
atgtttttgt actctcaaga tttaagtaac tgtacaacac ctagaagcat ttgagcgtat   2100
attgattggt tttgtactc tcaagattta agtaactgta caacaatttt gccccttctt   2160
tgccccttga ctaggttttt gtactctcaa gatttaagta actgtacaac accattagca   2220
atcatttgtg cccattgagt gtttttgtac tctcaagatt taagtaactg tacagtttga   2280
ttcaacataa aaagccagtt caattgaact tggcttt                            2317
```

<210> SEQ ID NO 685
<211> LENGTH: 29
<212> TYPE: DNA
<213> ORGANISM: Streptococcus thermophilus

<400> SEQUENCE: 685
tacgtttgaa aagaatatca aatcaatga 29

<210> SEQ ID NO 686
<211> LENGTH: 30
<212> TYPE: DNA
<213> ORGANISM: Streptococcus phage 858

<400> SEQUENCE: 686
tccactcacg tacaaatagt gagcgtactc 30

<210> SEQ ID NO 687
<211> LENGTH: 30
<212> TYPE: DNA
<213> ORGANISM: Streptococcus phage 858

<400> SEQUENCE: 687
caacacattc aacagattaa tgaagaatac 30

<210> SEQ ID NO 688
<211> LENGTH: 63
<212> TYPE: DNA
<213> ORGANISM: Streptococcus thermophilus

<400> SEQUENCE: 688
caaggacagt tattgatttt ataatcacta tgtgggtata aaaacgtcaa aatttcattt 60
gag 63

<210> SEQ ID NO 689
<211> LENGTH: 66
<212> TYPE: DNA
<213> ORGANISM: Streptococcus thermophilus

<400> SEQUENCE: 689
gtttttgtac tctcaagatt taagtaactg tacaactcaa caattgcaac atcttataac 60
ccactt 66

<210> SEQ ID NO 690
<211> LENGTH: 30
<212> TYPE: DNA
<213> ORGANISM: Streptococcus phage 858

<400> SEQUENCE: 690
ttacgtttga aaagaatatc aaatcaatga 30

<210> SEQ ID NO 691
<211> LENGTH: 41
<212> TYPE: DNA
<213> ORGANISM: Streptococcus thermophilus

<400> SEQUENCE: 691
ttgattcaac ataaaaagcc agttcaattg aacttggctt t 41

<210> SEQ ID NO 692

<400> SEQUENCE: 692

000

<210> SEQ ID NO 693

<400> SEQUENCE: 693

000

<210> SEQ ID NO 694
<211> LENGTH: 66
<212> TYPE: DNA
<213> ORGANISM: Streptococcus thermophilus

<400> SEQUENCE: 694
gtttttgtac tctcaagatt taagtaactg tacaacttac gtttgaaaag aatatcaaat 60
caatga 66

<210> SEQ ID NO 695
<211> LENGTH: 36
<212> TYPE: DNA
<213> ORGANISM: Streptococcus thermophilus

<400> SEQUENCE: 695
gttgtacagt tacttaaatc ttgagagtac aaaaac 36

<210> SEQ ID NO 696
<211> LENGTH: 7
<212> TYPE: DNA
<213> ORGANISM: Streptococcus thermophilus
<220> FEATURE:
<221> NAME/KEY: misc_feature
<222> LOCATION: (1)..(2)
<223> OTHER INFORMATION: n is a, c, g, or t

<400> SEQUENCE: 696 nnagaaw 7

<210> SEQ ID NO 697
<211> LENGTH: 30
<212> TYPE: DNA
<213> ORGANISM: Streptococcus thermophilus

<400> SEQUENCE: 697
ttacgtttga aaagaatatc aaatcaatga 30

<210> SEQ ID NO 698
<211> LENGTH: 30
<212> TYPE: DNA
<213> ORGANISM: Streptococcus phage 858

<400> SEQUENCE: 698
ttacgtttga aaagaatatc aaatcaatga 30

<210> SEQ ID NO 699
<211> LENGTH: 35
<212> TYPE: DNA
<213> ORGANISM: Streptococcus thermophilus

<400> SEQUENCE: 699
tagaggtaat gacggcttac cgggtaaaga cgggg 35

<210> SEQ ID NO 700
<211> LENGTH: 35
<212> TYPE: DNA
<213> ORGANISM: Streptococcus thermophilus

<400> SEQUENCE: 700
tacgccagaa gaactagcga agaacatagt aggag 35

<210> SEQ ID NO 701

<211> LENGTH: 35
<212> TYPE: DNA
<213> ORGANISM: Streptococcus thermophilus

<400> SEQUENCE: 701
tgcaatttcc attagttctt gacgcccttt agggg 35

<210> SEQ ID NO 702
<211> LENGTH: 30
<212> TYPE: DNA
<213> ORGANISM: Streptococcus thermophilus

<400> SEQUENCE: 702
tgtagatagc gtgggtgcag agatgcacgg 30

<210> SEQ ID NO 703
<211> LENGTH: 30
<212> TYPE: DNA
<213> ORGANISM: Streptococcus thermophilus

<400> SEQUENCE: 703
tctaatccca ctaggaatag tgggtagtaa 30

<210> SEQ ID NO 704
<211> LENGTH: 30
<212> TYPE: DNA
<213> ORGANISM: Streptococcus thermophilus

<400> SEQUENCE: 704
tcgataaatc agccaaagta ttaagtggtt 30

<210> SEQ ID NO 705
<211> LENGTH: 30
<212> TYPE: DNA
<213> ORGANISM: Streptococcus thermophilus

<400> SEQUENCE: 705
cagcttgaaa tgtttattga agcagcagtg 30

<210> SEQ ID NO 706
<211> LENGTH: 30
<212> TYPE: DNA
<213> ORGANISM: Streptococcus thermophilus

<400> SEQUENCE: 706
ttatatcgaa gaacgactga aagagcttga 30

<210> SEQ ID NO 707
<211> LENGTH: 30
<212> TYPE: DNA
<213> ORGANISM: Streptococcus thermophilus

<400> SEQUENCE: 707
tccaagttat ttgaggagtt attaagacat 30

<210> SEQ ID NO 708
<211> LENGTH: 30
<212> TYPE: DNA
<213> ORGANISM: Streptococcus thermophilus

<400> SEQUENCE: 708
taccgaaacg actggtttga aaaattcaag 30

```
<210> SEQ ID NO 709
<211> LENGTH: 30
<212> TYPE: DNA
<213> ORGANISM: Streptococcus thermophilus

<400> SEQUENCE: 709

agttgattgc gtaatcaacc atctccataa                                  30

<210> SEQ ID NO 710
<211> LENGTH: 30
<212> TYPE: DNA
<213> ORGANISM: Streptococcus thermophilus

<400> SEQUENCE: 710

cttcaaatgt actgcaaggc tgcaaaagta                                  30

<210> SEQ ID NO 711
<211> LENGTH: 30
<212> TYPE: DNA
<213> ORGANISM: Streptococcus thermophilus

<400> SEQUENCE: 711

ttttccgtct tcttttttag caaagatacg                                  30

<210> SEQ ID NO 712
<211> LENGTH: 30
<212> TYPE: DNA
<213> ORGANISM: Streptococcus thermophilus

<400> SEQUENCE: 712

tgtttcaagg tttcgggtcc aagtatcatt                                  30

<210> SEQ ID NO 713
<211> LENGTH: 30
<212> TYPE: DNA
<213> ORGANISM: Streptococcus thermophilus

<400> SEQUENCE: 713

aaatcagttt tttgttcaga aacttgttct                                  30

<210> SEQ ID NO 714
<211> LENGTH: 30
<212> TYPE: DNA
<213> ORGANISM: Streptococcus thermophilus

<400> SEQUENCE: 714

tagaggtaat gacggcttac cgggtaaaga                                  30

<210> SEQ ID NO 715
<211> LENGTH: 30
<212> TYPE: DNA
<213> ORGANISM: Streptococcus thermophilus

<400> SEQUENCE: 715

gaagtattag gtctctcaaa agatgatatt                                  30

<210> SEQ ID NO 716
<211> LENGTH: 30
<212> TYPE: DNA
<213> ORGANISM: Streptococcus thermophilus

<400> SEQUENCE: 716

taaactatga aattttataa tttttgaaca                                  30
```

<210> SEQ ID NO 717
<211> LENGTH: 29
<212> TYPE: DNA
<213> ORGANISM: Streptococcus thermophilus

<400> SEQUENCE: 717
aacccaataa ttacagtgaa gcacaatag 29

<210> SEQ ID NO 718
<211> LENGTH: 31
<212> TYPE: DNA
<213> ORGANISM: Streptococcus thermophilus

<400> SEQUENCE: 718
aattgtgtcg gtctttttta ttgtttttac c 31

<210> SEQ ID NO 719
<211> LENGTH: 30
<212> TYPE: DNA
<213> ORGANISM: Streptococcus thermophilus

<400> SEQUENCE: 719
ctcgttaatt gcaagtttgg tcggcacgtt 30

<210> SEQ ID NO 720
<211> LENGTH: 30
<212> TYPE: DNA
<213> ORGANISM: Streptococcus thermophilus

<400> SEQUENCE: 720
ttgtggcaca aacaaaatga attaaagatt 30

<210> SEQ ID NO 721
<211> LENGTH: 29
<212> TYPE: DNA
<213> ORGANISM: Streptococcus thermophilus

<400> SEQUENCE: 721
acaagcaaag attacaaccg ctggtgcta 29

<210> SEQ ID NO 722
<211> LENGTH: 30
<212> TYPE: DNA
<213> ORGANISM: Streptococcus thermophilus

<400> SEQUENCE: 722
accaagtagc atttgagcaa agatagattg 30

<210> SEQ ID NO 723
<211> LENGTH: 5
<212> TYPE: DNA
<213> ORGANISM: Streptococcus thermophilus
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t

<400> SEQUENCE: 723 nggng 5

<210> SEQ ID NO 724
<211> LENGTH: 35
<212> TYPE: DNA
<213> ORGANISM: Streptococcus thermophilus

<400> SEQUENCE: 724
tgctcgactt gttaaaaaaa ctactgaaga tggcg 35

<210> SEQ ID NO 725
<211> LENGTH: 39
<212> TYPE: DNA
<213> ORGANISM: Streptococcus thermophilus

<400> SEQUENCE: 725
ttacgtttga aaagaatatc aaatcaatga cgagaaaga 39

<210> SEQ ID NO 726
<211> LENGTH: 39
<212> TYPE: DNA
<213> ORGANISM: Streptococcus thermophilus

<400> SEQUENCE: 726
ttacgtttga aaagaatatc aaattaatga cgagaaaga 39

<210> SEQ ID NO 727
<211> LENGTH: 39
<212> TYPE: DNA
<213> ORGANISM: Streptococcus thermophilus

<400> SEQUENCE: 727
ttacgtttga aaagaatatc aaatcaacga cgagaaaga 39

<210> SEQ ID NO 728
<211> LENGTH: 39
<212> TYPE: DNA
<213> ORGANISM: Streptococcus thermophilus

<400> SEQUENCE: 728
ttacgtttga aaagaatatc aaatcaatga cgagagaga 39

<210> SEQ ID NO 729
<211> LENGTH: 39
<212> TYPE: DNA
<213> ORGANISM: Streptococcus thermophilus

<400> SEQUENCE: 729
ttacgtttga aaagaatatc aaatctatga cgagaaaga 39

<210> SEQ ID NO 730
<211> LENGTH: 39
<212> TYPE: DNA
<213> ORGANISM: Streptococcus thermophilus

<400> SEQUENCE: 730
ttacgtttga aaagaatatc aattcaatga cgagaaaga 39

<210> SEQ ID NO 731
<211> LENGTH: 78
<212> TYPE: DNA
<213> ORGANISM: Streptococcus thermophilus

<400> SEQUENCE: 731
ttacgtttga aaagaatatc aaattaatgg cgagaaagat tacgtttgaa aagaatatca 60
aattaatggc gagaaaga 78

<210> SEQ ID NO 732
<211> LENGTH: 78
<212> TYPE: DNA
<213> ORGANISM: Streptococcus thermophilus

<400> SEQUENCE: 732
ttacgtttga aaagaacatc aaattaatga cgagaaagat tacgtttgaa aagaacatca 60
aattaatgac gagaaaga 78

<210> SEQ ID NO 733
<211> LENGTH: 39
<212> TYPE: DNA
<213> ORGANISM: Streptococcus thermophilus

<400> SEQUENCE: 733
ctcagtcgtt actggtgaac cagtttcaat tgagaaaaa 39

<210> SEQ ID NO 734
<211> LENGTH: 39
<212> TYPE: DNA
<213> ORGANISM: Streptococcus thermophilus

<400> SEQUENCE: 734
ctcagtcgtt actggtgaac cagtttcaat tgaaaaaaa 39

<210> SEQ ID NO 735
<211> LENGTH: 39
<212> TYPE: DNA
<213> ORGANISM: Streptococcus thermophilus

<400> SEQUENCE: 735
ctcagtcgtt actggtgaac cagtttcgat tgagaaaaa 39

<210> SEQ ID NO 736
<211> LENGTH: 39
<212> TYPE: DNA
<213> ORGANISM: Streptococcus thermophilus

<400> SEQUENCE: 736
ctcagtcgtt actggtgaac cagtttcaat tgagagaaa 39

<210> SEQ ID NO 737
<211> LENGTH: 78
<212> TYPE: DNA
<213> ORGANISM: Streptococcus thermophilus

<400> SEQUENCE: 737
ctcagtcgtt actggtgaac cggtttcaat tgaaaaaaac tcagtcgtta ctggtgaacc 60
ggtttcaatt gaaaaaaa 78

<210> SEQ ID NO 738
<211> LENGTH: 39
<212> TYPE: DNA
<213> ORGANISM: Streptococcus thermophilus

<400> SEQUENCE: 738
gcccttctaa ttggattacc ttccgaggtg ttagaattc 39

<210> SEQ ID NO 739
<211> LENGTH: 39

<212> TYPE: DNA
<213> ORGANISM: Streptococcus thermophilus

<400> SEQUENCE: 739
gcccttctaa ttggattacc ttccgaggtg ttagagttc 39

<210> SEQ ID NO 740
<211> LENGTH: 39
<212> TYPE: DNA
<213> ORGANISM: Streptococcus thermophilus

<400> SEQUENCE: 740
gcccttctaa ttggattacc ttccgatgtg ttagaattc 39

<210> SEQ ID NO 741
<211> LENGTH: 39
<212> TYPE: DNA
<213> ORGANISM: Streptococcus thermophilus

<400> SEQUENCE: 741
gcccttctaa ttggattacc ttccgagttg ttagaattc 39

<210> SEQ ID NO 742
<211> LENGTH: 38
<212> TYPE: DNA
<213> ORGANISM: Streptococcus thermophilus

<400> SEQUENCE: 742
gcccttctaa ttggattacc ttccgagtgt tagaattc 38

<210> SEQ ID NO 743
<211> LENGTH: 39
<212> TYPE: DNA
<213> ORGANISM: Streptococcus thermophilus

<400> SEQUENCE: 743
attgtctatt acgacaacat ggaagatgat gtagaaatt 39

<210> SEQ ID NO 744
<211> LENGTH: 39
<212> TYPE: DNA
<213> ORGANISM: Streptococcus thermophilus

<400> SEQUENCE: 744
attgtctatt acgacaacat ggaagatgat gtataaatt 39

<210> SEQ ID NO 745
<211> LENGTH: 39
<212> TYPE: DNA
<213> ORGANISM: Streptococcus thermophilus

<400> SEQUENCE: 745
attgtctatt acgacaacat ggaagattat gtagaaatt 39

<210> SEQ ID NO 746
<211> LENGTH: 3
<212> TYPE: DNA
<213> ORGANISM: Streptococcus thermophilus

<400> SEQUENCE: 746 att 3

<210> SEQ ID NO 747

<211> LENGTH: 39
<212> TYPE: DNA
<213> ORGANISM: Streptococcus thermophilus

<400> SEQUENCE: 747
attgtctatt acgacaacat ggaagatgat gtaaaaatt 39

<210> SEQ ID NO 748
<211> LENGTH: 39
<212> TYPE: DNA
<213> ORGANISM: Streptococcus thermophilus

<400> SEQUENCE: 748
ttatatcgaa gaacgactga aagagcttga gaagaaaaa 39

<210> SEQ ID NO 749
<211> LENGTH: 39
<212> TYPE: DNA
<213> ORGANISM: Streptococcus thermophilus

<400> SEQUENCE: 749
ttatatcgaa gaacgactga aagagcttga gaataaaaa 39

<210> SEQ ID NO 750
<211> LENGTH: 10
<212> TYPE: DNA
<213> ORGANISM: Streptococcus phage 858

<400> SEQUENCE: 750
aaagaaaaaa 10

<210> SEQ ID NO 751
<211> LENGTH: 10
<212> TYPE: DNA
<213> ORGANISM: Streptococcus phage 2972

<400> SEQUENCE: 751
ctaaaaggat 10

<210> SEQ ID NO 752
<211> LENGTH: 10
<212> TYPE: DNA
<213> ORGANISM: Streptococcus phage 2972

<400> SEQUENCE: 752
cgagaaagat 10

<210> SEQ ID NO 753
<211> LENGTH: 10
<212> TYPE: DNA
<213> ORGANISM: Streptococcus phage 2972

<400> SEQUENCE: 753
tgagaaaaaa 10

<210> SEQ ID NO 754
<211> LENGTH: 30
<212> TYPE: DNA
<213> ORGANISM: Streptococcus thermophilus

<400> SEQUENCE: 754
agtttctttg tcagactcta acacagccgc 30

-continued

<210> SEQ ID NO 755
<211> LENGTH: 10
<212> TYPE: DNA
<213> ORGANISM: Streptococcus phage 2972

<400> SEQUENCE: 755
tcagaaagtt 10

<210> SEQ ID NO 756
<211> LENGTH: 10
<212> TYPE: DNA
<213> ORGANISM: Streptococcus phage 2972

<400> SEQUENCE: 756
ttagaattcc 10

<210> SEQ ID NO 757
<211> LENGTH: 30
<212> TYPE: DNA
<213> ORGANISM: Streptococcus thermophilus

<400> SEQUENCE: 757
aagcaagttg atatatttct ctttctttat 30

<210> SEQ ID NO 758
<211> LENGTH: 10
<212> TYPE: DNA
<213> ORGANISM: Streptococcus phage 2972

<400> SEQUENCE: 758
taagaaaacg 10

<210> SEQ ID NO 759
<211> LENGTH: 29
<212> TYPE: DNA
<213> ORGANISM: Streptococcus thermophilus

<400> SEQUENCE: 759
cgttttcagt cattggtggt ttgtcagcg 29

<210> SEQ ID NO 760
<211> LENGTH: 10
<212> TYPE: DNA
<213> ORGANISM: Streptococcus phage 2972

<400> SEQUENCE: 760
aaagaaataa 10

<210> SEQ ID NO 761
<211> LENGTH: 10
<212> TYPE: DNA
<213> ORGANISM: Streptococcus phage 2972

<400> SEQUENCE: 761
tcagaatatg 10

<210> SEQ ID NO 762
<211> LENGTH: 30
<212> TYPE: DNA
<213> ORGANISM: Streptococcus thermophilus

<400> SEQUENCE: 762
aaatcaacgt acatcccgat ataggcacga 30

<210> SEQ ID NO 763
<211> LENGTH: 10
<212> TYPE: DNA
<213> ORGANISM: Streptococcus phage 2972

<400> SEQUENCE: 763
ttagaatcag 10

<210> SEQ ID NO 764
<211> LENGTH: 30
<212> TYPE: DNA
<213> ORGANISM: Streptococcus thermophilus

<400> SEQUENCE: 764
gacatatcga cgtatcgtga ttatcccatt 30

<210> SEQ ID NO 765
<211> LENGTH: 10
<212> TYPE: DNA
<213> ORGANISM: Streptococcus phage 2972

<400> SEQUENCE: 765
caagaaaaca 10

<210> SEQ ID NO 766
<211> LENGTH: 31
<212> TYPE: DNA
<213> ORGANISM: Streptococcus thermophilus

<400> SEQUENCE: 766
tgaagtatta ggtctctcaa aagatgatat t 31

<210> SEQ ID NO 767
<211> LENGTH: 10
<212> TYPE: DNA
<213> ORGANISM: Streptococcus phage 2972

<400> SEQUENCE: 767
gtagaatact 10

<210> SEQ ID NO 768
<211> LENGTH: 10
<212> TYPE: DNA
<213> ORGANISM: Streptococcus phage 2972

<400> SEQUENCE: 768
ttagaatgga 10

<210> SEQ ID NO 769
<211> LENGTH: 30
<212> TYPE: DNA
<213> ORGANISM: Streptococcus thermophilus

<400> SEQUENCE: 769
gcaacactca aacgttgcaa acgcaagctt 30

<210> SEQ ID NO 770
<211> LENGTH: 10
<212> TYPE: DNA
<213> ORGANISM: Streptococcus phage 2972

<400> SEQUENCE: 770
cgagaatatc 10

<210> SEQ ID NO 771
<211> LENGTH: 30
<212> TYPE: DNA
<213> ORGANISM: Streptococcus thermophilus

<400> SEQUENCE: 771
ctcagtcgtt actggtgaac cagtttcaat 30

<210> SEQ ID NO 772
<211> LENGTH: 10
<212> TYPE: DNA
<213> ORGANISM: Streptococcus phage 2972

<400> SEQUENCE: 772
atagaaagtt 10

<210> SEQ ID NO 773
<211> LENGTH: 10
<212> TYPE: DNA
<213> ORGANISM: Streptococcus phage 2972

<400> SEQUENCE: 773
tcagaagcta 10

<210> SEQ ID NO 774
<211> LENGTH: 10
<212> TYPE: DNA
<213> ORGANISM: Streptococcus phage 2972

<400> SEQUENCE: 774
ccagaaattg 10

<210> SEQ ID NO 775
<211> LENGTH: 10
<212> TYPE: DNA
<213> ORGANISM: Streptococcus phage 2972

<400> SEQUENCE: 775
gaggaaatca 10

<210> SEQ ID NO 776
<211> LENGTH: 30
<212> TYPE: DNA
<213> ORGANISM: Streptococcus thermophilus

<400> SEQUENCE: 776
gatgtcactg agtgtctaag cattgcgtac 30

<210> SEQ ID NO 777
<211> LENGTH: 2317
<212> TYPE: DNA
<213> ORGANISM: Streptococcus thermophilus

<400> SEQUENCE: 777
caaggacagt tattgatttt ataatcacta tgtgggtata aaaacgtcaa aatttcattt 60
gaggtttttg tactctcaag atttaagtaa ctgtacaact tacgtttgaa aagaatatca 120
aatcaatgag tttttgtact ctcaagattt aagtaactgt acaactgttt gacagcaaat 180
caagattcga attgtgtttt tgtactctca agatttaagt aactgtacaa caatgacgag 240
gagctattgg cacaacttac agtttttgta ctctcaagat ttaagtaact gtacaaccga 300

-continued

```
tttgacaatc tgctgaccac tgttatcgtt tttgtactct caagatttaa gtaactgtac    360
aacacacttg gcaggcttat tactcaacag cgagtttttg tactctcaag atttaagtaa    420
ctgtacaacc tgttccttgt tcttttgttg tatcttttcg tttttgtact ctcaagattt    480
aagtaactgt acaacttcat tcttccgttt ttgtttgcga atcctgtttt tgtactctca    540
agatttaagt aactgtacaa cgctggcgag gaaacgaaca aggcctcaac agtttttgta    600
ctctcaagat ttaagtaact gtacaaccat agagtggaaa actagaaaca gattcaagtt    660
tttgtactct caagatttaa gtaactgtac aacataatgc cgttgaatta cacggcaagg    720
tcagtttttg tactctcaag atttaagtaa ctgtacaacg agcgagctcg aaataatctt    780
aattacaagg tttttgtact ctcaagattt aagtaactgt acaacgttcg ctagcgtcat    840
gtggtaacgt atttagtttt tgtactctca agatttaagt aactgtacaa cggcgtccca    900
atcctgatta atacttactc ggtttttgta ctctcaagat ttaagtaact gtacaacaac    960
acagcaagac aagaggatga tgctatggtt tttgtactct caagatttaa gtaactgtac   1020
aaccgacaca agaacgtatg caagagttca aggtttttgt actctcaaga tttaagtaac   1080
tgtacaacac aattcttcat ccggtaactg ctcaagtggt ttttgtactc tcaagattta   1140
agtaactgta caacaattaa gggcatagaa agggagacaa catggttttt gtactctcaa   1200
gatttaagta actgtacaac cgatatttaa aatcattttc ataacttcat gtttttgtac   1260
tctcaagatt taagtaactg tacaacgcag tatcagcaag caagctgtta gttactgttt   1320
ttgtactctc aagatttaag taactgtaca acataaacta tgaaatttta taatttttaa   1380
gagtttttgt actctcaaga tttaagtaac tgtacaacaa taatttatgg tatagcttaa   1440
tatcattggt ttttgtactc tcaagattta agtaactgta caactgcatc gagcacgttc   1500
gagtttaccg tttcgttttt gtactctcaa gatttaagta actgtacaac tctatatcga   1560
ggtcaactaa caattatgct gtttttgtac tctcaagatt taagtaactg tacaacaatc   1620
gttcaaattc tgttttaggt acatttgttt ttgtactctc aagatttaag taactgtaca   1680
acaatcaata cgacaagagt taaaatggtc ttgtttttgt actctcaaga tttaagtaac   1740
tgtacaacgc ttagctgtcc aatccacgaa cgtggatggt ttttgtactc tcaagattta   1800
agtaactgta caaccaacca acggtaacag ctacttttta cagtgttttt gtactctcaa   1860
gatttaagta actgtacaac ataactgaag gataggagct tgtaaagtct gtttttgtac   1920
tctcaagatt taagtaactg tacaactaat gctacatctc aaaggatgat cccagagttt   1980
ttgtactctc aagatttaag taactgtaca acaagtagtt gatgacctct acaatggttt   2040
atgtttttgt actctcaaga tttaagtaac tgtacaacac ctagaagcat ttgagcgtat   2100
attgattggt ttttgtactc tcaagattta agtaactgta caacaatttt gccccttctt   2160
tgccccttga ctaggttttt gtactctcaa gatttaagta actgtacaac accattagca   2220
atcatttgtg cccattgagt gtttttgtac tctcaagatt taagtaactg tacagtttga   2280
ttcaacataa aaagccagtt caattgaact tggcttt                             2317
```

<210> SEQ ID NO 778
<211> LENGTH: 10
<212> TYPE: DNA
<213> ORGANISM: Streptococcus phage 2972

<400> SEQUENCE: 778

```
atagaaaagt                                                             10
```

<210> SEQ ID NO 779
<211> LENGTH: 29
<212> TYPE: DNA
<213> ORGANISM: Streptococcus thermophilus

<400> SEQUENCE: 779
caattaacac agcaattaac acagtatat 29

<210> SEQ ID NO 780
<211> LENGTH: 10
<212> TYPE: DNA
<213> ORGANISM: Streptococcus phage 2972

<400> SEQUENCE: 780
acagaaattg 10

<210> SEQ ID NO 781
<211> LENGTH: 30
<212> TYPE: DNA
<213> ORGANISM: Streptococcus thermophilus

<400> SEQUENCE: 781
atgccattct ttaaagaggc tttactcgtt 30

<210> SEQ ID NO 782
<211> LENGTH: 10
<212> TYPE: DNA
<213> ORGANISM: Streptococcus phage 2972

<400> SEQUENCE: 782
aaagaaaacg 10

<210> SEQ ID NO 783
<211> LENGTH: 30
<212> TYPE: DNA
<213> ORGANISM: Streptococcus thermophilus

<400> SEQUENCE: 783
gttggcggac tactccttcg aggggttgat 30

<210> SEQ ID NO 784
<211> LENGTH: 10
<212> TYPE: DNA
<213> ORGANISM: Streptococcus phage 2972

<400> SEQUENCE: 784
ccagaaatta 10

<210> SEQ ID NO 785
<211> LENGTH: 29
<212> TYPE: DNA
<213> ORGANISM: Streptococcus thermophilus

<400> SEQUENCE: 785
gaagcacctc ttgcgttgat aaaagtatt 29

<210> SEQ ID NO 786
<211> LENGTH: 10
<212> TYPE: DNA
<213> ORGANISM: Streptococcus phage 2972

<400> SEQUENCE: 786
gcagaaaatg 10

<210> SEQ ID NO 787
<211> LENGTH: 29
<212> TYPE: DNA
<213> ORGANISM: Streptococcus thermophilus

<400> SEQUENCE: 787
acatatcgac gtatcgtgat tatcccatt 29

<210> SEQ ID NO 788
<211> LENGTH: 10
<212> TYPE: DNA
<213> ORGANISM: Streptococcus phage 2972

<400> SEQUENCE: 788
caagaaaaca 10

<210> SEQ ID NO 789
<211> LENGTH: 10
<212> TYPE: DNA
<213> ORGANISM: Streptococcus phage 2972

<400> SEQUENCE: 789
gaagaaaaaa 10

<210> SEQ ID NO 790
<211> LENGTH: 30
<212> TYPE: DNA
<213> ORGANISM: Streptococcus thermophilus

<400> SEQUENCE: 790
tttcatcgtc aatttccatg ttataaatct 30

<210> SEQ ID NO 791
<211> LENGTH: 10
<212> TYPE: DNA
<213> ORGANISM: Streptococcus phage 2972

<400> SEQUENCE: 791
ctagaaactg 10

<210> SEQ ID NO 792
<211> LENGTH: 9
<212> TYPE: DNA
<213> ORGANISM: Streptococcus phage 2972

<400> SEQUENCE: 792 gtagaatac 9

<210> SEQ ID NO 793
<211> LENGTH: 29
<212> TYPE: DNA
<213> ORGANISM: Streptococcus thermophilus

<400> SEQUENCE: 793
attggcatga tttcaatttt aattgggat 29

<210> SEQ ID NO 794
<211> LENGTH: 10
<212> TYPE: DNA
<213> ORGANISM: Streptococcus phage 2972

<400> SEQUENCE: 794
gtagaaaaag 10

-continued

```
<210> SEQ ID NO 795
<211> LENGTH: 9
<212> TYPE: DNA
<213> ORGANISM: Streptococcus phage 2972

<400> SEQUENCE: 795

gaagaaata                                                              9


<210> SEQ ID NO 796
<211> LENGTH: 10
<212> TYPE: DNA
<213> ORGANISM: Streptococcus phage 2972

<400> SEQUENCE: 796

gaagaaaatc                                                            10


<210> SEQ ID NO 797
<211> LENGTH: 10
<212> TYPE: DNA
<213> ORGANISM: Streptococcus phage 2972

<400> SEQUENCE: 797

gtagaaattt                                                            10


<210> SEQ ID NO 798
<211> LENGTH: 10
<212> TYPE: DNA
<213> ORGANISM: Streptococcus phage 858

<400> SEQUENCE: 798

ccagaaaata                                                            10
```